US008535927B1

(12) United States Patent
Jones et al.

(10) Patent No.: US 8,535,927 B1
(45) Date of Patent: *Sep. 17, 2013

(54) MICROCOCCINEAE SERINE PROTEASE POLYPEPTIDES AND COMPOSITIONS THEREOF

(75) Inventors: Brian E. Jones, Leidschendam (NL); Marc Kolkman, Oegstgeest (NL); Chris Leeflang, The Hague (NL); Hiroshi Oh, Cincinnati, OH (US); Ayrookaran J. Poulose, Belmont, CA (US); Eugene S. Sadlowski, Cincinnati, OH (US); Andrew Shaw, San Francisco, CA (US); Leo van Marrewijk, Zoetermeer (NL); Wilhelmus A. H. Van Der Kleij, The Hague (NL)

(73) Assignee: Danisco US Inc., Palo Alto, CA (US)

( * ) Notice: Subject to any disclaimer, the term of this patent is extended or adjusted under 35 U.S.C. 154(b) by 1321 days.

This patent is subject to a terminal disclaimer.

(21) Appl. No.: 10/576,331

(22) PCT Filed: Nov. 19, 2004

(86) PCT No.: PCT/US2004/039066
§ 371 (c)(1),
(2), (4) Date: Jul. 18, 2007

(87) PCT Pub. No.: WO2005/052146
PCT Pub. Date: Jun. 9, 2005

Related U.S. Application Data

(60) Provisional application No. 60/523,609, filed on Nov. 19, 2003.

(51) Int. Cl.
*C12N 9/48* (2006.01)
*C11D 3/386* (2006.01)

(52) U.S. Cl.
USPC ........................................ 435/212; 510/306

(58) Field of Classification Search
None
See application file for complete search history.

(56) References Cited

U.S. PATENT DOCUMENTS

| 3,840,433 | A | 10/1974 | Aunstrup et al. |
| 3,986,926 | A | 10/1976 | Monsheimer et al. |
| 4,430,243 | A | 2/1984 | Bragg |
| 4,435,307 | A | 3/1984 | Barbesgaard et al. |
| 4,533,359 | A | 8/1985 | Kondo et al. |
| 4,683,195 | A | 7/1987 | Mullis et al. |
| 4,965,188 | A | 10/1990 | Mullis et al. |
| 4,977,252 | A | 12/1990 | Chiu |
| 5,147,642 | A | 9/1992 | Lotz et al. |
| 5,217,878 | A * | 6/1993 | van Eekelen et al. ........ 435/69.1 |
| 5,264,366 | A | 11/1993 | Ferrari et al. |
| RE34,606 | E | 5/1994 | Estell et al. |
| 5,314,692 | A | 5/1994 | Haarasilta et al. |
| 5,322,770 | A | 6/1994 | Gelfand |
| 5,324,653 | A | 6/1994 | Van Eekelen et al. |
| 5,340,735 | A | 8/1994 | Christianson et al. |
| 5,354,559 | A | 10/1994 | Morehouse |
| 5,364,770 | A | 11/1994 | Berka et al. |
| 5,401,657 | A | 3/1995 | Jones et al. |
| 5,486,303 | A | 1/1996 | Capeci et al. |
| 5,489,392 | A | 2/1996 | Capeci et al. |
| 5,500,364 | A | 3/1996 | Christianson et al. |
| 5,516,448 | A | 5/1996 | Capeci et al. |
| 5,565,422 | A | 10/1996 | Del Greco et al. |
| 5,569,645 | A | 10/1996 | Dinniwell et al. |
| 5,574,005 | A | 11/1996 | Welch et al. |
| 5,576,282 | A | 11/1996 | Miracle et al. |
| 5,595,967 | A | 1/1997 | Miracle et al. |
| 5,597,936 | A | 1/1997 | Perkins et al. |
| 5,612,055 | A | 3/1997 | Bedford et al. |
| 5,646,028 | A | 7/1997 | Leigh |
| 5,646,101 | A | 7/1997 | MacBeath |
| 5,686,014 | A | 11/1997 | Baillely et al. |
| 5,691,297 | A | 11/1997 | Nassano et al. |
| 5,695,679 | A | 12/1997 | Christie et al. |
| 5,698,504 | A | 12/1997 | Christie et al. |
| 5,700,676 | A | 12/1997 | Bott et al. |
| 5,705,464 | A | 1/1998 | Scheper et al. |

(Continued)

FOREIGN PATENT DOCUMENTS

| EP | 0214761 A2 | 3/1984 |
| EP | 0218272 A1 | 4/1984 |

(Continued)

OTHER PUBLICATIONS

Shimoi et al, Molecular structure of *Rarobacter faecitabidus* protease I. A yeast-lytic serine protease having mannose-binding activity. J Biol Chem. Dec. 15, 1992;267(35):25189-95.*
Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Sigma, Inc. Catalogue 1997 p. 1159.*
U.S. Appl. No. 09/554,992, filed May 23, 2000, Schellenberger, Volker.
U.S. Appl. No. 09/699,250, filed Feb. 5, 2002, Caldwell, Robert et al.
U.S. Appl. No. 09/927,161, filed Dec. 5, 2002, Diaz-Torres, Maria R. et al.

(Continued)

*Primary Examiner* — Sheridan Swope
(74) *Attorney, Agent, or Firm* — Danisco US, Inc.

(57) ABSTRACT

The present invention provides novel serine proteases, novel genetic material encoding these enzymes, and proteolytic proteins obtained from *Micrococcineae* spp., including but not limited to *Cellulomonas* spp. and variant proteins developed therefrom. In particular, the present invention provides protease compositions obtained from a *Cellulomonas* spp, DNA encoding the protease, vectors comprising the DNA encoding the protease, host cells transformed with the vector DNA, and an enzyme produced by the host cells. The present invention also provides cleaning compositions (e.g., detergent compositions), animal feed compositions, and textile and leather processing compositions comprising protease(s) obtained from a *Micrococcineae* spp., including but not limited to *Cellulomonas* spp. In alternative embodiments, the present invention provides mutant (i.e., variant) proteases derived from the wild-type proteases described herein. These mutant proteases also find use in numerous applications.

31 Claims, 24 Drawing Sheets

(56) References Cited

U.S. PATENT DOCUMENTS

| | | | |
|---|---|---|---|
| 5,710,115 A | 1/1998 | Patel et al. | |
| 5,795,764 A | 8/1998 | Christgau et al. | |
| 5,801,039 A | 9/1998 | Maurer et al. | |
| 5,855,625 A | 1/1999 | Maurer et al. | |
| 5,874,276 A | 2/1999 | Fowler et al. | |
| 5,879,584 A | 3/1999 | Bianchetti et al. | |
| 5,935,826 A | 8/1999 | Blue et al. | |
| 5,955,340 A | 9/1999 | Bott et al. | |
| 5,965,384 A | 10/1999 | Boel et al. | |
| 6,132,970 A | 10/2000 | Stemmer | |
| 6,225,464 B1 | 5/2001 | Hiler et al. | |
| 6,287,839 B1 | 9/2001 | Jones et al. | |
| 6,306,812 B1 | 10/2001 | Perkins et al. | |
| 6,312,936 B1 | 11/2001 | Poulose et al. | |
| 6,326,348 B1 | 12/2001 | Vinson et al. | |
| 6,376,450 B1 | 4/2002 | Ghosh et al. | |
| 6,440,991 B1 | 8/2002 | Zhu et al. | |
| 6,465,235 B1 | 10/2002 | Bott et al. | |
| 6,482,628 B1 | 11/2002 | Poulose et al. | |
| 6,566,114 B1 | 5/2003 | Kauppinen et al. | |
| 6,602,842 B2 | 8/2003 | Cuperus et al. | |
| 6,605,458 B1 | 8/2003 | Hansen et al. | |
| 6,610,642 B2 | 8/2003 | Ghosh et al. | |
| 7,378,256 B2 * | 5/2008 | Kim et al. | 435/69.1 |

FOREIGN PATENT DOCUMENTS

| | | |
|---|---|---|
| EP | 0134 267 A1 | 3/1985 |
| EP | 238023 A2 | 9/1987 |
| EP | 258068 A2 | 2/1988 |
| EP | 305216 A1 | 1/1989 |
| EP | 331376 A2 | 3/1989 |
| EP | 0 495 257 A1 | 7/1992 |
| EP | 505920 A1 | 9/1992 |
| EP | 0305216 B1 | 2/1995 |
| EP | 0 922 499 A2 | 6/1999 |
| EP | 0784703 B1 | 7/1999 |
| GB | 1296839 | 11/1972 |
| GB | 1372034 | 10/1974 |
| GB | 2233665 A | 1/1991 |
| GB | 2250289 | 6/1992 |
| JP | 04-327274 A | 11/1992 |
| WO | WO 88/06623 | 9/1988 |
| WO | WO 88/09367 | 12/1988 |
| WO | WO 89/04552 | 5/1989 |
| WO | WO 89/06270 | 7/1989 |
| WO | WO 90/00192 | 1/1990 |
| WO | WO 90/09446 | 8/1990 |
| WO | WO 90/12118 | 10/1990 |
| WO | WO 91/16422 | 10/1991 |
| WO | WO 92/05249 | 4/1992 |
| WO | WO 92/21760 | 12/1992 |
| WO | WO 94/12621 | 6/1994 |
| WO | WO 94/25576 | 11/1994 |
| WO | WO 95/01426 | 1/1995 |
| WO | WO 95/23221 | 8/1995 |
| WO | WO 96/11285 | 4/1996 |
| WO | WO 96/10646 | 11/1996 |
| WO | WO 96/34946 | 11/1996 |
| WO | WO 97/07770 | 3/1997 |
| WO | WO 97/11151 | 3/1997 |
| WO | WO 98/22500 | 5/1998 |
| WO | WO 99/34011 | 7/1999 |
| WO | WO 00/32601 | 6/2000 |
| WO | WO 01/58276 A2 | 8/2001 |
| WO | WO 02/14490 | 2/2002 |
| WO | WO 02/50245 A2 | 6/2002 |
| WO | WO 02/055717 A2 | 7/2002 |
| WO | WO 03/008650 A1 | 1/2003 |
| WO | WO 03/062380 | 7/2003 |
| WO | WO 2004/072279 | 8/2004 |
| WO | WO 2005/028636 | 3/2005 |
| WO | WO 2005/052146 | 6/2005 |
| WO | WO 2005/052161 | 6/2005 |
| WO | WO 2005/124012 | 12/2005 |

OTHER PUBLICATIONS

U.S. Appl. No. 10/804,785, filed Mar. 19, 2004, Goedegebuur, Rozenlaan.

Altschul, S. et al., "Local Alignment Statistics," *Meth. Enzymol.* 266:460-480, 1996.

Altschul. S, et al., "Basic Local Alignment Search Tool," *J. Mol. Biol.* 215:403-410, 1990.

Beaucage S. et al., "Deoxyneucleoside Phosporamidites—a new class of key intermediates for Deoxypolynucleotide Synthesis" *Tetrahedron Lett.* 22(20):1859-1862, 1981.

Benton, W. et al., "Screening λgt Recombinant Clones by Hubridization to Single Plaques in situ," *Science* 196(4286):180-182. 1977.

Cerny, G. "Method for the Distinction of Gramnegative from Grampositive Bacteria." *Eur. J. Appl. Microbiol.* 3:223-225, 1976.

Cerny, G. "Studies on the Aminopeptidase Test for the Distinction of Gram-Negative from Gram-Positive Bacteria," *Eur. J. Appl. Microbiol.*, 5:113-122, 1978.

Chamberlin, M. et al., "New RNA Polymerase from *Escherichia coli* Infected Bacteriophage T7," *Nature* 228:227-231, 1970.

Christianson, T. et al., "Peptide Mapping of Subtilisins as a Practical Tool for Locating Protein Sequence Errors during Extensive Protein Engineering Projects," *Anal. Biochem.* 223:11929, 1994.

Collins, M. "Isoprenoid Quinone Analyses in Bacterial Classification and Identification," in Goodfellow, M. et al., (eds), *Chemical Methods in Bacterial Systematics*, London: Academic Press, pp. 267-287, 1985.

Collins, M. et al., "Distribution of Isoprenoid Quinone Structural Types in Bacteria and Their Taxonomic Implications," *Microbial. Rev.*, 45(2):316-354, 1981.

Dartois, V. et al., "Cloning, nucleotide sequence and expression in *Escherichia coli* of a lipase gene from *Bacillus subtilis* 168," *Biochem. Biophys. Acta* 1131:253-260, 1992.

Del Mar, E. et al., "A Sensitive New Substrate for Chymotrypsin," *Anal. Biochem.*, 99:316-320, 1979.

Devereux, J. et al., "A comprehensive set of sequence analysis programs for the VAX," *Nucl. Acids Res.* 12(1):387-395. 1984.

Dussault, H.P, "An improved technique for staining red halophilic bacteria," *J. Bacteriol.* 70:484-485, 1955.

Felsenstein J. "Confidence Limits on Phylogenies: An Approach Using the Bootstrap," *Evol.* 39(4):783-789, 1985.

Feng, D.-F. et al., "Progressive Sequence Alignment as a Prerequisite to Correct Phylogenetic Trees," *J. Mol. Evol.* 25:351-360, 1987.

Fernandez-Abalos, J. et al., "Posttranslational processing of the xylanase Xys1L from *Streptomyces halstedii* JM8 is carried out by secreted serine proteases," *Microbiol.*, 149:1623-1632, 2003.

Ferrari, E. et al., "Genetics," in Hardwood et al, (eds.), *Bacillus*, New York: Plenum Publishing Corp., pp. 57-72, 1989.

Gregersen, T. "Rapid Method for Distinction of Gram-Negative from Gram-Positive Bacteria," *Eur. J. Appl. Microbiol. Biotechnol.*, 5:123-127, 1978.

Grunstein, M. et al., "Colony Hybridization: A method for the isolation of cloned DNAs that contain a specific gene," *Proc. Natl. Acad. Sci. USA*, 72(10):3961-3965, 1975.

Guerout-Fleury, A.-M. et al., "Antibiotic-resistance cassettes for *Bacillus subtilis*," *Gene* 167:335-336, 1995.

Haas, M. et al., "Cloning expression and characterization of a cDNA encoding a lipase from *Rhizopus delemar*," *Gene* 109:107-113, 1991.

Halebian, S. et al., "Rapid Method That Aids in Distinguishing Gram-Positive from Gram-Negative Anaerobic Bacteria," *J. Clin. Microbiol.*, 13(3):444-448, 1981.

Henikoff, S. et al., "Amino acid substitution matrices from protein blocks," *Proc. Natl. Acad. Sci.*, 89:10915-10919, 1992.

Higgins, Desmond et al., "Fast and sensitive multiple sequence alignment on a microcomputer," *CABIOS Comm.*, 5(2):151-153, 1989.

Hong, S.:XP002327071 retrieved from EBI Database accession No. AF515832 abstract, Database EMBL 'Online! (Jun. 20, 2002).

Jukes T. et al., "Evolution of protein molecules," in Munro, H. (ed.), *Mammalian Protein Metabolism*, New York: Academic Press, pp. 21-132, 1969.

Kacian, D. et al., "A Replicating RNA Molecule Suitable for a Detailed Analysis of Extracellular Evolution and Replication," *Proc. Natl. Acad. Sci. USA*, 69(10):3038-3042, 1972.

Kalisz, H. "Microbial Proteinases," in Fiechter, A. et al., (eds.), *Advances in Biochemical Engineering/Biotechnology*, vol. 36, pp. 1-65, 1988.

Karlin, S. et al., "Applications and statistics for multiple high-scoring segments in molecular sequences," *Proc. Natl. Acad. Sci. USA* 90:5873-5877, 1993.

Kraut, J. "Serine Proteases: Structure and Mechanism of Catalysis," *Ann. Rev. Biochem.* 46:331-358, 1977.

Kugimiya, W. et al., "Cloning and Sequence Analysis of cDNA encoding *Rhizopus niveus* Lipase," *Biosci. Biotech. Biochem.*, 56(5):716-719, 1992.

Lao, G. et, al. "Cloning, Sequencing, and Expression of a *Thermomonospora fusca* Protease Gene in *Streptomyces lividans*," *Appl. Environ. Microbiol.*, 62(11):4256-4259, 1996.

Lee, Y.-C. et al., "Requirement of a COOH-terminal pro-sequence for the extracellular secretion of aqualysin I (a thermophilic subtilisin-type protease) in *Thermus thermophilus*," *FEMS Microbiol. Lett.*, 120:69-74, 1994.

Longshaw, C. et al., "*Kytococcus sedentarius*, the organism associated with pitted keratolysis, produces two keratin-degrading enzymes," *J. Appl. Microbiol.* 93(5):810-816. 2002.

Matthes, Hans et al., "Simultaneous rapid chemical synthesis of over one hundred oligonucleotides on a microscale," *EMBO J.*, 3(4):801-805, 1984.

Mine, O. et al., "Use of degenerate primers and heat-soaked polymerase chain reaction (PCR) to clone a serine protease antigen from *Dermatophilus congolensis*," *Immunol. Cell Biol.*, 75(5):484-491, 1997.

Needham-VanDevanter, D. et al., "Characterization of an adduct between CC-1065 and a defined oligodeoxynucleotide duplex," *Nucl. Acids Res.*, 12(15):6159-6168, 1984.

Needleman, S. et al., "A General Method Applicable to the Search for Similarities in the Amino Acid Sequence of Two Proteins," *J. Mol, Biol.*, 48:443-453, 1970.

Oledzka, G. et al., "High-level expression, secretion, and purification of the thermostable aqualysin I from *Thermus aquaticus* YT-1 in *Pichia pastoris*," *Protein Expr. Purific.*, 29:223-229, 2003.

Palmeros, B. et al., "A family of removable cassettes designed to obtain antibiotic-resistance-free genomic modifications of *Escherichia coli* and other bacteria," *Gene*, 247:255-264, 2000.

Pearson, W. et al., "Improved tools for biological sequence comparison," *Proc. Natl. Acad. Sci.*, 85:2444-2448, 1988.

Raoult, D. et al., Database NCBI 'Online!, XP002327070, Database accession No. AA044722 abstract (Aug. 11, 2003).

Sackin, M. "Computer Programs for Classification and Identification," *Meth, Microbiol.*, 19:459-494, 1987.

Saeki K. et al., "Purification and characterization of an alkaline protease from *Oerskovia xanthineolytica* TK-1," *J. Ferment. Bioeng.*, 77(5):554-556, 1994.

Saitou, Naruya et al., "The Neighbor-joining Method: A New Method Reconstructing Phylogenetic Trees," *Mol. Biol, Evol.*, 4(4):406-425, 1987.

Sakamoto, S. et al., "Efficient Production of Thermus protease aqualysin I in *Escherichia coli*: effects of cloned gene structure and two-stage culture," *Appl. Microbiol. Biotechnol.*, 45:94-101, 1996.

Sakamoto, S. et al., "Expression of Aqualysin I (a Thermophilic Protease) in Soluble Form in *Escherchia coli* under a Bacteriophage T7 Promoter," *Biosci. Biotechnol. Biochem.*, 59(8):1438-1443, 1995.

Sambrook, J. et al., "Molecular Cloning: A Laboratory Manual", Second Ed., Plainview, NY: Cold Spring Harbor Laboratory Press, pp. 16.7-16.8, 1989.

Segalas, I. et al., "A particularly labile Asp-Pro bond in the green mamba muscarinic toxin MTX2. Effect of protein conformation on the rate of cleavage," *FEBS Lett.*, 371:171-175, 1995.

Shaw A. et al., "A Novel Combination of Two Classic Catalytic Schemes," *J. Mol. Biol.*, 320:303-309, 2002.

Shimada, Y. et al., "cDNA Molecular Cloning of *Geotrichum candidum* Lipase," *J. Biochem.*, 106:383-388, 1989.

Shimoi, H. et al, "Molecular structure of *Rarobacter faecitabidus* protease I: A yeast-lytic serine protease having mannose-binding activity," *J. Biol. Chem.*, 267(35):25189-25195, 1992.

Smith, T. et al., "Comparison of Biosequences," *Adv. Appl. Math.*, 2:482-489, 1981.

Sneath, P. et al., "The Estimation of Taxonomic Resemblance," in Sneath. P. et al., *Numencal Taxonomy*, San Francisco: W.H. Freeman & Co., pp. 114-187, 1973.

Stroud, R. "A Family of Protein-Cutting Proteins," *Sci. Amer.*, 131:74-88, 1974.

Trieu-Cuot, P. et al., "Nucleotide sequence of the *Streptococcus faecalis* plasmid gene encoding the 3'5"—aminoglycoside phosphotransferase type III," *Gene*, 23:331-341, 1983.

Van de Peer, Y. et al., "Treecon for Windows: a software package for the construction and drawing of evolutionary trees for the Microsoft Windows environment," *CABIOS Comput. Appl. Biosci.*, 10(5):569-570, 1994.

Van der Laan, J. et al., "Cloning, Characterization, and Multiple Chromosomal Integration of a Bacillus Alkaline Protease Gene," *Appl. Environ. Microbiol.* 57(4):901-909, 1991.

Voskuil, M. et al,. "The—16 region, a vital sequence for the utilization of a promoter in *Bacillus subtilis* and *Escherichia coli*," *Mol. Microbiol.* 17(2):271-279, 1995.

Wu, D. et al., "The Ligation Amplification Reaction (LAR)—Amplification of Specific DNA Sequences Using Sequential Rounds of Template-Dependent Ligation," *Genomics*, 4:560-569, 1989.

Yamaguchi, S. et al., "Cloning and structure of the mono- and diacylglycerol lipase-encoding gene from *Penicillium camembertii* U-150," *Gene*, 103:61-67, 1991.

Screen, S.E., et al., "Cloning, Expression, and Substrate Specificity of a Fungal Chymotrypsin," *J. Biol. Chem.* 276(9): 6689-6694 (2000).

Sidhu, S.S., et al., "*Streptomyces griseus* Protease C." *J. Biol. Chem.* 269(31): 20167-20171 (1994).

GenPept Accession CAB44651 located at http://www.ncbi.nlm.nih.gov/protein/5042248?sat=OLD04&satkey=616966 (Mar. 3, 2000).

GenPept Accession CAB60729, located at http://www.ncbi.nlm.nih.gov/protein/6433954?sat=OLD04&satkey=617118 (Mar. 3, 2000).

GenPept Accession AAA26813, located at http://www//ncbi.nlm.nih.gov/protein/AAA26813 (Aug. 26, 1994).

GenPept Accession AAM55224, located at http://www.ncbi.nlm.nih.gov/protein/AAM55224 (Jun. 20, 2002).

GenPept Accession CAA52206, located at http://www.ncbi.nlm.nih.gov/protein/395197?sat=0&satkey=454972 (Jul. 26, 1993).

GenPept Accession CAA52205, located at http://www.ncbi.nlm.nih.gov/protein/395199?satkey=454973 (Jul. 26, 1993).

U.S. Appl. No. 10/567,331, filed Jul. 18, 2007, Jones.

U.S. Appl. No. 11/583,334, filed Oct. 19, 2006, Wofgang.

Duckworthm, et al., "Phylogenetic diversity of soda lake alkaliphiles", FEMS Microbiol. Ecol., 19:181-191, [1996].

Dynan, et al., "Control of eukaryotic messenger RNA synthesis by sequence-specific DNA-binding proteins", Nature 316:774-78, [1985].

EMBL Database Accession No. CAM33240; Cellulomonas bogoriensis preprocellulomonadin, [2007] http://www.ebi.ae.uk/ena/data/view/CAM33240&display=text.

Foreman, et al., "Transcriptional regulation of biomass-degrading enzymes in the filamentous fungus Trichoderma reesei" J. Biol. Chem., 278:31988-97 [2003].

Karlin, S. et al., "Applications and statistics for multiple high-scoring segments in molecular sequences", Proc. Natl. Acad. Sci. USA 90:5873-5877, [1993].

Kim, et al., "A carboxy-terminal pro-sequence of aqualysin I prevents proper folding of the protease domain on its secretion by *Saccharomyces cerevisiae*", Biochem. Biophys. Res. Commun., 231:535-539 [1997].

Needleman, S. et al., "A General Method Applicable to the Search for Similarities in the Amino Acid Sequence of Two Proteins," *J. Mol. Biol.*, 48:443-453, [1970].

NP_787753.GenBank Accession, [2003] http://www.ncbi.nlm.nih.gov/protein/28493592?sat=24&satkey=5208676.

Pearson, W. et al., "Improved tools for biological sequence comparison", Proc. Natl. Acad. Sci., 85:2444-2448, [1988].

Sambrook J. et al., "Molecular Cloning: A Laboratory Manual", Second Ed., Planview, N.Y. Cold Spring Harbor Laboratory Press, pp. 16.7-16.8, [1989].

Sigma, Inc. Catalogue, "Biochemicals and reagents for life science research", 1997 p. 1159.

Sneath, et al., "The Estimation of Taxonomic Resemblance", Numerical Taxonomy The Principles and Practice of Numerical Classification, 114-187, [1973].

Yamaguchi, S. et al.. "Cloning and structure of the mono- and diacylglycerol lipase-encoding gene from *Penicillium camembertii* U-150," *Gene*, 103:61-67, 1991.

International Preliminary Report on Patentability and Written Opinion of the International Search Authority for PCT/US2004/039006 mailed May 22, 2006.

International Preliminary Report on Patentability and Written Opinion of the International Search Authority for PCT/US2007/018909 mailed Apr. 22, 2009.

International Search Report for PCT/US2007/018909 mailed Feb. 12, 2008.

\* cited by examiner

SEQUENCE LISTING

<160> NUMBER OF SEQ ID NOS: 656

<210> SEQ ID NO 1
<211> LENGTH: 1680
<212> TYPE: DNA
<213> ORGANISM: Cellulomonas strain 69B4

<400> SEQUENCE: 1

```
gcgcgctgcg cccacgacga cgccgtccgc cgttcgccgg cgtacctgcg ttggctcacc      60
acccaccaga tcgacctcca taacgaggcc gtatgaccag aaagggatct gccaccgccc     120
accagcacgc tcctaacctc cgagcaccgg cgaccgccgg gtgcgatgaa agggacgaac     180
cgagatgaca ccacgcacag tcacgcgggc cctggccgtg gccaccgcag ccgccacact     240
cctggcaggc ggcatggccg cccaggccaa cgagcccgca ccacccggga gcgcgagcgc     300
accgccacgc ctggccgaga agctcgaccc cgacctcctc gaggccatgg agcgcgacct     360
gggcctcgac gcggaggaag ccgccgccac cctggcgttc cagcacgacg cagccgagac     420
cggcgaggcc ctcgccgaag agctcgacga ggacttcgcc ggcacctggg tcgaggacga     480
cgtcctgtac gtcgccacca ccgacgagga cgccgtcgag gaggtcgagg gcgaaggcgc     540
cacggccgtc accgtcgagc actccctggc cgacctcgag gcctggaaga ccgtcctcga     600
cgccgccctc gagggccacg acgacgtgcc cacctggtac gtcgacgtcc cgaccaacag     660
cgtcgtcgtc gccgtcaagg ccggagccca ggacgtcgcc gccggcctcg tcgaaggtgc     720
cgacgtcccg tccgacgccg tgaccttcgt cgagaccgac gagacccccgc ggaccatgtt     780
cgacgtgatc ggcggcaacg cctacaccat cggggggcgc agccgctgct cgatcgggtt     840
cgcggtcaac ggcgggttca tcaccgccgg ccactgcggc cgcaccggcg ccaccaccgc     900
caacccacc gggaccttcg ccgggtccag cttcccgggc aacgactacg cgttcgtccg     960
taccggggcc ggcgtgaacc tgctggccca ggtcaacaac tactccggtg gccgcgtcca    1020
ggtcgccggg cacaccgcgg cccccgtcgg ctcggccgtg tgccggtccg ggtcgaccac    1080
cgggtggcac tgcggcacca tcactgcgct caactcctcg gtcacctacc ccgagggcac    1140
cgtccgcggc ctgatccgca ccaccgtctg cgccgagccc ggcgactccg gtggctcgct    1200
gctcgccggc aaccaggccc agggcgtcac gtccggcggc tccggcaact gccgcaccgg    1260
tggcaccacg ttcttccagc cggtcaaccc catcctccag gcgtacggcc tgaggatgat    1320
caccacggac tcgggcagca gcccggcccc tgcaccgacc tcctgcaccg gctacgcccg    1380
caccttcacc gggaccctcg cggccggccg ggccgccgcc cagcccaacg gtcctacgt     1440
gcaggtcaac cggtccggga cccacagcgt gtgcctcaac gggccctccg gtgcggactt    1500
cgacctctac gtgcagcgct ggaacggcag ctcctgggtg accgtcgccc agagcacctc    1560
ccccggctcc aacgagacca tcacctaccg cggcaacgcc ggctactacc gctacgtggt    1620
caacgccgcg tccggctccg gtgcctacac catggggctc accctcccct gacgtagcgc    1680
```

<210> SEQ ID NO 2
<211> LENGTH: 1488
<212> TYPE: DNA
<213> ORGANISM: Cellulomonas strain 69B4

<400> SEQUENCE: 2

```
atgacaccac gcacagtcac gcgggccctg ccgtggcca ccgcagccgc cacactcctg      60
gcaggcggca tggccgccca ggccaacgag cccgcaccac ccgggagcgc gagcgcaccg     120
ccacgcctgg ccgagaagct cgaccccgac ctcctcgagg ccatggagcg cgacctgggc    180
ctcgacgcgg aggaagccgc cgccaccctg gcgttccagc acgacgcagc cgagaccggc    240
gaggccctcg ccgaagagct cgacgaggac ttcgccggca cctgggtcga ggacgacgtc    300
ctgtacgtcg ccaccaccga cgaggacgcc gtcgaggagg tcgagggcga aggcgccacg    360
gccgtcaccg tcgagcactc cctggccgac ctcgaggcct ggaagaccgt cctcgacgcc    420
gccctcgagg ccacgacga cgtgcccacc tggtacgtcg acgtcccgac caacagcgtc    480
gtcgtcgccg tcaaggccgg agcccaggac gtcgccgccg gcctcgtcga aggtgccgac    540
gtcccgtccg acgccgtgac cttcgtcgag accgacgaga cccgcggac catgttcgac    600
gtgatcggcg gcaacgccta ccatcgggg gggcgcagcc gctgctcgat cgggttcgcg    660
gtcaacggcg ggttcatcac cgccggccac tgccgccgca ccggcgccac caccgccaac    720
cccaccggga ccttcgccgg gtccagcttc ccgggcaacg actacgcgtt cgtccgtacc    780
ggggccggcg tgaacctgct ggcccaggtc aacaactact ccggtggccg cgtccaggtc    840
gccgggcaca ccgcggcccc cgtcggctcg gccgtgtgcc ggtccgggtc gaccaccggg    900
tggcactgcg gcaccatcac ctgcgctcaac tcctcggtca cctacccga gggcaccgtc    960
cgcggcctga tccgcaccac cgtctgcgcc gagcccggcg actccggtgg ctcgctgctc   1020
gccggcaacc aggcccaggg cgtcacgtcc ggcggctccg gcaactgccg caccggtggc   1080
accacgttct tccagccggt caaccccatc ctccaggcgt acggcctgag gatgatcacc   1140
acggactcgg gcagcagccc ggcccctgca ccgacctcct gcaccggcta cgcccgcacc   1200
ttcaccggga ccctcgcggc cggccgggcc gccgcccagc caacgggtc ctacgtgcag   1260
gtcaaccggt ccgggaccca cagcgtgtgc ctcaacgggc cctccggtgc ggacttcgac   1320
ctctacgtgc agcgctggaa cggcagctcc tgggtgaccg tcgcccagag cacctccccc   1380
ggctccaacg agaccatcac ctaccgcggc aacgccggct actaccgcta cgtggtcaac   1440
gccgcgtccg gctccggtgc ctacaccatg gggctcaccc tcccctga                1488
```

<210> SEQ ID NO 3
<211> LENGTH: 1404
<212> TYPE: DNA
<213> ORGANISM: Cellulomonas spp.

<400> SEQUENCE: 3

```
aacgagcccg caccacccgg gagcgcgagc gcaccgccac gcctggccga gaagctcgac      60
cccgacctcc tcgaggccat ggagcgcgac ctgggcctcg acgcggagga agccgccgcc    120
accctggcgt tccagcacga cgcagccgag accggcgagg ccctcgccga agagctcgac    180
gaggacttcg ccggcacctg gtcgaggac gacgtcctgt acgtcgccac caccgacgag    240
gacgccgtcg aggaggtcga gggcgaaggc gccacggccg tcaccgtcga gcactccctg    300
gccgacctcg aggcctggaa gaccgtcctc gacgccgccc tcgagggcca cgacgacgtg    360
cccacctggt acgtcgacgt cccgaccaac agcgtcgtcg tcgccgtcaa ggccggagcc    420
```

-continued

```
caggacgtcg ccgccggcct cgtcgaaggt gccgacgtcc cgtccgacgc cgtgaccttc      480
gtcgagaccg acgagacccc gcggaccatg ttcgacgtga tcggcggcaa cgcctacacc      540
atcggggggc gcagccgctg ctcgatcggg ttcgcggtca acggcgggtt catcaccgcc      600
ggccactgcg gccgcaccgg cgccaccacc gccaaccccca ccgggacctt cgccgggtcc     660
agcttcccgg gcaacgacta cgcgttcgtc cgtaccgggg ccggcgtgaa cctgctggcc      720
caggtcaaca actactccgg tggccgcgtc caggtcgccg ggcacaccgc ggcccccgtc      780
ggctcggccg tgtgccggtc cgggtcgacc accgggtggc actgcggcac catcactgcg      840
ctcaactcct cggtcaccta ccccgagggc accgtccgcg gcctgatccg caccaccgtc      900
tgcgccgagc ccggcgactc cggtggctcg ctgctcgccg gcaaccaggc ccagggcgtc      960
acgtccggcg gctccggcaa ctgccgcacc ggtggcacca cgttcttcca gccggtcaac     1020
cccatcctcc aggcgtacgg cctgaggatg atcaccacgg actcgggcag cagcccggcc     1080
cctgcaccga cctcctgcac cggctacgcc cgcaccttca ccgggaccct cgcggccggc     1140
cgggccgccg cccagcccaa cgggtcctac gtgcaggtca accggtccgg gacccacagc     1200
gtgtgcctca acgggccctc cggtgcggac ttcgacctct acgtgcagcg ctggaacggc     1260
agctcctggg tgaccgtcgc ccagagcacc tcccccggct ccaacgagac catcacctac     1320
cgcggcaacg ccggctacta ccgctacgtg gtcaacgccg cgtccggctc cggtgcctac     1380
accatggggc tcaccctccc ctga                                             1404

<210> SEQ ID NO 4
<211> LENGTH: 567
<212> TYPE: DNA
<213> ORGANISM: Cellulomonas spp.

<400> SEQUENCE: 4
ttcgacgtga tcggcggcaa cgcctacacc atcggggggc gcagccgctg ctcgatcggg       60
ttcgcggtca acggcgggtt catcaccgcc ggccactgcg gccgcaccgg cgccaccacc      120
gccaaccccca ccgggacctt cgccgggtcc agcttcccgg gcaacgacta cgcgttcgtc     180
cgtaccgggg ccggcgtgaa cctgctggcc caggtcaaca actactccgg tggccgcgtc      240
caggtcgccg ggcacaccgc ggcccccgtc ggctcggccg tgtgccggtc cgggtcgacc      300
accgggtggc actgcggcac catcactgcg ctcaactcct cggtcaccta ccccgagggc      360
accgtccgcg gcctgatccg caccaccgtc tgcgccgagc ccggcgactc cggtggctcg      420
ctgctcgccg gcaaccaggc ccagggcgtc acgtccggcg gctccggcaa ctgccgcacc      480
ggtggcacca cgttcttcca gccggtcaac cccatcctcc aggcgtacgg cctgaggatg      540
atcaccacgg actcgggcag cagcccg                                          567

<210> SEQ ID NO 5
<211> LENGTH: 83
<212> TYPE: DNA
<213> ORGANISM: Cellulomonas strain 69B4

<400> SEQUENCE: 5
atgacaccac cacagtcacg cgggccctgg ccgtggccac cgcagccgcc acactcctgg       60
caggcggcat ggccgcccag gcc                                               83

<210> SEQ ID NO 6
<211> LENGTH: 495
<212> TYPE: PRT
<213> ORGANISM: Cellulomonas strain 69B4
```

-continued

```
<400> SEQUENCE: 6

Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala Asn Glu Pro Ala
            20                  25                  30

Pro Pro Gly Ser Ala Ser Ala Pro Arg Leu Ala Glu Lys Leu Asp
        35                  40                  45

Pro Asp Leu Leu Glu Ala Met Glu Arg Asp Leu Gly Leu Asp Ala Glu
    50                  55                  60

Glu Ala Ala Ala Thr Leu Ala Phe Gln His Asp Ala Ala Glu Thr Gly
65                  70                  75                  80

Glu Ala Leu Ala Glu Glu Leu Asp Glu Asp Phe Ala Gly Thr Trp Val
                85                  90                  95

Glu Asp Asp Val Leu Tyr Val Ala Thr Thr Asp Glu Asp Ala Val Glu
            100                 105                 110

Glu Val Glu Gly Glu Gly Ala Thr Ala Val Thr Val Glu His Ser Leu
        115                 120                 125

Ala Asp Leu Glu Ala Trp Lys Thr Val Leu Asp Ala Ala Leu Glu Gly
130                 135                 140

His Asp Asp Val Pro Thr Trp Tyr Val Asp Val Pro Thr Asn Ser Val
145                 150                 155                 160

Val Val Ala Val Lys Ala Gly Ala Gln Asp Val Ala Ala Gly Leu Val
                165                 170                 175

Glu Gly Ala Asp Val Pro Ser Asp Ala Val Thr Phe Val Glu Thr Asp
            180                 185                 190

Glu Thr Pro Arg Thr Met Phe Asp Val Ile Gly Gly Asn Ala Tyr Thr
        195                 200                 205

Ile Gly Gly Arg Ser Arg Cys Ser Ile Gly Phe Ala Val Asn Gly Gly
    210                 215                 220

Phe Ile Thr Ala Gly His Cys Gly Arg Thr Gly Ala Thr Ala Asn
225                 230                 235                 240

Pro Thr Gly Thr Phe Ala Gly Ser Ser Phe Pro Gly Asn Asp Tyr Ala
                245                 250                 255

Phe Val Arg Thr Gly Ala Gly Val Asn Leu Leu Ala Gln Val Asn Asn
            260                 265                 270

Tyr Ser Gly Gly Arg Val Gln Val Ala Gly His Thr Ala Ala Pro Val
        275                 280                 285

Gly Ser Ala Val Cys Arg Ser Gly Ser Thr Thr Gly Trp His Cys Gly
    290                 295                 300

Thr Ile Thr Ala Leu Asn Ser Ser Val Thr Tyr Pro Glu Gly Thr Val
305                 310                 315                 320

Arg Gly Leu Ile Arg Thr Thr Val Cys Ala Glu Pro Gly Asp Ser Gly
                325                 330                 335

Gly Ser Leu Leu Ala Gly Asn Gln Ala Gln Gly Val Thr Ser Gly Gly
            340                 345                 350

Ser Gly Asn Cys Arg Thr Gly Gly Thr Thr Phe Phe Gln Pro Val Asn
        355                 360                 365

Pro Ile Leu Gln Ala Tyr Gly Leu Arg Met Ile Thr Thr Asp Ser Gly
    370                 375                 380

Ser Ser Pro Ala Pro Ala Pro Thr Ser Cys Thr Gly Tyr Ala Arg Thr
385                 390                 395                 400

Phe Thr Gly Thr Leu Ala Gly Arg Ala Ala Gln Pro Asn Gly
                405                 410                 415
```

```
Ser Tyr Val Gln Val Asn Arg Ser Gly Thr His Ser Val Cys Leu Asn
            420                 425                 430

Gly Pro Ser Gly Ala Asp Phe Asp Leu Tyr Val Gln Arg Trp Asn Gly
        435                 440                 445

Ser Ser Trp Val Thr Val Ala Gln Ser Thr Ser Pro Gly Ser Asn Glu
        450                 455                 460

Thr Ile Thr Tyr Arg Gly Asn Ala Gly Tyr Tyr Arg Tyr Val Val Asn
465                 470                 475                 480

Ala Ala Ser Gly Ser Gly Ala Tyr Thr Met Gly Leu Thr Leu Pro
                485                 490                 495

<210> SEQ ID NO 7
<211> LENGTH: 467
<212> TYPE: PRT
<213> ORGANISM: Cellulomonas strain 69B4

<400> SEQUENCE: 7

Asn Glu Pro Ala Pro Pro Gly Ser Ala Ser Ala Pro Pro Arg Leu Ala
1               5                   10                  15

Glu Lys Leu Asp Pro Asp Leu Leu Glu Ala Met Glu Arg Asp Leu Gly
            20                  25                  30

Leu Asp Ala Glu Glu Ala Ala Thr Leu Ala Phe Gln His Asp Ala
        35                  40                  45

Ala Glu Thr Gly Glu Ala Leu Ala Glu Glu Leu Asp Glu Asp Phe Ala
50                  55                  60

Gly Thr Trp Val Glu Asp Asp Val Leu Tyr Val Ala Thr Thr Asp Glu
65              70                  75                  80

Asp Ala Val Glu Glu Val Glu Gly Gly Ala Thr Ala Val Thr Val
                85                  90                  95

Glu His Ser Leu Ala Asp Leu Glu Ala Trp Lys Thr Val Leu Asp Ala
            100                 105                 110

Ala Leu Glu Gly His Asp Asp Val Pro Thr Trp Tyr Val Asp Val Pro
        115                 120                 125

Thr Asn Ser Val Val Ala Val Lys Ala Gly Ala Gln Asp Val Ala
130                 135                 140

Ala Gly Leu Val Glu Gly Ala Asp Val Pro Ser Asp Ala Val Thr Phe
145                 150                 155                 160

Val Glu Thr Asp Glu Thr Pro Arg Thr Met Phe Asp Val Ile Gly Gly
                165                 170                 175

Asn Ala Tyr Thr Ile Gly Gly Arg Ser Arg Cys Ser Ile Gly Phe Ala
            180                 185                 190

Val Asn Gly Gly Phe Ile Thr Ala Gly His Cys Gly Arg Thr Gly Ala
        195                 200                 205

Thr Thr Ala Asn Pro Thr Gly Thr Phe Ala Gly Ser Ser Phe Pro Gly
210                 215                 220

Asn Asp Tyr Ala Phe Val Arg Thr Gly Ala Gly Val Asn Leu Leu Ala
225                 230                 235                 240

Gln Val Asn Asn Tyr Ser Gly Gly Arg Val Gln Val Ala Gly His Thr
                245                 250                 255

Ala Ala Pro Val Gly Ser Ala Val Cys Arg Ser Gly Ser Thr Thr Gly
            260                 265                 270

Trp His Cys Gly Thr Ile Thr Ala Leu Asn Ser Ser Val Thr Tyr Pro
        275                 280                 285

Glu Gly Thr Val Arg Gly Leu Ile Arg Thr Thr Val Cys Ala Glu Pro
290                 295                 300
```

```
Gly Asp Ser Gly Gly Ser Leu Leu Ala Gly Asn Gln Ala Gln Gly Val
305                 310                 315                 320

Thr Ser Gly Gly Ser Gly Asn Cys Arg Thr Gly Gly Thr Thr Phe Phe
                325                 330                 335

Gln Pro Val Asn Pro Ile Leu Gln Ala Tyr Gly Leu Arg Met Ile Thr
            340                 345                 350

Thr Asp Ser Gly Ser Ser Pro Ala Pro Ala Pro Thr Ser Cys Thr Gly
                355                 360                 365

Tyr Ala Arg Thr Phe Thr Gly Thr Leu Ala Ala Gly Arg Ala Ala Ala
            370                 375                 380

Gln Pro Asn Gly Ser Tyr Val Gln Val Asn Arg Ser Gly Thr His Ser
385                 390                 395                 400

Val Cys Leu Asn Gly Pro Ser Gly Ala Asp Phe Asp Leu Tyr Val Gln
                405                 410                 415

Arg Trp Asn Gly Ser Ser Trp Val Thr Val Ala Gln Ser Thr Ser Pro
                420                 425                 430

Gly Ser Asn Glu Thr Ile Thr Tyr Arg Gly Asn Ala Gly Tyr Tyr Arg
                435                 440                 445

Tyr Val Val Asn Ala Ala Ser Gly Ser Gly Ala Tyr Thr Met Gly Leu
450                 455                 460

Thr Leu Pro
465

<210> SEQ ID NO 8
<211> LENGTH: 189
<212> TYPE: PRT
<213> ORGANISM: Cellulomonas strain 69B4

<400> SEQUENCE: 8

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
                20                  25                  30

Cys Gly Arg Thr Gly Ala Thr Thr Ala Asn Pro Thr Gly Thr Phe Ala
            35                  40                  45

Gly Ser Ser Phe Pro Gly Asn Asp Tyr Ala Phe Val Arg Thr Gly Ala
        50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
        115                 120                 125

Thr Val Cys Ala Glu Pro Gly Asp Ser Gly Gly Ser Leu Leu Ala Gly
130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp Ser Gly Ser Ser Pro
            180                 185

<210> SEQ ID NO 9
<211> LENGTH: 28
```

```
<212> TYPE: PRT
<213> ORGANISM: Cellulomonas strain 69B4

<400> SEQUENCE: 9

Met Thr Pro Arg Thr Val Thr Arg Ala Leu Ala Val Ala Thr Ala Ala
1               5                   10                  15

Ala Thr Leu Leu Ala Gly Gly Met Ala Ala Gln Ala
            20                  25

<210> SEQ ID NO 10
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t

<400> SEQUENCE: 10
acnacsggst ggcrgtgcgg cac                                           23

<210> SEQ ID NO 11
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (2)..(17)
<223> OTHER INFORMATION: n is a, c, g, or t

<400> SEQUENCE: 11
angngccgcc ggagtcncc                                                19

<210> SEQ ID NO 12
<211> LENGTH: 58
<212> TYPE: PRT
<213> ORGANISM: Cellulomonas strain 69B4

<400> SEQUENCE: 12

Asp Gly Trp Asp Cys Gly Thr Ile Thr Ala Leu Asn Ser Ser Val Thr
1               5                   10                  15

Tyr Pro Glu Gly Thr Val Arg Gly Leu Ile Arg Thr Thr Val Cys Ala
            20                  25                  30

Glu Pro Gly Asp Ser Gly Gly Ser Leu Leu Ala Gly Asn Gln Ala Gln
        35                  40                  45

Gly Val Thr Ser Gly Asp Ser Gly Gly Ser
    50                  55

<210> SEQ ID NO 13
<211> LENGTH: 177
<212> TYPE: DNA
<213> ORGANISM: Cellulomonas strain 69B4

<400> SEQUENCE: 13
acgacggctg ggactgcggc accatcactg cgctcaactc ctcggtcacc taccccgagg      60
gcaccgtccg cggcctgatc cgcaccaccg tctgcgccga gcccggcgac tccggtggct     120
cgctgctcgc cggcaaccag gcccagggcg tcacgtccgg cgactccggc ggctcat        177

<210> SEQ ID NO 14
<211> LENGTH: 32
```

```
<212> TYPE: DNA
<213> ORGANISM: Artificial Sequence
<220> FEATURE:
<223> OTHER INFORMATION: primer

<400> SEQUENCE: 14
cggggtaggt gaccgaggag ttgagcgcag tg                                    32

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
gctcgccggc aaccaggccc agggcgtcac gtc                                   33

<210> SEQ ID NO 16
<211> LENGTH: 34
<212> TYPE: DNA
<213> ORGANISM: Artificial Sequence
<220> FEATURE:
<223> OTHER INFORMATION: primer

<400> SEQUENCE: 16
aacggcgggt tcatcaccgc cggccactgc ggcc                                  34

<210> SEQ ID NO 17
<211> LENGTH: 14
<212> TYPE: PRT
<213> ORGANISM: Artificial Sequence
<220> FEATURE:
<223> OTHER INFORMATION: N-terminus of the mature chain determined by
      MALDI-TOF analysis

<400> SEQUENCE: 17

Phe Asp Val Ile Gly Gly Asn Ala Tyr Thr Ile Gly Gly Arg
1               5                   10

<210> SEQ ID NO 18

<400> SEQUENCE: 18

000

<210> SEQ ID NO 19
<211> LENGTH: 184
<212> TYPE: PRT
<213> ORGANISM: Streptomyces griseus

<400> SEQUENCE: 19

Thr Pro Leu Ile Ala Gly Gly Glu Ala Ile Thr Thr Gly Gly Ser Arg
1               5                   10                  15

Cys Ser Leu Gly Phe Asn Val Ser Val Asn Gly Val Ala His Ala Leu
            20                  25                  30

Thr Ala Gly His Cys Thr Asn Ile Ser Ala Ser Trp Ser Ile Gly Thr
        35                  40                  45

Arg Thr Gly Thr Ser Phe Pro Asn Asn Asp Tyr Gly Ile Ile Arg His
    50                  55                  60

Ser Asn Pro Ala Ala Ala Asp Gly Arg Val Tyr Leu Tyr Asn Gly Ser
65                  70                  75                  80

Tyr Gln Asp Ile Thr Thr Ala Gly Asn Ala Phe Val Gly Gln Ala Val
                85                  90                  95
```

```
Gln Arg Ser Gly Ser Thr Thr Gly Leu Arg Ser Gly Ser Val Thr Gly
            100                 105                 110

Leu Asn Ala Thr Val Asn Tyr Gly Ser Ser Gly Ile Val Tyr Gly Met
            115                 120                 125

Ile Gln Thr Asn Val Cys Ala Glu Pro Gly Asp Ser Gly Ser Leu
        130                 135                 140

Phe Ala Gly Ser Thr Ala Leu Gly Leu Thr Ser Gly Ser Gly Asn
145                 150                 155                 160

Cys Arg Thr Gly Gly Thr Thr Phe Tyr Gln Pro Val Thr Glu Ala Leu
                165                 170                 175

Ser Ala Tyr Gly Ala Thr Val Leu
            180

<210> SEQ ID NO 20
<211> LENGTH: 174
<212> TYPE: PRT
<213> ORGANISM: Streptomyces fradiae

<400> SEQUENCE: 20

Ile Ala Gly Gly Glu Ala Ile Tyr Ala Ala Gly Gly Gly Arg Cys Ser
1               5                   10                  15

Leu Gly Phe Asn Val Arg Ser Ser Gly Ala Thr Tyr Ala Leu Thr
            20                  25                  30

Ala Gly His Cys Thr Glu Ile Ala Ser Thr Trp Tyr Thr Asn Ser Gly
            35                  40                  45

Gln Thr Ser Leu Leu Gly Thr Arg Ala Gly Thr Ser Phe Pro Gly Asn
        50                  55                  60

Asp Tyr Gly Leu Ile Arg His Ser Asn Ala Ser Ala Ala Asp Gly Arg
65                  70                  75                  80

Val Tyr Leu Tyr Asn Gly Ser Tyr Arg Asp Ile Thr Gly Ala Gly Asn
                85                  90                  95

Ala Tyr Val Gly Gln Thr Val Gln Arg Ser Gly Ser Thr Thr Gly Leu
            100                 105                 110

His Ser Gly Arg Val Thr Gly Leu Asn Ala Thr Val Asn Tyr Gly Gly
            115                 120                 125

Gly Asp Ile Val Ser Gly Leu Ile Gln Thr Asn Val Cys Ala Glu Pro
        130                 135                 140

Gly Asp Ser Gly Gly Ala Leu Phe Ala Gly Ser Thr Ala Leu Gly Leu
145                 150                 155                 160

Thr Ser Gly Gly Ser Gly Asn Cys Arg Thr Gly Gly Thr Thr
                165                 170

<210> SEQ ID NO 21
<211> LENGTH: 188
<212> TYPE: PRT
<213> ORGANISM: Streptomyces lividans

<400> SEQUENCE: 21

Asn Lys Leu Ile Gln Gly Gly Asp Ala Ile Tyr Ala Ser Ser Trp Arg
1               5                   10                  15

Cys Ser Leu Gly Phe Asn Val Arg Thr Ser Ser Gly Ala Glu Tyr Phe
            20                  25                  30

Leu Thr Ala Gly His Cys Thr Asp Gly Ala Gly Ala Trp Arg Ala Ser
            35                  40                  45

Ser Gly Gly Thr Val Ile Gly Gln Thr Ala Gly Ser Ser Phe Pro Gly
        50                  55                  60

Asn Asp Tyr Gly Ile Val Gln Tyr Thr Gly Ser Val Ser Arg Pro Gly
```

```
                65                  70                  75                  80
Thr Ala Asn Gly Val Asp Ile Thr Arg Ala Ala Thr Pro Ser Val Gly
                    85                  90                  95
Thr Thr Val Ile Arg Asp Gly Ser Thr Thr Gly Thr His Ser Gly Arg
                100                 105                 110
Val Thr Ala Leu Asn Ala Thr Val Asn Tyr Gly Gly Asp Val Val
        115                 120                 125
Gly Gly Leu Ile Gln Thr Thr Val Cys Ala Glu Pro Gly Asp Ser Gly
        130                 135                 140
Gly Ser Leu Tyr Gly Ser Asn Gly Thr Ala Tyr Gly Leu Thr Ser Gly
145                 150                 155                 160
Gly Ser Gly Asn Cys Ser Ser Gly Gly Thr Thr Phe Phe Gln Pro Val
                165                 170                 175
Thr Glu Ala Leu Ser Ala Tyr Gly Val Ser Val Tyr
                180                 185

<210> SEQ ID NO 22
<211> LENGTH: 188
<212> TYPE: PRT
<213> ORGANISM: Streptomyces coelicolor

<400> SEQUENCE: 22

Asn Lys Leu Ile Gln Gly Gly Asp Ala Ile Tyr Ala Ser Ser Trp Arg
1               5                   10                  15
Cys Ser Leu Gly Phe Asn Val Arg Thr Ser Ser Gly Ala Glu Tyr Phe
                20                  25                  30
Leu Thr Ala Gly His Cys Thr Asp Gly Ala Gly Ala Trp Arg Ala Ser
            35                  40                  45
Ser Gly Gly Thr Val Ile Gly Gln Thr Ala Gly Ser Ser Phe Pro Gly
        50                  55                  60
Asn Asp Tyr Gly Ile Val Gln Tyr Thr Gly Ser Val Ser Arg Pro Gly
65                  70                  75                  80
Thr Ala Asn Gly Val Asp Ile Thr Arg Ala Ala Thr Pro Ser Val Gly
                    85                  90                  95
Thr Thr Val Ile Arg Asp Gly Ser Thr Thr Gly Thr His Ser Gly Arg
                100                 105                 110
Val Thr Ala Leu Asn Ala Thr Val Asn Tyr Gly Gly Asp Val Val
        115                 120                 125
Gly Gly Leu Ile Gln Thr Thr Val Cys Ala Glu Pro Gly Asp Ser Gly
        130                 135                 140
Gly Ser Leu Tyr Gly Ser Asn Gly Thr Ala Tyr Gly Leu Thr Ser Gly
145                 150                 155                 160
Gly Ser Gly Asn Cys Ser Ser Gly Gly Thr Thr Phe Phe Gln Pro Val
                165                 170                 175
Thr Glu Ala Leu Ser Ala Tyr Gly Val Ser Val Tyr
                180                 185

<210> SEQ ID NO 23
<211> LENGTH: 189
<212> TYPE: PRT
<213> ORGANISM: Streptomyces albogriseolus

<400> SEQUENCE: 23

Thr Lys Leu Ile Gln Gly Gly Asp Ala Ile Tyr Ala Ser Ser Trp Arg
1               5                   10                  15
Cys Ser Leu Gly Phe Asn Val Arg Ser Ser Gly Val Asp Tyr Phe
                20                  25                  30
```

```
Leu Thr Ala Gly His Cys Thr Asp Gly Ala Gly Thr Trp Tyr Ser Asn
        35                  40                  45

Ser Ala Arg Thr Thr Ala Ile Gly Ser Thr Ala Gly Ser Ser Phe Pro
 50                  55                  60

Gly Asn Asp Tyr Gly Ile Val Arg Tyr Thr Gly Ser Val Ser Arg Pro
 65                  70                  75                  80

Gly Thr Ala Asn Gly Val Asp Ile Thr Arg Ala Ala Thr Pro Ser Val
                 85                  90                  95

Gly Thr Thr Val Ile Arg Asp Gly Ser Thr Gly Thr His Ser Gly
                100                 105                 110

Arg Val Thr Ala Leu Asn Ala Thr Val Asn Tyr Gly Gly Asp Ile
                115                 120                 125

Val Ser Gly Leu Ile Gln Thr Val Cys Ala Glu Pro Gly Asp Ser
                130                 135                 140

Gly Gly Pro Leu Tyr Gly Ser Asn Gly Thr Ala Tyr Gly Leu Thr Ser
145                 150                 155                 160

Gly Gly Ser Gly Asn Cys Ser Ser Gly Thr Thr Phe Phe Gln Pro
                165                 170                 175

Val Thr Glu Ala Leu Ser Ala Tyr Gly Val Ser Val Tyr
                180                 185

<210> SEQ ID NO 24
<211> LENGTH: 188
<212> TYPE: PRT
<213> ORGANISM: Streptomyces griseus

<400> SEQUENCE: 24

Thr Lys Leu Ile Ser Gly Gly Asp Ala Ile Tyr Ser Ser Thr Gly Arg
 1               5                  10                  15

Cys Ser Leu Gly Phe Asn Val Arg Ser Gly Ser Thr Tyr Tyr Phe Leu
                 20                  25                  30

Thr Ala Gly His Cys Thr Asp Gly Ala Thr Thr Trp Trp Ala Asn Ser
        35                  40                  45

Ala Arg Thr Thr Val Leu Gly Thr Thr Ser Gly Ser Ser Phe Pro Asn
 50                  55                  60

Asn Asp Tyr Gly Ile Val Arg Tyr Thr Asn Thr Thr Ile Pro Lys Asp
 65                  70                  75                  80

Gly Thr Val Gly Gly Gln Asp Ile Thr Ser Ala Ala Asn Ala Thr Val
                 85                  90                  95

Gly Met Ala Val Thr Arg Arg Gly Ser Thr Thr Gly Thr His Ser Gly
                100                 105                 110

Ser Val Thr Ala Leu Asn Ala Thr Val Asn Tyr Gly Gly Gly Asp Val
                115                 120                 125

Val Tyr Gly Met Ile Arg Thr Asn Val Cys Ala Glu Pro Gly Asp Ser
                130                 135                 140

Gly Gly Pro Leu Tyr Ser Gly Thr Arg Ala Ile Gly Leu Thr Ser Gly
145                 150                 155                 160

Gly Ser Gly Asn Cys Ser Ser Gly Gly Thr Thr Phe Phe Gln Pro Val
                165                 170                 175

Thr Glu Ala Leu Ser Ala Tyr Gly Val Ser Val Tyr
                180                 185

<210> SEQ ID NO 25
<211> LENGTH: 188
<212> TYPE: PRT
<213> ORGANISM: Streptomyces griseus
```

```
<400> SEQUENCE: 25

Val Leu Gly Gly Gly Ala Ile Tyr Gly Gly Ser Arg Cys Ser Ala
1               5                   10                  15

Ala Phe Asn Val Thr Lys Gly Gly Ala Arg Tyr Phe Val Thr Ala Gly
            20                  25                  30

His Cys Thr Asn Ile Ser Ala Asn Trp Ser Ala Ser Ser Gly Gly Ser
        35                  40                  45

Val Val Gly Val Arg Glu Gly Thr Ser Phe Pro Thr Asn Asp Tyr Gly
    50                  55                  60

Ile Val Arg Tyr Thr Asp Gly Ser Pro Ala Gly Thr Val Asp Leu
65                  70                  75                  80

Tyr Asn Gly Ser Thr Gln Asp Ile Ser Ser Ala Ala Asn Ala Val Val
            85                  90                  95

Gly Gln Ala Ile Lys Lys Ser Gly Ser Thr Thr Lys Val Thr Ser Gly
            100                 105                 110

Thr Val Thr Ala Val Asn Val Thr Val Asn Tyr Gly Asp Gly Pro Val
            115                 120                 125

Tyr Asn Met Gly Arg Thr Thr Ala Cys Ser Ala Gly Asp Ser Gly
        130                 135                 140

Gly Ala His Phe Ala Gly Ser Val Ala Leu Gly Ile His Ser Gly Ser
145                 150                 155                 160

Ser Gly Cys Ser Gly Thr Ala Gly Ser Ala Ile His Gln Pro Val Thr
                165                 170                 175

Lys Ala Leu Ser Ala Tyr Gly Val Thr Val Tyr Leu
            180                 185

<210> SEQ ID NO 26
<211> LENGTH: 190
<212> TYPE: PRT
<213> ORGANISM: Streptomyces fradiae

<400> SEQUENCE: 26

Gln Arg Glu Val Ala Gly Gly Asp Ala Ile Tyr Gly Gly Ser Arg
1               5                   10                  15

Cys Ser Ala Ala Phe Asn Val Thr Lys Asn Gly Val Arg Tyr Phe Leu
            20                  25                  30

Thr Ala Gly His Cys Thr Asn Leu Ser Ser Thr Trp Ser Ser Thr Ser
        35                  40                  45

Gly Gly Thr Ser Ile Gly Val Arg Glu Gly Thr Ser Phe Pro Thr Asn
    50                  55                  60

Asp Tyr Gly Ile Val Arg Tyr Thr Thr Thr Asn Val Asp Gly Arg
65                  70                  75                  80

Val Asn Leu Tyr Asn Gly Gly Tyr Gln Asp Ile Ala Ser Ala Ala Asp
            85                  90                  95

Ala Val Val Gly Gln Ala Ile Lys Lys Ser Gly Ser Thr Thr Lys Val
            100                 105                 110

Thr Ser Gly Thr Val Ser Ala Val Asn Val Thr Val Asn Tyr Ser Asp
            115                 120                 125

Gly Pro Val Tyr Gly Met Val Arg Thr Thr Ala Cys Ser Ala Gly Gly
            130                 135                 140

Asp Ser Gly Gly Ala His Phe Ala Gly Ser Val Ala Leu Gly Ile His
145                 150                 155                 160

Ser Gly Ser Ser Gly Cys Thr Gly Thr Asn Gly Ser Ala Ile His Gln
                165                 170                 175
```

```
Pro Val Arg Glu Ala Leu Ser Ala Tyr Gly Val Asn Val Tyr
            180                 185                 190
```

<210> SEQ ID NO 27
<211> LENGTH: 190
<212> TYPE: PRT
<213> ORGANISM: Streptomyces albogriseolus

<400> SEQUENCE: 27

```
Lys Pro Phe Ile Ala Gly Gly Asp Ala Ile Thr Gly Asn Gly Gly Arg
1               5                   10                  15

Cys Ser Leu Gly Phe Asn Val Thr Lys Gly Gly Glu Pro His Phe Leu
            20                  25                  30

Thr Ala Gly His Cys Thr Glu Gly Ile Ser Thr Trp Ser Asp Ser Ser
            35                  40                  45

Gly Gln Val Ile Gly Glu Asn Ala Ala Ser Ser Phe Pro Gly Asp Asp
        50                  55                  60

Tyr Gly Leu Val Lys Tyr Thr Ala Asp Val Ala His Pro Ser Gln Val
65                  70                  75                  80

Asn Leu Tyr Asp Gly Ser Ser Gln Ser Ile Ser Gly Ala Ala Glu Ala
                85                  90                  95

Ala Val Gly Met Gln Val Thr Arg Ser Gly Ser Thr Thr Gln Val His
            100                 105                 110

Ser Gly Thr Val Thr Gly Leu Asp Ala Thr Val Asn Tyr Gly Asn Gly
            115                 120                 125

Asp Ile Val Asn Gly Leu Ile Gln Thr Asp Val Cys Ala Glu Pro Gly
        130                 135                 140

Asp Ser Gly Gly Ser Leu Phe Ser Gly Asp Lys Ala Val Gly Leu Thr
145                 150                 155                 160

Ser Gly Gly Ser Gly Asp Cys Thr Ser Gly Thr Thr Phe Phe Gln
                165                 170                 175

Pro Val Thr Glu Ala Leu Ser Ala Thr Gly Thr Gln Ile Gly
            180                 185                 190
```

<210> SEQ ID NO 28
<211> LENGTH: 190
<212> TYPE: PRT
<213> ORGANISM: Streptomyces coelicolor

<400> SEQUENCE: 28

```
Lys Pro Phe Val Ala Gly Gly Asp Ala Ile Thr Gly Gly Gly Gly Arg
1               5                   10                  15

Cys Ser Leu Gly Phe Asn Val Thr Lys Gly Gly Glu Pro Tyr Phe Ile
            20                  25                  30

Thr Ala Gly His Cys Thr Glu Ser Ile Ser Thr Trp Ser Asp Ser Ser
            35                  40                  45

Gly Asn Val Ile Gly Glu Asn Ala Ala Ser Ser Phe Pro Asn Asp
        50                  55                  60

Tyr Gly Leu Val Lys Tyr Thr Ala Asp Val Asp His Pro Ser Glu Val
65                  70                  75                  80

Asn Leu Tyr Asn Gly Ser Ser Gln Ala Ile Ser Gly Ala Ala Glu Ala
                85                  90                  95

Thr Val Gly Met Gln Val Thr Arg Ser Gly Ser Thr Thr Gln Val His
            100                 105                 110

Asp Gly Thr Val Thr Gly Leu Asp Ala Thr Val Asn Tyr Gly Asn Gly
            115                 120                 125

Asp Ile Val Asn Gly Leu Ile Gln Thr Asp Val Cys Ala Glu Pro Gly
```

```
            130                 135                 140
Asp Ser Gly Gly Ser Leu Phe Ser Gly Asp Gln Ala Ile Gly Leu Thr
145                 150                 155                 160

Ser Gly Gly Ser Gly Asp Cys Thr Ser Gly Gly Glu Thr Phe Phe Gln
                165                 170                 175

Pro Val Thr Glu Ala Leu Ser Ala Thr Gly Thr Gln Ile Gly
            180                 185                 190

<210> SEQ ID NO 29
<211> LENGTH: 191
<212> TYPE: PRT
<213> ORGANISM: Streptomyces griseus

<400> SEQUENCE: 29

Thr Pro Leu Ile Ala Gly Gly Asp Ala Ile Trp Gly Ser Gly Ser Arg
1               5                   10                  15

Cys Ser Leu Gly Phe Asn Val Val Lys Gly Gly Glu Pro Tyr Phe Leu
            20                  25                  30

Thr Ala Gly His Cys Thr Glu Ser Val Thr Ser Trp Ser Asp Thr Gln
        35                  40                  45

Gly Gly Ser Glu Ile Gly Ala Asn Glu Gly Ser Ser Phe Pro Glu Asn
50                  55                  60

Asp Tyr Gly Leu Val Lys Tyr Thr Ser Asp Thr Ala His Pro Ser Glu
65                  70                  75                  80

Val Asn Leu Tyr Asp Gly Ser Thr Gln Ala Ile Thr Gln Ala Gly Asp
            85                  90                  95

Ala Thr Val Gly Gln Ala Val Thr Arg Ser Gly Ser Thr Thr Gln Val
        100                 105                 110

His Asp Gly Glu Val Thr Ala Leu Asp Ala Thr Val Asn Tyr Gly Asn
    115                 120                 125

Gly Asp Ile Val Asn Gly Leu Ile Gln Thr Thr Val Cys Ala Glu Pro
130                 135                 140

Gly Asp Ser Gly Gly Ala Leu Phe Ala Gly Asp Thr Ala Leu Gly Leu
145                 150                 155                 160

Thr Ser Gly Gly Ser Gly Asp Cys Ser Ser Gly Gly Thr Thr Phe Phe
                165                 170                 175

Gln Pro Val Pro Glu Ala Leu Ala Ala Tyr Gly Ala Glu Ile Gly
            180                 185                 190

<210> SEQ ID NO 30
<211> LENGTH: 200
<212> TYPE: PRT
<213> ORGANISM: Streptomyces lividans

<400> SEQUENCE: 30

Lys Thr Phe Ala Ser Gly Gly Asp Ala Ile Phe Gly Gly Gly Ala Arg
1               5                   10                  15

Cys Ser Leu Gly Phe Asn Val Thr Ala Gly Asp Gly Ser Ala Ala Phe
            20                  25                  30

Leu Thr Arg Gly His Cys Gly Gly Ala Thr Met Trp Ser Asp Ala
        35                  40                  45

Gln Gly Gly Gln Pro Ile Ala Thr Val Asp Gln Ala Val Phe Pro Pro
50                  55                  60

Glu Gly Asp Phe Gly Leu Val Arg Tyr Asp Gly Pro Ser Thr Glu Ala
65                  70                  75                  80

Pro Ser Glu Val Asp Leu Gly Asp Gln Thr Leu Pro Ile Ser Gly Ala
            85                  90                  95
```

```
Ala Glu Ala Ser Val Gly Gln Glu Val Phe Arg Met Gly Ser Thr Thr
            100                 105                 110

Gly Leu Ala Asp Gly Gln Val Leu Gly Leu Asp Val Thr Val Asn Tyr
        115                 120                 125

Pro Glu Gly Thr Val Thr Gly Leu Ile Gln Thr Asp Val Cys Ala Glu
    130                 135                 140

Pro Gly Asp Ser Gly Gly Ser Leu Phe Thr Arg Asp Gly Leu Ala Ile
145                 150                 155                 160

Arg Leu Thr Ser Gly Gly Thr Arg Asp Cys Thr Ser Gly Gly Glu Thr
                165                 170                 175

Phe Phe Gln Pro Val Thr Thr Ala Leu Ala Ala Val Gly Gly Thr Leu
            180                 185                 190

Gly Gly Glu Asp Gly Gly Asp Gly
        195                 200

<210> SEQ ID NO 31
<211> LENGTH: 201
<212> TYPE: PRT
<213> ORGANISM: Streptomyces coelicolor

<400> SEQUENCE: 31

Lys Thr Phe Ala Ser Gly Gly Asp Ala Ile Phe Gly Gly Gly Ala Arg
1               5                   10                  15

Cys Ser Leu Gly Phe Asn Val Thr Ala Gly Asp Gly Ser Pro Ala Phe
            20                  25                  30

Leu Thr Ala Gly His Cys Gly Val Ala Ala Asp Gln Trp Ser Asp Ala
        35                  40                  45

Gln Gly Gly Gln Pro Ile Ala Thr Val Asp Gln Ala Val Phe Pro Gly
    50                  55                  60

Glu Gly Asp Phe Ala Leu Val Arg Tyr Asp Asp Pro Ala Thr Glu Ala
65                  70                  75                  80

Pro Ser Glu Val Asp Leu Gly Asp Gln Thr Leu Pro Ile Ser Gly Ala
                85                  90                  95

Ala Glu Ala Ala Val Gly Gln Glu Val Phe Arg Met Gly Ser Thr Thr
            100                 105                 110

Gly Leu Ala Asp Gly Gln Val Leu Gly Leu Asp Ala Thr Val Asn Tyr
        115                 120                 125

Pro Glu Gly Met Val Thr Gly Leu Ile Gln Thr Asp Val Cys Ala Glu
    130                 135                 140

Pro Gly Asp Ser Gly Gly Ser Leu Phe Thr Arg Asp Gly Leu Ala Ile
145                 150                 155                 160

Gly Leu Thr Ser Gly Gly Ser Gly Asp Cys Thr Val Gly Gly Glu Thr
                165                 170                 175

Phe Phe Gln Pro Val Thr Thr Ala Leu Ala Ala Val Gly Ala Thr Leu
            180                 185                 190

Gly Gly Glu Asp Gly Gly Ala Gly Ala
        195                 200

<210> SEQ ID NO 32
<211> LENGTH: 68
<212> TYPE: PRT
<213> ORGANISM: Streptomyces platensis

<400> SEQUENCE: 32

Val Asp Gly Leu Ile Gln Thr Asp Val Cys Ala Glu Pro Gly Asp Ser
1               5                   10                  15
```

```
Gly Gly Ala Leu Phe Asp Gly Asp Ala Ala Ile Gly Leu Thr Ser Gly
            20                  25                  30

Gly Ser Gly Asp Cys Ser Gln Gly Glu Thr Phe Phe Gln Pro Val
        35                  40                  45

Thr Glu Ala Leu Lys Ala Tyr Gly Ala Gln Ile Gly Gly Gln Gly
 50                  55                  60

Glu Pro Pro Glu
 65

<210> SEQ ID NO 33
<211> LENGTH: 201
<212> TYPE: PRT
<213> ORGANISM: Streptomyces coelicolor

<400> SEQUENCE: 33

Thr Thr Arg Leu Asn Gly Ala Glu Pro Ile Leu Ser Thr Ala Gly Arg
 1               5                  10                  15

Cys Ser Ala Gly Phe Asn Val Thr Asp Gly Thr Ser Asp Phe Ile Leu
            20                  25                  30

Thr Ala Gly His Cys Gly Pro Thr Gly Ser Val Trp Phe Gly Asp Arg
        35                  40                  45

Pro Gly Asp Gly Gln Val Gly Arg Thr Val Ala Gly Ser Phe Pro Gly
 50                  55                  60

Asp Asp Phe Ser Leu Val Glu Tyr Ala Asn Lys Ala Gly Asp Gly
 65                  70                  75              80

Ala Asp Val Val Ala Val Gly Asp Gly Lys Gly Val Arg Ile Thr Gly
                85                  90                  95

Ala Gly Glu Pro Ala Val Gly Gln Arg Val Phe Arg Ser Gly Ser Thr
            100                 105                 110

Ser Gly Leu Arg Asp Gly Arg Val Thr Ala Leu Asp Ala Thr Val Asn
        115                 120                 125

Tyr Pro Glu Gly Thr Val Thr Gly Leu Ile Glu Thr Asp Val Cys Ala
    130                 135                 140

Glu Pro Gly Asp Ser Gly Gly Pro Met Phe Ser Glu Gly Val Ala Leu
145                 150                 155                 160

Gly Val Thr Ser Gly Gly Ser Gly Asp Cys Ala Lys Gly Gly Thr Thr
                165                 170                 175

Phe Phe Gln Pro Leu Pro Glu Ala Met Ala Ser Leu Gly Val Arg Leu
            180                 185                 190

Ile Val Pro Gly Arg Glu Gly Ala Ala
        195                 200

<210> SEQ ID NO 34
<211> LENGTH: 188
<212> TYPE: PRT
<213> ORGANISM: Metarhizium anisopliae

<400> SEQUENCE: 34

Ala Thr Val Gln Gly Gly Asp Val Tyr Tyr Ile Asn Arg Ser Ser Arg
 1               5                  10                  15

Cys Ser Ile Gly Phe Ala Val Thr Thr Gly Phe Val Ser Ala Gly His
            20                  25                  30

Cys Gly Gly Ser Gly Ala Ser Ala Thr Thr Ser Gly Glu Ala Leu
        35                  40                  45

Gly Thr Phe Ser Gly Ser Val Phe Pro Gly Ser Ala Asp Met Ala Tyr
 50                  55                  60

Val Arg Thr Val Ser Gly Thr Val Leu Arg Gly Tyr Ile Asn Gly Tyr
```

```
                 65                  70                  75                  80
Gly Gln Gly Ser Phe Pro Val Ser Gly Ser Glu Ala Ala Val Gly
                85                  90                  95
Ala Ser Ile Cys Arg Ser Gly Ser Thr Thr Gln Val His Cys Gly Thr
               100                 105                 110
Ile Gly Ala Lys Gly Ala Thr Val Asn Tyr Pro Gln Gly Ala Val Ser
               115                 120                 125
Gly Leu Thr Arg Thr Ser Val Cys Ala Glu Pro Gly Asp Ser Gly Gly
               130                 135                 140
Ser Phe Tyr Ser Gly Ser Gln Ala Gln Gly Val Thr Ser Gly Gly Ser
145                 150                 155                 160
Gly Asp Cys Ser Arg Gly Gly Thr Thr Tyr Phe Gln Pro Val Asn Arg
               165                 170                 175
Ile Leu Gln Thr Tyr Gly Leu Thr Leu Val Thr Ala
               180                 185

<210> SEQ ID NO 35
<211> LENGTH: 195
<212> TYPE: PRT
<213> ORGANISM: Streptomyces griseus

<400> SEQUENCE: 35

Ala Asp Ile Arg Gly Gly Asp Ala Tyr Tyr Met Asn Gly Ser Gly Arg
1               5                   10                  15
Cys Ser Val Gly Phe Ser Val Thr Arg Gly Thr Gln Asn Gly Phe Ala
               20                  25                  30
Thr Ala Gly His Cys Gly Arg Val Gly Thr Thr Thr Asn Gly Val Asn
               35                  40                  45
Gln Gln Ala Gln Gly Thr Phe Gln Gly Ser Thr Phe Pro Gly Arg Asp
           50                  55                  60
Ile Ala Trp Val Ala Thr Asn Ala Asn Trp Thr Pro Arg Pro Leu Val
65                  70                  75                  80
Asn Gly Tyr Gly Arg Gly Asp Val Thr Val Ala Gly Ser Thr Ala Ser
                85                  90                  95
Val Val Gly Ala Ser Val Cys Arg Ser Gly Ser Thr Thr Gly Trp His
               100                 105                 110
Cys Gly Thr Ile Gln Gln Leu Asn Thr Ser Val Thr Tyr Pro Glu Gly
               115                 120                 125
Thr Ile Ser Gly Val Thr Arg Thr Ser Val Cys Ala Glu Pro Gly Asp
               130                 135                 140
Ser Gly Gly Ser Tyr Ile Ser Gly Ser Gln Ala Gln Gly Val Thr Ser
145                 150                 155                 160
Gly Gly Ser Gly Asn Cys Ser Ser Gly Gly Thr Thr Tyr Phe Gln Pro
               165                 170                 175
Ile Asn Pro Leu Leu Gln Ala Tyr Gly Leu Thr Leu Val Thr Ser Gly
               180                 185                 190
Gly Gly Thr
       195

<210> SEQ ID NO 36
<211> LENGTH: 197
<212> TYPE: PRT
<213> ORGANISM: Streptomyces coelicolor

<400> SEQUENCE: 36

Tyr Asp Leu Arg Gly Gly Glu Ala Tyr Tyr Ile Asn Asn Ser Ser Arg
1               5                   10                  15
```

```
Cys Ser Ile Gly Phe Pro Ile Thr Lys Gly Thr Gln Gln Gly Phe Ala
             20                  25                  30

Thr Ala Gly His Cys Gly Arg Ala Gly Ser Ser Thr Thr Gly Ala Asn
         35                  40                  45

Arg Val Ala Gln Gly Thr Phe Gln Gly Ser Ile Phe Pro Gly Arg Asp
 50                  55                  60

Met Ala Trp Val Ala Thr Asn Ser Ser Trp Thr Ala Thr Pro Tyr Val
 65                  70                  75                  80

Leu Gly Ala Gly Gly Gln Asn Val Gln Val Thr Gly Ser Thr Ala Ser
                 85                  90                  95

Pro Val Gly Ala Ser Val Cys Arg Ser Gly Ser Thr Thr Gly Trp His
            100                 105                 110

Cys Gly Thr Val Thr Gln Leu Asn Thr Ser Val Thr Tyr Gln Glu Gly
            115                 120                 125

Thr Ile Ser Pro Val Thr Arg Thr Thr Val Cys Ala Glu Pro Gly Asp
130                 135                 140

Ser Gly Gly Ser Phe Ile Ser Gly Ser Gln Ala Gln Gly Val Thr Ser
145                 150                 155                 160

Gly Gly Ser Gly Asp Cys Arg Thr Gly Gly Glu Thr Phe Phe Gln Pro
                165                 170                 175

Ile Asn Ala Leu Leu Gln Asn Tyr Gly Leu Thr Leu Lys Thr Thr Gly
            180                 185                 190

Gly Asp Gly Gly
        195

<210> SEQ ID NO 37
<211> LENGTH: 189
<212> TYPE: PRT
<213> ORGANISM: Streptomyces spp.

<400> SEQUENCE: 37

Tyr Asp Leu Val Gly Asp Ala Tyr Tyr Ile Gly Asn Gly Arg Cys
1               5                  10                  15

Ser Ile Gly Phe Ser Val Arg Gln Gly Ser Thr Pro Gly Phe Val Thr
             20                  25                  30

Ala Gly His Cys Gly Ser Val Gly Asn Ala Thr Thr Gly Phe Asn Arg
         35                  40                  45

Val Ser Gln Gly Thr Phe Arg Gly Ser Trp Phe Pro Gly Arg Asp Met
 50                  55                  60

Ala Trp Val Ala Val Asn Ser Asn Trp Thr Pro Thr Ser Leu Val Arg
 65                  70                  75                  80

Asn Ser Gly Ser Gly Val Arg Val Thr Gly Ser Thr Gln Ala Thr Val
                 85                  90                  95

Gly Ser Ser Ile Cys Arg Ser Gly Ser Thr Thr Gly Trp Arg Cys Gly
            100                 105                 110

Thr Ile Gln Gln His Asn Thr Ser Val Thr Tyr Pro Gln Gly Thr Ile
            115                 120                 125

Thr Gly Val Thr Arg Thr Ser Ala Cys Ala Gln Pro Gly Asp Ser Gly
            130                 135                 140

Gly Ser Phe Ile Ser Gly Thr Gln Ala Gln Gly Val Thr Ser Gly Gly
145                 150                 155                 160

Ser Gly Asn Cys Ser Ile Gly Gly Thr Thr Phe His Gln Pro Val Asn
                165                 170                 175

Pro Ile Leu Ser Gln Tyr Gly Leu Thr Leu Val Arg Ser
            180                 185
```

<210> SEQ ID NO 38
<211> LENGTH: 187
<212> TYPE: PRT
<213> ORGANISM: Streptomyces spp.

<400> SEQUENCE: 38

Tyr Asp Leu Val Gly Gly Asp Ala Tyr Met Gly Gly Arg Cys
1               5                   10                  15

Ser Val Gly Phe Ser Val Thr Gln Gly Ser Thr Pro Gly Phe Ala Thr
            20                  25                  30

Ala Gly His Cys Gly Thr Val Gly Thr Ser Thr Thr Gly Tyr Asn Gln
            35                  40                  45

Ala Ala Gln Gly Thr Phe Glu Glu Ser Ser Phe Pro Gly Asp Asp Met
50                  55                  60

Ala Trp Val Ser Val Asn Ser Asp Trp Asn Thr Thr Pro Thr Val Asn
65                  70                  75                  80

Glu Gly Glu Val Thr Val Ser Gly Ser Thr Glu Ala Ala Val Gly Ala
                85                  90                  95

Ser Ile Cys Arg Ser Gly Ser Thr Thr Gly Trp His Cys Gly Thr Ile
            100                 105                 110

Gln Gln His Asn Thr Ser Val Thr Tyr Pro Glu Gly Thr Ile Thr Gly
            115                 120                 125

Val Thr Arg Thr Ser Val Cys Ala Glu Pro Gly Asp Ser Gly Gly Ser
130                 135                 140

Tyr Ile Ser Gly Ser Gln Ala Gln Gly Val Thr Ser Gly Gly Ser Gly
145                 150                 155                 160

Asn Cys Thr Ser Gly Gly Thr Thr Tyr His Gln Pro Ile Asn Pro Leu
                165                 170                 175

Leu Ser Ala Tyr Gly Leu Asp Leu Val Thr Gly
            180                 185

<210> SEQ ID NO 39
<211> LENGTH: 193
<212> TYPE: PRT
<213> ORGANISM: Streptomyces coelicolor

<400> SEQUENCE: 39

Glu Asp Leu Val Gly Gly Asp Ala Tyr Tyr Ile Asp Asp Gln Ala Arg
1               5                   10                  15

Cys Ser Ile Gly Phe Ser Val Thr Lys Asp Asp Gln Glu Gly Phe Ala
            20                  25                  30

Thr Ala Gly His Cys Gly Asp Pro Gly Ala Thr Thr Thr Gly Tyr Asn
            35                  40                  45

Glu Ala Asp Gln Gly Thr Phe Gln Ala Ser Thr Phe Pro Gly Lys Asp
50                  55                  60

Met Ala Trp Val Gly Val Asn Ser Asp Trp Thr Ala Thr Pro Asp Val
65                  70                  75                  80

Lys Ala Glu Gly Gly Glu Lys Ile Gln Leu Ala Gly Ser Val Glu Ala
                85                  90                  95

Leu Val Gly Ala Ser Val Cys Arg Ser Gly Ser Thr Thr Gly Trp His
            100                 105                 110

Cys Gly Thr Ile Gln Gln His Asp Thr Ser Val Thr Tyr Pro Glu Gly
            115                 120                 125

Thr Val Asp Gly Leu Thr Glu Thr Thr Val Cys Ala Glu Pro Gly Asp
130                 135                 140

```
Ser Gly Gly Pro Phe Val Ser Gly Val Gln Ala Gln Gly Thr Thr Ser
145                 150                 155                 160

Gly Gly Ser Gly Asp Cys Thr Asn Gly Thr Thr Phe Tyr Gln Pro
                165                 170                 175

Val Asn Pro Leu Leu Ser Asp Phe Gly Leu Thr Leu Lys Thr Thr Ser
            180                 185                 190

Ala

<210> SEQ ID NO 40
<211> LENGTH: 187
<212> TYPE: PRT
<213> ORGANISM: Thermobifida fusca

<400> SEQUENCE: 40

Leu Ala Ala Ile Ile Gly Gly Asn Pro Tyr Tyr Phe Gly Asn Tyr Arg
1               5                   10                  15

Cys Ser Ile Gly Phe Ser Val Arg Gln Gly Ser Gln Thr Gly Phe Ala
                20                  25                  30

Thr Ala Gly His Cys Gly Ser Thr Gly Thr Arg Val Ser Ser Pro Ser
            35                  40                  45

Gly Thr Val Ala Gly Ser Tyr Phe Pro Gly Arg Asp Met Gly Trp Val
        50                  55                  60

Arg Ile Thr Ser Ala Asp Thr Val Thr Pro Leu Val Asn Arg Tyr Asn
65                  70                  75                  80

Gly Gly Thr Val Thr Val Thr Gly Ser Gln Glu Ala Ala Thr Gly Ser
                85                  90                  95

Ser Val Cys Arg Ser Gly Ala Thr Thr Gly Trp Arg Cys Gly Thr Ile
                100                 105                 110

Gln Ser Lys Asn Gln Thr Val Arg Tyr Ala Glu Gly Thr Val Thr Gly
            115                 120                 125

Leu Thr Arg Thr Thr Ala Cys Ala Glu Gly Gly Asp Ser Gly Gly Pro
        130                 135                 140

Trp Leu Thr Gly Ser Gln Ala Gln Gly Val Thr Ser Gly Gly Thr Gly
145                 150                 155                 160

Asp Cys Arg Ser Gly Ile Thr Phe Phe Gln Pro Ile Asn Pro Leu
                165                 170                 175

Leu Ser Tyr Phe Gly Leu Gln Leu Val Thr Gly
            180                 185

<210> SEQ ID NO 41
<211> LENGTH: 198
<212> TYPE: PRT
<213> ORGANISM: Lysobacter enzymogenes

<400> SEQUENCE: 41

Ala Asn Ile Val Gly Gly Ile Glu Tyr Ser Ile Asn Asn Ala Ser Leu
1               5                   10                  15

Cys Ser Val Gly Phe Ser Val Thr Arg Gly Ala Thr Lys Gly Phe Val
                20                  25                  30

Thr Ala Gly His Cys Gly Thr Val Asn Ala Thr Ala Arg Ile Gly Gly
            35                  40                  45

Ala Val Val Gly Thr Phe Ala Ala Arg Val Phe Pro Gly Asn Asp Arg
        50                  55                  60

Ala Trp Val Ser Leu Thr Ser Ala Gln Thr Leu Leu Pro Arg Val Ala
65                  70                  75                  80

Asn Gly Ser Ser Phe Val Thr Val Arg Gly Ser Thr Glu Ala Ala Val
                85                  90                  95
```

```
Gly Ala Ala Val Cys Arg Ser Gly Arg Thr Thr Gly Tyr Gln Cys Gly
            100                 105                 110

Thr Ile Thr Ala Lys Asn Val Thr Ala Asn Tyr Ala Glu Gly Ala Val
            115                 120                 125

Arg Gly Leu Thr Gln Gly Asn Ala Cys Met Gly Arg Gly Asp Ser Gly
        130                 135                 140

Gly Ser Trp Ile Thr Ser Ala Gly Gln Ala Gln Gly Val Met Ser Gly
145                 150                 155                 160

Gly Asn Val Gln Ser Asn Gly Asn Asn Cys Gly Ile Pro Ala Ser Gln
                165                 170                 175

Arg Ser Ser Leu Phe Glu Arg Leu Gln Pro Ile Leu Ser Gln Tyr Gly
            180                 185                 190

Leu Ser Leu Val Thr Gly
            195
```

<210> SEQ ID NO 42
<211> LENGTH: 189
<212> TYPE: PRT
<213> ORGANISM: Streptomyces coelicolor

<400> SEQUENCE: 42

```
Ala Ala Gly Thr Val Gly Gly Asp Pro Tyr Tyr Thr Gly Asn Val Arg
1               5                   10                  15

Cys Ser Ile Gly Phe Ser Val His Gly Gly Phe Val Thr Ala Gly His
            20                  25                  30

Cys Gly Arg Ala Gly Ala Gly Val Ser Gly Trp Asp Arg Ser Tyr Ile
        35                  40                  45

Gly Thr Phe Gln Gly Ser Ser Phe Pro Asp Asn Asp Tyr Ala Trp Val
    50                  55                  60

Ser Val Gly Ser Gly Trp Trp Thr Val Pro Val Val Leu Gly Trp Gly
65                  70                  75                  80

Thr Val Ser Asp Gln Leu Val Arg Gly Ser Asn Val Ala Pro Val Gly
                85                  90                  95

Ala Ser Ile Cys Arg Ser Gly Ser Thr Thr His Trp His Cys Gly Thr
            100                 105                 110

Val Leu Ala His Asn Glu Thr Val Asn Tyr Ser Asp Gly Ser Val Val
            115                 120                 125

His Gln Leu Thr Lys Thr Ser Val Cys Ala Glu Gly Gly Asp Ser Gly
        130                 135                 140

Gly Ser Phe Ile Ser Gly Asp Gln Ala Gln Gly Val Thr Ser Gly Gly
145                 150                 155                 160

Trp Gly Asn Cys Ser Ser Gly Gly Glu Thr Trp Phe Gln Pro Val Asn
                165                 170                 175

Glu Ile Leu Asn Arg Tyr Gly Leu Thr Leu His Thr Ala
            180                 185
```

<210> SEQ ID NO 43
<211> LENGTH: 197
<212> TYPE: PRT
<213> ORGANISM: Rarobacter faecitabidus

<400> SEQUENCE: 43

```
Val Ile Val Pro Val Arg Asp Tyr Trp Gly Gly Asp Ala Leu Ser Gly
1               5                   10                  15

Cys Thr Leu Ala Phe Pro Val Tyr Gly Gly Phe Leu Thr Ala Gly His
            20                  25                  30
```

```
Cys Ala Val Glu Gly Lys Gly His Ile Leu Lys Thr Glu Met Thr Gly
         35                  40                  45

Gly Gln Ile Gly Thr Val Glu Ala Ser Gln Phe Gly Asp Gly Ile Asp
 50                  55                  60

Ala Ala Trp Ala Lys Asn Tyr Gly Asp Trp Asn Gly Arg Gly Arg Val
 65                  70                  75                  80

Thr His Trp Asn Gly Gly Gly Val Asp Ile Lys Gly Ser Asn Glu
                 85                  90                  95

Ala Ala Val Gly Ala His Met Cys Lys Ser Gly Arg Thr Thr Lys Trp
                100                 105                 110

Thr Cys Gly Tyr Leu Leu Arg Lys Asp Val Ser Val Asn Tyr Gly Asn
                115                 120                 125

Gly His Ile Val Thr Leu Asn Glu Thr Ser Ala Cys Ala Leu Gly Gly
            130                 135                 140

Asp Ser Gly Gly Ala Tyr Val Trp Asn Asp Gln Ala Gln Gly Ile Thr
145                 150                 155                 160

Ser Gly Ser Asn Met Asp Thr Asn Asn Cys Arg Ser Phe Tyr Gln Pro
                165                 170                 175

Val Asn Thr Val Leu Asn Lys Trp Lys Leu Ser Leu Val Thr Ser Thr
                180                 185                 190

Asp Val Thr Thr Ser
        195

<210> SEQ ID NO 44
<211> LENGTH: 191
<212> TYPE: PRT
<213> ORGANISM: Streptomyces coelicolor

<400> SEQUENCE: 44

Asp Pro Pro Leu Arg Ser Gly Leu Ala Ile Tyr Gly Thr Asn Val Arg
 1               5                  10                  15

Cys Ser Ser Ala Phe Met Ala Tyr Ser Gly Ser Tyr Tyr Met Met Met
                 20                  25                  30

Thr Ala Gly His Cys Ala Glu Asp Ser Ser Tyr Trp Glu Val Pro Thr
         35                  40                  45

Tyr Ser Tyr Gly Tyr Gln Gly Val Gly His Val Ala Asp Tyr Thr Phe
 50                  55                  60

Gly Tyr Tyr Gly Asp Ser Ala Ile Val Arg Val Asp Asp Pro Gly Phe
 65                  70                  75                  80

Trp Gln Pro Arg Gly Trp Val Tyr Pro Ser Thr Arg Ile Thr Asn Trp
                 85                  90                  95

Asp Tyr Asp Tyr Val Gly Gln Tyr Val Cys Lys Gln Gly Ser Thr Thr
                100                 105                 110

Gly Tyr Thr Cys Gly Gln Ile Thr Glu Thr Asn Ala Thr Val Ser Tyr
            115                 120                 125

Pro Gly Arg Thr Leu Thr Gly Met Thr Trp Ser Thr Ala Cys Asp Ala
130                 135                 140

Pro Gly Asp Ser Gly Ser Gly Val Tyr Asp Gly Ser Thr Ala His Gly
145                 150                 155                 160

Ile Leu Ser Gly Gly Pro Asn Ser Gly Cys Gly Met Ile His Glu Pro
                165                 170                 175

Ile Ser Arg Ala Leu Ala Asp Arg Gly Val Thr Leu Leu Ala Gly
                180                 185                 190

<210> SEQ ID NO 45
<211> LENGTH: 20
```

```
<212> TYPE: DNA
<213> ORGANISM: Artificial Sequence
<220> FEATURE:
<223> OTHER INFORMATION: primer

<400> SEQUENCE: 45
tgcgccgagc ccggcgactc                                            20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gagtcgccgg gctcggcgca                                            20

<210> SEQ ID NO 47
<211> LENGTH: 26
<212> TYPE: DNA
<213> ORGANISM: Artificial Sequence
<220> FEATURE:
<223> OTHER INFORMATION: primer

<400> SEQUENCE: 47
ttccccggca acgactacgc gtgggt                                     26

<210> SEQ ID NO 48
<211> LENGTH: 26
<212> TYPE: DNA
<213> ORGANISM: Artificial Sequence
<220> FEATURE:
<223> OTHER INFORMATION: primer

<400> SEQUENCE: 48
acccacgcgt agtcgttgcc ggggaa                                     26

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gccgctgctc gatcgggttc                                            20

<210> SEQ ID NO 50
<211> LENGTH: 24
<212> TYPE: DNA
<213> ORGANISM: Artificial Sequence
<220> FEATURE:
<223> OTHER INFORMATION: primer

<400> SEQUENCE: 50
gcagttgccg gagccgccgg acgt                                       24

<210> SEQ ID NO 51
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: n is a, c, g, or t
```

<400> SEQUENCE: 51
tsggsgncrt ggtt                                                                14

<210> SEQ ID NO 52
<211> LENGTH: 12
<212> TYPE: PRT
<213> ORGANISM: Artificial Sequence
<220> FEATURE:
<223> OTHER INFORMATION: synthetic

<400> SEQUENCE: 52

Leu Arg Met Ile Thr Thr Asp Ser Gly Ser Ser Pro
1               5                   10

<210> SEQ ID NO 53
<211> LENGTH: 555
<212> TYPE: DNA
<213> ORGANISM: Cellulomonas flavigena

<400> SEQUENCE: 53
gtcgacgtca tcgggggcaa cgcgtactac atcgggtcgc gctcgcggtg ctcgatcggg    60
ttcgcggtcg agggcgggtt cgtcaccgcg gggcactgcg ggcgcgcggg cgcgagcacg   120
tcgtcaccgt cggggacctt ccgcggctcg tcgttcccg gcaacgacta cgcgtgggtc    180
caggtcgcct cgggcaacac gccgcgcggg ctggtgaaca ccactcgggg cggcacggtg   240
cgcgtcaccg gctcgcagca ggccgcggtc ggctcgtacg tgtgccgatc gggcagcacg   300
acgggatggc ggtgcggcta cgtccgggcg tacaacacga ccgtgcggta cgcggagggc   360
tcggtctcgg gcctcatccg cacgagcgtg tgcgccgagc cgggcgactc cggcggctcg   420
ctggtcgccg gcacgcaggc ccaggcgtc acgtcgggcg gtccggcaa ctgccgctac    480
gggggcacga cgtacttcca gcccgtgaac gagatcctgc aggaccagcc cgggccgtcg   540
accacgcgtg cccta                                                    555

<210> SEQ ID NO 54
<211> LENGTH: 185
<212> TYPE: PRT
<213> ORGANISM: Cellulomonas flavigena

<400> SEQUENCE: 54

Val Asp Val Ile Gly Gly Asn Ala Tyr Tyr Ile Gly Ser Arg Ser Arg
1               5                   10                  15

Cys Ser Ile Gly Phe Ala Val Glu Gly Gly Phe Val Thr Ala Gly His
            20                  25                  30

Cys Gly Arg Ala Gly Ala Ser Thr Ser Ser Pro Ser Gly Thr Phe Arg
        35                  40                  45

Gly Ser Ser Phe Pro Gly Asn Asp Tyr Ala Trp Val Gln Val Ala Ser
    50                  55                  60

Gly Asn Thr Pro Arg Gly Leu Val Asn Asn His Ser Gly Gly Thr Val
65                  70                  75                  80

Arg Val Thr Gly Ser Gln Gln Ala Ala Val Gly Ser Tyr Val Cys Arg
                85                  90                  95

Ser Gly Ser Thr Thr Gly Trp Arg Cys Gly Tyr Val Arg Ala Tyr Asn
            100                 105                 110

Thr Thr Val Arg Tyr Ala Glu Gly Ser Val Ser Gly Leu Ile Arg Thr
        115                 120                 125

Ser Val Cys Ala Glu Pro Gly Asp Ser Gly Gly Ser Leu Val Ala Gly
    130                 135                 140

Thr Gln Ala Gln Gly Val Thr Ser Gly Gly Ser Gly Asn Cys Arg Tyr
145                 150                 155                 160

Gly Gly Thr Thr Tyr Phe Gln Pro Val Asn Glu Ile Leu Gln Asp Gln
            165                 170                 175

Pro Gly Pro Ser Thr Thr Arg Ala Leu
        180                 185

<210> SEQ ID NO 55
<211> LENGTH: 1009
<212> TYPE: DNA
<213> ORGANISM: Cellulomonas biazotea

<400> SEQUENCE: 55

```
taaaacagac ggccagtgaa tttgtaatac gactcactat aggcgaattg aatttagcgg      60
ccgcgaattc gcccttacct atagggcacg cgtggtcgac ggccctgggc tggtacgtcg     120
acgtcactac caacacggtc gtcgtcaacg ccaccgccct cgccgtggcc caggcgaccg     180
agatcgtcgc cgccgcaacg gtgcccgccg acgccgtccg ggtcgtcgag accaccgagg     240
cgccccgcac gttcatcgac gtcatcggcg gcaaccgtta ccggatcaac aacacctcgc     300
gctgctcggt cggcttcgcc gtcagcggcg gcttcgtcac cgccgggcac tgcggcacga     360
ccggcgcgac cacgacgaaa ccgtccggca cgttcgccgg ctcgtcgttc cccggcaacg     420
actacgcgtg ggtgcgcgtc gcgtccggca cacccccggt cggcgccgtg aacaactaca     480
gcggcggcac cgtggccgtc gccggctcga cgcaggcgac cgtcggtgcg tccgtctgcc     540
gctccggctc caccacgggg tggcgctgcg ggacgatcca ggcgttcaac tccaccgtca     600
actacgcgca gggcagcgtc tccggcctca tccgcacgaa cgtgtgcgcc gagcccggcg     660
actccggcgg ctcgctcatc gccggcaacc aggcccaggg cctgacgtcc ggcgggtcgg     720
gcaactgcac caccggcggg acgacgtact ccagcccgt caacgaggcg ctctccgcct     780
acggcctgac gctcgtcacg tcgtccggcg gcggcggtgg cggcggcacg acctgcaccg     840
ggtacgcgcg gacctacacc ggctcgctcg cctcgcggca gtccgccgtc cagccgtccg     900
gcagctatgt gaccgtcggg tccagcggca ccatccgcgt ctgcctcgac ggcccgagcg     960
ggacggactt cgacctgtac ctgcagaagt ggaacgggtc cgcgtgggc             1009
```

<210> SEQ ID NO 56
<211> LENGTH: 335
<212> TYPE: PRT
<213> ORGANISM: Cellulomonas biazotea

<400> SEQUENCE: 56

Lys Gln Thr Ala Ser Glu Phe Val Ile Arg Leu Thr Ile Gly Glu Leu
1               5                   10                  15

Asn Leu Ala Ala Ala Asn Ser Pro Leu Pro Ile Gly His Ala Trp Ser
            20                  25                  30

Thr Ala Leu Gly Trp Tyr Val Asp Val Thr Thr Asn Thr Val Val Val
        35                  40                  45

Asn Ala Thr Ala Leu Ala Val Ala Gln Ala Thr Glu Ile Val Ala Ala
    50                  55                  60

Ala Thr Val Pro Ala Asp Ala Val Arg Val Val Glu Thr Thr Glu Ala
65                  70                  75                  80

Pro Arg Thr Phe Ile Asp Val Ile Gly Gly Asn Arg Tyr Arg Ile Asn
                85                  90                  95

Asn Thr Ser Arg Cys Ser Val Gly Phe Ala Val Ser Gly Gly Phe Val
            100                 105                 110

```
Thr Ala Gly His Cys Gly Thr Thr Gly Ala Thr Thr Lys Pro Ser
            115                 120                 125
Gly Thr Phe Ala Gly Ser Ser Phe Pro Gly Asn Asp Tyr Ala Trp Val
130                 135                 140
Arg Val Ala Ser Gly Asn Thr Pro Val Gly Val Asn Asn Tyr Ser
145                 150                 155                 160
Gly Gly Thr Val Ala Val Ala Gly Ser Thr Gln Ala Thr Val Gly Ala
                165                 170                 175
Ser Val Cys Arg Ser Gly Ser Thr Thr Gly Trp Arg Cys Gly Thr Ile
                180                 185                 190
Gln Ala Phe Asn Ser Thr Val Asn Tyr Ala Gln Gly Ser Val Ser Gly
                195                 200                 205
Leu Ile Arg Thr Asn Val Cys Ala Glu Pro Gly Asp Ser Gly Gly Ser
            210                 215                 220
Leu Ile Ala Gly Asn Gln Ala Gln Gly Leu Thr Ser Gly Gly Ser Gly
225                 230                 235                 240
Asn Cys Thr Thr Gly Gly Thr Thr Tyr Phe Gln Pro Val Asn Glu Ala
                245                 250                 255
Leu Ser Ala Tyr Gly Leu Thr Leu Val Thr Ser Ser Gly Gly Gly
                260                 265                 270
Gly Gly Gly Thr Thr Cys Thr Gly Tyr Ala Arg Thr Tyr Thr Gly Ser
                275                 280                 285
Leu Ala Ser Arg Gln Ser Ala Val Gln Pro Ser Gly Ser Tyr Val Thr
            290                 295                 300
Val Gly Ser Ser Gly Thr Ile Arg Val Cys Leu Asp Gly Pro Ser Gly
305                 310                 315                 320
Thr Asp Phe Asp Leu Tyr Leu Gln Lys Trp Asn Gly Ser Ala Trp
                325                 330                 335

<210> SEQ ID NO 57
<211> LENGTH: 474
<212> TYPE: DNA
<213> ORGANISM: Cellulomonas fimi

<400> SEQUENCE: 57
gtggacgtga tcggcggcga cgcctactac atcggcggcc gcagccgctg ttcgatcggg      60
ttcgccgtca ccgggggctt cgtgaccgcc gggcactgcg gccgcaccgg cgcggccacg     120
acgagcccgt cgggcacgtt cgccggctcg agcttcccgg caacgactac gcgtgggtg      180 cgggtcgcgt cgggcaacac gcccgtcggc gcggtgaaca actacagcgg cggcacggtc     240
gccgtcgccg gctcgaccca ggccgccgtc ggtgcgaccg tgtgccgctc gggctccacc     300
accggctggc ggtgcggcac catccaggcg ttcaacgcga ccgtcaacta cgccgagggc     360
agcgtctccg gcctcatccg cacgaacgtg tgcgccgagc ccggcgactc gggcggctcg     420
ctcgtcgccg gcaaccaggc gcagggcatg acgtccggcg gctccgacaa ctgc           474

<210> SEQ ID NO 58
<211> LENGTH: 144
<212> TYPE: PRT
<213> ORGANISM: Cellulomonas fimi

<400> SEQUENCE: 58

Val Asp Val Ile Gly Gly Asp Ala Tyr Tyr Ile Gly Gly Arg Ser Arg
1               5                   10                  15
Cys Ser Ile Gly Phe Ala Val Thr Gly Gly Phe Val Thr Ala Gly His
                20                  25                  30
```

```
Cys Gly Arg Thr Gly Ala Ala Thr Thr Ser Pro Ser Gly Thr Phe Ala
            35                  40                  45

Gly Ser Ser Phe Pro Gly Asn Asp Tyr Ala Trp Val Arg Val Ala Ser
 50                  55                  60

Gly Asn Thr Pro Val Gly Ala Val Asn Asn Tyr Ser Gly Gly Thr Val
 65                  70                  75                  80

Ala Val Ala Gly Ser Thr Gln Ala Ala Val Gly Ala Thr Val Cys Arg
                85                  90                  95

Ser Gly Ser Thr Thr Gly Trp Arg Cys Gly Thr Ile Gln Ala Phe Asn
            100                 105                 110

Ala Thr Val Asn Tyr Ala Glu Gly Ser Val Ser Gly Leu Ile Arg Thr
            115                 120                 125

Asn Val Cys Ala Glu Pro Gly Asp Ser Gly Gly Ser Leu Val Ala Gly
            130                 135                 140

<210> SEQ ID NO 59
<211> LENGTH: 462
<212> TYPE: DNA
<213> ORGANISM: Cellulomonas gelida

<400> SEQUENCE: 59
ctcgcgggca accaggcgca gggcgtgacg tcgggcgggt cgggcaactg ctcgtcgggc        60
gggacgacgt acttccagcc cgtcaacgag gccctccggg tgtacgggct cacgctcgtg       120
acctctgacg gtgggggcac cgagccgccg ccgaccgggt gccagggcta tgcgcggacc       180
taccagggca gcgtctcggc cgggacgtcg gtcgcgcagc cgaacggttc gtacgtcacg       240
accgggggcg ggacgcaccg ggtgtgcctg agcggaccgg cgggcacgga cctggacctg       300
tacctgcaga agtggaacgg gtactcgtgg gccagcgtcg cgcagtcgac gtcgcctggt       360
gccacggagg cggtcacgta caccgggacc gccggctact accgctacgt ggtccacgcg       420
tacgcgggtt cggggcgta cacctgggg cgacgaccc cg                             462

<210> SEQ ID NO 60
<211> LENGTH: 154
<212> TYPE: PRT
<213> ORGANISM: Cellulomonas gelida

<400> SEQUENCE: 60

Leu Ala Gly Asn Gln Ala Gln Gly Val Thr Ser Gly Gly Ser Gly Asn
 1               5                   10                  15

Cys Ser Ser Gly Gly Thr Thr Tyr Phe Gln Pro Val Asn Glu Ala Leu
            20                  25                  30

Arg Val Tyr Gly Leu Thr Leu Val Thr Ser Asp Gly Gly Gly Thr Glu
         35                  40                  45

Pro Pro Pro Thr Gly Cys Gln Gly Tyr Ala Arg Thr Tyr Gln Gly Ser
 50                  55                  60

Val Ser Ala Gly Thr Ser Val Ala Gln Pro Asn Gly Ser Tyr Val Thr
 65                  70                  75                  80

Thr Gly Gly Gly Thr His Arg Val Cys Leu Ser Gly Pro Ala Gly Thr
                85                  90                  95

Asp Leu Asp Leu Tyr Leu Gln Lys Trp Asn Gly Tyr Ser Trp Ala Ser
            100                 105                 110

Val Ala Gln Ser Thr Ser Pro Gly Ala Thr Glu Ala Val Thr Tyr Thr
            115                 120                 125

Gly Thr Ala Gly Tyr Tyr Arg Tyr Val Val His Ala Tyr Ala Gly Ser
            130                 135                 140
```

Gly Ala Tyr Thr Leu Gly Ala Thr Thr Pro
145                 150

<210> SEQ ID NO 61
<211> LENGTH: 257
<212> TYPE: DNA
<213> ORGANISM: Cellulomonas iranensis

<400> SEQUENCE: 61
ttccccggca acgactacgc gtgggtccag gtcgggtcgg gcgacacccc ccgcggcctg    60
gtcaacaact acgcgggcgg caccgtgcgg gtcaccgggt cgcagcaggc cgcggtcggc   120
gcgtacgtct gccggtcggg cagcacgacg ggctggcgct gcggcaccgt gcaggcctac   180
aacgcgtcgg tccgctacgc cgagggcacc gtctcgggcc tcatccgcac caacgtctgc   240
gccgagcccg gcgactc                                                  257

<210> SEQ ID NO 62
<211> LENGTH: 85
<212> TYPE: PRT
<213> ORGANISM: Cellulomonas iranensis

<400> SEQUENCE: 62

Phe Pro Gly Asn Asp Tyr Ala Trp Val Gln Val Gly Ser Gly Asp Thr
1               5                   10                  15

Pro Arg Gly Leu Val Asn Asn Tyr Ala Gly Gly Thr Val Arg Val Thr
            20                  25                  30

Gly Ser Gln Gln Ala Ala Val Gly Ala Tyr Val Cys Arg Ser Gly Ser
        35                  40                  45

Thr Thr Gly Trp Arg Cys Gly Thr Val Gln Ala Tyr Asn Ala Ser Val
    50                  55                  60

Arg Tyr Ala Glu Gly Thr Val Ser Gly Leu Ile Arg Thr Asn Val Cys
65                  70                  75                  80

Ala Glu Pro Gly Asp
                85

<210> SEQ ID NO 63
<211> LENGTH: 904
<212> TYPE: DNA
<213> ORGANISM: Cellulomonas cellasea

<400> SEQUENCE: 63
gtcgggcggg tccggcaact gccgctacgg gggcacgacg tacttccagc ccgtgaacga    60
gatcctgcag gcctacggtc tgcgtctcgt cctgggctga cacgctcgcg gcgggcccgg   120
ctcgacgcgg ccgccccgtc ggcccgggtc gccgcctggt acgtcgacgt gccgaccaac   180
aagctcgtcg tcgagtcggt cggcgacacc gcggcggccg ccgacgccgt cgccgccgcg   240
ggcctgcctg ccgacgccgt gacgctcgcg accaccgagg cgccacggac gttcgtcgac   300
gtcatcggcg gcaacgcgta ctacatcaac gcgagcagcc gctgctcggt cggcttcgcg   360
gtcgagggcg ggttcgtcac cgcgggccac tgcgggcgcg cgggcgcgag cacgtcgtca   420
ccgtcgggga ccttccgcgg ctcgtcgttc cccggcaacg actacgcgtg gtccaggtc    480 gcctcgggca cacgccgcg cgggctggtg aacaaccact cgggcggcac ggtgcgcgtc   540
accggctcgc agcaggccgc ggtcggctcg tacgtgtgcc gatcgggcag cacgacggga   600
tggcggtgcg gctacgtccg ggcgtacaac acgaccgtgc ggtacgcgga gggctcggtc   660
tcgggcctca tccgcacgag cgtgtgcgcc gagccgggcg actccggcgg ctcgctggtc   720

```
gccggcacgc aggcccaggg cgtcacgtcg ggcgggtccg gcaactgccg ctacggggc    780 acgacgtact tccagcccgt gaacgagatc ctgcaggcct acggtctgcg tctcgtcctg    840
ggctgacacg ctcgcggcgg gccctcccct gcccgtcgcg cgccggcccc accagcccgg    900
gccg                                                                  904
```

<210> SEQ ID NO 64
<211> LENGTH: 300
<212> TYPE: PRT
<213> ORGANISM: Cellulomonas cellasea

<400> SEQUENCE: 64

```
Val Gly Arg Val Arg Gln Leu Pro Leu Arg Gly His Asp Val Leu Pro
1               5                   10                  15

Ala Arg Glu Arg Asp Pro Ala Gly Leu Arg Ser Ala Ser Arg Pro Gly
            20                  25                  30

Leu Thr Arg Ser Arg Arg Ala Arg Leu Asp Ala Ala Gly Pro Ser Ala
        35                  40                  45

Arg Val Ala Ala Trp Tyr Val Asp Val Pro Thr Asn Lys Leu Val Val
    50                  55                  60

Glu Ser Val Gly Asp Thr Ala Ala Ala Asp Ala Val Ala Ala Ala
65                  70                  75                  80

Gly Leu Pro Ala Asp Ala Val Thr Leu Ala Thr Thr Glu Ala Pro Arg
                85                  90                  95

Thr Phe Val Asp Val Ile Gly Gly Asn Ala Tyr Tyr Ile Asn Ala Ser
            100                 105                 110

Ser Arg Cys Ser Val Gly Phe Ala Val Glu Gly Gly Phe Val Thr Ala
        115                 120                 125

Gly His Cys Gly Arg Ala Gly Ala Ser Thr Ser Pro Ser Gly Thr
    130                 135                 140

Phe Arg Gly Ser Ser Phe Pro Gly Asn Asp Tyr Ala Trp Val Gln Val
145                 150                 155                 160

Ala Ser Gly Asn Thr Pro Arg Gly Leu Val Asn Asn His Ser Gly Gly
                165                 170                 175

Thr Val Arg Val Thr Gly Ser Gln Gln Ala Ala Val Gly Ser Tyr Val
            180                 185                 190

Cys Arg Ser Gly Ser Thr Thr Gly Trp Arg Cys Gly Tyr Val Arg Ala
        195                 200                 205

Tyr Asn Thr Thr Val Arg Tyr Ala Glu Gly Ser Val Ser Gly Leu Ile
    210                 215                 220

Arg Thr Ser Val Cys Ala Glu Pro Gly Asp Ser Gly Gly Ser Leu Val
225                 230                 235                 240

Ala Gly Thr Gln Ala Gln Gly Val Thr Ser Gly Gly Ser Gly Asn Cys
                245                 250                 255

Arg Tyr Gly Gly Thr Thr Tyr Phe Gln Pro Val Asn Glu Ile Leu Gln
            260                 265                 270

Ala Tyr Gly Leu Arg Leu Val Leu Gly His Ala Arg Gly Gly Pro Ser
        275                 280                 285

Pro Ala Arg Arg Ala Pro Ala Pro Pro Ala Arg Ala
    290                 295                 300
```

<210> SEQ ID NO 65
<211> LENGTH: 429
<212> TYPE: DNA
<213> ORGANISM: Cellulomonas xylanilytica

<400> SEQUENCE: 65

```
cgctgctcga tcgggttcgc cgtgacgggc ggcttcgtga ccgccggcca ctgcggacgg       60
tccggcgcga cgacgacgtc gccgagcggc acgttcgccg ggtccagctt tcccggcaac      120
gactacgcct gggtccgcgc ggcctcgggc aacacgccgg tcggtgcggt gaaccgctac      180
gacggcagcc gggtgaccgt ggccgggtcc accgacgcgg ccgtcggtgc cgcggtctgc      240 cggtcgggt cgacgaccgc gtggggctgc ggcacgatcc agtcccgcgg cgcgagcgtc       300
acgtacgccc agggcaccgt cagcgggctc atccgcacca acgtgtgcgc cgagccgggt      360
gactccgggg ggtcgctgat cgcgggcacc caggcgcggg gcgtgacgtc cggcggctcc      420
ggcaactgc                                                              429

<210> SEQ ID NO 66
<211> LENGTH: 143
<212> TYPE: PRT
<213> ORGANISM: Cellulomonas xylanilytica

<400> SEQUENCE: 66

Arg Cys Ser Ile Gly Phe Ala Val Thr Gly Gly Phe Val Thr Ala Gly
1               5                   10                  15

His Cys Gly Arg Ser Gly Ala Thr Thr Thr Ser Pro Ser Gly Thr Phe
            20                  25                  30

Ala Gly Ser Ser Phe Pro Gly Asn Asp Tyr Ala Trp Val Arg Ala Ala
        35                  40                  45

Ser Gly Asn Thr Pro Val Gly Ala Val Asn Arg Tyr Asp Gly Ser Arg
    50                  55                  60

Val Thr Val Ala Gly Ser Thr Asp Ala Ala Val Gly Ala Ala Val Cys
65                  70                  75                  80

Arg Ser Gly Ser Thr Thr Ala Trp Gly Cys Gly Thr Ile Gln Ser Arg
                85                  90                  95

Gly Ala Ser Val Thr Tyr Ala Gln Gly Thr Val Ser Gly Leu Ile Arg
            100                 105                 110

Thr Asn Val Cys Ala Glu Pro Gly Asp Ser Gly Gly Ser Leu Ile Ala
        115                 120                 125

Gly Thr Gln Ala Arg Gly Val Thr Ser Gly Gly Ser Gly Asn Cys
    130                 135                 140

<210> SEQ ID NO 67
<211> LENGTH: 1284
<212> TYPE: DNA
<213> ORGANISM: Oerskovia turbata

<400> SEQUENCE: 67
atggcacgat cattctggag gacgctcgcc acggcgtgcg ccgcgacggc actggttgcc       60
ggccccgcag cgctcaccgc gaacgccgcg acgcccaccc ccgacacccc gaccgtttca      120
ccccagacct cctcgaaggt ctcgcccgag gtgctccgcg ccctccagcg ggacctgggg      180
ctgagcgcca aggacgcgac gaagcgtctg gcgttccagt ccgacgcggc gagcaccgag      240
gacgctctcg ccgacagcct ggacgcctac gcgggcgcct gggtcgaccc tgcgaggaac      300
accctgtacg tcggcgtcgc cgacagggcc gaggccaagg aggtccgttc ggccggagcg      360 accccgtgg tcgtcgacca cacgctcgcc gagctcgaca cgtggaaggc ggcgctcgac       420
ggtgagctca acgacccgc gggcgtcccg agctggttcg tcgacgtcac gaccaaccag       480
gtcgtcgtca acgtgcacga cggcggacgc gccctcgcgg agctggctgc cgcgagcgcg      540
ggcgtgcccg ccgacgccat cacctacgtg acgacgaccg aggctcctcg tcccctcgtc      600
```

-continued

```
gacgtggtgg gcggcaacgc gtacaccatg ggttcgggcg ggcgctgctc ggtcggcttc    660
gcggtgaacg ggggcttcat cacgccggg cactgcggct cggtcggcac ccgcacctcg    720
gggccgggcg gcacgttccg ggggtcgaac ttccccggca acgactacgc ctgggtgcag    780
gtcgacgcgg gtaacacccc ggtcggcgcg gtcaacaact acagcggtgg gcgcgtcgcg    840
gtcgcagggt cgacggccgc gcccgtgggg gcctcggtct gccggtccgg ttccacgacg    900
ggctggcact gcggcaccat cggcgcgtac aacacctcgg tgacgtaccc gcagggcacc    960
gtctcggggc tcatccgcac gaacgtgtgc gccgagcccg gcgactcggg cggctcgctc   1020
ctcgcgggca accaggcgca gggcgtgacc tcgggcgggt cgggcaactg ctcgtcgggc   1080
gggacgacgt acttccagcc cgtcaacgag gccctcgggg ggtacgggct cacgctcgtg   1140
acctctgacg gtgggggccc gagccgccgc cgaccgggtg ccagggctat gcgcggacct   1200
accagggcag cgtctcggcc gggacgtcgg tcgcgcagcg aacggttcgt acgtcacgac   1260
cgggggcggg cgaccgggtg tgcc                                          1284
```

<210> SEQ ID NO 68
<211> LENGTH: 428
<212> TYPE: PRT
<213> ORGANISM: Oerskovia turbata

<400> SEQUENCE: 68

```
Met Ala Arg Ser Phe Trp Arg Thr Leu Ala Thr Ala Cys Ala Ala Thr
  1               5                  10                  15

Ala Leu Val Ala Gly Pro Ala Ala Leu Thr Ala Asn Ala Ala Thr Pro
             20                  25                  30

Thr Pro Asp Thr Pro Thr Val Ser Pro Gln Thr Ser Ser Lys Val Ser
         35                  40                  45

Pro Glu Val Leu Arg Ala Leu Gln Arg Asp Leu Gly Leu Ser Ala Lys
     50                  55                  60

Asp Ala Thr Lys Arg Leu Ala Phe Gln Ser Asp Ala Ala Ser Thr Glu
 65                  70                  75                  80

Asp Ala Leu Ala Asp Ser Leu Asp Ala Tyr Ala Gly Ala Trp Val Asp
                 85                  90                  95

Pro Ala Arg Asn Thr Leu Tyr Val Gly Val Ala Asp Arg Ala Glu Ala
            100                 105                 110

Lys Glu Val Arg Ser Ala Gly Ala Thr Pro Val Val Asp His Thr
            115                 120                 125

Leu Ala Glu Leu Asp Thr Trp Lys Ala Ala Leu Asp Gly Glu Leu Asn
        130                 135                 140

Asp Pro Ala Gly Val Pro Ser Trp Phe Val Asp Val Thr Thr Asn Gln
145                 150                 155                 160

Val Val Val Asn Val His Asp Gly Gly Arg Ala Leu Ala Glu Leu Ala
                165                 170                 175

Ala Ala Ser Ala Gly Val Pro Ala Asp Ala Ile Thr Tyr Val Thr Thr
            180                 185                 190

Thr Glu Ala Pro Arg Pro Leu Val Asp Val Val Gly Gly Asn Ala Tyr
        195                 200                 205

Thr Met Gly Ser Gly Gly Arg Cys Ser Val Gly Phe Ala Val Asn Gly
    210                 215                 220

Gly Phe Ile Thr Ala Gly His Cys Gly Ser Val Gly Thr Arg Thr Ser
225                 230                 235                 240

Gly Pro Gly Gly Thr Phe Arg Gly Ser Asn Phe Pro Gly Asn Asp Tyr
                245                 250                 255
```

```
Ala Trp Val Gln Val Asp Ala Gly Asn Thr Pro Val Gly Ala Val Asn
            260                 265                 270

Asn Tyr Ser Gly Gly Arg Val Ala Val Ala Gly Ser Thr Ala Ala Pro
        275                 280                 285

Val Gly Ala Ser Val Cys Arg Ser Gly Ser Thr Thr Gly Trp His Cys
    290                 295                 300

Gly Thr Ile Gly Ala Tyr Asn Thr Ser Val Thr Tyr Pro Gln Gly Thr
305                 310                 315                 320

Val Ser Gly Leu Ile Arg Thr Asn Val Cys Ala Glu Pro Gly Asp Ser
            325                 330                 335

Gly Gly Ser Leu Leu Ala Gly Asn Gln Ala Gln Gly Val Thr Ser Gly
        340                 345                 350

Gly Ser Gly Asn Cys Ser Ser Gly Thr Thr Tyr Phe Gln Pro Val
    355                 360                 365

Asn Glu Ala Leu Gly Gly Tyr Gly Leu Thr Leu Val Thr Ser Asp Gly
370                 375                 380

Gly Gly Pro Ser Arg Arg Arg Pro Gly Ala Arg Ala Met Arg Gly Pro
385                 390                 395                 400

Thr Arg Ala Ala Ser Arg Pro Gly Arg Arg Ser Arg Ser Glu Arg Phe
            405                 410                 415

Val Arg His Asp Arg Gly Arg Ala Thr Gly Cys Ala
            420                 425

<210> SEQ ID NO 69
<211> LENGTH: 524
<212> TYPE: DNA
<213> ORGANISM: Oerskovia jenensis

<400> SEQUENCE: 69
gccgctgctc ggtcggcttc gcggtgaacg gcggcttcgt caccgcaggc cactgcggga      60
cggtgggcac ccgcacctcg gggccggggcg gcacgttccg cgggtcgagc ttccccggca    120
acgactacgc ctgggtgcag gtcgacgcgg ggaacacccc ggtcggggcc gtcaacaact    180
acagcggtgg acgcgtcgcg gtcgcgggct cgacggccgc acccgtgggt tcctcggtct    240
gccggtccgg ttccacgacg ggctggcgct gcggcacgat cgcggcctac aacagctcgg    300
tgacgtaccc gcaggggacc gtctccgggc tcatccgcac caacgtgtgc cgagccgg     360 gcgactcggg cggctcgctc ctcgcgggca accaggcaca gggcctgacg tcgggcgggt    420
cgggcaactg ctcgtcgggc ggcacgacgt acttccagcc cgtcaacgag gcgctctcgg    480
cctacggcct cacgctcgtg acctccggcg gcaggggcaa ctgc                    524

<210> SEQ ID NO 70
<211> LENGTH: 174
<212> TYPE: PRT
<213> ORGANISM: Oerskovia jenensis

<400> SEQUENCE: 70

Arg Cys Ser Val Gly Phe Ala Val Asn Gly Gly Phe Val Thr Ala Gly
1               5                   10                  15

His Cys Gly Thr Val Gly Thr Arg Thr Ser Gly Pro Gly Gly Thr Phe
            20                  25                  30

Arg Gly Ser Ser Phe Pro Gly Asn Asp Tyr Ala Trp Val Gln Val Asp
        35                  40                  45

Ala Gly Asn Thr Pro Val Gly Ala Val Asn Asn Tyr Ser Gly Gly Arg
    50                  55                  60

Val Ala Val Ala Gly Ser Thr Ala Ala Pro Val Gly Ser Ser Val Cys
```

```
                65                  70                  75                  80
Arg Ser Gly Ser Thr Thr Gly Trp Arg Cys Gly Thr Ile Ala Ala Tyr
                    85                  90                  95
Asn Ser Ser Val Thr Tyr Pro Gln Gly Thr Val Ser Gly Leu Ile Arg
                    100                 105                 110
Thr Asn Val Cys Ala Glu Pro Gly Asp Ser Gly Ser Leu Leu Ala
            115                 120                 125
Gly Asn Gln Ala Gln Gly Leu Thr Ser Gly Ser Asn Cys Ser
        130                 135                 140
Ser Gly Gly Thr Thr Tyr Phe Gln Pro Val Asn Glu Ala Leu Ser Ala
145                 150                 155                 160
Tyr Gly Leu Thr Leu Val Thr Ser Gly Gly Arg Gly Asn Cys
                165                 170

<210> SEQ ID NO 71
<211> LENGTH: 984
<212> TYPE: DNA
<213> ORGANISM: Cellulosimicrobium cellulans

<400> SEQUENCE: 71
ccacgggcgg cgggtcgggc agcgcgctcg tcgggctcgc gggcaagtgc atcgacgtcc       60
ccgggtccga cttcagtgac ggcaagcgcc tccagctgtg acgtgcaac gggtcgcagg      120
cagcgctgga cgttcgaagc cgacggcacc gtacgcgcgg gcggcaagtg catggacgtc      180
gcgtgggcgc cgcggccgac ggcacggcgc tccagctcgc gaactgcacg gcaacgcggc      240
ccagaagttc gtgctcaacg gcgcgggcga cctcgtgtcg gtgctggcga caaagtgcg      300
tcgacgccgc cgggtgcgca ccgaggtact cgcggcgccg tacgagctca cggcgacgtg      360
cgcggcggcg accgctacat cacacgggac ccgggcgcgt cgtcgggctc ggcctgctcg      420
atcgggtacg ccgtccaggg cggcttcgtc acggcggggc actgcggacg cggcgggaca      480
aggagagtgc tcaccgcgag ctgggcgcgc atggggacgg tccaggcggc gtcgttcccc      540
ggccacgact acgcgtgggt gcgcgtcgac gccgggttct ccccgtccc gcgggtgaac      600
aactacgccg cggcaccgt cgacgtcgcc ggctcggccg aggcgccgt gggtgcgtcg       660
gtgtgccgct cgggcgccac gaccggctgg cgctgcggcg tcatcgagca aagaacatc      720
accgtcaact acgcaacgg cgacgttccc ggcctcgtgc gcggcagcgc gtgcgcggag      780
ggcggcgact cgggcgggtc ggtgatctcc ggcaaccagg cgcagggcgt cacgtcgggc      840
aggatcaacg actgctcgaa cggcggcaag ttcctctacc agcccgatcg acggcctgtc      900
gctcgtgacc acgggcggcg ggtcgggcag cgcgctcgtc gggctcgcgg gcaagtgcat      960
cgacgtcccc gggtccgact tcag                                            984

<210> SEQ ID NO 72
<211> LENGTH: 328
<212> TYPE: PRT
<213> ORGANISM: Cellulosimicrobium cellulans

<400> SEQUENCE: 72

Pro Arg Ala Ala Gly Arg Ala Arg Ser Ser Gly Ser Arg Ala Ser
1               5                   10                  15
Ala Ser Thr Ser Pro Gly Pro Ser Val Thr Ala Ser Ala Ser Ser
                20                  25                  30
Cys Gly Arg Ala Thr Gly Arg Arg Gln Arg Trp Thr Phe Glu Ala Asp
            35                  40                  45
Gly Thr Val Arg Ala Gly Gly Lys Cys Met Asp Val Ala Trp Ala Pro
```

```
                50                  55                  60
Arg Pro Thr Ala Arg Arg Ser Ser Arg Thr Ala Arg Gln Arg Gly
 65                  70                  75                  80

Pro Glu Val Arg Ala Gln Arg Arg Gly Arg Pro Arg Val Gly Ala Gly
                 85                  90                  95

Glu Gln Ser Ala Ser Thr Pro Pro Gly Ala His Arg Gly Thr Arg Gly
                100                 105                 110

Ala Val Arg Ala His Gly Asp Val Arg Gly Gly Asp Arg Tyr Ile Thr
                115                 120                 125

Arg Asp Pro Gly Ala Ser Ser Gly Ser Ala Cys Ser Ile Gly Tyr Ala
130                 135                 140

Val Gln Gly Gly Phe Val Thr Ala Gly His Cys Gly Arg Gly Gly Thr
145                 150                 155                 160

Arg Arg Val Leu Thr Ala Ser Trp Ala Arg Met Gly Thr Val Gln Ala
                165                 170                 175

Ala Ser Phe Pro Gly His Asp Tyr Ala Trp Val Arg Val Asp Ala Gly
                180                 185                 190

Phe Ser Pro Val Pro Arg Val Asn Asn Tyr Ala Gly Gly Thr Val Asp
                195                 200                 205

Val Ala Gly Ser Ala Glu Ala Pro Val Gly Ala Ser Val Cys Arg Ser
210                 215                 220

Gly Ala Thr Thr Gly Trp Arg Cys Gly Val Ile Glu Gln Lys Asn Ile
225                 230                 235                 240

Thr Val Asn Tyr Gly Asn Gly Asp Val Pro Gly Leu Val Arg Gly Ser
                245                 250                 255

Ala Cys Ala Glu Gly Gly Asp Ser Gly Gly Ser Val Ile Ser Gly Asn
                260                 265                 270

Gln Ala Gln Gly Val Thr Ser Gly Arg Ile Asn Asp Cys Ser Asn Gly
                275                 280                 285

Gly Lys Phe Leu Tyr Gln Pro Asp Arg Arg Pro Val Ala Arg Asp His
                290                 295                 300

Gly Arg Arg Val Gly Gln Arg Ala Arg Arg Ala Arg Gly Gln Val His
305                 310                 315                 320

Arg Arg Pro Arg Val Arg Leu Gln
                325

<210> SEQ ID NO 73
<211> LENGTH: 257
<212> TYPE: DNA
<213> ORGANISM: Promicromonospora citrea

<400> SEQUENCE: 73
ttccccggca acgactacgc gtgggtgaac acgggcacgg acgacaccct cgtcggcgcc      60
gtgaacaact acagcggcgg cacggtcaac gtcgcgggct cgacccgtgc cgccgtcggc     120
gcgacggtct gccgctcggg ctccacgacc ggctggcact gcggcaccat ccaggcgctg     180
aacgcgtcgg tcacctacgc cgagggcacc gtgagcggcc tcatccgcac caacgtgtgc     240
gccgagcccg cgactc                                                    257

<210> SEQ ID NO 74
<211> LENGTH: 85
<212> TYPE: PRT
<213> ORGANISM: Promicromonospora citrea

<400> SEQUENCE: 74

Phe Pro Gly Asn Asp Tyr Ala Trp Val Asn Thr Gly Thr Asp Asp Thr
```

-continued

```
                1               5                  10                 15
Leu Val Gly Ala Val Asn Asn Tyr Ser Gly Gly Thr Val Asn Val Ala
                       20                 25                 30

Gly Ser Thr Arg Ala Ala Val Gly Ala Thr Val Cys Arg Ser Gly Ser
                35                 40                 45

Thr Thr Gly Trp His Cys Gly Thr Ile Gln Ala Leu Asn Ala Ser Val
            50                 55                 60

Thr Tyr Ala Glu Gly Thr Val Ser Gly Leu Ile Arg Thr Asn Val Cys
65                 70                 75                 80

Ala Glu Pro Gly Asp
                85

<210> SEQ ID NO 75
<211> LENGTH: 257
<212> TYPE: DNA
<213> ORGANISM: Promicromonospora sukumoe

<400> SEQUENCE: 75
ttccccggca acgactacgc gtgggtgaac gtcggctccg acgacacccc gatcggtgcg      60
gtcaacaact acagcggcgg caccgtgaac gtcgcgggct cgacccaggc cgccgtcggc     120
tccaccgtct gccgctccgg ttccacgacc ggctggcact gcggcaccat ccaggccttc     180
aacgcgtcgg tcacctacgc cgagggcacc gtgtccggcc tgatccgcac caacgtctgc     240
gccgagcccg gcgactc                                                   257

<210> SEQ ID NO 76
<211> LENGTH: 85
<212> TYPE: PRT
<213> ORGANISM: Promicromonospora sukumoe

<400> SEQUENCE: 76

Phe Pro Gly Asn Asp Tyr Ala Trp Val Asn Val Gly Ser Asp Thr
1               5                  10                 15

Pro Ile Gly Ala Val Asn Asn Tyr Ser Gly Gly Thr Val Asn Val Ala
                       20                 25                 30

Gly Ser Thr Gln Ala Ala Val Gly Ser Thr Val Cys Arg Ser Gly Ser
                35                 40                 45

Thr Thr Gly Trp His Cys Gly Thr Ile Gln Ala Phe Asn Ala Ser Val
            50                 55                 60

Thr Tyr Ala Glu Gly Thr Val Ser Gly Leu Ile Arg Thr Asn Val Cys
65                 70                 75                 80

Ala Glu Pro Gly Asp
                85

<210> SEQ ID NO 77
<211> LENGTH: 430
<212> TYPE: DNA
<213> ORGANISM: Xylanibacterium ulmi

<400> SEQUENCE: 77
gccgctgctc gatcgggttc gccgtgacgg gcggcttcgt gaccgccggc cactgcggac      60
ggtccggcgc gacgacgacg tccgcgagcg gcacgttcgc cgggtccagc tttcccggca     120
acgactacgc ctgggtccgc gcggcctcgg gaacacgccg gtcggtgcgg tgaaccgcta     180
cgacggcagc cgggtgaccg tggccgggtc caccgacgcg ccgtcggtg ccgcggtctg      240 ccggtcgggg tcgacgaccg cgtggcgctg cggcacgatc cagtcccgcg gcgcgacggt     300
cacgtacgcc cagggcaccg tcagcgggct catccgcacc aacgtgtgcg ccgagccggg     360
```

```
tgactccggg gggtcgctga tcgcgggcac ccaggcgcag ggcgtgacgt ccggcggctc    420
cggcaactgc                                                          430
```

<210> SEQ ID NO 78
<211> LENGTH: 141
<212> TYPE: PRT
<213> ORGANISM: Xylanibacterium ulmi

<400> SEQUENCE: 78

```
Arg Cys Ser Ile Gly Phe Ala Val Thr Gly Gly Phe Val Thr Ala Gly
1               5                   10                  15

His Cys Gly Arg Ser Gly Ala Thr Thr Thr Ser Ala Ser Gly Thr Phe
            20                  25                  30

Ala Gly Ser Ser Phe Pro Gly Asn Asp Tyr Ala Trp Val Arg Ala Ala
        35                  40                  45

Ser Gly Asn Thr Pro Val Gly Ala Val Asn Arg Tyr Asp Gly Ser Arg
    50                  55                  60

Val Thr Val Ala Gly Ser Thr Asp Ala Ala Val Gly Ala Ala Val Cys
65                  70                  75                  80

Arg Ser Gly Ser Thr Thr Ala Trp Arg Cys Gly Thr Ile Gln Ser Arg
                85                  90                  95

Gly Ala Thr Val Thr Tyr Ala Gln Gly Thr Val Ser Gly Leu Ile Arg
            100                 105                 110

Thr Asn Val Cys Ala Glu Pro Gly Asp Ser Gly Gly Ser Leu Ile Ala
        115                 120                 125

Gly Thr Gln Ala Gln Gly Val Thr Ser Gly Gly Ser Gly
    130                 135                 140
```

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79

```
acccacgcgt agtcgttgcc                                               20
```

<210> SEQ ID NO 80
<211> LENGTH: 24
<212> TYPE: DNA
<213> ORGANISM: Artificial Sequence
<220> FEATURE:
<223> OTHER INFORMATION: primer

<400> SEQUENCE: 80

```
acccacgcgt agtcgtkgcc gggg                                          24
```

<210> SEQ ID NO 81
<211> LENGTH: 18
<212> TYPE: DNA
<213> ORGANISM: Artificial Sequence
<220> FEATURE:
<223> OTHER INFORMATION: primer

<400> SEQUENCE: 81

```
tcgtcgtggt cgcgccgg                                                 18
```

<210> SEQ ID NO 82
<211> LENGTH: 17
<212> TYPE: DNA

```
<213> ORGANISM: Artificial Sequence
<220> FEATURE:
<223> OTHER INFORMATION: primer

<400> SEQUENCE: 82
cgacgtgctc gcgcccg                                                   17

<210> SEQ ID NO 83
<211> LENGTH: 18
<212> TYPE: DNA
<213> ORGANISM: Artificial Sequence
<220> FEATURE:
<223> OTHER INFORMATION: primer

<400> SEQUENCE: 83
cgcgcccagc tcgcggtg                                                  18

<210> SEQ ID NO 84
<211> LENGTH: 22
<212> TYPE: DNA
<213> ORGANISM: Artificial Sequence
<220> FEATURE:
<223> OTHER INFORMATION: primer

<400> SEQUENCE: 84
cggccccgag gtgcgggtgc cg                                             22

<210> SEQ ID NO 85
<211> LENGTH: 22
<212> TYPE: DNA
<213> ORGANISM: Artificial Sequence
<220> FEATURE:
<223> OTHER INFORMATION: primer

<400> SEQUENCE: 85
cagcgtctcc ggcctcatcc gc                                             22

<210> SEQ ID NO 86
<211> LENGTH: 22
<212> TYPE: DNA
<213> ORGANISM: Artificial Sequence
<220> FEATURE:
<223> OTHER INFORMATION: primer

<400> SEQUENCE: 86
ctcggtctcg ggcctcatcc gc                                             22

<210> SEQ ID NO 87
<211> LENGTH: 22
<212> TYPE: DNA
<213> ORGANISM: Artificial Sequence
<220> FEATURE:
<223> OTHER INFORMATION: primer

<400> SEQUENCE: 87
cgacgttccc ggcctcgtgc gc                                             22

<210> SEQ ID NO 88
<211> LENGTH: 22
<212> TYPE: DNA
<213> ORGANISM: Artificial Sequence
<220> FEATURE:
<223> OTHER INFORMATION: primer

<400> SEQUENCE: 88
caccgtctcg gggctcatcc gc                                             22
```

```
<210> SEQ ID NO 89
<211> LENGTH: 20
<212> TYPE: DNA
<213> ORGANISM: Artificial Sequence
<220> FEATURE:
<223> OTHER INFORMATION: primer

<400> SEQUENCE: 89
agcarcgtgt gcgccgagcc                                              20

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
ggcagcgcgt gcgcggaggg                                              20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
gccgctgctc gatcgggttc                                              20

<210> SEQ ID NO 92
<211> LENGTH: 24
<212> TYPE: DNA
<213> ORGANISM: Artificial Sequence
<220> FEATURE:
<223> OTHER INFORMATION: primer

<400> SEQUENCE: 92
gcagttgccg gagccgccgg acgt                                         24

<210> SEQ ID NO 93
<211> LENGTH: 24
<212> TYPE: DNA
<213> ORGANISM: Artificial Sequence
<220> FEATURE:
<223> OTHER INFORMATION: primer

<400> SEQUENCE: 93
tgcgccgagc ccggcgactc cggc                                         24

<210> SEQ ID NO 94
<211> LENGTH: 27
<212> TYPE: DNA
<213> ORGANISM: Artificial Sequence
<220> FEATURE:
<223> OTHER INFORMATION: primer

<400> SEQUENCE: 94
ggcacgacgt acttccagcc cgtgaac                                      27

<210> SEQ ID NO 95
<211> LENGTH: 33
<212> TYPE: DNA
<213> ORGANISM: Artificial Sequence
<220> FEATURE:
<223> OTHER INFORMATION: primer
```

```
<400> SEQUENCE: 95
gacccacgcg tagtcgttgc cggggaacga cga                                33

<210> SEQ ID NO 96
<211> LENGTH: 33
<212> TYPE: DNA
<213> ORGANISM: Artificial Sequence
<220> FEATURE:
<223> OTHER INFORMATION: primer

<400> SEQUENCE: 96
gaaggtcccc gacggtgacg acgtgctcgc gcc                                33

<210> SEQ ID NO 97
<211> LENGTH: 30
<212> TYPE: DNA
<213> ORGANISM: Artificial Sequence
<220> FEATURE:
<223> OTHER INFORMATION: primer

<400> SEQUENCE: 97
caggcgcagg gcgtgacctc gggcgggtcg                                    30

<210> SEQ ID NO 98
<211> LENGTH: 29
<212> TYPE: DNA
<213> ORGANISM: Artificial Sequence
<220> FEATURE:
<223> OTHER INFORMATION: primer

<400> SEQUENCE: 98
ggcgggacga cgtacttcca gcccgtcaa                                     29

<210> SEQ ID NO 99
<211> LENGTH: 30
<212> TYPE: DNA
<213> ORGANISM: Artificial Sequence
<220> FEATURE:
<223> OTHER INFORMATION: primer

<400> SEQUENCE: 99
cacccacgcg tagtcgtggc cggggaacga                                    30

<210> SEQ ID NO 100
<211> LENGTH: 33
<212> TYPE: DNA
<213> ORGANISM: Artificial Sequence
<220> FEATURE:
<223> OTHER INFORMATION: primer

<400> SEQUENCE: 100
gaagccgccc tggacggcgt acccgatcga gca                                33

<210> SEQ ID NO 101
<211> LENGTH: 30
<212> TYPE: DNA
<213> ORGANISM: Artificial Sequence
<220> FEATURE:
<223> OTHER INFORMATION: primer

<400> SEQUENCE: 101
tgcgcggagg gcggcgactc gggcgggtcg                                    30

<210> SEQ ID NO 102
<211> LENGTH: 30
<212> TYPE: DNA
```

```
<213> ORGANISM: Artificial Sequence
<220> FEATURE:
<223> OTHER INFORMATION: primer

<400> SEQUENCE: 102
ttcctctacc agcccgtcaa cccgatccta                                      30

<210> SEQ ID NO 103
<211> LENGTH: 33
<212> TYPE: DNA
<213> ORGANISM: Artificial Sequence
<220> FEATURE:
<223> OTHER INFORMATION: primer

<400> SEQUENCE: 103
cgccgcgggg acgaacccgc cctcgaccgc gaa                                  33

<210> SEQ ID NO 104
<211> LENGTH: 30
<212> TYPE: DNA
<213> ORGANISM: Artificial Sequence
<220> FEATURE:
<223> OTHER INFORMATION: primer

<400> SEQUENCE: 104
cgcgtagtcg ttgccgggga acgacgagcc                                      30

<210> SEQ ID NO 105
<211> LENGTH: 30
<212> TYPE: DNA
<213> ORGANISM: Artificial Sequence
<220> FEATURE:
<223> OTHER INFORMATION: primer

<400> SEQUENCE: 105
ggcctcatcc gcacgagcgt gtgcgccgag                                      30

<210> SEQ ID NO 106
<211> LENGTH: 36
<212> TYPE: DNA
<213> ORGANISM: Artificial Sequence
<220> FEATURE:
<223> OTHER INFORMATION: primer

<400> SEQUENCE: 106
acgtcgggcg ggtccggcaa ctgccgctac gggggc                               36

<210> SEQ ID NO 107
<211> LENGTH: 39
<212> TYPE: DNA
<213> ORGANISM: Artificial Sequence
<220> FEATURE:
<223> OTHER INFORMATION: primer

<400> SEQUENCE: 107
gagcccgtac acccggaggg cctcgttgac gggctggaa                            39

<210> SEQ ID NO 108
<211> LENGTH: 30
<212> TYPE: DNA
<213> ORGANISM: Artificial Sequence
<220> FEATURE:
<223> OTHER INFORMATION: primer

<400> SEQUENCE: 108
cgtcacgccc tgcgcctggt tgcccgcgag                                      30
```

```
<210> SEQ ID NO 109
<211> LENGTH: 38
<212> TYPE: DNA
<213> ORGANISM: Artificial Sequence
<220> FEATURE:
<223> OTHER INFORMATION: primer

<400> SEQUENCE: 109
tccagcccgt caacgaggcc ctccgggtgt acgggctc                              38

<210> SEQ ID NO 110
<211> LENGTH: 33
<212> TYPE: DNA
<213> ORGANISM: Artificial Sequence
<220> FEATURE:
<223> OTHER INFORMATION: primer

<400> SEQUENCE: 110
acgtcggtcg cgcagccgaa cggttcgtac gtc                                   33

<210> SEQ ID NO 111
<211> LENGTH: 30
<212> TYPE: DNA
<213> ORGANISM: Artificial Sequence
<220> FEATURE:
<223> OTHER INFORMATION: primer

<400> SEQUENCE: 111
cgtggtcgcg ccggtcgtgc cgcagtgccc                                       30

<210> SEQ ID NO 112
<211> LENGTH: 36
<212> TYPE: DNA
<213> ORGANISM: Artificial Sequence
<220> FEATURE:
<223> OTHER INFORMATION: primer

<400> SEQUENCE: 112
gacgacgacc gtgttggtag tgacgtcgac gtacca                                36

<210> SEQ ID NO 113
<211> LENGTH: 30
<212> TYPE: DNA
<213> ORGANISM: Artificial Sequence
<220> FEATURE:
<223> OTHER INFORMATION: primer

<400> SEQUENCE: 113
tccaccacgg ggtggcgctg cgggacgatc                                       30

<210> SEQ ID NO 114
<211> LENGTH: 30
<212> TYPE: DNA
<213> ORGANISM: Artificial Sequence
<220> FEATURE:
<223> OTHER INFORMATION: primer

<400> SEQUENCE: 114
gtgtgcgccg agcccggcga ctccggcggc                                       30

<210> SEQ ID NO 115
<211> LENGTH: 36
<212> TYPE: DNA
<213> ORGANISM: Artificial Sequence
<220> FEATURE:
<223> OTHER INFORMATION: primer
```

```
<400> SEQUENCE: 115
gctcgggccc ccaccgtcag aggtcacgag cgtgag                              36

<210> SEQ ID NO 116
<211> LENGTH: 36
<212> TYPE: DNA
<213> ORGANISM: Artificial Sequence
<220> FEATURE:
<223> OTHER INFORMATION: primer

<400> SEQUENCE: 116
atggcacgat cattctggag gacgctcgcc acggcg                              36

<210> SEQ ID NO 117
<211> LENGTH: 33
<212> TYPE: DNA
<213> ORGANISM: Artificial Sequence
<220> FEATURE:
<223> OTHER INFORMATION: primer

<400> SEQUENCE: 117
tgctcgatcg ggtacgccgt ccagggcggc ttc                                 33

<210> SEQ ID NO 118
<211> LENGTH: 30
<212> TYPE: DNA
<213> ORGANISM: Artificial Sequence
<220> FEATURE:
<223> OTHER INFORMATION: primer

<400> SEQUENCE: 118
taggatcggg ttgacgggct ggtagaggaa                                     30

<210> SEQ ID NO 119
<211> LENGTH: 36
<212> TYPE: DNA
<213> ORGANISM: Artificial Sequence
<220> FEATURE:
<223> OTHER INFORMATION: primer

<400> SEQUENCE: 119
tggtacgtcg acgtcactac caacacggtc gtcgtc                              36

<210> SEQ ID NO 120
<211> LENGTH: 30
<212> TYPE: DNA
<213> ORGANISM: Artificial Sequence
<220> FEATURE:
<223> OTHER INFORMATION: primer

<400> SEQUENCE: 120
gccgccggag tcgccgggct cggcgcacac                                     30

<210> SEQ ID NO 121
<211> LENGTH: 30
<212> TYPE: DNA
<213> ORGANISM: Artificial Sequence
<220> FEATURE:
<223> OTHER INFORMATION: primer

<400> SEQUENCE: 121
gtsgacgtsa tcggsggsaa cgcstactac                                     30

<210> SEQ ID NO 122
<211> LENGTH: 18
<212> TYPE: DNA
```

```
<213> ORGANISM: Artificial Sequence
<220> FEATURE:
<223> OTHER INFORMATION: primer
<220> FEATURE:
<221> NAME/KEY: misc_feature
<222> LOCATION: (13)..(16)
<223> OTHER INFORMATION: n is a, c, g, or t

<400> SEQUENCE: 122
sgcsgtsgcs ggnganga                                                 18

<210> SEQ ID NO 123
<211> LENGTH: 27
<212> TYPE: DNA
<213> ORGANISM: Artificial Sequence
<220> FEATURE:
<223> OTHER INFORMATION: primer

<400> SEQUENCE: 123
gtsgaygtsa tcggcggcga ygcstac                                       27

<210> SEQ ID NO 124
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (10)..(16)
<223> OTHER INFORMATION: n is a, c, g, or t

<400> SEQUENCE: 124
sgasgcgtan ccctgncc                                                 18

<210> SEQ ID NO 125
<211> LENGTH: 189
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1, 8-16, 24, 35, 36, 38, 39, 41-44, 48, 61-64, 66, 67,
      69-71, 81, 87, 89, 93, 109-111, 113, 116
<223> OTHER INFORMATION: Xaa can be any naturally occurring amino acid
<220> FEATURE:
<221> NAME/KEY: VARIANT
<222> LOCATION: 4, 19, 28, 108, 126
<223> OTHER INFORMATION: Xaa is Ile or Val
<220> FEATURE:
<221> NAME/KEY: VARIANT
<222> LOCATION: 7, 157
<223> OTHER INFORMATION: Xaa is Asn or Asp
<220> FEATURE:
<221> NAME/KEY: VARIANT
<222> LOCATION: 92, 99, 143
<223> OTHER INFORMATION: Xaa is Ser or Ala
<220> FEATURE:
<221> NAME/KEY: VARIANT
<222> LOCATION: 112, 156
<223> OTHER INFORMATION: Xaa is Asn or Gly
<220> FEATURE:
<221> NAME/KEY: VARIANT
<222> LOCATION: 21
<223> OTHER INFORMATION: Xaa is Phe or Tyr
<220> FEATURE:
<221> NAME/KEY: VARIANT
<222> LOCATION: 40
<223> OTHER INFORMATION: Xaa is Thr or Val
<220> FEATURE:
<221> NAME/KEY: VARIANT
<222> LOCATION: 59
<223> OTHER INFORMATION: Xaa is Phe or Trp
```

```
<220> FEATURE:
<221> NAME/KEY: VARIANT
<222> LOCATION: 65
<223> OTHER INFORMATION: Xaa is Gly or Asp
<220> FEATURE:
<221> NAME/KEY: VARIANT
<222> LOCATION: 68
<223> OTHER INFORMATION: Xaa is Leu or Phe
<220> FEATURE:
<221> NAME/KEY: VARIANT
<222> LOCATION: 74
<223> OTHER INFORMATION: Xaa is Asn or Arg
<220> FEATURE:
<221> NAME/KEY: VARIANT
<222> LOCATION: 75
<223> OTHER INFORMATION: Xaa is Tyr or His
<220> FEATURE:
<221> NAME/KEY: VARIANT
<222> LOCATION: 76
<223> OTHER INFORMATION: Xaa is Ser or Asp
<220> FEATURE:
<221> NAME/KEY: VARIANT
<222> LOCATION: 78
<223> OTHER INFORMATION: Xaa is Gly or Ser
<220> FEATURE:
<221> NAME/KEY: VARIANT
<222> LOCATION: 79
<223> OTHER INFORMATION: Xaa is Arg or Thr
<220> FEATURE:
<221> NAME/KEY: VARIANT
<222> LOCATION: 83
<223> OTHER INFORMATION: Xaa is Ala or Thr
<220> FEATURE:
<221> NAME/KEY: VARIANT
<222> LOCATION: 85
<223> OTHER INFORMATION: Xaa is His or Ser
<220> FEATURE:
<221> NAME/KEY: VARIANT
<222> LOCATION: 86
<223> OTHER INFORMATION: Xaa is Thr or Gln
<220> FEATURE:
<221> NAME/KEY: VARIANT
<222> LOCATION: 102
<223> OTHER INFORMATION: Xaa is Gly or Ala
<220> FEATURE:
<221> NAME/KEY: VARIANT
<222> LOCATION: 104
<223> OTHER INFORMATION: Xaa is His or Arg
<220> FEATURE:
<221> NAME/KEY: VARIANT
<222> LOCATION: 107
<223> OTHER INFORMATION: Xaa is Thr or Tyr
<220> FEATURE:
<221> NAME/KEY: VARIANT
<222> LOCATION: 114
<223> OTHER INFORMATION: Xaa is Ser or Thr
<220> FEATURE:
<221> NAME/KEY: VARIANT
<222> LOCATION: 118
<223> OTHER INFORMATION: Xaa is Pro or Ala
<220> FEATURE:
<221> NAME/KEY: VARIANT
<222> LOCATION: 119
<223> OTHER INFORMATION: Xaa is Glu or Gln
<220> FEATURE:
<221> NAME/KEY: VARIANT
<222> LOCATION: 121
<223> OTHER INFORMATION: Xaa is Thr, Ser, or Asp
<220> FEATURE:
<221> NAME/KEY: VARIANT
<222> LOCATION: 123
<223> OTHER INFORMATION: Xaa is Arg or Ser
<220> FEATURE:
<221> NAME/KEY: VARIANT
<222> LOCATION: 128
<223> OTHER INFORMATION: Xaa is Thr or Gly
<220> FEATURE:
<221> NAME/KEY: VARIANT
<222> LOCATION: 129
<223> OTHER INFORMATION: Xaa is Thr, Asn, or Ser
```

```
<220> FEATURE:
<221> NAME/KEY: VARIANT
<222> LOCATION: 130
<223> OTHER INFORMATION: Xaa is Val or Ala
<220> FEATURE:
<221> NAME/KEY: VARIANT
<222> LOCATION: 134
<223> OTHER INFORMATION: Xaa is Pro or Gly
<220> FEATURE:
<221> NAME/KEY: VARIANT
<222> LOCATION: 141
<223> OTHER INFORMATION: Xaa is Leu or Val
<220> FEATURE:
<221> NAME/KEY: VARIANT
<222> LOCATION: 142
<223> OTHER INFORMATION: Xaa is Leu, Val, or Ile
<220> FEATURE:
<221> NAME/KEY: VARIANT
<222> LOCATION: 145
<223> OTHER INFORMATION: Xaa is Asn or Thr
<220> FEATURE:
<221> NAME/KEY: VARIANT
<222> LOCATION: 148
<223> OTHER INFORMATION: Xaa is Gln or Arg
<220> FEATURE:
<221> NAME/KEY: VARIANT
<222> LOCATION: 150
<223> OTHER INFORMATION: Xaa is Val or Leu
<220> FEATURE:
<221> NAME/KEY: VARIANT
<222> LOCATION: 154
<223> OTHER INFORMATION: Xaa is Gly or Arg
<220> FEATURE:
<221> NAME/KEY: VARIANT
<222> LOCATION: 155
<223> OTHER INFORMATION: Xaa is Ser or Ile
<220> FEATURE:
<221> NAME/KEY: VARIANT
<222> LOCATION: 159, 160, 163-166, 169-189
<223> OTHER INFORMATION: Xaa can be any naturally occurring amino acid

<400> SEQUENCE: 125

Xaa Asp Val Xaa Gly Gly Xaa Xaa Xaa Xaa Xaa Xaa Xaa Xaa Xaa
1               5                   10                  15

Cys Ser Xaa Gly Xaa Ala Val Xaa Gly Gly Phe Xaa Thr Ala Gly His
            20                  25                  30

Cys Gly Xaa Xaa Gly Xaa Xaa Xaa Xaa Xaa Xaa Xaa Gly Thr Phe Xaa
            35                  40                  45

Gly Ser Ser Phe Pro Gly Asn Asp Tyr Ala Xaa Val Xaa Xaa Xaa Xaa
50                  55                  60

Xaa Xaa Xaa Xaa Xaa Xaa Xaa Val Asn Xaa Xaa Xaa Gly Xaa Xaa Val
65                  70                  75                  80

Xaa Val Xaa Gly Xaa Xaa Xaa Ala Xaa Val Gly Xaa Xaa Val Cys Arg
            85                  90                  95

Ser Gly Xaa Thr Thr Xaa Trp Xaa Cys Gly Xaa Xaa Xaa Xaa Xaa
            100                 105                 110

Xaa Xaa Val Xaa Tyr Xaa Xaa Gly Xaa Val Xaa Gly Leu Xaa Arg Xaa
            115                 120                 125

Xaa Xaa Cys Ala Glu Xaa Gly Asp Ser Gly Gly Ser Xaa Xaa Xaa Gly
    130                 135                 140

Xaa Gln Ala Xaa Gly Xaa Thr Ser Gly Xaa Xaa Xaa Xaa Cys Xaa Xaa
145                 150                 155                 160

Gly Gly Xaa Xaa Xaa Xaa Gln Pro Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa
            180                 185
```

```
<210> SEQ ID NO 126
<211> LENGTH: 16
<212> TYPE: PRT
<213> ORGANISM: Cellulomonas cellasea
<220> FEATURE:
<221> NAME/KEY: VARIANT
<222> LOCATION: (1)..(1)
<223> OTHER INFORMATION: Xaa is Ile or Tyr

<400> SEQUENCE: 126

Xaa Ala Trp Asp Ala Phe Ala Glu Asn Val Val Asp Trp Ser Ser Arg
1               5                   10                  15

<210> SEQ ID NO 127
<211> LENGTH: 17
<212> TYPE: PRT
<213> ORGANISM: Cellulomonas cellasea

<400> SEQUENCE: 127

Tyr Gly Gly Thr Thr Tyr Phe Gln Pro Val Asn Glu Ile Leu Gln Ala
1               5                   10                  15

Tyr

<210> SEQ ID NO 128
<211> LENGTH: 11
<212> TYPE: PRT
<213> ORGANISM: Cellulomonas flavigena
<220> FEATURE:
<221> NAME/KEY: VARIANT
<222> LOCATION: (4)..(11)
<223> OTHER INFORMATION: Xaa is Ile or Tyr

<400> SEQUENCE: 128

Val Asp Val Xaa Gly Gly Asn Ala Tyr Tyr Xaa
1               5                   10

<210> SEQ ID NO 129
<211> LENGTH: 9
<212> TYPE: PRT
<213> ORGANISM: Cellulomonas fimi
<220> FEATURE:
<221> NAME/KEY: VARIANT
<222> LOCATION: (4)..(4)
<223> OTHER INFORMATION: Xaa is Ile or Tyr

<400> SEQUENCE: 129

Val Asp Val Xaa Gly Gly Asp Ala Tyr
1               5

<210> SEQ ID NO 130
<211> LENGTH: 305
<212> TYPE: DNA
<213> ORGANISM: Aspergillus niger
<220> FEATURE:
<221> NAME/KEY: misc_feature
<222> LOCATION: (186)..(186)
<223> OTHER INFORMATION: n is a, c, g, or t

<400> SEQUENCE: 130
tcgaacttca tgttcgagtt cttgttcacg tagaagccgg agatgtgaga ggtgatctgg      60
aactgctcac cctcgttggt ggtgacctgg aggtaaagca agtgacccct ctggcggagg     120
tggtaaggaa cggggttcca cggggagaga gagatggcct tgacggtctt ggaaggggaa     180
gcttcngcgc gggggaggat ggtcttgaga gaggggagc tagtaatgtc gtacttggac     240
agggagtgct cctcctccga cgcatcagcc acctcagcgg gatggcatc gtgcagagac     300 agacc                                                                305
```

<210> SEQ ID NO 131
<211> LENGTH: 1488
<212> TYPE: DNA
<213> ORGANISM: Cellulomonas strain 69B4

<400> SEQUENCE: 131

```
atgacaccac gaactgtcac aagagctctg gctgtggcaa cagcagctgc tacactcttg      60
gctgggggta tggcagcaca agctaacgaa ccggctcctc aggatctgc atcagcccct     120
ccacgattag ctgaaaaact tgaccctgac ttacttgaag caatggaacg cgatctgggg     180
ttagatgcag aggaagcagc tgcaacgtta gcttttcagc atgacgcagc tgaaacggga     240
gaggctcttg ctgaggaact cgacgaagat ttcgcgggca cgtgggttga agatgatgtg     300
ctgtatgttg caaccactga tgaagatgct gttgaagaag tcgaaggcga aggagcaact     360
gctgtgactg ttgagcattc tcttgctgat ttagaggcgt ggaagacggt tttggatgct     420
gcgctggagg tcatgatga tgtgcctacg tggtacgtcg acgtgcctac gaattcggta     480
gtcgttgctg taaaggcagg agcgcaggat gtagctgcag acttgtgga aggcgctgat     540
gtgccatcag atgcggtcac ttttgtagaa acggacgaaa cgcctagaac gatgttcgac     600
gtaattggag gcaacgcata tactattggc ggccggtcta gatgttctat cggattcgca     660
gtaaacggtg gcttcattac tgccggtcac tgcggaagaa caggagccac tactgccaat     720
ccgactggca catttgcagg tagctcgttt ccgggaaatg attatgcatt cgtccgaaca     780
ggggcaggag taaatttgct tgcccaagtc aataactact cgggcggcag agtccaagta     840
gcaggacata cggccgcacc agttggatct gctgtatgcc gctcaggtag cactacaggt     900
tggcattgcg gaactatcac ggcgctgaat tcgtctgtca cgtatccaga gggaacagtc     960
cgaggactta tccgcacgac ggtttgtgcc gaaccaggtg atagcggagg tagcctttta    1020
gcgggaaatc aagcccaagg tgtcacgtca ggtggttctg gaaattgtcg acgggggga    1080
acaacattct ttcaaccagt caacccgatt ttgcaggctt acggcctgag aatgattacg    1140
actgactctg gaagttcccc tgctccagca cctacatcat gtacaggcta cgcaagaacg    1200
ttcacaggaa ccctcgcagc aggaagagca gcagctcaac cgaacggtag ctatgttcag    1260
gtcaaccgga gcggtacaca ttccgtctgt ctcaatggac ctagcggtgc ggactttgat    1320
ttgtatgtgc agcgatggaa tggcagtagc tgggtaaccg tcgctcaatc gacatcgccg    1380
ggaagcaatg aaaccattac gtaccgcgga aatgctggat attatcgcta cgtggttaac    1440
gctgcgtcag gatcaggagc ttacacaatg ggactcaccc tcccctga              1488
```

<210> SEQ ID NO 132
<211> LENGTH: 6
<212> TYPE: PRT
<213> ORGANISM: Artificial Sequence
<220> FEATURE:
<223> OTHER INFORMATION: linker

<400> SEQUENCE: 132

Asp Asp Asn Asp Pro Ile
1               5

<210> SEQ ID NO 133
<211> LENGTH: 1020
<212> TYPE: DNA
<213> ORGANISM: Artificial Sequence
<220> FEATURE:
<223> OTHER INFORMATION: synthetic -continued

```
<400> SEQUENCE: 133
gtgagaagca aaaaattgtg gatcagcttg ttgtttgcgt taacgttaat ctttacgatg      60
gcgttcagca acatgagcgc gcaggctgat gattattcag ttgtagagga acatgggcaa     120
ctaagtatta gtaacggtga attagtcaat gaacgaggcg aacaagttca gttaaaaggg     180
atgagttccc atggtttgca atggtacggt caatttgtaa actatgaaag catgaaatgg     240
ctaagagatg attggggaat aactgtattc cgagcagcaa tgtatacctc ttcaggagga     300
tatattgacg atccatcagt aaaggaaaaa gtaaagaga ctgttgaggc tgcgatagac      360
cttggcatat atgtgatcat tgattggcat atcctttcag acaatgaccc gaatatatat     420
aaagaagaag cgaaggattt ctttgatgaa atgtcagagt tgtatggaga ctatccgaat     480
gtgatatacg aaattgcaaa tgaaccgaat ggtagtgatg ttacgtggga caatcaaata     540
aaaccgtatg cagaagaagt gattccggtt attcgtgaca atgaccctaa taacattgtt     600
attgtaggta caggtacatg gagtcaggat gtccatcatg cagccgataa tcagcttgca     660
gatcctaacg tcatgtatgc atttcatttt tatgcaggaa cacatggaca aaatttacga     720
gaccaagtag attatgcatt agatcaagga gcagcgatat ttgttagtga atgggggaca     780
agtgcagcta caggtgatgg tggtgtgttt ttagatgaag cacaagtgtg gattgacttt     840
atggatgaaa gaaatttaag ctgggccaac tggtctctaa cgcataagga tgagtcatct     900
gcagcgttaa tgccaggtgc aaatccaact ggtggttgga cagaggctga actatctcca     960
tctggtacat ttgtgaggga aaaataaga gaatcagcat ctgacaacaa tgatcccata    1020

<210> SEQ ID NO 134
<211> LENGTH: 340
<212> TYPE: PRT
<213> ORGANISM: Artificial Sequence
<220> FEATURE:
<223> OTHER INFORMATION: synthetic

<400> SEQUENCE: 134

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Asp Asp Tyr
                20                  25                  30

Ser Val Val Glu Glu His Gly Gln Leu Ser Ile Ser Asn Gly Glu Leu
            35                  40                  45

Val Asn Glu Arg Gly Glu Gln Val Gln Leu Lys Gly Met Ser Ser His
        50                  55                  60

Gly Leu Gln Trp Tyr Gly Gln Phe Val Asn Tyr Glu Ser Met Lys Trp
65                  70                  75                  80

Leu Arg Asp Asp Trp Gly Ile Thr Val Phe Arg Ala Ala Met Tyr Thr
                85                  90                  95

Ser Ser Gly Gly Tyr Ile Asp Asp Pro Ser Val Lys Glu Lys Val Lys
            100                 105                 110

Glu Thr Val Glu Ala Ala Ile Asp Leu Gly Ile Tyr Val Ile Ile Asp
        115                 120                 125

Trp His Ile Leu Ser Asp Asn Asp Pro Asn Ile Tyr Lys Glu Glu Ala
    130                 135                 140

Lys Asp Phe Phe Asp Glu Met Ser Glu Leu Tyr Gly Asp Tyr Pro Asn
145                 150                 155                 160

Val Ile Tyr Glu Ile Ala Asn Glu Pro Asn Gly Ser Asp Val Thr Trp
                165                 170                 175

Asp Asn Gln Ile Lys Pro Tyr Ala Glu Glu Val Ile Pro Val Ile Arg
```

```
                    180                 185                 190
Asp Asn Asp Pro Asn Asn Ile Val Ile Val Gly Thr Gly Thr Trp Ser
                195                 200                 205
Gln Asp Val His His Ala Ala Asp Asn Gln Leu Ala Asp Pro Asn Val
            210                 215                 220
Met Tyr Ala Phe His Phe Tyr Ala Gly Thr His Gly Gln Asn Leu Arg
225                 230                 235                 240
Asp Gln Val Asp Tyr Ala Leu Asp Gln Gly Ala Ala Ile Phe Val Ser
                245                 250                 255
Glu Trp Gly Thr Ser Ala Ala Thr Gly Asp Gly Gly Val Phe Leu Asp
            260                 265                 270
Glu Ala Gln Val Trp Ile Asp Phe Met Asp Glu Arg Asn Leu Ser Trp
            275                 280                 285
Ala Asn Trp Ser Leu Thr His Lys Asp Glu Ser Ser Ala Ala Leu Met
            290                 295                 300
Pro Gly Ala Asn Pro Thr Gly Gly Trp Thr Glu Ala Glu Leu Ser Pro
305                 310                 315                 320
Ser Gly Thr Phe Val Arg Glu Lys Ile Arg Glu Ser Ala Ser Asp Asn
                325                 330                 335
Asn Asp Pro Ile
            340

<210> SEQ ID NO 135
<211> LENGTH: 30
<212> TYPE: PRT
<213> ORGANISM: Cellulomonas strain 69B4

<400> SEQUENCE: 135

Met Arg Ser Lys Lys Arg Thr Val Thr Arg Ala Leu Ala Val Ala Thr
1               5                   10                  15
Ala Ala Ala Thr Leu Leu Ala Gly Gly Met Ala Ala Gln Ala
            20                  25                  30

<210> SEQ ID NO 136
<211> LENGTH: 30
<212> TYPE: PRT
<213> ORGANISM: Cellulomonas strain 69B4

<400> SEQUENCE: 136

Met Arg Ser Lys Lys Leu Trp Ile Ser Leu Leu Leu Ala Val Ala Thr
1               5                   10                  15
Ala Ala Ala Thr Leu Leu Ala Gly Gly Met Ala Ala Gln Ala
            20                  25                  30

<210> SEQ ID NO 137
<211> LENGTH: 40
<212> TYPE: DNA
<213> ORGANISM: Artificial Sequence
<220> FEATURE:
<223> OTHER INFORMATION: primer

<400> SEQUENCE: 137
ctagctaggt accatgacac cacgaactgt cacaagagct                40

<210> SEQ ID NO 138
<211> LENGTH: 40
<212> TYPE: DNA
<213> ORGANISM: Artificial Sequence
<220> FEATURE:
<223> OTHER INFORMATION: primer
```

<400> SEQUENCE: 138
gtgtgcaagc tttcagggga gggtgagtcc cattgtgtaa                               40

<210> SEQ ID NO 139
<211> LENGTH: 40
<212> TYPE: DNA
<213> ORGANISM: Artificial Sequence
<220> FEATURE:
<223> OTHER INFORMATION: primer

<400> SEQUENCE: 139
ctagctaggt accatgacac cacgaactgt cacaagagct                               40

<210> SEQ ID NO 140
<211> LENGTH: 37
<212> TYPE: DNA
<213> ORGANISM: Artificial Sequence
<220> FEATURE:
<223> OTHER INFORMATION: primer

<400> SEQUENCE: 140
gtgtgcaagc tttcaagggg aacttccaga gtcagtc                                  37

<210> SEQ ID NO 141
<211> LENGTH: 53
<212> TYPE: DNA
<213> ORGANISM: Artificial Sequence
<220> FEATURE:
<223> OTHER INFORMATION: primer

<400> SEQUENCE: 141
tcatgcaggg taccatgaga agcaagaagc gaactgtcac aagagctctg gct                53

<210> SEQ ID NO 142
<211> LENGTH: 40
<212> TYPE: DNA
<213> ORGANISM: Artificial Sequence
<220> FEATURE:
<223> OTHER INFORMATION: primer

<400> SEQUENCE: 142
gtgtgcaagc tttcagggga gggtgagtcc cattgtgtaa                               40

<210> SEQ ID NO 143
<211> LENGTH: 53
<212> TYPE: DNA
<213> ORGANISM: Artificial Sequence
<220> FEATURE:
<223> OTHER INFORMATION: primer

<400> SEQUENCE: 143
tcatgcaggg taccatgaga agcaagaagc gaactgtcac aagagctctg gct                53

<210> SEQ ID NO 144
<211> LENGTH: 37
<212> TYPE: DNA
<213> ORGANISM: Artificial Sequence
<220> FEATURE:
<223> OTHER INFORMATION: primer

<400> SEQUENCE: 144
gtgtgcaagc tttcaagggg aacttccaga gtcagtc                                  37

<210> SEQ ID NO 145
<211> LENGTH: 74
<212> TYPE: DNA

```
<213> ORGANISM: Artificial Sequence
<220> FEATURE:
<223> OTHER INFORMATION: primer

<400> SEQUENCE: 145
tcatgcaggg taccatgaga agcaagaagt tgtggatcag tttgctgctg gctgtggcaa    60
cagcagctgc taca                                                      74

<210> SEQ ID NO 146
<211> LENGTH: 40
<212> TYPE: DNA
<213> ORGANISM: Artificial Sequence
<220> FEATURE:
<223> OTHER INFORMATION: primer

<400> SEQUENCE: 146
gtgtgcaagc tttcagggga gggtgagtcc cattgtgtaa                          40

<210> SEQ ID NO 147
<211> LENGTH: 74
<212> TYPE: DNA
<213> ORGANISM: Artificial Sequence
<220> FEATURE:
<223> OTHER INFORMATION: primer

<400> SEQUENCE: 147
tcatgcaggg taccatgaga agcaagaagt tgtggatcag tttgctgctg gctgtggcaa    60
cagcagctgc taca                                                      74

<210> SEQ ID NO 148
<211> LENGTH: 37
<212> TYPE: DNA
<213> ORGANISM: Artificial Sequence
<220> FEATURE:
<223> OTHER INFORMATION: primer

<400> SEQUENCE: 148
gtgtgcaagc tttcaagggg aacttccaga gtcagtc                             37

<210> SEQ ID NO 149
<211> LENGTH: 38
<212> TYPE: DNA
<213> ORGANISM: Artificial Sequence
<220> FEATURE:
<223> OTHER INFORMATION: primer

<400> SEQUENCE: 149
ccataccgga tccaaacgaa ccggctcctc caggatct                            38

<210> SEQ ID NO 150
<211> LENGTH: 39
<212> TYPE: DNA
<213> ORGANISM: Artificial Sequence
<220> FEATURE:
<223> OTHER INFORMATION: primer

<400> SEQUENCE: 150
ctcgagttaa gcttttaagg ggaacttcca gagtcagtc                           39

<210> SEQ ID NO 151
<211> LENGTH: 48
<212> TYPE: DNA
<213> ORGANISM: Artificial Sequence
<220> FEATURE:
<223> OTHER INFORMATION: primer
```

-continued

<400> SEQUENCE: 151
tgagctgcta gcaaaaggag agggtaaaga atgacaccac gaactgtc    48

<210> SEQ ID NO 152
<211> LENGTH: 36
<212> TYPE: DNA
<213> ORGANISM: Artificial Sequence
<220> FEATURE:
<223> OTHER INFORMATION: primer

<400> SEQUENCE: 152
cgtacatccc gggtcagggg agggtgagtc ccattg    36

<210> SEQ ID NO 153
<211> LENGTH: 48
<212> TYPE: DNA
<213> ORGANISM: Artificial Sequence
<220> FEATURE:
<223> OTHER INFORMATION: primer

<400> SEQUENCE: 153
tgagctgcta gcaaaaggag agggtaaaga atgacaccac gaactgtc    48

<210> SEQ ID NO 154
<211> LENGTH: 38
<212> TYPE: DNA
<213> ORGANISM: Artificial Sequence
<220> FEATURE:
<223> OTHER INFORMATION: primer

<400> SEQUENCE: 154
catgcatccc gggttaaggg gaacttccag agtcagtc    38

<210> SEQ ID NO 155
<211> LENGTH: 45
<212> TYPE: DNA
<213> ORGANISM: Artificial Sequence
<220> FEATURE:
<223> OTHER INFORMATION: primer

<400> SEQUENCE: 155
tgagctgcta gcaaaaggag agggtaaaga atgagaagca agaag    45

<210> SEQ ID NO 156
<211> LENGTH: 36
<212> TYPE: DNA
<213> ORGANISM: Artificial Sequence
<220> FEATURE:
<223> OTHER INFORMATION: primer

<400> SEQUENCE: 156
cgtacatccc gggtcagggg agggtgagtc ccattg    36

<210> SEQ ID NO 157
<211> LENGTH: 45
<212> TYPE: DNA
<213> ORGANISM: Artificial Sequence
<220> FEATURE:
<223> OTHER INFORMATION: primer

<400> SEQUENCE: 157
tgagctgcta gcaaaaggag agggtaaaga atgagaagca agaag    45

<210> SEQ ID NO 158
<211> LENGTH: 38
<212> TYPE: DNA

```
<213> ORGANISM: Artificial Sequence
<220> FEATURE:
<223> OTHER INFORMATION: primer

<400> SEQUENCE: 158
catgcatccc gggttaaggg gaacttccag agtcagtc                         38

<210> SEQ ID NO 159
<211> LENGTH: 45
<212> TYPE: DNA
<213> ORGANISM: Artificial Sequence
<220> FEATURE:
<223> OTHER INFORMATION: primer

<400> SEQUENCE: 159
tgagctgcta gcaaaaggag agggtaaaga atgagaagca agaag                 45

<210> SEQ ID NO 160
<211> LENGTH: 36
<212> TYPE: DNA
<213> ORGANISM: Artificial Sequence
<220> FEATURE:
<223> OTHER INFORMATION: primer

<400> SEQUENCE: 160
cgtacatccc gggtcagggg agggtgagtc ccattg                           36

<210> SEQ ID NO 161
<211> LENGTH: 45
<212> TYPE: DNA
<213> ORGANISM: Artificial Sequence
<220> FEATURE:
<223> OTHER INFORMATION: primer

<400> SEQUENCE: 161
tgagctgcta gcaaaaggag agggtaaaga atgagaagca agaag                 45

<210> SEQ ID NO 162
<211> LENGTH: 38
<212> TYPE: DNA
<213> ORGANISM: Artificial Sequence
<220> FEATURE:
<223> OTHER INFORMATION: primer

<400> SEQUENCE: 162
catgcatccc gggttaaggg gaacttccag agtcagtc                         38

<210> SEQ ID NO 163
<211> LENGTH: 40
<212> TYPE: DNA
<213> ORGANISM: Artificial Sequence
<220> FEATURE:
<223> OTHER INFORMATION: primer

<400> SEQUENCE: 163
tgcagtctgc tagcaaaagg agagggtaaa gagtgagaag                       40

<210> SEQ ID NO 164
<211> LENGTH: 38
<212> TYPE: DNA
<213> ORGANISM: Artificial Sequence
<220> FEATURE:
<223> OTHER INFORMATION: primer

<400> SEQUENCE: 164
catgcatccc gggttaaggg gaacttccag agtcagtc                         38
```

<210> SEQ ID NO 165
<211> LENGTH: 50
<212> TYPE: DNA
<213> ORGANISM: Artificial Sequence
<220> FEATURE:
<223> OTHER INFORMATION: primer

<400> SEQUENCE: 165
ttatgcgagg ctagcaaaag gagagggtaa agagtgagaa gcaaaaaacg           50

<210> SEQ ID NO 166
<211> LENGTH: 42
<212> TYPE: DNA
<213> ORGANISM: Artificial Sequence
<220> FEATURE:
<223> OTHER INFORMATION: primer

<400> SEQUENCE: 166
taaagagtga gaagcaaaaa acgcacagtc acgcgggccc tg                   42

<210> SEQ ID NO 167
<211> LENGTH: 35
<212> TYPE: DNA
<213> ORGANISM: Artificial Sequence
<220> FEATURE:
<223> OTHER INFORMATION: primer

<400> SEQUENCE: 167
gtcctctgtt aacttacggg ctgctgcccg agtcc                           35

<210> SEQ ID NO 168
<211> LENGTH: 41
<212> TYPE: DNA
<213> ORGANISM: Artificial Sequence
<220> FEATURE:
<223> OTHER INFORMATION: primer

<400> SEQUENCE: 168
gcaacatgtc tgcgcaggct aacgaaccgg ctcctccagg a                    41

<210> SEQ ID NO 169
<211> LENGTH: 35
<212> TYPE: DNA
<213> ORGANISM: Artificial Sequence
<220> FEATURE:
<223> OTHER INFORMATION: primer

<400> SEQUENCE: 169
gacatgacat aagcttaagg ggaacttcca gagtc                           35

<210> SEQ ID NO 170
<211> LENGTH: 25
<212> TYPE: DNA
<213> ORGANISM: Artificial Sequence
<220> FEATURE:
<223> OTHER INFORMATION: primer

<400> SEQUENCE: 170
gagccgaatt catatacctg ccgtt                                      25

<210> SEQ ID NO 171
<211> LENGTH: 41
<212> TYPE: DNA
<213> ORGANISM: Artificial Sequence
<220> FEATURE:
<223> OTHER INFORMATION: primer -continued

<400> SEQUENCE: 171
tcctggagga gccggttcgt tagcctgcgc agacatgttg c        41

<210> SEQ ID NO 172
<211> LENGTH: 5713
<212> TYPE: DNA
<213> ORGANISM: Artificial Sequence
<220> FEATURE:
<223> OTHER INFORMATION: synthetic

<400> SEQUENCE: 172

| | | | | | |
|---|---|---|---|---|---|
| catcacatat | acctgccgtt | cactattatt | tagtgaaatg | agatattatg | atattttctg | 60 |
| aattgtgatt | aaaaaggcaa | ctttatgccc | atgcaacaga | aactataaaa | aatacagaga | 120 |
| atgaaaagaa | acagatagat | ttttagttc | tttaggcccg | tagtctgcaa | atccttttat | 180 |
| gattttctat | caaacaaaag | aggaaaatag | accagttgca | atccaaacga | gagtctaata | 240 |
| gaatgaggtc | acagaatagt | cttttaagta | agtctactct | gaattttttt | aaaaggagag | 300 |
| ggtaaagagt | gagaagcaaa | aaattgtgga | tcagcttgtt | gtttgcgtta | acgttaatct | 360 |
| ttacgatggc | gttcagcaac | atgtctgcgc | aggctaacga | accggctcct | ccaggatctg | 420 |
| catcagcccc | tccacgatta | gctgaaaaac | ttgaccctga | cttacttgaa | gcaatggaac | 480 |
| gcgatctggg | gttagatgca | gaggaagcag | ctgcaacgtt | agcttttcag | catgacgcag | 540 |
| ctgaaacggg | agaggctctt | gctgaggaac | tcgacgaaga | tttcgcgggc | acgtgggttg | 600 |
| aagatgatgt | gctgtatgtt | gcaaccactg | atgaagatgc | tgttgaagaa | gtcgaaggcg | 660 |
| aaggagcaac | tgctgtgact | gttgagcatt | ctcttgctga | tttagaggcg | tggaagacgg | 720 |
| ttttggatgc | tgcgctggag | ggtcatgatg | atgtgcctac | gtggtacgtc | gacgtgccta | 780 |
| cgaattcggt | agtcgttgct | gtaaaggcag | gagcgcagga | tgtagctgca | ggacttgtgg | 840 |
| aaggcgctga | tgtgccatca | gatgcggtca | cttttgtaga | aacggacgaa | acgcctagaa | 900 |
| cgatgttcga | cgtaattgga | ggcaacgcat | atactattgg | cggccggtct | agatgttcta | 960 |
| tcggattcgc | agtaaacggt | ggcttcatta | ctgccggtca | ctgcggaaga | acaggagcca | 1020 |
| ctactgccaa | tccgactggc | acatttgcag | gtagctcgtt | tccgggaaat | gattatgcat | 1080 |
| tcgtccgaac | aggggcagga | gtaaatttgc | ttgcccaagt | caataactac | tcgggcggca | 1140 |
| gagtccaagt | agcaggacat | acggccgcac | cagttggatc | tgctgtatgc | cgctcaggta | 1200 |
| gcactacagg | ttggcattgc | ggaactatca | cggcgctgaa | ttcgtctgtc | acgtatccag | 1260 |
| agggaacagt | ccgaggactt | atccgcacga | cggtttgtgc | cgaaccaggt | gatagcggag | 1320 |
| gtagccttt | agcgggaaat | caagcccaag | tgtcacgtc | aggtggttct | ggaaattgtc | 1380 |
| ggacgggggg | aacaacattc | tttcaaccag | tcaacccgat | tttgcaggct | tacgcctga | 1440 |
| gaatgattac | gactgactct | ggaagttccc | cttaagctta | aaaaaccggc | cttggccccg | 1500 |
| ccggtttttt | attattttc | ttcctccgca | tgttcaatcc | gctccataat | cgacggatgg | 1560 |
| ctccctctga | aaattttaac | gagaaacggc | gggttgaccc | ggctcagtcc | cgtaacggcc | 1620 |
| aagtcctgaa | acgtctcaat | cgccgcttcc | cggtttccgg | tcagctcaat | gccgtaacgg | 1680 |
| tcggcggcgt | tttcctgata | ccgggagacg | gcattcgtaa | tcggatcccg | gacgcatcgt | 1740 |
| ggccggcatc | accggcgcca | caggtgcggt | tgctggcgcc | tatatcgccg | acatcaccga | 1800 |
| tggggaagat | cgggctcgcc | acttcgggct | catgagcgct | tgtttcggcg | tgggtatggt | 1860 |
| ggcaggcccc | gtggccgggg | gactgttggg | cgccatctcc | ttgcatgcac | cattccttgc | 1920 |
| ggcggcggtg | ctcaacggcc | tcaacctact | actgggctgc | ttcctaatgc | aggagtcgca | 1980 |

```
taagggagag cgtcgaccga tgcccttgag agccttcaac ccagtcagct ccttccggtg    2040
ggcgcggggc atgactatcg tcgccgcact tatgactgtc ttctttatca tgcaactcgt    2100
aggacaggtg ccggcagcgc tctgggtcat tttcggcgag gaccgctttc gctggagcgc    2160
gacgatgatc ggcctgtcgc ttgcggtatt cggaatcttg cacgccctcg ctcaagcctt    2220
cgtcactggt cccgccacca aacgtttcgg cgagaagcag gccattatcg ccggcatggc    2280
ggccgacgcg ctgggctacg tcttgctggc gttcgcgacg cgaggctgga tggccttccc    2340
cattatgatt cttctcgctt ccggcggcat cgggatgccc gcgttgcagg ccatgctgtc    2400
caggcaggta gatgacgacc atcagggaca gcttcaagga tcgctcgcgg ctcttaccag    2460
cctaacttcg atcactggac cgctgatcgt cacggcgatt tatgccgcct cggcgagcac    2520
atggaacggg ttggcatgga ttgaggcgcc gccctatacc ttatttatgt tacagtaata    2580
ttgactttta aaaaggatt gattctaatg aagaaagcag acaagtaagc ctcctaaatt    2640
cactttagat aaaaatttag gaggcatatc aaatgaactt taataaaatt gatttagaca    2700
attggaagag aaaagagata tttaatcatt atttgaacca acaaacgact tttagtataa    2760
ccacagaaat tgatattagt gttttatacc gaaacataaa acaagaagga tataaatttt    2820
accctgcatt tatttcttta gtgacaaggg tgataaactc aaatacagct tttagaactg    2880
gttacaatag cgacggagag ttaggttatt gggataagtt agagccactt tatacaattt    2940
ttgatggtgt atctaaaaca ttctctggta tttggactcc tgtaaagaat gacttcaaag    3000
agttttatga tttataccct tctgatgtag agaaatataa tggttcgggg aaattgtttc    3060
ccaaaacacc tatacctgaa aatgcttttt ctctttctat tattccatgg acttcattta    3120
ctgggtttaa cttaaatatc aataataata gtaattaccc tctacccatt attacagcag    3180
gaaaattcat taataaaggt aattcaatat atttaccgct atctttacag gtacatcatt    3240
ctgtttgtga tggttatcat gcaggattgt ttatgaactc tattcaggaa ttgtcagata    3300
ggcctaatga ctggctttta taatatgaga taatgccgac tgtacttttt acagtcggtt    3360
ttctaatgtc actaacctgc cccgttagtt gaagaaggtt tttatattac agctccagat    3420
cctgcctcgc gcgtttcggt gatgacggtg aaaacctctg acacatgcag ctcccggaga    3480
cggtcacagc ttgtctgtaa gcggatgccg ggagcagaca gcccgtcag ggcgcgtcag    3540 cgggtgttgg cgggtgtcgg ggcgcagcca tgacccagtc acgtagcgat gcggagtgt    3600 atactggctt aactatgcgg catcagagca gattgtactg agagtgcacc atatgcggtg    3660
tgaaataccg cacagatgcg taaggagaaa ataccgcatc aggcgctctt ccgcttcctc    3720
gctcactgac tcgctgcgct cggtcgttcg gctgcggcga gcggtatcag ctcactcaaa    3780
ggcggtaata cggttatcca cagaatcagg ggataacgca ggaaagaaca tgtgagcaaa    3840
aggccagcaa aaggccagga accgtaaaaa ggccgcgttg ctggcgtttt tccataggct    3900
ccgcccccct gacgagcatc acaaaaatcg acgctcaagt cagaggtggc gaaacccgac    3960
aggactataa agataccagg cgtttccccc tggaagctcc ctcgtgcgct ctcctgttcc    4020
gaccctgccg cttaccggat acctgtccgc ctttctccct tcgggaagcg tggcgctttc    4080
tcatagctca cgctgtaggt atctcagttc ggtgtaggtc gttcgctcca agctgggctg    4140
tgtgcacgaa ccccccgttc agcccgaccg ctgcgcctta ccggtaact atcgtcttga    4200 gtccaacccg gtaagacacg acttatcgcc actggcagca gccactggta acaggattag    4260
cagagcgagg tatgtaggcg gtgctacaga gttcttgaag tggtggccta actacggcta    4320
cactagaagg acagtatttg gtatctgcgc tctgctgaag ccagttacct tcggaaaaag    4380
```

```
agttggtagc tcttgatccg gcaaacaaac caccgctggt agcggtggtt ttttgtttg      4440 caagcagcag attacgcgca gaaaaaagg atctcaagaa gatcctttga tcttttctac      4500
ggggtctgac gctcagtgga acgaaaactc acgttaaggg attttggtca tgagattatc    4560
aaaaaggatc ttcacctaga tccttttaaa ttaaaaatga gttttaaat caatctaaag     4620 tatatatgag taaacttggt ctgacagtta ccaatgctta atcagtgagg cacctatctc    4680
agcgatctgt ctatttcgtt catccatagt tgcctgactc cccgtcgtgt agataactac    4740
gatacgggag ggcttaccat ctggccccag tgctgcaatg ataccgcgag acccacgctc    4800
accggctcca gatttatcag caataaacca gccagccgga agggccgagc gcagaagtgg    4860
tcctgcaact ttatccgcct ccatccagtc tattaattgt tgccgggaag ctagagtaag    4920
tagttcgcca gttaatagtt tgcgcaacgt tgttgccatt gctgcaggca tcgtggtgtc    4980
acgctcgtcg tttggtatgg cttcattcag ctccggttcc caacgatcaa ggcgagttac    5040
atgatccccc atgttgtgca aaaagcggt tagctccttc ggtcctccga tcgttgtcag     5100
aagtaagttg gccgcagtgt tatcactcat ggttatggca gcactgcata attctcttac    5160
tgtcatgcca tccgtaagat gcttttctgt gactggtgag tactcaacca agtcattctg    5220
agaatagtgt atgcggcgac cgagttgctc ttgcccggcg tcaacacggg ataataccgc    5280
gccacatagc agaactttaa aagtgctcat cattggaaaa cgttcttcgg ggcgaaaact    5340
ctcaaggatc ttaccgctgt tgagatccag ttcgatgtaa cccactcgtg cacccaactg    5400
atcttcagca tctttacctt tcaccagcgt tctgggtga gcaaaacag gaaggcaaaa      5460 tgccgcaaaa aagggaataa gggcgacacg gaaatgttga atactcatac tcttcctttt    5520
tcaatattat tgaagcattt atcagggtta ttgtctcatg agcggataca tatttgaatg    5580
tatttagaaa aataaacaaa tagggggttcc gcgcacattt ccccgaaaag tgccacctga   5640
cgtctaagaa accattatta tcatgacatt aacctataaa aataggcgta tcacgaggcc    5700
ctttcgtctt caa                                                       5713

<210> SEQ ID NO 173
<211> LENGTH: 33
<212> TYPE: PRT
<213> ORGANISM: Artificial Sequence
<220> FEATURE:
<223> OTHER INFORMATION: synthetic

<400> SEQUENCE: 173

Met Lys Lys Arg Thr Val Thr Arg Ala Leu Ala Val Ala Thr Ala Ala
1               5                   10                  15

Ala Thr Leu Leu Ala Gly Gly Met Ala Ala Gln Ala Asn Glu Pro Ala
            20                  25                  30

Pro

<210> SEQ ID NO 174
<211> LENGTH: 36
<212> TYPE: PRT
<213> ORGANISM: Artificial Sequence
<220> FEATURE:
<223> OTHER INFORMATION: synthetic

<400> SEQUENCE: 174

Met Lys Lys Pro Leu Gly Arg Thr Val Thr Arg Ala Leu Ala Val Ala
1               5                   10                  15

Thr Ala Ala Ala Thr Leu Leu Ala Gly Gly Met Ala Ala Gln Ala Asn
            20                  25                  30
```

-continued

Glu Pro Ala Pro
          35

<210> SEQ ID NO 175
<211> LENGTH: 32
<212> TYPE: PRT
<213> ORGANISM: Artificial Sequence
<220> FEATURE:
<223> OTHER INFORMATION: synthetic

<400> SEQUENCE: 175

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala Asn Glu Pro Ala Pro
            20                  25                  30

<210> SEQ ID NO 176
<211> LENGTH: 40
<212> TYPE: DNA
<213> ORGANISM: Artificial Sequence
<220> FEATURE:
<223> OTHER INFORMATION: primer

<400> SEQUENCE: 176
agggaaccga atgaagaaac gaactgtcac aagagctctg                              40

<210> SEQ ID NO 177
<211> LENGTH: 40
<212> TYPE: DNA
<213> ORGANISM: Artificial Sequence
<220> FEATURE:
<223> OTHER INFORMATION: primer

<400> SEQUENCE: 177
cagagctctt gtgacagttc gtttcttcat tcggttccct                              40

<210> SEQ ID NO 178
<211> LENGTH: 40
<212> TYPE: DNA
<213> ORGANISM: Artificial Sequence
<220> FEATURE:
<223> OTHER INFORMATION: primer

<400> SEQUENCE: 178
aatgaagaaa ccgttggggc gaactgtcac aagagctctg                              40

<210> SEQ ID NO 179
<211> LENGTH: 40
<212> TYPE: DNA
<213> ORGANISM: Artificial Sequence
<220> FEATURE:
<223> OTHER INFORMATION: primer

<400> SEQUENCE: 179
cagagctctt gtgacagttc gccccaacgg tttcttcatt                              40

<210> SEQ ID NO 180
<211> LENGTH: 42
<212> TYPE: DNA
<213> ORGANISM: Artificial Sequence
<220> FEATURE:
<223> OTHER INFORMATION: primer

<400> SEQUENCE: 180
agttcatcga tcgcatcggc taacgaaccg gctcctccag ga                           42

```
<210> SEQ ID NO 181
<211> LENGTH: 42
<212> TYPE: DNA
<213> ORGANISM: Artificial Sequence
<220> FEATURE:
<223> OTHER INFORMATION: primer

<400> SEQUENCE: 181
tcctggagga gccggttcgt tagccgatgc gatcgatgaa ct                42

<210> SEQ ID NO 182
<211> LENGTH: 34
<212> TYPE: DNA
<213> ORGANISM: Artificial Sequence
<220> FEATURE:
<223> OTHER INFORMATION: primer

<400> SEQUENCE: 182 tcaggggat cctagattct gttaacttaa cgtt                          34

<210> SEQ ID NO 183
<211> LENGTH: 28
<212> TYPE: DNA
<213> ORGANISM: Artificial Sequence
<220> FEATURE:
<223> OTHER INFORMATION: primer

<400> SEQUENCE: 183
gtgctgtttt atcctttacc ttgtctcc                                28

<210> SEQ ID NO 184
<211> LENGTH: 29
<212> TYPE: DNA
<213> ORGANISM: Artificial Sequence
<220> FEATURE:
<223> OTHER INFORMATION: primer

<400> SEQUENCE: 184
agttaagcaa tcagatcttc ttcaggtta                               29

<210> SEQ ID NO 185
<211> LENGTH: 47
<212> TYPE: DNA
<213> ORGANISM: Artificial Sequence
<220> FEATURE:
<223> OTHER INFORMATION: primer

<400> SEQUENCE: 185
cattgaaagg ggaggagaat catgagaagc aagaagcgaa ctgtcac           47

<210> SEQ ID NO 186
<211> LENGTH: 47
<212> TYPE: DNA
<213> ORGANISM: Artificial Sequence
<220> FEATURE:
<223> OTHER INFORMATION: primer

<400> SEQUENCE: 186
gtgacagttc gcttcttgct tctcatgatt ctcctcccct ttcaatg           47

<210> SEQ ID NO 187
<211> LENGTH: 36
<212> TYPE: DNA
<213> ORGANISM: Artificial Sequence
<220> FEATURE:
<223> OTHER INFORMATION: primer

<400> SEQUENCE: 187
```
ctttaccttg tctccaagct taaaataaaa aaacgg        36

<210> SEQ ID NO 188
<211> LENGTH: 28
<212> TYPE: DNA
<213> ORGANISM: Artificial Sequence
<220> FEATURE:
<223> OTHER INFORMATION: primer

<400> SEQUENCE: 188
gcgcaggatg tagcagctgg acttgtgg        28

<210> SEQ ID NO 189
<211> LENGTH: 28
<212> TYPE: DNA
<213> ORGANISM: Artificial Sequence
<220> FEATURE:
<223> OTHER INFORMATION: primer

<400> SEQUENCE: 189
ccacaagtcc agctgctaca tcctgcgc        28

<210> SEQ ID NO 190
<211> LENGTH: 42
<212> TYPE: DNA
<213> ORGANISM: Artificial Sequence
<220> FEATURE:
<223> OTHER INFORMATION: primer

<400> SEQUENCE: 190
gcctcattct gcagcttcag caaacgaacc ggctcctcca gg        42

<210> SEQ ID NO 191
<211> LENGTH: 45
<212> TYPE: DNA
<213> ORGANISM: Artificial Sequence
<220> FEATURE:
<223> OTHER INFORMATION: primer

<400> SEQUENCE: 191
cgtcctctgt taactcagtc gtcacttcca gagtcagtcg taatc        45

<210> SEQ ID NO 192
<211> LENGTH: 39
<212> TYPE: DNA
<213> ORGANISM: Artificial Sequence
<220> FEATURE:
<223> OTHER INFORMATION: primer

<400> SEQUENCE: 192
atcctactcg aggcttttct tttggaagaa aatatagggg        39

<210> SEQ ID NO 193
<211> LENGTH: 35
<212> TYPE: DNA
<213> ORGANISM: Artificial Sequence
<220> FEATURE:
<223> OTHER INFORMATION: primer

<400> SEQUENCE: 193
tggaatctcg aggttttatc ctttaccttg tctcc        35

<210> SEQ ID NO 194
<211> LENGTH: 136
<212> TYPE: DNA
<213> ORGANISM: Artificial Sequence

```
<220> FEATURE:
<223> OTHER INFORMATION: primer

<400> SEQUENCE: 194 accccoctcg aggctttct tttggaagaa aatatagggg aaatggtact tgttaaaaat     60
tcggaatatt tatacaatat catatgtttc acattgaaag gggaggagaa tcatgaaaca    120
acaaaaacgg ctttac                                                   136

<210> SEQ ID NO 195
<211> LENGTH: 118
<212> TYPE: DNA
<213> ORGANISM: Artificial Sequence
<220> FEATURE:
<223> OTHER INFORMATION: primer

<400> SEQUENCE: 195
gtcgacctcg aggttttatc ctttaccttg tctccaagct taaaataaaa aaacggattt     60
ccttcaggaa atccgtcctc tgttaactca agggggaactt ccagagtcag tcgtaatc     118

<210> SEQ ID NO 196
<211> LENGTH: 135
<212> TYPE: DNA
<213> ORGANISM: Artificial Sequence
<220> FEATURE:
<223> OTHER INFORMATION: primer

<400> SEQUENCE: 196 accccoctcg aggctttct tttggaagaa aatatagggg aaatggtact tgttaaaaat     60
tcggaatatt tatacaatat catatgtttc acattgaaag gggaggagaa tcatgacacc    120
acgaactgtc acaag                                                    135

<210> SEQ ID NO 197
<211> LENGTH: 34
<212> TYPE: DNA
<213> ORGANISM: Artificial Sequence
<220> FEATURE:
<223> OTHER INFORMATION: primer

<400> SEQUENCE: 197
attagtctcg aggatcgacc ggaccgcaac ctcc                                34

<210> SEQ ID NO 198
<211> LENGTH: 55
<212> TYPE: DNA
<213> ORGANISM: Artificial Sequence
<220> FEATURE:
<223> OTHER INFORMATION: primer

<400> SEQUENCE: 198
cgatggcatt cagcgattcc gcttctgcta acgaaccggc tcctccagga tctgc          55

<210> SEQ ID NO 199
<211> LENGTH: 55
<212> TYPE: DNA
<213> ORGANISM: Artificial Sequence
<220> FEATURE:
<223> OTHER INFORMATION: primer

<400> SEQUENCE: 199
gcagatcctg gaggagccgg ttcgttagca gaagcggaat cgctgaatgc catcg           55

<210> SEQ ID NO 200
<211> LENGTH: 45
```

```
<212> TYPE: DNA
<213> ORGANISM: Artificial Sequence
<220> FEATURE:
<223> OTHER INFORMATION: primer

<400> SEQUENCE: 200
actagtaagc ggatgaacga gcccgcacca cccgggagcg cgagc          45

<210> SEQ ID NO 201
<211> LENGTH: 42
<212> TYPE: DNA
<213> ORGANISM: Artificial Sequence
<220> FEATURE:
<223> OTHER INFORMATION: primer

<400> SEQUENCE: 201
ggcgcgcctt aggggagggt gagccccatg gtgtaggcac cg             42

<210> SEQ ID NO 202
<211> LENGTH: 45
<212> TYPE: DNA
<213> ORGANISM: Artificial Sequence
<220> FEATURE:
<223> OTHER INFORMATION: primer

<400> SEQUENCE: 202
actagtaagc ggatgaacga gcccgcacca cccgggagcg cgagc          45

<210> SEQ ID NO 203
<211> LENGTH: 40
<212> TYPE: DNA
<213> ORGANISM: Artificial Sequence
<220> FEATURE:
<223> OTHER INFORMATION: primer

<400> SEQUENCE: 203
ggcgcgcctt acgggctgct gcccgagtcc gtggtgatca                40

<210> SEQ ID NO 204
<211> LENGTH: 47
<212> TYPE: DNA
<213> ORGANISM: Artificial Sequence
<220> FEATURE:
<223> OTHER INFORMATION: primer

<400> SEQUENCE: 204
actagtaagc ggatgttcga cgtgatcggc ggcaacgcct acaccat        47

<210> SEQ ID NO 205
<211> LENGTH: 40
<212> TYPE: DNA
<213> ORGANISM: Artificial Sequence
<220> FEATURE:
<223> OTHER INFORMATION: primer

<400> SEQUENCE: 205
ggcgcgcctt acgggctgct gcccgagtcc gtggtgatca                40

<210> SEQ ID NO 206
<211> LENGTH: 30
<212> TYPE: DNA
<213> ORGANISM: Artificial Sequence
<220> FEATURE:
<223> OTHER INFORMATION: primer

<400> SEQUENCE: 206
atgacaccac gaactgtcac aagagctctg                           30
```

<210> SEQ ID NO 207
<211> LENGTH: 30
<212> TYPE: DNA
<213> ORGANISM: Artificial Sequence
<220> FEATURE:
<223> OTHER INFORMATION: primer

<400> SEQUENCE: 207
aacgaaccgg ctcctccagg atctgcatca                                        30

<210> SEQ ID NO 208
<211> LENGTH: 39
<212> TYPE: DNA
<213> ORGANISM: Artificial Sequence
<220> FEATURE:
<223> OTHER INFORMATION: primer

<400> SEQUENCE: 208
aggggaactt ccagagtcag tcgtaatcat tctcaggcc                              39

<210> SEQ ID NO 209
<211> LENGTH: 33
<212> TYPE: DNA
<213> ORGANISM: Artificial Sequence
<220> FEATURE:
<223> OTHER INFORMATION: primer

<400> SEQUENCE: 209
ggggagggtg agtcccattg tgtaagctcc tga                                    33

<210> SEQ ID NO 210
<211> LENGTH: 66
<212> TYPE: DNA
<213> ORGANISM: Artificial Sequence
<220> FEATURE:
<223> OTHER INFORMATION: primer

<400> SEQUENCE: 210
accgcgactg ctagcaacgt catctccaag cgcggcggtg gcaacgaacc ggctcctcca       60
ggatct                                                                  66

<210> SEQ ID NO 211
<211> LENGTH: 66
<212> TYPE: DNA
<213> ORGANISM: Artificial Sequence
<220> FEATURE:
<223> OTHER INFORMATION: primer

<400> SEQUENCE: 211
accgcgactg ctagcaacgt catctccaag cgcggcggtg gcaacgaacc ggctcctcca       60
ggatct                                                                  66

<210> SEQ ID NO 212
<211> LENGTH: 54
<212> TYPE: DNA
<213> ORGANISM: Artificial Sequence
<220> FEATURE:
<223> OTHER INFORMATION: primer

<400> SEQUENCE: 212
ccgccaggtg tcggtcacct aaggggaact tccagagtca gtcgtaatca ttct             54

<210> SEQ ID NO 213
<211> LENGTH: 90

-continued

```
<212> TYPE: DNA
<213> ORGANISM: Artificial Sequence
<220> FEATURE:
<223> OTHER INFORMATION: synthetic

<400> SEQUENCE: 213
atgagaagca agaagcgaac tgtcacaaga gctctggctg tggcaacagc agctgctaca      60
ctcttggctg ggggtatggc agcacaagct                                       90

<210> SEQ ID NO 214
<211> LENGTH: 389
<212> TYPE: PRT
<213> ORGANISM: Cellulomonas strain 69B4

<400> SEQUENCE: 214
```

Met Arg Ser Lys Lys Arg Thr Val Thr Arg Ala Leu Ala Val Ala Thr
1               5                   10                  15

Ala Ala Ala Thr Leu Leu Ala Gly Gly Met Ala Gln Ala Asn Glu
            20                  25                  30

Pro Ala Pro Pro Gly Ser Ala Ser Ala Pro Pro Arg Leu Ala Glu Lys
        35                  40                  45

Leu Asp Pro Asp Leu Leu Glu Ala Met Glu Arg Asp Leu Gly Leu Asp
    50                  55                  60

Ala Glu Glu Ala Ala Thr Leu Ala Phe Gln His Asp Ala Ala Glu
65                  70                  75                  80

Thr Gly Glu Ala Leu Ala Glu Glu Leu Asp Glu Asp Phe Ala Gly Thr
                85                  90                  95

Trp Val Glu Asp Asp Val Leu Tyr Val Ala Thr Thr Asp Glu Asp Ala
            100                 105                 110

Val Glu Glu Val Glu Gly Glu Gly Ala Thr Ala Val Thr Val Glu His
        115                 120                 125

Ser Leu Ala Asp Leu Glu Ala Trp Lys Thr Val Leu Asp Ala Ala Leu
    130                 135                 140

Glu Gly His Asp Asp Val Pro Thr Trp Tyr Val Asp Val Pro Thr Asn
145                 150                 155                 160

Ser Val Val Val Ala Val Lys Ala Gly Ala Gln Asp Val Ala Ala Gly
                165                 170                 175

Leu Val Glu Gly Ala Asp Val Pro Ser Asp Ala Val Thr Phe Val Glu
            180                 185                 190

Thr Asp Glu Thr Pro Arg Thr Met Phe Asp Val Ile Gly Gly Asn Ala
        195                 200                 205

Tyr Thr Ile Gly Gly Arg Ser Arg Cys Ser Ile Gly Phe Ala Val Asn
    210                 215                 220

Gly Gly Phe Ile Thr Ala Gly His Cys Gly Arg Thr Gly Ala Thr Thr
225                 230                 235                 240

Ala Asn Pro Thr Gly Thr Phe Ala Gly Ser Ser Phe Pro Gly Asn Asp
                245                 250                 255

Tyr Ala Phe Val Arg Thr Gly Ala Gly Val Asn Leu Leu Ala Gln Val
            260                 265                 270

Asn Asn Tyr Ser Gly Gly Arg Val Gln Val Ala Gly His Thr Ala Ala
        275                 280                 285

Pro Val Gly Ser Ala Val Cys Arg Ser Gly Ser Thr Thr Gly Trp His
    290                 295                 300

Cys Gly Thr Ile Thr Ala Leu Asn Ser Ser Val Thr Tyr Pro Glu Gly
305                 310                 315                 320

Thr Val Arg Gly Leu Ile Arg Thr Thr Val Cys Ala Glu Pro Gly Asp

```
                    325                 330                 335
Ser Gly Gly Ser Leu Leu Ala Gly Asn Gln Ala Gln Gly Val Thr Ser
            340                 345                 350

Gly Gly Ser Gly Asn Cys Arg Thr Gly Gly Thr Thr Phe Phe Gln Pro
        355                 360                 365

Val Asn Pro Ile Leu Gln Ala Tyr Gly Leu Arg Met Ile Thr Thr Asp
    370                 375                 380

Ser Gly Ser Ser Pro
385

<210> SEQ ID NO 215
<211> LENGTH: 29
<212> TYPE: DNA
<213> ORGANISM: Artificial Sequence
<220> FEATURE:
<223> OTHER INFORMATION: primer

<400> SEQUENCE: 215
gcaatcagat cttccttcag gttatgacc                                        29

<210> SEQ ID NO 216
<211> LENGTH: 30
<212> TYPE: DNA
<213> ORGANISM: Artificial Sequence
<220> FEATURE:
<223> OTHER INFORMATION: primer

<400> SEQUENCE: 216
gcatcgaaga tctgattgct taactgcttc                                       30

<210> SEQ ID NO 217
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 217
gaaacgccta gaacgatgnn sgacgtaatt ggaggcaac                             39

<210> SEQ ID NO 218
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 218
acgcctagaa cgatgttcnn sgtaattgga ggcaacgca                             39

<210> SEQ ID NO 219
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
```

<223> OTHER INFORMATION: n is a, c, g, or t

<400> SEQUENCE: 219
cctagaacga tgttcgacnn sattggaggc aacgcatat                              39

<210> SEQ ID NO 220
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 220
agaacgatgt tcgacgtann sggaggcaac gcatatact                              39

<210> SEQ ID NO 221
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 221
acgatgttcg acgtaattnn sggcaacgca tatactatt                              39

<210> SEQ ID NO 222
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 222
atgttcgacg taattggann saacgcatat actattggc                              39

<210> SEQ ID NO 223
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 223
ttcgacgtaa ttggaggcnn sgcatatact attggcggc                              39

<210> SEQ ID NO 224
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 224
gacgtaattg gaggcaacnn statactatt ggcggccgg                                39

<210> SEQ ID NO 225
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 225
gtaattggag gcaacgcann sactattggc ggccggtct                                39

<210> SEQ ID NO 226
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 226
attggaggca acgcatatnn sattggcggc cggtctaga                                39

<210> SEQ ID NO 227
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 227
ggaggcaacg catatactnn sggcggccgg tctagatgt                                39

<210> SEQ ID NO 228
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 228
ggcaacgcat atactattnn sggccggtct agatgttct                                39

<210> SEQ ID NO 229
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 229
aacgcatata ctattggcnn scggtctaga tgttctatc                                    39

<210> SEQ ID NO 230
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 230
gcatatacta ttggcggcnn stctagatgt tctatcgga                                    39

<210> SEQ ID NO 231
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 231
tatactattg gcggccggnn sagatgttct atcggattc                                    39

<210> SEQ ID NO 232
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 232
actattggcg gccggtctnn stgttctatc ggattcgca                                    39

<210> SEQ ID NO 233
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 233
attggcggcc ggtctagann stctatcgga ttcgcagta                                    39

<210> SEQ ID NO 234
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 234
ggcggccggt ctagatgtnn satcggattc gcagtaaac                               39

<210> SEQ ID NO 235
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 235
ggccggtcta gatgttctnn sggattcgca gtaaacggt                               39

<210> SEQ ID NO 236
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 236
cggtctagat gttctatcnn sttcgcagta aacggtggc                               39

<210> SEQ ID NO 237
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 237
tctagatgtt ctatcggann sgcagtaaac ggtggcttc                               39

<210> SEQ ID NO 238
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 238
agatgttcta tcggattcnn sgtaaacggt ggcttcatt                               39

<210> SEQ ID NO 239
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 239
tgttctatcg gattcgcann saacggtggc ttcattact                              39

<210> SEQ ID NO 240
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 240
tctatcggat tcgcagtann sggtggcttc attactgcc                              39

<210> SEQ ID NO 241
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 241
atcggattcg cagtaaacnn sggcttcatt actgccggt                              39

<210> SEQ ID NO 242
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 242
ggattcgcag taaacggtnn sttcattact gccggtcac                              39

<210> SEQ ID NO 243
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 243
ttcgcagtaa acggtggcnn sattactgcc ggtcactgc                              39

<210> SEQ ID NO 244
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 244
gcagtaaacg gtggcttcnn sactgccggt cactgcgga                                    39

<210> SEQ ID NO 245
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 245
gtaaacggtg gcttcattnn sgccggtcac tgcggaaga                                    39

<210> SEQ ID NO 246
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 246
aacggtggct tcattactnn sggtcactgc ggaagaaca                                    39

<210> SEQ ID NO 247
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 247
ggtggcttca ttactgccnn scactgcgga agaacagga                                    39

<210> SEQ ID NO 248
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 248
ggcttcatta ctgccggtnn stgcggaaga acaggagcc                                    39

<210> SEQ ID NO 249
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 249
ttcattactg ccggtcacnn sggaagaaca ggagccact                                39

<210> SEQ ID NO 250
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 250
attactgccg gtcactgcnn sagaacagga gccactact                                39

<210> SEQ ID NO 251
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 251
actgccggtc actgcggann sacaggagcc actactgcc                                39

<210> SEQ ID NO 252
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 252
gccggtcact gcggaagann sggagccact actgccaat                                39

<210> SEQ ID NO 253
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 253
ggtcactgcg gaagaacann sgccactact gccaatccg                                39

<210> SEQ ID NO 254
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 254
cactgcggaa gaacaggann sactactgcc aatccgact                     39

<210> SEQ ID NO 255
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 255
tgcggaagaa caggagccnn sactgccaat ccgactggc                     39

<210> SEQ ID NO 256
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 256
ggaagaacag gagccactnn sgccaatccg actggcaca                     39

<210> SEQ ID NO 257
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 257
agaacaggag ccactactnn saatccgact ggcacattt                     39

<210> SEQ ID NO 258
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 258
acaggagcca ctactgccnn sccgactggc acatttgca                     39

<210> SEQ ID NO 259
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 259
ggagccacta ctgccaatnn sactggcaca tttgcaggt                              39

<210> SEQ ID NO 260
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 260
gccactactg ccaatccgnn sggcacattt gcaggtagc                              39

<210> SEQ ID NO 261
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 261
actactgcca atccgactnn sacatttgca ggtagctcg                              39

<210> SEQ ID NO 262
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 262
actgccaatc cgactggcnn stttgcaggt agctcgttt                              39

<210> SEQ ID NO 263
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 263
gccaatccga ctggcacann sgcaggtagc tcgtttccg                              39

<210> SEQ ID NO 264
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 264
aatccgactg gcacatttnn sggtagctcg tttccggga                                   39

<210> SEQ ID NO 265
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 265
ccgactggca catttgcann sagctcgttt ccgggaaat                                   39

<210> SEQ ID NO 266
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 266
actggcacat ttgcaggtnn stcgtttccg ggaaatgat                                   39

<210> SEQ ID NO 267
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 267
ggcacatttg caggtagcnn stttccggga aatgattat                                   39

<210> SEQ ID NO 268
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 268
acatttgcag gtagctcgnn sccgggaaat gattatgca                                   39

<210> SEQ ID NO 269
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

```
<223> OTHER INFORMATION: n is a, c, g, or t

<400> SEQUENCE: 269
tttgcaggta gctcgtttnn sggaaatgat tatgcattc                              39

<210> SEQ ID NO 270
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 270
gcaggtagct cgtttccgnn saatgattat gcattcgtc                              39

<210> SEQ ID NO 271
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 271
ggtagctcgt ttccgggann sgattatgca ttcgtccga                              39

<210> SEQ ID NO 272
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 272
agctcgtttc cgggaaatnn statgcattc gtccgaaca                              39

<210> SEQ ID NO 273
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 273
tcgtttccgg gaaatgatnn sgcattcgtc cgaacaggg                              39

<210> SEQ ID NO 274
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
```

<223> OTHER INFORMATION: n is a, c, g, or t

<400> SEQUENCE: 274
tttccgggaa atgattatnn sttcgtccga acaggggca                    39

<210> SEQ ID NO 275
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 275
ccgggaaatg attatgcann sgtccgaaca ggggcagga                    39

<210> SEQ ID NO 276
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 276
ggaaatgatt atgcattcnn scgaacaggg gcaggagta                    39

<210> SEQ ID NO 277
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 277
aatgattatg cattcgtcnn sacaggggca ggagtaaat                    39

<210> SEQ ID NO 278
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 278
gattatgcat tcgtccgann sggggcagga gtaaatttg                    39

<210> SEQ ID NO 279
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 279
tatgcattcg tccgaacann sgcaggagta aatttgctt                                    39

<210> SEQ ID NO 280
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 280
gcattcgtcc gaacagggnn sggagtaaat ttgcttgcc                                    39

<210> SEQ ID NO 281
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 281
ttcgtccgaa caggggcann sgtaaatttg cttgcccaa                                    39

<210> SEQ ID NO 282
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 282
gtccgaacag gggcaggann saatttgctt gcccaagtc                                    39

<210> SEQ ID NO 283
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 283
cgaacagggg caggagtann sttgcttgcc caagtcaat                                    39

<210> SEQ ID NO 284
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 284 acagggcag gagtaaatnn scttgcccaa gtcaataac                    39

<210> SEQ ID NO 285
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 285
ggggcaggag taaatttgnn sgcccaagtc aataactac                    39

<210> SEQ ID NO 286
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 286
gcaggagtaa atttgcttnn scaagtcaat aactactcg                    39

<210> SEQ ID NO 287
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 287
ggagtaaatt tgcttgccnn sgtcaataac tactcgggc                    39

<210> SEQ ID NO 288
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 288
gtaaatttgc ttgcccaann saataactac tcgggcggc                    39

<210> SEQ ID NO 289
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 289
aatttgcttg cccaagtcnn saactactcg ggcggcaga                    39

<210> SEQ ID NO 290
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 290
ttgcttgccc aagtcaatnn stactcgggc ggcagagtc                    39

<210> SEQ ID NO 291
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 291
cttgcccaag tcaataacnn stcgggcggc agagtccaa                    39

<210> SEQ ID NO 292
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 292
gcccaagtca ataactacnn sggcggcaga gtccaagta                    39

<210> SEQ ID NO 293
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 293
caagtcaata actactcgnn sggcagagtc caagtagca                    39

<210> SEQ ID NO 294
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

```
<223> OTHER INFORMATION: n is a, c, g, or t

<400> SEQUENCE: 294
gtcaataact actcgggcnn sagagtccaa gtagcagga                          39

<210> SEQ ID NO 295
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 295
aataactact cgggcggcnn sgtccaagta gcaggacat                          39

<210> SEQ ID NO 296
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 296
aactactcgg gcggcagann scaagtagca ggacatacg                          39

<210> SEQ ID NO 297
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 297
tactcgggcg gcagagtcnn sgtagcagga catacggcc                          39

<210> SEQ ID NO 298
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 298
tcgggcggca gagtccaann sgcaggacat acggccgca                          39

<210> SEQ ID NO 299
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
```

-continued

<223> OTHER INFORMATION: n is a, c, g, or t

<400> SEQUENCE: 299
ggcggcagag tccaagtann sggacatacg gccgcacca                39

<210> SEQ ID NO 300
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 300
ggcagagtcc aagtagcann scatacggcc gcaccagtt                39

<210> SEQ ID NO 301
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 301
agagtccaag tagcaggann sacggccgca ccagttgga                39

<210> SEQ ID NO 302
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 302
gtccaagtag caggacatnn sgccgcacca gttggatct                39

<210> SEQ ID NO 303
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 303
caagtagcag gacatacgnn sgcaccagtt ggatctgct                39

<210> SEQ ID NO 304
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 304
gtagcaggac atacggccnn sccagttgga tctgctgta                                    39

<210> SEQ ID NO 305
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 305
gcaggacata cggccgcann sgttggatct gctgtatgc                                    39

<210> SEQ ID NO 306
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 306
ggacatacgg ccgcaccann sggatctgct gtatgccgc                                    39

<210> SEQ ID NO 307
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 307
catacggccg caccagttnn stctgctgta tgccgctca                                    39

<210> SEQ ID NO 308
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 308
acggccgcac cagttggann sgctgtatgc cgctcaggt                                    39

<210> SEQ ID NO 309
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 309
gccgcaccag ttggatctnn sgtatgccgc tcaggtagc                                      39

<210> SEQ ID NO 310
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 310
gcaccagttg gatctgctnn stgccgctca ggtagcact                                      39

<210> SEQ ID NO 311
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 311
ccagttggat ctgctgtann scgctcaggt agcactaca                                      39

<210> SEQ ID NO 312
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 312
gttggatctg ctgtatgcnn stcaggtagc actacaggt                                      39

<210> SEQ ID NO 313
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 313
ggatctgctg tatgccgcnn sggtagcact acaggttgg                                      39

<210> SEQ ID NO 314
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 314
tctgctgtat gccgctcann sagcactaca ggttggcat                                39

<210> SEQ ID NO 315
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 315
gctgtatgcc gctcaggtnn sactacaggt tggcattgc                                39

<210> SEQ ID NO 316
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 316
gtatgccgct caggtagcnn sacaggttgg cattgcgga                                39

<210> SEQ ID NO 317
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 317
tgccgctcag gtagcactnn sggttggcat tgcggaact                                39

<210> SEQ ID NO 318
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 318
cgctcaggta gcactacann stggcattgc ggaactatc                                39

<210> SEQ ID NO 319
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 319
tcaggtagca ctacaggtnn scattgcgga actatcacg     39

<210> SEQ ID NO 320
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 320
ggtagcacta caggttggnn stgcggaact atcacggcg     39

<210> SEQ ID NO 321
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 321
agcactacag gttggcatnn sggaactatc acggcgctg     39

<210> SEQ ID NO 322
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 322
actacaggtt ggcattgcnn sactatcacg gcgctgaat     39

<210> SEQ ID NO 323
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 323
acaggttggc attgcggann satcacggcg ctgaattcg     39

<210> SEQ ID NO 324
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 324
ggttggcatt gcggaactnn sacggcgctg aattcgtct       39

<210> SEQ ID NO 325
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 325
tggcattgcg gaactatcnn sgcgctgaat tcgtctgtc       39

<210> SEQ ID NO 326
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 326
cattgcggaa ctatcacgnn sctgaattcg tctgtcacg       39

<210> SEQ ID NO 327
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 327
tgcggaacta tcacggcgnn saattcgtct gtcacgtat       39

<210> SEQ ID NO 328
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 328
ggaactatca cggcgctgnn stcgtctgtc acgtatcca       39

<210> SEQ ID NO 329
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 329
actatcacgg cgctgaatnn stctgtcacg tatccagag        39

<210> SEQ ID NO 330
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 330
atcacggcgc tgaattcgnn sgtcacgtat ccagaggga        39

<210> SEQ ID NO 331
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 331
acggcgctga attcgtctnn sacgtatcca gagggaaca        39

<210> SEQ ID NO 332
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 332
gcgctgaatt cgtctgtcnn statccagag ggaacagtc        39

<210> SEQ ID NO 333
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 333
ctgaattcgt ctgtcacgnn sccagaggga acagtccga        39

<210> SEQ ID NO 334
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 334
aattcgtctg tcacgtatnn sgagggaaca gtccgagga                                39

<210> SEQ ID NO 335
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 335
tcgtctgtca cgtatccann sggaacagtc cgaggactt                                39

<210> SEQ ID NO 336
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 336
tctgtcacgt atccagagnn sacagtccga ggacttatc                                39

<210> SEQ ID NO 337
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 337
gtcacgtatc cagagggann sgtccgagga cttatccgc                                39

<210> SEQ ID NO 338
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 338
acgtatccag agggaacann scgaggactt atccgcacg                                39

<210> SEQ ID NO 339
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 339
tatccagagg gaacagtcnn sggacttatc cgcacgacg                                39

<210> SEQ ID NO 340
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 340
ccagagggaa cagtccgann scttatccgc acgacggtt                                39

<210> SEQ ID NO 341
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 341
gagggaacag tccgaggann satccgcacg acggtttgt                                39

<210> SEQ ID NO 342
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 342
ggaacagtcc gaggacttnn scgcacgacg gtttgtgcc                                39

<210> SEQ ID NO 343
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 343
acagtccgag gacttatcnn sacgacggtt tgtgccgaa                                39

<210> SEQ ID NO 344
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 344
gtccgaggac ttatccgcnn sacggtttgt gccgaacca     39

<210> SEQ ID NO 345
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 345
cgaggactta tccgcacgnn sgtttgtgcc gaaccaggt     39

<210> SEQ ID NO 346
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 346
ggacttatcc gcacgacgnn stgtgccgaa ccaggtgat     39

<210> SEQ ID NO 347
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 347
cttatccgca cgacggttnn sgccgaacca ggtgatagc     39

<210> SEQ ID NO 348
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 348
atccgcacga cggtttgtnn sgaaccaggt gatagcgga     39

<210> SEQ ID NO 349
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 349
cgcacgacgg tttgtgccnn sccaggtgat agcggaggt                               39

<210> SEQ ID NO 350
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 350
acgacggttt gtgccgaann sggtgatagc ggaggtagc                               39

<210> SEQ ID NO 351
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 351
acggtttgtg ccgaaccann sgatagcgga ggtagcctt                               39

<210> SEQ ID NO 352
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 352
gtttgtgccg aaccaggtnn sagcggaggt agccttta                                39

<210> SEQ ID NO 353
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 353
tgtgccgaac caggtgatnn sggaggtagc cttttagcg                               39

<210> SEQ ID NO 354
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 354
gccgaaccag gtgatagcnn sggtagcctt ttagcggga                          39

<210> SEQ ID NO 355
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 355
gaaccaggtg atagcggann sagcctttta gcgggaaat                          39

<210> SEQ ID NO 356
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 356
ccaggtgata gcggaggtnn sctttagcg ggaaatcaa                           39

<210> SEQ ID NO 357
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 357
ggtgatagcg gaggtagcnn sttagcggga aatcaagcc                          39

<210> SEQ ID NO 358
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 358
gatagcggag gtagccttnn sgcgggaaat caagcccaa                          39

<210> SEQ ID NO 359
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 359
agcggaggta gccttttann sggaaatcaa gcccaaggt          39

<210> SEQ ID NO 360
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 360
ggaggtagcc ttttagcgnn saatcaagcc caaggtgtc          39

<210> SEQ ID NO 361
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 361
ggtagccttt tagcgggann scaagcccaa ggtgtcacg          39

<210> SEQ ID NO 362
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 362
agccttttag cgggaaatnn sgcccaaggt gtcacgtca          39

<210> SEQ ID NO 363
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 363
cttttagcgg gaaatcaann scaaggtgtc acgtcaggt          39

<210> SEQ ID NO 364
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 364
ttagcgggaa atcaagccnn sggtgtcacg tcaggtggt                                39

<210> SEQ ID NO 365
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 365
gcgggaaatc aagcccaann sgtcacgtca ggtggttct                                39

<210> SEQ ID NO 366
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 366
ggaaatcaag cccaaggtnn sacgtcaggt ggttctgga                                39

<210> SEQ ID NO 367
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 367
aatcaagccc aaggtgtcnn stcaggtggt tctggaaat                                39

<210> SEQ ID NO 368
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 368
caagcccaag gtgtcacgnn sggtggttct ggaaattgt                                39

<210> SEQ ID NO 369
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 369
gcccaaggtg tcacgtcann sggttctgga aattgtcgg                              39

<210> SEQ ID NO 370
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 370
caaggtgtca cgtcaggtnn stctggaaat tgtcggacg                              39

<210> SEQ ID NO 371
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 371
ggtgtcacgt caggtggtnn sggaaattgt cggacgggg                              39

<210> SEQ ID NO 372
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 372
gtcacgtcag gtggttctnn saattgtcgg acgggggga                              39

<210> SEQ ID NO 373
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 373
acgtcaggtg gttctggann stgtcggacg gggggaaca                              39

<210> SEQ ID NO 374
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 374
tcaggtggtt ctggaaatnn scggacgggg ggaacaaca          39

<210> SEQ ID NO 375
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 375
ggtggttctg gaaattgtnn sacgggggga acaacattc          39

<210> SEQ ID NO 376
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 376
ggttctggaa attgtcggnn sggggggaaca acattcttt         39

<210> SEQ ID NO 377
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 377
tctggaaatt gtcggacgnn sggaacaaca ttctttcaa          39

<210> SEQ ID NO 378
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 378
ggaaattgtc ggacggggnn sacaacattc tttcaacca          39

<210> SEQ ID NO 379
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

```
<223> OTHER INFORMATION: n is a, c, g, or t

<400> SEQUENCE: 379
aattgtcgga cgggggganm sacattcttt caaccagtc                     39

<210> SEQ ID NO 380
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 380
tgtcggacgg gggaacann sttctttcaa ccagtcaac                      39

<210> SEQ ID NO 381
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 381
cggacggggg gaacaacann stttcaacca gtcaacccg                     39

<210> SEQ ID NO 382
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 382 acgggggaa caacattcnn scaaccagtc aacccgatt                      39

<210> SEQ ID NO 383
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 383 ggggaacaa cattctttnn sccagtcaac ccgattttg                      39

<210> SEQ ID NO 384
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
```

<223> OTHER INFORMATION: n is a, c, g, or t

<400> SEQUENCE: 384
ggaacaacat tctttcaann sgtcaacccg attttgcag             39

<210> SEQ ID NO 385
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 385
acaacattct ttcaaccann saacccgatt ttgcaggct             39

<210> SEQ ID NO 386
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 386
acattctttc aaccagtcnn sccgattttg caggcttac             39

<210> SEQ ID NO 387
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 387
ttctttcaac cagtcaacnn sattttgcag gcttacggc             39

<210> SEQ ID NO 388
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 388
tttcaaccag tcaacccgnn sttgcaggct tacggcctg             39

<210> SEQ ID NO 389
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

```
<223> OTHER INFORMATION: n is a, c, g, or t

<400> SEQUENCE: 389
caaccagtca acccgattnn scaggcttac ggcctgaga                                39

<210> SEQ ID NO 390
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 390
ccagtcaacc cgattttgnn sgcttacggc ctgagaatg                                39

<210> SEQ ID NO 391
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 391
gtcaacccga ttttgcagnn stacggcctg agaatgatt                                39

<210> SEQ ID NO 392
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 392
aacccgattt tgcaggctnn sggcctgaga atgattacg                                39

<210> SEQ ID NO 393
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 393
ccgattttgc aggcttacnn sctgagaatg attacgact                                39

<210> SEQ ID NO 394
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
```

<223> OTHER INFORMATION: n is a, c, g, or t

<400> SEQUENCE: 394
attttgcagg cttacggcnn sagaatgatt acgactgac                                  39

<210> SEQ ID NO 395
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 395
ttgcaggctt acggcctgnn satgattacg actgactct                                  39

<210> SEQ ID NO 396
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 396
caggcttacg gcctgagann sattacgact gactctgga                                  39

<210> SEQ ID NO 397
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 397
gcttacggcc tgagaatgnn sacgactgac tctggaagt                                  39

<210> SEQ ID NO 398
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 398
tacggcctga gaatgattnn sactgactct ggaagttcc                                  39

<210> SEQ ID NO 399
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 399
ggcctgagaa tgattacgnn sgactctgga agttcccct					39

<210> SEQ ID NO 400
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 400
ctgagaatga ttacgactnn stctggaagt tcccctta					39

<210> SEQ ID NO 401
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 401
agaatgatta cgactgacnn sggaagttcc ccttaaccc					39

<210> SEQ ID NO 402
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 402
atgattacga ctgactctnn sagttcccct taacccaac					39

<210> SEQ ID NO 403
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 403
attacgactg actctggann stcccttaa cccaacaga					39

<210> SEQ ID NO 404
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

-continued

<223> OTHER INFORMATION: n is a, c, g, or t

<400> SEQUENCE: 404
acgactgact ctggaagtnn sccttaaccc aacagagga                          39

<210> SEQ ID NO 405
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 405
actgactctg gaagttccnn staacccaac agaggacgg                          39

<210> SEQ ID NO 406
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 406
gttgcctcca attacgtcsn ncatcgttct aggcgtttc                          39

<210> SEQ ID NO 407
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 407
tgcgttgcct ccaattacsn ngaacatcgt tctaggcgt                          39

<210> SEQ ID NO 408
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 408
atatgcgttg cctccaatsn ngtcgaacat cgttctagg                          39

<210> SEQ ID NO 409
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 409
agtatatgcg ttgcctccsn ntacgtcgaa catcgttct        39

<210> SEQ ID NO 410
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 410
aatagtatat gcgttgccsn naattacgtc gaacatcgt        39

<210> SEQ ID NO 411
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 411
gccaatagta tatgcgttsn ntccaattac gtcgaacat        39

<210> SEQ ID NO 412
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 412
gccgccaata gtatatgcsn ngcctccaat tacgtcgaa        39

<210> SEQ ID NO 413
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 413
ccggccgcca atagtatasn ngttgcctcc aattacgtc        39

<210> SEQ ID NO 414
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 414
agaccggccg ccaatagtsn ntgcgttgcc tccaattac					39

<210> SEQ ID NO 415
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 415
tctagaccgg ccgccaatsn natatgcgtt gcctccaat					39

<210> SEQ ID NO 416
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 416
acatctagac cggccgccsn nagtatatgc gttgcctcc					39

<210> SEQ ID NO 417
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 417
agaacatcta gaccggccsn naatagtata tgcgttgcc					39

<210> SEQ ID NO 418
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 418
gatagaacat ctagaccgsn ngccaatagt atatgcgtt					39

<210> SEQ ID NO 419
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

-continued

<223> OTHER INFORMATION: n is a, c, g, or t

<400> SEQUENCE: 419
tccgatagaa catctagasn ngccgccaat agtatatgc                              39

<210> SEQ ID NO 420
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 420
gaatccgata gaacatctsn nccggccgcc aatagtata                              39

<210> SEQ ID NO 421
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 421
tgcgaatccg atagaacasn nagaccggcc gccaatagt                              39

<210> SEQ ID NO 422
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 422
tactgcgaat ccgatagasn ntctagaccg gccgccaat                              39

<210> SEQ ID NO 423
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 423
gtttactgcg aatccgatsn nacatctaga ccggccgcc                              39

<210> SEQ ID NO 424
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 424
accgtttact gcgaatccsn nagaacatct agaccggcc					39

<210> SEQ ID NO 425
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 425
gccaccgttt actgcgaasn ngatagaaca tctagaccg					39

<210> SEQ ID NO 426
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 426
gaagccaccg tttactgcsn ntccgataga acatctaga					39

<210> SEQ ID NO 427
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 427
aatgaagcca ccgtttacsn ngaatccgat agaacatct					39

<210> SEQ ID NO 428
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 428
agtaatgaag ccaccgttsn ntgcgaatcc gatagaaca					39

<210> SEQ ID NO 429
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 429
ggcagtaatg aagccaccsn ntactgcgaa tccgataga                                39

<210> SEQ ID NO 430
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 430
accggcagta atgaagccsn ngtttactgc gaatccgat                                39

<210> SEQ ID NO 431
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 431
gtgaccggca gtaatgaasn naccgtttac tgcgaatcc                                39

<210> SEQ ID NO 432
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 432
gcagtgaccg gcagtaatsn ngccaccgtt tactgcgaa                                39

<210> SEQ ID NO 433
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 433
tccgcagtga ccggcagtsn ngaagccacc gtttactgc                                39

<210> SEQ ID NO 434
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 434
tcttccgcag tgaccggcsn naatgaagcc accgtttac                           39

<210> SEQ ID NO 435
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 435
tgttcttccg cagtgaccsn nagtaatgaa gccaccgtt                           39

<210> SEQ ID NO 436
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 436
tcctgttctt ccgcagtgsn nggcagtaat gaagccacc                           39

<210> SEQ ID NO 437
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 437
ggctcctgtt cttccgcasn naccggcagt aatgaagcc                           39

<210> SEQ ID NO 438
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 438
agtggctcct gttcttccsn ngtgaccggc agtaatgaa                           39

<210> SEQ ID NO 439
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 439
agtagtggct cctgttctsn ngcagtgacc ggcagtaat                              39

<210> SEQ ID NO 440
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 440
ggcagtagtg gctcctgtsn ntccgcagtg accggcagt                              39

<210> SEQ ID NO 441
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 441
attggcagta gtggctccsn ntcttccgca gtgaccggc                              39

<210> SEQ ID NO 442
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 442
cggattggca gtagtggcsn ntgttcttcc gcagtgacc                              39

<210> SEQ ID NO 443
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 443
agtcggattg gcagtagtsn ntcctgttct tccgcagtg                              39

<210> SEQ ID NO 444
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 444
gccagtcgga ttggcagtsn nggctcctgt tcttccgca               39

<210> SEQ ID NO 445
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 445
tgtgccagtc ggattggcsn nagtggctcc tgttcttcc               39

<210> SEQ ID NO 446
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 446
aaatgtgcca gtcggattsn nagtagtggc tcctgttct               39

<210> SEQ ID NO 447
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 447
tgcaaatgtg ccagtcggsn nggcagtagt ggctcctgt               39

<210> SEQ ID NO 448
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 448
acctgcaaat gtgccagtsn nattggcagt agtggctcc               39

<210> SEQ ID NO 449
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 449
gctacctgca aatgtgccsn ncggattggc agtagtggc    39

<210> SEQ ID NO 450
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 450
cgagctacct gcaaatgtsn nagtcggatt ggcagtagt    39

<210> SEQ ID NO 451
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 451
aaacgagcta cctgcaaasn ngccagtcgg attggcagt    39

<210> SEQ ID NO 452
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 452
cggaaacgag ctacctgcsn ntgtgccagt cggattggc    39

<210> SEQ ID NO 453
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 453
tcccggaaac gagctaccsn naaatgtgcc agtcggatt    39

<210> SEQ ID NO 454
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 454
atttcccgga aacgagctsn ntgcaaatgt gccagtcgg    39

<210> SEQ ID NO 455
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 455
atcatttccc ggaaacgasn nacctgcaaa tgtgccagt    39

<210> SEQ ID NO 456
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 456
ataatcattt cccggaaasn ngctacctgc aaatgtgcc    39

<210> SEQ ID NO 457
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 457
tgcataatca tttcccggsn ncgagctacc tgcaaatgt    39

<210> SEQ ID NO 458
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 458
gaatgcataa tcatttccsn naaacgagct acctgcaaa    39

<210> SEQ ID NO 459
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 459
gacgaatgca taatcattsn ncggaaacga gctacctgc          39

<210> SEQ ID NO 460
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 460
tcggacgaat gcataatcsn ntcccggaaa cgagctacc          39

<210> SEQ ID NO 461
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 461
tgttcggacg aatgcatasn natttcccgg aaacgagct          39

<210> SEQ ID NO 462
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 462
ccctgttcgg acgaatgcsn natcatttcc cggaaacga          39

<210> SEQ ID NO 463
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 463 tgccctgtt cggacgaasn nataatcatt tcccggaaa          39

<210> SEQ ID NO 464
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 464
tcctgcccct gttcggacsn ntgcataatc atttcccgg         39

<210> SEQ ID NO 465
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 465
tactcctgcc cctgttcgsn ngaatgcata atcatttcc         39

<210> SEQ ID NO 466
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 466
atttactcct gccctgtsn ngacgaatgc ataatcatt         39

<210> SEQ ID NO 467
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 467
caaatttact cctgccccsn ntcggacgaa tgcataatc         39

<210> SEQ ID NO 468
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 468
aagcaaattt actcctgcsn ntgttcggac gaatgcata         39

<210> SEQ ID NO 469
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 469
ggcaagcaaa tttactccsn ncctgttcg gacgaatgc                               39

<210> SEQ ID NO 470
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 470
ttgggcaagc aaatttacsn ntgccctgt tcggacgaa                               39

<210> SEQ ID NO 471
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 471
gacttgggca agcaaattsn ntcctgcccc tgttcggac                              39

<210> SEQ ID NO 472
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 472
attgacttgg gcaagcaasn ntactcctgc cctgttcg                              39

<210> SEQ ID NO 473
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 473
gttattgact tgggcaagsn natttactcc tgcccctgt                              39

<210> SEQ ID NO 474
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 474
gtagttattg acttgggcsn ncaaatttac tcctgcccc                                      39

<210> SEQ ID NO 475
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 475
cgagtagtta ttgacttgsn naagcaaatt tactcctgc                                      39

<210> SEQ ID NO 476
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 476
gcccgagtag ttattgacsn nggcaagcaa atttactcc                                      39

<210> SEQ ID NO 477
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 477
gccgcccgag tagttattsn nttgggcaag caaatttac                                      39

<210> SEQ ID NO 478
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 478
tctgccgccc gagtagttsn ngacttgggc aagcaaatt                                      39

<210> SEQ ID NO 479
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 479
gactctgccg cccgagtasn nattgacttg ggcaagcaa                39

<210> SEQ ID NO 480
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 480
ttggactctg ccgcccgasn ngttattgac ttgggcaag                39

<210> SEQ ID NO 481
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 481
tacttggact ctgccgccsn ngtagttatt gacttgggc                39

<210> SEQ ID NO 482
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 482
tgctacttgg actctgccsn ncgagtagtt attgacttg                39

<210> SEQ ID NO 483
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 483
tcctgctact tggactctsn ngcccgagta gttattgac                39

<210> SEQ ID NO 484
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 484
atgtcctgct acttggacsn ngccgcccga gtagttatt                                    39

<210> SEQ ID NO 485
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 485
cgtatgtcct gctacttgsn ntctgccgcc cgagtagtt                                    39

<210> SEQ ID NO 486
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 486
ggccgtatgt cctgctacsn ngactctgcc gcccgagta                                    39

<210> SEQ ID NO 487
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 487
tgcggccgta tgtcctgcsn nttggactct gccgcccga                                    39

<210> SEQ ID NO 488
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 488
tggtgcggcc gtatgtccsn ntacttggac tctgccgcc                                    39

<210> SEQ ID NO 489
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 489
aactggtgcg gccgtatgsn ntgctacttg gactctgcc    39

<210> SEQ ID NO 490
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 490
tccaactggt gcggccgtsn ntcctgctac ttggactct    39

<210> SEQ ID NO 491
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 491
agatccaact ggtgcggcsn natgtcctgc tacttggac    39

<210> SEQ ID NO 492
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 492
agcagatcca actggtgcsn ncgtatgtcc tgctacttg    39

<210> SEQ ID NO 493
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 493
tacagcagat ccaactggsn nggccgtatg tcctgctac    39

<210> SEQ ID NO 494
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 494
gcatacagca gatccaacsn ntgcggccgt atgtcctgc					39

<210> SEQ ID NO 495
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 495
gcggcataca gcagatccsn ntggtgcggc cgtatgtcc					39

<210> SEQ ID NO 496
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 496
tgagcggcat acagcagasn naactggtgc ggccgtatg					39

<210> SEQ ID NO 497
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 497
acctgagcgg catacagcsn ntccaactgg tgcggccgt					39

<210> SEQ ID NO 498
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 498
gctacctgag cggcatacsn nagatccaac tggtgcggc					39

<210> SEQ ID NO 499
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 499
agtgctacct gagcggcasn nagcagatcc aactggtgc                                    39

<210> SEQ ID NO 500
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 500
tgtagtgcta cctgagcgsn ntacagcaga tccaactgg                                    39

<210> SEQ ID NO 501
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 501
acctgtagtg ctacctgasn ngcatacagc agatccaac                                    39

<210> SEQ ID NO 502
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 502
ccaacctgta gtgctaccsn ngcggcatac agcagatcc                                    39

<210> SEQ ID NO 503
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 503
atgccaacct gtagtgctsn ntgagcggca tacagcaga                                    39

<210> SEQ ID NO 504
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 504
gcaatgccaa cctgtagtsn nacctgagcg gcatacagc                            39

<210> SEQ ID NO 505
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 505
tccgcaatgc caacctgtsn ngctacctga gcggcatac                            39

<210> SEQ ID NO 506
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 506
agttccgcaa tgccaaccsn nagtgctacc tgagcggca                            39

<210> SEQ ID NO 507
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 507
gatagttccg caatgccasn ntgtagtgct acctgagcg                            39

<210> SEQ ID NO 508
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 508
cgtgatagtt ccgcaatgsn nacctgtagt gctacctga                            39

<210> SEQ ID NO 509
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 509
cgccgtgata gttccgcasn nccaacctgt agtgctacc            39

<210> SEQ ID NO 510
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 510
cagcgccgtg atagttccsn natgccaacc tgtagtgct            39

<210> SEQ ID NO 511
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 511
attcagcgcc gtgatagtsn ngcaatgcca acctgtagt            39

<210> SEQ ID NO 512
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 512
cgaattcagc gccgtgatsn ntccgcaatg ccaacctgt            39

<210> SEQ ID NO 513
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 513
agacgaattc agcgccgtsn nagttccgca atgccaacc            39

<210> SEQ ID NO 514
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 514
gacagacgaa ttcagcgcsn ngatagttcc gcaatgcca    39

<210> SEQ ID NO 515
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 515
cgtgacagac gaattcagsn ncgtgatagt tccgcaatg    39

<210> SEQ ID NO 516
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 516
atacgtgaca gacgaattsn ncgccgtgat agttccgca    39

<210> SEQ ID NO 517
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 517
tggatacgtg acagacgasn ncagcgccgt gatagttcc    39

<210> SEQ ID NO 518
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 518
ctctggatac gtgacagasn nattcagcgc cgtgatagt    39

<210> SEQ ID NO 519
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 519
tccctctgga tacgtgacsn ncgaattcag cgccgtgat          39

<210> SEQ ID NO 520
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 520
tgttccctct ggatacgtsn nagacgaatt cagcgccgt          39

<210> SEQ ID NO 521
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 521
gactgttccc tctggatasn ngacagacga attcagcgc          39

<210> SEQ ID NO 522
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 522
tcggactgtt ccctctggsn ncgtgacaga cgaattcag          39

<210> SEQ ID NO 523
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 523
tcctcggact gttccctcsn natacgtgac agacgaatt          39

<210> SEQ ID NO 524
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

```
<223> OTHER INFORMATION: n is a, c, g, or t

<400> SEQUENCE: 524
aagtcctcgg actgttccsn ntggatacgt gacagacga                               39

<210> SEQ ID NO 525
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 525
gataagtcct cggactgtsn nctctggata cgtgacaga                               39

<210> SEQ ID NO 526
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 526
gcggataagt cctcggacsn ntccctctgg atacgtgac                               39

<210> SEQ ID NO 527
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 527
cgtgcggata agtcctcgsn ntgttccctc tggatacgt                               39

<210> SEQ ID NO 528
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 528
cgtcgtgcgg ataagtccsn ngactgttcc ctctggata                               39

<210> SEQ ID NO 529
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
```

<223> OTHER INFORMATION: n is a, c, g, or t

<400> SEQUENCE: 529
aaccgtcgtg cggataagsn ntcggactgt tccctctgg                                39

<210> SEQ ID NO 530
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 530
acaaaccgtc gtgcggatsn ntcctcggac tgttccctc                                39

<210> SEQ ID NO 531
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 531
ggcacaaacc gtcgtgcgsn naagtcctcg gactgttcc                                39

<210> SEQ ID NO 532
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 532
ttcggcacaa accgtcgtsn ngataagtcc tcggactgt                                39

<210> SEQ ID NO 533
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 533
tggttcggca caaaccgtsn ngcggataag tcctcggac                                39

<210> SEQ ID NO 534
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

-continued

<223> OTHER INFORMATION: n is a, c, g, or t

<400> SEQUENCE: 534
acctggttcg gcacaaacsn ncgtgcggat aagtcctcg                                  39

<210> SEQ ID NO 535
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 535
atcacctggt tcggcacasn ncgtcgtgcg gataagtcc                                  39

<210> SEQ ID NO 536
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 536
gctatcacct ggttcggcsn naaccgtcgt gcggataag                                  39

<210> SEQ ID NO 537
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 537
tccgctatca cctggttcsn nacaaaccgt cgtgcggat                                  39

<210> SEQ ID NO 538
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 538
acctccgcta tcacctggsn nggcacaaac cgtcgtgcg                                  39

<210> SEQ ID NO 539
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 539
gctacctccg ctatcaccsn nttcggcaca aaccgtcgt                        39

<210> SEQ ID NO 540
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 540
aaggctacct ccgctatcsn ntggttcggc acaaaccgt                        39

<210> SEQ ID NO 541
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 541
taaaaggcta cctccgctsn nacctggttc ggcacaaac                        39

<210> SEQ ID NO 542
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 542
cgctaaaagg ctacctccsn natcacctgg ttcggcaca                        39

<210> SEQ ID NO 543
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 543
tcccgctaaa aggctaccsn ngctatcacc tggttcggc                        39

<210> SEQ ID NO 544
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 544
atttcccgct aaaaggctsn ntccgctatc acctggttc                                  39

<210> SEQ ID NO 545
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 545
ttgatttccc gctaaaagsn nacctccgct atcacctgg                                  39

<210> SEQ ID NO 546
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 546
ggcttgattt cccgctaasn ngctacctcc gctatcacc                                  39

<210> SEQ ID NO 547
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 547
ttgggcttga tttcccgcsn naaggctacc tccgctatc                                  39

<210> SEQ ID NO 548
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 548
accttgggct tgatttccsn ntaaaggct acctccgct                                   39

<210> SEQ ID NO 549
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 549
gacaccttgg gcttgattsn ncgctaaaag gctacctcc                                  39

<210> SEQ ID NO 550
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 550
cgtgacacct tgggcttgsn ntcccgctaa aaggctacc                                  39

<210> SEQ ID NO 551
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 551
tgacgtgaca ccttgggcsn natttcccgc taaaaggct                                  39

<210> SEQ ID NO 552
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 552
acctgacgtg acaccttgsn nttgatttcc cgctaaaag                                  39

<210> SEQ ID NO 553
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 553
accacctgac gtgacaccsn nggcttgatt tcccgctaa                                  39

<210> SEQ ID NO 554
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 554
agaaccacct gacgtgacsn nttgggcttg atttcccgc                    39

<210> SEQ ID NO 555
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 555
tccagaacca cctgacgtsn naccttgggc ttgatttcc                    39

<210> SEQ ID NO 556
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 556
atttccagaa ccacctgasn ngacaccttg ggcttgatt                    39

<210> SEQ ID NO 557
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 557
acaatttcca gaaccaccsn ncgtgacacc ttgggcttg                    39

<210> SEQ ID NO 558
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 558
ccgacaattt ccagaaccsn ntgacgtgac accttgggc                    39

<210> SEQ ID NO 559
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 559
cgtccgacaa tttccagasn nacctgacgt gacaccttg                    39

<210> SEQ ID NO 560
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 560
ccccgtccga caatttccsn naccacctga cgtgacacc                    39

<210> SEQ ID NO 561
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 561 tcccccgtc cgacaattsn nagaaccacc tgacgtgac                     39

<210> SEQ ID NO 562
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 562
tgttcccccc gtccgacasn ntccagaacc acctgacgt                    39

<210> SEQ ID NO 563
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 563
tgttgttccc cccgtccgsn natttccaga accacctga                    39

<210> SEQ ID NO 564
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 564
gaatgttgtt cccccgtsn nacaatttcc agaaccacc                    39

<210> SEQ ID NO 565
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 565
aaagaatgtt gttcccccsn nccgacaatt tccagaacc                   39

<210> SEQ ID NO 566
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 566
ttgaaagaat gttgttccsn ncgtccgaca atttccaga                   39

<210> SEQ ID NO 567
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 567
tggttgaaag aatgttgtsn nccccgtccg acaatttcc                   39

<210> SEQ ID NO 568
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 568
gactggttga aagaatgtsn ntcccccgt ccgacaatt                    39

<210> SEQ ID NO 569
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 569
gttgactggt tgaaagaasn ntgttccccc cgtccgaca          39

<210> SEQ ID NO 570
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 570
cgggttgact ggttgaaasn ntgttgttcc cccgtccg          39

<210> SEQ ID NO 571
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 571
aatcgggttg actggttgsn ngaatgttgt tcccccgt          39

<210> SEQ ID NO 572
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 572
caaaatcggg ttgactggsn naaagaatgt tgttccccc          39

<210> SEQ ID NO 573
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 573
ctgcaaaatc gggttgacsn nttgaaagaa tgttgttcc          39

<210> SEQ ID NO 574
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 574
agcctgcaaa atcgggttsn ntggttgaaa gaatgttgt                              39

<210> SEQ ID NO 575
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 575
gtaagcctgc aaaatcggsn ngactggttg aaagaatgt                              39

<210> SEQ ID NO 576
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 576
gccgtaagcc tgcaaaatsn ngttgactgg ttgaaagaa                              39

<210> SEQ ID NO 577
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 577
caggccgtaa gcctgcaasn ncgggttgac tggttgaaa                              39

<210> SEQ ID NO 578
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 578
tctcaggccg taagcctgsn naatcgggtt gactggttg                              39

<210> SEQ ID NO 579
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 579
cattctcagg ccgtaagcsn ncaaaatcgg gttgactgg          39

<210> SEQ ID NO 580
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 580
aatcattctc aggccgtasn nctgcaaaat cgggttgac          39

<210> SEQ ID NO 581
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 581
cgtaatcatt ctcaggccsn nagcctgcaa aatcgggtt          39

<210> SEQ ID NO 582
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 582
agtcgtaatc attctcagsn ngtaagcctg caaaatcgg          39

<210> SEQ ID NO 583
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 583
gtcagtcgta atcattctsn ngccgtaagc ctgcaaaat          39

<210> SEQ ID NO 584
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 584
agagtcagtc gtaatcatsn ncaggccgta agcctgcaa    39

<210> SEQ ID NO 585
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 585
tccagagtca gtcgtaatsn ntctcaggcc gtaagcctg    39

<210> SEQ ID NO 586
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 586
acttccagag tcagtcgtsn ncattctcag gccgtaagc    39

<210> SEQ ID NO 587
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 587
ggaacttcca gagtcagtsn naatcattct caggccgta    39

<210> SEQ ID NO 588
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 588
aggggaactt ccagagtcsn ncgtaatcat tctcaggcc    39

<210> SEQ ID NO 589
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 589
ttaaggggaa cttccagasn nagtcgtaat cattctcag                39

<210> SEQ ID NO 590
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 590
gggttaaggg gaacttccsn ngtcagtcgt aatcattct                39

<210> SEQ ID NO 591
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 591
gttgggttaa ggggaactsn nagagtcagt cgtaatcat                39

<210> SEQ ID NO 592
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 592
tctgttgggt taaggggasn ntccagagtc agtcgtaat                39

<210> SEQ ID NO 593
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 593
tcctctgttg ggttaaggsn nacttccaga gtcagtcgt                39

<210> SEQ ID NO 594
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 594
ccgtcctctg ttgggttasn nggaacttcc agagtcagt        39

<210> SEQ ID NO 595
<211> LENGTH: 39
<212> TYPE: DNA
<213> ORGANISM: Artificial Sequence
<220> FEATURE:
<223> OTHER INFORMATION: primer

<400> SEQUENCE: 595
gcatatacta ttggcggcct gtctagatgt tctatcgga        39

<210> SEQ ID NO 596
<211> LENGTH: 38
<212> TYPE: DNA
<213> ORGANISM: Artificial Sequence
<220> FEATURE:
<223> OTHER INFORMATION: primer

<400> SEQUENCE: 596
actattggcg gccggtctca gtgttctatc ggattcgc        38

<210> SEQ ID NO 597
<211> LENGTH: 37
<212> TYPE: DNA
<213> ORGANISM: Artificial Sequence
<220> FEATURE:
<223> OTHER INFORMATION: primer

<400> SEQUENCE: 597
ctgccggtca ctgcggattt acaggagcca ctactgc        37

<210> SEQ ID NO 598
<211> LENGTH: 38
<212> TYPE: DNA
<213> ORGANISM: Artificial Sequence
<220> FEATURE:
<223> OTHER INFORMATION: primer

<400> SEQUENCE: 598
atgattatgc attcgtctca acaggggcag gagtaaat        38

<210> SEQ ID NO 599
<211> LENGTH: 40
<212> TYPE: DNA
<213> ORGANISM: Artificial Sequence
<220> FEATURE:
<223> OTHER INFORMATION: primer

<400> SEQUENCE: 599
ataactactc gggcggcaca gtccaagtag caggacatac        40

<210> SEQ ID NO 600
<211> LENGTH: 37
<212> TYPE: DNA
<213> ORGANISM: Artificial Sequence
<220> FEATURE:
<223> OTHER INFORMATION: primer

<400> SEQUENCE: 600
atccagaggg aacagtcctg ggacttatcc gcacgac        37

<210> SEQ ID NO 601

-continued

```
<211> LENGTH: 39
<212> TYPE: DNA
<213> ORGANISM: Artificial Sequence
<220> FEATURE:
<223> OTHER INFORMATION: primer

<400> SEQUENCE: 601
cagtccgagg acttatccag acgacggttt gtgccgaac                              39

<210> SEQ ID NO 602
<211> LENGTH: 38
<212> TYPE: DNA
<213> ORGANISM: Artificial Sequence
<220> FEATURE:
<223> OTHER INFORMATION: primer

<400> SEQUENCE: 602
gtggttctgg aaattgtcag acgggggaa caacattc                                38

<210> SEQ ID NO 603
<211> LENGTH: 37
<212> TYPE: DNA
<213> ORGANISM: Artificial Sequence
<220> FEATURE:
<223> OTHER INFORMATION: primer

<400> SEQUENCE: 603
tgcaggctta cggcctgcag atgattacga ctgactc                                37

<210> SEQ ID NO 604
<211> LENGTH: 38
<212> TYPE: DNA
<213> ORGANISM: Artificial Sequence
<220> FEATURE:
<223> OTHER INFORMATION: primer

<400> SEQUENCE: 604
ttggcggccg gtctagatca tctatcggat tcgcagta                               38

<210> SEQ ID NO 605
<211> LENGTH: 38
<212> TYPE: DNA
<213> ORGANISM: Artificial Sequence
<220> FEATURE:
<223> OTHER INFORMATION: primer

<400> SEQUENCE: 605
tcattactgc cggtcactca ggaagaacag gagccact                               38

<210> SEQ ID NO 606
<211> LENGTH: 37
<212> TYPE: DNA
<213> ORGANISM: Artificial Sequence
<220> FEATURE:
<223> OTHER INFORMATION: primer

<400> SEQUENCE: 606
cagttggatc tgctgtatct cgctcaggta gcactac                                37

<210> SEQ ID NO 607
<211> LENGTH: 37
<212> TYPE: DNA
<213> ORGANISM: Artificial Sequence
<220> FEATURE:
<223> OTHER INFORMATION: primer

<400> SEQUENCE: 607
```
cactacaggt tggcattcag gaactatcac ggcgctg                            37

<210> SEQ ID NO 608
<211> LENGTH: 38
<212> TYPE: DNA
<213> ORGANISM: Artificial Sequence
<220> FEATURE:
<223> OTHER INFORMATION: primer

<400> SEQUENCE: 608
cttatccgca cgacggtttc agccgaacca ggtgatag                           38

<210> SEQ ID NO 609
<211> LENGTH: 37
<212> TYPE: DNA
<213> ORGANISM: Artificial Sequence
<220> FEATURE:
<223> OTHER INFORMATION: primer

<400> SEQUENCE: 609
caggtggttc tggaaattca cggacggggg gaacaac                            37

<210> SEQ ID NO 610
<211> LENGTH: 19
<212> TYPE: DNA
<213> ORGANISM: Artificial Sequence
<220> FEATURE:
<223> OTHER INFORMATION: primer

<400> SEQUENCE: 610
tgcctcacat ttgtgccac                                                19

<210> SEQ ID NO 611
<211> LENGTH: 19
<212> TYPE: DNA
<213> ORGANISM: Artificial Sequence
<220> FEATURE:
<223> OTHER INFORMATION: primer

<400> SEQUENCE: 611
caggatgtag ctgcaggac                                                19

<210> SEQ ID NO 612
<211> LENGTH: 19
<212> TYPE: DNA
<213> ORGANISM: Artificial Sequence
<220> FEATURE:
<223> OTHER INFORMATION: primer

<400> SEQUENCE: 612
ctcggttatg agttagttc                                                19

<210> SEQ ID NO 613
<211> LENGTH: 50
<212> TYPE: DNA
<213> ORGANISM: Artificial Sequence
<220> FEATURE:
<223> OTHER INFORMATION: primer

<400> SEQUENCE: 613
cagagacaga cccccggagg taaccatggc acgatcattc tggaggacgc              50

<210> SEQ ID NO 614
<211> LENGTH: 50
<212> TYPE: DNA
<213> ORGANISM: Artificial Sequence
<220> FEATURE:

```
<223> OTHER INFORMATION: primer

<400> SEQUENCE: 614
gcgtcctcca gaatgatcgt gccatggtta cctccggggg tctgtctctg        50

<210> SEQ ID NO 615
<211> LENGTH: 55
<212> TYPE: DNA
<213> ORGANISM: Artificial Sequence
<220> FEATURE:
<223> OTHER INFORMATION: primer

<400> SEQUENCE: 615
atccgctcgc ggatccccat tgtcagctcg ggcccccacc gtcagaggtc acgag   55

<210> SEQ ID NO 616
<211> LENGTH: 42
<212> TYPE: DNA
<213> ORGANISM: Artificial Sequence
<220> FEATURE:
<223> OTHER INFORMATION: primer

<400> SEQUENCE: 616
gcagcctgaa ctagttgcga tcctctagag atcgaacttc at                42

<210> SEQ ID NO 617
<211> LENGTH: 56
<212> TYPE: DNA
<213> ORGANISM: Artificial Sequence
<220> FEATURE:
<223> OTHER INFORMATION: primer

<400> SEQUENCE: 617
agaccgacga gaccccgcgg accatggtcg acgtcatcgg cggcaacgcg tactac   56

<210> SEQ ID NO 618
<211> LENGTH: 56
<212> TYPE: DNA
<213> ORGANISM: Artificial Sequence
<220> FEATURE:
<223> OTHER INFORMATION: primer

<400> SEQUENCE: 618
tcagccgatc cgctcgcgga tccccattgt cagcccagga cgagacgcag accgta   56

<210> SEQ ID NO 619
<211> LENGTH: 56
<212> TYPE: DNA
<213> ORGANISM: Artificial Sequence
<220> FEATURE:
<223> OTHER INFORMATION: primer

<400> SEQUENCE: 619
gtagtacgcg ttgccgccga tgacgtcgac catggtccgc ggggtctcgt cggtct   56

<210> SEQ ID NO 620
<211> LENGTH: 48
<212> TYPE: DNA
<213> ORGANISM: Artificial Sequence
<220> FEATURE:
<223> OTHER INFORMATION: primer

<400> SEQUENCE: 620
gcagcctgaa ctagttgcga tcctctagag atcgaacttc atgttcga         48

<210> SEQ ID NO 621
```

```
<211> LENGTH: 53
<212> TYPE: DNA
<213> ORGANISM: Artificial Sequence
<220> FEATURE:
<223> OTHER INFORMATION: primer

<400> SEQUENCE: 621
accgacgaga ccccgcggac catgcacggc gacgtgcgcg gcggcgaccg cta        53

<210> SEQ ID NO 622
<211> LENGTH: 53
<212> TYPE: DNA
<213> ORGANISM: Artificial Sequence
<220> FEATURE:
<223> OTHER INFORMATION: primer

<400> SEQUENCE: 622
tagcggtcgc cgccgcgcac gtcgccgtgc atggtccgcg gggtctcgtc ggt        53

<210> SEQ ID NO 623
<211> LENGTH: 59
<212> TYPE: DNA
<213> ORGANISM: Artificial Sequence
<220> FEATURE:
<223> OTHER INFORMATION: primer

<400> SEQUENCE: 623
tcagccgatc cgctcgcgga tccccattgt cagcgagccc gacgagcgcg ctgcccgac    59

<210> SEQ ID NO 624
<211> LENGTH: 184
<212> TYPE: PRT
<213> ORGANISM: Cellulomonas strain 69B4

<400> SEQUENCE: 624
```

Phe Asp Val Ile Gly Gly Asn Ala Tyr Thr Ile Gly Gly Arg Ser Arg
1               5                   10                  15

Cys Ser Ile Gly Phe Ala Val Asn Gly Gly Phe Ile Thr Ala Gly His
            20                  25                  30

Cys Gly Arg Thr Gly Ala Thr Thr Ala Asn Pro Thr Gly Thr Phe Ala
        35                  40                  45

Gly Ser Ser Phe Pro Gly Asn Asp Tyr Ala Phe Val Arg Thr Gly Ala
    50                  55                  60

Gly Val Asn Leu Leu Ala Gln Val Asn Asn Tyr Ser Gly Gly Arg Val
65                  70                  75                  80

Gln Val Ala Gly His Thr Ala Ala Pro Val Gly Ser Ala Val Cys Arg
                85                  90                  95

Ser Gly Ser Thr Thr Gly Trp His Cys Gly Thr Ile Thr Ala Leu Asn
            100                 105                 110

Ser Ser Val Thr Tyr Pro Glu Gly Thr Val Arg Gly Leu Ile Arg Thr
        115                 120                 125

Thr Val Cys Ala Glu Pro Gly Asp Ser Gly Ser Leu Leu Ala Gly
    130                 135                 140

Asn Gln Ala Gln Gly Val Thr Ser Gly Gly Ser Gly Asn Cys Arg Thr
145                 150                 155                 160

Gly Gly Thr Thr Phe Phe Gln Pro Val Asn Pro Ile Leu Gln Ala Tyr
                165                 170                 175

Gly Leu Arg Met Ile Thr Thr Asp
            180

```
<210> SEQ ID NO 625
```

```
<211> LENGTH: 187
<212> TYPE: PRT
<213> ORGANISM: Streptomyces griseus

<400> SEQUENCE: 625
```

| | | | | | | | | | | | | | | | |
|---|---|---|---|---|---|---|---|---|---|---|---|---|---|---|---|
| Val | Leu | Gly | Gly | Gly | Ala | Ile | Tyr | Gly | Gly | Gly | Ser | Arg | Cys | Ser | Ala |
| 1 | | | | 5 | | | | | 10 | | | | | 15 | |
| Ala | Phe | Asn | Val | Thr | Lys | Gly | Gly | Ala | Arg | Tyr | Phe | Val | Thr | Ala | Gly |
| | | | 20 | | | | | 25 | | | | | 30 | | |
| His | Cys | Thr | Asn | Ile | Ser | Ala | Asn | Trp | Ser | Ala | Ser | Ser | Gly | Gly | Ser |
| | | | | 35 | | | | | 40 | | | | | 45 | |
| Val | Val | Gly | Val | Arg | Glu | Gly | Thr | Ser | Phe | Pro | Thr | Asn | Asp | Tyr | Gly |
| | | | 50 | | | | | 55 | | | | | 60 | | |
| Ile | Val | Arg | Tyr | Thr | Asp | Gly | Ser | Ser | Pro | Ala | Gly | Thr | Val | Asp | Leu |
| 65 | | | | | 70 | | | | | 75 | | | | | 80 |
| Tyr | Asn | Gly | Ser | Thr | Gln | Asp | Ile | Ser | Ala | Ala | Asn | Ala | Val | Val | |
| | | | | 85 | | | | | 90 | | | | | 95 | |
| Gly | Gln | Ala | Ile | Lys | Lys | Ser | Gly | Ser | Thr | Thr | Lys | Val | Thr | Ser | Gly |
| | | | 100 | | | | | 105 | | | | | 110 | | |
| Thr | Val | Thr | Ala | Val | Asn | Val | Thr | Val | Asn | Tyr | Gly | Asp | Gly | Pro | Val |
| | | | | 115 | | | | | 120 | | | | | 125 | |
| Tyr | Asn | Met | Val | Arg | Thr | Thr | Ala | Cys | Ser | Ala | Gly | Gly | Asp | Ser | Gly |
| | | | 130 | | | | | 135 | | | | | 140 | | |
| Gly | Ala | His | Phe | Ala | Gly | Ser | Val | Ala | Leu | Gly | Ile | His | Ser | Gly | Ser |
| 145 | | | | | 150 | | | | | 155 | | | | | 160 |
| Ser | Gly | Cys | Ser | Gly | Thr | Ala | Gly | Ser | Ala | Ile | His | Gln | Pro | Val | Thr |
| | | | | 165 | | | | | 170 | | | | | 175 | |
| Glu | Ala | Leu | Ser | Ala | Tyr | Gly | Val | Thr | Val | Tyr | | | | | |
| | | | 180 | | | | | 185 | | | | | | | |

```
<210> SEQ ID NO 626
<211> LENGTH: 185
<212> TYPE: PRT
<213> ORGANISM: Streptomyces griseus

<400> SEQUENCE: 626
```

| | | | | | | | | | | | | | | | |
|---|---|---|---|---|---|---|---|---|---|---|---|---|---|---|---|
| Ile | Ser | Gly | Gly | Asp | Ala | Ile | Tyr | Ser | Ser | Thr | Gly | Arg | Cys | Ser | Leu |
| 1 | | | | 5 | | | | | 10 | | | | | 15 | |
| Gly | Phe | Asn | Val | Arg | Ser | Gly | Ser | Thr | Tyr | Tyr | Phe | Leu | Thr | Ala | Gly |
| | | | 20 | | | | | 25 | | | | | 30 | | |
| His | Cys | Thr | Asp | Gly | Ala | Thr | Thr | Trp | Trp | Ala | Asn | Ser | Ala | Arg | Thr |
| | | | | 35 | | | | | 40 | | | | | 45 | |
| Thr | Val | Leu | Gly | Thr | Thr | Ser | Gly | Ser | Ser | Phe | Pro | Asn | Asn | Asp | Tyr |
| | | | 50 | | | | | 55 | | | | | 60 | | |
| Gly | Ile | Val | Arg | Tyr | Thr | Asn | Thr | Thr | Ile | Pro | Lys | Asp | Gly | Thr | Val |
| 65 | | | | | 70 | | | | | 75 | | | | | 80 |
| Gly | Gly | Gln | Asp | Ile | Thr | Ser | Ala | Ala | Asn | Ala | Thr | Val | Gly | Met | Ala |
| | | | | 85 | | | | | 90 | | | | | 95 | |
| Val | Thr | Arg | Arg | Gly | Ser | Thr | Thr | Gly | Thr | His | Ser | Gly | Ser | Val | Thr |
| | | | 100 | | | | | 105 | | | | | 110 | | |
| Ala | Leu | Asn | Ala | Thr | Val | Asn | Tyr | Gly | Gly | Gly | Asp | Val | Val | Tyr | Gly |
| | | | | 115 | | | | | 120 | | | | | 125 | |
| Met | Ile | Arg | Thr | Asn | Val | Cys | Ala | Glu | Pro | Gly | Asp | Ser | Gly | Gly | Pro |
| | | | 130 | | | | | 135 | | | | | 140 | | |
| Leu | Tyr | Ser | Gly | Thr | Arg | Ala | Ile | Gly | Leu | Thr | Ser | Gly | Gly | Ser | Gly |
| 145 | | | | | 150 | | | | | 155 | | | | | 160 |

Asn Cys Ser Ser Gly Gly Thr Thr Phe Phe Gln Pro Val Thr Glu Ala
            165                 170                 175

Leu Val Ala Tyr Gly Val Ser Val Tyr
            180                 185

<210> SEQ ID NO 627
<211> LENGTH: 198
<212> TYPE: PRT
<213> ORGANISM: Lysobacter enzymogenes

<400> SEQUENCE: 627

Ala Asn Ile Val Gly Gly Ile Glu Tyr Ser Ile Asn Asn Ala Ser Leu
1               5                   10                  15

Cys Ser Val Gly Phe Ser Val Thr Arg Gly Ala Thr Lys Gly Phe Val
            20                  25                  30

Thr Ala Gly His Cys Gly Thr Val Asn Ala Thr Ala Arg Ile Gly Gly
            35                  40                  45

Ala Val Val Gly Thr Phe Ala Ala Arg Val Phe Pro Gly Asn Asp Arg
        50                  55                  60

Ala Trp Val Ser Leu Thr Ser Ala Gln Thr Leu Leu Pro Arg Val Ala
65                  70                  75                  80

Asn Gly Ser Ser Phe Val Thr Val Arg Gly Ser Thr Glu Ala Ala Val
            85                  90                  95

Gly Ala Ala Val Cys Arg Ser Gly Arg Thr Thr Gly Tyr Gln Cys Gly
            100                 105                 110

Thr Ile Thr Ala Lys Asn Val Thr Ala Asn Tyr Ala Glu Gly Ala Val
            115                 120                 125

Arg Gly Leu Thr Gln Gly Asn Ala Cys Met Gly Arg Gly Asp Ser Gly
            130                 135                 140

Gly Ser Trp Ile Thr Ser Ala Gly Gln Ala Gln Gly Val Met Ser Gly
145                 150                 155                 160

Gly Asn Val Gln Ser Asn Gly Asn Asn Cys Gly Ile Pro Ala Ser Gln
            165                 170                 175

Arg Ser Ser Leu Phe Glu Arg Leu Gln Pro Ile Leu Ser Gln Tyr Gly
            180                 185                 190

Leu Ser Leu Val Thr Gly
            195

<210> SEQ ID NO 628
<211> LENGTH: 191
<212> TYPE: PRT
<213> ORGANISM: Streptomyces fradiae

<400> SEQUENCE: 628

Ile Ala Gly Gly Glu Ala Ile Tyr Ala Ala Gly Gly Arg Cys Ser
1               5                   10                  15

Leu Gly Phe Asn Val Arg Ser Ser Gly Ala Thr Tyr Ala Leu Thr
            20                  25                  30

Ala Gly His Cys Thr Glu Ile Ala Ser Thr Trp Tyr Thr Asn Ser Gly
            35                  40                  45

Gln Thr Ser Leu Leu Gly Thr Arg Ala Gly Thr Ser Phe Pro Gly Asn
        50                  55                  60

Asp Tyr Gly Leu Ile Arg His Ser Asn Ala Ser Ala Asp Gly Arg
65                  70                  75                  80

Val Tyr Leu Tyr Asn Gly Ser Tyr Arg Asp Ile Thr Gly Ala Gly Asn
            85                  90                  95

Ala Tyr Val Gly Gln Thr Val Gln Arg Ser Gly Ser Thr Thr Gly Leu

-continued

```
                 100                 105                 110
His Ser Gly Arg Val Thr Gly Leu Asn Ala Thr Val Asn Tyr Gly Gly
        115                 120                 125

Gly Asp Ile Val Ser Gly Leu Ile Gln Thr Asn Val Cys Ala Glu Pro
130                 135                 140

Gly Asp Ser Gly Gly Ala Leu Phe Ala Gly Ser Thr Ala Leu Gly Leu
145                 150                 155                 160

Thr Ser Gly Gly Ser Gly Asn Cys Arg Thr Gly Thr Thr Phe Phe
                165                 170                 175

Gln Pro Val Thr Glu Ala Leu Ser Ala Tyr Gly Val Ser Ile Leu
                180                 185                 190

<210> SEQ ID NO 629
<211> LENGTH: 181
<212> TYPE: PRT
<213> ORGANISM: Streptomyces griseus

<400> SEQUENCE: 629

Ile Ala Gly Gly Glu Ala Ile Thr Thr Gly Gly Ser Arg Cys Ser Leu
1               5                   10                  15

Gly Phe Asn Val Ser Val Asn Gly Val Ala His Ala Leu Thr Ala Gly
                20                  25                  30

His Cys Thr Asn Ile Ser Ala Ser Trp Ser Ile Gly Thr Arg Thr Gly
            35                  40                  45

Thr Ser Phe Pro Asn Asn Asp Tyr Gly Ile Ile Arg His Ser Asn Pro
        50                  55                  60

Ala Ala Ala Asp Gly Arg Val Tyr Leu Tyr Asn Gly Ser Tyr Gln Asp
65                  70                  75                  80

Ile Thr Thr Ala Gly Asn Ala Phe Val Gly Gln Ala Val Gln Arg Ser
                85                  90                  95

Gly Ser Thr Thr Gly Leu Arg Ser Gly Ser Val Thr Gly Leu Asn Ala
            100                 105                 110

Thr Val Asn Tyr Gly Ser Ser Gly Ile Val Tyr Gly Met Ile Gln Thr
        115                 120                 125

Asn Val Cys Ala Gln Pro Gly Asp Ser Gly Gly Ser Leu Phe Ala Gly
    130                 135                 140

Ser Thr Ala Leu Gly Leu Thr Ser Gly Gly Ser Gly Asn Cys Arg Thr
145                 150                 155                 160

Gly Gly Thr Thr Phe Tyr Gln Pro Val Thr Glu Ala Leu Ser Ala Tyr
                165                 170                 175

Gly Ala Thr Val Leu
            180

<210> SEQ ID NO 630
<211> LENGTH: 6
<212> TYPE: PRT
<213> ORGANISM: Artificial Sequence
<220> FEATURE:
<223> OTHER INFORMATION: synthetic

<400> SEQUENCE: 630

Pro Arg Thr Met Phe Asp
1               5

<210> SEQ ID NO 631
<211> LENGTH: 10
<212> TYPE: PRT
<213> ORGANISM: Cellulomonas strain 69B4
```

```
<400> SEQUENCE: 631

Phe Asp Val Ile Gly Gly Asn Ala Tyr Thr
1               5                   10

<210> SEQ ID NO 632
<211> LENGTH: 9
<212> TYPE: PRT
<213> ORGANISM: Cellulomonas strain 69B4

<400> SEQUENCE: 632

Thr Ala Asn Pro Thr Gly Thr Phe Ala
1               5

<210> SEQ ID NO 633
<211> LENGTH: 12
<212> TYPE: PRT
<213> ORGANISM: Cellulomonas strain 69B4

<400> SEQUENCE: 633

Phe Ala Gly Ser Ser Phe Pro Gly Asn Asp Tyr Ala
1               5                   10

<210> SEQ ID NO 634
<211> LENGTH: 14
<212> TYPE: PRT
<213> ORGANISM: Cellulomonas strain 69B4

<400> SEQUENCE: 634

Phe Ala Gly Ser Ser Phe Pro Gly Asn Asp Tyr Ala Phe Val
1               5                   10

<210> SEQ ID NO 635
<211> LENGTH: 10
<212> TYPE: PRT
<213> ORGANISM: Cellulomonas strain 69B4

<400> SEQUENCE: 635

Arg Thr Gly Ala Gly Val Asn Leu Leu Ala
1               5                   10

<210> SEQ ID NO 636
<211> LENGTH: 9
<212> TYPE: PRT
<213> ORGANISM: Cellulomonas strain 69B4

<400> SEQUENCE: 636

Phe Phe Gln Pro Val Asn Pro Ile Leu
1               5

<210> SEQ ID NO 637
<211> LENGTH: 11
<212> TYPE: PRT
<213> ORGANISM: Cellulomonas strain 69B4

<400> SEQUENCE: 637

Phe Phe Gln Pro Val Asn Pro Ile Leu Gln Ala
1               5                   10

<210> SEQ ID NO 638
<211> LENGTH: 13
<212> TYPE: PRT
<213> ORGANISM: Cellulomonas strain 69B4

<400> SEQUENCE: 638

Phe Phe Gln Pro Val Asn Pro Ile Leu Gln Ala Tyr Gly
```

-continued

<210> SEQ ID NO 639
<211> LENGTH: 255
<212> TYPE: PRT
<213> ORGANISM: Streptomyces griseus

<400> SEQUENCE: 639

```
Ala Asp Ile Arg Gly Gly Asp Ala Tyr Tyr Met Asn Gly Ser Gly Arg
1               5                   10                  15
Cys Ser Val Gly Phe Ser Val Thr Arg Gly Thr Gln Asn Gly Phe Ala
            20                  25                  30
Thr Ala Gly His Cys Gly Arg Val Gly Thr Thr Thr Asn Gly Val Asn
        35                  40                  45
Gln Gln Ala Gln Gly Thr Phe Gln Gly Ser Thr Phe Pro Gly Arg Asp
    50                  55                  60
Ile Ala Trp Val Ala Thr Asn Ala Asn Trp Thr Pro Arg Pro Leu Val
65                  70                  75                  80
Asn Gly Tyr Gly Arg Gly Asp Val Thr Val Ala Gly Ser Thr Ala Ser
                85                  90                  95
Val Val Gly Ala Ser Val Cys Arg Ser Gly Ser Thr Thr Gly Trp His
            100                 105                 110
Cys Gly Thr Ile Gln Gln Leu Asn Thr Ser Val Thr Tyr Pro Glu Gly
        115                 120                 125
Thr Ile Ser Gly Val Thr Arg Thr Ser Val Cys Ala Glu Pro Gly Asp
    130                 135                 140
Ser Gly Gly Ser Tyr Ile Ser Gly Ser Gln Ala Gln Gly Val Thr Ser
145                 150                 155                 160
Gly Gly Ser Gly Asn Cys Ser Ser Gly Thr Thr Tyr Phe Gln Pro
                165                 170                 175
Ile Asn Pro Leu Leu Gln Ala Tyr Gly Leu Thr Leu Val Thr Ser Gly
                180                 185                 190
Gly Gly Thr Pro Thr Asp Pro Pro Thr Thr Pro Pro Thr Asp Ser Pro
            195                 200                 205
Gly Gly Thr Trp Ala Val Gly Thr Ala Tyr Ala Ala Gly Ala Thr Val
        210                 215                 220
Thr Tyr Gly Gly Ala Thr Tyr Arg Cys Leu Gln Ala His Thr Ala Gln
225                 230                 235                 240
Pro Gly Trp Thr Pro Ala Asp Val Pro Ala Leu Trp Gln Arg Val
                245                 250                 255
```

<210> SEQ ID NO 640
<211> LENGTH: 185
<212> TYPE: PRT
<213> ORGANISM: Streptomyces griseus

<400> SEQUENCE: 640

```
Ile Ser Gly Gly Asp Ala Ile Tyr Ser Ser Thr Gly Arg Cys Ser Leu
1               5                   10                  15
Gly Phe Asn Val Arg Ser Gly Ser Thr Tyr Tyr Phe Leu Thr Ala Gly
            20                  25                  30
His Cys Thr Asp Gly Ala Thr Thr Trp Trp Ala Asn Ser Ala Arg Thr
        35                  40                  45
Thr Val Leu Gly Thr Thr Ser Gly Ser Ser Phe Pro Asn Asn Asp Tyr
    50                  55                  60
Gly Ile Val Arg Tyr Thr Asn Thr Thr Ile Pro Lys Asp Gly Thr Val
65                  70                  75                  80
```

```
Gly Gly Gln Asp Ile Thr Ser Ala Ala Asn Ala Thr Val Met Ala
                85                  90                  95

Val Thr Arg Arg Gly Ser Thr Thr Gly Thr His Ser Gly Ser Val Thr
            100                 105                 110

Ala Leu Asn Ala Thr Val Asn Tyr Gly Gly Gly Asp Val Val Tyr Gly
            115                 120                 125

Met Ile Arg Thr Asn Val Cys Ala Glu Pro Gly Asp Ser Gly Gly Pro
    130                 135                 140

Leu Tyr Ser Gly Thr Arg Ala Ile Gly Leu Thr Ser Gly Gly Ser Gly
145                 150                 155                 160

Asn Cys Ser Ser Gly Gly Thr Thr Phe Phe Gln Pro Val Thr Glu Ala
                165                 170                 175

Leu Ser Ala Tyr Gly Val Ser Val Tyr
            180                 185

<210> SEQ ID NO 641
<211> LENGTH: 181
<212> TYPE: PRT
<213> ORGANISM: Streptomyces griseus

<400> SEQUENCE: 641

Ile Ala Gly Gly Glu Ala Ile Thr Thr Gly Gly Ser Arg Cys Ser Leu
1               5                   10                  15

Gly Phe Asn Val Ser Val Asn Gly Val Ala His Ala Leu Thr Ala Gly
                20                  25                  30

His Cys Thr Asn Ile Ser Ala Ser Trp Ser Ile Gly Thr Arg Thr Gly
            35                  40                  45

Thr Ser Phe Pro Asn Asn Asp Tyr Gly Ile Ile Arg His Ser Asn Pro
    50                  55                  60

Ala Ala Ala Asp Gly Arg Val Tyr Leu Tyr Asn Gly Ser Tyr Gln Asp
65                  70                  75                  80

Ile Thr Thr Ala Gly Asn Ala Phe Val Gly Gln Ala Val Gln Arg Ser
                85                  90                  95

Gly Ser Thr Thr Gly Leu Arg Ser Gly Ser Val Thr Gly Leu Asn Ala
            100                 105                 110

Thr Val Asn Tyr Gly Ser Ser Gly Ile Val Tyr Gly Met Ile Gln Thr
            115                 120                 125

Asn Val Cys Ala Glu Pro Gly Asp Ser Gly Gly Ser Leu Phe Ala Gly
    130                 135                 140

Ser Thr Ala Leu Gly Leu Thr Ser Gly Gly Ser Gly Asn Cys Arg Thr
145                 150                 155                 160

Gly Gly Thr Thr Phe Tyr Gln Pro Val Thr Glu Ala Leu Ser Ala Tyr
                165                 170                 175

Gly Ala Thr Val Leu
            180

<210> SEQ ID NO 642
<211> LENGTH: 188
<212> TYPE: PRT
<213> ORGANISM: Streptomyces griseus

<400> SEQUENCE: 642

Ile Ala Gly Gly Asp Ala Ile Trp Gly Ser Gly Ser Arg Cys Ser Leu
1               5                   10                  15

Gly Phe Asn Val Val Lys Gly Gly Glu Pro Tyr Phe Leu Thr Ala Gly
                20                  25                  30
```

```
His Cys Thr Glu Ser Val Thr Ser Trp Ser Asp Thr Gln Gly Gly Ser
        35                  40                  45

Glu Ile Gly Ala Asn Glu Gly Ser Ser Phe Pro Glu Asn Asp Tyr Gly
 50                  55                  60

Leu Val Lys Tyr Thr Ser Asp Thr Ala His Pro Ser Glu Val Asn Leu
 65                  70                  75                  80

Tyr Asp Gly Ser Thr Gln Ala Ile Thr Gln Ala Gly Asp Ala Thr Val
                85                  90                  95

Gly Gln Ala Val Thr Arg Ser Gly Ser Thr Thr Gln Val His Asp Gly
                100                 105                 110

Glu Val Thr Ala Leu Asp Ala Thr Val Asn Tyr Gly Asn Gly Asp Ile
            115                 120                 125

Val Asn Gly Leu Ile Gln Thr Thr Val Cys Ala Glu Pro Gly Asp Ser
130                 135                 140

Gly Gly Ala Leu Phe Ala Gly Asp Thr Ala Leu Gly Leu Thr Ser Gly
145                 150                 155                 160

Gly Ser Gly Asp Cys Ser Ser Gly Gly Thr Thr Phe Phe Gln Pro Val
                165                 170                 175

Pro Glu Ala Leu Ala Ala Tyr Gly Ala Glu Ile Gly
            180                 185

<210> SEQ ID NO 643
<211> LENGTH: 198
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (9)..(10)
<223> OTHER INFORMATION: Xaa can be any naturally occurring amino acid
<220> FEATURE:
<221> NAME/KEY: VARIANT
<222> LOCATION: (12)..(12)
<223> OTHER INFORMATION: Xaa can be any naturally occurring amino acid
<220> FEATURE:
<221> NAME/KEY: VARIANT
<222> LOCATION: (22)..(23)
<223> OTHER INFORMATION: Xaa can be any naturally occurring amino acid
<220> FEATURE:
<221> NAME/KEY: VARIANT
<222> LOCATION: (25)..(27)
<223> OTHER INFORMATION: Xaa can be any naturally occurring amino acid
<220> FEATURE:
<221> NAME/KEY: VARIANT
<222> LOCATION: (37)..(38)
<223> OTHER INFORMATION: Xaa can be any naturally occurring amino acid
<220> FEATURE:
<221> NAME/KEY: VARIANT
<222> LOCATION: (43)..(51)
<223> OTHER INFORMATION: Xaa can be any naturally occurring amino acid
<220> FEATURE:
<221> NAME/KEY: VARIANT
<222> LOCATION: (55)..(56)
<223> OTHER INFORMATION: Xaa can be any naturally occurring amino acid
<220> FEATURE:
<221> NAME/KEY: VARIANT
<222> LOCATION: (62)..(62)
<223> OTHER INFORMATION: Xaa can be any naturally occurring amino acid
<220> FEATURE:
<221> NAME/KEY: VARIANT
<222> LOCATION: (73)..(79)
<223> OTHER INFORMATION: Xaa can be any naturally occurring amino acid
<220> FEATURE:
<221> NAME/KEY: VARIANT
<222> LOCATION: (82)..(82)
<223> OTHER INFORMATION: Xaa can be any naturally occurring amino acid
<220> FEATURE:
<221> NAME/KEY: VARIANT
<222> LOCATION: (84)..(84)
```

```
<223> OTHER INFORMATION: Xaa can be any naturally occurring amino acid
<220> FEATURE:
<221> NAME/KEY: VARIANT
<222> LOCATION: (86)..(87)
<223> OTHER INFORMATION: Xaa can be any naturally occurring amino acid
<220> FEATURE:
<221> NAME/KEY: VARIANT
<222> LOCATION: (89)..(89)
<223> OTHER INFORMATION: Xaa can be any naturally occurring amino acid
<220> FEATURE:
<221> NAME/KEY: VARIANT
<222> LOCATION: (92)..(92)
<223> OTHER INFORMATION: Xaa can be any naturally occurring amino acid
<220> FEATURE:
<221> NAME/KEY: VARIANT
<222> LOCATION: (95)..(95)
<223> OTHER INFORMATION: Xaa can be any naturally occurring amino acid
<220> FEATURE:
<221> NAME/KEY: VARIANT
<222> LOCATION: (97)..(97)
<223> OTHER INFORMATION: Xaa can be any naturally occurring amino acid
<220> FEATURE:
<221> NAME/KEY: VARIANT
<222> LOCATION: (100)..(100)
<223> OTHER INFORMATION: Xaa can be any naturally occurring amino acid
<220> FEATURE:
<221> NAME/KEY: VARIANT
<222> LOCATION: (103)..(103)
<223> OTHER INFORMATION: Xaa can be any naturally occurring amino acid
<220> FEATURE:
<221> NAME/KEY: VARIANT
<222> LOCATION: (111)..(111)
<223> OTHER INFORMATION: Xaa can be any naturally occurring amino acid
<220> FEATURE:
<221> NAME/KEY: VARIANT
<222> LOCATION: (113)..(113)
<223> OTHER INFORMATION: Xaa can be any naturally occurring amino acid
<220> FEATURE:
<221> NAME/KEY: VARIANT
<222> LOCATION: (127)..(127)
<223> OTHER INFORMATION: Xaa can be any naturally occurring amino acid
<220> FEATURE:
<221> NAME/KEY: VARIANT
<222> LOCATION: (129)..(129)
<223> OTHER INFORMATION: Xaa can be any naturally occurring amino acid
<220> FEATURE:
<221> NAME/KEY: VARIANT
<222> LOCATION: (132)..(132)
<223> OTHER INFORMATION: Xaa can be any naturally occurring amino acid
<220> FEATURE:
<221> NAME/KEY: VARIANT
<222> LOCATION: (155)..(155)
<223> OTHER INFORMATION: Xaa can be any naturally occurring amino acid
<220> FEATURE:
<221> NAME/KEY: VARIANT
<222> LOCATION: (179)..(179)
<223> OTHER INFORMATION: Xaa can be any naturally occurring amino acid
<220> FEATURE:
<221> NAME/KEY: VARIANT
<222> LOCATION: (191)..(198)
<223> OTHER INFORMATION: Xaa can be any naturally occurring amino acid

<400> SEQUENCE: 643

Ile Ala Gly Gly Asp Ala Ile Tyr Xaa Xaa Gly Xaa Ser Arg Cys Ser
1               5                   10                  15

Leu Gly Phe Asn Val Xaa Xaa Gly Xaa Xaa Xaa Tyr Phe Leu Thr Ala
                20                  25                  30

Gly His Cys Thr Xaa Xaa Gly Thr Thr Trp Xaa Xaa Xaa Xaa Xaa Xaa
            35                  40                  45

Xaa Xaa Xaa Ile Gly Thr Xaa Gly Ser Ser Phe Pro Xaa Asn Asp
    50                  55                  60

Tyr Gly Ile Val Arg Tyr Thr Ala Xaa Xaa Xaa Xaa Xaa Xaa Xaa Val
65                  70                  75                  80

Asn Xaa Tyr Xaa Gly Xaa Xaa Gln Xaa Ile Thr Xaa Ala Gly Xaa Ala
```

```
                    85                  90                  95
Xaa Val Gly Xaa Ala Val Xaa Arg Ser Gly Ser Thr Thr Gly Xaa His
                100                 105                 110

Xaa Gly Ser Val Thr Ala Leu Asn Ala Thr Val Asn Tyr Gly Xaa Gly
            115                 120                 125

Xaa Ile Val Xaa Gly Leu Ile Arg Thr Thr Val Cys Ala Glu Pro Gly
        130                 135                 140

Asp Ser Gly Gly Ser Leu Phe Ala Gly Ser Xaa Ala Leu Gly Leu Thr
145                 150                 155                 160

Ser Gly Gly Ser Gly Asn Cys Ser Ser Gly Gly Thr Thr Phe Phe Gln
                165                 170                 175

Pro Val Xaa Glu Ala Leu Ser Ala Tyr Gly Leu Thr Val Ile Xaa Xaa
            180                 185                 190

Xaa Xaa Xaa Xaa Xaa Xaa
        195

<210> SEQ ID NO 644
<211> LENGTH: 513
<212> TYPE: PRT
<213> ORGANISM: Thermus aquaticus

<400> SEQUENCE: 644

Met Arg Lys Thr Tyr Trp Leu Met Ala Leu Phe Ala Val Leu Val Leu
1               5                   10                  15

Gly Gly Cys Gln Met Ala Ser Arg Ser Asp Pro Thr Pro Thr Leu Ala
                20                  25                  30

Glu Ala Phe Trp Pro Lys Glu Ala Pro Val Tyr Gly Leu Asp Asp Pro
            35                  40                  45

Glu Ala Ile Pro Gly Arg Tyr Ile Val Val Phe Lys Lys Gly Lys Gly
    50                  55                  60

Gln Ser Leu Leu Gln Gly Gly Ile Thr Thr Leu Gln Ala Arg Leu Ala
65                  70                  75                  80

Pro Gln Gly Val Val Val Thr Gln Ala Tyr Thr Gly Ala Leu Gln Gly
                85                  90                  95

Phe Ala Ala Glu Met Ala Pro Gln Ala Leu Glu Ala Phe Arg Gln Ser
                100                 105                 110

Pro Asp Val Glu Phe Ile Glu Ala Asp Lys Val Val Arg Ala Trp Ala
            115                 120                 125

Thr Gln Ser Pro Ala Pro Trp Gly Leu Asp Arg Ile Asp Gln Arg Asp
    130                 135                 140

Leu Pro Leu Ser Asn Ser Tyr Thr Tyr Thr Ala Thr Gly Arg Gly Val
145                 150                 155                 160

Asn Val Tyr Val Ile Asp Thr Gly Ile Arg Thr His Arg Glu Phe
                165                 170                 175

Gly Gly Arg Ala Arg Val Gly Tyr Asp Ala Leu Gly Gly Asn Gly Gln
                180                 185                 190

Asp Cys Asn Gly His Gly Thr His Val Ala Gly Thr Ile Gly Gly Val
            195                 200                 205

Thr Tyr Gly Val Ala Lys Ala Val Asn Leu Tyr Ala Val Arg Val Leu
    210                 215                 220

Asp Cys Asn Gly Ser Gly Ser Thr Ser Gly Val Ile Ala Gly Val Asp
225                 230                 235                 240

Trp Val Thr Arg Asn His Arg Arg Pro Ala Val Ala Asn Met Ser Leu
                245                 250                 255

Gly Gly Gly Val Ser Thr Ala Leu Asp Asn Ala Val Lys Asn Ser Ile
```

-continued

```
                260                 265                 270
Ala Ala Gly Val Val Tyr Ala Val Ala Gly Asn Asp Asn Ala Asn
            275                 280                 285
Ala Cys Asn Tyr Ser Pro Ala Arg Val Ala Glu Ala Leu Thr Val Gly
            290                 295                 300
Ala Thr Thr Ser Ser Asp Ala Arg Ala Ser Phe Ser Asn Tyr Gly Ser
305                 310                 315                 320
Cys Val Asp Leu Phe Ala Pro Gly Ala Ser Ile Pro Ser Ala Trp Tyr
                325                 330                 335
Thr Ser Asp Thr Ala Thr Gln Thr Leu Asn Gly Thr Ser Met Ala Thr
            340                 345                 350
Pro His Val Ala Gly Val Ala Ala Leu Tyr Leu Glu Gln Asn Pro Ser
            355                 360                 365
Ala Thr Pro Ala Ser Val Ala Ser Ala Ile Leu Asn Gly Ala Thr Thr
            370                 375                 380
Gly Arg Leu Ser Gly Ile Gly Ser Gly Ser Pro Asn Arg Leu Leu Tyr
385                 390                 395                 400
Ser Leu Leu Ser Ser Gly Ser Gly Ser Thr Ala Pro Cys Thr Ser Cys
                405                 410                 415
Ser Tyr Tyr Thr Gly Ser Leu Ser Gly Pro Gly Asp Tyr Asn Phe Gln
            420                 425                 430
Pro Asn Gly Thr Tyr Tyr Tyr Ser Pro Ala Gly Thr His Arg Ala Trp
            435                 440                 445
Leu Arg Gly Pro Ala Gly Thr Asp Phe Asp Leu Tyr Leu Trp Arg Trp
            450                 455                 460
Asp Gly Ser Arg Trp Leu Thr Val Gly Ser Ser Thr Gly Pro Thr Ser
465                 470                 475                 480
Glu Glu Ser Leu Ser Tyr Ser Gly Thr Ala Gly Tyr Tyr Leu Trp Arg
                485                 490                 495
Ile Tyr Ala Tyr Ser Gly Ser Gly Met Tyr Glu Phe Trp Leu Gln Arg
            500                 505                 510
Pro

<210> SEQ ID NO 645
<211> LENGTH: 495
<212> TYPE: PRT
<213> ORGANISM: Cellulomonas strain 69B4

<400> SEQUENCE: 645

Met Thr Pro Arg Thr Val Thr Arg Ala Leu Ala Val Ala Thr Ala Ala
1               5                   10                  15
Ala Thr Leu Leu Ala Gly Gly Met Ala Ala Gln Ala Asn Glu Pro Ala
            20                  25                  30
Pro Pro Gly Ser Ala Ser Ala Pro Pro Arg Leu Ala Glu Lys Leu Asp
            35                  40                  45
Pro Asp Leu Leu Glu Ala Met Glu Arg Asp Leu Gly Leu Asp Ala Glu
            50                  55                  60
Glu Ala Ala Ala Thr Leu Ala Phe Gln His Asp Ala Ala Glu Thr Gly
65                  70                  75                  80
Glu Ala Leu Ala Glu Glu Leu Asp Glu Asp Phe Ala Gly Thr Trp Val
                85                  90                  95
Glu Asp Asp Val Leu Tyr Val Ala Thr Thr Asp Glu Asp Ala Val Glu
            100                 105                 110
Glu Val Glu Gly Glu Gly Ala Thr Ala Val Thr Val Glu His Ser Leu
            115                 120                 125
```

Ala Asp Leu Glu Ala Trp Lys Thr Val Leu Asp Ala Ala Leu Glu Gly
        130                 135                 140

His Asp Asp Val Pro Thr Trp Tyr Val Asp Val Pro Thr Asn Ser Val
145                 150                 155                 160

Val Val Ala Val Lys Ala Gly Ala Gln Asp Val Ala Ala Gly Leu Val
                165                 170                 175

Glu Gly Ala Asp Val Pro Ser Asp Ala Val Thr Phe Val Glu Thr Asp
            180                 185                 190

Glu Thr Pro Arg Thr Met Phe Asp Val Ile Gly Gly Asn Ala Tyr Thr
        195                 200                 205

Ile Gly Gly Arg Ser Arg Cys Ser Ile Gly Phe Ala Val Asn Gly Gly
    210                 215                 220

Phe Ile Thr Ala Gly His Cys Gly Arg Thr Gly Ala Thr Thr Ala Asn
225                 230                 235                 240

Pro Thr Gly Thr Phe Ala Gly Ser Ser Phe Pro Gly Asn Asp Tyr Ala
                245                 250                 255

Phe Val Arg Thr Gly Ala Gly Val Asn Leu Leu Ala Gln Val Asn Asn
            260                 265                 270

Tyr Ser Gly Gly Arg Val Gln Val Ala Gly His Thr Ala Ala Pro Val
        275                 280                 285

Gly Ser Ala Val Cys Arg Ser Gly Ser Thr Thr Gly Trp His Cys Gly
    290                 295                 300

Thr Ile Thr Ala Leu Asn Ser Ser Val Thr Tyr Pro Glu Gly Thr Val
305                 310                 315                 320

Arg Gly Leu Ile Arg Thr Thr Val Cys Ala Glu Pro Gly Asp Ser Gly
                325                 330                 335

Gly Ser Leu Leu Ala Gly Asn Gln Ala Gln Gly Val Thr Ser Gly Gly
            340                 345                 350

Ser Gly Asn Cys Arg Thr Gly Gly Thr Thr Phe Phe Gln Pro Val Asn
        355                 360                 365

Pro Ile Leu Gln Ala Tyr Gly Leu Arg Met Ile Thr Thr Asp Ser Gly
    370                 375                 380

Ser Ser Pro Ala Pro Ala Pro Thr Ser Cys Thr Gly Tyr Ala Arg Thr
385                 390                 395                 400

Phe Thr Gly Thr Leu Ala Ala Gly Arg Ala Ala Gln Pro Asn Gly
                405                 410                 415

Ser Tyr Val Gln Val Asn Arg Ser Gly Thr His Ser Val Cys Leu Asn
            420                 425                 430

Gly Pro Ser Gly Ala Asp Phe Asp Leu Tyr Val Gln Arg Trp Asn Gly
        435                 440                 445

Ser Ser Trp Val Thr Val Ala Gln Ser Thr Ser Pro Gly Ser Asn Glu
    450                 455                 460

Thr Ile Thr Tyr Arg Gly Asn Ala Gly Tyr Tyr Arg Tyr Val Val Asn
465                 470                 475                 480

Ala Ala Ser Gly Ser Gly Ala Tyr Thr Met Gly Leu Thr Leu Pro
                485                 490                 495

<210> SEQ ID NO 646
<211> LENGTH: 510
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (3)..(509)

<223> OTHER INFORMATION: Xaa can be any naturally occurring amino acid

<400> SEQUENCE: 646

```
Met Ala Xaa Xaa Ala Xaa Xaa Leu Leu Ala Gly Xaa Xaa Xaa Ala Xaa
1               5                   10                  15

Xaa Xaa Asp Pro Xaa Pro Xaa Ala Xaa Ala Xaa Xaa Pro Lys Xaa
            20                  25                  30

Ala Xaa Xaa Xaa Xaa Xaa Asp Xaa Xaa Glu Ala Ile Xaa Xaa Xaa Xaa
        35                  40                  45

Xaa Leu Xaa Xaa Xaa Xaa Ala Xaa Ala Xaa Xaa Xaa Xaa Gln Xaa Xaa
    50                  55                  60

Xaa Xaa Xaa Xaa Xaa Xaa Xaa Leu Ala Xaa Xaa Xaa Xaa Xaa Leu Xaa
65                  70                  75                  80

Xaa Xaa Phe Xaa Gly Xaa Xaa Xaa Xaa Xaa Xaa Xaa Xaa Xaa Xaa
        85                  90                  95

Xaa Xaa Xaa Glu Xaa Xaa Xaa Xaa Xaa Xaa Asp Xaa Glu Xaa Xaa Xaa
            100                 105                 110

Ala Xaa Xaa Val Xaa Xaa Ala Xaa Ala Xaa Xaa Xaa Xaa Xaa Xaa Xaa
        115                 120                 125

Xaa Leu Asp Xaa Xaa Xaa Xaa Xaa Xaa Xaa Leu Xaa Xaa Xaa Xaa Tyr
130                 135                 140

Xaa Xaa Xaa Xaa Thr Xaa Xaa Xaa Xaa Xaa Val Xaa Xaa Ile Xaa Xaa
145                 150                 155                 160

Gly Xaa Xaa Xaa Xaa Xaa Xaa Xaa Xaa Xaa Xaa Ala Xaa Val Xaa
        165                 170                 175

Xaa Asp Ala Leu Xaa Xaa Xaa Xaa Xaa Asp Xaa Xaa Xaa Xaa Xaa Xaa
        180                 185                 190

Xaa Met Xaa Xaa Xaa Ile Gly Gly Xaa Xaa Tyr Xaa Ile Ala Xaa Xaa
    195                 200                 205

Xaa Xaa Xaa Xaa Xaa Xaa Xaa Xaa Xaa Cys Xaa Xaa Xaa Xaa Ala
        210                 215                 220

Xaa Xaa Gly Xaa Xaa Xaa Xaa Xaa Xaa Xaa Xaa Arg Xaa Xaa Xaa
225                 230                 235                 240

Xaa Xaa Ala Xaa Xaa Xaa Xaa Ser Xaa Ala Gly Xaa Xaa Xaa Xaa Ala
        245                 250                 255

Xaa Asp Xaa Ala Xaa Xaa Ser Xaa Ala Ala Xaa Xaa Xaa Xaa
        260                 265                 270

Xaa Xaa Xaa Xaa Asn Xaa Xaa Ala Asn Xaa Xaa Asn Tyr Ser Xaa Ala
        275                 280                 285

Arg Val Xaa Xaa Ala Xaa Xaa Ala Ala Xaa Xaa Xaa Ser Xaa Xaa
        290                 295                 300

Xaa Xaa Ser Xaa Ser Xaa Xaa Gly Xaa Xaa Xaa Xaa Xaa Xaa Xaa Xaa
305                 310                 315                 320

Xaa Ala Xaa Xaa Xaa Ser Xaa Xaa Tyr Xaa Xaa Xaa Thr Xaa Xaa Xaa
        325                 330                 335

Xaa Ile Xaa Xaa Thr Xaa Xaa Ala Xaa Pro Xaa Xaa Ala Gly Xaa Ala
        340                 345                 350

Xaa Leu Xaa Xaa Xaa Gln Xaa Xaa Xaa Xaa Thr Xaa Ala Xaa Xaa Ala
        355                 360                 365

Xaa Xaa Xaa Xaa Xaa Gly Xaa Thr Xaa Xaa Xaa Xaa Xaa Xaa Xaa
        370                 375                 380

Xaa Xaa Ala Xaa Xaa Xaa Xaa Leu Xaa Ser Xaa Xaa Ser Xaa Gly Ser
385                 390                 395                 400

Xaa Xaa Xaa Xaa Xaa Xaa Thr Ser Cys Ser Xaa Tyr Xaa Xaa Ser Xaa
```

-continued

```
                    405                 410                 415
Ser Gly Xaa Xaa Xaa Gly Xaa Xaa Xaa Gln Pro Asn Gly Ser
        420                 425                 430

Tyr Xaa Xaa Xaa Xaa Ala Gly Thr His Xaa Xaa Xaa Leu Xaa Gly
    435                 440                 445

Pro Ala Gly Xaa Asp Phe Asp Leu Tyr Leu Xaa Arg Trp Xaa Gly Ser
        450                 455                 460

Xaa Trp Leu Thr Val Ala Xaa Ser Thr Xaa Pro Xaa Ser Xaa Glu Ser
465                 470                 475                 480

Ile Ser Tyr Xaa Gly Xaa Ala Gly Tyr Tyr Xaa Trp Xaa Ile Xaa Ala
                485                 490                 495

Xaa Ser Gly Ser Gly Xaa Tyr Xaa Xaa Xaa Leu Xaa Xaa Pro
            500                 505                 510

<210> SEQ ID NO 647
<211> LENGTH: 190
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (6)..(188)
<223> OTHER INFORMATION: Xaa can be any naturally occurring amino acid

<400> SEQUENCE: 647

Asp Val Ile Gly Gly Xaa Xaa Tyr Xaa Ile Xaa Xaa Xaa Xaa Arg Xaa
1               5                   10                  15

Xaa Xaa Xaa Xaa Cys Ser Ile Gly Phe Ala Val Xaa Gly Gly Phe Val
            20                  25                  30

Thr Ala Gly His Cys Gly Arg Xaa Gly Ala Xaa Xaa Xaa Xaa Xaa
        35                  40                  45

Thr Ser Xaa Pro Xaa Gly Thr Phe Xaa Gly Ser Ser Phe Pro Gly Asn
    50                  55                  60

Asp Tyr Ala Trp Val Gln Val Ala Ser Gly Asn Thr Pro Val Gly Ala
65                  70                  75                  80

Val Asn Asn Tyr Ser Gly Gly Thr Val Xaa Val Ala Gly Ser Thr Xaa
                85                  90                  95

Ala Ala Val Gly Ala Ser Val Cys Arg Ser Gly Ser Thr Thr Gly Trp
            100                 105                 110

Arg Cys Gly Thr Ile Xaa Ala Tyr Asn Ala Ser Val Xaa Tyr Ala Glu
        115                 120                 125

Gly Thr Val Ser Gly Leu Ile Arg Thr Asn Val Cys Ala Glu Pro Gly
    130                 135                 140

Asp Ser Gly Gly Ser Leu Leu Ala Gly Asn Gln Ala Gln Gly Val Thr
145                 150                 155                 160

Ser Gly Gly Ser Gly Asn Cys Xaa Xaa Gly Gly Thr Thr Tyr Phe Gln
                165                 170                 175

Pro Val Asn Xaa Xaa Leu Xaa Xaa Tyr Gly Leu Xaa Leu Val
            180                 185                 190

<210> SEQ ID NO 648
<211> LENGTH: 368
<212> TYPE: PRT
<213> ORGANISM: Thermobifida fusca

<400> SEQUENCE: 648

Met Asn His Ser Ser Arg Arg Thr Thr Ser Leu Leu Phe Thr Ala Ala
1               5                   10                  15
```

```
Leu Ala Ala Thr Ala Leu Val Ala Ala Thr Thr Pro Ala Ser Ala Gln
             20                  25                  30

Glu Leu Ala Leu Lys Arg Asp Leu Gly Leu Ser Asp Ala Glu Val Ala
         35                  40                  45

Glu Leu Arg Ala Ala Glu Ala Val Glu Leu Glu Glu Glu Leu
     50                  55                  60

Arg Asp Ser Leu Gly Ser Asp Phe Gly Val Tyr Leu Asp Ala Asp
 65              70                  75                  80

Thr Thr Glu Ile Thr Val Ala Val Thr Asp Pro Ala Ala Val Ser Arg
                 85                  90                  95

Val Asp Ala Asp Asp Val Thr Val Asp Val Asp Phe Gly Glu Thr
                100                 105                 110

Ala Leu Asn Asp Phe Val Ala Ser Leu Asn Ala Ile Ala Asp Thr Ala
                115                 120                 125

Asp Pro Lys Val Thr Gly Trp Tyr Thr Asp Leu Glu Ser Asp Ala Val
            130                 135                 140

Val Ile Thr Thr Leu Arg Gly Gly Thr Pro Ala Ala Glu Glu Leu Ala
145                 150                 155                 160

Glu Arg Ala Gly Leu Asp Glu Arg Ala Arg Ile Val Glu Glu Asp
                165                 170                 175

Glu Glu Pro Gln Ser Leu Ala Ala Ile Ile Gly Gly Asn Pro Tyr Tyr
                180                 185                 190

Phe Gly Asn Tyr Arg Cys Ser Ile Gly Phe Ser Val Arg Gln Gly Ser
            195                 200                 205

Gln Thr Gly Phe Ala Thr Ala Gly His Cys Gly Ser Thr Gly Thr Arg
        210                 215                 220

Val Ser Ser Pro Ser Gly Thr Val Ala Gly Ser Tyr Phe Pro Gly Arg
225                 230                 235                 240

Asp Met Gly Trp Val Arg Ile Thr Ser Ala Asp Thr Val Thr Pro Leu
                245                 250                 255

Val Asn Arg Tyr Asn Gly Gly Thr Val Thr Val Thr Gly Ser Gln Glu
                260                 265                 270

Ala Ala Thr Gly Ser Ser Val Cys Arg Ser Gly Ala Thr Thr Gly Trp
            275                 280                 285

Arg Cys Gly Thr Ile Gln Ser Lys Asn Gln Thr Val Arg Tyr Ala Glu
        290                 295                 300

Gly Thr Val Thr Gly Leu Thr Arg Thr Thr Ala Cys Ala Glu Gly Gly
305                 310                 315                 320

Asp Ser Gly Gly Pro Trp Leu Thr Gly Ser Gln Ala Gln Val Thr
                325                 330                 335

Ser Gly Gly Thr Gly Asp Cys Arg Ser Gly Ile Thr Phe Phe Gln
            340                 345                 350

Pro Ile Asn Pro Leu Leu Ser Tyr Phe Gly Leu Gln Leu Val Thr Gly
            355                 360                 365

<210> SEQ ID NO 649
<211> LENGTH: 382
<212> TYPE: PRT
<213> ORGANISM: Streptomyces spp.

<400> SEQUENCE: 649

Met Arg His Thr Gly Arg Asn Ala Ile Gly Ala Ala Ile Ala Ala Ser
 1               5                  10                  15

Ala Leu Ala Phe Ala Leu Val Pro Ser Gln Ala Ala Ala Asn Asp Thr
             20                  25                  30
```

```
Leu Thr Glu Arg Ala Glu Ala Val Ala Asp Leu Pro Ala Gly Val
        35                  40                  45

Leu Asp Ala Met Glu Arg Asp Leu Gly Leu Ser Gln Glu Ala Gly
 50                  55                  60

Leu Lys Leu Val Ala Glu His Asp Ala Ala Leu Gly Glu Thr Leu
 65                  70                  75                  80

Ser Ala Asp Leu Asp Ala Phe Ala Gly Ser Trp Leu Ala Glu Gly
                 85                  90                  95

Glu Leu Val Val Ala Thr Thr Ser Glu Ala Glu Ala Glu Ile Thr
                100                 105                 110

Glu Ala Gly Ala Thr Ala Glu Val Val Asp His Thr Leu Ala Glu Leu
            115                 120                 125

Asp Ser Val Lys Asp Ala Leu Asp Thr Ala Ala Glu Ser Tyr Asp Thr
        130                 135                 140

Thr Asp Ala Pro Val Trp Tyr Val Asp Val Thr Thr Asn Gly Val Val
145                 150                 155                 160

Leu Leu Thr Ser Asp Val Thr Glu Ala Glu Gly Phe Val Glu Ala Ala
                165                 170                 175

Gly Val Asn Ala Ala Val Asp Ile Gln Thr Ser Asp Glu Gln Pro
            180                 185                 190

Gln Ala Phe Tyr Asp Leu Val Gly Gly Asp Ala Tyr Tyr Met Gly Gly
        195                 200                 205

Gly Arg Cys Ser Val Gly Phe Ser Val Thr Gln Gly Ser Thr Pro Gly
    210                 215                 220

Phe Ala Thr Ala Gly His Cys Gly Thr Val Gly Thr Ser Thr Thr Gly
225                 230                 235                 240

Tyr Asn Gln Ala Ala Gln Gly Thr Phe Glu Ser Ser Phe Pro Gly
                245                 250                 255

Asp Asp Met Ala Trp Val Ser Val Asn Ser Asp Trp Asn Thr Thr Pro
            260                 265                 270

Thr Val Asn Glu Gly Glu Val Thr Val Ser Gly Ser Thr Glu Ala Ala
                275                 280                 285

Val Gly Ala Ser Ile Cys Arg Ser Gly Ser Thr Thr Gly Trp His Cys
        290                 295                 300

Gly Thr Ile Gln Gln His Asn Thr Ser Val Thr Tyr Pro Glu Gly Thr
305                 310                 315                 320

Ile Thr Gly Val Thr Arg Thr Ser Val Cys Ala Glu Pro Gly Asp Ser
                325                 330                 335

Gly Gly Ser Tyr Ile Ser Gly Ser Gln Ala Gln Gly Val Thr Ser Gly
            340                 345                 350

Gly Ser Gly Asn Cys Thr Ser Gly Gly Thr Thr Tyr His Gln Pro Ile
        355                 360                 365

Asn Pro Leu Leu Ser Ala Tyr Gly Leu Asp Leu Val Thr Gly
        370                 375                 380

<210> SEQ ID NO 650
<211> LENGTH: 388
<212> TYPE: PRT
<213> ORGANISM: Streptomyces spp.

<400> SEQUENCE: 650

Met Arg Leu Lys Gly Arg Thr Val Ala Ile Gly Ser Ala Leu Ala Ala
 1               5                  10                  15

Ser Ala Leu Ala Leu Ser Leu Val Pro Ala Asn Ala Ser Ser Glu Leu
                20                  25                  30
```

Pro Ser Ala Glu Thr Ala Lys Ala Asp Ala Leu Val Glu Gln Leu Pro
                35                  40                  45

Ala Gly Met Val Asp Ala Met Glu Arg Asp Leu Gly Val Pro Ala Ala
    50                  55                  60

Glu Val Gly Asn Gln Leu Val Ala Glu His Ala Ala Val Leu Glu
65                  70                  75                  80

Glu Ser Leu Ser Glu Asp Leu Ser Gly Tyr Ala Gly Ser Trp Ile Val
                85                  90                  95

Glu Gly Thr Ser Glu His Val Val Ala Thr Asp Arg Ala Glu Ala
            100                 105                 110

Ala Glu Ile Thr Ala Ala Gly Ala Thr Ala Thr Val Val Glu His Ser
            115                 120                 125

Leu Ala Glu Leu Glu Ala Val Lys Asp Ile Leu Asp Glu Ala Ala Thr
    130                 135                 140

Ala Asn Pro Glu Asp Ala Ala Pro Val Trp Tyr Val Asp Val Thr Thr
145                 150                 155                 160

Asn Glu Val Val Val Leu Ala Ser Asp Val Pro Ala Ala Glu Ala Phe
                165                 170                 175

Val Ala Ala Ser Gly Ala Asp Ala Ser Thr Val Arg Val Glu Arg Ser
            180                 185                 190

Asp Glu Ser Pro Gln Pro Phe Tyr Asp Leu Val Gly Gly Asp Ala Tyr
        195                 200                 205

Tyr Ile Gly Asn Gly Arg Cys Ser Ile Gly Phe Ser Val Arg Gln Gly
    210                 215                 220

Ser Thr Pro Gly Phe Val Thr Ala Gly His Cys Gly Ser Val Gly Asn
225                 230                 235                 240

Ala Thr Thr Gly Phe Asn Arg Val Ser Gln Gly Thr Phe Arg Gly Ser
                245                 250                 255

Trp Phe Pro Gly Arg Asp Met Ala Trp Val Ala Val Asn Ser Asn Trp
            260                 265                 270

Thr Pro Thr Ser Leu Val Arg Asn Ser Gly Ser Gly Val Arg Val Thr
        275                 280                 285

Gly Ser Thr Gln Ala Thr Val Gly Ser Ser Ile Cys Arg Ser Gly Ser
    290                 295                 300

Thr Thr Gly Trp Arg Cys Gly Thr Ile Gln Gln His Asn Thr Ser Val
305                 310                 315                 320

Thr Tyr Pro Gln Gly Thr Ile Thr Gly Val Thr Arg Thr Ser Ala Cys
                325                 330                 335

Ala Gln Pro Gly Asp Ser Gly Gly Ser Phe Ile Ser Gly Thr Gln Ala
            340                 345                 350

Gln Gly Val Thr Ser Gly Gly Ser Gly Asn Cys Ser Ile Gly Gly Thr
        355                 360                 365

Thr Phe His Gln Pro Val Asn Pro Ile Leu Ser Gln Tyr Gly Leu Thr
    370                 375                 380

Leu Val Arg Ser
385

<210> SEQ ID NO 651
<211> LENGTH: 458
<212> TYPE: PRT
<213> ORGANISM: Streptomyces lividans

<400> SEQUENCE: 651

Met Val Gly Arg His Ala Ala Arg Ser Arg Arg Ala Ala Leu Thr Ala
1               5                   10                  15

Leu Gly Ala Leu Val Leu Thr Ala Leu Pro Ser Ala Ala Ser Ala Ala
            20                  25                  30

Pro Pro Pro Val Pro Gly Pro Arg Pro Ala Val Ala Arg Thr Pro Asp
            35                  40                  45

Ala Ala Thr Ala Pro Ala Arg Met Leu Ser Ala Met Glu Arg Asp Leu
 50                  55                  60

Arg Leu Ala Pro Gly Gln Ala Ala Arg Pro Val Asn Glu Ala Glu
 65                  70                  75                  80

Ala Gly Thr Arg Ala Gly Met Leu Arg Asn Thr Leu Gly Asp Arg Phe
                 85                  90                  95

Ala Gly Ala Trp Val Ser Gly Ala Thr Ser Ala Glu Leu Thr Val Ala
                100                 105                 110

Thr Thr Asp Ala Ala Asp Thr Ala Ala Ile Glu Ala Gln Gly Ala Lys
            115                 120                 125

Ala Ala Val Val Gly Arg Asn Leu Ala Glu Leu Arg Ala Val Lys Glu
            130                 135                 140

Lys Leu Asp Ala Ala Ala Val Arg Thr Arg Thr Arg Gln Thr Pro Val
145                 150                 155                 160

Trp Tyr Val Asp Val Lys Thr Asn Arg Val Thr Val Gln Ala Thr Gly
                165                 170                 175

Ala Ser Ala Ala Ala Ala Phe Val Glu Ala Ala Gly Val Pro Ala Ala
                180                 185                 190

Asp Val Gly Val Arg Val Ser Pro Asp Gln Pro Arg Val Leu Glu Asp
            195                 200                 205

Leu Val Gly Gly Asp Ala Tyr Tyr Ile Asp Asp Gln Ala Arg Cys Ser
210                 215                 220

Ile Gly Phe Ser Val Thr Lys Asp Asp Gln Gly Phe Ala Thr Ala
225                 230                 235                 240

Gly His Cys Gly Asp Pro Gly Ala Thr Thr Gly Tyr Asn Glu Ala
                245                 250                 255

Asp Gln Gly Thr Phe Gln Ala Ser Thr Phe Pro Gly Lys Asp Met Ala
            260                 265                 270

Trp Val Gly Val Asn Ser Asp Trp Thr Ala Thr Pro Asp Val Lys Ala
            275                 280                 285

Glu Gly Gly Glu Lys Ile Gln Leu Ala Gly Ser Val Glu Ala Leu Val
290                 295                 300

Gly Ala Ser Val Cys Arg Ser Gly Ser Thr Thr Gly Trp His Cys Gly
305                 310                 315                 320

Thr Ile Gln Gln His Asp Thr Ser Val Thr Tyr Pro Glu Gly Thr Val
                325                 330                 335

Asp Gly Leu Thr Gly Thr Thr Val Cys Ala Glu Pro Gly Asp Ser Gly
            340                 345                 350

Gly Pro Phe Val Ser Gly Val Gln Ala Gln Gly Thr Thr Ser Gly Gly
            355                 360                 365

Ser Gly Asp Cys Thr Asn Gly Gly Thr Thr Phe Tyr Gln Pro Val Asn
370                 375                 380

Pro Leu Leu Ser Asp Phe Gly Leu Thr Leu Lys Thr Thr Ser Ala Ala
385                 390                 395                 400

Thr Gln Thr Pro Ala Pro Gln Asp Asn Ala Ala Asp Ala Trp Thr
                405                 410                 415

Ala Gly Arg Val Tyr Glu Val Gly Thr Thr Val Ser Tyr Asp Gly Val
            420                 425                 430

Arg Tyr Arg Cys Leu Gln Ser His Gln Ala Gln Gly Val Gly Ser Pro

-continued

```
              435                 440                 445
Ala Ser Val Pro Ala Leu Trp Gln Arg Val
        450                 455

<210> SEQ ID NO 652
<211> LENGTH: 458
<212> TYPE: PRT
<213> ORGANISM: Streptomyces coelicolor A3(2)

<400> SEQUENCE: 652

Met Val Gly Arg His Ala Ala Arg Ser Arg Ala Ala Leu Thr Ala
1               5                   10                  15

Leu Gly Ala Leu Val Leu Thr Ala Leu Pro Ser Ala Ala Ser Ala Ala
            20                  25                  30

Pro Pro Pro Val Pro Gly Pro Arg Pro Ala Val Ala Arg Thr Pro Asp
        35                  40                  45

Ala Ala Thr Ala Pro Ala Arg Met Leu Ser Ala Met Glu Arg Asp Leu
    50                  55                  60

Arg Leu Ala Pro Gly Gln Ala Ala Arg Leu Val Asn Glu Ala Glu
65                  70                  75                  80

Ala Gly Thr Arg Ala Gly Met Leu Arg Asn Thr Leu Gly Asp Arg Phe
                85                  90                  95

Ala Gly Ala Trp Val Ser Gly Ala Thr Ser Ala Glu Leu Thr Val Ala
            100                 105                 110

Thr Thr Asp Ala Ala Asp Thr Ala Ala Ile Glu Ala Gln Gly Ala Lys
        115                 120                 125

Ala Ala Val Val Gly Arg Asn Leu Ala Glu Leu Arg Ala Val Lys Glu
    130                 135                 140

Lys Leu Asp Ala Ala Ala Val Arg Thr Arg Thr Arg Gln Thr Pro Val
145                 150                 155                 160

Trp Tyr Val Asp Val Lys Thr Asn Arg Val Thr Val Gln Ala Thr Gly
                165                 170                 175

Ala Ser Ala Ala Ala Ala Phe Val Glu Ala Ala Gly Val Pro Ala Ala
            180                 185                 190

Asp Val Gly Val Arg Val Ser Pro Asp Gln Pro Arg Val Leu Glu Asp
        195                 200                 205

Leu Val Gly Gly Asp Ala Tyr Tyr Ile Asp Asp Gln Ala Arg Cys Ser
    210                 215                 220

Ile Gly Phe Ser Val Thr Lys Asp Asp Gln Glu Gly Phe Ala Thr Ala
225                 230                 235                 240

Gly His Cys Gly Asp Pro Gly Ala Thr Thr Thr Gly Tyr Asn Glu Ala
                245                 250                 255

Asp Gln Gly Thr Phe Gln Ala Ser Thr Phe Pro Gly Lys Asp Met Ala
            260                 265                 270

Trp Val Gly Val Asn Ser Asp Trp Thr Ala Thr Pro Asp Val Lys Ala
        275                 280                 285

Glu Gly Gly Glu Lys Ile Gln Leu Ala Gly Ser Val Glu Ala Leu Val
    290                 295                 300

Gly Ala Ser Val Cys Arg Ser Gly Ser Thr Thr Gly Trp His Cys Gly
305                 310                 315                 320

Thr Ile Gln Gln His Asp Thr Ser Val Thr Tyr Pro Glu Gly Thr Val
                325                 330                 335

Asp Gly Leu Thr Glu Thr Thr Val Cys Ala Glu Pro Gly Asp Ser Gly
            340                 345                 350

Gly Pro Phe Val Ser Gly Val Gln Ala Gln Gly Thr Thr Ser Gly Gly
```

```
              355                 360                 365
Ser Gly Asp Cys Thr Asn Gly Gly Thr Thr Phe Tyr Gln Pro Val Asn
    370                 375                 380

Pro Leu Leu Ser Asp Phe Gly Leu Thr Leu Lys Thr Thr Ser Ala Ala
385                 390                 395                 400

Thr Gln Thr Pro Ala Pro Gln Asp Asn Ala Ala Asp Ala Trp Thr
            405                 410                 415

Ala Gly Arg Val Tyr Glu Val Gly Thr Thr Val Ser Tyr Asp Gly Val
            420                 425                 430

Arg Tyr Arg Cys Leu Gln Ser His Gln Ala Gln Gly Val Gly Ser Pro
            435                 440                 445

Ala Ser Val Pro Ala Leu Trp Gln Arg Val
    450                 455

<210> SEQ ID NO 653
<211> LENGTH: 456
<212> TYPE: PRT
<213> ORGANISM: Streptomyces avermitilis MA-4680

<400> SEQUENCE: 653

Met Val His Arg His Val Gly Ala Gly Cys Ala Gly Leu Ser Val Leu
1               5                   10                  15

Ala Thr Leu Val Leu Thr Gly Leu Pro Ala Ala Ala Ile Glu Pro
            20                  25                  30

Pro Gly Pro Ala Pro Ala Pro Ser Ala Val Gln Pro Leu Gly Ala Gly
            35                  40                  45

Asn Pro Ser Thr Ala Val Leu Gly Ala Leu Gln Arg Asp Leu His Leu
50                  55                  60

Thr Asp Thr Gln Ala Lys Thr Arg Leu Val Asn Glu Met Glu Ala Gly
65                  70                  75                  80

Thr Arg Ala Gly Arg Leu Gln Asn Ala Leu Gly Lys His Phe Ala Gly
            85                  90                  95

Ala Trp Val His Gly Ala Ala Ser Ala Asp Leu Thr Val Ala Thr Thr
            100                 105                 110

His Ala Thr Asp Ile Pro Ala Ile Thr Ala Gly Gly Ala Thr Ala Val
            115                 120                 125

Val Val Lys Thr Gly Leu Asp Asp Leu Lys Gly Ala Lys Lys Lys Leu
            130                 135                 140

Asp Ser Ala Val Ala His Gly Gly Thr Ala Val Asn Thr Pro Val Arg
145                 150                 155                 160

Tyr Val Asp Val Arg Thr Asn Arg Val Thr Leu Gln Ala Arg Ser Arg
                165                 170                 175

Ala Ala Ala Asp Ala Leu Ile Ala Ala Gly Val Asp Ser Gly Leu
            180                 185                 190

Val Asp Val Lys Val Ser Glu Asp Arg Pro Arg Ala Leu Phe Asp Ile
            195                 200                 205

Arg Gly Gly Asp Ala Tyr Tyr Ile Asp Asn Thr Ala Arg Cys Ser Val
            210                 215                 220

Gly Phe Ser Val Thr Lys Gly Asn Gln Gln Gly Phe Ala Thr Ala Gly
225                 230                 235                 240

His Cys Gly Arg Ala Gly Ala Pro Thr Ala Gly Phe Asn Glu Val Ala
                245                 250                 255

Gln Gly Thr Val Gln Ala Ser Val Phe Pro Gly His Asp Met Ala Trp
            260                 265                 270

Val Gly Val Asn Ser Asp Trp Thr Ala Thr Pro Asp Val Ala Gly Ala
```

```
                    275                 280                 285
Ala Gly Gln Asn Val Ser Ile Ala Gly Ser Val Gln Ala Ile Val Gly
    290                 295                 300

Ala Ala Ile Cys Arg Ser Gly Ser Thr Thr Gly Trp His Cys Gly Thr
305                 310                 315                 320

Val Glu Glu His Asp Thr Ser Val Thr Tyr Glu Gly Thr Val Asp
                325                 330                 335

Gly Leu Thr Arg Thr Thr Val Cys Ala Glu Pro Gly Asp Ser Gly Gly
            340                 345                 350

Ser Phe Val Ser Gly Ser Gln Ala Gln Gly Val Thr Ser Gly Gly Ser
            355                 360                 365

Gly Asp Cys Thr Arg Gly Gly Thr Thr Tyr Tyr Gln Pro Val Asn Pro
    370                 375                 380

Ile Leu Ser Thr Tyr Gly Leu Thr Leu Lys Thr Ser Thr Ala Pro Thr
385                 390                 395                 400

Asp Thr Pro Ser Asp Pro Val Asp Gln Ser Gly Val Trp Ala Ala Gly
                405                 410                 415

Arg Val Tyr Glu Val Gly Ala Gln Val Thr Tyr Ala Gly Val Thr Tyr
            420                 425                 430

Gln Cys Leu Gln Ser His Gln Ala Gln Gly Val Trp Gln Pro Ala Ala
            435                 440                 445

Thr Pro Ala Leu Trp Gln Arg Leu
    450                 455

<210> SEQ ID NO 654
<211> LENGTH: 458
<212> TYPE: PRT
<213> ORGANISM: Streptomyces lividans

<400> SEQUENCE: 654

Met Pro His Arg His Arg His Arg Ala Val Gly Ala Ala Val Ala
1               5                   10                  15

Ala Thr Ala Ala Leu Leu Val Ala Gly Leu Ser Gly Ser Ala Ser Ala
            20                  25                  30

Gly Thr Ala Pro Ala Gly Ser Ala Pro Thr Ala Ala Glu Thr Leu Arg
        35                  40                  45

Thr Asp Ala Ala Pro Pro Ala Leu Leu Lys Ala Met Gln Arg Asp Leu
    50                  55                  60

Gly Ile Asp Arg Arg Gln Ala Glu Arg Leu Val Asn Glu Ala Glu
65                  70                  75                  80

Ala Gly Ala Thr Ala Gly Arg Leu Arg Ala Ala Leu Gly Gly Asp Phe
                85                  90                  95

Ala Gly Ala Trp Val Arg Gly Ala Glu Ser Gly Thr Leu Thr Val Ala
            100                 105                 110

Thr Thr Asp Ala Gly Asp Val Ala Ala Val Glu Ala Arg Gly Ala Glu
        115                 120                 125

Ala Lys Val Val Arg His Ser Leu Ala Asp Leu Asp Ala Ala Lys Ala
    130                 135                 140

Arg Leu Asp Thr Ala Ala Ala Gly Leu Asn Thr Ala Asp Ala Pro Val
145                 150                 155                 160

Trp Tyr Val Asp Thr Arg Thr Asn Thr Val Val Glu Ala Ile Arg
                165                 170                 175

Pro Ala Ala Ala Arg Ser Leu Leu Thr Ala Ala Gly Val Asp Gly Ser
            180                 185                 190

Leu Ala His Val Lys Asn Arg Thr Glu Arg Pro Arg Thr Phe Tyr Asp
```

```
                195                 200                 205
Leu Arg Gly Gly Glu Ala Tyr Tyr Ile Asn Asn Ser Ser Arg Cys Ser
210                 215                 220

Ile Gly Phe Pro Ile Thr Lys Gly Thr Gln Gln Gly Phe Ala Thr Ala
225                 230                 235                 240

Gly His Cys Asp Arg Ala Gly Ser Ser Thr Thr Gly Ala Asn Arg Val
                245                 250                 255

Ala Gln Gly Thr Phe Gln Gly Ser Ile Phe Pro Gly Arg Asp Met Ala
                260                 265                 270

Trp Val Ala Thr Asn Ser Ser Trp Thr Ala Thr Pro Tyr Val Leu Gly
            275                 280                 285

Ala Gly Gly Gln Asn Val Gln Val Thr Gly Ser Thr Ala Ser Pro Val
            290                 295                 300

Gly Ala Ser Val Cys Arg Ser Gly Ser Thr Thr Gly Trp His Cys Gly
305                 310                 315                 320

Thr Val Thr Gln Leu Asn Thr Ser Val Thr Tyr Gln Glu Gly Thr Ile
                325                 330                 335

Ser Pro Val Thr Arg Thr Thr Val Cys Ala Glu Pro Gly Asp Ser Gly
                340                 345                 350

Gly Ser Phe Ile Ser Gly Ser Gln Ala Gln Gly Val Thr Ser Gly Gly
            355                 360                 365

Ser Gly Asp Cys Arg Thr Gly Gly Thr Phe Phe Gln Pro Ile Asn
370                 375                 380

Ala Leu Leu Gln Asn Tyr Gly Leu Thr Leu Lys Thr Thr Gly Gly Asp
385                 390                 395                 400

Asp Gly Gly Asp Asp Gly Gly Glu Glu Pro Gly Gly Thr Trp Ala
                405                 410                 415

Ala Gly Thr Val Tyr Gln Pro Gly Asp Thr Val Thr Tyr Gly Gly Ala
                420                 425                 430

Thr Phe Arg Cys Leu Gln Gly His Gln Ala Tyr Ala Gly Trp Glu Pro
            435                 440                 445

Pro Asn Val Pro Ala Leu Trp Gln Arg Val
    450                 455

<210> SEQ ID NO 655
<211> LENGTH: 463
<212> TYPE: PRT
<213> ORGANISM: Streptomyces coelicolor A3(2)

<400> SEQUENCE: 655

Met Pro His Arg His Arg His His Arg Ala Val Gly Ala Ala Val Ala
1               5                   10                  15

Ala Thr Ala Ala Leu Leu Val Ala Gly Leu Ser Gly Ser Ala Ser Ala
                20                  25                  30

Gly Thr Ala Pro Ala Gly Ser Ala Pro Thr Ala Ala Glu Thr Leu Arg
            35                  40                  45

Thr Asp Ala Ala Pro Pro Ala Leu Leu Lys Ala Met Gln Arg Asp Leu
50                  55                  60

Gly Leu Asp Arg Arg Gln Ala Glu Arg Arg Leu Val Asn Glu Ala Glu
65                  70                  75                  80

Ala Gly Ala Thr Ala Gly Arg Leu Arg Ala Ala Leu Gly Gly Asp Phe
                85                  90                  95

Ala Gly Ala Trp Val Arg Gly Ala Glu Ser Gly Thr Leu Thr Val Ala
                100                 105                 110

Thr Thr Asp Ala Gly Asp Val Ala Ala Ile Glu Ala Arg Gly Ala Glu
```

```
                115             120                 125
Ala Lys Val Val Arg His Ser Leu Ala Asp Leu Asp Ala Ala Lys Ala
130                 135                 140

Arg Leu Asp Thr Ala Ala Ala Gly Leu Asn Thr Ala Asp Ala Pro Val
145                 150                 155                 160

Trp Tyr Val Asp Thr Arg Thr Asn Thr Val Val Glu Ala Ile Arg
                165                 170                 175

Pro Ala Ala Ala Arg Ser Leu Leu Thr Ala Ala Gly Val Asp Gly Ser
                180                 185                 190

Leu Ala His Val Lys Asn Arg Thr Glu Arg Pro Arg Thr Phe Tyr Asp
                195                 200                 205

Leu Arg Gly Gly Glu Ala Tyr Tyr Ile Asn Asn Ser Ser Arg Cys Ser
210                 215                 220

Ile Gly Phe Pro Ile Thr Lys Gly Thr Gln Gln Gly Phe Ala Thr Ala
225                 230                 235                 240

Gly His Cys Gly Arg Ala Gly Ser Ser Thr Thr Gly Ala Asn Arg Val
                245                 250                 255

Ala Gln Gly Thr Phe Gln Gly Ser Ile Phe Pro Gly Arg Asp Met Ala
                260                 265                 270

Trp Val Ala Thr Asn Ser Ser Trp Thr Ala Thr Pro Tyr Val Leu Gly
                275                 280                 285

Ala Gly Gly Gln Asn Val Gln Val Thr Gly Ser Thr Ala Ser Pro Val
                290                 295                 300

Gly Ala Ser Val Cys Arg Ser Gly Ser Thr Thr Gly Trp His Cys Gly
305                 310                 315                 320

Thr Val Thr Gln Leu Asn Thr Ser Val Thr Tyr Gln Glu Gly Thr Ile
                325                 330                 335

Ser Pro Val Thr Arg Thr Thr Val Cys Ala Glu Pro Gly Asp Ser Gly
                340                 345                 350

Gly Ser Phe Ile Ser Gly Ser Gln Ala Gln Val Thr Ser Gly Gly
                355                 360                 365

Ser Gly Asp Cys Arg Thr Gly Gly Glu Thr Phe Phe Gln Pro Ile Asn
                370                 375                 380

Ala Leu Leu Gln Asn Tyr Gly Leu Thr Leu Lys Thr Thr Gly Gly Asp
385                 390                 395                 400

Asp Gly Gly Gly Asp Asp Gly Gly Gly Asp Gly Gly Glu Glu Pro
                405                 410                 415

Gly Gly Thr Trp Ala Ala Gly Thr Val Tyr Gln Pro Gly Asp Thr Val
                420                 425                 430

Thr Tyr Gly Gly Ala Thr Phe Arg Cys Leu Gln Gly His Gln Ala Tyr
                435                 440                 445

Ala Gly Trp Glu Pro Pro Asn Val Pro Ala Leu Trp Gln Arg Val
                450                 455                 460

<210> SEQ ID NO 656
<211> LENGTH: 457
<212> TYPE: PRT
<213> ORGANISM: Streptomyces griseus

<400> SEQUENCE: 656

Met Glu Arg Thr Thr Leu Arg Arg Arg Ala Leu Val Ala Gly Thr Ala
1               5                   10                  15

Thr Val Ala Val Gly Ala Leu Ala Leu Ala Gly Leu Thr Gly Val Ala
                20                  25                  30

Ser Ala Asp Pro Ala Ala Thr Ala Ala Pro Pro Val Ser Ala Asp Ser
```

-continued

```
                35                      40                      45
Leu Ser Pro Gly Met Leu Ala Ala Leu Glu Arg Asp Leu Gly Leu Asp
 50                      55                      60
Glu Asp Ala Ala Arg Ser Arg Ile Ala Asn Glu Tyr Arg Ala Ala Ala
 65                      70                      75                      80
Val Ala Ala Gly Leu Glu Lys Ser Leu Gly Ala Arg Tyr Ala Gly Ala
                 85                      90                      95
Arg Val Ser Gly Ala Lys Ala Thr Leu Thr Val Ala Thr Asp Ala
                100                     105                     110
Ser Glu Ala Ala Arg Ile Thr Glu Ala Gly Ala Arg Ala Glu Val Val
                115                     120                     125
Gly His Ser Leu Asp Arg Phe Glu Gly Val Lys Lys Ser Leu Asp Lys
130                     135                     140
Ala Ala Leu Asp Lys Ala Pro Lys Asn Val Pro Val Trp Tyr Val Asp
145                     150                     155                     160
Val Ala Ala Asn Arg Val Val Asn Ala Ala Ser Pro Ala Ala Gly
                165                     170                     175
Gln Ala Phe Leu Lys Val Ala Gly Val Asp Arg Gly Leu Val Thr Val
                180                     185                     190
Ala Arg Ser Ala Glu Gln Pro Arg Ala Leu Ala Asp Ile Arg Gly Gly
                195                     200                     205
Asp Ala Tyr Tyr Met Asn Gly Ser Gly Arg Cys Ser Val Gly Phe Ser
                210                     215                     220
Val Thr Arg Gly Thr Gln Asn Gly Phe Ala Thr Ala Gly His Cys Gly
225                     230                     235                     240
Arg Val Gly Thr Thr Asn Gly Val Asn Gln Gln Ala Gln Gly Thr
                245                     250                     255
Phe Gln Gly Ser Thr Phe Pro Gly Arg Asp Ile Ala Trp Val Ala Thr
                260                     265                     270
Asn Ala Asn Trp Thr Pro Arg Pro Leu Val Asn Gly Tyr Gly Arg Gly
                275                     280                     285
Asp Val Thr Val Ala Gly Ser Thr Ala Ser Val Gly Ala Ser Val
                290                     295                     300
Cys Arg Ser Gly Ser Thr Thr Gly Trp His Cys Gly Thr Ile Gln Gln
305                     310                     315                     320
Leu Asn Thr Ser Val Thr Tyr Pro Glu Gly Thr Ile Ser Gly Val Thr
                325                     330                     335
Arg Thr Ser Val Cys Ala Glu Pro Gly Asp Ser Gly Ser Tyr Ile
                340                     345                     350
Ser Gly Ser Gln Ala Gln Gly Val Thr Ser Gly Ser Gly Asn Cys
                355                     360                     365
Ser Ser Gly Gly Thr Thr Tyr Phe Gln Pro Ile Asn Pro Leu Leu Gln
370                     375                     380
Ala Tyr Gly Leu Thr Leu Val Ser Gly Gly Thr Pro Thr Asp
385                     390                     395                     400
Pro Pro Thr Thr Pro Pro Thr Asp Ser Pro Gly Gly Thr Trp Ala Val
                405                     410                     415
Gly Thr Ala Tyr Ala Ala Gly Ala Thr Val Thr Tyr Gly Gly Ala Thr
                420                     425                     430
Tyr Arg Cys Leu Gln Ala His Thr Ala Gln Pro Gly Trp Thr Pro Ala
                435                     440                     445
Asp Val Pro Ala Leu Trp Gln Arg Val
450                     455
```

MICROCOCCINEAE SERINE PROTEASE POLYPEPTIDES AND COMPOSITIONS THEREOF

The present application claims priority under 35 U.S.C. §119, to co-pending U.S. Provisional Patent Application Ser. No. 60/523,609, filed Nov. 19, 2003.

SEQUENCE LISTING

The sequence listing submitted via EFS, in compliance with 37 C.F.R. §1.52(e), is incorporated herein by reference. The sequence listing text file submitted via EFS contains the file "SequenceListing_amd" created on May 7, 2012, which is 315,161 bytes in size.

FIELD OF THE INVENTION

The present invention provides novel serine proteases, novel genetic material encoding these enzymes, and proteolytic proteins obtained from *Micrococcineae* spp., including but not limited to *Cellulomonas* spp. and variant proteins developed therefrom. In particular, the present invention provides protease compositions obtained from a *Cellulomonas* spp, DNA encoding the protease, vectors comprising the DNA encoding the protease, host cells transformed with the vector DNA, and an enzyme produced by the host cells. The present invention also provides cleaning compositions (e.g., detergent compositions), animal feed compositions, and textile and leather processing compositions comprising protease(s) obtained from a *Micrococcineae* spp., including but not limited to *Cellulomonas* spp. In alternative embodiments, the present invention provides mutant (i.e., variant) proteases derived from the wild-type proteases described herein. These mutant proteases also find use in numerous applications.

BACKGROUND OF THE INVENTION

Serine proteases are a subgroup of carbonyl hydrolases comprising a diverse class of enzymes having a wide range of specificities and biological functions (See e.g., Stroud, Sci. Amer., 131:74-88). Despite their functional diversity, the catalytic machinery of serine proteases has been approached by at least two genetically distinct families of enzymes: 1) the subtilisins; and 2) the mammalian chymotrypsin-related and homologous bacterial serine proteases (e.g., trypsin and *S. griseus* trypsin). These two families of serine proteases show remarkably similar mechanisms of catalysis (See e.g., Kraut, Ann. Rev. Biochem., 46:331-358 [1977]). Furthermore, although the primary structure is unrelated, the tertiary structure of these two enzyme families brings together a conserved catalytic triad of amino acids consisting of serine, histidine and aspartate. The subtilisins and chymotrypsin-related serine proteases both have a catalytic triad comprising aspartate, histidine and serine. In the subtilisin-related proteases the relative order of these amino acids, reading from the amino to carboxy terminus, is aspartate-histidine-serine. However, in the chymotrypsin-related proteases, the relative order is histidine-aspartate-serine. Much research has been conducted on the subtilisins, due largely to their usefulness in cleaning and feed applications. Additional work has been focused on the adverse environmental conditions (e.g., exposure to oxidative agents, chelating agents, extremes of temperature and/or pH) which can adversely impact the functionality of these enzymes in various applications. Nonetheless, there remains a need in the art for enzyme systems that are able to resist these adverse conditions and retain or have improved activity over those currently known in the art.

SUMMARY OF THE INVENTION

The present invention provides novel serine proteases, novel genetic material encoding these enzymes, and proteolytic proteins obtained from *Micrococcineae* spp., including but not limited to *Cellulomonas* spp. and variant proteins developed therefrom. In particular, the present invention provides protease compositions obtained from a *Cellulomonas* spp, DNA encoding the protease, vectors comprising the DNA encoding the protease, host cells transformed with the vector DNA, and an enzyme produced by the host cells. The present invention also provides cleaning compositions (e.g., detergent compositions), animal feed compositions, and textile and leather processing compositions comprising protease(s) obtained from a *Micrococcineae* spp., including but not limited to *Cellulomonas* spp. In alternative embodiments, the present invention provides mutant (i.e., variant) proteases derived from the wild-type proteases described herein. These mutant proteases also find use in numerous applications.

The present invention provides isolated serine proteases obtained from a member of the *Micrococcineae*. In some embodiments, the proteases are cellulomonadins. In some preferred embodiments, the protease is obtained from an organism selected from the group consisting of *Cellulomonas, Oerskovia, Cellulosimicrobium, Xylanibacterium,* and *Promicromonospora*. In some particularly preferred embodiments, the protease is obtained so from *Cellulomonas* 69B4. In further embodiments, the protease comprises the amino acid sequence set forth in SEQ ID NO:8. In additional embodiments, the present invention provides isolated serine proteases comprising at least 45% amino acid identity with serine protease comprising SEQ ID NO:8. In some embodiments, the isolated serine proteases comprise at least 50% identity, preferably at least 55%, more preferably at least 60%, yet more preferably at least 65%, even more preferably at least 70%, more preferably at least 75%, still more preferably at least 80%, more preferably 85%, yet more preferably 90%, even more preferably at least 95%, and most preferably 99% identity.

The present invention also provides compositions comprising isolated serine proteases having immunological cross-reactivity with the serine proteases obtained from the *Micrococcineae*. In some preferred embodiments, the serine proteases have immunological cross-reactivity with serine protease obtained from *Cellulomonas* 69B4. In alternative embodiments, the serine proteases have immunological cross-reactivity with serine protease comprising the amino acid sequence set forth in SEQ ID NO:8. In still further embodiments, the serine proteases have cross-reactivity with fragments (i.e., portions) of any of the serine proteases obtained from the *Micrococcineae*, the *Cellulomonas* 69B4 protease, and/or serine protease comprising the amino acid sequence set forth in SEQ ID NO:8.

In some embodiments, the present invention provides the amino acid sequence set forth in SEQ ID NO:8, wherein the sequence comprises substitutions at least one amino acid position selected from the group comprising positions 2, 8, 10, 11, 12, 13, 14, 15, 16, 24, 26, 31, 33, 35, 36, 38, 39, 40, 43, 46, 49, 51, 54, 61, 64, 65, 67, 70, 71, 76, 78, 79, 81, 83, 85, 86, 90, 93, 99, 100, 105, 107, 109, 112, 113, 116, 118, 119, 121, 123, 127, 145, 155, 159, 160, 163, 165, 170, 174, 179, 183, 184, 185, 186, 187, and 188. In alternative embodiments, the sequence comprises substitutions at least one amino acid position selected from the group comprising positions 1, 4, 22, 27, 28, 30, 32, 41, 47, 48, 55, 59, 63, 66, 69, 75, 77, 80, 84, 87, 88, 89, 92, 96, 110, 111, 114, 115, 117, 128, 134, 144, 143, 146, 151, 154, 156, 158, 161, 166, 176, 177, 181, 182, 187, and 189.

In some preferred embodiments, the present invention provides protease variants having an amino acid sequence comprising at least one substitution of an amino acid made at a position equivalent to a position in a *Cellulomonas* 69B4 protease comprising the amino acid sequence set forth in SEQ ID NO:8. In alternative embodiments, the present invention provides protease variants having an amino acid sequence comprising at least one substitution of an amino acid made at a position equivalent to a position in a *Cellulomonas* 69B4 protease comprising at least a portion of SEQ ID NO:8. In some embodiments, the substitutions are made at positions equivalent to positions 2, 8, 10, 11, 12, 13, 14, 15, 16, 24, 26, 31, 33, 35, 36, 38, 39, 40, 43, 46, 49, 51, 54, 61, 64, 65, 67, 70, 71, 76, 78, 79, 81, 83, 85, 86, 90, 93, 99, 100, 105, 107, 109, 112, 113, 116, 118, 119, 121, 123, 127, 145, 155, 159, 160, 163, 165, 170, 174, 179, 183, 184, 185, 186, 187, and 188 in a *Cellulomonas* 69B4 protease having an amino acid sequence set forth in SEQ ID NO:8. In alternative embodiments, the substitutions are made at positions equivalent to positions 1, 4, 22, 27, 28, 30, 32, 41, 47, 48, 55, 59, 63, 66, 69, 75, 77, 80, 84, 87, 88, 89, 92, 96, 110, 111, 114, 115, 117, 128, 134, 144, 143, 146, 151, 154, 156, 158, 161, 166, 176, 177, 181, 182, 187, and 189, in a *Cellulomonas* 69B4 protease having an amino acid sequence set forth in SEQ ID NO:8. In some preferred embodiments, the protease variants comprise the amino acid sequence comprising SEQ ID NO:8, wherein at least one amino acid position at positions selected from the group consisting of 14, 16, 35, 36, 65, 75, 76, 79, 123, 127, 159, and 179, are substituted with another amino acid. In some particularly preferred embodiments, the proteases comprise at least one mutation selected from the group consisting of R14L, R16I, R16L, R16Q, R35F, T36S, G65Q, Y75G, N76L, N76V, R79T, R123L, R123Q, R127A, R127K, R127Q, R159K, R159Q, and R179Q. In some alternative preferred embodiments, the proteases comprise multiple mutations selected from the group consisting of R16Q/R35F/ R159Q, R16Q/R123L, R14LJR127Q/R159Q, R14L/R179Q, R123L/R127Q/R179Q, R16Q/R79T/R127Q, and R16Q/ R79T. In some particularly preferred embodiments, the proteases comprise the following mutations R123L, R127Q, and R179Q.

The present invention also provides protease variants having amino acid sequences comprising at least one substitution selected from the group consisting of T36I, A38R, N170Y, N73T, G77T, N24A, T36G, N24E, L69S, T36N, T36S, E119R, N74G, T36W, S76W, N24T, N24Q, T36P, S76Y, T36H, G54D, G78A, S187P, R179V, N24V, V90P, T36D, L69H, G65P, G65R, N7L, W103M, N55F G186E, A70H, S76V, G186V, R159F, T36Y, T36V, G65V, N24M, S51A, G65Y, Q71I, V66H, P118A, T116F, A38F, N24H, V66D, S76L, G177M, G186I, H85Q, Q71K, Q71G, G65S, A38D, P118F, A38S, G65T, N67G, T36R, P118R, S114G, Y75I, I181H, G65Q, Y75G, T36F, A38H, R179M, T183I, G78S, A64W, Y75F, G77S, N24L, W103I, V3L, Q81V, R179D, G54R, T36L, Q71M, A70S, G49F, G54L, G54H, G78H, R179I, Q81K, V90I, A38L, N67L, T109I, R179N, V66I, G78T, R179Y, S187T, N67K, N73S, E119K, V3I, Q71H, I1Q, A64H, R14E, R179T, L69V, V150L, Q71A, G65L, Q71N, V905, A64N, I11A, N145I, H85T, A64Y, N145Q, V66L, S92G, S188M, G78D, N67A, N7S, V80H, G54K, A70D, P118H, D2G, G54M, Q81K, D2Q, V66E, I479P, A38N, N145E, R179L, T109H, R179K, V66A, G54A, G78N, T109A, R179A, N7A, R179E, H104K, A64R, and V80L. In further embodiments, wherein the amino acid sequence of the protease variants so comprise at least one substitution selected from the group consisting of H85R, H85L, T62I, N67H, G54I, N24F, T40V, T86A, G63V, G54Q, A64F, G77Y, R35F, T129S, R61M, I126L, S76N, T182V, R79G, T109P, R127F, R123E, P118I, T109R, I71S, T183K, N67T, P89N, F1T, A64K, G78I, T109L, G78V, A64M, A64S, T10G, G77N, A64L, N67D, S76T, N42H, D184F, D184R, S76I, S78R, A38K, W2I, V3T, T107S, A38V, F47I, N55Q, S76E, P118Q, ss T109G, Q71D, P118K, N67S, Q167N, N145G, I28L, I11T, A64I, G49K, G49A, G65A, N170D, H85K, S185I, I181N, V80F, L69W, S76R, D184H, V150M, T183M, N67Q, S51Q, A38Y, T107V, N145T, Q71F, A83N, S76A, N67R, T151L, T163L, S51F, Q81I, F47M, A41N, P118E, N67Y, T107M, N73H, 67V, G63W, T10K, I181G, S187E, T107H, D2A, L142V, A143N, A8G, S187L, V90A, G49L, N170L, G65H, T36C, Q12W, S76Q, A143S, F1A, N7H, S185V, A110T, N55K, N67F, N7I, A110S, N170A, Q81D, A64Q, Q71L, A38I, N112I, V90T, N145L, A64T, I11S, A30S, R123I, D2H, V66M, Q71R, V90L, L68W, N24S, R159E, V66N, D184Q, E133Q, A64V, D2N, G13M, T40S, S76K, G177S, G63Q, S15F, A8K, A70G, and A38G. In some preferred embodiments, these variants have improved casein hydrolysis performance as compared to wild-type *Cellulomonas* 69B4 protease.

The present invention also provides protease variants having amino acid sequences comprising at least one substitution selected from the group consisting of R35E, R35D, R14E, R14D, Q167E, G49C, S15R, S15H, I11W, S15C, G49Q, R35Q, R35V, G49E, R123D, R123Y, G49H, A38D, R35S, F47R, R123c, T151L, R14T, R35T, R123E, G49A, G49V, D56L, R35N, R35A, G12D, R35c, R123N, T46V, R123H, S155C, T121E, R127E, S113C, R123T, R16E, T46F, T121L, A38C, T46E, R123W, T44E, N55G, A8G, E119G, R35P, R14G, F59W, R127S, R61E, R14S, S155W, R123F, R123S, G49N, R127D, E119Y, A48E, N170D, R159T, S99A, G120, P118R, F165W, R127G, R35H, G12N, A22C, G12V, R16T, Y57G, T100A, T46Y, R159E, E119R, T107R, T151C, G54C, E119T, R61V, I11E, R14I, R61M, S15E, A22S, R16C, T36C, R16V, L125Q, M180L, R123Q, R14A, R14Q, R35M, R127K, R159Q, N112P, G124D, R179E, G49L, A41D, G177D, R123V, E119V, T10L, T109E, R179D, G12S, T10C, G91Q, S15Y, S155Y, R14C, T163D, T121F, R14N, F165E, N24E, A41C, R61T, G12I, P118K, T46C, I11T, R159D, N170C, R159V, S155I, I11Q, D2P, T100R, R159S, S114C, R16D, and P134R. In alternative embodiments, the protease variants have amino acid sequences comprising at least one substitution selected from the group consisting of S99G, T100K, R127A, F1P, S155V, T128A, F165H, G177E, A70M, S140P, A87E, D2I, R159K, T36V, R179c, E119N, T10Y, I172A, ABT, F47V, W103L, R61K, D2V, R179V, D2T, R159N, E119A, G54E, R16Q, G49S, R16I, S51L, S155E, S15M, R179I, T10Q, G12H, R159c, R179T, T163C, R159A, A132S, N157D, G13E, L141M, A41T, R123M, R14M, ABR, Q81P, N24T, T10D, A88F, R61Q, S99K, R179Y, T121A, N112E, S155T, T151V, S99Q, T10E, S92T, T109K, T44C, R123A, A87C, S15F, S155F, D56F, T10F, A83H, R179M, T121D, G13D, P118C, G49F, Q174C, S114E, T86E, F1N, T115C, R127c, R123K, V66N, G12Y, S113A, S15N, A175T, R79T, R123G, R179S, R179N, R123I, P118A, S187E, N112D, A70G, E119L, E119S, R159M, R14H, R179F, A64C, A41S, R179W, N24G, T100Q, P118W, Q81G, G49K, R14L, N55A, R35K, R79V, D2M, T160D, A83D, R179L, S51A, G12S, S99H, N42D, S188E, T10M, L125Q, T116N, A70P, Q174S, G65D, S113D, E119Q, A83E, N170L, Q81A, S51C, P118G, Q174T, I28V, S15G, and T116G. In some preferred embodiments, these variants have improved LAS stability as compared to wild-type *Cellulomonas* 69B4 protease.

The present invention also provides protease variants having amino acid sequences comprising at least one substitution selected from the group consisting of G26I, G26K, G26Q, G26V, G26W, F27V, F27W, I28P, T29E, T129W, T40D, T40Q, R43D, P43H, P43K, P43L, A22C, T40H, P89W, G91L, S18E, F59K, A30M, A30N, G31M, C33M, G161L, G161V, P43N, G26E, N73P, G84C, G84P, G45V, C33L, Y9E, Y9P, A147E, C158H, I28W, A48P, A22S, T62R, S137R, S155P, S155R, G156I, G156L, Q81A, R96c, I4D, I4P, A70P, C105E, C105G, C105K, C105M, C105N, C105S, T128A, T128V, T128G, S140P, G12D, C33N, C33E, T164G, G45A, G156P, S99A, Q167L, S155W, I28T, R96F, A30P, R123W, T40P, T39R, C105P, T100A, C105W, S155K, T46Y, R123F, I4G, S155Y, T46V, A93S, Y57N, Q81S, G186S, G31H, T10Y, G31V, A83H, A38D, R123Y, R79T, C158G, G31Y, Q81P, R96E, A30Y, R159A, A22T, T40N, Y57M, G31N, Q81G, T164L, T121E, T10F, Q146P, R123N, V3R, P43G, Q81H, Q81D, G161I, C158M; N24T, T10W, T128S, T160I, Y176P, S155F, T128C, L125A, P168Y, T62G, F166S, S188A, Q81F, T46W, A70G, and A38G. In alternative embodiments, the protease variants have amino acid sequences comprising at least one substitution selected from the group consisting of S188E, S188V, Y117K, Y117Q, Y117R, Y117V, R127K, R127Q, R123L, T86S, R123I, Q81E, L125M, H32A, S188T, N74F, C33D, F27I, A83M, Q71Y, R123T, V90A, F59W, L141C, N170E, T46F, S51V, G162P, S185R, A41S, R79V, T151C, T107S, T129Y, M180L, F166C, C105T, T160E, P89A, R159T, T183P, S188M, T10L, G25S, N24S, E119L, T107L, T107Q, G161K, G15Q, S15R, G153K, G153V, S188G, A83E, G186P, T121D, G49A, S15C, C105Y, C105A, R127F, Q71A, T10C, R179K, T86I, W103N, A87S, F166A, A83F, R123Q, A132C, A143H, T163I, T39V, A93D, V90M, R123K, P134W, G177N, V115I, S155T, T110D, G105L, N170D, T107A, G84V, G84M, L111K, P168I, G154L, T183I, S99G, S15T, A8G, S15N, P189S, S188C, T100Q, A110G, A121A, G12A, R159V, G31A, G154R, T182L, V15L, T160Q, T107F, R159Q, G144A, S92T, T101S, A83R, G12HM S15H, T116Q, T36V, G154, Q81C, V130T, T183A, P118Y, A87E, T86M, V150N, and N24E. In some preferred embodiments, these variants have improved thermostability as compared to wild-type *Cellulomonas* 69B4 protease.

The present invention also provides protease variants having amino acid sequences comprising at least one substitution selected from the group consisting of T36I, I172T, N24E, N170Y, G77T, G186N, I181L, N73T, A38R, N74G, N24A, G54D, S76R, R123E, I59E, N112E, R35E, R179V, R123D, N24T, R179T, R14L, A38D, V90P, R14Q, R123I, R179D, S76V, R79G, R35L, S76E, S76Y, R79D, R79P, R35Q, R179N, N112D, R179E, G65P, Y75G, V90S, R179M, R35F, R123F, A64I, N24Q, R14I, R179A, R127A, R179I, N170D, R35A, R159T, T109E, R14D, N67D, G49A, N112Q, G78D, T121E, L69S, T116E, V90I, T36S, T36G, N145E, T86D, S51D, R179K, T107E, T129S, L142V, R79A, R79E, A38H, T107S, R123A, N55E, R123L, R159N, G65D, R14N, G65Q, R123Q, N24V, R14G, T116Q, A38N, R159Q, R179Y, A83E, N112L, S99N, G78A, T10N, H85Q, R35Q, N24L, N24H, G49S, R79L, S76T, S76L, G65S, N55F, R79V, G65T, R123N, T86E, Y75F, F1T, S76N, S99V, R79T, N112V, R79M, T107V, R79S, G54E, G65V, R127Q, R159D, T107H, H85T, R35T, T36N, Q81E, R123H, S76I, A38F, V90T, and R14T. In alternative embodiments, the protease variants have amino acid sequences comprising at least one substitution selected from the group consisting of G65L, S99D, T107M, S113T, S99T, G77S, R14M, A64N, R61M, A70D, Q71G, A93D, S92G, N112Y, S15W, R159K, N67G, T10E, R127H, A64Y, R159c, A38L, T160E, T183E, R127S, A8E, S51Q, N7L, G63D, A38S, R35H, R14K, T107I, G12D, A64L, S76W, A41N, R35M, A64V, A38Y, T183I, W103M, A41D, R127K, T36D, R61T, G65Y, G13S, R35Y, R123T, A64H, G49H, A70H, A64F, R127Y, R61E, A64P, T121D, V115A, R123Y, T101S, T182V, H85L, N24M, R127E, N145D, Q71H, S76Q, A64T, G49F, A64Q, T10D, F1D, A70G, R35W, Q71D, N121I, A64M, T36H, A8G, T107N, R35S, N67T, S92A, N170L, N67E, S114A, R14A, R14S, Q81D, S51H, R123S, A93S, R127F, I19V, T40V, S185N, R123G, R179L, S51V, T163D, T109I, A64S, V72I, N67S, R159S, H85M, T109G, Q71S, R61H, T107A, Q81V, V90N, T109A, A38T, N145T, R159A, A110S, Q81H, A48E, S51T, A64W, R159L, N67H, A93E, T116F, R61S, R123V, V3L, and R159Y. In some preferred embodiments, these variants have improved keratin hydrolysis activity as compared to wild-type *Cellulomonas* 69B4 protease.

The present invention also provides protease variants having amino acid sequences comprising at least one substitution selected from the group consisting of T36I, P89D, A93T, A93S, T36N, N73T, T36G, R159F, T36S, A38R, S99W, S76W, T36P, G77T, G54D, R127A, R159E, H85Q, T36D, S76L, S99N, Y75G, S76Y, R127S, N24E, R127Q, D184F, N170Y, N24A, S76T, H85L, Y75F, S76V, L69S, R159K, R127K, G65P, N74G, R159H, G65Q, G186V, A48Q, T36H, N67L, F114I, R127L, T36Y, S76I, S114G, R127H, S187P, V3L, G78D, R123I, I181Q, R35F, H85R, R127Y, N67S, Q81P, R123F, R159N, S99A, S76D, A132V, R127F, A143N, S92A, N24T, R79P, S76N, R14M, G186E, N24Q, N67A, R127T, H85K, G65T, G65Y, R179V, Y75, I11Q, A38L, T36L, R159Y, R159D, N24V, G65S, N157D, G186I, G54Q, N67Y, R127G, S76A, A38S, T109E, V66H, T116F, R123L, G49A, A64T, T36W, D184H, S99D, G161K, P134E, A64F, N67G, S99T, D2Q, S76E, R16Q, G54N, N67V, R35L, Q71I, N7L, N112E, L69H, N24H, G54I, R16L, N24M, A64Y, S113A, H85F, R79G, I11A, T121D, R61V, and G65L. In alternative embodiments, the protease variants have amino acid sequences comprising at least one substitution selected from the group consisting of N67Q, S187Q, Q71H, T163D, R61K, R159V, Q71F, V31F, V90I, R79D, T160E, R123Q, A38Y, S113G, A88F, A70G, I11T, G78A, N24L, S92G, R14L, D184R, G54L, N112L, H85Y, R16N, G77S, R179T, V80L, G65V, T121E, Q71D, R16G, P89N, N42H, G49F, I11S, R61M, R159c, G65R, T183I, A93D, L111E, S51Q, G78N, N67T, A38N, T40V, A64W, R159L, T10E, R179K, R123E, V90P, A64N, G161E, H85T, ABG, L142V, A41N, S185I, Q71L, A64T, R16I, A38D, G54M, N112Q, R16A, R14E, V80H, N170D, S99G, R179N, S15E, G49H, A70P, A64S, G54A, S185W, R61H, T10Q, A38F, N170L, T10L, N67F, G12D, D184T, R14N, S187E, R14P, N112D, S140A, N112G G49S, L111N, N67M, V150L, G12Y, R123K, P89V, V66D, G77N, S51T, A8D, I181H, T86N, R179D, N55F, N24S, D184L, R61S, N67K, G186L, F1T, R159A, I11L, R61T, D184Q, A93E, Q71T, R179E, L69W, T163I, S188Q, L125V, A38V, R35A, P134G, A64V, N145D, V90T, and A143S. In some preferred embodiments, these variants have improved BMI performance as compared to wild-type *Cellulomonas* 69B4 protease.

The present invention also provides protease variants having amino acid sequences comprising at least one substitution selected from the group consisting of T36I, N170Y, A38R, R79P, G77T, L69S, N73T, S76V, S76Y, R179V, T36N, N55F, R159F, G54D, G65P, L69H, T36G, G177M, N24E, N74G, R159E, T36S, Y75G, S76I, S76D, ABR, A24A, V90P, R159c, G65Q, T121E, A8V, S76L, T109E, R179M, ABT, T107N, G186E, S76W, R123E, A38F, T36P, N67G, Y75F, S76N, R179I, S187P, N67V, V90S, R127A, R179Y, R35F, N145S, G65S, R61M, S51A, R179N, R123D, N24T, N55E, R79c, G186V, R123I, G161E, G65Y, A38S, R14L, V90I, R79G, N145E, N67L, R127S, R150Y, M180D, N67T, A93D, T121D, Q81V, I109I, A93E; T107S, R179T, R179L, R179K, R159D; R179A, R79E, R123F, R79D, T36D, A64N, L142V, T109A, I172V, A83N, T85A, R179D, A38L, I126L, R127Q, R127L, L69W, R127K, G65T, R127H, P134A, N67D, R14M, N24Q, A143N, N55S, N67M, S51D, S76E, T163D, A38D, R159K, T183I, G63V, ABS, T107M, H85Q, N112E, N67F, N67S, A64H, T86I, P134E, T182V, N67Y, A64S, G78D, V90T, R61T, R16Q, G65R, T86L, V90N, R159Q, G54I, S76C, R179E, V66D, L69V, R127Y, R35L, R14E, and T86F. In alternative embodiments, the protease variants have amino acid sequences comprising at least one substitution selected from the group consisting of G186I, A64Q, T109G, G64L, N24L, A8E, N112D, A38H, R179W, S114G, R123L, ABL, T129S, N170D, R159N, N67C, S92C, T107A, G54E, T107E, T36V, R127T, ABN, H85L, A110S, N170C, A64R, A132V, T36Y, G63D, W103M, T151V, R123P, W103Y, S76T, S1871", R127F, N67A, P171M, A70S, R159H, S76Q, L125V, G54Q, G49L, R14I, R14Q, A83I, V90L, T183E, R159A, T101S, G65D, G54A, T107Q, Q71M, T86E, N24M, N55Q, R61V, P134D, R96K, A88F, N145Q, A64M, A64T, N24V, S140A, A8H, A64I, R123Q, T183Q, N24H, A64W, T62I, T129G, R35A, T40V, I11T, A38N, N145G, A175T, G77Q, T109H, A8P, R35E, T109N, A110T, N67Q, G63P, H859, S92G, A175V, S51Q, G63Q, T116F, G65A, R79L, N145P, L69Q, Q146D, A83D, F166Y, R123A, T121L, R123H, A70P, T182W, S76A, A64F, T107H, G186L, Q81I, R123K, A64L, N67R, V3L, S187E, S161K, T86M, I4M, G77N, G49A, A41N, G54M, T107V, Q81E, A38I, T109L, T183K, A70G, Q71D, T183L, Q81H, A64V, A93Q, S188E, S51F, G186P, G186T, R159L, P134G, N145T, N55V, V66E, R159V, Y176L, and R16L. In some preferred embodiments, these variants have improved BMI performance under low pH conditions, as compared to wild-type *Cellulomonas* 69B4 protease.

The present invention also provides serine proteases comprising at least a portion of an amino acid sequence selected from the group consisting of SEQ ID NO:8, SEQ ID NO:6, SEQ ID NO:7, and SEQ ID NO:9. In some embodiments, the nucleotide sequences encoding these serine proteases comprise a nucleotide sequence selected from the group consisting of SEQ ID NO:1, SEQ ID NO:2, SEQ ID NO:3, SEQ ID NO:4, and SEQ ID NO:5. In some embodiments, the serine proteases are variants having amino acid sequences that are similar to that set forth in SEQ ID NO:8. In some preferred embodiments, the proteases are obtained from a member of the *Micrococcineae*. In some particularly preferred embodiments, the proteases are obtained from an organism selected from the group consisting of *Cellulomonas, Oerskovia, Cellulosimicrobium, Xylanibacterium,* and *Promicromonospora*. In some particularly preferred embodiments, the protease is obtained from variants of *Cellulomonas* 69B4.

The present invention also provides isolated protease variants having amino acid sequences comprising at least one substitution of an amino acid made at a position equivalent to a position in a *Cellulomonas* 69B4 protease comprising the amino acid sequence set forth in SEQ ID NO:8, wherein the amino acid of the protease comprises Arg14, Ser15, Arg16, Cys17, His32, Cys33, Phe52, Asp56, Thr100, Val115, Thr116, Tyr117, Pro118, Glu119, Ala132, Glu133, Pro134, Gly135, Asp136, Ser137, Thr151, Ser152, Gly153, Gly154, Ser155, Gly156, Asn157, Thr164, and Phe165. In some embodiments, the catalytic triad of the proteases comprises His 32, Asp56, and Ser137. In alternative embodiments, the proteases comprise Cys131, Ala132, Glu133, Pro134, Gly135, Thr15I, Ser152, Gly153, Gly154, Ser155, Gly156, Asn157 and Gly 162, Thr 163, and Thr164. In some preferred embodiments, the amino acid sequence of the proteases comprise Phe52, Tyr117, Pro118 and Glu119. In some particularly preferred embodiments, the amino acids sequences of the proteases have main-chain to main-chain hydrogen bonding from Gly 154 to the substrate main-chain.

In embodiments, the proteases of the present invention comprise three disulfide bonds. In some preferred embodiments, the disulfide bonds are located between C17 and C38, C95 and C105, and C131 and C158. In some particularly preferred embodiments, the disulfide bonds are located between C17 and C38, C95 and C105, and C131 and C158 of SEQ ID NO:8. In alternative protease variant embodiments, the disulfide bonds are located at positions equivalent to the disulfide bonds in SEQ ID NO:8.

The present invention also provides isolated protease variants having amino acid sequences comprising at least one substitution of an amino acid made at a position equivalent to a position in a *Cellulomonas* 69B4 protease comprising the amino acid sequence set forth in SEQ ID NO:8, wherein the variants have altered substrate specificities as compared to wild-type *Cellulomonas* 69B4 protease. In some further preferred embodiments, the variants have altered pIs as compared to wild-type *Cellulomonas* 69B4 protease. In additional preferred embodiments, the variants have improved stability as compared to wild-type *Cellulomonas* 69B4 protease. In still further preferred embodiments, the variants exhibit altered surface properties. In some particularly preferred embodiments, the variants exhibit altered surface properties as compared to wild-type *Cellulomonas* 69B4 protease. In additional particularly preferred embodiments, the variants comprise mutations at least one substitution at sites selected from the group consisting of 1, 2, 4, 7, 8, 10, 11, 12, 13, 14, 15, 16, 22, 24, 25, 32, 34, 35, 36, 37, 38, 39, 40, 41, 42, 43, 44, 45, 46, 47, 48, 49, 50, 51, 52, 53, 54, 55, 57, 59, 61, 62, 63, 64, 65, 66, 67, 68, 69, 71, 73, 74, 75, 76, 77, 78, 79, 80, 81, 83, 84, 85, 86, 87, 88, 89, 90, 91, 92, 93, 95, 99, 100, 101, 102, 103, 104, 105, 106, 107, 108, 109, 110, 111, 112, 113, 114, 115, 116, 117, 118, 119, 120, 121, 123, 124, 126, 127, 128, 130, 131, 132, 133, 134, 135, 137, 143, 144, 145, 146, 147, 148, 152, 153, 154, 155, 156, 157, 158, 159, 160, 161, 162, 163, 164, 165, 166, 167, 168, 170, 171, 173, 174, 175, 176, 177, 178, 179, 180, 181, 182, 183, and 184.

The present invention also provides protease variants having at least one improved property as compared to the wild-type protease. In some particularly preferred embodiments, the variants are variants of a serine protease obtained from a member of the *Micrococcineae*. In some particularly preferred embodiments, the proteases are obtained from an organism selected from the group consisting of *Cellulomonas, Oerskovia, Cellulosimicrobium, Xylanibacterium,* and *Promicromonospora*. In some particularly preferred embodiments, the protease is obtained from variants of *Cellulomonas* 69B4. In some preferred embodiments, at least one improved property is selected from the group consisting of acid stability, thermostability, casein hydrolysis, keratin hydrolysis, cleaning performance, and LAS stability.

The present invention also provides expression vectors comprising a polynucleotide sequence encoding protease variants having amino acid sequences comprising at least one substitution of an amino acid made at a position equivalent to a position in a *Cellulomonas* 69B4 protease comprising the amino acid sequence set forth in SEQ ID NO:8. In further embodiments, the present invention provides host cells comprising these expression vectors. In some particularly preferred embodiments, the host cells are selected from the group consisting of *Bacillus* sp., *Streptomyces* sp., *Aspergillus* sp., and *Trichoderma* sp. The present invention also provides the serine proteases produced by the host cells.

The present invention also provides variant proteases comprising an amino acid sequence selected from the group consisting of SEQ ID NOS:54, 56, 58, 60, 62, 64, 66, 68, 70, 72, 74, 76, and 78, In some preferred embodiments, the amino acid sequence is encoded by a polynucleotide sequence selected from the group consisting of SEQ ID NOS:53, 55, 57, 59, 61, 63, 65, 67, 69, 71, 73, 75, and 77. In further embodiments, the present invention provides expression vectors comprising a polynucleotide sequence encoding at least one protease variant. In additional embodiments, the present invention provides host cells comprising these expression vectors. In some particularly preferred embodiments, the host cells are selected from the group consisting of *Bacillus*. sp., *Streptomyces* sp., *Aspergillus* sp., and *Trichoderma* sp. The present invention also provides the serine proteases produced by the host cells.

The present invention also provides compositions comprising at least a portion of an isolated serine protease of obtained from a member of the *Micrococcineae*, wherein the protease is encoded by a polynucleotide sequence selected from the group consisting of SEQ ID NO:1, SEQ ID NO:2, SEQ ID NO:3, and SEQ ID NO:4. In some preferred embodiments, the sequence comprises at least a portion of SEQ ID NO:1. In further embodiments, the present invention provides host cells comprising these expression vectors. In some particularly preferred embodiments, the host cells are selected from the group consisting of *Bacillus* sp., *Streptomyces* sp., *Aspergillus* sp., and *Trichoderma* sp. The present invention also provides the serine proteases produced by the host cells.

The present invention also provides variant serine proteases, wherein the proteases comprise at least one substitution corresponding to the amino acid positions in SEQ ID NO:8, and wherein variant proteases have better performance in at least one property selected from the group consisting of keratin hydrolysis, thermostability, casein activity, LAS stability, and cleaning, as compared to wild-type *Cellulomonas* 69B4 protease.

The present invention also provides isolated polynucleotides comprising a nucleotide sequence (i) having at least 70% identity to SEQ ID NO:4, or (ii) being capable of hybridizing to a probe derived from the nucleotide sequence set forth in SEQ ID NO:4, under conditions of intermediate to high stringency, or (iii) being complementary to the nucleotide sequence set forth in SEQ ID NO:4. In embodiments, the present invention provides expression vectors encoding at least one such polynucleotide. In further embodiments, the present invention provides host cells comprising these expression vectors. In some particularly preferred embodiments, the host cells are selected from the group consisting of *Bacillus* sp., *Streptomyces* sp., *Aspergillus* sp., and *Trichoderma* sp. The present invention also provides the serine proteases produced by the host cells. In further embodiments, the present invention provides polynucleotides that are complementary to at least a portion of the sequence set forth in SEQ ID NO:4.

The present invention also provides methods of producing an enzyme having protease activity, comprising: transforming a host cell with an expression vector comprising a polynucleotide having at least 70% sequence identity to SEQ ID NO:4; cultivating the transformed host cell under conditions suitable for host cell. In some embodiments, the host cell is selected from the group consisting of *Streptomyces*, *Aspergillus*, *Trichoderma* and *Bacillus* species.

The present invention also provides probes comprising 4 to 150 nucleotide sequence substantially identical to a corresponding fragment of SEQ ID NO:4, wherein the probe is used to detect a nucleic acid sequence coding for an enzyme having proteolytic activity, and wherein the nucleic acid sequence is obtained from a member of the *Micrococcineae*. In some embodiments, the *Micrococcineae* is a *Cellulomonas* spp. In some preferred embodiments, the *Cellulomonas* is *Cellulomonas* strain 69B4.

The present invention also provides cleaning compositions comprising at least one serine protease obtained from a member of the *Micrococcineae*. In some embodiments, ate least one protease is obtained from an organism selected from the group consisting of *Cellulomonas*, *Oerskovia*, *Cellulosimicrobium*, *Xylanibacterium*, and *Promicromonospora*. In some preferred embodiments, the protease is obtained from *Cellulomonas* 69B4. In some particularly preferred embodiments, at least one protease comprises the amino acid sequence set forth in SEQ ID NO:8. In some further embodiments, the present invention provides isolated serine proteases comprising at least 45% amino acid identity with serine protease comprising SEQ ID NO:8. In some embodiments, the isolated serine proteases comprise at least 50% identity, preferably at least 55%, more preferably at least 60%, yet more preferably at least 65%, even more preferably at least 70%, more preferably at least 75%, still more preferably at least 80%, more preferably 85%, yet more preferably 90%, even more preferably at least 95%, and most preferably 99% identity. 75.

The present invention further provides cleaning compositions comprising at least one serine protease, wherein at least one of the serine proteases has immunological cross-reactivity with the serine protease obtained from a member of the *Micrococcineae*. In some preferred embodiments, the serine proteases have immunological cross-reactivity with serine protease obtained from *Cellulomonas* 69B4. In alternative embodiments, the serine proteases have immunological cross-reactivity with serine protease comprising the amino acid sequence set forth in SEQ ID NO:8. In still further embodiments, the serine proteases have cross-reactivity with fragments (i.e., portions) of any of the serine proteases obtained from the *Micrococcineae*, the *Cellulomonas* 69B4 protease, and/or serine protease comprising the amino acid sequence set forth in SEQ ID NO:8.

The present invention further provides cleaning compositions comprising at least one serine protease, wherein the protease is a variant protease having an amino acid sequence comprising at least one substitution of an amino acid made at a position equivalent to a position in a *Cellulomonas* 69B4 protease having an amino acid sequence set forth in SEQ ID NO:8. In some embodiments, the substitutions are made at positions equivalent to positions 2, 8, 10, 11, 12, 13, 14, 15, 16, 24, 26, 31, 33, 35, 36, 38, 39, 40, 43, 46, 49, 51, 54, 61, 64, 65, 67, 70, 71, 76, 78, 79, 81, 83, 85, 86, 90, 93, 99, 100, 105, 101, 109, 112, 113, 116, 118, 119, 121, 123, 127, 145, 155, 159, 160, 163, 165, 170, 174, 179, 183, 184, 185, 186, 187, and 188 in a *Cellulomonas* 69B4 protease comprising an amino acid sequence set forth in SEQ ID NO:8. In alternative embodiments, the substitutions are made at positions equivalent to positions 1, 4, 22, 27, 28, 30, 32, 41, 47, 48, 55, 59, 63, 66, 69, 75, 77, 80, 84, 87, 88, 89, 92, 96, 110, 111, 114, 115, 117, 128, 134, 144, 143, 146, 151, 154, 156, 158, 161, 166, 176, 177, 181, 182, 187, and 189, in a *Cellulomonas* 69B4 protease comprising an amino acid sequence set forth in SEQ ID NO:8. In further embodiments, the protease comprises at least one amino acid substitutions at positions 14, 16, 35, 36, 65, 75, 76, 79, 123, 127, 159, and 179, in an equivalent amino acid sequence to that set forth in SEQ ID NO:8. In still further embodiments, the protease comprises at least one mutation selected from the group consisting of R14L, R16I, R16L, R16Q, R35F, T36S, G65Q, Y75G, N76L, N76V, R79T, R123L, R123Q, R127A, R127K, R127Q, R159K, R159Q, and R179Q. In yet additional embodiments, the protease comprises a set of mutations selected from the group consisting of the sets R16Q/R35F/R159Q, R16Q/R123L, R14L/R127Q/R159Q, R14L/R179Q, R123L/R9127Q/R179Q, R16Q/R79T/R127Q, and R16Q/R79T. In some particularly preferred embodiments, the protease comprises the following mutations R123L, R127Q, and R179Q. In some particularly preferred embodiments, the variant serine as proteases comprise at least one substitution corresponding to the amino acid positions in SEQ ID NO:8, and wherein the variant proteases have better performance in at least one property selected from the group consisting of keratin hydrolysis, thermostability, casein activity, LAS stability, and cleaning, as compared to wild-type *Cellulomonas* 69B4 protease. In some embodiments, the variant protease comprises an amino acid sequence selected from the group consisting of SEQ ID NOS:54, 56, 58, 60, 62, 64, 66, 68, 70, 72, 74, 76, and 78. In alternative embodiments, the variant protease amino acid sequence is encoded by a polynucleotide sequence selected from the group consisting of SEQ ID NOS:53, 55, 57, 59, 61, 63, 65, 67, 69, 71, 73, 75, and 77.

The present invention also provides cleaning compositions comprising a cleaning effective amount of a proteolytic enzyme, the enzyme comprising an amino acid sequence having at least 70% sequence identity to SEQ ID NO:4, and a suitable cleaning formulation. In some preferred embodiments, the cleaning compositions further comprise one or more additional enzymes or enzyme derivatives selected from the group consisting of proteases, amylases, lipases, mannanases, pectinases, cutinases, oxidoreductases, hemicellulases, and cellulases.

The present invention also provides compositions comprising at least one serine protease obtained from a member of the *Micrococcineae*, wherein the compositions further comprise at least one stabilizer. In some embodiments, the stabilizer is selected from the group consisting of borax and glycerol. In some embodiments, the present invention provides competitive inhibitors suitable to stabilize the enzyme of the present invention to anionic surfactants. In some embodiments, at least one protease is obtained from an organism selected from the group consisting of *Cellulomonas, Oerskovia, Cellulosimicrobium, Xylanibacterium,* and *Promicromonospora*. In some preferred embodiments, the protease is obtained from *Cellulomonas* 69B4. In some particularly preferred embodiments, at least one protease comprises the amino acid sequence set forth in SEQ ID NO:8.

The present invention further provides compositions comprising at least one serine protease obtained obtained from a member of the *Micrococcineae*, wherein the serine protease is an autolytically stable variant. In some embodiments, at least one variant protease is obtained from an organism selected from the group consisting of *Cellulomonas, Oerskovia, Cellulosimicrobium, Xylanibacterium,* and *Promicromonospora*. In some preferred embodiments, the variant protease is obtained from *Cellulomonas* 69B4. In some particularly preferred embodiments, at least one variant protease comprises the amino acid sequence set forth in SEQ ID NO:8.

The present invention also provides cleaning compositions comprising at least 0.0001 weight percent of the serine protease of the present invention, and optionally, an adjunct ingredient. In some embodiments, the composition comprises an adjunct ingredient. In some preferred embodiments, the composition comprises a sufficient amount of a pH modifier to provide the composition with a neat pH of from about 3 to about 5, the composition being essentially free of materials that hydrolyze at a pH of from about 3 to about 5. In some particularly preferred embodiments, the materials that hydrolyze comprise a surfactant material. In additional embodiments, the cleaning composition is a liquid composition. In further embodiments, the surfactant material comprises a sodium alkyl sulfate surfactant that comprises an ethylene oxide moiety.

The present invention additionally provides cleaning compositions that comprise at least one acid stable enzyme, the cleaning composition comprising a sufficient amount of a pH modifier to provide the composition with a neat pH of from about 3 to about 5, the composition being essentially free of materials that hydrolyze at a pH of from about 3 to about 5. In further embodiments, the materials that hydrolyze comprise a surfactant material. In some preferred embodiments, the cleaning composition being a liquid composition. In yet additional embodiments, the surfactant material comprises a sodium alkyl sulfate surfactant that comprises an ethylene oxide moiety. In some embodiments, the cleaning composition comprises a suitable adjunct ingredient. In some additional embodiments, the composition comprises a suitable adjunct ingredient. In some preferred embodiments, the composition comprises from about 0.001 to about 0.5 weight % of ASP.

In some alternatively preferred embodiments, the composition comprises from about 0.01 to about 0.1 weight percent of ASP.

The present invention also provides methods of cleaning, the comprising the steps of: a) contacting a surface and/or an article comprising a fabric with the cleaning composition comprising the serine protease of the present invention at an appropriate concentration; and b) optionally washing and/or rinsing the surface or material. In alternative embodiments, any suitable composition provided herein finds use in these methods.

The present invention also provides animal feed comprising at least one serine protease obtained from a member of the *Micrococcineae*. In some embodiments, at least one protease is obtained from an organism selected from the group consisting of *Cellulomonas, Oerskovia, Cellulosimicrobium, Xylanibacterium,* and *Promicromonospora*. In some preferred embodiments, the protease is obtained from *Cellulomonas* 69B4. In some particularly preferred embodiments, at least one protease comprises the amino acid sequence set forth in SEQ ID NO:8.

The present invention provides an isolated polypeptide having proteolytic activity, (e.g., a protease) having the amino acid sequence set forth in SEQ ID NO:8. In some embodiments, the present invention provides isolated polypeptides having approximately 40% to 98% identity with the sequence set forth in SEQ ID NO:8. In some preferred embodiments, the polypeptides have approximately 50% to 95% identity with the sequence set forth in SEQ ID NO:8. In some additional preferred embodiments, the polypeptides have approximately 60% to 90% identity with the sequence set forth in SEQ ID NO:8. In yet additional embodiments, the polypeptides have approximately 65% to 85% identity with the sequence set forth in SEQ ID NO:8. In some particularly preferred embodiments, the polypeptides have approximately 90% to 95% identity with the sequence set forth in SEQ ID NO:8.

The present invention further provides proteases obtained from bacteria of the suborder *Micrococcineae*. In some preferred embodiments, the proteases are obtained from members of the family Promicromonosporaceae. In yet further embodiments; the proteases are obtained from any member of the genera *Xylanimicrobium, Xylanibacterium, Xylanimonas, Myceligenerans*, and *Promicromonospora*. In some preferred embodiments, the proteases are obtained from members of the family Cellulomonadaceae. In some particularly preferred embodiments, the proteases are obtained from members of the genera *Cellulomonas* and *Oerskovia*. In some further preferred embodiments, the proteases are derived from *Cellulomonas* spp. In some embodiments, the *Cellulomonas* spp. is selected from *Cellulomonas fimi, Cellulomonas biazotea, Cellulomonas cellasea, Cellulomonas hominis, Cellulomonas flavigena, Cellulomonas persica, Cellulomonas iranensis, Cellulomonas gelida, Cellulomonas humilata, Cellulomonas turbata, Cellulomonas uda, Cellulomonas fermentans, Cellulomonas xylanilytica, Cellulomonas humilata* and *Cellulomonas* strain 69B4 (DSM 16035).

In alternative embodiments, the proteases are derived from *Oerskovia* spp. In some preferred embodiments, the *Oerskovia* spp. is selected from *Oerskovia jenensis, Oerskovia paurometabola, Oerskovia enterophila, Oerskovia turbata* and *Oerskovia turbata* strain DSM so 20577.

In some embodiments, the proteases have apparent molecular weights of about 17 kD to 21 kD as determined by a matrix assisted laser desorption/ionizaton—time of flight ("MALDI-TOF") spectrophotometer.

The present invention further provides isolated polynucleotides that encode proteases comprise an amino acid sequence comprising at least 40% amino acid sequence identity to SEQ ID NO:8. In some embodiments, the proteases have at least 50% amino acid sequence identity to SEQ ID NO:8. In some embodiments, the proteases have at least 60% amino acid sequence identity to SEQ ID NO:8. In some embodiments, the proteases have at least 70% amino acid sequence identity to SEQ ID NO:8. In some embodiments, the proteases have at least 80% amino acid sequence identity to SEQ ID NO:8. In some embodiments, the proteases have at least 90% amino acid sequence identity to SEQ ID NO:8. In some embodiments, the proteases have at least 95% amino acid sequence identity to SEQ ID NO:8. The present invention also provides expression vectors comprising any of the polynucleotides provided above.

The present invention further provides host cells transformed with the expression vectors of the present invention, such that at least one protease is expressed by the host cells. In some embodiments, the host cells are bacteria, while in other embodiments, the host cells are fungi. In some preferred embodiments, the bacterial host cells are selected from the group consisting of the genera *Bacillus* and *Streptomyces*. In some alternative preferred embodiments, the fungal host cells are members of the genus *Trichoderma*, while in other alternative preferred embodiments, the fungal host cells are members of the genus *Aspergillus*.

The present invention also provides isolated polynucleotides comprising a nucleotide sequence (i) having at least 70% identity to SEQ ID NOS:3 or 4, or (ii) being capable of hybridizing to a probe derived from the nucleotide sequence disclosed in SEQ ID NOS: 3 or 4, under conditions of medium to high stringency, or (iii) being complementary to the nucleotide sequence disclosed in SEQ ID NOS:3 or 4. In some embodiments, the present invention provides vectors comprising such polynucleotide. In further embodiments, the present invention provides host cells transformed with such vector.

The present invention further provides methods for producing at least one enzyme having protease activity, comprising: the steps of transforming a host cell with an expression vector comprising a polynucleotide comprising at least 70% sequence identity to SEQ ID NO:4, cultivating the transformed host cell under conditions suitable for the host cell to produce the protease; and recovering the protease. In some preferred embodiments, the host cell is a *Streptomyces* spp, while in other embodiments, the host cell is a *Bacillus* spp, a *Trichoderma* spp., and/or a *Aspergillus* spp. In some embodiments, the *Streptomyces* spp. is *Streptomyces lividans*. In alternative embodiments, the host cell is *T. reesei*. In further embodiments, the *Aspergillus* spp. is *A. niger*.

The present invention also provides fragments (i.e., portions) of the DNA encoding the proteases provided herein. These fragments find use in obtaining partial length DNA fragments capable of being used to isolate or identify polynucleotides encoding mature protease enzyme described herein from Cellulomonas 69B4, or a segment thereof having proteolytic activity. In some embodiments, portions of the DNA provided in SEQ ID NO:1 find use in obtaining homologous fragments of DNA from other species, and particularly from *Micrococcineae* spp. which encode a protease or portion thereof having proteolytic activity.

The present invention further provides at least one probe comprising a polynucleotide substantially identical to a fragment of SEQ ID NOS:1, 2, 3 or 4, wherein the probe is used to detect a nucleic acid sequence coding for an enzyme having proteolytic activity, and wherein the nucleic acid sequence is obtained from a bacterial source. In some embodiments, the bacterial source is a *Cellulomonas* spp. In some preferred embodiments, the bacterial source is *Cellulomonas* strain 69B4.

The present invention further provides compositions comprising at least one of the proteases provided herein. In some preferred embodiments, the compositions are cleaning compositions. In some embodiments, the present invention provides cleaning compositions comprising a cleaning effective amount of at least one protease comprising an amino acid sequence having at least 40% sequence identity to SEQ ID NO:8, at least 90% sequence identity to SEQ ID NO:8, and/or having an amino acid sequence of SEQ ID NO:8. In some embodiments, the cleaning compositions further comprise at least one suitable cleaning adjunct. In some embodiments, the protease is derived from a *Cellulomonas* sp. In some preferred embodiments, the *Cellulomonas* spp. is selected from *Cellulomonas fimi, Cellulomonas biazotea, Cellulomonas cellasea, Cellulomonas hominis, Cellulomonas flavigena, Cellulomonas persica, Cellulomonas iranensis, Cellulomonas gelida, Cellulomonas humilata, Cellulomonas turbata, Cellulomonas uda*, and *Cellulomonas* strain 69B4 (DSM 16035). In some particularly preferred embodiments, the *Cellulomonas* spp is Cellulomonas strain 69B4. In still further embodiments, the cleaning composition further comprises at least one additional enzymes or enzyme derivatives selected from the group consisting of protease, amylase, lipase, mannanase and cellulase.

The present invention also provides isolated naturally occurring proteases comprising an amino acid sequence having at least 45% sequence identity to SEQ ID NO:8, at least 60% sequence identity to SEQ ID NO:8, at least 75% sequence identity to SEQ ID NO:8, at least 90% sequence identity to SEQ ID NO:8, at least 95% sequence identity to SEQ ID NO:8, and/or having the sequence identity of SEQ ID NO:8, the protease being isolated from a *Cellulomonas* spp. In some embodiments, the protease is isolated from *Cellulomonas* strain 69B4 (DSM 16035).

In additional embodiments, the present invention provides engineered variants of the serine proteases of the present invention. In some embodiments, the engineered variants are genetically modified using recombinant DNA technologies, while in other embodiments, the variants are naturally occurring. The present invention further encompasses engineered variants of homologous enzymes. In some embodiments, the engineered variant homologous proteases are genetically modified using recombinant DNA technologies, while in other embodiments, the variant homologous proteases are naturally occurring.

The present invention also provides serine proteases that immunologically cross-react with the Cellulomonas 69B4 protease (i.e., ASP) of the present invention. Indeed, it is intended that the present invention encompass fragments (e.g., epitopes) of the ASP protease that stimulate an immune response in animals (including, but not limited to humans) and/or are recognized by antibodies of any class. The present invention further encompasses epitopes on proteases that are cross-reactive with ASP epitopes. In some embodiments, the ASP epitopes are recognized by antibodies, but do not stimulate an immune response in animals (including, but not limited to humans), while in other embodiments, the ASP epitopes stimulate an immune response in at least one animal species (including, but not limited to humans) and are recognized by antibodies' of any class. The present invention also provides means and compositions for identifying and assessing cross-reactive epitopes.

The present invention further provides at least one polynucleotide encoding a signal peptide (i) having at least 70% sequence identity to SEQ ID NO:9, or (ii) being capable of hybridizing to a probe derived from the polypeptide sequence encoding SEQ ID NO:9, under conditions of medium to high stringency, or (iii) being complementary to the polypeptide sequence provided in SEQ ID NO:9. In further embodiments, the present invention provides at vectors comprising the polynucleotide described above. In yet additional embodiments, a host cell is provided that is transformed with the vector.

The present invention also provides methods for producing proteases, comprising: (a) transforming a host cell with an expression vector comprising a polynucleotide having at least 70% sequence identity to SEQ ID NO:4, at least 95% sequence identity to SEQ ID NO:4, and/or having a polynucleotide sequence of SEQ ID NO:4; (b) cultivating the transformed host cell under conditions suitable for the host cell to produce the protease; and (c) recovering the protease. In some embodiments, the host cell is a *Bacillus* species (e.g., *B. subtilis, B. clausii*, or *B. licheniformis*). In alternative embodiments, the host cell is a *Streptomyces* spp., (e.g., *Streptomyces lividans*). In additional embodiments, the host cell is a *Trichoderma* spp., (e.g., *Trichoderma reesei*). In yet further embodiments, the host cell is a *Aspergillus* spp. (e.g., *Aspergillus niger*).

As will be appreciated, an advantage of the present invention is that a polynucleotide has been isolated which provides the capability of isolating further polynucleotides which encode proteins having serine protease activity, wherein the backbone is substantially identical to that of the Cellulomonas protease of the present invention.

In further embodiments, the present invention provides means to produce host cells that are capable of producing the serine proteases of the present invention in relatively large quantities. In particularly preferred embodiments, the present invention provides means to produce protease with various commercial applications where degradation or synthesis of polypeptides are desired, including cleaning compositions, as well as feed components, textile processing, leather finishing, grain processing, meat processing, cleaning, preparation of protein hydrolysates, digestive aids, microbicidal compositions, bacteriostatic composition, fungistatic compositions, personal care products, including oral care, hair care, and/or skin care.

The present invention further provides enzyme compositions have comparable or improved wash performance, as compared to presently used subtilisin proteases. Other objects and advantages of the present invention are apparent from the present Specification.

The present invention provides an isolated polypeptide having proteolytic activity, (e.g., a protease) having the amino acid sequence set forth in SEQ ID NO:8. In some embodiments, the present invention provides isolated polypeptides having approximately 40% to 98% identity with the sequence set forth in SEQ ID NO:8. In some preferred embodiments, the polypeptides have approximately 50% to 95% identity with the sequence set forth in SEQ ID NO:8. In some additional preferred embodiments, the polypeptides have approximately 60% to 90% identity with the sequence set forth in SEQ ID NO:8. In yet additional embodiments, the polypeptides have approximately 65% to 85% identity with the sequence set forth in SEQ ID NO:8. In some particularly preferred embodiments, the polypeptides have approximately 90% to 95% identity with the sequence set forth in SEQ ID NO:8.

The present invention further provides proteases obtained from bacteria of the suborder *Micrococcineae*. In some preferred embodiments, the proteases are obtained from members of the family Promicromonosporaceae. In yet further embodiments, the proteases are obtained from any member of the genera *Xylanimicrobium, Xylanibacterium, Xylanimonas, Myceligenerans*, and *Promicromonospora*. In some preferred embodiments, the proteases are obtained from members of the family Cellulomonadaceae. In some particularly preferred embodiments, the proteases are obtained from members of the genera *Cellulomonas* and *Oerskovia*. In some further preferred embodiments, the proteases are derived from *Cellulomonas* spp. In some embodiments, the *Cellulomonas* spp. is selected from *Cellulomonas fimi, Cellulomonas biazotea, Cellulomonas cellasea, Cellulomonas hominis, Cellulomonas flavigena, Cellulomonas persica, Cellulomonas iranensis, Cellulomonas gelida, Cellulomonas humilata, Cellulomonas turbata, Cellulomonas uda, Cellulomonas fermentans, Cellulomonas xylanilytica, Cellulomonas humilata* and *Cellulomonas* strain 69B4 (DSM 16035).

In alternative embodiments, the proteases are derived from *Oerskovia* spp. In some preferred embodiments, the *Oerskovia* spp. is selected from *Oerskovia jenensis, Oerskovia paurometabola, Oerskovia enterophila, Oerskovia turbata* and *Oerskovia turbata* strain DSM 20577.

In some embodiments, the proteases have apparent molecular weights of about 17 kD to 21 kD as determined by a matrix assisted laser desorption/ionizaton—time of flight ("MALDI-TOF") spectrophotometer.

The present invention further provides isolated polynucleotides that encode proteases comprise an amino acid sequence comprising at least 40% amino acid sequence identity to SEQ ID NO:8. In some embodiments, the proteases have at least 50% amino acid sequence identity to SEQ ID NO:8. In some embodiments, the proteases have at least 60% amino acid sequence identity to SEQ ID NO:8. In some embodiments, the proteases have at least 70% amino acid sequence identity to SEQ ID NO:8. In some embodiments, the proteases have at least 80% amino acid sequence identity to SEQ ID NO:8. In some embodiments, the proteases have at least 90% amino acid sequence identity to SEQ ID NO:8. In some embodiments, the proteases have at least 95% amino acid sequence identity to SEQ ID NO:8. The present invention also provides expression vectors comprising any of the polynucleotides provided above.

The present invention further provides host cells transformed with the expression vectors of the present invention, such that at least one protease is expressed by the host cells. In some embodiments, the host cells are bacteria, while in other embodiments, the host cells are fungi. In some preferred embodiments, the bacterial host cells are selected from the group consisting of the genera *Bacillus* and *Streptomyces*. In some alternative preferred embodiments, the fungal host cells are members of the genus *Trichoderma*, while in other alternative preferred embodiments, the fungal host cells are members of the genus *Aspergillus*.

The present invention also provides isolated polynucleotides comprising a nucleotide sequence (i) having at least 70% identity to SEQ ID NOS:3 or 4, or (ii) being capable of hybridizing to a probe derived from the nucleotide sequence disclosed in SEQ ID NOS: 3 or 4, under conditions of medium to high stringency, or (iii) being complementary to the nucleotide sequence disclosed in SEQ ID NOS:3 or 4. In some embodiments, the present invention provides vectors comprising such polynucleotide. In further embodiments, the present invention provides host cells transformed with such vector.

The present invention further provides methods for producing at least one enzyme having protease activity, comprising: the steps of transforming a host cell with an expression vector comprising a polynucleotide comprising at least 70% sequence identity to SEQ ID NO:4, cultivating the transformed host cell under conditions suitable for the host cell to produce the protease; and recovering the protease. In some preferred embodiments, the host cell is a *Streptomyces* spp, while in other embodiments, the host cell is a *Bacillus* spp, a *Trichoderma* spp., and/or a *Aspergillus* spp. In some embodiments, the *Streptomyces* spp. is *Streptomyces lividans*. In alternative embodiments, the host cell is *T. reesei*. In further embodiments, the *Aspergillus* spp. is *A. niger*.

The present invention also provides fragments (i.e., portions) of the DNA encoding the proteases provided herein: These fragments find use in obtaining partial length DNA fragments capable of being used to isolate or identify polynucleotides encoding mature protease enzyme described herein from Cellulomonas 69B4, or a segment thereof having proteolytic activity. In some embodiments, portions of the DNA provided in SEQ ID NO:1 find use in obtaining homologous fragments of DNA from other species, and particularly from *Micrococcineae* spp. which encode a protease or portion thereof having proteolytic activity.

The present invention further provides at least one probe comprising a polynucleotide substantially identical to a fragment of SEQ ID NOS:1, 2, 3 or 4, wherein the probe is used to detect a nucleic acid sequence coding for an enzyme having proteolytic activity, and wherein the nucleic acid sequence is obtained from a bacterial source. In some embodiments, the bacterial source is a *Cellulomonas* spp. In some preferred embodiments, the bacterial source is *Cellulomonas* strain 69B4.

The present invention further provides compositions comprising at least one of the proteases provided herein. In some preferred embodiments, the compositions are cleaning compositions. In some embodiments, the present invention provides cleaning compositions comprising a cleaning effective amount of at least one protease comprising an amino acid sequence having at least 40% sequence identity to SEQ ID NO:8, at least 90% sequence identity to SEQ ID NO:8, and/or having an amino acid sequence of SEQ ID NO:8. In some embodiments, the cleaning compositions further comprise at least one suitable cleaning adjunct. In some embodiments, the protease is derived from a *Cellulomonas* sp. In some preferred embodiments, the *Cellulomonas* spp. is selected from *Cellulomonas fimi*, *Cellulomonas biazotea*, *Cellulomonas cellasea*, *Cellulomonas hominis*, *Cellulomonas flavigena*, *Cellulomonas persica*, *Cellulomonas iranensis*, *Cellulomonas gelida*, *Cellulomonas humilata*, *Cellulomonas turbata*, *Cellulomonas uda*, and *Cellulomonas* strain 69B4 (DSM 16035). In some particularly preferred embodiments, the *Cellulomonas* spp is *Cellulomonas* strain 69B4. In still further embodiments, the cleaning composition further comprises at least one additional enzymes or enzyme derivatives selected from the group consisting of protease, amylase, lipase, mannanase and cellulase.

The present invention also provides isolated naturally occurring proteases comprising an amino acid sequence having at least 45% sequence identity to SEQ ID NO:8, at least 60% sequence identity to SEQ ID NO:8, at least 75% sequence identity to SEQ ID NO:8, at least 90% sequence identity to SEQ ID NO:8, at least 95% sequence identity to SEQ ID NO:8, and/or having the sequence identity of SEQ ID NO:8, the protease being isolated from a *Cellulomonas* spp. In some embodiments, the protease is isolated from *Cellulomonas* strain 69B4 (DSM 16035).

In additional embodiments, the present invention provides engineered variants of the serine proteases of the present invention. In some embodiments, the engineered variants are genetically modified using recombinant DNA technologies, while in other embodiments, the variants are naturally occurring. The present invention further encompasses engineered variants of homologous enzymes. In some embodiments, the engineered variant homologous proteases are genetically modified using recombinant DNA technologies, while in other embodiments, the variant homologous proteases are naturally occurring.

The present invention also provides serine proteases that immunologically cross-react with the ASP protease of the present invention. Indeed, it is intended that the present invention encompass fragments (e.g., epitopes) of the ASP protease that stimulate an immune response in animals (including, but not limited to humans) and/or are recognized by antibodies of any class. The present invention further encompasses epitopes on proteases that are cross-reactive with ASP epitopes. In some embodiments, the ASP epitopes are recognized by antibodies, but do not stimulate an immune response in animals (including, but not limited to humans), while in other embodiments, the ASP epitopes stimulate an immune response in at least one animal species (including, but not limited to humans) and are recognized by antibodies of any class. The present invention also provides means and compositions for identifying and assessing cross-reactive epitopes.

The present invention further provides at least one polynucleotide encoding a signal peptide (i) having at least 70% sequence identity to SEQ ID NO:9, or (ii) being capable of hybridizing to a probe derived from the polypeptide sequence encoding SEQ ID NO:9, under conditions of medium to high stringency, or (iii) being complementary to the polypeptide sequence provided in SEQ ID NO:9. In further embodiments, the present invention provides at vectors comprising the polynucleotide described above. In yet additional embodiments, a host cell is provided that is transformed with the vector.

The present invention also provides methods for producing proteases, comprising: (a) transforming a host cell with an expression vectorcomprising a polynucleotide having at least 70% sequence identity to SEQ ID NO:4, at least 95% sequence identity to SEQ ID NO:4, and/or having a polynucleotide sequence of SEQ ID NO:4; (b) cultivating the transformed host cell under conditions suitable for the host cell to produce the protease; and (c) recovering the protease. In some embodiments, the host cell is a *Bacillus* species (e.g., *B. subtilis, B. clausii,* or *B. licheniformis*). In alternative embodiments, the host cell is a *Streptomyces* spp., (e.g., *Streptomyces lividans*). In additional embodiments, the host cell is a *Trichoderma* spp., (e.g., *Trichoderma reesei*). In yet further embodiments, the host cell is a *Aspergillus* spp., (e.g., *Aspergillus niger*).

As will be appreciated, an advantage of the present invention is that a polynucleotide has been isolated which provides the capability of isolating further polynucleotides which encode proteins having serine protease activity, wherein the backbone is substantially identical to that of the Cellulomonas protease of the invention.

In further embodiments, the present invention provides means to produce host cells that are capable of producing the serine proteases of the present invention in relatively large quantities. In particularly preferred embodiments, the present invention provides means to produce protease with various commercial applications where degradation or synthesis of polypeptides are desired, including cleaning compositions, as well as feed components, textile processing, leather finishing, grain processing, meat processing, cleaning, preparation of protein hydrolysates, digestive aids, microbicidal compositions, bacteriostatic composition, fungistatic compositions, personal care products, including oral care, hair care, and/or skin care.

The present invention further provides enzyme compositions have comparable or improved wash performance, as compared to presently used subtilisin proteases. Other objects and advantages of the present invention are apparent from the present Specification.

DESCRIPTION OF THE INVENTION

Figure 1:
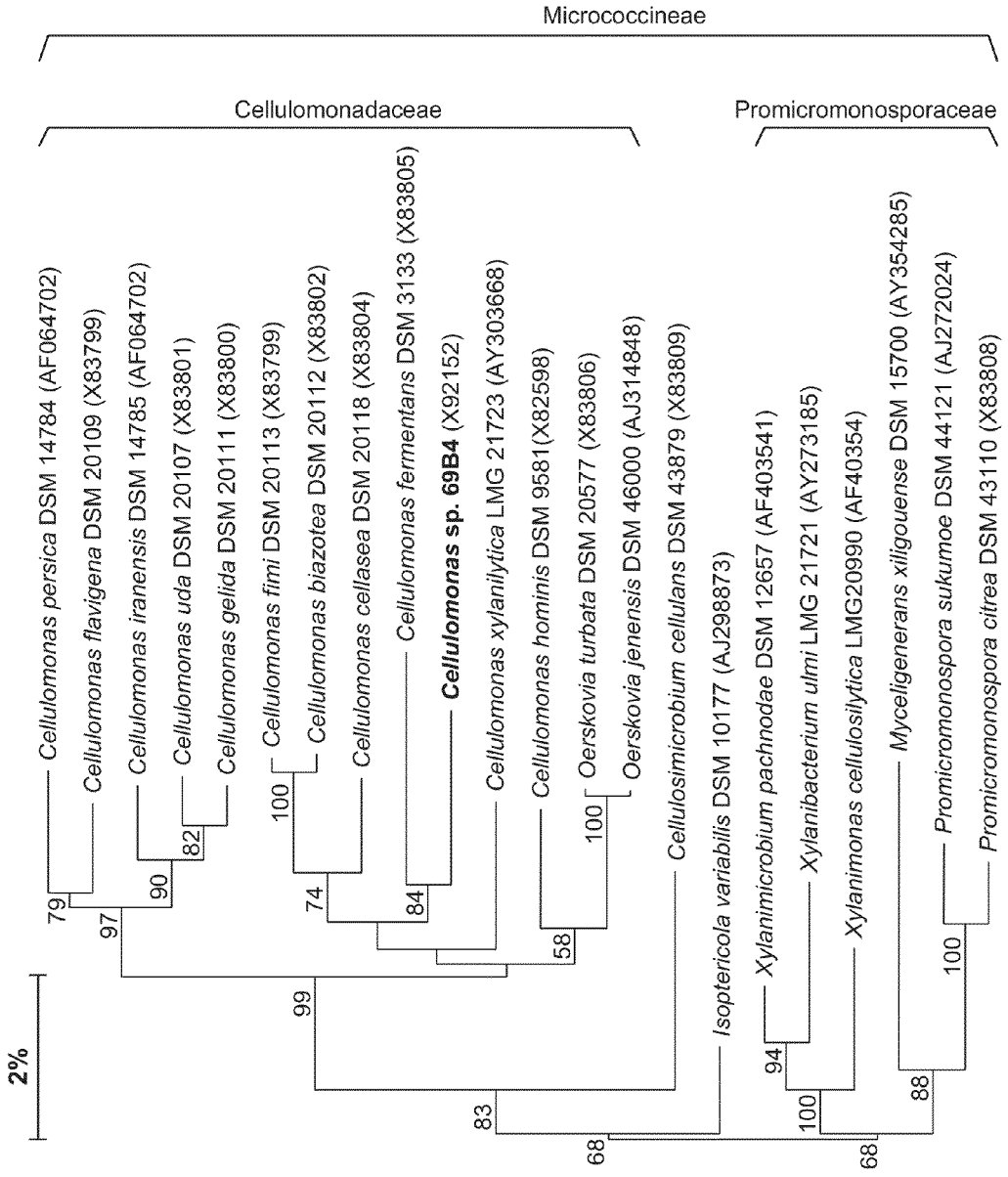
FIG. 1 provides an unrooted phylogenetic tree illustrating the relationship of novel strain 69B4 to members of the family Cellulomonadaceae and other related genera of the suborder *Micrococcineae*.

The present invention provides novel serine proteases, novel genetic material encoding these enzymes, and proteolytic proteins obtained from *Micrococcineae* spp., including but not limited to *Cellulomonas* spp. and variant proteins developed therefrom. In particular, the present invention provides protease compositions obtained from a *Cellulomonas* spp, DNA encoding the protease, vectors comprising the DNA encoding the protease, host cells transformed with the vector DNA, and an enzyme produced by the host cells. The present invention also provides cleaning compositions (e.g., detergent compositions), animal feed compositions, and textile and leather processing compositions comprising protease(s) obtained from a *Micrococcineae* spp., including but not limited to *Cellulomonas* spp. In alternative embodiments, the present invention provides mutant (i.e., variant) proteases derived from the wild-type proteases described herein. These mutant proteases also find use in numerous applications:

Gram-positive alkalophilic bacteria have been isolated from in and around alkaline soda lakes (See e.g., U.S. Pat. No. 5,401,657, herein incorporated by reference). These alkalophilic were analyzed according to the principles of numerical taxonomy with respect to each other and also a collection of known bacteria, and taxonomically characterized. Six natural clusters or phenons of alkalophilic bacteria were generated. Amongst the strains isolated was a strain identified as 69B4.

*Cellulomonas* spp. are Gram-positive bacteria classified as members of the family Cellulomonadaceae, Suborder *Micrococcineae*, Order Actinomycetales, Class Actinobacteria. *Cellulomonas* grows as slender, often irregular rods that may occasionally show branching, but no mycelium is formed. In addition, there is no aerial growth and no spores are formed. *Cellulomonas* and *Streptomyces* are only distantly related at a genetic level. The large genetic (genomic) distinction between Cellulomonas and *Streptomyces* is reflected in a great difference in phenotypic properties. While serine proteses in *Streptomyces* have been previously examined, there apparently have been no reports of any serine proteases (approx. MW 18,000 to 20,000) secreted by *Cellulomonas* spp. In addition, there apparently have been no previous reports of Cellulomonas proteases being used in the cleaning and/or feed industry.

*Streptomyces* are Gram-positive bacteria classified as members of the Family Streptomycetaceae, Suborder Streptomycineae, Order Actinomycetales, class Actinobacteria. *Streptomyces* grows as an extensively branching primary or substrate mycelium and an abundant aerial mycelium that at maturity bear characteristic spores. Streptogrisins are serine proteases secreted in large amounts from a wide variety of *Streptomyces* species. The amino acid sequences of *Streptomyces* proteases have been determined from at least 9 different species of *Streptomyces* including *Streptomyces griseus* Streptogrisin C (accession no. P52320); alkaline proteinase (EC 3.4.21.-) from *Streptomyces* sp. (accession no. PC2053); alkaline serine proteinase I from *Streptomyces* sp. (accession no. S34672), serine protease from *Streptomyces lividans* (accession no. CAD4208); putative serine protease from *Streptomyces coelicolor* A3(2) (accession no. NP_625129); putative serine protease from *Streptomyces avermitilis* MA-4680 (accession no. NP_822175); serine protease from *Streptomyces lividans* (accession no. CAD42809); putative serine protease precursor from *Streptomyces coelicolor* A3(2) (accession no. NP_628830)). A purified native alkaline protease having an apparent molecular weight of 19,000 daltons and isolated from *Streptomyces griseus* var. *alcalophilus* protease and cleaning compositions comprised thereof have been described (See e.g., U.S. Pat. No. 5,646,028, incorporated herein by reference).

The present invention provides protease enzymes produced by these organisms. Importantly, these enzymes have good stability and proteolytic activity. These enzymes find use in various applications, including but not limited to cleaning compositions, animal feed, textile processing and etc. The present invention also provides means to produce these enzymes. In some preferred embodiments, the proteases of the present invention are in pure or relatively pure form.

The present invention also provides nucleotide sequences which are suitable to produce the proteases of the present invention in recombinant organisms. In some embodiments, recombinant production provides means to produce the proteases in quantities that are commercially viable.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The practice of the present invention employs, unless otherwise indicated, conventional techniques of protein purification, molecular biology, microbiology, recombinant DNA techniques and protein sequencing, all of which are within the skill of those in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

I. Definitions

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the such analysis of protease or protelytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms "ASP protease," "Asp protease," and "Asp," refer to the serine proteases described herein. In some preferred embodiments, the Asp protease is the protease designed herein as 69B4 protease obtained from *Cellulomonas* strain 69B4. Thus, in preferred embodiments, the term "69B4 protease" refers to a naturally occurring mature protease derived from *Cellulomonas* strain 69B4 (DSM 16035) having substantially identical amino acid sequences as provided in SEQ ID NO:8. In alternative embodiments, the present invention provides portions of the ASP protease.

The term "Cellulomonas protease homologues" refers to naturally occurring proteases having substantially identical amino acid sequences to the mature protease derived from *Cellulomonas* strain 69B4 or polynucleotide sequences which encode for such naturally occurring proteases, and which proteases retain the functional characteristics of a serine protease encoded by such nucleic acids. In some embodiments, these protease homologues are referred to as "cellulomonadins."

As used herein, the terms "protease variant," "ASP variant," "ASP protease variant," and "69B protease variant" are used in reference to proteases that are similar to the wild-type ASP, particularly in their function, but have mutations in their amino acid sequence that make them different in sequence from the wild-type protease.

As used herein, "*Cellulomonas* ssp." refers to all of the species within the genus "*Cellulomonas*," which are Gram-positive bacteria classified as members of the Family Cellulomonadaceae, Suborder *Micrococcineae*, Order Actinomycetales, Class Actinobacteria. It is recognized that the genus *Cellulomonas* continues to undergo taxonomical reorganization. Thus, it is intended that the genus include species that have been reclassified As used herein, "*Streptomyces* ssp." refers to all of the species within the genus "*Streptomyces*," which are Gram-positive bacteria classified as members of the Family Streptomycetaceae, Suborder Streptomycineae, Order Actinomycetales, class Actinobacteria. It is recognized that the genus *Streptomyces* continues to undergo taxonomical reorganization. Thus, it is intended that the genus include species that have been reclassified As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracil, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes; and/or introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$; See e.g., Guerot-Fleury, Gene, 167:335-337 [1995]; Palmeros et al., Gene 247:255-264 [2000]; and Trieu-Cuot et al., Gene, 23:331-341 [1983]). Other markers useful in accordance with the invention include, but are not limited to auxotrophic markers, such as tryptophan; and detection markers, such asp-galactosidase.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment), that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, an "analogous sequence" is one wherein the function of the gene is essentially the same as the gene based on the *Cellulomonas* strain 69B4 protease. Additionally, analogous genes include at least 45%, 50%, 55%, 60%, 65%, 70%, 75%, 80%, 85%, 90%, 95%, 97%, 98%, 99% or 100% sequence identity with the sequence of the *Cellulomonas* strain 69B4 protease. Alternately, analogous sequences have an alignment of between 70 to 100% of the genes found in the *Cellulomonas* strain 69B4 protease region and/or have at least between 5-10 genes found in the region aligned with the genes in the *Cellulomonas* strain 69B4 chromosome. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps.

Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gape introduced by WU-Blast-2 to maximize the alignment score are ignored).

Thus, "percent (%) nucleic acid sequence identity" is defined as the percentage of nucleotide residues in a candidate sequence that are identical with the nucleotide residues of the starting sequence (i.e., the sequence of interest). A preferred method utilizes the so BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while an intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the dell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. In some embodiments, a flanking sequence is present on only a single side (either 3' or 5'), while in preferred embodiments, it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene which permits the amplification of that gene under appropriate, growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase; the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative position's of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, "protein of interest" and "polypeptide of interest" refer to a protein/polypeptide that is desired and/or being assessed. In some embodiments, the protein of interest is expressed intracellularly, while in other embodiments, it is a secreted polypeptide. In particularly preferred embodiments, these enzyme include the serine proteases of the present invention. In some embodiments, the protein of interest is a secreted polypeptide which is fused to a signal peptide (i.e., an amino-terminal extension on a protein to be secreted). Nearly all secreted proteins use an amino-terminal protein extension which plays a crucial role in the targeting to and translocation of precursor proteins across the membrane. This extension is proteolytically removed by a signal peptidase during or immediately following membrane transfer.

As used herein, the term "heterologous protein" refers to a protein or polypeptide that does not naturally occur in the host cell. Examples of heterologous proteins include enzymes such as hydrolases including proteases. In some embodiments, the gene encoding the proteins are naturally occurring genes, while in other embodiments, mutated and/or synthetic genes are used.

As used herein, "homologous protein" refers to a protein or polypeptide native or naturally occurring in a cell. In preferred embodiments, the cell is a Gram-positive cell, while in particularly preferred embodiments, the cell is a *Bacillus* host cell. In alternative embodiments, the homologous protein is a native protein produced by other organisms, including but not limited to *E. coli, Streptomyces, Trichoderma*, and *Aspergillus*. The invention encompasses host cells producing the homologous protein via recombinant DNA technology.

As used herein, an "operon region" comprises a group of contiguous genes that are transcribed as a single transcription unit from a common promoter, and are thereby subject to co-regulation. In some embodiments, the operon includes a regulator gene. In most preferred embodiments, operons that are highly expressed as measured by RNA levels, but have an unknown or unnecessary function are used.

As used herein, an "antimicrobial region" is a region containing at least one gene that encodes an antimicrobial protein.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences.

As is known in the art, a DNA can be transcribed by an RNA polymerase to produce RNA, but an RNA can be reverse transcribed by reverse transcriptase to produce a DNA. Thus a DNA can encode a RNA and vice versa.

The term "regulatory segment" or "regulatory sequence" or "expression control sequence" refers to a polynucleotide sequence of DNA that is operatively linked with a polynucleotide sequence of DNA that encodes the amino acid sequence of a polypeptide chain to effect the expression of the encoded amino acid sequence. The regulatory sequence can inhibit, repress, or promote the expression of the operably linked polynucleotide sequence encoding the amino acid.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence will result in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "substantially the same signal activity" refers to the signal activity, as indicated by substantially the same secretion of the protease into the fermentation medium, for example a fermentation medium protease level being at least 50%, at least 60%, at least 70%, at least 80%, at least 90%, at least 95%, at least 98% of the secreted protease levels in the fermentation medium as provided by the signal sequence of SEQ ID NOS:5 and/or 9.

The term "mature" form of a protein or peptide refers to the final functional form of the protein or peptide. To exemply, a mature form of the protease of the present invention at least includes the amino acid sequence identical to residue positions 1-189 of SEQ ID NO:8.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from Cellulomonas" refers to those enzymes having proteolytic activity which are naturally-produced by Cellulomonas, as well as to serine proteases like those produced by Cellulomonas sources but which through the use of genetic engineering techniques are produced by non-Cellulomonas organisms transformed with a nucleic acid encoding said serine proteases.

A "derivative" within the scope of this definition generally retains the characteristic proteolytic activity observed in the wild-type, native or parent form to the extent that the derivative is useful for similar purposes as the wild-type, native or parent form. Functional derivatives of serine protease encompass naturally occurring, synthetically or recombinantly produced peptides or peptide fragments which have the general characteristics of the serine protease of the present invention.

The term "functional derivative" refers to a derivative of a nucleic acid which has the functional characteristics of a nucleic acid which encodes serine protease. Functional derivatives of a nucleic acid which encode serine protease of the present invention encompass naturally occurring, synthetically or recombinantly produced nucleic acids or fragments and encode serine protease characteristic of the present invention. Wild type nucleic acid encoding serine proteases according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The phrase "equivalent," in this context, refers to serine proteases enzymes that are encoded by a polynucleotide capable of hybridizing to the polynucleotide having the sequence as shown in SEQ ID NO:1, under conditions of medium to maximal stringency. For example, being equivalent means that an equivalent mature serine protease comprises at least 70%, at least 75%, at least 80%, at least 85%, at least 90%, at least 91%, at least 92%, at least 93%, at least 94%, at least 95%, at least 96%, at least 97%, at least 98% and/or at least 99% sequence identity to the mature Cellulomonas serine protease having as the amino acid sequence of SEQ ID NO:8.

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78 [1985]). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations which were not members of the predefined set of mutations. In some embodiments, the methods include those set forth in U.S. patent application Ser. No. 09/699,250, filed Oct. 26, 2000, hereby incorporated by reference. In alternative embodiments, combinatorial mutagenesis methods encompass commercially available kits (e.g., QuikChange® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the term "starting gene" refers to a gene of interest that encodes a protein of interest that is to be improved and/or changed using the present invention.

As used herein, the term "multiple sequence alignment" ("MSA") refers to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence resulting from an MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

As used herein, the term "initial hit" refers to a variant that was identified by screening a combinatorial consensus mutagenesis library. In preferred embodiments, initial hits have improved performance characteristics, as compared to the starting gene.

As used herein, the term "improved hit" refers to a variant that was identified by screening an enhanced combinatorial consensus mutagenesis library.

As used herein, the terms "improving mutation" and "performance-enhancing mutation" refer to a mutation that leads to improved performance when it is introduced into the starting gene. In some preferred embodiments, these mutations are identified by sequencing hits that were identified during the screening step of the method. In most embodiments, mutations that are more frequently found in hits are likely to be improving mutations, as compared to an unscreened combinatorial consensus mutagenesis library.

As used herein, the term "enhanced combinatorial consensus mutagenesis library" refers to a CCM library that is designed and constructed based on screening and/or sequencing results from an earlier round of CCM mutagenesis and screening. In some embodiments, the enhanced CCM library is based on the sequence of an initial hit resulting from an earlier round of CCM. In additional embodiments, the enhanced CCM is designed such that mutations that were frequently observed in initial hits from earlier rounds of mutagenesis and screening are favored. In some preferred embodiments, this is accomplished by omitting primers that encode performance-reducing mutations or by increasing the concentration of primers that encode performance-enhancing mutations relative to other primers, that were used in earlier CCM libraries.

As used herein, the term "performance-reducing mutations" refer to mutations in the combinatorial consensus mutagenesis library that are less frequently found in hits resulting from screening as compared to an unscreened combinatorial consensus mutagenesis library. In preferred embodiments, the screening process removes and/or reduces the abundance of variants that contain "performance-reducing mutations."

As used herein, the term "functional assay" refers to an assay that provides an indication of a protein's activity. In particularly preferred embodiments, the term refers to assay systems in which a protein is analyzed for its ability to function in its usual capacity. For example, in the case of enzymes, a functional assay involves determining the effectiveness of the enzyme in catalyzing a reaction.

As used herein, the term "target property" refers to the property of the starting gene that is to be altered. It is not intended that the present invention be limited to any particular target property. However, in some preferred embodiments, the target property is the stability of a gene product (e.g., resistance to denaturation, proteolysis or other degradative factors), while in other embodiments, the level of production in a production host is altered. Indeed, it is contemplated that any property of a starting gene will find use in the present invention.

The term "property" or grammatical equivalents thereof in the context of a nucleic acid, as used herein, refer to any characteristic or attribute of a nucleic acid that can be selected or detected. These properties include, but are not limited to, a property affecting binding to a polypeptide, a property conferred on a cell comprising a particular nucleic acid, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, etc., of a nucleic acid may be altered to produce desired characteristics or to identify undesirable characteristics.

The term "property" or grammatical equivalents thereof in the context of a polypeptide, as used herein, refer to any characteristic or attribute of a polypeptide that can be selected or detected. These properties include, but are not limited to oxidative stability, substrate specificity, catalytic activity, thermal stability, alkaline stability, pH activity profile, resistance to proteolytic degradation, $K_M$, $K_{cat}$, $K_{cat}/k_M$ ratio, protein folding, inducing an immune response, ability to bind to a ligand, ability to bind to a receptor, ability to be secreted, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease.

As used herein, the term "screening" has its usual meaning in the art and is, in general a multi-step process. In the first step, a mutant nucleic acid or variant polypeptide therefrom is provided. In the second step, a property of the mutant nucleic acid or variant polypeptide is determined. In the third step, the determined property is compared to a property of the corresponding precursor nucleic acid, to the property of the corresponding naturally occurring polypeptide or to the property of the starting material (e.g., the initial sequence) for the generation of the mutant nucleic acid.

It will be apparent to the skilled artisan that the screening procedure for obtaining a nucleic acid or protein with an altered property depends upon the property of the starting material the modification of which the generation of the mutant nucleic acid is intended to facilitate. The skilled artisan will therefore appreciate that the invention is not limited to any specific property to be screened for and that the following description of properties lists illustrative examples only. Methods for screening for any particular property are generally described in the art. For example, one can measure binding, pH, specificity, etc., before and after mutation, wherein a change indicates an alteration. Preferably, the screens are performed in a high-throughput manner, including multiple samples being screened simultaneously, including, but not limited to assays utilizing chips, phage display, and multiple substrates and/or indicators.

As used herein, in some embodiments, screens encompass selection steps in which variants of interest are enriched from a population of variants. Examples of these embodiments include the selection of variants that confer a growth advantage to the host organism, as well as phage display or any other method of display, where variants can be captured from a population of variants based on their binding or catalytic properties. In a preferred embodiment, a library of variants is exposed to stress (heat, protease, denaturation) and subsequently variants that are still intact are identified in a screen or enriched by selection. It is intended that the term encompass any suitable means for selection. Indeed, it is not intended that the present invention be limited to any particular method of screening.

As used herein, the term "targeted randomization" refers to a process that produces a plurality of sequences where one or several positions have been randomized. In some embodiments, randomization is complete (i.e., all four nucleotides, A, T, G, and C can occur at a randomized position. In alternative embodiments, randomization of a nucleotide is limited to a subset of the four nucleotides. Targeted randomization can be applied to one or several codons of a sequence, coding for one or several proteins of interest. When expressed, the resulting libraries produce protein populations in which one or more amino acid positions can contain a mixture of all 20 amino acids or a subset of amino acids, as determined by the randomization scheme of the randomized codon. In some embodiments, the individual members of a population resulting from targeted randomization differ in the number of amino acids, due to targeted or random insertion or deletion of codons. In further embodiments, synthetic amino acids are included in the protein populations produced. In some preferred embodiments, the majority of members of a population resulting from targeted randomization show greater sequence homology to the consensus sequence than the starting gene. In some embodiments, the sequence encodes one or more proteins fo interest. In alternative embodiments, the proteins have differing biological functions. In some preferred embodiments, the incoming sequence comprises at least one selectable marker.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions which will match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their precursor sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

As used herein, the phrase "contiguous mutations" refers to mutations which are presented within the same oligonucleotide primer. For example, contiguous mutations may be adjacent or nearby each other, however, they will be introduced into the resulting mutant template nucleic acids by the same primer.

As used herein, the phrase "discontiguous mutations" refers to mutations which are presented in separate oligonucleotide primers. For example, discontiguous mutations will be introduced into the resulting mutant template nucleic acids by separately prepared oligonucleotide primers.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein engineering project. The wild-type sequence may encode either a homologous or heterologous protein. A homologous protein is one the host cell would produce without intervention. A heterologous protein is one that the host cell would not produce but for the intervention.

As used herein, the term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the epitope that the intact antibody binds and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least 50%, 60%, 70%, 75%, 80%, 85%, 90%, 92%, 95%, 96%, 97%, 98% or 99% proteolytic activity after contact with a bleaching or oxidizing agent over a given time period, for example, at least 1 minute, 3 minutes, 5 minutes, 8 minutes, 12 minutes, 16 minutes, 20 minutes, etc. In some embodiments, the stability is measured as described in the Examples.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least 50%, 60%, 70%, 75%, 80%, 85%, 90%, 92%, 95%, 96%, 97%, 98% or 99% proteolytic activity after contact with a chelating agent over a given time period, for example, at least 10 minutes, 20 minutes, 40 minutes, 60 minutes, 100 minutes, etc. In some embodiments, the chelator stability is measured as described in the Examples.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed altered temperatures. Altered temperatures includes increased or decreased temperatures. In some embodiments, the proteases retain at least 50%, 60%, 70%, 75%, 80%, 85%, 90%, 92%, 95%, 96%, 97%, 98% or 99% proteolytic activity after exposure to altered temperatures over a given time period, for example, at least 60 minutes, 120 minutes, 180 minutes, 240 minutes, 300 minutes, etc. In some embodiments, the thermostability is determined as described in the Examples.

The term "enhanced stability" in the context of an oxidation, chelator, thermal and/or pH stable protease refers to a higher retained proteolytic activity over time as compared to other serine proteases (e.g., subtilisin proteases) and/or wild-type enzymes.

The term "diminished stability" in the context of an oxidation, chelator, thermal and/or pH stable protease refers to a lower retained proteolytic activity over time as compared to other serine proteases (e.g., subtilisin proteases) and/or wild-type enzymes.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pretreat types.

It is to be understood that the test methods described in the Examples herein are used to determine the respective values of the parameters of the present invention, as such invention is described and claimed herein.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

The term "enhanced performance" in the context of cleaning activity refers to an increased or greater cleaning activity of certain enzyme sensitive stains such as egg, milk, grass or blood, as determined by usual evaluation after a standard wash cycle and/or multiple wash cycles.

The term "diminished performance" in the context of cleaning activity refers to an decreased or lesser cleaning activity of certain enzyme sensitive stains such as egg, milk, grass or blood, as determined by usual evaluation after a standard wash cycle.

The term "comparative performance" in the context of cleaning activity refers to at least 60%, at least 70%, at least 80% at least 90% at least 95% of the cleaning activity of a comparative subtilisin protease (e.g., commercially available proteases), including but not limited to OPTIMASE™ protease (Genencor), PURAFECT™ protease products (Genencor), SAVINASE™ protease (Novozymes), BPN'-variants (See e.g., U.S. Pat. No. Re 34,606), RELASE™, DURAZYM™, EVERLASE™, KANNASE™ protease (Novozymes), MAXACAL™; MAXAPEM™, PROPERASE™ proteases (Genencor; See also, U.S. Pat. No. Re 34,606, U.S. Pat. Nos. 5,700,676; 5,955,340; 6,312,936; 6,482,628), and *B. lentus* variant protease products [for example those described in WO 92/21760, WO 95/23221 and/or WO 97/07770 (Henkel). Exemplary subtilisin protease variants include, but are not limited to those having substitutions or deletions at residue positions equivalent to positions 76, 101, 103, 104, 120, 159, 167, 170, 194, 195, 217, 232, 235, 236, 245, 248, and/or 252 of BPN'. Cleaning performance can be determined by comparing the proteases of the present invention with those subtilisin proteases in various cleaning assays concerning enzyme sensitive stains such as grass, blood or milk as determined by usual spectrophotometric or analytical methodologies after standard wash cycle conditions.

As used herein, a "low detergent concentration" system includes detergents where less than about 800 ppm of detergent components are present in the wash water. Japanese detergents are typically considered low detergent concentration systems, as they have usually have approximately 667 ppm of detergent components present in the wash water.

As used herein, a "medium detergent concentration" systems includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" systems includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or more preferably, 5%, by weight of the composition. In some embodiments, the inorganic filler salts are selected from the alkali and alkaline-earth-metal salts of sulfates and chlorides. A preferred filler salt is sodium sulfate.

II. Serine Protease Enzymes and Nucleic Acid Encoding Serine Protease Enzymes

The present invention provides isolated polynucleotides encoding amino acid sequences, encoding proteases. In some embodiments, these polynucleotides comprise at least 65% amino acid sequence identity, preferably at least 70% amino acid sequence identity, more preferably at least 75% amino acid sequence identity, still more preferably at least 80% amino acid sequence identity, more preferably at least 85% amino acid sequence identity, even more preferably at least 90% amino acid sequence identity, more preferably at least 92% amino acid sequence identity, yet more preferably at least 95% amino acid sequence identity, more preferably at least 97% amino acid sequence identity, still more preferably at least 98% amino acid sequence identity, and most preferably at least 99% amino acid sequence identity to an amino acid sequence as shown in SEQ ID NOS:6-8, (e.g., at least a portion of the amino acid sequence encoded by the polynucleotide having proteolytic activity, including the mature protease catalyzing the hydrolysis of peptide linkages of substrates), and/or demonstrating comparable or enhanced washing performance under identified wash conditions.

In some embodiments, the percent identity (amino acid sequence, nucleic acid sequence, gene sequence) is determined by a direct comparison of the sequence information between two molecules by aligning the sequences, counting the exact number of matches between the two aligned sequences, dividing by the length of the shorter sequence, and multiplying the result by 100. Readily available computer programs find use in these analysis, such as those described above. Programs for determining nucleotide sequence identity are available in the Wisconsin Sequence Analysis Package, Version 8 (Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., J. Mol. Biol., 215:403-410 (1990). Software for performing BLAST analyses is publicly available through the National Center for Biotechnology Information (www.ncbi.nlm.nih.gov). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff & Henikoff, *Proc. Natl. Acad. Sci. USA* 89:10915 (1989)) alignments (B) of 50, expectation (E) of 10, M'S, N'-4, and a comparison of both strands.

The BLAST algorithm then performs a statistical analysis of the similarity between two sequences (See e.g., Karlin and Altschul, Proc. Nat'l. Acad. Sci. USA 90:5873-5787 [1993]). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

In some embodiments of the present invention, sequences were analyzed by BLAST and protein translation sequence tools. In some experiments, the preferred version was BLAST (Basic BLAST version 2.0). The program' chosen was "BlastX", and the database chosen was "nr". Standard/default parameter values were employed.

In some preferred embodiments, the present invention encompasses the approximately 1621 base pairs in length polynucleotide set forth in SEQ. ID NO:1. A start codon is shown in bold in SEQ ID NO:1. In another embodiment of the present invention, the polynucleotides encoding these amino acid sequences comprise a 1485 base pair portion (residues 1-1485 of SEQ ID NO:2) that, if expressed, is believed to encode a signal sequence (nucleotides 1-84 of SEQ ID NO:5) encoding amino acids 1-28 of SEQ ID NO:9; an N-terminal prosequence (nucleotides 84-594 encoding amino acid residues 29-198 of SEQ ID NO:6); a mature protease sequence (nucleotides 595-1161 of SEQ ID NO:2 encoding amino acid residues 1-189 of SEQ ID NO:8); and a C-terminal prosequence (nucleotides 1162-1486 encoding amino acid residues 388-495 of SEQ ID NO:6). Alternatively, the signal peptide, the N-terminal pro-sequence, mature serine protease sequence and C-terminal pro-sequence is numbered in relation to the amino acid residues of the mature protease of SEQ ID NO:6 being numbered 1-189, i.e., signal peptide (residues −198 to −171), an N-terminal pro sequence (residues −171 to −1), the mature serine protease sequence (residues 1-189) and a C-terminal pro-sequence (residues 190-298). In another embodiment of the present invention, the polynucleotide encoding an amino acid sequence having proteolytic activity comprises a nucleotide sequence of nucleotides 1 to 1485 of the portion of SEQ ID NO:2 encoding the signal peptide and precursor protease. In another embodiment of the present invention, the polynucleotide encoding an amino acid sequence comprises the sequence of nucleotides 1 to 1412 of the polynucleotide encoding the precursor Cellulomonas protease (SEQ ID NO:3). In yet another embodiment, the polynucleotide encoding an amino acid sequence comprises the sequence of nucleotides 1 to 587 of the portion of the polynucleotide encoding the mature Cellulomonas protease (SEQ ID NO:4).

As will be understood by the skilled artisan, due to the degeneracy of the genetic code, a variety of polynucleotides can encode the signal peptide, precursor protease and/or mature protease provided in SEQ ID NOS:6, 7, and/or 8, respectively, or a protease having the % sequence identity described above. Another embodiment of the present invention encompasses a polynucleotide comprising a nucleotide sequence having at least 70% sequence identity, at least 75% sequence identity, at least 80% sequence identity, at least 85% sequence identity, at least 90% sequence identity, at least 92% sequence identity, at least 95% sequence identity, at least 97% sequence identity, at least 98% sequence identity and at least 99% sequence identity to the polynucleotide sequence of SEQ ID NOS:2, 3, and/or 4, respectively, encoding the signal peptide and precursor protease, the precursor protease and/or the mature protease, respectively.

In additional embodiments, the present invention provides fragments or portions of DNA that encodes proteases, so long as the encoded fragment retains proteolytic activity. Another embodiment of the present invention encompasses polynucleotides having at least 20% of the sequence length, at least 30% of the sequence length, at least 40% of the sequence length, at least 50% of the sequence length, at least 60% of the sequence length, 70% of the sequence length, at least 75% of the sequence length, at least 80% of the sequence length, at least 85% of the sequence length, at least 90% of the sequence length, at least 92% of the sequence length, at least 95% of the sequence length, at least 97% of the sequence length, at least 98% of the sequence length and at least 99% of the sequence of the polynucleotide sequence of SEQ ID NO:2, or residues 185-1672 of SEQ ID NO:1, encoding the precursor protease. In alternative embodiments, these fragments or portions of the sequence length are contiguous portions of the sequence length, useful for shuffling of the DNA sequence in recombinant DNA sequences (See e.g., U.S. Pat. No. 6,132,970)

Another embodiment of the invention includes fragments of the DNA described herein that find use according to art recognized techniques in obtaining partial length DNA fragments capable of being used to isolate or identify polynucleotides encoding mature protease enzyme described herein from Cellulomonas 6964, or a segment thereof having proteolytic activity. Moreover, the DNA provided in SEQ ID NO:1 finds use in identifying homologous fragments of DNA from other species, and particularly from *Cellulomonas* spp. which encode a protease or portion thereof having proteolytic activity.

In addition, the present invention encompasses using primer or probe sequences constructed from SEQ ID NO:1, or a suitable portion or fragment thereof (e.g., at least about 5-20 or 10-15 contiguous nucleotides), as a probe or primer for screening nucleic acid of either genomic or cDNA origin. In some embodiments, the present invention provides DNA probes of the desired length (i.e., generally between 100 and 1000 bases in length), based on the sequences in SEQ ID NOS1, 2, 3, and/or 4.

In some embodiments, the DNA fragments are electrophoretically isolated, cut from the gel, and recovered from the agar matrix of the gel. In preferred embodiments, this purified fragment of DNA is then labeled (using, for example, the Megaprime labeling system according to the instructions of the manufacturer) to incorporate $P^{32}$ in the DNA. The labeled probe is denatured by heating to 95° C. for a given period of time (e.g., 5 minutes), and immediately added to the membrane and prehybridization solution. The hybridization reaction proceeds for an appropriate time and under appropriate conditions (e.g., 18 hours at 37° C.), with gentle shaking or rotation. The membrane is rinsed (e.g., twice in SSC/0.3% SDS) and then washed in an appropriate wash solution with gentle agitation. The stringency desired is a reflection of the conditions under which the membrane (filter) is washed. In some embodiments herein, "low-stringency" conditions involve washing with a solution of 0.2×SSC/0.1% SDS at 20° C. for 15 minutes, while in other embodiments, "medium-stringency" conditions, involve a further washing step comprising washing with a solution of 0.2×SSC/0.1% SDS at 37° C. for 30 minutes, while in other embodiments, "high-stringency" conditions involve a further washing step comprising washing with a solution of 0.2×SSC/0.1% SDS at 37° C. for 45 minutes, and in further embodiments, "maximum-stringency" conditions involve a further washing step comprising washing with a solution of 0.2×SSC/0.1% SDS at 37° C. for 60 minutes. Thus, various embodiments of the present invention provide polynucleotides capable of hybridizing to a probed derived from the nucleotide sequence provided in SEQ ID NOS:1, 2, 3, 4, and/or 5, under conditions of medium, high and/or maximum stringency.

After washing, the membrane is dried and the bound probe detected. If $P^{32}$ or another radioisotope is used as the labeling agent, the bound probe is detected by autoradiography. Other techniques for the visualization of other probes are well-known to those of skill in the art. The detection of a bound probe indicates a nucleic acid sequence has the desired homology, and therefore identity to SEQ ID NOS:1, 2, 3, 4, and/or 5, and is encompassed by the present invention. Accordingly, the present invention provides methods for the detection of nucleic acid encoding a protease encompassed by the present invention which comprises hybridizing part or all of a nucleic acid sequence of SEQ ID NOS:1, 2, 3, 4, and/or 5 with other nucleic acid of either genomic or cDNA origin.

As indicated above, in other embodiments, hybridization conditions are based on the melting temperature (Tm) of the nucleic acid binding complex, to confer a defined "stringency" as explained below. "Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As known to those of skill in the art, medium, high and/or maximum stringency hybridization are chosen such that conditions are optimized to identify or detect polynucleotide sequence homologues or equivalent polynucleotide sequences.

In yet additional embodiments, the present invention provides nucleic acid constructs (i.e., expression vectors) comprising the polynucleotides encoding the proteases of the present invention. In further embodiments, the present invention provides host cells transformed with at least one of these vectors.

In further embodiments, the present invention provides polynucleotide sequences further encoding a signal sequence. In some embodiments, invention encompasses polynucleotides having signal activity comprising a nucleotide sequence having at least 65% sequence identity, at least 70% sequence identity, preferably at least 75% sequence identity, more preferably at least 80% sequence identity, still further preferably at least 85% sequence identity, even more preferably at least 90% sequence identity, more preferably at least 95% sequence identity, more preferably at least 97% sequence identity, at least 98% sequence identity, and most preferably at least 99% sequence identity to SEQ ID NO:5. Thus, in these embodiments, the present invention provides a sequence with a putative signal sequence, and polynucleotides being capable of hybridizing to a probe derived from the nucleotide sequence disclosed in SEQ ID NO:5 under conditions of medium, high and/or maximal stringency, wherein the signal sequences have substantially the same signal activity as the signal sequence encoded by the polynucleotide of the present invention.

In some embodiments, the signal activity is indicated by substantially the same level of secretion of the protease into the fermentation medium, as the starting material. For example, in some embodiments, the present invention provides fermentation medium protease levels at least 50%, at least 60%, at least 70%, at least 80%, at least 90%, at least 95%, or at least 98% of the secreted protease levels in the fermentation medium as provided by the signal sequence of SEQ ID NO:3. In some embodiments, the secreted protease levels are ascertained by protease activity analyses such as the pNA assay (See e.g., Del Mar, [1979], infra). Additional means for determining the levels of secretion of a heterologous or homologous protein in a Gram-positive host cell and detecting secreted proteins include using either polyclonal or monoclonal antibodies specific for the protein. Examples include enzyme-linked immunosorbent assay (ELISA), radioimmunoassay (RIA) and fluorescent activated cell sorting (FACS), as well-known those in the art.

In further embodiments, the present invention provides polynucleotides, encoding an amino acid sequence of a signal peptide (nucleotides 1-84 of SEQ ID NO:5), as shown in SEQ ID NO:9, nucleotide residue positions 1 to 85 of SEQ ID NO:2, and for SEQ ID NO:5. The invention further encompasses nucleic acid sequences which hybridize to the nucleic acid sequence shown in SEQ ID NO:5 under low, medium, high stringency and/or maximum stringency conditions, but which have substantially the same signal activity as the sequence. The present invention encompasses all such polynucleotides.

In further embodiments, the present invention provides polynucleotides that are complementary to the nucleotide sequences described herein. Exemplary complementary nucleotide sequences include those that are provided in SEQ ID NOS:1-5.

Further aspects of the present invention encompass polypeptides having proteolytic activity comprising 65% amino acid sequence identity, at least 70% sequence identity, at least 75% amino acid sequence identity, at least 80% amino acid sequence identity, at least 85% amino acid sequence identity, at least 90% amino acid sequence identity, at least 92% amino acid sequence identity, at least 95% amino acid sequence identity, at least 97% amino acid sequence identity, at least 98% amino acid sequence identity and at least 99% amino acid sequence identity to the amino acid sequence of SEQ ID NO: 6 (i.e., the signal and precursor protease), SEQ ID NO:7 (i.e., the precursor protease), and/or of SEQ ID NO:8 (i.e., the mature protease). The proteolytic activity of these polypeptides is determined using methods known in the art and include such methods as those used to assess detergent function. In further embodiments, the polypeptides are isolated. In additional embodiments of the present invention, the polypeptides comprise amino acid sequences that identical to amino acid sequence selected from the group consisting of the amino acid sequences of SEQ ID NOS:6, 7, or 8. In some further embodiments, the polypeptides are identical to portions of SEQ ID NOS:6, 7 or 8.

In some embodiments, the present invention provides isolated polypeptides having proteolytic activity, comprising the amino acid sequence approximately 495 amino acids in length, as provided in SEQ ID NO:6. In further embodiments, the present invention encompasses polypeptides having proteolytic activity comprising the amino acid sequence approximately 467 amino acids in length provided in SEQ ID NO:7. In some embodiments, these amino acid sequences comprise a signal sequence (amino acids 1-28 of SEQ ID NO:9); and a precursor protease (amino acids 1-467 of SEQ ID NO:7). In additional embodiments, the present invention encompasses polypeptides comprising an N-terminal prosequence (amino acids 1-170 of SEQ ID NO:7), a mature protease sequence (amino acids 1-189 of SEQ ID NO:8), and a C-terminal prosequence (amino acids 360-467 of SEQ ID NO:7). In still further embodiments, the present invention encompasses polypeptides comprising a precursor protease sequence (e.g., amino acids 1-467 of SEQ ID NO:7). In yet another embodiment, the present invention encompasses polypeptides comprising a mature protease sequence comprising amino acids (e.g., 1-189 of SEQ ID NO:8).

In further embodiments, the present invention provides polypeptides and/or proteases comprising amino acid sequences of the above described sequence derived from bacterial species including, but not limited to *Micrococcineae* which are identified through amino acid sequence homology studies. In some embodiments, an amino acid residue of a precursor *Micrococcineae* protease is equivalent to a residue of *Cellulomonas* strain 69B4, if it is either homologous (i.e., corresponding in position in either primary or tertiary structure) or analogous to a specific residue or portion of that residue in *Cellulomonas* strain 69B4 protease (i.e., having the same or similar functional capacity to combine, react, or interact chemically).

In some preferred embodiments, in order to establish homology to primary structure, the amino acid sequence of a precursor protease is directly compared to the Cellulomonas strain 69B4 mature protease amino acid sequence and particularly to a set of conserved residues which are discerned to be invariant in all or a large majority of Cellulomonas like proteases for which sequence is known. After aligning the conserved residues, allowing for necessary insertions and deletions in order to maintain alignment (i.e., avoiding the elimination of conserved residues through arbitrary deletion and insertion), the residues corresponding to particular amino acids in the mature protease (SEQ ID NO:8) and *Cellulomonas* 69B4 protease are determined. Alignment of conserved residues preferably should conserve 100% of such residues. However, alignment of greater than 75% or as little as 45% of conserved residues is also adequate to define equivalent residues. However, conservation of the catalytic triad, His32/Asp56/Ser137 of SEQ ID NO:8 should be maintained.

For example, in some embodiments, the amino acid sequence of proteases from *Cellulomonas* strain 69B4, and other *Micrococcineae* spp. described above are aligned to provide the maximum amount of homology between amino acid sequences. A comparison of these sequences indicates that there are a number of conserved residues contained in each sequence. These are the residues that are identified and utilized to establish the equivalent residue positions of amino acids identified in the precursor or mature *Micrococcineae* protease in question.

These conserved residues are used to ascertain the corresponding amino acid residues of *Cellulomonas* strain 69B4 protease in one or more in *Micrococcineae* homologues (e.g.,

*Cellulomonas cellasea* (DSM 20118) and/or a *Cellulomonas homologue* herein). These particular amino acid sequences are aligned with the sequence of *Cellulomonas* 69B4 protease to produce the maximum homology of conserved residues. By this alignment, the sequences and particular residue positions of *Cellulomonas* 69B4 are observed in comparison with other *Cellulomonas* spp. Thus, the equivalent amino acid for the catalytic triad (e.g., in *Cellulomonas* 69B4 protease) is identifiable in the other *Micrococcineae* spp. In some embodiments of the present invention, the protease homologs comprise the equivalent of His32/Asp56/Ser137 of SEQ ID NO:8.

Another indication that two polypeptides are substantially identical is that the first polypeptide is immunologically cross-reactive with the second polypeptide. Methodologies for determining immunological cross-reactivity are described in the art and are described in the Examples herein. Typically, polypeptides that differ by conservative amino acid substitutions are immunologically cross-reactive. Thus, a polypeptide is substantially identical to a second polypeptide, for example, where the two peptides differ only by a conservative substitution.

The present invention encompasses proteases obtained from various sources. In some preferred embodiments, the proteases are obtained from bacteria, while in other embodiments, the proteases are obtained from fungi.

In some particularly preferred embodiments, the bacterial source is selected from the members of the suborder *Micrococcineae*. In some embodiments, the bacterial source is the family Promicromonosporaceae. In some preferred embodiments, the Promicromonosporaceae spp. includes and/or is selected from the group consisting of *Promicromonospora citrea* (DSM 431.10), *Promicromonospora sukumoe* (DSM 44121), *Promicromonospora aerolata* (CCM 7043), *Promicromonospora vindobonensis* (CCM 7044), *Myceligenerans xiligouense* (DSM 15700), *Isoptericola variabilis* (DSM 10177, basonym *Cellulosimicrobium variabile*), *Cellulosimicrobium cellulans* (DSM 20424, basonym *Nocardia cellulans, Cellulomonas cellulans*), *Cellulosimicrobium funkei, Xylanimonas cellulosilytica* (LMG 20990), *Xylanibacterium ulmi* (LMG 21721), and *Xylanimicrobium pachnodae* (DSM 12657, basonym *Promicromonospora pachnodae*).

In other particularly preferred embodiments, the bacterial source is the family Cellulomonadaceae. In some preferred embodiments, the Cellulomonadaceae spp. includes and/or is selected from the group of *Cellulomonas fimi* (ATCC 484, DSM 20113), *Cellulomonas biazotea* (ATCC 486, DSM 20112), *Cellulomonas cellasea* (ATCC 487, 21681, DSM 20118), *Cellulomonas denverensis, Cellulomonas hominis* (DSM 9581), *Cellulomonas flavigena* (ATCC 482, DSM 20109), *Cellulomonas persica* (ATCC 700642, DSM 14784), *Cellulomonas iranensis* (ATCC 700643, DSM 14785); *Cellulomonas fermentans* (ATCC 43279, DSM 3133), *Cellulomonas gelida* (ATCC 488, DSM 20111, DSM 20110), *Cellulomonas humilata* (ATCC 25174, basonym *Actinomyces humiferus*), *Cellulomonas uda* (ATCC 491, DSM 20107), *Cellulomonas xylanilytica* (LMG 21723), *Cellulomonas septica, Cellulomonas parahominis, Oerskovia turbata* (ATCC 25835, DSM 20577, synonym *Cellulomonas turbata*), *Oerskovia jenensis* (DSM 46000), *Oerskovia enterophila* (ATCC 35307, DSM 43852, basonym *Promicromonospora enterophila*), *Oerskovia paurometabola* (DSM 14281), and *Cellulomonas* strain 69B4 (DSM 16035). In further embodiments, the bacterial source also includes and/or is selected from the group of *Thermobifida* spp., *Rarobacter* spp., and/or *Lysobacter* spp. In yet additional embodiments, the *Thermobifida* spp. is *Thermobifida fusca* (basonym *Thermomonospora*

*fusca*) (tfpA, AAC23545; See, Lao et. al, Appl. Environ. Microbiol., 62: 4256-4259 [1996]). In an alternative embodiment, the *Rarobacter* spp. is *Rarobacter faecitabidus* (RP1, A45053; See e.g., Shimoi et al., J. Biol. Chem., 267:25189-25195 [1992]). In yet another embodiment, the *Lysobacter* spp. is *Lysobacter enzymogenes*.

In further embodiments, the present invention provides polypeptides and/or polynucleotides obtained and/or isolated from fungal sources. In some embodiments, the fungal source includes a *Metarhizium* spp. In some preferred embodiments, the fungal source is a *Metarhizium anisopliae* (CHY1 (CAB60729).

In another embodiment, the present invention provides polypeptides and/or polynucleotides derived from a *Cellulomonas* strain selected from cluster 2 of the taxonomic classification described in U.S. Pat. No. 5,401,657, herein incorporated by reference. In U.S. Pat. No. 5,401,657, twenty strains of bacteria isolated from in and around alkaline lakes were assigned to the type of bacteria known as Gram-positive bacteria on the basis of: (1) the Dussault modification of the Gram's staining reaction (Dussault, J. Bacteriol., 70:484-485 [1955]); (2) the KOH sensitivity test (Gregersen, Eur. J. Appl. Microbiol. Biotechnol., 5:123-127 [1978]; Halebian et al., J. Clin. Microbiol., 13:444-448 [1981]; and (3) the aminopeptidase reaction (Cerny, Eur. J. Appl. Microbiol., 3:223-225 [1976]; Cerny, Eur. J. Appl. Microbiol., 5:113-122 [1978]). In addition, in most cases, confirmation was also made on the basis of quinone analysis (Collins and Jones, Microbiol. Rev., 45:316-354 [1981]) using the method described by Collins (See, Collins, In Goodfellow and Minnikin (eds), *Chemical Methods in Bacterial Systematics*, Academic Press, London [1985], pp. 267-288). In addition, strains can be tested for 200 characters and the results analyzed using the principles of numerical taxonomy (See e.g., Sneath and Sokal, *Numerical Taxonomy*, W.H. Freeman & Co., San Francisco, Calif. [1973]). Exemplary characters tested, testing methods, and codification methods are also described in U.S. Pat. No. 5,401,657.

As described in U.S. Pat. No. 5,401,657, the phenetic data, consisting of 200 unit characters was scored and set out in the form of an "n.times.t" matrix, whose t columns represent the "t" bacterial strains to be grouped on the basis of resemblances, and whose "n" rows are the unit characters. Taxonomic resemblance of the bacterial strains was estimated by means of a similarity coefficient (Sneath and Sokal, supra, pp. 114-187). Although many different coefficients have been used for biological classification, only a few have found regular use in bacteriology. Three association Coefficients (See e.g., Sneath and Sokal, supra, at p. 129), namely, the Gower, Jaccard and Simple Matching coefficients were applied. These have been frequently applied to the analysis of bacteriological data and are widely accepted by those skilled in the art, as they have been shown to result in robust classifications.

The coded data were analyzed using the TAXPAK program package (Sackin; Meth. Microbiol., 19:459-494 [1987]), run on a DEC VAX computer at the University of Leicester, U.K.

A similarity matrix was constructed for all pairs of strains using the Gower Coefficient ($S_G$) with the option of permitting negative matches (See, Sneath and Sokal, supra, at pp. 135-136), using the RTBNSIM program in TAXPAK. As the primary instrument of analysis and the one upon which most of the taxonomic data presented herein are based, the Gower Coefficient was chosen over other coefficients for generating similarity matrices because it is applicable to all types of characters or data, namely, two-state, multistate (ordered and qualitative), and quantitative.

Cluster analysis of the similarity matrix was accomplished using the Unweighted Pair Group Method with Arithmetic Averages (UPGMA) algorithm, also known as the Unweighted Average Linkage procedure, by running the SMATCLST sub-routine in TAXPAK.

Dendrograms illustrate the levels of similarity between bacterial strains In some embodiments, dendrograms are obtained by using the DENDGR program in TAXPAK. The phenetic data were re-analyzed using the Jaccard Coefficient ($S_J$) (Sneath and Sokal, supra, at p. 131) and Simple Matching Coefficient ($S_{SM}$) (Sneath, P. H. A. and Sokal, R. R., ibid, P. 132) by running the RTBNSIM program in TAXPAK. An additional two dendrograms were obtained by using the SMATCLST with UPGMA option and DENDGR sub-routines in TAXPAK.

Using the $S_G$/UPGMA method, six natural clusters or phenons of alkalophilic bacteria were generated at the 79% similarity level. These six clusters included 15 of the 20 alkalophilic bacteria isolated from alkaline lakes. Although the choice of 79% for the level of delineation was arbitrary, it was in keeping with current practices in numerical taxonomy (See e.g., Austin Priest, *Modern Bacterial Taxonomy*, Van Nostrand Reinhold, Wokingham, U.K., [1986], p. 37). Placing the delineation at a lower percentage would combine groups of clearly unrelated organisms whose definition is not supported by the data. At the 79% level, 3 of the clusters exclusively contain novel alkalophilic bacteria representing 13 of the newly isolated strains (potentially representing new taxa). Protease 69B4 was classified as in cluster 2 by this method.

The significance of the clustering at this level was supported by the results of the TESTDEN program. This program tests the significance of all dichotomous pairs of clusters (comprising 4 or more strains) in a UPGMA generated dendrogram with Squared Euclidean distances, or their complement as a measurement and assuming that the clusters are hyperspherical. The critical overlap was set at 0.25%. The separation of the clusters is highly significant.

The $S_J$ coefficient is a useful adjunct to the $S_G$ coefficient, as it can be used to detect phenons in the latter that are based on negative matches or distortions owing to undue weight being put on potentially subjective qualitative data. Consequently, the $S_J$ coefficient is useful for confirming the validity of clusters defined initially by the use of the $S_G$ coefficient. The Jaccard Coefficient is particularly useful in comparing biochemically unreactive organisms (Austin and Priest, supra, at p. 37). In addition, there may be some question about the admissibility of matching negative character states (See, Sneath and Sokal, supra, at p. 131), in which case the Simple Matching Coefficient is a widely applied alternative. Strain 69B4 was classified as in cluster 2 by this method.

In the main, all of the clusters (especially the clusters of the new bacteria) generated by the $S_G$/UPGMA method were recovered in the dendrograms produced by the $S_J$/UPGMA method (cophenetic correlation, 0.795), and the $S_{SM}$/UPGMA method (cophenetic correlation, 0.814). The main effect of these transformations was to gather all the *Bacillus* strains in a single large cluster which further serves to emphasize the separation between the alkalophilic *Bacillus* species and the new alkalophilic bacteria, and the uniqueness of the latter. Based on these methodologies, 6984 is considered to be a cluster 2 bacterium.

In other aspects of the present invention, the polynucleotide is derived from a bacteria having a 16S rRNA gene nucleotide sequence at least 70%, 75%, 80%, 85%, 88%, 90%, 92%, 95%, 98% sequence identity with the 16S rRNA gene nucleotide sequence of *Cellulomonas* strain 69B4. The sequence of the 16S rRNA gene is deposited at GenBank under Accession Number X92152.

FIG. 1 provides an unrooted phylogenetic tree illustrating the relationship of novel strain 69B4 to members of the family Cellulomonadaceae (including *Cellulomonas* strain 69B4 and other related genera of the suborder *Micrococcineae*. The dendrogram was constructed from aligned 16S rDNA sequences (1374 nt) using TREECONW v.1.3b (Van de Peer and De Wachter, Comput. Appl. Biosci., 10: 569-570 [1994]). Distance estimations were calculated using the substitution rate calibration of Jukes and Cantor (Jukes and Cantor, "Evolution of protein molecules," In, Munro (ed.), *Mammalian Protein Metabolism*, Academic Press, NY, at pp. 21-132, [1969]) and tree topology inferred by the Neighbor-Joining algorithm (Saitou and Nei, Mol. Biol. Evol., 4:406-425 [1987]). The numbers at the nodes refer to bootstrap values from 100 resampled data sets (Felsenstein, Evol., 39:783-789 [1985]) and the scale bar indicates 2 nucleotide substitutions in 100 nt.

The strain 69B4 exhibits the closest 16S rDNA relationship to members of *Cellulomonas* and *Oerskovia* of the family Cellulomonadaceae. The closest relatives are believed to be *C. cellasea* (DSM 20118) and *C. fimi* (DSM 20113), with at least 95% sequence identity with the 16S rRNA gene nucleotide sequence of *Cellulomonas* strain 69B4 (e.g., 96% and 95% identity respectively) to strain 69B4 16S rRNA gene sequence.

In some preferred embodiments of the present invention, the *Cellulomonas* spp. is *Cellulomonas* strain 69B4 (DSM16035). This strain was originally isolated from a sample of sediment and water from the littoral zone of Lake Bogoria, Kenya at Acacia Camp (Lat. 0° 12'N, Long. 36° 07'E) collected on 10 Oct. 1988. The water temperature was 33° C., pH 10.5 with a conductivity of 44 mS/cm. *Cellulomonas* strain 69B4 was determined to have the phenotypic characteristics described below. Fresh cultures were Gram-positive, slender, generally straight, rod-shaped bacteria, approximately 0.5-0.7 μm×1.8-4 μm. Older cultures contained mainly short rods and coccoid cells. Cells occasionally occurred in pairs or as V-forms, but primary branching was not observed. Endospores were not detected. On alkaline GAM agar the strain forms opaque, glistening, pale-yellow coloured, circular and convex or domed colonies, with entire margins, about 2 mm in diameter after 2-3 days incubation at 37° C. The colonies were viscous or slimy with a tendency to dump when scraped with a loop. On neutral Tryptone Soya Agar, strain growth was less vigorous, giving translucent yellow colonies, generally <1 mm in diameter. The cultures were facultatively anaerobic, as they were capable of growth under strictly anaerobic conditions. However, growth under anaerobic conditions was markedly reduced compared to aerobic growth. The strain also appeared to be negative in standard oxidase, urease, aminopeptidase, and KOH tests. In addition, nitrate was not reduced, although the organisms were catalase positive and DNase was produced under alkaline conditions. The preferred temperature range for growth was 20-37° C., with an optimum temperature at around 30-37° C. No growth was observed at 15° C. or 45° C.

The strain is alkalophilic and slightly halophilic. The strain may also be characterized as having growth occurring at pH values between 6.0 and 10.5 with an optimum around pH 9-10. No growth was observed at pH 11 or pH 5.5. Growth below pH 7 was less vigorous and abundant than that of cultures grown at the optimal temperature. The strain was observed to grow in medium containing 0-8% (w/v) NaCl. Furthermore, the strain may also be characterized as a chemoorganotroph, since it grew on complex substrates such as yeast extract and peptone; and hydrolyzed starch, gelatin, casein, carboxymethylcellulose and amorphous cellulose.

The strain was observed to have metabolism that was respiratory and also fermentative. Acid was produced both aerobically and anaerobically from (API 50CH): L-arabinose, D-xylose, D-glucose, D-fructose, D-mannose, rhamnose' (weak), cellobiose, maltose, sucrose, trehalose, gentiobiose, D-turanose, D-lyxose and 5-keto-gluconate (weak). Amygdalin, arbutin, salicin and esculin are also utilized. The strain was unable to utilize: ribose, lactose, galactose, melibiose, D-raffinose, glycogen, glycerol, erythritol, inositol, mannitol, sorbitol, xylitol, arabitol, gluconate and lactate.

The strain was determined to be susceptible to ampicillin, chloramphenicol, erythromycin, fusidic acid, methicillin, novobiocin, streptomycin, tetracycline, sulphafurazole, oleandomycin, polymixin, rifampicin, vancomycin and bacitracin; but resistant to gentamicin, nitrofurantoin, nalidixic acid, sulphmethoxazole, trimethoprim, penicillin G, neomycin and kanamycin.

The following enzymes, aside from the protease of the present invention, were observed to be produced (ApiZym, API Coryne); C4-esterase, C8-esterase/lipase, leucine arylamidase, alpha-chymotrypsin, alpha-glucosidase, beta-glucosidase and pyrazinamidase.

The strain was observed to exhibit the following chemotaxonomic characteristics. Major fatty acids (>10% of total) were C16:1 (28.1%), C18:0 (31.1%), C18:1 (13.9%). N-saturated (79.1%), n-unsaturated (19.9%). Fatty acids with even numbers of carbons accounted for 98%. Main polar lipid components: phosphatidylglycerol (PG) and 3 unidentified glycolipids (alpha-napthol positive) were present; DPG, PGP, PI and PE were not detected. Menaquinones MK-4, MK-6, MK-7 and MK-9 were the main isoprenoids present. The cell wall peptidoglycan type was A4β with L-ornithine as diamino acid and D-aspartic acid in the interpeptide bridge. With regard to toxicity evaluation, there are no known toxicity or pathogenicity issues associated with bacteria of the genus *Cellulomonas*.

Although there may be variations in the sequence of a naturally occurring enzyme within a given species of organism, enzymes of a specific type produced by organisms of the same species generally are substantially identical with respect to substrate specificity and/or proteolytic activity levels under given conditions (e.g., temperature, pH, water hardness, oxidative conditions, chelating conditions, and concentration), etc. Thus, for the purposes of the present invention, it is contemplated that other strains and species of *Cellulomonas* also produce the *Cellulomonas* protease of the present invention and thus provide useful sources for the proteases of the present invention. Indeed, as presented herein, it is contemplated that other members of the *Micrococcineae* will find use in the present invention.

In some embodiments, the proteolytic polypeptides of this invention are characterized physicochemically, while in other embodiments, they are characterized based on their functionally, while in further embodiments, they are characterized using both sets of properties. Physicochemical characterization takes advantages of well known techniques such as SDS electrophoresis, gel filtration, amino acid composition, mass spectrometry (e.g., MALDI-TOF-MS, LC-ES-MS/MS, etc.), and sedimentation to determine the molecular weight of proteins, isoelectric focusing to determine the pI of proteins, amino acid sequencing to determine the amino acid sequences of protein, crystallography studies to determine the tertiary structures of proteins, and antibody binding to determine antigenic epitopes present in proteins.

In some embodiments, functional characteristics are determined by techniques well known to the practitioner in the protease field and include, but are not limited to, hydrolysis of various commercial substrates, such as di-methyl casein ("DMC") and/or AAPF-pNA. This preferred technique for functional characterization is described in greater detail in the Examples provided herein.

Figure 3:
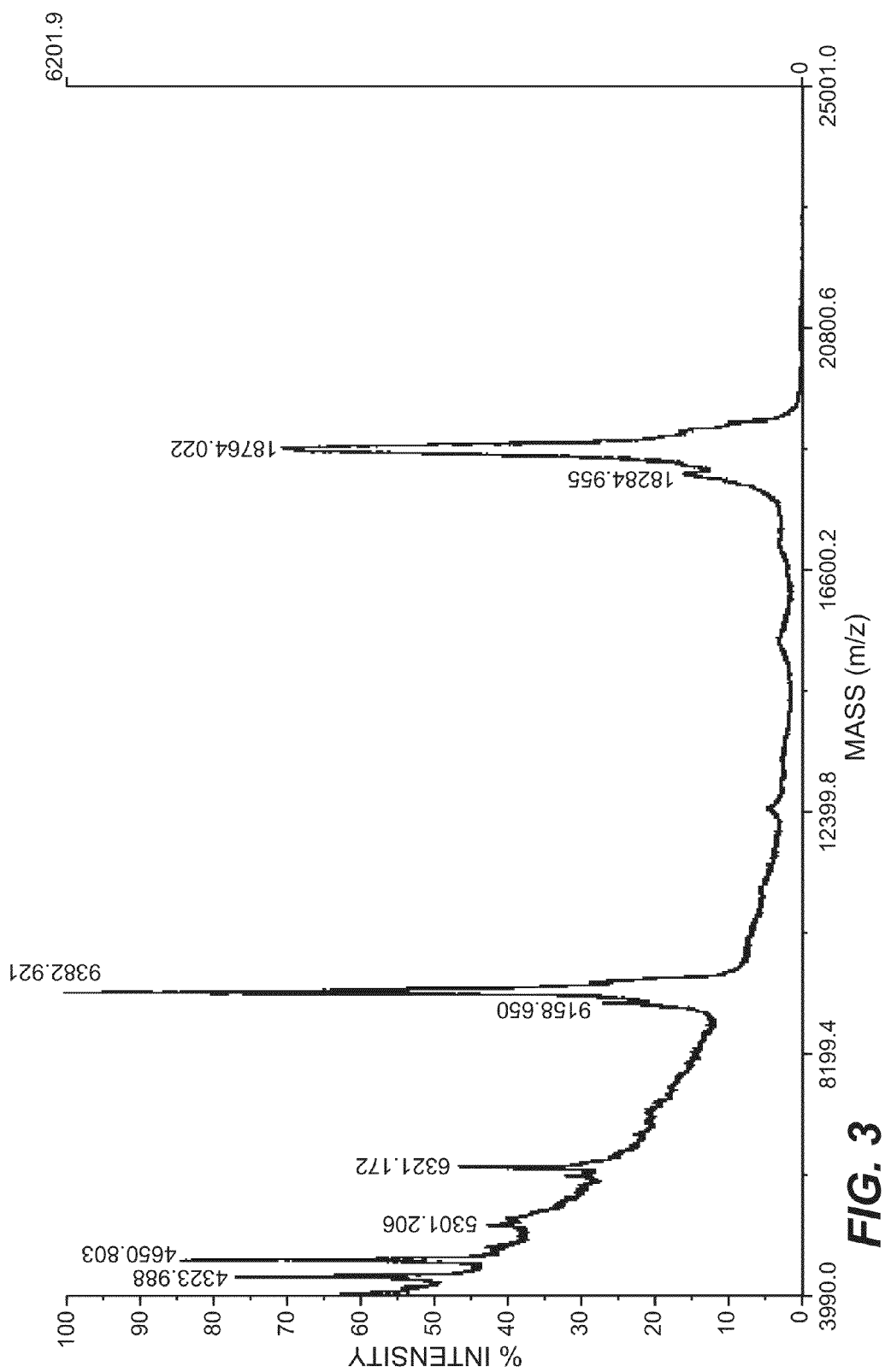
FIG. 3 provides a MALDI TOF spectrum of a protease derived from Cellulomonas strain 69B4

In some embodiments of the present invention, the protease has a molecular weight of about 17 kD to about 21 kD, for example about 18 kD to 19 kD, for example 18700 daltons to 18800 daltons, for example about 18764 daltons, as determined by MALDI-TOF-MS). In another aspect of the present invention, the protease measured MALDI-TOF-MS spectrum as set forth in FIG. 3.

The mature protease also displays proteolytic activity (e.g., hydrolytic activity on a substrate having peptide linkages) such as DMC. In further embodiments, proteases of the present invention provide enhanced wash performance under identified conditions. Although the present invention encompasses the protease 69B as described herein, in some embodiments, the proteases of the present invention exhibit at least 50%, 60%, 70%, 75%, 80%, 85%, 90%, 92%, 95%, 96%, 97%, 98% or 99% proteolytic activity as compared to the proteolytic activity of 69B4. In some embodiments, the proteases display at least 50%, 60%, 70%, 75%, 80%, 85%, 90%, 92%, 95%, 96%, 97%, 98% or 99% proteolytic activity as compared to the proteolytic activity of proteases sold under the tradenames SAVINASE® (Novzymes) or PURAFECT® (Genencor) under the same conditions. In some embodiments, the proteases of the present invention display comparative or enhanced wash performance under identified conditions as compared to 69B4 under the same conditions. In some preferred embodiments, the proteases of the present invention display comparative or enhanced wash performance under identified conditions, as compared to proteases sold under the tradenames SAVINASE® (Novozymes) or PURAFECT® (Genencor) under the same conditions.

In yet further embodiments, the proteases and/or polynucleotides encoding the proteases of the present invention are provided purified form (i.e., present in a particular composition in a higher or lower concentration than exists in a naturally occurring or wild type organism), or in combination with components not normally present upon expression from a naturally occurring or wild-type organism. However, it is not intended that the present invention be limited to proteases of any specific purity level, as ranges of protease purity find use in various applications in which the proteases of the present inventing are suitable.

III. Obtaining Polynucleotides Encoding *Micrococcineae* (e.g., *Cellulomonas*) Proteases of the Present Invention In some embodiments, nucleic acid encoding a protease of the present invention is obtained by standard procedures known in the art from, for example, cloned DNA (e.g., a DNA ulibraryn), chemical synthesis, cDNA cloning, PCR, cloning of genomic DNA or fragments thereof, or purified from a desired cell, such as a bacterial or fungal species (See, for example, Sambrook et al., supra [1989]; and Glover and Hames (eds.), *DNA Cloning: A Practical Approach*, Vols 1 and 2, Second Edition). Synthesis of polynucleotide sequences is well known in the art (See e.g., Beaucage and Caruthers, Tetrahedron Lett., 22:1859-1862 [1981]), including the use of automated synthesizers (See e.g., Needham-VanDevanter et al., Nucl. Acids Res., 12:6159-6168 [1984]). DNA sequences can also be custom made and ordered from a variety of commercial sources. As described in greater detail herein, in some embodiments, nucleic acid sequences derived from genomic DNA contain regulatory regions in addition to coding regions.

In some embodiments involving the molecular cloning of the gene from genomic DNA, DNA fragments are generated, some of which comprise at least a portion of the desired gene. In some embodiments, the DNA is cleaved at specific sites using various restriction enzymes. In some alternative embodiments, DNAse is used in the presence of manganese to fragment the DNA, or the DNA is physically sheared (e.g., by sonication). The linear DNA fragments created are then be separated according to size and amplified by standard techniques, including but not limited to, agarose and polyacrylamide gel electrophoresis, PCR and column chromatography.

Once nucleic acid fragments are generated, identification of the specific DNA fragment encoding a protease may be accomplished in a number of ways. For example, in some embodiments, a proteolytic hydrolyzing enzyme encoding the asp gene or its specific RNA, or a fragment thereof, such as a probe or primer, is isolated, labeled, and then used in hybridization assays well known to those in the art, to detect a generated gene (See e.g., Benton and Davis, Science 196: 180 [1977]; and Grunstein and Hogness, Proc. Natl. Acad. Sci. USA 723961 [1975]). In preferred embodiments, DNA fragments sharing substantial sequence similarity to the probe hybridize under medium to high stringency.

In some preferred embodiments, amplification is accomplished using PCR, as known in the art. In some preferred embodiments, a nucleic acid sequence of at least about 4 nucleotides and as many as about 60 nucleotides from SEQ ID NOS:1, 2, 3 and/or 4 (i.e., fragments), preferably about 12 to 30 nucleotides, and more preferably about 25 nucleotides are used in any suitable combinations as PCR primer. These same fragments also find use as probes in hybridization and product detection methods.

In some embodiments, isolation of nucleic acid constructs of the invention from a cDNA or genomic library utilizes PCR with using degenerate oligonucleotide primers prepared on the basis of the amino acid sequence of the protein having the amino acid sequence as shown in SEQ ID NOS:1-5. The primers can be of any segment length, for example at least 4, at least 5, at least 8, at least 15, at least 20, nucleotides in length. Exemplary probes in the present application utilized a primer comprising a TTGWHCGT and a GDSGG polynucleotide sequence as more fully described in Examples.

In view of the above, it will be appreciated that the polynucleotide sequences provided herein and based on the polynucleotide sequences provided in SEQ ID NOS:1-5 are useful for obtaining identical or homologous fragments of polynucleotides from other species, and particularly from bacteria that encode enzymes having the serine protease activity expressed by protease 69B4.

IV. Expression and Recovery of Serine Proteases of the Present Invention

Any suitable means for expression and recovery of the serine proteases of the present invention find use herein. Indeed, those of skill in the art know many methods suitable for cloning a *Cellulomonas*-derived polypeptide having proteolytic activity, as well as an additional enzyme (e.g., a second peptide having proteolytic activity, such as a protease, cellulase, mannanase, or amylase, etc.). Numerous methods are also known in the art for introducing at least one (e.g., multiple) copies of the polynucleotide(s) encoding the enzyme(s) of the present invention in conjunction with any additional sequences desired, into the genes or genome of host cells.

In general, standard procedures for cloning of genes and introducing exogenous proteases encoding, regions (including multiple copies of the exogenous encoding regions) into said genes find use in obtaining a *Cellulomonas* 69B4 protease derivative or homologue thereof. Indeed, the present Specification, including the Examples provides such teaching: However, additional methods known in the art are also suitable (See e.g., Sambrook et al. supra (1989); Ausubel et al., supra [1995]; and Harwood and Cutting, (eds.) *Molecular Biological Methods for Bacillus*," John Wiley and Sons, [1990]; and WO 96/34946).

In some preferred embodiments, the polynucleotide sequences of the present invention are expressed by operatively linking them to an expression control sequence in an appropriate expression vector and employed by that expression vector to transform an appropriate host according to techniques well established in the art. In some embodiments, the polypeptides produced on expression of the DNA sequences of this invention are isolated from the fermentation of cell cultures and purified in a variety of ways according to well established techniques in the art. Those of skill in the art are capable of selecting the most appropriate isolation and purification techniques.

More particularly, the present invention provides constructs, vectors comprising polynucleotides described herein, host cells transformed with such vectors, proteases expressed by such host cells, expression methods and systems for the production of serine protease enzymes derived from microorganisms, in particular, members of the *Micrococcineae*, including but not limited to Cellulomonas species. In some embodiments, the polynucleotide(s) encoding serine protease(s) are used to produce recombinant host cells suitable for the expression of the serine protease(s). In some preferred embodiments, the expression hosts are capable of producing the protease(s) in commercially viable quantities.

IV. Recombinant Vectors

As indicated above, in some embodiments, the present invention provides vectors comprising the aforementioned polynucleotides. In some embodiments, the vectors (i.e., constructs) of the invention encoding the protease are of genomic origin (e.g., prepared though use of a genomic library and screening for DNA sequences coding for all or part of the protease by hybridization using synthetic oligonucleotide probes in accordance with standard techniques). In some preferred embodiments, the DNA sequence encoding the protease is obtained by isolating chromosomal DNA from the *Cellulomonas* strain 69B4 and amplifying the sequence by PCR methodology (See, the Examples).

In alternative embodiments, the nucleic acid construct of the invention encoding the protease is prepared synthetically by established standard methods (See e.g., Beaucage and Caruthers, Tetra. Lett. 22:1859-1869 [1981]; and Matthes et al., EMBO J., 3:801-805 [1984]). According to the phosphoramidite method, oligonucleotides are synthesized (e.g., in an automatic DNA synthesizer), purified, annealed, ligated and cloned in suitable vectors.

In additional embodiments, the nucleic acid construct is of mixed synthetic and genomic origin. In some embodiments, the construct is prepared by ligating fragments of synthetic or genomic DNA (as appropriate), wherein the fragments correspond to various parts of the entire nucleic acid construct, in accordance with standard techniques.

In further embodiments, the present invention provides vectors comprising at least one DNA construct of the present invention. In some embodiments, the present invention encompasses recombinant vectors. It is contemplated that any suitable vector will find use in the present invention, including autonomously replicating vector a well as vectors that integrate (either transiently or stably) within the host cell genome). Indeed, a wide variety of vectors, and expression cassettes suitable for the cloning, transformation and expression in fungal (mold and yeast), bacterial, insect and plant cells are known to those of skill in the art. Typically, the vector or cassette contains sequences directing transcription and translation of the nucleic acid, a selectable marker, and sequences allowing autonomous replication or chromosomal integration. In some embodiments, suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Figure 5:
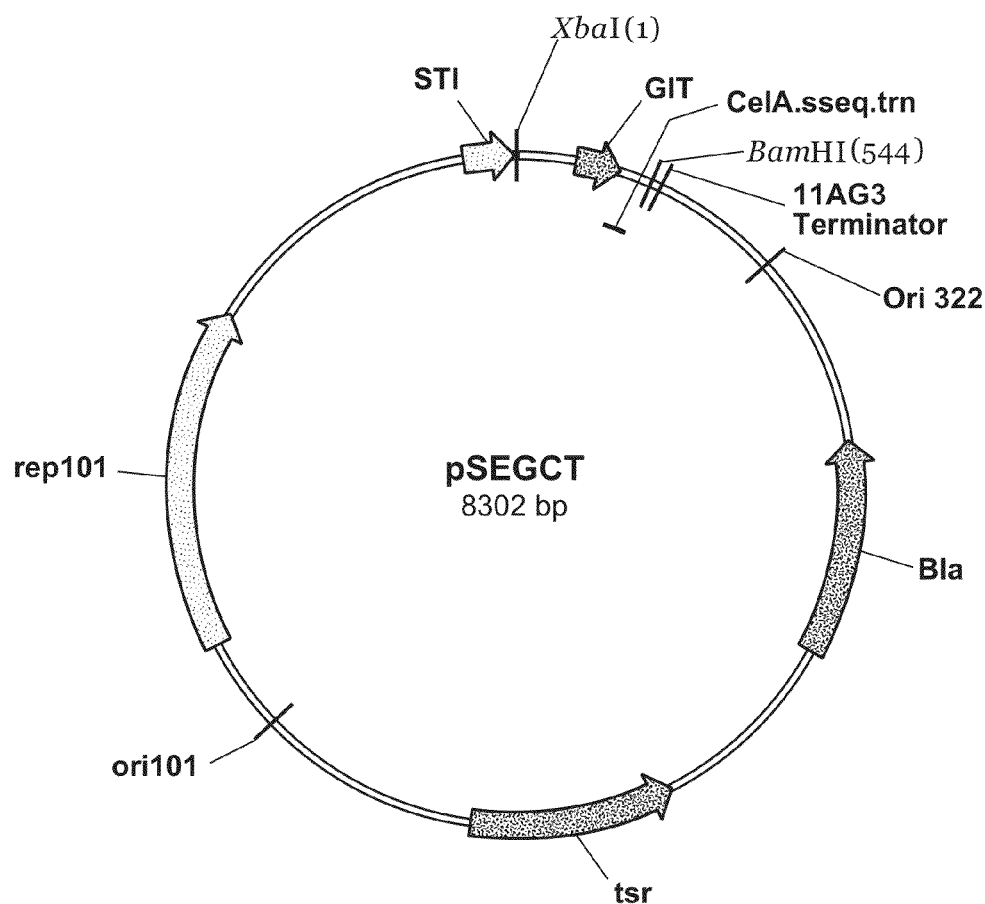
FIG. 5 provides the plasmid map of the pSEGCT vector.
Figure 5:
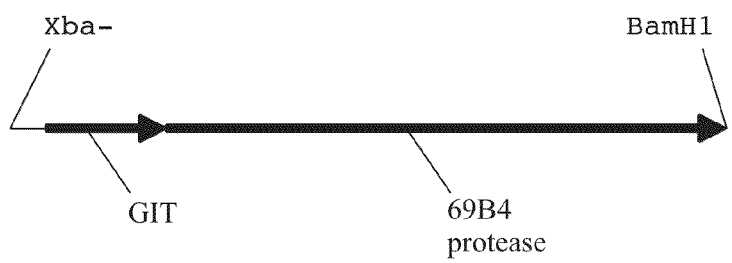
Figure 6:
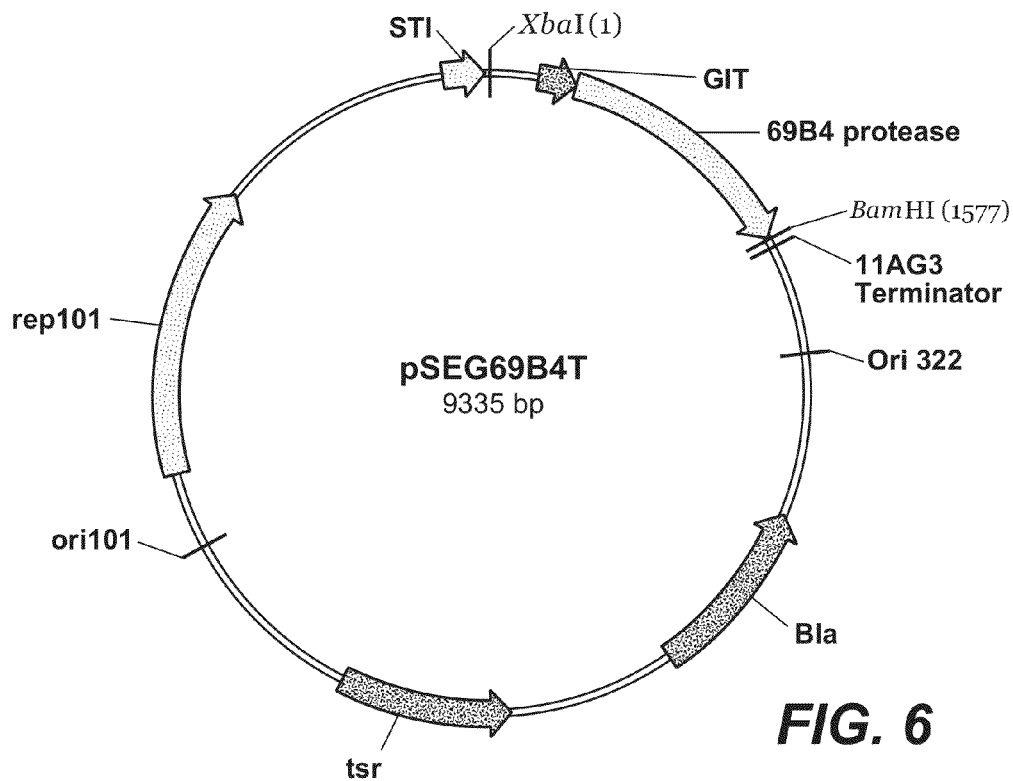
FIG. 6 provides the plasmid map of the pSEGCT69B4 vector.

The vector is preferably an expression vector in which the DNA sequence encoding the protease of the invention is operably linked to additional segments required for transcription of the DNA. In some preferred embodiments, the expression vector is derived from plasmid or viral DNA, or in alternative embodiments, contains elements of both. Exemplary vectors include, but are not limited to pSEGCT, pSEACT, and/or pSEA4CT, as well as all of the vectors described in the Examples herein. Construction of such vectors is described herein, and methods are well known in the art (See e.g., U.S. Pat. No. 6,287,839; and WO 02/50245). In some preferred embodiments, the vector pSEGCT (about 8302 bp; See, FIG. 5) finds use in the construction of a vector comprising the polynucleotides described herein (e.g., pSEG69B4T; See, FIG. 6). In alternative preferred embodiments, the vector pSEA469B4CT (See, FIG. 7) finds use in the construction of a vector comprising the polynucleotides described herein. Indeed, it is intended that all of the vectors described herein will find use in the present invention.

In some embodiments, the additional segments required for transcription include regulatory segments (e.g., promoters, secretory segments, inhibitors, global regulators, etc.), as known in the art. One example includes any DNA sequence that shows transcriptional activity in the host cell of choice and is derived from genes encoding proteins either homologous or heterologous to the host cell. Specifically, examples of suitable promoters for use in bacterial host cells include but are not limited to the promoter of the *Bacillus stearothermophilus* maltogenic amylase gene, the *Bacillus amyloliquefaciens* (BAN) amylase gene, the *Bacillus subtilis* alkaline protease gene, the *Bacillus clausii* alkaline protease gene the *Bacillus pumilus* xylosidase gene, the *Bacillus thuringiensis* cryIIIA, and the *Bacillus licheniformis* alpha-amylase gene. Additional promoters include the A4 promoter, as described herein. Other promoters that find use in the present invention include, but are not limited to phage Lambda $P_R$ or $P_L$ promoters, as well as the *E. coli* lac, trp or tac promoters.

In some embodiments, the promoter is derived from a gene encoding said protease or a fragment thereof having substantially the same promoter activity as said sequence. The invention further encompasses nucleic acid sequences which hybridize to the promoter sequences under intermediate, high, and/or maximum stringency conditions, or which have at least about 90% homology and preferably about 95% homology to such promoter, but which have substantially the same promoter activity. In some embodiments, this promoter is used to promote the expression of either the protease and/or a heterologous DNA sequence (e.g., another enzyme in addition to the protease of the present invention). In additional embodiments, the vector also comprises at least one selectable marker.

In some embodiments, the recombinant vectors of the invention further comprise a DNA sequence enabling the vector to replicate in the host cell. In some preferred embodiments involving bacterial host cells, these sequences comprise all the sequences needed to allow plasmid replication (e.g., ori and/or rep sequences).

In some particularly preferred embodiments, signal sequences (e.g., leader sequence or pre sequence) are also included in the vector, in order to direct a polypeptide of the present invention into the secretory pathway of the host cells. In some more preferred embodiments, a secretory signal sequence is joined to the-DNA sequence encoding the precursor protease in the correct reading frame (See e.g., SEQ ID NOS:1 and 2). Depending on whether the protease is to be expressed intracellularly or is secreted, a polynucleotide sequence or expression vector of the invention is engineered with or without a natural polypeptide signal sequence or a signal sequence which functions in bacteria (e.g., *Bacillus* sp.), fungi (e.g., *Trichoderma*), other prokaryoktes or eukaryotes. In some embodiments, expression is achieved by either removing or partially removing the signal sequence In some embodiments involving secretion from bacterial cells, the signal peptide is a naturally occurring signal peptide, or a functional part thereof, while in other embodiments, it is a synthetic peptide. Suitable signal peptides include but are not limited to sequences derived from *Bacillus licheniformis* alpha-amylase, *Bacillus clausii* alkaline protease, and *Bacillus amyloliquefaciens* amylase. One preferred signal sequence is the signal peptide derived from *Cellulomonas* strain 69B4, as described herein. Thus, in some particularly preferred embodiments, the signal peptide comprises the signal peptide from the protease described herein. This signal finds use in facilitating the secretion of the 69B4 protease and/or a heterologous DNA sequence (e.g. a second protease, such as another wild-type protease, a BPN' variant protease, a GG36 variant protease, a lipase, a cellulase, a mannanase, etc.). In some embodiments, these second enzymes are encoded by the DNA sequence and/or the amino acid sequences known in the art (See e.g., U.S. Pat. Nos. 6,465, 235, 6,287,839, 5,965,384, and 5,795,764; as well as WO 98/22500, WO 92/05249, EP 0305216B1, and WO 94/25576). Furthermore, it is contemplated that in some embodiments, the signal sequence peptide is also be operatively linked to an endogenous sequence to activate and secrete such endogenous encoded protease.

The procedures used to ligate the DNA sequences coding for the present protease, the promoter and/or secretory signal sequence, respectively, and to insert them into suitable vectors containing the information necessary for replication, are well known to those skilled in the art. As indicated above, in some embodiments, the nucleic acid construct is prepared using PCR with specific primers.

V. Host Cells

As indicated above, in some embodiments, the present invention also provides host cells transformed with the vectors described above. In some embodiments, the polynucleotide encoding the protease(s) of the present invention that is introduced into the host cell is homologous, while in other embodiments, the polynucleotide is heterologous to the host. In some embodiments in which the polynucleotide is homologous to the host cell (e.g., additional copies of the native protease produced by the host cell are introduced), it is operably connected to another homologous or heterologous promoter sequence. In alternative embodiments, another secretory signal sequence, and/or terminator sequence find use in the present invention. Thus, in some embodiments, the polypeptide DNA sequence comprises multiple copies of a homologous polypeptide sequence, a heterologous polypeptide sequence from another organism, or synthetic polypeptide sequence(s). Indeed, it is not intended that the present invention be limited to any particular host cells and/or vectors.

Indeed, the host cell into which the DNA construct of the present invention is introduced may be any cell which is capable of producing the present alkaline protease, including, but not limited to bacteria, fungi, and higher eukaryotic cells.

Examples of bacterial host cells which find use in the present invention include, but are not limited to Gram-positive bacteria such as *Bacillus, Streptomyces*, and *Thermobifida*, for example strains of *B. subtilis, B. licheniformis, B. lentus, B. brevis, B. stearothermophilus, B. clausii, B. amyloliquefaciens, B. coagulans, B. circulans, B. lautus, B. megaterium, B. thuringiensis, S. griseus, S. lividans, S. coelicolor, S. avermitilis* and *T. fusca*; as well as Gram-negative bacteria such as members of the Enterobacteriaceae (e.g., *Escherichia coli*). In some particularly preferred embodiments, the host cells are *B. subtilis, B. clausii*, and/or *B. licheniformis*. In additional preferred embodiments, the host cells are strains of *S. lividans* (e.g., TK23 and/or TK21). Any suitable method for transformation of the bacteria find use in the present invention, including but not limited to protoplast transformation, use of competent cells, etc., as known in the art. In some preferred embodiments, the method provided in U.S. Pat. No. 5,264,366 (incorporated by reference herein), finds used in the present invention. For *S. lividans*, one preferred means for transformation and protein expression is that described by Fernandez-Abalos et al. (See, Fernandez-Abalos et al., Microbiol., 149:1623-1632 [2003]; See also, Hopwood, et al., Genetic Manipulation of Streptomyces: Laboratory Manual, Innis [1985], both of which are incorporated by reference herein). Of course, the methods described in the Example herein find use in the present invention.

Examples of fungal host cells which find use in the present invention include, but are not limited to *Trichoderma* spp. and *Aspergillus* spp. In some particularly preferred embodiments, the host cells are *Trichoderma reesei* and/or *Aspergillus niger*. In some embodiments, transformation and expression in *Aspergillus* is performed as described in U.S. Pat. No. 5,364,770, herein incorporated by reference. Of course, the methods described in the Example herein find use in the present invention.

In some embodiments, particular promoter and signal sequences are needed to provide effective transformation and expression of the protease(s) of the present invention. Thus, in some preferred embodiments involving the use of *Bacillus* host cells, the aprE promoter is used in combination with known *Bacillus*-derived signal and other regulatory sequences. In some preferred embodiments involving expression in *Aspergillus*, the glaA promoter is used. In some embodiments involving *Streptomyces* host cells, the glucose isomerase (GI) promoter of *Actinoplanes missouriensis* is used, while in other embodiments, the A4 promoter is used.

In some embodiments involving expression in bacteria such as *E. coli*, the protease is retained in the cytoplasm, typically as insoluble granules (i.e., inclusion bodies). However, in other embodiments, the protease is directed to the periplasmic space by a bacterial secretion sequence. In the former case, the cells are lysed, and the granules are recovered and denatured after which the protease is refolded by diluting the denaturing agent. In the latter case, the protease is recovered from the periplasmic space by disrupting the cells (e.g., by sonication or osmotic shock), to release the contents of the periplasmic space and recovering the protease.

In preferred embodiments, the transformed host cells of the present invention are cultured in a suitable nutrient medium under conditions permitting the expression of the present protease, after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the protease produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention will find use. Indeed, it is not intended that the present invention be limited to any particular purification method.

VI. Applications for Serine Protease Enzymes

As described in greater detail herein, the proteases of the present invention have important characteristics that make them very suitable for certain applications. For example, the proteases of the present invention have enhanced thermal stability, enhanced oxidative stability, and enhanced chelator stability, as compared to some currently used proteases.

Thus, these proteases find use in cleaning compositions. Indeed, under certain wash conditions, the present proteases exhibit comparative or enhanced wash performance as compared with currently used subtilisin proteases. Thus, it is contemplated that the cleaning and/or enzyme compositions of the present invention will be provided in a variety of cleaning compositions. In some embodiments, the proteases of the present invention are utilized in the same manner as subtilisin proteases (i.e., proteases currently in use). Thus, the present proteases find use in various cleaning compositions, as well as animal feed applications, leather processing (e.g., bating), protein hydrolysis, and in textile uses. The identified proteases also find use in personal care applications.

Thus, the proteases of the present invention find use in a number of industrial applications, in particular within the cleaning, disinfecting, animal feed, and textile/leather industries. In some embodiments, the protease(s) of the present invention are combined with detergents, builders, bleaching agents and other conventional ingredients to produce a variety of novel cleaning compositions useful in the laundry and other cleaning arts such as, for example, laundry detergents (both powdered and liquid), laundry pre-soaks, all fabric bleaches, automatic dishwashing detergents (both liquid and powdered), household cleaners, particularly bar and liquid soap applications, and drain openers. In addition, the protease find use in the cleaning of contact lenses, as well as other items, by contacting such materials with an aqueous solution of the cleaning composition. In addition these naturally occurring proteases can be used, for example in peptide hydrolysis, waste treatment, textile applications, medical device cleaning, biofilm removal and as fusion-cleavage enzymes in protein production, etc. The composition of these products is not critical to the present invention, as long as the protease(s) maintain their function in the setting used. In some embodiments, the compositions are readily prepared by combining a cleaning effective amount of the protease or an enzyme composition comprising the protease enzyme preparation with the conventional components of such compositions in their art recognized amounts.

A. Cleaning Compositions

The cleaning composition of the present invention may be advantageously employed for example, in laundry applications, hard surface cleaning, automatic dishwashing applications, as well as cosmetic applications such as dentures, teeth, hair and skin. However, due to the unique advantages of increased effectiveness in lower temperature solutions and the superior color-safety profile, the enzymes of the present invention are ideally suited for laundry applications such as the bleaching of fabrics. Furthermore, the enzymes of the present invention may be employed in both granular and liquid compositions.

The enzymes of the present invention may also be employed in a cleaning additive product. A cleaning additive product including the enzymes of the present invention is ideally suited for inclusion in a wash process when additional bleaching effectiveness is desired. Such instances may include, but are not limited to low temperature solution cleaning application. The additive product may be, in its simplest form, one or more proteases, including ASP. Such additive may be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to, methanol, ethanol, propanol and isopropanol. The compositions may contain from about 5% to about 90% of such materials. Acidic fillers can be used to reduce pH. Alternatively, the cleaning additive may include activated peroxygen source defined below or the adjunct ingredients as fully defined below.

The present cleaning compositions and cleaning additives require an effective amount of the ASP enzyme and/or variants provided herein. The required level of enzyme may be achieved by the addition of one or more species of the enzymes of the present invention. Typically the present cleaning compositions will comprise at least 0.0001 weight percent, from about 0.0001 to about 1, from about 0.001 to about 0.5, or even from about 0.01 to about 0.1 weight percent of at least one of the enzymes of the present invention.

The cleaning compositions herein will typically be formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to 16 moles of ethylene oxide. Such cleaning compositions typically comprise a sufficient amount of a pH modifier, such as sodium hydroxide, monoethanolamine or hydrochloric acid, to provide such cleaning composition with a neat pH, of from about 3 to about 5. Such compositions typically comprise at least one acid stable enzyme. Said compositions may be liquids or solids. The pH of such liquid compositions is measured as a neat pH. The pH of such solid compositions is measured as a 10% solids solution of said composition wherein the solvent is distilled water. In these embodiments, all pH measurements are taken at 20° C.

When the serine protease(s) is/are employed in a granular composition or liquid, it may be desirable for the enzyme to be in the form of an encapsulated particle to protect such enzyme from other components of the granular composition during storage. In addition, encapsulation is also a means of controlling the availability of the enzyme during the cleaning process and may enhance performance of the enzymes provided herein. In this regard, the serine proteases of the present invention may be encapsulated with any encapsulating material known in the art.

The encapsulating material typically encapsulates at least part of the catalyst for the enzymes of the present invention. Typically, the encapsulating material is water-soluble and/or water-dispersible. The encapsulating material may have a glass transition temperature (Tg) of 0° C. or higher. Glass transition temperature is described in more detail in WO 97/11151, especially from page 6, line 25 to page 7, line 2.

The encapsulating material is may be selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. When the encapsulating material is a carbohydrate, it may be typically selected from the group consisting of monosaccharides, oligosaccharides, polysaccharides, and combinations thereof. Typically, the encapsulating material is a starch. Suitable starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark Expancel®, and those supplied by PQ Corp. of Valley Forge, Pa. U.S.A. under the tradename PM 6545, PM 6550, PM 7220, PM 7228, Extendospheres®, Luxsil®, Q-cel® and Sphericel®.

As described herein, the proteases of the present invention find particular use in the cleaning industry, including, but not limited to laundry and dish detergents. These applications place enzymes under various environmental stresses. The proteases of the present invention provide advantages over many currently used enzymes, due to their stability under various conditions.

Indeed, there are a variety of wash conditions including varying detergent formulations, wash water volumes, wash water temperatures, and lengths of wash time, to which proteases involved in washing are exposed. In addition, detergent formulations used in different geographical areas have different concentrations of their relevant components present in the wash water. For example, a European detergent typically has about 4500-5000 ppm of detergent components in the wash water, while a Japanese detergent typically has approximately 667 ppm of detergent components in the wash water. In North America, particularly the United States, detergents typically have about 975 ppm of detergent components present in the wash water.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water. Brazil typically has approximately 1500 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan can be between 10 and 30° C. (e.g., about 20° C.), whereas the temperature of wash water in Europe is typically between 30 and 60° C. (e.g., about 40° C.).

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than 10.5 (for example 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness; but less than European water hardness. For examples North American water hardness can be between 3 to 10 grains, 3-8 grains or about 6 grains. Japanese water hardness is typically lower than North American water hardness, usually less than 4, for example 3 grains-per gallon mixed $Ca^{2+}/Mg^{2+}$.

Accordingly, in some embodiments, the present invention provides proteases that show surprising wash performance in at least one set of wash conditions (e.g., water temperature, water hardness, and/or detergent concentration). In some embodiments, the proteases of the present invention are comparable in wash performance to subtilisin proteases. In some embodiments, the proteases of the present invention exhibit enhanced wash performance as compared to subtilisin proteases. Thus, in some preferred embodiments of the present invention, the proteases provided herein exhibit enhanced oxidative stability, enhanced thermal stability, and/or enhanced chelator stability.

In some preferred embodiments, the present invention provides the ASP protease, as well as homologues and variants fo the protease. These proteases find use in any applications in which it is desired to clean protein based stains from textiles or fabrics.

In some embodiments, the cleaning compositions of the present invention are formulated as hand and machine laundry detergent compositions including laundry additive compositions, and compositions suitable for use in the pretreatment of stained fabrics, rinse-added fabric softener compositions, and compositions for use in general household hard surface cleaning operations, as well as dishwashing operations. Those in the art are familiar with different formulations which can be used as cleaning compositions. In preferred embodiments, the proteases of the present invention comprise comparative or enhanced performance in detergent compositions (i.e., as compared to other proteases). In some embodiments, cleaning performance is evaluated by comparing the proteases of the present invention with subtilisin proteases in various cleaning assays that utilize enzyme-sensitive stains such as egg, grass, blood, milk, etc., in standard methods. Indeed, those in the art are familiar with the spectrophotometric and other analytical methodologies used to assess detergent performance under standard wash cycle conditions.

Assays that find use in the present invention include, but are not limited to those described in WO 99/34011, and U.S. Pat. No. 6,605,458 (See e.g., Example 3). In U.S. Pat. No. 6,605,458, at Example 3, a detergent dose of 3.0 g/l at pH10.5, wash time 15 minutes, at 15 C, water hardness of 6° dH, 10 nM enzyme concentration in 150 ml glass beakers with stirring rod, 5 textile pieces (phi 2.5 cm) in 50 ml, EMPA 117 test material from Center for Test Materials Holland are used. The measurement of reflectance "R" on the test material was done at 460 nm using a Macbeth ColorEye 7000 photometer. Additional methods are provided in the Examples herein. Thus, these methods also find use in the present invention.

The addition of proteases of the invention to conventional cleaning compositions does not create any special use limitation. In other words, any temperature and pH suitable for the detergent is also suitable for the present compositions, as long as the pH is within the range set forth herein, and the temperature is below the described protease's denaturing temperature. In addition, proteases of the present invention find use in cleaning compositions that do not include detergents, again either alone or in combination with builders and stabilizers.

When used in cleaning compositions or detergents, oxidative stability is a further consideration. Thus, in some applications, the stability is enhanced, diminished, or comparable to subtilisin proteases as desired for various uses. In some preferred embodiments, enhanced oxidative stability is desired. Some of the proteases of the present invention find particular use in such applications.

When used in cleaning compositions or detergents, thermal stability is a further ao consideration. Thus, in some applications, the stability is enhanced, diminished, or comparable to subtilisin proteases as desired for various uses. In some preferred embodiments, enhanced thermostability is desired. Some of the proteases of the present invention find particular use in such applications.

When used in cleaning compositions or detergents, chelator stability is a further consideration. Thus, in some applications, the stability is enhanced, diminished, or comparable to subtilisin proteases as desired for various uses. In some preferred embodiments, enhanced chelator stability is desired. Some of the proteases of the present invention find particular use in such applications.

In some embodiments of the present invention, naturally occurring proteases are provided which exhibit modified enzymatic activity at different pHs when compared to subtilisin proteases. A pH-activity profile is a plot of pH against enzyme activity and may be constructed as described in the Examples and/or by methods known in the art. In some embodiments, it is desired to obtain naturally occurring proteases with broader profiles (i.e., those having greater activity at range of pHs than a comparable subtilisin protease). In other embodiments, the enzymes have no significantly greater activity at any pH, or naturally occurring homologues with sharper profiles (i.e., those having enhanced activity when compared to subtilisin proteases at a given pH, and lesser activity elsewhere). Thus, in various embodiments, the proteases of the present invention have differing pH optima and/or ranges. It is not intended that the present invention be limited to any specific pH or pH range.

In some embodiments of the present invention, the cleaning compositions comprise, proteases of the present invention at a level from 0.00001% to 10% of 69B4 and/or other protease of the present invention by weight of the composition and the balance (e.g., 99.999% to 90.0%) comprising cleaning adjunct materials by weight of composition. In other aspects of the present invention, the cleaning compositions of the present invention comprise, the 69B4 and/or other proteases at a level of 0.0001% to 10%, 0.001% to 5%, 0.001% to 2%, 0.005% to 0.5% 69B4 or other protease of the present invention by weight of the composition and the balance of the cleaning composition (e.g., 99.9999% to 90.0%, 99.999% to 98%, 99.995% to 99.5% by weight) comprising cleaning adjunct materials.

In some embodiments, preferred cleaning compositions, in addition to the protease preparation of the invention, comprise one or more additional enzymes or enzyme derivatives which provide cleaning performance and/or fabric care benefits. Such enzymes include, but are not limited to other proteases, lipases, cutinases, amylases, cellulases, peroxidases, oxidases (e.g. laccases), and/or mannanases.

Any other protease suitable for use in alkaline solutions finds use in the compositions of the present invention. Suitable proteases include those of animal, vegetable or microbial origin. In particularly preferred embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., subtilisin, lentus, amyloliquefaciens, subtilisin Carlsberg, subtilisin 309, subtilisin 147 and subtilisin 168). Additional examples include those mutant proteases described in U.S. Pat. Nos. RE 34,606, 5,955,340, 5,700,676, 6,312,936, and 6,482,628, all of which are incorporated herein by reference. Additional protease examples include, but are not limited to trypsin (e.g., of porcine or bovine origin), and the *Fusarium* protease described in WO 89/06270. Preferred commercially available protease enzymes include those sold under the trade names MAXATASE®, MAXACAL™, MAXAPEM™, OPTICLEAN®, OPTIMASE®, PROPERASE®, PURAFECT® and PURAFECT® OXP (Genencor), those sold under the trade names ALCALASE®, SAVINASE®, PRIMASE®, DURAZYM™, RELASE® and ESPERASE® (Novozymes); and those sold under the trade name BLAP™ (Henkel Kommanditgesellschaft auf Aktien, Duesseldorf, Germany. Various proteases are described in WO95/23221, WO 92/21760, and U.S. Pat. Nos. 5,801,039, 5,340,735, 5,500,364, 5,855,625. An additional BPN' variant ("BPN'-var 1" and "BPN-variant 1"; as referred to herein) is described in U.S. Pat. No. RE 34,606. An additional GG36-variant ("GG36-var.1" and "GG36-variant 1"; as referred to herein) is described in U.S. Pat. Nos. 5,955,340 and 5,700,676. A further GG36-variant is described in U.S. Pat. Nos. 6,312,936 and 6,482,628. In one aspect of the present invention, the cleaning compositions of the present invention comprise additional protease enzymes at a level from 0.00001% to 10% of additional protease by weight of the composition and 99.999% to 90.0% of cleaning adjunct materials by weight of composition. In other embodiments of the present invention, the cleaning compositions of the present invention also comprise, proteases at a level of 0.0001% to 10%, 0.001% to 5%, 0.001% to 2%, 0.005% to 0.5% 69B4 protease (or its homologues or variants) by weight of the composition and the balance of the cleaning composition (e.g., 99.9999% to 90.0%, 99.999% to 98%, 99.995% to 99.5% by weight) comprising cleaning adjunct materials.

In addition, any lipase suitable for use in alkaline solutions finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and so EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), a *Pseudomonas* lipase such as *P. alcaligenes* and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipolytic enzymes such as cutinases also find use in some embodiments of the present invention, including but not limited to the cutinase derived from *Pseudomonas mendocina* (See, WO 88/09367), or cutinase derived from *Fusarium solani pisi* (See, WO 90/09446).

Additional suitable lipases include commercially available lipases such as M1 LIPASE™, LUMA FAST™, and LIPOMAX™ (Genencor); LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from 0.00001% to 10% of additional lipase by weight of the composition and the balance of cleaning adjunct materials by weight of composition. In other aspects of the present invention, the cleaning compositions of the present invention also comprise, lipases at a level of 0.0001% to 10%, 0.001% to 5%, 0.001% to 2%, 0.005% to 0.5% lipase by weight of the composition.

Any amylase (alpha and/or beta) suitable for use in alkaline solutions also find use in some embodiments of the present invention. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296,839). Commercially available amylases that find use in the present invention include, but are not limited to DURAMYL®, TERMAMYL®, FUNGAMYL® and BAN™ (Novozymes) and RAPIDASE® and MAXAMYL® P (Genencor International).

In some embodiments of the present invention, the cleaning compositions of the so present invention further comprise amylases at a level from 0.00001% to 10% of additional amylase by weight of the composition and the balance of cleaning adjunct materials by weight of composition. In other aspects of the present invention, the cleaning compositions of the present invention also comprise, amylases at a level of 0.0001% to 10%, 0.001% to 5%, 0.001% to 2%, 0.005% to 0.5% amylase by weight of the composition.

Any cellulase suitable for use in alkaline solutions find use in embodiments of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257).

Commercially available cellulases that find use in the present include, but are not limited to CELLUZYME® (Novozymes), and KAC-500(B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276).

In some embodiments, the cleaning compositions of the present invention can further comprise cellulases at a level from 0.00001% to 10% of additional cellulase by weight of the composition and the balance of cleaning adjunct materials by weight of composition. In other aspects of the present invention, the cleaning compositions of the present invention also comprise cellulases at a level of 0.0001% to 10%, 0.001% to 5%, 0.001% to 2%, 0.005% to 0.5% cellulase by weight of the composition.

Any mannanase suitable for use in detergent compositions and or alkaline solutions find use in the present invention. Suitable mannanases include, but are not limited to those of bacterial or fungal origin. Chemically or genetically modified mutants are included in some embodiments. Various mannanases are known which find use in the present invention (See e.g., U.S. Pat. No. 6,566,114, U.S. Pat. No. 6,602,842, and U.S. Pat. No. 6,440,991, all of which are incorporated herein by reference).

In some embodiments, the cleaning compositions of the present invention can further comprise mannanases at a level from 0.00001% to 10% of additional mannanase by weight of the composition and the balance of cleaning adjunct materials by weight of composition. In other aspects of the present invention, the cleaning compositions of the present invention also comprise, mannanases at a level of 0.0001% to 10%, 0.001% to 5%, 0.001% to 2%, 0.005% to 0.5% mannanase by weight of the composition.

In some embodiments, peroxidases are used in combination with hydrogen peroxide or a source thereof (e.g., a percarbonate, perborate or persulfate). In alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments.

In some embodiments, the cleaning compositions of the present invention can further comprise peroxidase and/or oxidase enzymes at a level from 0.00001% to 10% of additional peroxidase and/or oxidase by weight of the composition and the balance of cleaning adjunct materials by weight of composition. In other aspects of the present invention, the cleaning compositions of the present invention also comprise, peroxidase and/or oxidase enzymes at a level of 0.0001% to 10%, 0.001% to 5%, 0.001% to 2%, 0.005% to 0.5% peroxidase and/or oxidase enzymes by weight of the composition.

Mixtures of the above mentioned enzymes are encompassed herein, in particular a mixture of a the 69B4 enzyme, one or more additional proteases, at least one amylase, at least one lipase, at least one mannanase, and/or at least one cellulase. Indeed, it is contemplated that various mixtures of these enzymes will find use in the present invention.

It is contemplated that the varying levels of the protease and one or more additional enzymes may both independently range to 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610, 642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below.

If the cleaning adjunct materials are not compatible with the proteases of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapulation, tablets, physical separation, etc.).

Preferably an effective amount of one or more protease(s) provided herein are included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the protease of the present invention find use are described in greater detail below. In embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials).

The compositions of the present invention also find use detergent additive products in solid or liquid form. Such additive products are intended to supplement and/or boost the performance of conventional detergent compositions and can be added at any stage of the cleaning process.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, the density of the laundry detergent compositions herein ranges from 400 to 1200 g/liter, while in other embodiments, it ranges from 500 to 950 g/liter of composition measured at 20° C.

In some embodiments, various cleaning compositions such as those provided in U.S. Pat. No. 6,605,458 find use with the proteases of the present invention. Thus, in some embodiments, the compositions comprising at least one protease of the present invention is a compact granular fabric cleaning composition, while in other embodiments, the composition is a granular fabric cleaning composition useful in the laundering of colored fabrics, in further embodiments, the composition is a granular-fabric cleaning composition which provides softening through the wash capacity, in additional embodiments, the composition is a heavy duty liquid fabric cleaning composition.

In some embodiments, the compositions comprising at least one protease of the present invention are fabric cleaning compositions such as those described in U.S. Pat. Nos. 6,610,642 and 6,376,450. In addition, the proteases of the present invention find use in granular laundry detergent compositions of particular utility under European or Japanese washing conditions (See e.g., U.S. Pat. No. 6,610,642).

In alternative embodiments, the present invention provides hard surface cleaning compositions comprising at least one protease provided herein. Thus, in some embodiments, the compositions comprising at least one protease of the present invention is a hard surface cleaning composition such as those described in U.S. Pat. Nos. 6,610,642, 6,376,450, and 6,376,450.

In yet further embodiments, the present invention provides dishwashing compositions comprising at least one protease provided herein. Thus, in some embodiments, the compositions comprising at least one protease of the present invention is a hard surface cleaning composition such as those in U.S. Pat. Nos. 6,610,642 and 6,376,450.

In still further embodiments, the present invention provides dishwashing compositions comprising at least one protease provided herein. Thus, in some embodiments, the compositions comprising at least one protease of the present invention comprise oral care compositions such as those in U.S. Pat. Nos. 6,376,450, and 6,376,450.

The formulations and descriptions of the compounds and cleaning adjunct materials contained in the aforementioned U.S. Pat. Nos. 6,376,450, 6,605,458, 6,605,458, and 6,610,642, all of which are expressly incorporated by reference herein. Still further examples are set forth in the Examples below.

I) Processes of Making and Using the Cleaning Composition of the Present Invention The cleaning compositions of the present invention can be formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition may be adjusted via the addition of a material such as monoethanolamine or an acidic material such as HCl.

II) Adjunct Materials in Addition to the Serine Proteases of the Present Invention While not essential for the purposes of the present invention, the non-limiting list of adjuncts illustrated hereinafter are suitable for use in the instant cleaning compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. It is understood that such adjuncts are in addition to the serine proteases of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, that are incorporated by reference. The aforementioned adjunct ingredients may constitute the balance of the cleaning compositions of the present invention.

Surfactants

The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When a low pH cleaning composition, such as composition having a neat pH of from about 3 to about 5, is desired, such composition typically does not contain alkyl ethoxylated sulfate as it is believed that such surfactant may be hydrolyzed by such compositions the acidic contents.

The surfactant is typically present at a level of from about 0.1% to about 60%, from about 1% to about 50% or even from about 5% to about 40% by weight of the subject cleaning composition.

Builders

The cleaning compositions of the present invention may comprise one or more detergent builders or builder systems. When a builder is used, the subject cleaning composition will typically comprise at least about 1%, from about 3% to about 60% or even from about 5% to about 40% builder by weight of the subject cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof.

Chelating Agents

The cleaning compositions herein may contain a chelating agent, Suitable chelating agents include copper, iron and/or manganese chelating agents and mixtures thereof.

When a chelating agent is used, the cleaning composition may comprise from about 0.1% to about 15% or even from about 3.0% to about 10% chelating agent by weight of the subject cleaning composition.

Deposition Aid

The cleaning compositions herein may contain a deposition aid. Suitable deposition aids include, polyethylene glycol, polypropylene glycol, polycarboxylate, soil release polymers such as polytelephthalic acid, clays such as Kaolinite, montmorillonite, atapulgite, illite, bentonite, halloysite, and mixtures thereof.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in a subject cleaning composition, the dye transfer inhibiting agents may be present at levels from about 0.0001% to about 10%, from about 0.01% to about 5% or even from about 0.1% to about 3% by weight of the cleaning composition.

Dispersants

The cleaning compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes

The cleaning compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenol oxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is cocktail of conventional applicable enzymes like protease, lipase, cutinase and/or cellulase in conjunction with amylase.

Enzyme Stabilizers

Enzymes for use in detergents can be stabilized by various techniques. The enzymes employed herein can be stabilized by the presence of water-soluble sources of calcium and/or magnesium ions in the finished compositions that provide such ions to the enzymes.

Catalytic Metal Complexes

The cleaning compositions of the present invention may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936, and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexadecane.

Suitable transition metal MRLs are readily prepared by known procedures, such as taught for example in WO 00/332601, and U.S. Pat. No. 6,225,464.

III) Processes of Making and Using Cleaning Compositions

The cleaning compositions of the present invention can be formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference.

IV) Method of Use

The cleaning compositions disclosed herein of can be used to clean a situs inter alia a surface or fabric. Typically at least a portion of the situs is contacted with an embodiment of the present cleaning composition, in neat form or diluted in a wash liquor, and then the situs is optionally washed and/or rinsed. For purposes of the present invention, washing includes but is not limited to, scrubbing, and mechanical agitation. The fabric may comprise most any fabric capable of being laundered in normal consumer use conditions. The disclosed cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

B. Animal Feed

Still further, the present invention provides compositions and methods for the production of a food or animal feed, characterized in that protease according to the invention is mixed with food or animal feed. In some embodiments, the protease is added as a dry product before processing, while in other embodiments it is added as a liquid before or after processing. In some embodiments, in which a dry powder is used, the enzyme is diluted as a liquid onto a dry carrier such as milled grain. The proteases of the present invention find use as components of animal feeds and/or additives such as those described U.S. Pat. No. 5,612,055, U.S. Pat. No. 5,314,692. and U.S. Pat. No. 5,147,642, all of which are hereby incorporated by reference.

The enzyme feed additive according to the present invention is suitable for preparation in a number of methods. For example, in some embodiments, it is prepared simply by mixing different enzymes having the appropriate activities to produce an enzyme mix. In some embodiments; this enzyme mix is mixed directly with a feed, while in other embodiments, it is impregnated onto a cereal-based carrier material such as milled wheat, maize or soya flour. The present invention also encompasses these impregnated carriers, as they find use as enzyme feed additives.

In some alternative embodiments, a cereal-based carrier (e.g., milled wheat or maize) is impregnated either simultaneously or sequentially with enzymes having the appropriate activities. For example, in some embodiments, a milled wheat carrier is first sprayed with a xylanase, secondly with a protease, and optionally with a β-glucanase. The present invention also encompasses these impregnated carriers, as they find use as enzyme feed additives. In preferred embodiments, these impregnated carriers comprise at least one protease of the present invention.

In some embodiments, the feed additive of the present invention is directly mixed with the animal feed, while in alternative embodiments, it is mixed with one or more other feed additives such as a vitamin feed additive, a mineral feed additive, and/or an amino acid feed additive. The resulting feed additive including several different types of components is then mixed in an appropriate amount with the feed.

In some preferred embodiments, the feed additive of the present invention, including cereal-based carriers is normally mixed in amounts of 0.01-50 g per kilogram of feed, more preferably 0.1-10 g/kilogram, and most preferably about 1 g/kilogram.

In alternative embodiments, the enzyme feed additive of the present invention involves construction of recombinant microorganisms that produces the desired enzyme(s) in the desired relative amounts. In some embodiments, this is accomplished by increasing the copy number of the gene encoding at least one protease of the present invention, and/or by using a suitably strong promoter operatively linked to the polynucleotide encoding the protease(s). In further embodiments, the recombinant microorganism strain has certain enzyme activities deleted (e.g., cellulases, endoglucanases, etc.), as desired.

In additional embodiments, the enzyme feed additives provided by the present invention also include other enzymes, including but not limited to at least one xylanase, α-amylase, glucoamylase, pectinase, mannanase, α-galactosidase, phytase, and/or lipase. In some embodiments, the enzymes having the desired activities are mixed with the xylanase and protease either before impregnating these on a cereal-based carrier or alternatively such enzymes are impregnated simultaneously or sequentially on such a cereal-based carrier. The carrier is then in turn mixed with a cereal-based feed to prepare the final feed. In alternative embodiments, the enzyme feed additive is formulated as a solution of the individual enzyme activities and then mixed with a feed material pre-formed as pellets or as a mash.

In still further embodiments, the enzyme feed additive is included in animals' diets by incorporating it into a second (i.e., different) feed or the animals' drinking water. Accordingly, it is not essential that the enzyme mix provided by the present invention be incorporated into the cereal-based feed itself, although such incorporation forms a particularly preferred embodiment of the present invention. The ratio of the units of xylanase activity per g of the feed additive to the units of protease activity per g of the feed additive is preferably 1:0.001-1,000, more preferably 1:0.01-100, and most preferably 1:0.1-10. As indicated above, the enzyme mix provided by the present invention is preferably finds use as a feed additive in the preparation of a cereal-based feed.

In some embodiments, the cereal-based feed comprises at least 25% by weight, or more preferably at least 35% by weight, wheat or maize or a combination of both of these cereals. The feed further comprises a protease (i.e., at least one protease of the present invention) in such an amount that the feed includes a protease in such an amount that the feed includes 100-100,000 units of protease activity per kg.

Cereal-based feeds provided the present invention according to the present invention find use as feed for a variety of non-human animals, including poultry (e.g., turkeys, geese, ducks, chickens, etc.), livestock (e.g., pigs, sheep, cattle, goats, etc.), and companion animals (e.g., horses, dogs, cats, rabbits, mice, etc.). The feeds are particularly suitable for poultry and pigs, and in particular broiler chickens.

C. Textile and Leather Treatment

The present invention also provides compositions for the treatment of textiles that include at least one of the proteases of the present invention. In some embodiments, at least one protease of the present invention is a component of compositions suitable for the treatment of silk or wool (See e.g., U.S. RE Pat. No. 216,034, EP 134,267, U.S. Pat. No. 4,533,359, and EP 344,259).

In addition, the proteases of the present invention find use in a variety of applications where it is desirable to separate phosphorous from phytate. Accordingly, the present invention also provides methods producing wool or animal hair material with improved properties. In some preferred embodiments, these methods comprise the steps of pretreating wool, wool fibres or animal hair material in a process selected from the group consisting of plasma treatment processes and the Delhey process; and subjecting the pretreated wool or animal hair material to a treatment with a proteolytic enzyme (e.g., at least one protease of the present invention) in an amount effective for improving the properties. In some embodiments, the proteolytic enzyme treatment occurs prior to the plasma treatment, while in other embodiments, it occurs after the plasma treatment. In some further embodiments, it is conducted as a separate step, while in other embodiments, it is conducted in combination with the scouring or the dyeing of the wool or animal hair material. In additional embodiments, at least one surfactant and/or at least one softener is present during the enzyme treatment step, while in other embodiments, the surfactant(s) and/or softener(s) are incorporated in a separate step wherein the wool or animal hair material is subjected to a softening treatment.

In some embodiments, the compositions of the present invention find us in methods for shrink-proofing wool fibers (See e.g., JP 4-327274). In some embodiments, the compositions are used in methods for shrink-proofing treatment of wool fibers by subjecting the fibers to a low-temperature plasma treatment, followed by treatment with a shrink-proofing resin such as a block-urethane resin, polyamide epochlorohydrin resin, glyoxalic resin, ethylene-urea resin or acrylate resin, and then treatment with a weight reducing proteolytic enzyme for obtaining a softening effect). In some embodiments, the plasma treatment step is a low-temperature treatment, preferably a corona discharge treatment or a glow discharge treatment.

In some embodiments, the low-temperature plasma treatment is carried out by using a gas, preferably a gas selected from the group consisting of air, oxygen, nitrogen, ammonia, helium, or argon. Conventionally, air is used but it may be advantageous to use any of the other indicated gasses.

Preferably, the low-temperature plasma treatment is carried out at a pressure between about 0.1 torr and 5 torr for from about 2 seconds to about 300 seconds, preferably for about 5 seconds to about 100 seconds, more preferably from about 5 seconds to about 30 seconds.

As indicated above, the present invention finds use in conjunction with methods such as the Delhey process (See e.g., DE-A-43 32 692). In this process, the wool is treated in an aqueous solution of hydrogen peroxide in the presence of soluble wolframate, optionally followed by treatment in a solution or dispersion of synthetic polymers, for improving the anti-felting properties of the wool. In this method, the wool is treated in an aqueous solution of hydrogen peroxide (0.1-35% (w/w), preferably 2-10% (w/w)), in the presence of a 2-60% (w/w), preferably 8-20% (w/w) of a catalyst (preferably $Na_2 WO_4$), and in the presence of a nonionic wetting agent. Preferably, the treatment is carried out at pH 8-11, and room temperature. The treatment time depends on the concentrations of hydrogen peroxide and catalyst, but is preferably 2 minutes or less. After the oxidative treatment, the wool is rinsed with water. For removal of residual hydrogen peroxide, and optionally for additional bleaching, the wool is further treated in acidic solutions of reducing agents (e.g., sulfites, phosphites etc.).

In some embodiments, the enzyme treatment step carried out for between about 1 minute and about 120 minutes. This step is preferably carried out at a temperature of between about 20° C. and about 60° C., more preferably between about 30° C. and about 50° C. Alternatively, the wool is soaked in or padded with an aqueous enzyme solution and then subjected to steaming at a conventional temperature and pressure, typically for about 30 seconds to about 3 minutes. In some preferred embodiments, the proteolytic enzyme treatment is carried out in an acidic or neutral or alkaline medium which may include a buffer.

In alternative embodiments, the enzyme treatment step is conducted in the presence of one or more conventional anionic, non-ionic (e.g.; Dobanol; Henkel AG) or cationic surfactants. An example of a useful nonionic surfactant is Dobanol (from Henkel AG). In further embodiments, the wool or animal hair material is subjected to an ultrasound treatment, either prior to or simultaneous with the treatment with a proteolytic enzyme. In some preferred embodiments, the ultrasound treatment is carried out at a temperature of about 50° C. for about 5 minutes. In some preferred embodiments, the amount of proteolytic enzyme used in the enzyme treatment step is between about 0.2 w/w % and about 10 w/w %, based on the weight of the wool or animal hair material. In some embodiments, in order to the number of treatment steps, the enzyme treatment is carried out during dyeing and/or scouring of the wool or animal hair material, simply by adding the protease to the dyeing, rinsing and/or scouring bath. In some embodiments, enzyme treatment is carried out after the plasma treatment but in other embodiments, the two treatment steps are carried out in the opposite order.

Softeners conventionally used on wool are usually cationic softeners, either organic cationic softeners or silicone based products, but anionic or non-ionic softeners are also so useful. Examples of useful softeners include, but are not limited to polyethylene softeners and silicone softeners (i.e., dimethyl polysiloxanes (silicone oils)), H-polysiloxanes, silicone elastomers, aminofunctional dimethyl polysiloxanes, aminofunctional silicone elastomers, and epoxyfunctional dimethyl polysiloxanes, and organic cationic softeners (e.g. alkyl quarternary ammonium derivatives).

In additional embodiments, the present invention provides compositions for the treatment of an animal hide that includes at least one protease of the present invention. In some embodiments, the proteases of the present invention find use in compositions for treatment of animal hide, such as those described in WO 03/00865 (Insect Biotech Co., Taejeon-Si, Korea). In additional embodiments, the present invention provides methods for processing hides and/or skins into leather comprising enzymatic treatment of the hide or skin with the protease of the present invention (See e.g., WO 96/11285). In additional embodiments, the present invention provides compositions for the treatment of an animal skin or hide into leather that includes at least one protease of the present invention.

Hides and skins are usually received in the tanneries in the form of salted or dried raw hides or skins. The processing of hides or skins into leather comprises several different process steps including the steps of soaking, unhairing and bating. These steps constitute the wet processing and are performed in the beamhouse. Enzymatic treatment utilizing the proteases of the present invention are applicable at any time during the process involved in the processing of leather. However, proteases are usually employed during the wet processing (i.e., during soaking, unhairing and/or bating). Thus, in some preferred embodiments, the enzymatic treatment with at least one of the proteases of the present invention occurs during the wet processing stage.

In some embodiments, the soaking processes of the present invention are performed under conventional soaking conditions (e.g., at a pH in the range pH 6.0-11).

In some preferred embodiments, the range is pH 7.0-10.0. In alternative embodiments, the temperature is in the range of 20-30° C., while in other embodiments it is preferably in the range 24-28° C. In yet further embodiments, the reaction time is in the range 2-24 hours, while preferred range is 4-16 hours. In additional embodiments, tensides and/or preservatives are provided as desired.

The second phase of the bating step usually commences with the addition of the bate itself. In some embodiments, the enzymatic treatment takes place during bating. In some preferred embodiments, the enzymatic treatment takes place during bating, after the deliming phase. In some embodiments, the bating process of the presents invention is performed using conventional conditions (e.g., at a pH in the range pH 6.0-9.0). In some preferred embodiments, the pH range is 6.0 to 8.5. In further embodiments, the temperature is in the range of 20-30° C., while in preferred embodiments, the temperature is in the range of 25-28° C. In some embodiments, the reaction time is in the range of 20-90 minutes, while in other embodiments, it is in the range 40-80 minutes. Processes for the manufacture of leather are well known to those skilled in the art (See e.g., WO 94/069429 WO 90/1121189, U.S. Pat. No. 3,840,433, EP 505920, GB 2233665, and U.S. Pat. No. 3,986,926, all of which are herein incorporated by reference).

In further embodiments, the present invention provides bates comprising at least one protease of the present invention. A bate is an agent or an enzyme-containing preparation comprising the chemically active ingredients for use in beamhouse processes, in particular in the bating step of a process for the manufacture of leather. In some embodiments, the present invention provides bates comprising protease and suitable excipients. In some embodiments, agents including, but not limited to chemicals known and used in the art, e.g. diluents, emulgators, delimers and carriers. In some embodiments, the bate comprising at least one protease of the present invention is formulated as known in the art (See. e.g., GB-A2250289, WO 96/11285, and EP 0784703).

In some embodiments, the bate of the present invention contains from 0.00005 to 0.01 g of active protease per g of bate, while in other embodiments, the bate contains from 0.0002 to 0.004 g of active protease per g of bate.

Thus, the proteases of the present invention find use in numerous applications and settings.

EXPERIMENTAL

The present invention is described in further detail in the following Examples which are not in any way intended to limit the scope of the invention as claimed. The attached Figures are meant to be considered as integral parts of the specification and description of the invention. All references cited are herein specifically incorporated by reference for all that is described therein. The following Examples are offered to illustrate, but not to limit the claimed invention In the experimental disclosure which follows, the following abbreviations apply: PI (proteinase inhibitor), ppm (parts per million); M (molar); mM (millimolar); μM (micromolar);

nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); (HCl (hydrochloric acid); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN® 20); PEG (polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl] phosphine); Ci (Curies); mCi (milliCuries); µCi (microCuries); HPLC (high pressure liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (heavy duty liquid detergent, i.e., laundry detergent); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y.); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingeng, the Netherlands); Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco 15. Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc., Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); and Microsoft (Microsoft, Inc., Redmond, Wash.).

Example 1

Assays

In the following Examples, various assays were used, such as protein determinations, application-based tests, and stability-based tests. For ease in reading, the following assays are set forth below and referred to in the respective Examples. Any deviations from the protocols provided below in any of the experiments performed during the development of the present invention are indicated in the Examples.

Some of the detergents used in the following Examples had the following compositions. In Compositions I and II, the balance (to 100%) is perfume/dye and/or water. The pH of these compositions was from about 5 to about 7 for Composition I, and about 7.5 to about 8.5 Composition II. In Composition III, the balance (to 100%) comprised of water and/or the minors perfume, dye, brightener/SRPI/sodium carboxymethylcellulose/photobleach/MgSo$_4$/PVPVI/suds suppressor/high molecular PEG/clay.

DETERGENT COMPOSITIONS

| | Composition I | Composition II |
|---|---|---|
| LAS | 24.0 | 8.0 |
| $C_{12}$-$C_{15}$ $AE_{1.8}$S | — | 11.0 |
| $C_8$-$C_{10}$ propyl dimethyl amine | 2.0 | 2.0 |
| $C_{12}$-$C_{14}$ alkyl dimethyl amine oxide | — | — |
| $C_{12}$-$C_{15}$ AS | — | 7.0 |
| CFAA | — | 4.0 |
| $C_{12}$-$C_{14}$ Fatty alcohol ethoxylate | 12.0 | 1.0 |
| $C_{12}$-$C_{18}$ Fatty acid | 3.0 | 4.0 |
| Citric acid (anhydrous) | 6.0 | 3.0 |
| DETPMP | — | 1.0 |
| Monoethanolamine | 5.0 | 5.0 |
| Sodium hydroxide | — | 1.0 |
| 1 N HCl aqueous solution | #1 | — |
| Propanediol | 12.7 | 10. |
| Ethanol | 1.8 | 5.4 |
| DTPA | 0.5 | 0.4 |
| Pectin Lyase | — | 0.005 |
| Lipase | 0.1 | — |
| Amylase | 0.001 | — |
| Cellulase | — | 0.0002 |
| Protease A | — | — |
| Aldose Oxidase | — | — |
| DETBCHD | — | 0.01 |
| SRP1 | 0.5 | 0.3 |
| Boric acid | 2.4 | 2.8 |
| Sodium xylene sulfonate | — | — |
| DC 3225C | 1.0 | 1.0 |
| 2-butyl-octanol | 0.03 | 0.03 |
| Brightener 1 | 0.12 | 0.08 |

Composition III

| | |
|---|---|
| $C_{14}$-$C_{15}$ AS or sodium tallow alkyl sulfate | 3.0 |
| LAS | 8.0 |
| $C_{12}$-$C_{15}$ $AE_3$S | 1.0 |
| $C_{12}$-$C_{15}$ $E_5$ or $E_3$ | 5.0 |
| QAS | — |
| Zeolite A | 11.0 |
| SKS-6 (dry add) | 9.0 |
| MA/AA | 2.0 |
| AA | — |
| 3Na Citrate 2H$_2$O | — |
| Citric Acid (Anhydrous) | 1.5 |
| DTPA | — |
| EDDS | 0.5 |
| HEDP | 0.2 |
| PB1 | — |

Composition III

| | |
|---|---|
| Percarbonate | 3.8 |
| NOBS | — |
| NACA OBS | 2.0 |
| TAED | 2.0 |
| BB1 | 0.34 |
| BB2 | — |
| Anhydrous Na Carbonate | 8.0 |
| Sulfate | 2.0 |
| Silicate | — |
| Protease B | — |
| Protease C | — |
| Lipase | — |
| Amylase | — |
| Cellulase | — |
| Pectin Lyase | 0.001 |
| Aldose Oxidase | 0.05 |
| PAAC | — |

A. TCA Assay for Protein Content Determination in 96-Well Microtiter Plates

This assay was started using filtered culture supernatant from microtiter plates grown 4 days at 33° C. with shaking at 230 RPM and humidified aeration. A fresh 96-well flat bottom plate was used for the assay. First, 100 μL/well of 0.25 N HCl were placed in the wells. Then, 50 μL filtered culture broth were added to the wells. The light scattering/absorbance at 405 nm (use 5 sec mixing mode in the plate reader) was then determined, in order to provide the "blank" reading.

For the test, 100 μL/well 15% (w/v) TCA was placed in the plates and incubated between 5 and 30 min at room temperature. The light scattering/absorbance at 405 nm (use 5 sec mixing mode in the plate reader) was then determined.

The calculations were performed by subtracting the blank (i.e., no TCA) from the test reading with TCA. If desired, a standard curve can be created by calibrating the TCA readings with AAPF assays of clones with known conversion factors. However, the TCA results are linear with respect to protein concentration from 50 to 0.500 ppm and can thus be plotted directly against enzyme performance for the purpose of choosing good-performing variants.

B. suc-AAPF-pNA Assay of Proteases in 96-Well Microtiter Plates

In this assay system, the reagent solutions used were:
1. 100 mM Tris/HCl, pH 8.6, containing 0.005% TWEEN®-80 (Tris buffer)
2. 100 mM Tris buffer, pH 8.6, containing 10 mM CaCl$_2$ and 0.005% TWEEN®-80 (Tris buffer)
3. 160 mM suc-AAPF-pNA in DMSO (suc-AAPF-pNA stock solution) (Sigma: S-7388)

To prepare suc-AAPF-pNA working solution, 1 ml AAPF stock was added to 100 ml Tris/Ca buffer and mixed well for at least 10 seconds.

The assay was performed by adding 10 μl of diluted protease solution to each well, followed by the addition (quickly) of 190 μl 1 mg/ml AAPF-working solution. The solutions were mixed for 5 sec., and the absorbance change was read at 410 nm in an MTP reader, at 25° C. The protease activity was expressed as AU (activity=δOD·min$^{-1}$·ml$^{-1}$).

C. Keratin Hydrolysis Assay

In this assay system, the chemical and reagent solutions used were:

| | |
|---|---|
| Keratin | ICN 902111 |
| Detergent | Detergent Composition II |
| | 1.6 g. detergent is dissolved in 1000 ml |
| | water (pH = 8.2) 0.6 ml. CaCl2/MgCl2 of 10,000 |
| | gpg is added as well as 1190 mg |
| | HEPES, giving a hardness |

|  |  |
|---|---|
| | and buffer strength of 6 gpg and 5 mM respectively. The pH is adjusted to 8.2 with NaOH. |
| Picrylsulfonic acid (TNBS) | Sigma P-2297 (5% solution in water) |
| Reagent A | 45.4 g $Na_2B_4O_7 \cdot 10\ H_2O$ (Merck 6308) and 15 ml of 4N NaOH are dissolved together to a final volume of 1000 ml (by heating if needed) |
| Reagent B | 35.2 g $NaH_2PO_4 \cdot 1H_2O$ (Merck 6346) and 0.6 g $Na_2SO_3$ (Merck 6657) are dissolved together to a final volume of 1000 ml. |

Method:

Prior to the incubations, keratin was sieved on a 100 μm sieve in small portions at a time. Then, 10 g of the <100 μm keratin was stirred in detergent solution for at least 20 minutes at room temperature with regular adjustment of the pH to 8.2. Finally, the suspension was centrifuged for 20 minutes at room temperature (Sorvall, GSA rotor, 13,000 rpm). This procedure was then repeated. Finally, the wet sediment was suspended in detergent to a total volume of 200 ml., and the suspension was kept stirred during pipetting.

Prior to incubation, microtiter plates (MTPs) were filled with 200 μl substrate per well with a Biohit multichannel pipette and 1200 μl tip (6 dispenses of 200 μl and dispensed as fast as possible to avoid settling of keratin in the tips). Then, 10 μl of the filtered culture was added to the substrate containing MTPs. The plates were covered with tape, placed in an incubator and incubated at 20° C. for 3 hours at 350 rpm (Innova 4330 [New Brunswick]). Following incubation, the plates were centrifuged for 3 minutes at 3000 rpm (iSigma 6K 15 centrifuge). About 15 minutes before removal of the $1^{st}$ plate from the incubator, the TNBS reagent was prepared by mixing 1 ml TNBS solution per 50 ml of reagent A.

MTPs were filled with 60 μl TNBS reagent A per well. From the incubated plates, 10 μl was transferred to the MTPs with TNBS reagent A. The plates were covered with tape and shaken for 20 minutes in a bench shaker (BMG Thermostar) at room temperature and 500 rpm. Finally, 200 μl of reagent B was added to the wells, mixed for 1 minute on a shaker, and the absorbance at 405 nm was measured with the MTP-reader.

Calculation of the Keratin Hydrolyzing Activity:

The obtained absorbance value was corrected for the blank value (substrate without enzyme). The resulting absorbance provides a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

D. Microswatch Assay for Testing Protease Performance

All of the detergents used in these assays did not contain enzymes.

Detergent Preparations:

1. European Detergent Solution:

Milli-Q water was adjusted to 15 gpg water hardness (Ca/Mg=4/1), add 7.6 g/l ARIEL® Regular detergent and stir the detergent solution vigorously for at least 30 minutes. The detergent was filtered before use in the assay through a 0.22 μm filter (e.g. Nalgene top bottle filter).

2. Japanese Detergent Solution

Milli-Q water was adjusted to 3 gpg water hardness (Ca/Mg=3/1), add 0.66 g/l Detergent Composition III, the detergent solution was stirred vigorously for at least 30 minutes. The detergent was filtered before use in the assay through a 0.22 μm filter (e.g. Nalgene top bottle filter).

3. Cold Water Liquid Detergent (US Conditions):

Milli-Q water was adjusted to 6 gpg water hardness (Ca/Mg=3/1), add 1.60 g/l TIDE® LVJ-1 detergent and stir the detergent solution vigorously for at least 15 minutes. Add 5 mM Hepes buffer and set pH at 8.2. The detergent was filtered before use in the assay through a 0.22 μm filter (e.g. Nalgene top bottle filter).

4. Low pH Liquid Detergent (US Conditions):

Milli-Q water was adjusted to 6 gpg water hardness (Ca/Mg=3/1), 1.60 g/l Detergent Composition I, was added and the detergent solution stirred vigorously for at least 15 minutes. The pH was set at 6.0 using 1N NaOH solution. The detergent was filtered before use in the assay through a 0.22 μm filter (e.g. Nalgene top bottle filter).

Microswatches:

Microswatches of ¼" circular diameter were ordered and delivered by CFT Vlaardingen. The microswatches were pre-treated using the fixation method described below. Single microswatches were placed in each well of a 96-well microtiter plate vertically to expose the whole surface area (i.e., not flat on the bottom of the well).

Bleach Fixation ("Superfixed"):

In a 10 L stainless steel beaker containing 10 L of water, the water was heated to 60° C. for fixation of swatches used in European conditions (=Super fixed). For Japanese condition(s) and other conditions, the swatches were fixed at room temperature (=3K). Then, 10 ml of 30% hydrogen peroxide (1 ml/L of $H_2O_2$, final conc. of $H_2O_2$ is 300 ppm) were added. Then, 100 swatches (10 swatches/L) were added to the solution. The solution was allowed to sit for 30 minutes with occasional stirring and monitoring of the temperature. The swatches were rinsed 7-8 times with cold water and placed on bench to dry. A towel was placed on top of swatches, as this prevents the swatches from curling up. For the 3K swatches, the procedure is repeated (except the water was not heated and 10× the amount of hydrogen peroxide was added).

Alternative Fixation ("3K" Swatch Fixation):

This particular swatch fixation was done at room temperature, however the amount of 30% H2O2 added is 10× more than in the Superfixed Swatch Fixation. Bubble formation (frothing) will be visible and therefore it is necessary to use a bigger beaker to account for this. First, 8 liters of distilled water are placed in a 10 L beaker, and 80 ml of 30% hydrogen peroxide are added. The water and peroxide are mixed well with a ladle. Then, 40 pieces of EMPA 116 swatches were spread into a fan before adding into the solution to ensure uniform fixation. The swatches were swirled in the solution (using the ladle) for 30 minutes, continuously for the first five minutes and occasionally for the remaining 25 minutes. The solution was discarded and the swatches were rinsed 6 times with approximately 6 liters of distilled water each time. The swatches were placed on top of paper towels to dry. The air-dried swatches were punched using a ¼" circular die on an expulsion press. A single microswatch was placed vertically into each well of a 96-well microtiter plate to expose the whole surface area (i.e. not flat on the bottom of the well).

Enzyme Samples:

The enzyme samples were tested at appropriate concentrations for the respective geography, and diluted in 10 mM NaCl, 0.005% TWEEN®-80 solution.

Test Method:

The incubator was set at the desired temperature: 20° C. for cold water liquid conditions; 30° C. for low-pH liquid conditions; 40° C. for European conditions; 20° C. for Japanese and North American conditions. The pretreated and precut swatches were placed into the wells of a 96-well MTP, as described above. The enzyme samples were diluted, if needed, in 10 mM NaCl, 0.005% TWEEN®-80 to 20× the desired concentration. The desired detergent solutions were prepared as described above. Then, 190 µl of detergent solution were added to each well of the MTP. To this mixture, 10 µl of enzyme solution were added to each well (to provide a total volume to 200 µl/well). The MTP was sealed with a plate sealer and placed in an incubator for 60 minutes, with agitation at 350 rpm. Following incubation under the appropriate conditions, 100 µl of solution from each well were removed and placed into a fresh MTP. The new MTP containing 100 µl of solution/well was read at 405 nm in a MTP reader. Blank controls, as well as a control containing a microswatch and detergent but no enzyme were also included.

TABLE 1-1

Detergent Composition and Incubation Conditions in the µSwatch Assay.

| Geography | Reference Enzyme | Detergent | Water Hardness | Enzyme Dosage [ppm] | Temp. | Swatch |
|---|---|---|---|---|---|---|
| European | ASP GG36 | 7.6 g/l ARIEL® Regular | 15 gpg - Ca/Mg: 4/1 | 0.5-4 | 40° | Superfix |
| Japanese | ASP GG36 | 0.66 g/l Detergent Comp. III | 3 gpg - Ca/Mg: 3/1 | 0.5-4 | 20° | 3K |
| Cold Water Liquid | ASP | 1.6 g/l Tide® LVJ-1 | 6 gpg - Ca/Mg: 3/1 | 0.5-4 | 20° | 3K |
| Liquid Detergent Comp. I | ASP | 1.6 g/l Detergent Comp. I | 6 gpg - Ca/Mg: 3/1 | 0.5-4 | 30° | 3K |

**The stock solution was used at a concentration of 15,000 gpg
stock #1 = Ca/Mg 3:1
(1.92 M $Ca^{2+}$ = 282.3 g/L $CaCl_2 \cdot 2H_2O$; 0.64 M $Mg^{2+}$ = 30.1 g/L $MgCl_2 \cdot 6H_2O$)
stock #2 = Ca/Mg 4:1
(2.05 M $Ca^{2+}$ = 301.4 g/L $CaCl_2 \cdot 2H_2O$; 0.51 M $Mg^{2+}$ = 103.7 g/L $MgCl_2 \cdot 6H_2O$)

Calculation of the BMI Performance:

The obtained absorbance value was corrected for the blank value (obtained after incubation of microswatches in the absence of enzyme). The resulting absorbance was a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

D. Dimethylcasein Hydrolysis Assay (96 Wells)

In this assay system, the chemical and reagent solutions used were:

| | |
|---|---|
| Dimethylcasein (DMC): | Sigma C-9801 |
| TWEEN ®-80: | Sigma P-8074 |
| PIPES buffer (free acid): | Sigma P-1851; 15.1 g is dissolved in about 960 ml water; pH is adjusted: to 7.0 with 4N NaOH, 1 ml 5% TWEEN ®-80 is added and the volume brought up to 1000 ml. The final concentration of PIPES and TWEEN ®-80 is 50 mM and 0.005% respectively. |
| Picrylsulfonic acid (TNBS): | Sigma P-2297 (5% solution in water) |
| Reagent A: | 45.4 g $Na_2B_4O_7 \cdot 10 H_2O$ (Merck 6308) and 15 ml of 4N NaOH are dissolved together to a final volume of 1000 ml (by heating if needed) |
| Reagent B: | 35.2 g $NaH_2PO_4 \cdot 1H_2O$ (Merck 6346) and 0.6 g $Na_2SO_3$ (Merck 6657) are dissolved together to a final volume of 1000 ml. |

Method:

To prepare the substrate, 4 g DMC were dissolved in 400 ml PIPES buffer. The filtered culture supernatants were diluted with PIPES buffer; the final concentration of the controls in the growth plate was 20 ppm. Then, 10 µl of each diluted supernatant were added to 200 µl substrate in the wells of a MTP. The MTP plate was covered with tape, shaken for a few seconds and placed in an oven at 37° C. for 2 hours without agitation.

About 15 minutes before removal of the 1$^{st}$ plate from the oven, the TNBS reagent was prepared by mixing 1 ml TNBS solution per 50 ml of reagent A. MTPs were filled with 60 µl TNBS reagent A per well. The incubated plates were shaken for a few seconds, after which 10 µl were transferred to the MTPs with TNBS reagent A. The plates were covered with tape and shaken for 20 minutes in a bench shaker (BMG Thermostar) at room temperature and 500 rpm. Finally, 200 µl reagent B were added to the wells, mixed for 1 minute on a shaker, and the absorbance at 405 nm was determined using an MTP-reader.

Calculation of Dimethylcasein Hydrolyzing Activity:

The obtained absorbance value was corrected for the blank value (substrate without enzyme). The resulting absorbance is a measure for the hydrolytic activity. The (arbitrary) specific activity of a sample was calculated by dividing the absorbance and the determined protein concentration.

E. Thermostability Assay

This assay is based on the dimethylcasein hydrolysis, before and after heating of the buffered culture supernatant. The same chemical and reagent solutions were used as described in the dimethylcasein hydrolysis assay.

Method:

The filtered culture supernatants were diluted to 20 ppm in PIPES buffer (based on the concentration of the controls in the growth plates). Then, 50 µl of each diluted supernatant were placed in the empty wells of a MTP. The MTP plate was incubated in an iEMS incubator/shaker HT (Thermo Lab-systems) for 90 minutes at 60° C. and 400 rpm. The plates were cooled on ice for 5 minutes. Then, 10 µl of the solution was added to a fresh MTP containing 200 µl dimethylcasein substrate/well. This MTP was covered with tape, shaken for a few seconds and placed in an oven at 37° C. for 2 hours without agitation. The same detection method as used for the DMC hydrolysis assay was used.

Calculation of Thermostability:

The residual activity of a sample was expressed as the ratio of the final absorbance and the initial absorbance, both corrected for blanks.

F. LAS Stability Assay

LAS stability was measured after incubation of the test protease in the presence of 0.06% LAS (dodecylbenzenesulfonate sodium), and the residual activity was determined using the AAPF assay.

Reagents:
Dodecylbenzenesulfonate, Sodium salt (=LAS): Sigma D-2525
TWEEN®-80: Sigma P-8074
TRIS buffer (free acid): Sigma T-1378); 6.35 g is dissolved in about 960 ml water; pH is adjusted to 8.2 with 4N HCl. Final concentration of TRIS is 52.5 mM.
LAS stock solution: Prepare a 10.5% LAS solution in MQ water (=10.5 g per 100 ml MQ)
TRIS buffer-100 mM/pH 8.6 (100 mM Tris/0.005% Tween80)
TRIS-Ca buffer, pH 8.6 (100 mM Tris/10 mM CaCl2/0.005% Tween80)

Hardware:
Flat bottom MTPs: Costar (#9017)
Biomek FX
ASYS Multipipettor
Spectramax MTP Reader
iEMS Incubator/Shaker
Innova 4330 Incubator/Shaker
Biohit multichannel pipette
BMG Thermostar Shaker Method:

A 10 µl 0.063% LAS solution was prepared in 52.5 mM Tris buffer pH 8.2. The AAPF working solution was prepared by adding 1 ml of 100 mg/ml AAPF stock solution (in DMSO) to 100 ml (100 mM) TRIS buffer; pH 8.6. To dilute the supernatants, flat-bottomed plates were filled with dilution buffer and an aliquot of the supernatant was added and mixed well. The dilution ratio depended on the concentration of the ASP-controls in the growth plates (AAPF activity). The desired protein concentration was 80 ppm.

Ten µl of the diluted supernatant was added to 190 µl 0.063% LAS buffer/well. The MTP was covered with tape, shaken for a few seconds and placed in an incubator (Innova 4230) at 25° C., for 60 minutes at 200 rpm agitation. The initial activity (t=10 minutes) was determined after 10 minutes of incubation by transferring 10 µl of the mixture in each well to a fresh MTP containing 190 µl AAPF work solution. These solutions were mixed well and the AAPF activity was measured using a MTP Reader (20 readings in 5 minutes and 25° C.).

The final activity (t=60 minutes) was determined by removing another 10 µl of solution from the incubating plate after 60 minutes of incubation. The AAPF activity was then determined as described above. The calculations were performed as follows: the % Residual Activity was [t–60 value] *100/[t–10 value].

G. Scrambled Egg Hydrolysis Assay

Proteases release insoluble particles from scrambled egg, which was baked into the wells of 96-well microtiter plates. The scrambled egg coated wells were treated with a mixture of protease containing culture filtrate and ADW (automatic dishwash detergent) to determine the enzyme performance in scrambled egg removal. The rate of turbidity is a measure of the enzyme activity.

Materials:
Water bath
Oven with mechanical air circulation (Memmert ULE 400)
Incubator/shaker with amplitude of 0.25 cm (Multitron), equipped with MTP-holders and aluminum covers and bottoms
Biomek FX liquid-handling system (Beckman)
Micro plate reader (Molecular Devices Spectramax 340, SOFTmax Pro Software)
Nichiryo 8800 multi channel syringe dispenser+syringes
Micro titer plate tape
Single and multi channel pipettes with tips
Grade A medium eggs
$CaCl_2.2H_2O$ (Merck 102382); $MgCl_2.6H_2O$ (Merck105833); $Na_2CO_3$ (Merck 6392)

ADW product:
LH-powder (=Light House)

Procedure:

Three eggs were stirred with a fork in a glass beaker and 100 ml milk (at 4° C. or room temperature) was added. The beaker was placed in an 85° C. water bath, and the mixture was stirred constantly with a spoon. As the mixture became thicker, care was taken to scrape the solidifying material continuously from the walls and bottom of the beaker. When the mixture was slightly runny (after about 25 minutes) the beaker was removed from the bath. Another 40 ml milk was added to the mixture and blended with a hand mixer or blender for 2 minutes. The mixture was cooled to room temperature (an ice bath can be used). The substrate was then stirred with an additional amount of 5 to 15% water (usually 7.5%).

Test Method:

First, 50 µl of scrambled egg substrate were dispensed into each well of a MTP. The plates were allowed to dry at room temperature overnight (about 17 hours), baked in oven at 80° C. for 2 hours, then cooled to room temperature.

ADW product solution was prepared by dissolving 2.85 g of LH-powder into 1 L water. Only about 15 minutes dissolution time was needed and filtration of the solution was not needed. Then, 1.16 mL artificial hardness solution was added and 2120 mg $Na_2CO_3$ was dissolved in the solution.

Hardness solution was prepared by mixing 188.57 g $CaCl_2.2H_2O$ and 86.92 g $MgCl_2.6H_2O$ in 1 L demi water (equal to 1.28 M Ca+0.43 M Mg and totally 10000 gpg). The above-mentioned amounts of ADW, $CaCl_2$ and $MgCl_2$ were already proportionally increased values (200/190x) because of the addition of 10 µl supernatant to 190 µl ADW solution.

ADW solution (190 µl) was added to each well of the substrate plate. The MTPs were processed by adding 10 µl of supernatant to each well and sealing the'plate with tape. The plate was placed in a pre-warmed incubator/shaker and secured with a metal cover and clamp. The plate was then washed for 30 minutes at the appropriate temperature (50° C. for US) at 700 rpm. The plate was removed from the incubator/shaker. With gentle up and down movements of the liquid, about 125 µl of the warm supernatant were transferred to an empty flat bottom plate. After cooling, exactly 100 µl of the dispersion was dispensed into the wells of an empty flat bottom plate. The absorbance at 405 nm was determined using a microtiter plate reader.

Calculation of the Scrambled Egg Hydrolyzing Activity:

The obtained absorbance value was corrected for the blank value (substrate without enzyme). The resulting absorbance is a measure for the hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme. A performance index (PI) that is greater than 1 (PI>1) identifies a better variant (as compared to the standard [e.g., wild-type]), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

Example 2

Production of 69B4 Protease from the Gram-Positive Alkaliphilic Bacterium 69B4

This Example provides a description of the *Cellulomonas* strain 69B4 used to initially isolate the novel protease 69B4 provided by the present invention. The alkaliphilic microorganism *Cellulomonas* strain 69B.4, (DSM 16035) was isolated at 37° C. on an alkaline casein medium containing (g $L^{-1}$) (See e.g., Duckworth et al., FEMS Microbiol. Ecol., 19:181-191 [1996]).

| | |
|---|---|
| Glucose (Merck 1.08342) | 10 |
| Peptone (Difco 0118) | 5 |
| Yeast extract (Difco 0127) | 5 |
| $K_2HPO_4$ | 1 |
| $MgSO_4 \cdot 7H_2O$ | 0.2 |
| NaCl | 40 |
| $Na_2CO_3$ | 10 |
| Casein | 20 |
| Agar | 20 |

An additional alkaline cultivation medium (Grant Alkaliphile Medium) was also used to cultivate *Cellulomonas* strain 69B.4, as provided below:
Grant Alkaliphile Medium ("GAM") solution A (g $L^{-1}$)

| | |
|---|---|
| Glucose (Merck 1.08342) | 10 |
| Peptone (Difco 0118) | 5 |
| Yeast extract (Difco 0127) | 5 |
| $K_2HPO_4$ | 1 |
| $MgSO_4 \cdot 7H_2O$ | 0.2 |

Dissolved in 800 ml distilled water and sterilized by autoclaving
GAM solution B (g $L^1$)

| | |
|---|---|
| NaCl | 40 |
| $Na_2CO_3$ | 10 |

Dissolved in 200 ml distilled water and sterilized by autoclaving.
Complete GAM medium was prepared by mixing Solution A (800 ml) with Solution B (200 ml). Solid medium is prepared by the addition of agar (2% w/v).
Growth Conditions
From a freshly thawed glycerol vial of culture (stored as a frozen glycerol (20% v/v, stock stored at −80° C.), the microorganisms were inoculated using an inoculation loop on Grant Alkaliphile Medium (GAM) described above in agar plates and grown for at least 2 days at 37° C. One colony was then used to inoculate a 500 ml shake flask containing 100 ml of GAM at pH 10. This flask was then incubated at 37° C. in a rotary shaker at 280 rpm for 1-2 days until good growth (according to visual observation) was obtained. Then, 100 ml of broth culture was subsequently used to inoculate a 7 L fermentor containing 5 liters of GAM. The fermentations were run at 37° C. for 2-3 days in order to obtain maximal production of protease. Fully aerobic conditions were maintained throughout by injecting air, at a rate of 5 L/min, into the region of the impeller, which was rotating at about 500 rpm. The pH was set at pH 10 at the start, but was not controlled during the fermentation.
Preparation of 69B4 Crude Enzyme Samples
Culture broth was collected from the fermentor, and cells were removed by centrifugation for 30 min at 5000×g at 10° C. The resulting supernatant was clarified by depth filtration over Seitz EKS (SeitzSchenk Filtersystems). The resulting sterile culture supernatant was further concentrated approximately 10 times by ultra filtration using an ultra filtration cassette with a 10 kDa cut-off (Pall Omega 10 kDa Minisette; Pall). The resulting concentrated crude 69B4 samples were frozen and stored at −20° C. until further use.
Purification
The cell separated culture broth was dialyzed against 20 mM (2-(4-morpholino)-ethane sulfonic acid ("MES"), pH 5.4, 1 mM $CaCl_2$ using 8K Molecular Weight Cut Off (MWCO) Spectra-Por7 (Spectrum) dialysis tubing. The dialysis was performed overnight or until the conductivity of the sample was less than or equal to the conductivity of the MES buffer. The dialyzed enzyme sample was purified using a BioCad VISION (Applied Biosystems) with a 10×100 mm (7.845 mL) POROS High Density Sulfo-propyl (HS) 20 (20 micron) cation-exchange column (PerSeptive Biosystems). After loading the enzyme on the previously equilibrated column at 5 mL/min, the column was washed at 40 mL/min with a pH gradient from 25 mM MES, pH 6.2, 1 mM $CaCl_2$ to 25 mM (N-[2-hydroxyethyl]piperazine-N'-[2-ethane]sulfonic acid [$C_8H_{18}N_2O_4S$, CAS #7365-45-9]) ("HEPES") pH 8.0, 1 mM $CaCl_2$ in 25 column volumes. Fractions (8 mL) were collected across the run. The pH 8.0 wash step was held for 5 column volumes and then the enzyme was eluted using a gradient (0-100 mM NaCl in the same buffer in 35 column volumes). Protease activity in the fractions was monitored using the pNA assay (sAAPF-pNA assay; DelMar, et al., supra). Protease activity which eluted at 40 mM NaCl was concentrated and buffer exchanged (using a 5K MWCO VIVA Science 20 mL concentrator) into 20 mM MES, pH 5.8, 1 mM CaCl2. This material was used for further characterization of the enzyme.

Example 3

PCR Amplification of a Serine Protease Gene Fragment

In this Example, PCR amplification of a serine protease gene fragment is described.
Degenerate Primer Design
Based on alignments of published serine protease amino acid sequences, a range of degenerate primers were designed against conserved structural and catalytic regions. Such regions included those that were highly conserved among the serine proteases, as well as those known to be important for enzyme structure and function.
During the development of the present invention, protein sequences of nine published serine proteases (Streptogrisin C homologues) were aligned, as shown in below. The sequences were *Streptomyces griseus* Streptogrisin C (accession no. P52320); alkaline serine protease precursor from *Thermobifida fusca* (accession no. AAC23545); alkaline proteinase (EC 3.4.21.-) from *Streptomyces* sp. (accession no. PC2053); alkaline serine proteinase I from *Streptomyces* sp. (accession no. S34672); serine protease from *Streptomyces lividans* (accession no. CAD4208); putative serine protease from *Streptomyces coelicolor* A3(2) (accession no. NP_625129); putative serine protease from *Streptomyces avermitilis* MA-4680 (accession no. NP_822175); serine protease from *Streptomyces lividans* (accession no. CAD42809); putative serine protease precursor from *Streptomyces coelicolor* A3(2) (accession no. NP_628830). All of these sequences are publicly available from GenBank. These alignments are provided below. In this alignment, two conserved boxes are underlined and shown in bold.

```
AAC23545   (1)    --MNHSSR--RTTSLLFTAALAATALVAATTPAS----------------
PC2053     (1)    --MRHTGR-NAIGAAIAASALAFALVPSQAAAN------DTLTERAEAAV
S34672     (1)    --MRLKGRTVAIGSALAASALALSLVPANASSELP----SAETAKADALV
CAD42808   (1)    MVGRHAAR-SRRAALTALGALVLTALPSAASAAPPPVPGPRPAVARTPDA
NP_625129  (1)    MVGRHAAR-SRRAALTALGALVLTALPSAASAAPPPVPGPRPAVARTPDA
NP_822175  (1)    MVHRHVG--AGCAGLSVLATLVLTGLPAAAAIEPP-GPAPAPSAVQPLGA
CAD42809   (1)    MPHRHRHH-RAVGAAVAATAALLVAGLSGSASAGTAPAGSAPTAAETLRT
NP_628830  (1)    MPHRHRHH-RAVGAAVAATAALLVAGLSGSASAGTAPAGSAPTAAETLRT
P52320     (1)    ---MERTT-LRRRALVAGTATVAVGALALAGLTGVASADPAATAAPPVSA 51                                               100
AAC23545   (31)   -----AQELALKRDLGLSDAEVAELRAAEAEAVELEEELRDSLGSDFGGV
PC2053     (42)   ADLPAGVLDAMERDLGLSEQEAGLKLVAEHDAALLGETLSADLDAFAGSW
S34672     (45)   EQLPAGMVDAMERDLGVPAAEVGNQLVAEHEAAVLEESLSEDLSGYAGSW
CAD42808   (50)   ATAPARMLSAMERDLRLAPGQAAARPVNEAEAGTRAGMLRNTLGDRFAGA
NP_625129  (50)   ATAPARMLSAMERDLRLAPGQAAARLVNEAEAGTRAGMLRNTLGDRFAGA
NP_822175  (48)   GNPSTAVLGALQRDLHLTDTQAKTRLVNEMEAGTRAGRLQNALGKHFAGA
CAD42809   (50)   DAAPPALLKAMQRDLGIDRRQAERRLVNEAEAGATAGRLRAALGGDFAGA
NP_628830  (50)   DAAPPALLKAMQRDLGLDRRQAERRLVNEAEAGATAGRLRAALGGDFAGA
P52320     (47)   DSLSPGMLAALERDLGLDEDAARSRIANEYRAAAVAAGLEKSLGARYAGA 101                                              150
AAC23545   (76)   YLDADT-TEITVAVTDPAAVSRVDADDVTVDVVDFGETALNDFVASLNAI
PC2053     (92)   LAEGT---ELVVATTSEAEAAEITEAGATAEVVDHTLAELDSVKDALDTA
S34672     (95)   IVEGTS--EHVVATTDRAEAAEITAAGATATVVEHSLAELEAVKDILDEA
CAD42808   (100)  WVSGATSAELTVATTDAADTAAIEAQGAKAAVVGRNLAELRAVKEKLDAA
NP_625129  (100)  WVSGATSAELTVATTDAADTAAIEAQGAKAAVVGRNLAELRAVKEKLDAA
NP_822175  (98)   WVHGAASADLTVATTHATDIPAITAGGATAVVVKTGLDDLKGAKKKLDSA
CAD42809   (100)  WVRGAESGTLTVATTDAGDVAAVEARGAEAKVVRHSLADLDAAKARLDTA
NP_628830  (100)  WVRGAESGTLTVATTDAGDVAAIEARGAEAKVVRHSLADLDAAKARLDTA
P52320     (97)   RVSGAK-ATLTVATTDASEAARITEAGARAEVVGHSLDRFEGVKKSLDKA 151                                              200
AAC23545   (125)  ADT--ADPKVTGWYTDLESDAVVITTLRGGTPAAEELAERAGLDERAVRI
PC2053     (139)  AES-YDTTDAPVWYVDVTTNGVVLLTSD--VTEAEGFVEAAGVNAAAVDI
S34672     (143)  ATA-NPEDAAPVWYVDVTTNEVVVLASD--VPAAEEAFVAASGADASTVRV
CAD42808   (150)  AVR-TRTRQTPVWYVDVKTNRVTVQATG--ASAAAAFVEAAGVPAADVGV
NP_625129  (150)  AVR-TRTRQTPVWYVDVKTNRVTVQATG--ASAAAAFVEAAGVPAADVGV
NP_822175  (148)  VAHGGTAVNTPVRYVDVRTNRVTLQARS--RAAADALIAAAGVDSGLVDV
CAD42809   (150)  AAG-LNTADAPVWYVDTRTNTVVVEAIR--PAAARSLLTAAGVDGSLAHV
NP_628830  (150)  AAG-LNTADAPVWYVDTRTNTVVVEAIR--PAAARSLLTAAGVDGSLAHV
P52320     (146)  ALD-KAPKNVPVWYVDVAANRVVVNAAS--PAAGQAFLKVAGVDRGLVTV 201                                              250
AAC23545   (173)  VEEDEEPQSLAAIIGGNPYYFGN-YRCSIGFSVRQGSQTGFATAGHCGST
PC2053     (186)  QTSDEQPQAFYDLVGGDAYYMGG-GRCSVGFSVTQGSTPGFATAGHCGTV
S34672     (190)  ERSDESPQPFYDLVGGDAYYIGN-GRCSIGFSVRQGSTPGFVTAGHCGSV
CAD42808   (197)  RVSPDQPRVLEDLVGGDAYYIDDQARCSIGFSVTKDDQEGFATAGHCGDP
NP_625129  (197)  RVSPDQPRVLEDLVGGDAYYIDDQARCSIGFSVTKDDQEGFATAGHCGDP
NP_822175  (196)  KVSEDRPRALFDIRGGDAYYIDNTARCSVGFSVTKGNQQGFATAGHCGRA
CAD42809   (197)  KNRTERPRTFYDLRGGEAYYINNSSRCSIGFPITKGTQQGFATAGHCDRA
NP_628830  (197)  KNRTERPRTFYDLRGGEAYYINNSSRCSIGFPITKGTQQGFATAGHCGRA
P52320     (193)  ARSAEQPRALADIRGGDAYYMNGSGRCSVGFSVTRGTQNGFATAGRCGRV 251                                              300
AAC23545   (222)  GTRVS----SPSGTVAGSYFPGRDMGWVRITSADTVTPLVNRYNGGTVTV
PC2053     (235)  GTSTTGYNQAAQGTFEESSFPGDDMAWVSVNSDWNTTPTVNE--GE-VTV
S34672     (239)  GNATTGFNRVSQGTFRGSWFPGRDMAWVAVNSNWTPTSLVRNS-GSGVRV
CAD42808   (247)  GATTTGYNEADQGTFQASTFPGKDMAWVGVNSDWTATPDVKAEGGEKIQL
NP_625129  (247)  GATTTGYNEADQGTFQASTFPGKDMAWVGVNSDWTATPDVKAEGGEKIQL
NP_822175  (246)  GAPTAGFNEVAQGTVQASVFPGHDMAWVGVNSDWTATPDVAGAAGQNVSI
CAD42809   (247)  GSSTTGANRVAQGTFQGSIFPGRDMAWVATNSSWTATPYVLGAGGGQNVQV
NP_628830  (247)  GSSTTGANRVAQGTFQGSIFPGRDMAWVATNSSWTATPYVLGAGGGQNVQV
P52320     (243)  GTTTNGVNQQAQGTFQGSTFPGRDIAWVATNANWTPRPLVNGYGRGDVTV 301                                              350
AAC23545   (268)  TGSQEAATGSSVCRSGATTGWRCGTIQSKNQTVRYAEGTVTGLTRTTACA
PC2053     (282)  SGSTEAAVGASICRSGSTTGWHCGTIQQHNTSVTYPEGTITGVTRTSVCA
S34672     (288)  TGSTQATVGSSICRSGSTTGWRCGTIQQHNTSVTYPQGTITGVTRTSACA
CAD42808   (297)  AGSVEALVGASVCRSGSTTGWHCGTIQQHDTSVTYPEGTVDGLTGTTVCA
```

```
                    -continued
NP_625129 (297)  AGSVEALVGASVCRSGSTTGWHCGTIQQHDTSVTYPEGTVDGLTETTVCA
NP_822175 (296)  AGSVQAIVGAAICRSGSTTGWHCGTVEEHDTSVTYEEGTVDGLTRTTVCA
CAD42809  (297)  TGSTASPVGASVCRSGSTTGWHCGTVTQLNTSVTYQEGTISPVTRTTVCA
NP_628830 (297)  TGSTASPVGASVCRSGSTTGWHCGTVTQLNTSVTYQEGTISPVTRTTVCA
P52320    (293)  AGSTASVVGASVCRSGSTTGWHCGTIQQLNTSVTYPEGTISGVTRTSVCA 351                                               400
AAC23545  (318)  EGGDSGGPWLTGSQAQGVTSGGTGDCRSGGITFFQPINPLLSYFGLQLVT
PC2053    (332)  EPGDSGGSYISGSQAQGVTSGGSGNCTSGGTTYHQPINPLLSAYGLDLVT
S34672    (338)  QPGDSGGSFISGTQAQGVTSGGSGNCSIGGTTFHQPVNPILSQYGLTLVR
CAD42808  (347)  EPGDSGGPFVSGVQAQGTTSGGSGDCTNGGTTFYQPVNPLLSDFGLTLKT
NP_625129 (347)  EPGDSGGPFVSGVQAQGTTSGGSGDCTNGGTTFYQPVNPLLSDFGLTLKT
NP_822175 (346)  EPGDSGGSFVSGSQAQGVTSGGSGDCTRGGTTYYQPVNPILSTYGLTLKT
CAD42809  (347)  EPGDSGGSFISGSQAQGVTSGGSGDCRTGGGTFFQPINALLQNYGLTLKT
NP_628830 (347)  EPGDSGGSFISGSQAQGVTSGGSGDCRTGGETFFQPINALLQNYGLTLKT
P52320    (343)  EPGDSGGSYISGSQAQGVTSGGSGNCSSGGTTYFQPINPLLQAYGLTLVT 401                                               450
AAC23545  (368)  G-------------------------------------------------
PC2053    (382)  G-------------------------------------------------
S34672    (388)  S-------------------------------------------------
CAD42808  (397)  TSAATQTPAPQDNAAA------DAWTAGRVYEVGTTVSYDGVRYRCLQSH
NP_625129 (397)  TSAATQTPAPQDNAAA------DAWTAGRVYEVGTTVSYDGVRYRCLQSH
NP_822175 (396)  STAPTDTPSDPVDQSG-------VWAAGRVYEVGAQVTYAGVTYQCLQSH
CAD42809  (397)  TGGDDGGGDDGG-----EEPGG-TWAAGTVYQPGDTVTYGGATFRCLQGH
NP_628830 (397)  TGGDDGGGDDGGGDDGGEEPGG-TWAAGTVYQPGDTVTYGGATFRCLQGH
P52320    (393)  SGGGTPTDPPTTPPTDSP---GGTWAVGTAYAAGATVTYGGATYRCLQAH 451             468
AAC23545  (369)  ------------------  (SEQ ID NO: 648)
PC2053    (383)  ------------------  (SEQ ID NO: 649)
S34672    (389)  ------------------  (SEQ ID NO: 650)
CAD42808  (441)  QAQGVGSPASVPALWQRV  (SEQ ID NO: 651)
NP_625129 (441)  QAQGVGSPASVPALWQRV  (SEQ ID NO: 652)
NP_822175 (439)  QAQGVWQPAATPALWQRL  (SEQ ID NO: 653)
CAD42809  (441)  QAYAGWEPPNVPALWQRV  (SEQ ID NO: 654)
NP_628830 (446)  QAYAGWEPPNVPALWQRV  (SEQ ID NO: 655)
P52320    (440)  TAQPGWTPADVPALWQRV  (SEQ ID NO: 656)
```

Two particular regions were chosen to meet the criteria above, and a forward and a reverse primer were designed based on these amino acid regions. The specific amino acid regions used to design the primers are highlighted in black in the sequences shown in the alignments directly above. Using the genetic code for codon usage, degenerate nucleotide PCR primers were synthesized by MWG-Biotech. The degenerate primer sequences produced were:

```
        forward primer TTGWXCGT_FW:
                                (SEQ ID NO: 10)
        5' ACNACSGGSTGGCRGTGCGGCAC 3' reverse primer GDSGGX_RV:
                                (SEQ ID NO: 11)
        5'-ANGNGCCGCCGGAGTCNCC-3'
```

As all primers were synthesized in the 5'-3' direction and standard IUB code for mixed base sites was used (e.g., to designate "N" for A/C/T/G). Degenerate primers TTGWX-CGT_FW and GDSGGX_RV successfully amplified a 177 bp region from *Cellulomonas* sp. isolate 69B4 by PCR, as described below.

PCR Amplification of a Serine Protease Gene Fragment

Figure 13:
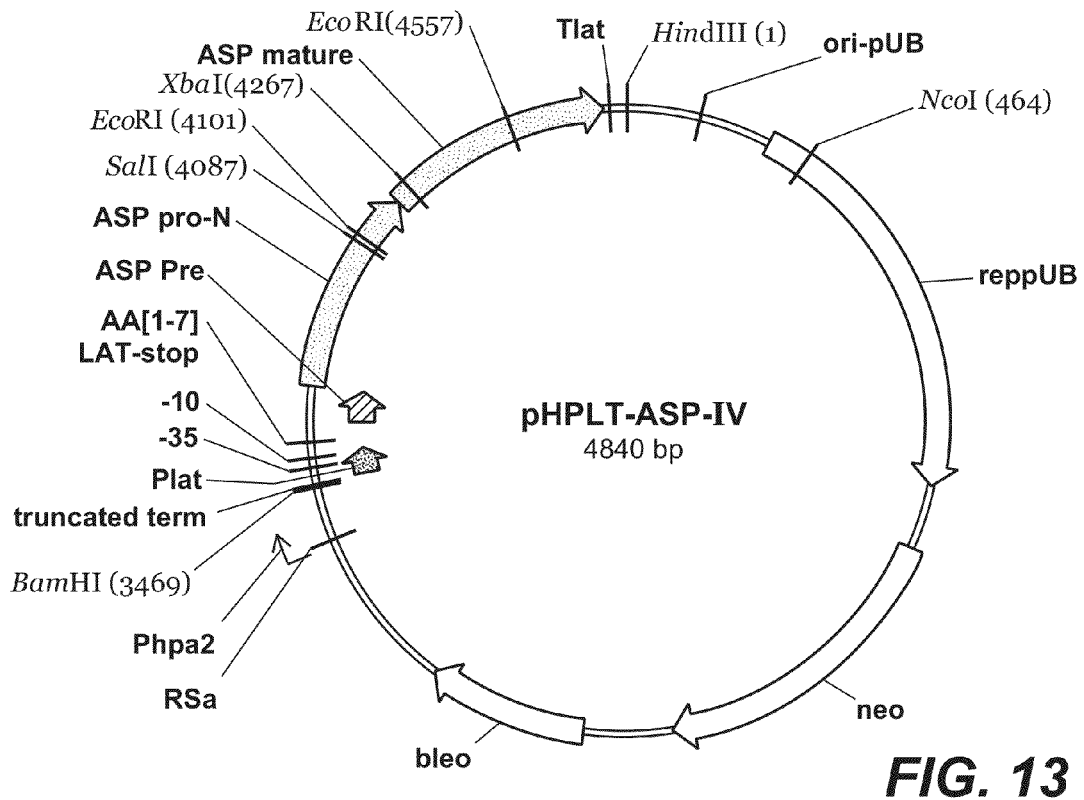
FIG. 13 provides the plasmid map of the pHPLT-ASP-IV vector.
Figure 14:
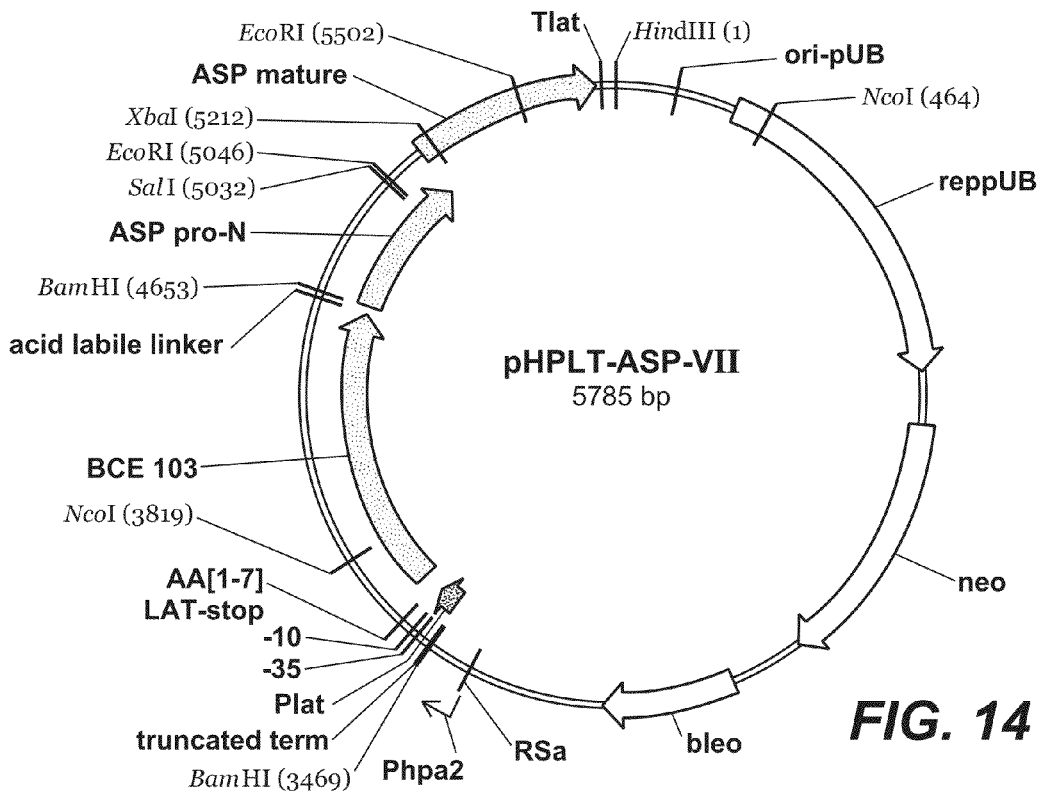
FIG. 14 provides the plasmid map of the pHPLT-ASP-VII vector.

*Cellulomonas* sp. isolate 69B4 genomic DNA was used as a template for PCR amplification of putative serine protease gene fragments using the above-described primers. PCR was carried out using High Fidelity Platinum Taq polymerase (Catalog number 11304-102; Invitrogen). Conditions were determined by individual experiments, but typically thirty cycles were run in a thermal cycler (MJ Research). Successful amplification was verified by electrophoresis of the PCR reaction on a 1% agarose TBE gel. A PCR product that was amplified from *Cellulomonas* sp. 69B4 with the primers TTGWXCGT_FW and GDSGGX_RV was purified by gel extraction using the Qiaquick Spin Gel Extraction kit (Catalogue 28704; Qiagen) according to the manufacturer's instructions. The purified PCR product was cloned into the commercially available pCR2.1TOPO vector System (Invitrogen) according to the manufacturer's instructions, and transformed into competent *E. coli* TOP10 cells. Colonies containing recombinant plasmids were visualized using blue/white selection. For rapid screening of recombinant transformants, plasmid DNA was prepared from cultures of putative positive (i.e., white) colonies. DNA was isolated using the Qiagen plasmid purification kit, and was sequenced by Baseclear. One of the clones contained a DNA insert of 177 bp that showed some homology with several streptogrisin-like protease genes of various *Streptomyces* species and also with serine protease genes from other bacterial species. The DNA and protein coding sequence of this 177 bp fragment is provided in FIG. 13.

Sequence Analysis

The sequences were analyzed by BLAST and other protein translation sequence tools. BLAST comparison at the nucleotide level showed various levels of identity to published serine protease sequences. Initially, nucleotide sequences were submitted to BLAST (Basic BLAST version 2.0). The program chosen was "BlastX", and the database chosen was "nr." Standard/default parameter values were employed. Sequence data for putative *Cellulomonas* 69B4 protease gene fragment was entered in FASTA format and the query submitted to BLAST to compare the sequences of the present invention to those already in the database. The results returned for the 177 bp fragment a high number of hits for protease genes from various *Streptomyces* spp., including *S. griseus, S. fividans, S. coelicolor, S. albogriseolus, S. platensis, S. fradiae*; and *Streptomyces* sp. It was concluded that further analysis of the 177 bp fragment cloned from *Cellulomonas* sp. isolate 69B4 was desired.

Example 4

Isolation of a Polynucleotide Sequence from the Genome of *Cellulomonas* 69B4 Encoding a Serine Protease by Inverse PCR In this Example, experiments conducted to isolate a polynucleotide sequence encoding a serine protease produced by *Cellulomonas* sp. 69B4 are described.
Inverse PCR of *Cellulomonas* sp. 69B4 Genomic DNA to Isolate the Gene Encoding *Cellulomonas* strain 69B4 Protease
Inverse PCR was used to isolate and clone the full-length serine protease gene from *Cellulomonas* sp. 6984. Based on the DNA sequence of the 177 bp fragment of the *Cellulomonas* protease gene described in Example 3, novel DNA primers were designed:

```
69B4int_RV1
                                     (SEQ ID NO: 14)
5'-CGGGGTAGGTGACCGAGGAGTTGAGCGCAGTG-3'

69B4int_FW2
                                     (SEQ ID NO: 15)
5'-GCTCGCCGGCAACCAGGCCCAGGGCGTCACGTC-3'
```

Chromosomal DNA of *Cellulomonas* sp. 69B4 was digested with the restriction enzymes ApaI, BamHI, BssHII, KpnI, NarI, NcoI, NheI, PvuI, SalI or SstII, purified using the Qiagen PCR purification kit (Qiagen, Catalogue #28106) and self-ligated with T4 DNA ligase (Invitrogen) according to the manufacturers' instructions. Ligation mixtures were purified using the Qiagen PCR purification kit, and PCR was performed with primers 69B4int_RV1 and 69B4int_FW2. PCR on DNA fragments that were digested with NcoI, and then self-ligated, resulting in a PCR product of approximately 1.3 kb. DNA sequence analysis (BaseClear) revealed that this DNA fragment covers the main part of a streptogrisin-like protease gene from *Cellulomonas*. This protease was designated as "69B4 protease," and the gene encoding *Cellulomonas* 69B4 protease was designated as the "asp gene." The entire sequence of the asp gene was derived by additional inverse PCR reactions with primer 69B40int_FW2 and an another primer: 69B4-for 4 (5' MC GGC GGG TTC ATC ACC GCC GGC CAC TGC GGC C 3' (SEQ ID NO:16). Inverse PCR with these primers on NcoI, BssHII, ApaI and PvuI digested and self-ligated DNA fragments of genomic DNA of *Cellulomonas* sp. 69B4 resulted in the identification of the entire sequence of the asp gene.
Nucleotide and Amino Acid Sequences
For convenience, various sequences are included below. First, the DNA sequence of the asp gene (SEQ ID NO:1) provided below encodes the signal peptide (SEQ ID NO:9) and the precursor serine protease (SEQ ID NO:7) derived from *Cellulomonas* strain 69B4 (DSM 16035). The initiating polynucleotide encoding the signal peptide of the Cellulomonas strain 69B4 protease is in bold (ATG).

```
                                                          (SEQ ID NO: 1)
  1    GCGCGCTGCG CCCACGACGA CGCCGTCCGC CGTTCGCCGG CGTACCTGCG TTGGCTCACC
       CGCGCGACGC GGGTGCTGCT GCGGCAGGCG GCAAGCGGCC GCATGGACGC AACCGAGTGG

61    ACCCACCAGA TCGACCTCCA TAACGAGGCC GTATGACCAG AAAGGGATCT GCCACCGCCC
       TGGGTGGTCT AGCTGGAGGT ATTGCTCCGG CATACTGGTC TTTCCCTAGA CGGTGGCGGG

121    ACCAGCACGC TCCTAACCTC CGAGCACCGG CGACCGCCGG GTGCGATGAA AGGGACGAAC
       TGGTCGTGCG AGGATTGGAG GCTCGTGGCC GCTGGCGGCC CACGCTACTT TCCCTGCTTG

181    CGAGATGACA CCACGCACAG TCACGCGGGC CCTGGCCGTG GCCACCGCAG CCGCCACACT
       GCTCTACTGT GGTGCGTGTC AGTGCGCCCG GGACCGGCAC CGGTGGCGTC GGCGGTGTGA

241    CCTGGCAGGC GGCATGGCCG CCCAGGCCAA CGAGCCCGCA CCACCCGGGA GCGCGAGCGC
       GGACCGTCCG CCGTACCGGC GGGTCCGGTT GCTCGGGCGT GGTGGGCCCT CGCGCTCGCG

301    ACCGCCACGC CTGGCCGAGA AGCTCGACCC CGACCTCCTC GAGGCCATGG AGCGCGACCT
       TGGCGGTGCG GACCGGCTCT TCGAGCTGGG GCTGGAGGAG CTCCGGTACC TCGCGCTGGA

361    GGGCCTCGAC GGGGAGGAAG CCGCCGCCAC CCTGGCGTTC CAGCACGACG CAGCCGAGAC
       CCCGGAGCTG CGCCTCCTTC GGCGGCGGTG GGACCGCAAG GTCGTGCTGC GTCGGCTCTG

421    CGGCGAGGCC CTCGCCGAAG AGCTCGACGA GGACTTCGCC GGCACCTGGG TCGAGGACGA
       GCCGCTCCGG GAGCGGCTTC TCGAGCTGCT CCTGAAGCGG CCGTGGACCC AGCTCCTGCT

481    CGTCCTGTAC GTCGCCACCA CCGACGAGGA CGCCGTCGAG GAGGTCGAGG GCGAAGGCGC
       GCAGGACATG CAGCCGGTGGT GGCTGCTCCT GCGGCAGCTC CTCCAGCTCC CGCTTCCGCG

541    CACGGCCGTC ACCGTCGAGC ACTCCCTGGC CGACCTCGAG GCCTGGAAGA CCGTCCTCGA
       GTGCCGGCAG TGGCAGCTCG TGAGGGACCG GCTGGAGCTC CGGACCTTCT GGCAGGAGCT

601    CGCCGCCCTC GAGGGCCACG ACGACGTGCC CACCTGGTAC GTCGACGTCC CGACCAACAG
       GCGGCGGGAG CTCCCGGTGC TGCTGCACGG GTGGACCATG CAGCTGCAGG GCTGGTTGTC

661    CGTCGTCGTC GCCGTCAAGG CCGGAGCCCA GGACGTCGCC GCCGGCCTCG TCGAAGGTGC
       GCAGCAGCAG CGGCAGTTCC GGCCTCGGGT CCTGCAGCGG CGGCCGGAGC AGCTTCCACG

721    CGACGTCCCG TCCGACGCCG TGACCTTCGT CGAGACCGAC GAGACCCCGC GGACCATGTT
       GCTGCAGGGC AGGCTGCGGC ACTGGAAGCA GCTCTGGCTG CTCTGGGGCG CCTGGTACAA

781    CGACGTGATC GGCGGCAACG CCTACACCAT CGGGGGCGC AGCCGCTGCT CGATCGGGTT
       GCTGCACTAG CCGCCGTTGC GGATGTGGTA GCCCCCGCG TCGGCGACGA GCTAGCCCAA
```

```
                                -continued
 841   CGCGGTCAAC GGCGGGTTCA TCACCGCCGG CCACTGCGGC CGCACCGGCG CCACCACCGC
       GCGCCAGTTG CCGCCCAAGT AGTGGCGGCC GGTGACGCCG GCGTGGCCGC GGTGGTGGCG 901   CAACCCCACC GGGACCTTCG CCGGGTCCAG CTTCCCGGGC AACGACTACG CGTTCGTCCG
       GTTGGGGTGG CCCTGGAAGC GGCCCAGGTC GAAGGGCCCG TTGCTGATGC GCAAGCAGGC 961   TACCGGGGCC GGCGTGAACC TGCTGGCCCA GGTCAACAAC TACTCCGGTG GCCGCGTCCA
       ATGGCCCCGG CCGCACTTGG ACGACCGGGT CCAGTTGTTG ATGAGGCCAC CGGCGCAGGT 1021   GGTCGCCGGG CACACCGCGG CCCCCGTCGG CTCGGCCGTG TGCCGGTCCG GGTCGACCAC
       CCAGCGGCCC GTGTGGCGCC GGGGGCAGCC GAGCCGGCAC ACGGCCAGGC CCAGCTGGTG 1081   CGGGTGGCAC TGCGGCACCA TCACTGCGCT CAACTCCTCG GTCACCTACC CCGAGGGCAC
       GCCCACCGTG ACGCCGTGGT AGTGACGCGA GTTGAGGAGC CAGTGGATGG GGCTCCCGTG 1141   CGTCCGCGGC CTGATCCGCA CCACCGTCTG CGCCGAGCCC GGCGACTCCG GTGGCTCGCT
       GCAGGCGCCG GACTAGGCGT GGTGGCAGAC GCGGCTCGGG CCGCTGAGGC CACCGAGCGA 1201   GCTCGCCGGC AACCAGGCCC AGGGCGTCAC GTCCGGCGGC TCCGGCAACT GCCGCACCGG
       CGAGCGGCCG TTGGTCCGGG TCCCGCAGTG CAGGCCGCCG AGGCCGTTGA CGGCGTGGCC 1261   TGGCACCACG TTCTTCCAGC CGGTCAACCC CATCCTCCAG GCGTACGCCC TGAGGATGAT
       ACCGTGGTGC AAGAAGGTCG GCCAGTTGGG GTAGGAGGTC CGCATGCCGG ACTCCTACTA 1321   CACCACGGAC TCGGGCAGCA GCCCGGCCCC TGCACCGACC TCCTGCACCG GCTACGCCCG
       GTGGTGCCTG AGCCCGTCGT CGGGCCGGGG ACGTGGCTGG AGGACGTGGC CGATGCGGGC 1381   CACCTTCACC GGGACCCTCG CGGCCGGCCG GGCCGCCGCC CAGCCCAACG GTCCTACGT
       GTGGAAGTGG CCCTGGGAGC GCCGGCCGGC CCGGCGGCGG GTCGGGTTGC CCAGGATGCA 1441   GCAGGTCAAC CGGTCCGGGA CCCACAGCGT GTGCCTCAAC GGGCCCTCCG GTGCGGACTT
       CGTCCAGTTG GCCAGGCCCT GGGTGTCGCA CACGGAGTTG CCCGGGAGGC CACGCCTGAA 1501   CGACCTCTAC GTGCAGCGCT GGAACGGCAG CTCCTGGGTG ACCGTCGCCC AGAGCACCTC
       GCTGGAGATG CACGTCGCGA CCTTGCCGTC GAGGACCCAC TGGCAGCGGG TCTCGTGGAG 1561   CCCCGGCTCC AACGAGACCA TCACCTACCG CGGCAACGCC GGCTACTACC GCTACGTGGT
       GGGGCCGAGG TTGCTCTGGT AGTGGATGGC GCCGTTGCGG CCGATGATGG CGATGCACCA 1621   CAACGCCGCG TCCGGCTCCG GTGCCTACAC CATGGGGCTC ACCCTCCCCT GACGTAGCGC
       GTTGCGGCGC AGGCCGAGGC CACGGATGTG GTACCCCGAG TGGGAGGGGA CTGCATCGCG
```

The following DNA sequence (SEQ ID NO:2) encodes the signal peptide (SEQ ID NO:9) that is operatively linked to the precursor protease (SEQ ID NO:7) derived from *Cellulomonas* strain 69B4 (DSM 16035). The initiating polynucleotide encoding the signal peptide of the *Cellulomonas* strain 69B4 protease is in bold (ATG). The asterisk indicates the termination codon (TGA), beginning with residue 1486. Residues 85, 595, and 1162, relate to the initial residues of the N terminal prosequence, mature sequence and Carboxyl terminal prosequence, respectively, are bolded and underlined.

```
                                                            (SEQ ID NO: 2)
   1   ATGACACCAC GCACAGTCAC GCGGGCCCTG GCCGTGGCCA CCGCAGCCGC CACACTCCTG
       TACTGTGGTG CGTGTCAGTG CGCCCGGGAC CGGCACCGGT GGCGTCGGCG GTGTGAGGAC

.85
  61   GCAGGCGGCA TGGCCGCCCA GGCCAACGAG CCCGCACCAC CCGGGAGCGC GAGCGCACCG
       CGTCCGCCGT ACCGGCGGGT CCGGTTGCTC GGGCGTGGTG GGCCCTCGCG CTCGCGTGGC

121   CCACGCCTGG CCGAGAAGCT CGACCCCGAC CTCCTCGAGG CCATGGAGCG CGACCTGGGC
       GGTGCGGACC GGCTCTTCGA GCTGGGGCTG GAGGAGCTCC GGTACCTCGC GCTGGACCCG

181   CTCGACGCGG AGGAAGCCGC CGCCACCCTG GCGTTCCAGC ACGACGCAGC CGAGACCGGC
       GAGCTGCGCC TCCTTCGGCG GCGGTGGGAC CGCAAGGTCG TGCTGCGTCG GCTCTGGCCG

241   GAGGCCCTCG CCGAAGAGCT CGACGAGGAC TTCGCCGGCA CCTGGGTCGA GGACGACGTC
       CTCCGGGAGC GGCTTCTCGA GCTGCTCCTG AAGCGGCCGT GGACCCAGCT CCTGCTGCAG

301   CTGTACGTCG CCACCACCGA CGAGGACGCC GTCGAGGAGG TCGAGGGCGA AGGCGCCACG
       GACATGCAGC GGTGGTGGCT GCTCCTGCGG CAGCTCCTCC AGCTCCCGCT TCCGCGGTGC

361   GCCGTCACCG TCGAGCACTC CCTGGCCGAC CTCGAGGCCT GGAAGACCGT CCTCGACGCC
       CGGCAGTGGC AGCTCGTGAG GGACCGGCTG GAGCTCCGGA CCTTCTGGCA GGAGCTGCGG

421   GCCCTGAGG GCCACGACGA CGTGCCCACC TGGTACGTCG ACGTCCCGAC CAACAGCGTC
       CGGGAGCTCC CGGTGCTGCT GCACGGGTGG ACCATGCAGC TGCAGGGCTG GTTGTCGCAG

481   GTCGTCGCCG TCAAGGCCGG AGCCCAGGAC GTCGCCGCCG GCCTCGTCGA AGGTGCCGAC
       CAGCAGCGGC AGTTCCGGCC TCGGGTCCTG CAGCGGCGGC CGGAGCAGCT TCCACGGCTG
                                                                    595
```

-continued

```
 541  GTCCCGTCCG ACGCCGTGAC CTTCGTCGAG ACCGACGAGA CCCCGCGGAC CATGTTCGAC
       CAGGGCAGGC TGCGGCACTG GAAGCAGCTC TGGCTGCTCT GGGGCGCCTG GTACAAGCTG

601  GTGATCGGCG GCAACGCCTA CACCATCGGG GGGCGCAGCC GCTGCTCGAT CGGGTTCGCG
       CACTAGCCGC CGTTGCGGAT GTGGTAGCCC CCCGCGTCGG CGACGAGCTA GCCCAAGCGC

661  GTCAACGGCG GGTTCATCAC CGCCGGCCAC TGCGGCCGCA CCGGCGCCAC CACCGCCAAC
       CAGTTGCCGC CCAAGTAGTG GCGGCCGGTG ACGCCGGCGT GGCCGCGGTG GTGGCGGTTG

721  CCCACCGGGA CCTTCGCCGG GTCCAGCTTC CCGGGCAACG ACTACGCGTT CGTCCGTACC
       GGGTGGCCCT GGAAGCGGCC CAGGTCGAAG GGCCCGTTGC TGATGCGCAA GCAGGCATGG

781  GGGGCCGGCG TGAACCTGCT GGCCCAGGTC AACAACTACT CCGGTGGCCG CGTCCAGGTC
       CCCCGGCCGC ACTTGGACGA CCGGGTCCAG TTGTTGATGA GGCCACCGGC GCAGGTCCAG

841  GCCGGGCACA CCGCGGCCCC CGTCGGCTCG GCCGTGTGCC GGTCCGGGTC GACCACCGGG
       CGGCCCGTGT GGCGCCGGGG GCAGCCGAGC CGGCACACGG CCAGGCCCAG CTGGTGGCCC

0901  TGGCACTGCG GCACCATCAC TGCGCTCAAC TCCTCGGTCA CCTACCCCGA GGGCACCGTC
       ACCGTGACGC CGTGGTAGTG ACGCGAGTTG AGGAGCCAGT GGATGGGGCT CCCGTGGCAG

0961  CGCGGCCTGA TCCGCACCAC CGTCTGCGCC GAGCCCGGCG ACTCCGGTGG CTCGCTGCTC
       GCGCCGGACT AGGCGTGGTG GCAGACGCGG CTCGGGCCGC TGAGGCCACC GAGCGACGAG

1021  GCCGGCAACC AGGCCCAGGG CGTCACGTCC GGCGGCTCCG GCAACTGCCG CACCGGTGGC
       CGGCCGTTGG TCCGGGTCCC GCAGTGCAGG CCGCCGAGGC CGTTGACGGC GTGGCCACCG

1081  ACCACGTTCT TCCAGCCGGT CAACCCCATC CTCCAGGCGT ACGGCCTGAG GATGATCACC
       TGGTGCAAGA AGGTCGGCCA GTTGGGGTAG GAGGTCCGCA TGCCGGACTC CTACTAGTGG 1162
1141  ACGGACTCGG GCAGCAGCCC GGCCCCTGCA CCGACCTCCT GCACCGGCTA CGCCCGCACC
       TGCCTGAGCC CGTCGTCGGG CCGGGGACGT GGCTGGAGGA CGTGGCCGAT GCGGGCGTGG

1201  TTCACCGGGA CCCTCGCGGC CGGCCGGGCC GCCGCCCAGC CAACGGGTC CTACGTGCAG
       AAGTGGCCCT GGGAGCGCCG GCCGGCCCGG CGGCGGGTCG GGTTGCCCAG GATGCACGTC

1261  GTCAACCGGT CCGGGACCCA CAGCGTGTGC CTCAACGGGC CCTCCGGTGC GGACTTCGAC
       CAGTTGGCCA GGCCCTGGGT GTCGCACACG GAGTTGCCCG GGAGGCCACG CCTGAAGCTG

1321  CTCTACGTGC AGCGCTGGAA CGGCAGCTCC TGGGTGACCG TCGCCCAGAG CACCTCCCCC
       GAGATGCACG TCGCGACCTT GCCGTCGAGG ACCCACTGGC AGCGGGTCTC GTGGAGGGGG

1381  GGCTCCAACG AGACCATCAC CTACCGCGGC AACGCCGGCT ACTACCGCTA CGTGGTCAAC
       CCGAGGTTGC TCTGGTAGTG GATGGCGCCG TTGCGGCCGA TGATGGCGAT GCACCAGTTG

1486*
1441  GCCGCGTCCG GCTCCGGTGC CTACACCATG GGGCTCACCC TCCCCTGA
       CGGCGCAGGC CGAGGCCACG GATGTGGTAC CCCGAGTGGG AGGGGACT
```

The following DNA sequence (SEQ ID NO:3) encodes the precursor protease derived from *Cellulomonas* strain 69B4 (DSM 16035).

```
                                                          (SEQ ID NO: 3)
   1  AACGAGCCCG CACCACCCGG GAGCGCGAGC GCACCGCCAC GCCTGGCCGA GAAGCTCGAC
       TTGCTCGGGC GTGGTGGGCC CTCGCGCTCG CGTGGCGGTG CGGACCGGCT CTTCGAGCTG

61  CCCGACCTCC TCGAGGCCAT GGAGCGCGAC CTGGCCCTCG ACGCGGAGGA AGCCGCCGCC
       GGGCTGGAGG AGCTCCGGTA CCTCGCGCTG GACCCGGAGC TGCGCCTCCT TCGGCGGCGG

121  ACCCTGGCGT TCCAGCACGA CGCAGCCGAG ACCGGCGAGG CCCTCGCCGA AGAGCTCGAC
       TGGGACCGCA AGGTCGTGCT GCGTCGGCTC TGGCCGCTCC GGGAGCGGCT TCTCGAGCTG

181  GAGGACTTCG CCGGCACCTG GGTCGAGGAC GACGTCCTGT ACGTCGCCAC CACCGACGAG
       CTCCTGAAGC GGCCGTGGAC CCAGCTCCTG CTGCAGGACA TGCAGCGGTG GTGGCTGCTC

241  GACGCCGTCG AGGAGGTCGA GGGCGAAGGC GCCACGGCCG TCACCGTCGA GCACTCCCTG
       CTGCGGCAGC TCCTCCAGCT CCCGCTTCCG CGGTGCCGGC AGTGGCAGCT CGTGAGGGAC

301  GCCGACCTCG AGGCCTGGAA GACCGTCCTC GACGCCGCCC TCGAGGGCCA CGACGACGTG
       CGGCTGGAGC TCCGGACCTT CTGGCAGGAG CTGCGGCGGG AGCTCCCGGT GCTGCTGCAC

361  CCCACCTGGT ACGTCGACGT CCCGACCAAC AGCGTCGTCG TCGCCGTCAA GGCCGGAGCC
       GGGTGGACCA TGCAGCTGCA GGGCTGGTTG TCGCAGCAGC AGCGGCAGTT CCGGCCTCGG

421  CAGGACGTCG CCGCCGGCCT CGTCGAAGGT GCCGACGTCC CGTCCGACGC CGTGACCTTC
       GTCCTGCAGC GGCGGCCGGA GCAGCTTCCA CGGCTGCAGG GCAGGCTGCG GCACTGGAAG
```

```
 481   GTCGAGACCG ACGAGACCCC GCGGACCATG TTCGACGTGA TCGGCGGCAA CGCCTACACC
       CAGCTCTGGC TGCTCTGGGG CGCCTGGTAC AAGCTGCACT AGCCGCCGTT GCGGATGTGG

541   ATCGGGGGGC GCAGCCGCTG CTCGATCGGG TTCGCGGTCA ACGGCGGGTT CATCACCGCC
       TAGCCCCCCG CGTCGGCGAC GAGCTAGCCC AAGCGCCAGT TGCCGCCCAA GTAGTGGCGG

601   GGCCACTGCG GCCGCACCGG CGCCACCACC GCCAACCCCA CCGGGACCTT CGCCGGGTCC
       CCGGTGACGC CGGCGTGGCC GCGGTGGTGG CGGTTGGGGT GGCCCTGGAA GCGGCCCAGG

661   AGCTTCCCGG GCAACGACTA CGCGTTCGTC CGTACCGGGG CCGGCGTGAA CCTGCTGGCC
       TCGAAGGGCC CGTTGCTGAT GCGCAAGCAG GCATGGCCCC GGCCGCACTT GGACGACCGG

721   CAGGTCAACA ACTACTCCGG TGGCCGCGTC CAGGTCGCCG GCACACCGC GGCCCCCGTC
       GTCCAGTTGT TGATGAGGCC ACCGGCGCAG GTCCAGCGGC CCGTGTGGCG CCGGGGGCAG

781   GGCTCGGCCG TGTGCCGGTC CGGGTCGACC ACCGGGTGGC ACTGCGGCAC CATCACTGCG
       CCGAGCCGGC ACACGGCCAG GCCCAGCTGG TGGCCCACCG TGACGCCGTG GTAGTGACGC

841   CTCAACTCCT CGGTCACCTA CCCCGAGGGC ACCGTCCGCG GCCTGATCCG CACCACCGTC
       GAGTTGAGGA GCCAGTGGAT GGGGCTCCCG TGGCAGGCGC CGGACTAGGC GTGGTGGCAG

901   TGCGCCGAGC CCGGCGACTC CGGTGGCTCG CTGCTCGCCG GCAACCAGGC CCAGGGCGTC
       ACGCGGCTCG GGCCGCTGAG GCCACCGAGC GACGAGCGGC CGTTGGTCCG GGTCCCGCAG

961   ACGTCCGGCG GCTCCGGCAA CTGCCGCACC GGTGGCACCA CGTTCTTCCA GCCGGTCAAC
       TGCAGGCCGC CGAGGCCGTT GACGGCGTGG CCACCGTGGT GCAAGAAGGT CGGCCAGTTG

1021   CCCATCCTCC AGGCGTACGG CCTGAGGATG ATCACCACGG ACTCGGGCAG CAGCCCGGCC
       GGGTAGGAGG TCCGCATGCC GGACTCCTAC TAGTGGTGCC TGAGCCCGTC GTCGGGCCGG

1081   CCTGCACCGA CCTCCTGCAC CGGCTACGCC CGCACCTTCA CCGGGACCCT CGCGGCCGGC
       GGACGTGGCT GGAGGACGTG GCCGATGCGG GCGTGGAAGT GGCCCTGGGA GCGCCGGCCG

1141   CGGGCCGCCG CCCAGCCCAA CGGGTCCTAC GTGCAGGTCA ACCGGTCCGG GACCCACAGC
       GCCCGGCGGC GGGTCGGGTT GCCCAGGATG CACGTCCAGT TGGCCAGGCC CTGGGTGTCG

1201   GTGTGCCTCA ACGGGCCCTC CGGTGCGGAC TTCGACCTCT ACGTGCAGCG CTGGAACGGC
       CACACGGAGT TGCCCGGGAG GCCACGCCTG AAGCTGGAGA TGCACGTCGC GACCTTGCCG

1261   AGCTCCTGGG TGACCGTCGC CCAGAGCACC TCCCCCGGCT CCAACGAGAC CATCACCTAC
       TCGAGGACCC ACTGGCAGCG GGTCTCGTGG AGGGGGCCGA GGTTGCTCTG GTAGTGGATG

1321   CGCGGCAACG CCGGCTACTA CCGCTACGTG GTCAACGCCG CGTCCGGCTC CGGTGCCTAC
       GCGCCGTTGC GGCCGATGAT GGCGATGCAC CAGTTGCGGC GCAGGCCGAG GCCACGGATG

1381   ACCATGGGGC TCACCCTCCC CTGA
       TGGTACCCCG AGTGGGAGGG GACT
```

The following DNA sequence (SEQ ID NO:4) encodes the mature protease derived from *Cellulomonas* strain 69B4 (DSM 16035).

```
                                                            (SEQ ID NO: 4)
  1   TTCGACGTGA TCGGCGGCAA CGCCTACACC ATCGGGGGGC GCAGCCGCTG CTCGATCGGG
      AAGCTGCACT AGCCGCCGTT GCGGATGTGG TAGCCCCCCG CGTCGGCGAC GAGCTAGCCC

61   TTCGCGGTCA ACGGCGGGTT CATCACCGCC GGCCACTGCG GCCGCACCGG CGCCACCACC
      AAGCGCCAGT TGCCGCCCAA GTAGTGGCGG CCGGTGACGC CGGCGTGGCC GCGGTGGTGG

121   GCCAACCCCA CCGGGACCTT CGCCGGGTCC AGCTTCCCGG GCAACGACTA CGCGTTCGTC
      CGGTTGGGGT GGCCCTGGAA GCGGCCCAGG TCGAAGGGCC CGTTGCTGAT GCGCAAGCAG

181   CGTACCGGGG CCGGCGTGAA CCTGCTGGCC CAGGTCAACA ACTACTCCGG TGGCCGCGTC
      GCATGGCCCC GGCCGCACTT GGACGACCGG GTCCAGTTGT TGATGAGGCC ACCGGCGCAG

241   CAGGTCGCCG GCACACCGC GGCCCCCGTC GGCTCGGCCG TGTGCCGGTC CGGGTCGACC
      GTCCAGCGGC CCGTGTGGCG CCGGGGGCAG CCGAGCCGGC ACACGGCCAG GCCCAGCTGG

301   ACCGGGTGGC ACTGCGGCAC CATCACTGCG CTCAACTCCT CGGTCACCTA CCCCGAGGGC
      TGGCCCACCG TGACGCCGTG GTAGTGACGC GAGTTGAGGA GCCAGTGGAT GGGGCTCCCG

361   ACCGTCCGCG GCCTGATCCG CACCACCGTC TGCGCCGAGC CCGGCGACTC CGGTGGCTCG
      TGGCAGGCGC CGGACTAGGC GTGGTGGCAG ACGCGGCTCG GCCGCTGAG GCCACCGAGC
```

```
421  CTGCTCGCCG GCAACCAGGC CCAGGGCGTC ACGTCCGGCG GCTCCGGCAA CTGCCGCACC
     GACGAGCGGC CGTTGGTCCG GGTCCCGCAG TGCAGGCCGC CGAGGCCGTT GACGGCGTGG

481  GGTGGCACCA CGTTCTTCCA GCCGGTCAAC CCCATCCTCC AGGCGTACGG CCTGAGGATG
     CCACCGTGGT GCAAGAAGGT CGGCCAGTTG GGGTAGGAGG TCCGCATGCC GGACTCCTAC

561  ATCACCACGG ACTCGGGCAG CAGCCCG
     TAGTGGTGCC TGAGCCCGTC GTCGGGC
```

The following DNA sequence (SEQ ID NO:5) encodes the signal peptide derived from *Cellulomonas* strain 69B4 (DSM 16035)

```
                                                              (SEQ ID NO: 5)
  1  ATGACACCAC CACAGTCAC GCGGGCCCTG GCCGTGGCCA CCGCAGCCGC CACACTCCTG
     TACTGTGGTG CGTGTCAGTG CGCCCGGGAC CGGCACCGGT GGCGTCGGCG GTGTGAGGAC

61  GCAGGCGGCA TGGCCGCCCA GGCC
     CGTCCGCCGT ACCGGCGGGT CCGG
```

The following sequence is the amino acid sequence (SEQ ID NO:6) of the signal sequence and precursor protease derived from *Cellulomonas* strain 69B4 (DSM 16035), including the signal sequence [segments 1a-c] (residues 1-28 [-198 to -171]), an N-terminal prosequence [segments 2a-r] (residues 29-198 [-170 to -1]), a mature protease [segments 3a-t] (residues 199-387 [1-189]), and a C-terminal prosequence [segments 4a-l] (residues 388-495 [190-398]) encoded by the DNA sequences set forth in SEQ ID NOS:1, 2, 3 and 4. The N-terminal sequence of the mature protease amino acid sequence is in bold.

```
                                                              (SEQ ID NO: 6)
  1  MTPRTVTRAL AVATAAATLL AGGMAAQA NE PAPPGSASAP PRLAEKLDPD
         1a         1b        1c    2a 2b          2c

51  LLEAMERDLG LDAEEAAATL AFQHDAAETG EALAEELDED FAGTWVEDDV
         2d         2e         2f         2g           2h

101  LYVATTDEDA VEEVEGEGAT AVTVEHSLAD LEAWKTVLDA ALEGHDDVPT
         2i         2j         2k         2l           2m

151  WYVDVPTNSV VVAVKAGAQD VAAGLVEGAD VPSDAVTFVE TDETPRTM FD
         2n         2o         2p         2q              2r 3a
201  VIGGNAYTIG GRSRCSIGFA VNGGFITAGH CGRTGATTAN PTGTFAGSSF
         3b         3c         3d         3e           3f

251  PGNDYAFVRT GAGVNLLAQV NNYSGGRVQV AGHTAAPVGS AVCRSGSTTG
         3g         3h         3i         3j           3k

301  WHCGTITALN SSVTYPEGTV RGLIRTTVCA EPGDSGGSLL AGNQAQGVTS
         3l         3m         3n         3o           3p

351  GGSGNCRTGG TTFFQPVNPI LQAYGLRMIT TDSGSSP APA PTSCTGYART
         3q         3r         3s         3t      4a 4b

401  FTGTLAAGRA AAQPNGSYVQ VNRSGTHSVC LNGPSGADFD LYVQRWNGSS
         4c         4d         4e         4f           4g

451  WVTVAQSTSP GSNETITYRG NAGYYRYVVN AASGSGAYTM GLTLP
             4h         4i         4j         4k     4l
```

The following sequence (SEQ ID NO:7) is the amino acid sequence of the precursor protease derived from *Cellulomonas* strain 69B4 (DSM 16035) (SEQ ID NO:7).

```
                                                       (SEQ ID NO: 7)
  1  NEPAPPGSAS  APPRLAEKLD  PDLLEAMERD.LGLDAEEAAA.TLAFQHDAAE

51  TGEALAEELD  EDFAGTWVED  DVLYVATTDE  DAVEEVEGEG  ATAVTVEHSL

101  ADLEAWKTVL  DAALEGHDDV  PTWYVDVPTN  SVVVAVKAGA  QDVAAGLVEG

151  ADVPSDAVTF  VETDETPRTM  FDVIGGNAYT  IGGRSRCSIG  FAVNGGFITA

201  GHCGRTGATT  ANPTGTFAGS  SFPGNDYAFV  RTGAGVNLLA  QVNNYSGGRV

251  QVAGHTAAPV  GSAVCRSGST  TGWHCGTITA  LNSSVTYPEG  TVRGLIRTTV

301  CAEPGDSGGS  LLAGNQAQGV  TSGGSGNCRT  GGTTFFQPVN  PILQAYGLRM

351  ITTDSGSSPA  PAPTSCTGYA  RTFTGTLAAG  RAAAQPNGSY  VQVNRSGTHS

401  VCLNGPSGAD  FDLYVQRWNG  SSWVTVAQST  SPGSNETITY  RGNAGYYRYV

451  VNAASGSGAY  TMGLTLP
```

The following sequence (SEQ ID NO:8) is the amino acid sequence of the mature protease derived from *Cellulomonas* strain 69B4 (DSM 16035). The catalytic triad residues H32, D56 and S132 are bolded and underlined.

```
                                                       (SEQ ID NO: 8)
  1  FDVIGGNAYT  IGGRSRCSIG  FAVNGGFITA  GHCGRTGATT  ANPTGTFAGS

51  SFPGNDYAFV  RTGAGVNLLA  QVNNYSGGRV  QVAGHTAAPV  GSAVCRSGST

101  TGWHCGTITA  LNSSVTYPEG  TVRGLIRTTV  CAEPGDSGGS  LLAGNQAQGV

151  TSGGSGNCRT  GGTTFFQPVN  PILQAYGLRM  ITTDSGSSP
```

The following sequence (SEQ ID NO:9) is the amino acid sequence of the signal peptide of the protease derived from *Cellulomonas* strain 6984 (DSM 16035).

```
          D   G   W      D   C   G      T   I   T   A      L   N   S      S   V   T      Y   P   E   G .
  1  ACGACGGCTG  GGACTGCGGC  ACCATCACTG  CGCTCAACTC  CTCGGTCACC  TACCCCGAGG
     TGCTGCCGAC  CCTGACGCCG  TGGTAGTGAC  GCGAGTTGAG  GAGCCAGTGG  ATGGGGCTCC

.  T   V   R      G   L   I      R   T   T   V      C   A   E      P   G   D      S   G   G   S .
 61  GCACCGTCCG  CGGCCTGATC  CGCACCACCG  TCTGCGCCGA  GCCCGGCGAC  TCCGGTGGCT
     CGTGGCAGGC  GCCGGACTAG  GCGTGGTGGC  AGACGCGGCT  CGGGCCGCTG  AGGCCACCGA

.  L   L   A      G   N   Q      A   Q   G   V      T   S   G      D   S   G      G   S
121  CGCTGCTCGC  CGGCAACCAG  GCCCAGGGCG  TCACGTCCGG  CGACTCCGGC  GGCTCAT
     GCGACGAGCG  GCCGTTGGTC  CGGGTCCCGC  AGTGCAGGCC  GCTGAGGCCG  CCGAGTA
```

```
  1  MTPRTVTRAL  AVATAAATLL  AGGMAAQA   (SEQ ID NO: 9)
```

The following sequence (SEQ ID NO:10) is the degenerate primer used to identify a 177 bp fragment of the protease of *Cellulomonas* strain 69B4.

```
                                       (SEQ ID NO: 10)
  TTGWXCGT_FW:  5' ACNACSGGSTGGCRGTGCGGCAC 3'
```

The following sequence (SEQ ID NO:11) is the reverse primer used to identity a 177 bp fragment of the protease derived from *Cellulomonas* strain 69B4.

```
                                       (SEQ ID NO: 11)
  GDSGGX_RV:  5'-ANGNGCCGCCGGAGTCNCC-3'
```

The following DNA (SEQ ID NO:13) and amino acid sequence of the 177 bp fragment (SEQ ID NO:12) encoding part of the protease gene derived from *Cellulomonas* strain 69B4. The sequences of the degenerate primers (SEQ ID NOS:10 and 11) are underlined and in bold.

Analysis of the Sequence of *Cellulomonas* sp. 69B4 Protease

A saturated sinapinic acid (3,5-dimethoxy-4-hydroxy cinnamic acid) ("SA") solution in a 1:1 v/v acetonitrile ("ACN")/0.1% formic acid solution was prepared. The resulting mixture was vortexed for 60 seconds and then centrifuged for 20 seconds at 14,000 rpm. Then, 5 μl of the matrix supernatant was transferred to a 0.5 ml Eppendorf tube and 1 μl of a 10 pmole/μl protease 69B4 sample was added to the SA matrix supernatant and vortexed for 5 seconds. Then, 1 μl of the analyte/matrix solution was transferred onto a sample plate and, after being completely dry, analyzed by a Voyager DE-STR (PerSeptive), matrix assisted laser desorption/ionization—time of flight (MALDI-TOF) mass spectrophotometer, with the following settings: Mode of operation: Linear; Extraction mode: Delayed; Polarity: Positive; Accelerating voltage: 25000 V; Extraction delay time: 350 nsec; Acquisition mass range: 4000-20000 Da; Number of laser shots: 100/spectrum; and Laser intensity: 2351. The resulting spectrum is provided in FIG. 4.

A tryptic map was produced using methods known in the art (Christianson et al., Anal. Biochem. 223:119-29 [1994]), modified as described herein. The protease solution, containing 10-50 µg protease was diluted 1:1 with chilled water in a 1.5 ml microtube. 1.0 N HCl was added to a final concentration of 0.1 N HCl, mixed thoroughly and incubated for 10 minutes on ice. Then, 50% trichloro-acetic acid ("TCA") was added to a final concentration of 10% TCA and mixed. The sample was incubated for 10 minutes on ice, centrifuged for two minutes and the supernatant discarded. Then, 1 ml of cold 90% acetone was added to resuspend the pellet. The resulting sample was then centrifuged for one minute, the supernatant quickly decanted and remaining liquid was removed by vacuum aspiration. The dry pellet was dissolved in 12 µl of 8.0 M urea solution (480 mg urea [Roche, catalog #1685899]) in 0.65 ml of ammonium bicarbonate solution (final concentration of bicarbonate: 0.5 M) and incubated for 3-5 minutes at 37° C. The solution was slowing diluted with 48 µl of a n-octyl-beta-D-glucopyranoside solution ("o-water") (200 mg of n-octyl-beta-D-glucopyranoside [$C_{14}H_{28}O_6$, f.w. 292.4] in 200 ml of water). Then, 2.0 µl of trypsin (2.5 mg/ml in 1 mM HCl) was added and the mixture was incubated for 15 minutes at 37° C. The proteolytic reaction was quenched with 6 µl of 10% trifluoroacetic acid ("TFA"). Insoluble material and bubbles were removed from the sample by centrifugation for one minute. The tryptic digest was separate by RP-HPLC on 2.1×150 mm C-18 column (5 µl particle size, 300 angstroms pore size). The elution gradient was formed from 0.1% (v/v) TFA in water and 0.08% (v/v) TFA in acetonitrile at a flow rate of 0.2 ml-min. The column compartment was heated to 50° C. Peptide elution was monitored at 215 nm and data were collected at 215 nm and 280 nm. The samples were then analyzed on a LCQ Advantage mass spectrometer with a Surveyor HPLC (both from Thermo Finnigan). The LCQ mass spectrophotometer was run with the following settings: Spray voltage: 4.5 kV; Capillary temperature: 225° C. Data processing was performed using TurboSEQUEST and Xcalibur (ThermoFinnigan). Sequencing of the tryptic digest portions was also performed in part by Argo BioAnalytica.

Analysis of the full sequence of the asp gene revealed that it encodes a prosequence protease of 495 amino acids (SEQ ID NO:6). The first 28 amino acids were predicted to form a signal peptide. The mass of the mature chain of 69B4 protease as produced by *Cellulomonas* strain 69B4 has a molecular weight of 18764 (determined by MALDI-TOF). The sequence of the N-terminus of the mature chain was also determined by MALDI-TOF analysis and starts with the sequence FDVIGGNAYTIGGR (SEQ ID NO:17). It is believed that the 69B4 protease has a unique precursor structure with $NH_2$— and COOH terminal pro-sequences, as is known to occur with some other enzymes (e.g., *T. aquaticus* aqualysin I; See e.g., Lee et al., FEMS Microbiol. Lett., 1:69-74 [1994]; Sakamoto et al., Biosci. Biotechnol. Biochem., 59:1438-1443 [1995]; Sakamoto et al., Appl. Microbiol. Biotechnol., 45:94-101 [1996]; Kim et al., Biochem. Biophys. Res. Commun., 231:535-539 [1997]; and Oledzka et al., Protein Expr. Purific., 29:223-229 [2003]). The predicted molecular weight of mature 69B4 protease as provided in SEQ ID NO:8, was 18776.42, which corresponds well with the molecular weight of the purified enzyme with proteolytic activity isolated from *Cellulomonas* sp. 69B4 18764). The prediction of the COON terminal pro-sequence in 69B4 protease was also based on an alignment of the 69B4 protease with *T. aquaticus* aqualysin I, provided below. In this alignment, the amino acid sequence of the *Cellulomonas* 69B4 signal sequence and precursor protease are aligned with the signal sequence and precursor protease Aqualysin I of *Thermus aquaticus* (COOH-terminal pro-sequence of Aqualysin I is underlined and in bold).

```
Aqualysin I   (1)    ----MRKTYWLMALFAVLVLGGCQMASRSDPTPTLAEAFWPKEAPVYGLD
69B4          (1)    MTPRTVTRALAVATAAATLLAGGMAAQANEPAPPGSASAPPRLAEKLDPD
Consensus     (1)        MA  A  LLAG   A   DP P  AA  PK A         D 51                                                100
Aqualysin I   (47)   DPEAIPGRYIVVFKKGKGQSLLQGGITTLQARLAPQGVVVTQAYTGALQG
69B4          (51)   LLEAMERDLGLDAEEAAATLAFQHDAAETGEALAEE---LDEDFAGTWVE
Consensus     (51)      EAI    L     A A   Q        LA      L    F G 101                                               150
Aqualysin I   (97)   FAAEMAPQALEAFRQSPDVEFIEADKVVRAWATQSPAPWGLDRIDQRDLP
69B4          (98)   DDVLYVATTDEDAVEEVEGEGATAVTVEHSLADLEANKTVLDAALEGHDD
Consensus     (101)         E    D E  A V  A A            LD 151                                               200
Aqualysin I   (147)  LSNSYTYTATGRGVNVYVIDTGIRTTHREFGGRARVGYDALGGNGQDCNG
69B4          (148)  VPTWYVDVPTNS--VVVAVKAGAQDVAAGLVEGADVPSDAVT--FVETDE
Consensus     (151)  L    Y  T     V  I G            A V DAL       D 201                                               250
Aqualysin I   (197)  HGTHVAGTIGGVTYGVAKAVNLYAVRVLDCNGSGSTSGVIAGVDWVTRNH
69B4          (194)  TPRTMFDVIGGNAYTIGGRS--------RCSIGFAVNGGFITAGHCGRTG
Consensus     (201)      M   IGG  Y IA         C     A G          R 251                                               300
Aqualysin I   (247)  RRPAVANMSLGGGVSTALDNAVKNSIAAGVVYAVAAGNDNANACNYSPAR
69B4          (236)  ATTANPTGTFAGSSFPGNDYAFVRTGAG--------VNLLAQVNNYSGGR
Consensus     (251)   A      S AG   A D A      S AA        N AN NYS AR 301                                               350
Aqualysin I   (297)  VAEALTVGATTSSDARASFSNYGSCVDLFAPGASIPSAWYTSDTATQTLN
69B4          (278)  VQVAGHTAAPVGSAVCRSGSTTGWHCGTIT--ALNSSVTYPEGTVRGLIR
Consensus     (301)  V  A   AA   S     S S G        A   S Y  T      I
```

-continued

```
                       351                                                400
Aqualysin I (347)      GTSMATPHVAGVAALYLEQNPSATPASVASAILNGATTGRLSGIGSGSPN
69B4        (326)      TTVCAEPGDSGGSLLAGNQAQGVTSGGSGNCRTGGTTFFQPVNPILQAYG
Consensus   (351)        T  AP  AG A L     Q    TA  A       G T           A 401                                                450
Aqualysin I (397)      ALLYSLLSSGSGSTAPCTSCSYYTGSLSG---PGDYNFQPNGTYYYSP-A
69B4        (376)      LRMITTDS-GSSPAPAPTSCTGYARTFTGTLAAGRAAAQPNGSYVQVNRS
Consensus   (401)         L S  S GS       TSCS Y  S SG     G      QPNGSY      A 451                                                500
Aqualysin I (443)      GTHRAWLRGPAGTDFDLYLWREDGSRELTVGSSTGPTSEESLSYSGTAGY
69B4        (425)      GTHSVCLNGPSGADFDLYVQRWNGSSWVTVAQSTSPGSNETITYRGNAGY
Consensus   (451)      GTH    L GPAG DFDLYL RW GS WLTVA  ST P S ESISY G AGY 501       521
Aqualysin I (493)      YLWRIYAYSGSGMYEFWLQRP (SEQ ID NO: 644)
69B4        (475)      YRYVVNAASGSGAYTMGLTLP   (SEQ ID NO: 645)
Consensus   (501)      Y W   I A SGSG Y    L  P (SEQ ID NO: 646)
```

The sequences of three internal peptides of the purified enzyme from *Cellulomonas* sp. 69B4 having proteolytic activity were determined by MALDI-TOF analysis. All three peptides were also identified in the translation product of the isolated asp gene, confirming the identification of the correct protease gene (See, SEQ ID NO:1, above).

Percentage Identity Comparison Between Asp and Streptogrisin

The deduced polypeptide product of the asp gene (mature chain) was used in homology analysis with other serine proteases using the BLAST program and settings as described in Example 3. The preliminary analyses showed identities of from about 44-48% (See, Table 4-1, below). Together with analysis of the translated sequence, these results provided evidence that the asp gene encodes a protease having less than 50% sequence identity with the mature chains of Streptogrisin-like serine proteases. An alignment of Asp with Streptogrisin A, Streptogrisin B, Streptogrisin C, Streptogrisin D of *Streptomyces griseus* is provided below. In this alignment, the amino acid sequences of *Cellulomonas* 69B4 mature protease ("69B4 mature") are aligned with mature proteases amino acid sequences of Streptogrisin C ("Sq-streptogrisinC_mature"), Streptogrisin B ("Sq—streptogrisinBmature"), Streptogrisin A ("Sq-streptogrisinAmature"), Streptogrisin D ("Sq—streptogrisinDmature") and consensus residues.

```
                              1                                                 50
69B4 mature            (1)    FDVIGGNAYTIGGRSRCSIGFAVN----GGFITAGHCGRTGATT------
Sg-StreptogrisinC mature (1)  ADIRGGDAYYNNGSGRCSVGFSVTRGTQNGFATAGHCGRVGTTTNG--VN
Sg-StreptogrisinBmature  (1)  --ISGGDAIYSST-GRCSLGFNVRSGSTYYFLTAGHCTDGATTWWANSAR
Sg-StreptogrisinAmature  (1)  --IAGGEAITTGG-SRCSLGFNVSVNGVAHALTAGHCTNISASWS-----
Sg-StreptogrisinDmature  (1)  --IAGGDAIWGSG-SRCSLGFNVVKGGEPYFLTAGHCTESVTSWSD-TQG
Consensus                (1)     IAGGDAIY   G SRCSLGFNV   G   YFLTAGHCT   GTTW 51                                                100
Asp mature             (41)   ANPTGTFAGSSFPGNDYAFVRTGAGVNLLAQVNNYSGGRVQVAGHTAAPV
Sg-StreptogrisinC mature (49) QQAQGTFQGSTFPGRDIAWVATNANWTPRPLVNGYGRGDVTVAGSTASVV
Sg-StreptogrisinBmature  (48) TTVLGTTSGSSFPNNDYGIVRYTNTTIPKDGTVGG----QDITSAANATV
Sg-StreptogrisinAmature  (43) ---IGTRTGTSFPNNDYGIIRHSNPAAADGRVYLYNGSYQDITTAGNAFV
Sg-StreptogrisinDmature  (47) GSEIGANEGSSFPENDYGLVKYTSDTAHPSEVNLYDGSTQAITQAGDATV
Consensus                (51)    IGT  GSSFP NDYGIVRYTA         VN Y G  Q IT AG A V 101                                               150
Asp mature             (91)   GSAVCRSGSTTGWHCGTITALNSSVTYPEG-TVRGLIRTTVCAEPGDSGG
Sg-StreptogrisinC mature (99) GASVCRSGSTTGWHCGTIQQLNTSVTYPEG-TISGVTRTSVCAEPGDSGQ
Sg-StreptogrisinBmature  (94) GMAVTRRGSTTGTHSGSVTALNATVNYGGGDVVYGNIRTNVCAEPGDSGG
Sg-StreptogrisinAmature  (90) GQAVQRSGSTTGLRSGSVTGLNATVNYGSSGIVYGMIQTNVCAEPGDSGG
Sg-StreptogrisinDmature  (97) GQAVTRSGSTTQVHDGEVTALDATVNYGNGDIVNGLIQTTVCAEPGDSGG
Consensus               (101) G AV RSGSTTG H  GSVTALNATVNYG G IV  GLIRTTVCAEPGDSGG 151                                               200
Asp mature            (140)   SLLAGNQAQGVTSGGSGNCRTGGTTFFQPVNPILQAYGLRMITTDSGSSP
Sg-StreptogrisinC mature(148) SYISGSQAQGVTSGGSGNCSSGGTTYFQPINPLLQAYGLTLVTSGGGTPT
Sg-StreptogrisinBmature (144) PLYSGTRAIGLTSGGSGNCSSGGTTFFQPVTEALSAYGVSVY--------
Sg-StreptogrisinAmature (140) SLFAGSTALGLTSGGSGNCRTGGTTFYQPVTEALSAYGATVL--------
Sg-StreptogrisinDmature (147) ALFAGDTALGLTSGGSGDCSSGGTTFFQPVPEALAAYGAEIG--------
Consensus               (151) SLFAGS ALGLTSGGSGNCSSGGTTFFQPV  EALSAYGLTVI 201                                               250
Asp mature            (190)   --------------------------------------------------
Sg-StreptogrisinC mature(198) DPPTTPPTDSPGGTWAVGTAYAAGATVTYGGATYRCLQAHTAQPGWTPAD
Sg-StreptogrisinBmature (186) --------------------------------------------------
Sg-StreptogrisinAmature (182) --------------------------------------------------
Sg-StreptogrisinDmature (189) --------------------------------------------------
Consensus               (201)
```

-continued

```
                                    251
Asp mature              (190)   --------  (SEQ ID NO: 8)
Sg-StreptogrisinC mature (248)  VPALWQRV  (SEQ ID NO: 639)
Sg-StreptogrisinBmature (186)   --------  (SEQ ID NO: 640)
Sg-StreptogrisinAmature (182)   --------  (SEQ ID NO: 641)
Sg-StreptogrisinDmature (189)   --------  (SEQ ID NO: 642)
Consensus               (251)   --------  (SEQ ID NO: 643)
```

TABLE 4-1

Percentage Identity: Comparison between *Cellulomonas* sp. 69B4 Protease Encoded by asp and Other Serine Proteases (identity between the mature chains)

| | Streptogrisin A *S. griseus* | Streptogrisin B *S. griseus* | Streptogrisin C *S. griseus* | Streptogrisin D *S. griseus* | Alphalytic endopeptidase *Lysobacter enzymogenes* |
|---|---|---|---|---|---|
| Asp protease *Cellulomonas* sp. Isolate 69B4 | 48% | 45% | 47% | 46% | 44% |

Additional protease sequences were also investigated. In these analyses, proteases homologous in protein sequence to the mature domain of ASP were searched for using BLAST. Those identified were then aligned using the multiple sequence alignment program clustalW. The numbers on the top of the alignment below refer to the amino-acid sequence of the mature ASP protease. The numbers at the side of the alignment are sequence identifiers, as described at the bottom of the alignment.

```
Sequence 1        10        20        30        40
    ASP   FDVIGGNAYTIGGRSRCSIGFAVN-----GGFITAGHCGRTGATTANPTG--------TF

2     TPLIAGGEAITTGGRCSLGFNV-SVNGVAHALTAGHCTNISASWS----------IGTR

3     --IAGGEAIYAAGGGRCSLGFNVRSSSGATYALTAGHCTEIASTWYTNSGQTSL--LGTR

4     NKLIQGGDAIYASSWRCSLGFNVRTSSGAEYFLTAGHCTDGAGAWRASSGGTV---IGQT

5     NKLIQGGDAIYASSWRCSLGFNVRTSSGAEYFLTAGHCTDGAGAWRASSGGTV---IGQT

6     TKLIQGGDAIYASSWRCSLGFNVRSSSGVDYFLTAGHCTDGAGTWYSNSARTTA--IGST

7     TKLISGGDAIYSSTGRCSLGFNVRSGS-TYYFLTAGHCTDGATTWWANSARTTV--LGTT

8     ---VLGGGAIYGGGSRCSAAFNV-TKGGARYFVTAGHCTNISANWSASSGGSV---VGVR

9     QREVAGGDAIYGGGSRCSAAFNV-TKNGVRYFLTAGHCTNLSSTWSSTSGGTS---IGVR

10    KPFIAGGDAITGNGGRCSLGFNVTKG-GEPHFLTAGHCTEGISTWSDSSG--QV--IGEN

11    KPFVAGGDAITGGGGRCSLGFNVTKG-GEPYFITAGHCTESISTWSDSSG--NV--IGEN

12    TPLIAGGDAIWGSGSRCSLGFNVVKG-GEPYFLTAGHCTESVTSWSDTQGG-SE--IGAN

13    KTFASGGDAIFGGGARCSLGFNVTAGDGSAAFLTRGHCGGGATMWSDAQGGQPI--ATVD

14    KTFASGGDAIFGGGARCSLGFNVTAGDGSPAFLTAGHCGVAADQWSDAQGGQPI--ATVD

15    ------------------------------------------------------------

16    TTRLNGAEPILSTAGRCSAGFNVTDG-TSDFILTAGHCGPTGSVWFGDRPGDGQ--VGRT

17    ATVQGGDVYYINRSSRCSIGFAVT-----TGFVSAGHCGGSGASATTSSGEAL----GTF

18    ADIRGGDAYYMNGSGRCSVGFSVTRG-TQNGFATAGHCGRVGTTTNGVNQQAQ----GTF

19    YDLRGGEAYYINNSSRCSIGFPITKG-TQQGFATAGHCGRAGSSTTGANRVAQ----GTF

20    YDLVGGDAYYIGN-GRCSIGFSVRQG-STPGFVTAGHCGSVGNATTGFNRVSQ----GTF

21    YDLVGGDAYYMGG-GRCSVGFSVTQG-STPGFATAGHCGTVGTSTTGYNQAAQ----GTF
```

```
 22   EDLVGGDAYYIDDQARCSIGFSVTKD-DQEGFATAGHCGDPGATTTGYNEADQ----GTF

23   LAAIIGGNPYYFGNYRCSIGFSVRQG-SQTGFATAGHCGSTGTRVSSPSG--------TV

24   ANIVGGIEYSINNASLCSVGFSVTRG-ATKGFVTAGHCGTVNATARIGGAVV-----GTF

25   AAGTVGGDPYYTGNVRCSIGFSVH-----GGFVTAGHCGRAGAGVSGWDRSYI----GTF

26   VIVPVRDYWGGDALSGCTLAFPVYGG-----FLTAGHCAVEGKGHILKTEMTGGQ-IGTV

27   DPPLRSGLAIYGTNVRCSSAFMAYSG-SSYYMMTAGHCAEDSSYWEVPTYSYGYQGVGHV 50        60        70        80        90       100
ASP   AGSSFPGN-DYAFVRTGAGVNLLAQVNNYSGGR-VQVAGHTAAPVGSAVCRSGSTTGWHC

2   TGTSFPNNDYGIIRHSNPAAA--DGRVYLYNGSYQDITTAGNAFVGQAVQRSGSTTGLRS

3   AGTSFPGNDYGLIRHSNASAA--DGRVYLYNGSYRDITGAGNAYVGQTVQRSGSTTGLHS

4   AGSSFPGNDYGIVQYTGS-------VSRPGTANGVDITRAATPSVGTTVIRDGSTTGTHS

5   AGSSFPGNDYGIVQYTGS-------VSRPGTANGVDITRAATPSVGTTVIRDGSTTGTHS

6   AGSSFPGNDYGIVRYTGS-------VSRPGTANGVDITRAATPSVGTTVIRDGSTTGTHS

7   SGSSFPNNDYGIVRYTNTT------IPKDGTVGGQDITSAANATVGMAVTRRGSTTGTHS

8   EGTSFPTNDYGIVRYTDGSSP--AGTVDLYNGSTQDISSAANAVVGQAIKKSGSTTKVTS

9   EGTSFPTNDYGIVRYTTTTNV--DGRVNLYNGGYQDIASAADAVVGQAIKKSGSTTKVTS

10   AASSFPDDYGLVKYTADVAH--PSQVNLYDGSSQSISGAAEAAVGMQVTRSGSTTQVHS

11   AASSFPDNDYGLVKYTADVDH--PSEVNLYNGSSQAISGAAEATVGMQVTRSGSTTQVHD

12   EGSSFPENDYGLVKYTSDTAH--PSEVNLYDGSTQAITQAGDATVGQAVTRSGSTTQVHD

13   QAVFPPEGDFGLVRYDGPSTE--APSEVDLGDQTLPISGAAEASVGQEVFRMGSTTGLAD

14   QAVFPGEGDFALVRYDDPATE--APSEVDLGDQTLPISGAAEAAVGQEVFRMGSTTGLAD

15   ------------------------------------------------------------

16   VAGSFFGDDFSLVEYANGKAGDGADVVAVGDGKGVRITGAGEPAVGQRVFRSGSTSGLRD

17   SGSVFPGSADMAYVRTVSGTVLRGYINGYGQGS-FPVSGSSEAAVGASICRSGSTTQVHC

18   QGSTFPGR-DIAWVATNANWTPRPLVNGYGRGD-VTVAGSTASVVGASVCRSGSTTGWHC

19   QGSIFPGR-DMAWVATNSSWTATPYVLGAGGQN-VQVTGSTASPVGASVCRSGSTTGWHC

20   RGSWFPGR-DMAWVAVNSNWTPTSLVRNSGSG--VRVTGSTQATVGSSICRSGSTTGWRC

21   EESSFPGD-DMAWVSVNSDWNTTPTVNEGE----VTVSGSTEAAVGASICRSGSTTGWHC

22   QASTFPGK-DMAWVGVNSDWTATPDVKAEGGEK-IQLAGSVEALVGASVCRSGSTTGWHC

23   AGSYFPGR-DMGWVRITSADTVTPLVNRYNGGT-VTVTGSQEAATGSSVCRSGATTGWRC

24   AARVFPGN-DRAWVSLTSAQTLLPRVANGSSF--VTVRGSTEAAVGAAVCRSGRTTGYQC

25   QGSSFPDN-DYAWVSVGSGWWTVPVVLGWGTVSDQLVRGSNVAPVGASICRSGSTTHWHC

26   EASQFGDGIDAAWAKNYGDWNGRGRVTHWNGGGGVDIKGSNEAAVGAHMCKSGRTTKWTC

27   ADYTFGYYGDSAIVRVDDPGF---WQPRGWVYPSTRITNWDYDYVGQYVCKQGSTTGYTC 110       120       130       140       150
ASP   GTITALNSSVTYPEGTV-RGLIRTTVCAEPGDSGGSLLAGN-QAQGVTSGGS--------

2   GSVTGLNATVNYGSSGIVYGMIQTNVCAEPGDSGGSLF-AGSTALGLTSGGS--------

3   GRVTGLNATVNYGGGDIVSGLIQTNVCAEPGDSGGALF-AGSTALGLTSGGS--------

4   GRVTALNATVNYGGGDVVGGLIQTTVCAEPGDSGGSLYGSNGTAYGLTSGGS--------

5   GRVTALNATVNYGGGDVVGGLIQTTVCAEPGDSGGSLYGSNGTAYGLTSGGS--------

6   GRVTALNATVNYGGGDIVSGLIQTTVCAEPGDSGGPLYGSNGTAYGLTSGGS--------
```

```
  7  GSVTALNATVNYGGGDVVYGMIRTNVCAEPGDSGGPLY-SGTRAIGLTSGGS--------

8  GTVTAVNVTVNYGDGP-VYNMGRTTACSAGGDSGGAHF-AGSVALGIHSGSS--------

9  GTVSAVNVTVNYSDGP-VYGMVRTTACSAGGDSGGAHF-AGSVALGIHSGSS--------

10  GTVTGLDATVNYGNGDIVNGLIQTDVCAEPGDSGGSLFSGDK-AVGLTSGGS--------

11  GTVTGLDATVNYGNGDIVNGLIQTDVCAEPGDSGGSLFSGDQ-AIGLTSGGS--------

12  GEVTALDATVNYGNGDIVNGLIQTTVCAEPGDSGGALFAGDT-ALGLTSGGS--------

13  GQVLGLDVTVNYPEG-TVTGLIQTDVCAEPGDSGGSLFTRDGLAIRLTSGGT--------

14  GQVLGLDATVNYPEG-MVTGLIQTDVCAEPGDSGGSLFTRDGLAIGLTSGGS--------

15  ----------------VDGLIQTDVCAEPGDSGGALFDGDA-AIGLTSGGS--------

16  GRVTALDATVNYPEG-TVTGLIETDVCAEPGDSGGPMFSEGV-ALGVTSGGS--------

17  GTIGAKGATVNYPQGAV-SGLTRTSVCAEPGDSGGSFYSGS-QAQGVTSGGS--------

18  GTIQQLNTSVTYPEGTI-SGVTRTSVCAEPGDSGGSYISGS-QAQGVTSGGS--------

19  GTVTQLNTSVTYQEGTI-SPVTRTTVCAEPGDSGGSFISGS-QAQGVTSGGS--------

20  GTIQQHNTSVTYPQGTI-TGVTRTSACAQPGDSGGSFISGT-QAQGVTSGGS--------

21  GTIQQHNTSVTYPEGTI-TGVTRTSVCAEPGDSGGSYISGS-QAQGVTSGGS--------

22  GTIQQHDTSVTYPEGTV-DGLTETTVCAEPGDSGGPFVSGV-QAQGTTSGGS--------

23  GTIQSKNQTVRYAEGTV-TGLTRTTACAEGGDSGGPWLTGS-QAQGVTSGGT--------

24  GTITAKNVTANYAEGAV-RGLTQGNACMGRGDSGGSWITSAGQAQGVMSGGNVQSNGNNC

25  GTVLAHNETVNYSDGSVVHQLTKTSVCAEGGDSGGSFISGD-QAQGVTSGGW--------

26  GYLLRKDVSVNYGNGHI-VTLNETSACALGGDSGGAYVWND-QAQGITSGSN--------

27  GQITETNATVSYPGRTL-TGMTWSTACDAPGDSGSGVYDGSTAHGILSGGPN--------

160       170       180      189
ASP  GNCRTGGTTFFQPVNPILQAYGLRMITTDSGSSP  (SEQ ID NO: 18)

2  GNCRTGGTTFYQPVTEALSAYGATVL--------  (SEQ ID NO: 19)

3  GNCRTGGTT-------------------------  (SEQ ID NO: 20)

4  GNCSSGGTTFFQPVTEALSAYGVSVY--------  (SEQ ID NO: 21)

5  GNCSSGGTTFFQPVTEALSAYGVSVY--------  (SEQ ID NO: 22)

6  GNCSSGGTTFFQPVTEALSAYGVSVY--------  (SEQ ID NO: 23)

7  GNCSSGGTTFFQPVTEALSAYGVSVY--------  (SEQ ID NO: 24)

8  GCSGTAGSAIHQPVTKALSAYGVTVYL-------  (SEQ ID NO: 25)

9  GCTGTNGSAIHQPVREALSAYGVNVY--------  (SEQ ID NO: 26)

10  GDCTSGGTTFFQPVTEALSATGTQIG--------  (SEQ ID NO: 27)

11  GDCTSGGETFFQPVTEALSATGTQIG--------  (SEQ ID NO: 28)

12  GDCSSGGTTFFQPVPEALAAYGAEIG--------  (SEQ ID NO: 29)

13  RDCTSGGETFFQPVTTALAAVGGTLGGEDGGDG-  (SEQ ID NO: 30)

14  GDCTVGGETFFQPVTTALAAVGATLGGEDGGAGA  (SEQ ID NO: 31)

15  GDCSQGGETFFQPVTEALKAYGAQIGGGQGEPPE  (SEQ ID NO: 32)

16  GDCAKGGTTFFQPLPEAMASLGVRLIVPGREGAA  (SEQ ID NO: 33)

17  GDCSRGGTTYFQPVNRILQTYGLTLVTA------  (SEQ ID NO: 34)

18  GNCSSGGTTYFQPINPLLQAYGLTLVTSGG--GT  (SEQ ID NO: 35)

19  GDCRTGGETFFQPINALLQNYGLTLKTTGGDDGG  (SEQ ID NO: 36)
```

```
20   GNCSIGGTTFHQPVNPILSQYGLTLVRS------ (SEQ ID NO: 37)

21   GNCTSGGTTYHQPINPLLSAYGLDLVTG------ (SEQ ID NO: 38)

22   GDCTNGGTTFYQPVNPLLSDFGLTLKTTSA---- (SEQ ID NO: 39)

23   GDCRSGGITFFQPINPLLSYFGLQLVTG------ (SEQ ID NO: 40)

24   GIPASQRSSLFERLQPILSQYGLSLVTG------ (SEQ ID NO: 41)

25   GNCSSGGETWFQPVNEILNRYGLTLHTA------ (SEQ ID NO: 42)

26   -MDTNNCRSFYQPVNTVLNKWKLSLVTSTDVTTS (SEQ ID NO: 43)

27   ----SGCGMIHEPISRALADRGVTLLAG------ (SEQ ID NO: 44)
```

In the above listing, the numbers correspond as follows:

| | |
|---|---|
| 1 | ASP Protease |
| 2 | Streptogrisin A (*Streptomyces griseus*) |
| 3 | Glutamyl endopeptidase (*Streptomyces fradiae*) |
| 4 | Streptogrisin B (*Streptomyces lividans*) |
| 5 | SAM-P20 (*Streptomyces coelicolor*) |
| 6 | SAM-P20 (*Streptomyces albogriseolus*) |
| 7 | Streptogrisin B (*Streptomyces griseus*) |
| 8 | Glutamyl endopeptidase II (*Streptomyces griseus*) |
| 9 | Glutamyl endopeptidase II (*Streptomyces fradiae*) |
| 10 | Streptogrisin D (*Streptomyces albogriseolus*) |
| 11 | Streptogrisin D (*Streptomyces coelicolor*) |
| 12 | Streptogrisin D (*Streptomyces griseus*) |
| 13 | Subfamily S1E unassigned peptidase (SalO protein) (*Streptomyces lividans*) |
| 14 | Subfamily S1E unassigned peptidase (SALO protein) (*Streptomyces coelicolor*) |
| 15 | Streptogrisin D (*Streptomyces platensis*) |
| 16 | Subfamily S1E unassigned peptidase (3SC5B7.10 protein)(*Streptomyces coelicolor*) |
| 17 | CHY1 protease (*Metarhizium anisopliae*) |
| 18 | Streptogrisin C (*Streptomyces griseus*) |
| 19 | Streptogrisin C (SCD40A.16c protein) (*Streptomyces coelicolor*) |
| 20 | Subfamily S1E unassigned peptidase (I) (*Streptomyces* sp.) |
| 21 | Subfamily S1E unassigned peptidase (II) (*Streptomyces* sp.) |
| 22 | Subfamily S1E unassigned peptidase (SCF43A.19 protein)(*Streptomyces coelicolor*) |
| 23 | Subfamily S1E unassigned peptidase (*Thermobifida fusca*; basonym *Thermomonospora fusca*) |
| 24 | Alpha-lytic endopeptidase (*Lysobacter enzymogenes*) |
| 25 | Subfamily S1E unassigned peptidase (SC10G8.13C protein) (*Streptomyces coelicolor*) |
| 26 | Yeast-lytic endopeptidase (*Rarobacter faecitabidus*) |
| 27 | Subfamily S1E unassigned peptidase (SC10A5.18 protein) (*Streptomyces coelicolor*) |

Example 5

Screening for Novel Homologues of 69B4 Protease by PCR

In this Example, methods used to screen for novel homologues of 69B4 protease are described. Bacterial strains of the suborder *Micrococcineae*, and in particular from the family Cellulomonadaceae and Promicromonosporaceae were ordered from the German culture collection, DSMZ (Braunschweig) and received as freeze dried cultures. Additional strains were received from the Belgian Coordinated Collections of Microorganisms, BCCM™/LMG (University of Ghent). The freeze-dried ampoules were opened according to DSMZ instructions and the material rehydrated with sterile physiological saline (1.5 ml) for 1 h. Well-mixed, rehydrated cell suspensions (300 µL) were transferred to sterile Eppendorf tubes for subsequent PCR.

PCR Methods i) Pretreatment of the Samples

The rehydrated microbial cell suspensions were placed in boiling water bath for 10 min. The suspensions were then centrifuged at 16000 rpm for 5 min. (Sigma 1-15 centrifuge) to remove cell debris and remaining cells, the clear supernatant fraction serving as template for the PCR reaction.

(ii) PCR Test Conditions

The DNA from these types of bacteria (Actinobacteria) is characteristically highly GC rich (typically >55 mol %), so addition of DMSO is a necessity. The chosen concentration based on earlier work with the *Cellulomonas* sp. strain 69B4 was 4% v/v DMSO.

(iii) PCR Primers (Chosen from the Following Pairs)

```
                               (SEQ ID NO: 45)
Prot-int_FW1   5'-TGCGCCGAGCCCGGCGACTC-3'

(SEQ ID NO: 46)
Prot-int_RV1   5'-GAGTCGCCGGGCTCGGCGCA-3'

(SEQ ID NO: 47)
Prot-int_FW2   5'-TTCCCCGGCAACGACTACGCGTGGGT-3'

(SEQ ID NO: 48)
Prot-int_RV2   5'-ACCCACGCGTAGTCGTTGCCGGGGAA-3'

(SEQ ID NO: 49)
Cellu-FW1      5'-GCCGCTGCTCGATCGGGTTC-3'

(SEQ ID NO: 50)
Cellu-RV1      5'-GCAGTTGCCGGAGCCGCCGGACGT-3'
```

(Iv) PCR Mixture (all Materials Supplied by Invitrogen)

| | |
|---|---|
| Template DNA | 4 µl |
| 10x PCR buffer | 5 µl |
| 50 mM MgSO4 | 2 µl |
| 10 mM dNTP's | 1 µl |
| Primers (10 µM soln.) | 1 µl each |
| Platinum Taq hifi polymerase | 0.5 µl |
| DMSO | 2 µl |
| MilliQ water | 33.5 µl |

(v) PCR Protocol

| | |
|---|---|
| 1) 94° C. | 5 min |
| 2) 94° C. | 30 sec |
| 3) 55° C. | 30 sec |
| 4) 68° C. | 3 min |

| 5) Repeat steps 2-4 repeat for 29 cycles | |
|---|---|
| 6) 68° C. | 10 min |
| 7) 15° C. | 1 min |

The amplified PCR products were examined by agarose gel electrophoresis. Distinct bands for each organism were excised from the gel, purified using the Qiagen gel extraction kit, and sequenced by BaseClear, using the same primer combinations.

(vi) Sequence Analysis

Nucleotide sequence data were analyzed and the DNA sequences were translated into amino acid sequences to review the homology to 69B4-mature protein. Sequence alignments were performed using AlignX, a component of Vector NTI suite 9.0.0. The results are compiled in Table 5-1. The numbering is that used in SEQ ID NO:8.

TABLE 5-1

Percent Identity of (translated) Amino Acid Sequences found in Natural Isolate Strains Compared to 69B4 Mature Protease

| Microorganism | No. of Amino Acids | Overlap Position | % Identity |
|---|---|---|---|
| *Cellulomonas flavigena* DSM 20109 | 101 | 34-134 | 62 |
| *Cellulomonas biazotea* DSM 20112 | 114 | 26-139 | 68 |
| *Cellulomonas fimi* DSM20113 | 109 | 32-140 | 72 |
| *Cellulomonas gelida* DSM 20111 | 48 | 142-189 | 69 |
| *Cellulomonas iranensis* DSM 14785 | 85 | 52-123 | 66 |
| *Cellulomonas cellasea* DSM 20109 | 102 | 32-133 | 63 |
| *Cellulomonas xylanilytica* LMG 21723 | 143 | 16-158 | 73 |
| *Oerskovia turbata* DSM 20577 | 111 | 34-144 | 74 |
| *Oerskovia jenensis* DSM 46000 | 129 | 22-150 | 70 |
| *Cellulosimicrobium cellulans* DSM 20424 | 134 | 35-168 | 53 |
| *Promicromonospora citrea* DSM 43110 | 85 | 52-136 | 75 |
| *Promicromonospora sukumoe* DSM 44121 | 85 | 52-136 | 73 |
| *Xylanibacterium ulmi* LMG 21721 | 141 | 16-156 | 64 |
| *Streptomyces griseus* ATCC 27001 | | No PCR product detected | |
| *Streptomyces griseus* ATCC 10137 | | | |
| *Streptomyces griseus* ATCC 23345 | | homologous to 69B4 protease | |
| *Streptomyces fradiae* ATCC 14544 | | | |
| *Streptomyces coelicolor* ATCC 10147 | | | |
| *Streptomyces lividans* TK23 | | | |

These results show that PCR primers based on polynucleotide sequences of the 69B4 protease gene (mature chain), SEQ ID NO:4 are successful in detecting homologous genes in bacterial strains of the suborder *Micrococcineae*, and in particular from the family Cellulomonadaceae and Promicromonosporaceae.

Figure 2:
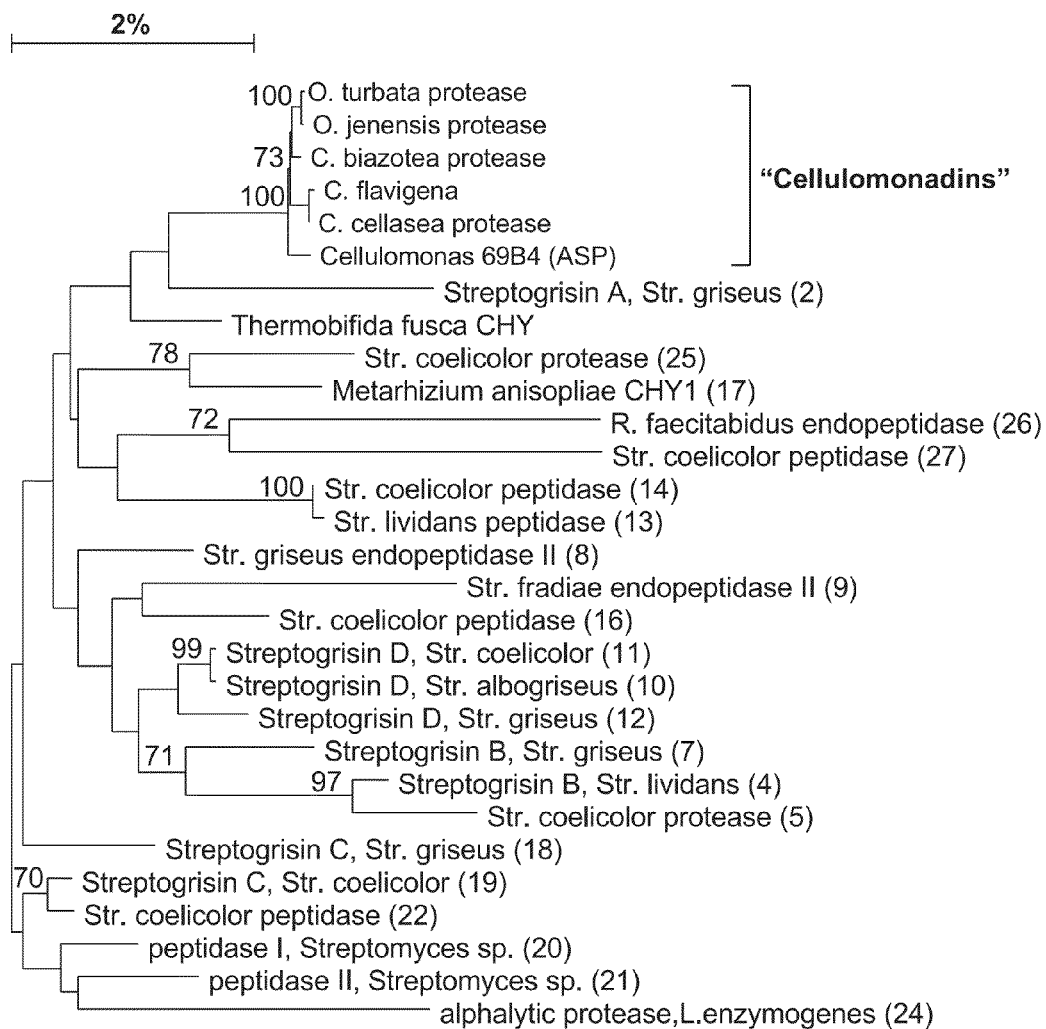
FIG. 2 provides a phylogenetic tree for ASP protease.

FIG. 2 provides a phylogeny tree of ASP protease. The phylogeny of this protease was examined by a variety of approaches from mature sequences of similar members of the chymotrypsin superfamily of proteins and ASP homologues for which significant mature sequence has been deduced. Using protein distance methods known in the art (See e.g., Kimura, *The Neutral Theory of Molecular Evolution*, Cambridge University Press, Cambridge, UK [1983]) similar trees were obtained either including or excluding gaps. The phylogenetic tree of FIG. 2 was constructed from aligned sequences (positions 16-181 of SEQ ID NO:8) using TREE-CONW v.1.3b (Van de Peer and De Wachter, Comput. Appl. Biosci., 10:569-570 [1994]) and with tree topology inferred by the Neighbor-Joining algorithm (Saitou and Nei, Mol. Biol. Evol., 4:406-425 [1987]). As indicated by this tree, the data indicate that the ASP series of homologous proteases ("cellulomonadins") forms a separate subfamily of proteins. In FIG. 2, the numbers provided in brackets correspond to the sequences provided herein.

The following is an alignment between the Cellulomonas 69B4 ASP protease and homologous proteases of related genera described herein.

```
                                           1                                                  50
         69B4(ASP)complete       (1)  MTPRTVTRALAVATAAATLLAGGMAAQANEPAPPGSASAPPRLAEKLDPD Cellulomonas gelida     (1)  --------------------------------------------------

Cellulomonas flavigena  (1)  --------------------------------------------------

Cellulomonas biazotea   (1)  --------------------------------------------------

Cellulomonas fimi       (1)  --------------------------------------------------

Cellulomonas iranensis  (1)  --------------------------------------------------

Cellulomonas cellasea   (1)  --------------------------------------------------

C. xylanilytica         (1)  --------------------------------------------------

Oerskovia turbata       (1)  MARSFWATLATACAATALVAGPAALTANAATPTPDTPTVSPQTSSKVSPE

Oerskovia jenensis      (1)  --------------------------------------------------

Cm. cellulans           (1)  --------------------------------------------------

Pm. citrea              (1)  --------------------------------------------------

Pm. sukumoe             (1)  --------------------------------------------------

69B4 (ASP) mature       (1)  --------------------------------------------------

Consensus               (1)
```

-continued

```
                                51                                                100
69B4(ASP)complete        (51)   LLEAMERDLGLDAEEAAATLAFQHDAAETGEALAEELDEDF-AGTWVEDD
Cellulomonas gelida       (1)   --------------------------------------------------
Cellulomonas flavigena    (1)   --------------------------------------------------
Cellulomonas biazotea     (1)   --------------------------------------------------
Cellulomonas fimi         (1)   --------------------------------------------------
Cellulomonas iranensis    (1)   --------------------------------------------------
Cellulomonas cellasea     (1)   -------------------------------------------------V
C. xylanilytica           (1)   --------------------------------------------------
Oerskovia turbata        (51)   VLRALQRDLGLSAKDATKRLAFQSDAASTEDALADSLDAYAGAWVDPARN
Oerskovia jenensis        (1)   --------------------------------------------------
Cm. cellulans             (1)   ---------------------PRAAGRAARSSGSRASAS
Pm. citrea                (1)   --------------------------------------------------
Pm. sukumoe               (1)   --------------------------------------------------
69B4 (ASP) mature         (1)   --------------------------------------------------
Consensus                (51)

101                                               150
69B4(ASP)complete       (100)   VLYVATTDEDAVEEVEGEGATAVTVEHSLADLEAWKTVLDAALEGHDDVP
Cellulomonas gelida       (1)   --------------------------------------------------
Cellulomonas flavigena    (1)   --------------------------------------------------
Cellulomonas biazotea     (1)   ---------------KQTASEFVIRLTIGELNLAAANSPLPIGHAWSTAL
Cellulomonas fimi         (1)   --------------------------------------------------
Cellulomonas iranensis    (1)   --------------------------------------------------
Cellulomonas cellasea     (2)   GRVRQLPLRGHDVLPARERDPAGLASASRPGLTRSRRARLDAAGPSARVA
C. xylanilytica           (1)   --------------------------------------------------
Oerskovia turbata       (101)   TLYVGVADRAEAKEVRSAGATPVVVDHTLAELDTWKAALDGELNDPAGVP
Oerskovia jenensis        (1)   --------------------------------------------------
Cm. cellulans            (19)   TSPGPTSVTASASSCGRATGRRQRWTFEADGTVRAGGKCMDVAWAPRPTA
Pm. citrea                (1)   --------------------------------------------------
Pm. sukumoe               (1)   --------------------------------------------------
69B4 (ASP) mature         (1)   --------------------------------------------------
Consensus               (101)

151                                               200
69B4(ASP)complete       (150)   TWYVDVPTNSVVVAVKAGAQDVAAGLVEGADVPSDAVTFVETDETPRTMF
Cellulomonas gelida       (1)   --------------------------------------------------
Cellulomonas flavigena    (1)   -------------------------------------------------V
Cellulomonas biazotea    (36)   GWYVDVTTNTVVVNATALAVAQATEIVAAATVPADAVRVVETTEAPRTFI
Cellulomonas fimi         (1)   -------------------------------------------------V
Cellulomonas iranensis    (1)   --------------------------------------------------
Cellulomonas cellasea    (52)   AWYVDVPTNKLVVESVG--DTAAAADAVAAAGLPADAVTLATTEAPRTFV
C. xylanilytica           (1)   --------------------------------------------------
Oerskovia turbata       (151)   SWFVDVTTNQVVVNVHDGGRALAELAAASAGVPADAITYVTTTEAPRPLV
```

```
                        -continued

O. jenenensis revi      (1)  --------------------------------------------------

Cm. cellulans          (69)  RASSSRTARQRGPEVRAQRRGRPRVGAGEQSASTPPGAHRGTRGAVRAHG

Pm. citrea              (1)  --------------------------------------------------

Pm. sukumoe             (1)  --------------------------------------------------

69B4 (ASP) mature       (1)  -------------------------------------------------F

Consensus             (151)

201                                             250
69B4(ASP)complete     (200)  DVIGGNAYTIGGRSR-----CSIGFAVNGGFITAGHCGRTGA-----TTA Cellulomonas gelida     (1)  --------------------------------------------------

Cellulomonas flavigena  (2)  DVIGGNAYYIGSRSR-----CSIGFAVEGGFVTAGHCGRAGA-----STS

Cellulomonas biazotea  (86)  DVIGGNRYRINNTSR-----CSVGFAVSGGFVTAGHCGTTGA-----TTT

C. fimi. revi           (2)  DVIGGDAYYIGGRSR-----CSIGFAVTGGFVTAGHCGRTGA-----ATT

C. iranensis revi       (1)  --------------------------------------------------

Cellulomonas cellasea (100)  DVIGGNAYYINASSR-----CSVGFAVEGGFVTAGHCGRAGA-----STS

C. xylanilytica         (1)  --------------R-----CSIGFAVTGGFVTAGHCGRSGA-----TTT

Oerskovia turbata     (201)  DVVGGNAYTMGSGGR-----CSVGFAVNGGFITAGHCGSVGT-----RTS

Oerskovia jenensis      (1)  --------------R-----CSVGFAVNGGFVTAGHCGTVGT-----RTS

Cm. cellulans         (119)  DVRGGDRYITRDPGASSGSACSIGYAVQGGFVTAGHCGRGGTRRVLTASW

Pm. citrea              (1)  --------------------------------------------------

Pm. sukumoe             (1)  --------------------------------------------------

69B4 (ASP) mature       (2)  DVIGGNAYTIGGRSR-----CSIGFAVNGGFITAGHCGRTGA-----TTA

Consensus             (201)  DVIGG  Y I   R     CSIGFAV GGFVTAGHCGR GA      TS 251                                             300
69B4(ASP)complete     (240)  NPTGTFAGSSFPGNDYAFVRTGAGVNLLAQVNNYSGGRVQVAGHTAAPVG Cellulomonas gelida     (1)  --------------------------------------------------

Cellulomonas flavigena (42)  SPSGTFRGSSFPGNDYAWVQVASGNTPRGLVNNHSGGTVRVTGSQQAAVG

Cellulomonas biazotea (126)  KPSGTFAGSSFPGNDYAWVRVASGNTPVGAVNNYSGGTVAVAGSTQATVG

Cellulomonas fimi      (42)  SPSGTFAGSSFPGNDYAWVRVASGNTPVGAVNNYSGGTVAVAGSTQAAVG

Cellulomonas iranensis  (1)  ----------FPGNDYAWVQVGSGDTPRGLVNNYAGGTVRVTGSQQAAVG

Cellulomonas cellasea (140)  SPSGTFRGSSFPGNDYAWVQVASGMTPRGLVNNHSGGTVRVTGSQQAAVG

C. xylanilytica        (27)  SPSGTFAGSSFPGNDYAWVRAASGNTPVGAVNRYDGSRVTVAGSTDAAVG

Oerskovia turbata     (241)  GPGGTFRGSNFPGNDYAWVQVDAGNTPVGAVNNYSGGRVAVAGSTAAPVG

Oerskovia jenensis     (27)  GPGGTFRGSSFPGNDYAWVQVDAGNTPVGAVNNYSGGRVAVAGSTAAPVG

Cm. cellulans         (169)  ARMGTVQAASFPGHDYAWVRVDAGFSPVPRVNNYAGGTVDVAGSAEAPVG

Pm. citrea              (1)  ----------FPGNDYAWVNTGTDDTLVGAVNNYSGGTVNVAGSTRAAVG

Pm. sukumoe             (1)  ----------FPGNDYAWVNVGSDDTPIGAVNNYSGGTVNVAGSTQAAVG

69B4 (ASP) mature      (42)  NPTGTFAGSSFPGNDYAFVRTGAGVNLLAQVNNYSGGRVQVAGHTAAPVG

Consensus             (251)   P GTF GSSFPGNDYAWVQVASGNTPVGAVNNYSGGTV VAGST AAVG 301                                             350
69B4(ASP)complete     (290)  SAVCRSGSTTGWHCGTITALNSSVTYPEGTVRGLIRTTVCAEPGDSGGSL Cellulomonas gelida     (1)  --------------------------------------------------

Cellulomonas flavigena (92)  SYVCRSGSTTGWRCGYVRAYNTTVRYAEGSVSGLIRTSVCAEPGDSGGSL
```

-continued

```
Cellulomonas biazotea    (176)  ASVCRSGSTTGWRCGTIQAFNSTVNYAQGSVSGLIRTNVCAEPGDSGGSL
Cellulomonas fimi         (92)  ATVCRSGSTTGWRCGTIQAFNATVNYAEGSVSGLIRTNVCAEPGDSGGSL
Cellulomonas iranensis    (41)  AYVCRSGSTTGWRCGTVQAYNASVRYAEGTVSGLIRTNVCAEPGD-----
Cellulomonas cellasea    (190)  SYVCRSGSTTGWRCGYVRAYNTTVRYAEGSVSGLIRTSVCAEPGDSGGSL
C. xylanilytica           (77)  AAVCRSGSTTAWGCGTIQSRGASVTYAQGTVSGLIRTNVCAEPGDSGGSL
Oerskovia turbata        (291)  ASVCRSGSTTGWHCGTIGAYNTSVTYPQGTVSGLIRTNVCAEPGDSGGSL
Oerskovia jenensis        (77)  SSVCRSGSTTGWRCGTIAAYNSSVTYPQGTVSGLIRTNVCAEPGDSGGSL
Cm. cellulans            (219)  ASVCRSGATTGWRCGVIEQKNITVNYGNGDVPGLVRGSACAEGGDSGGSV
Pm. citrea                (41)  ATVCRSGSTTGWHCGTIQALNASVTYAEGTVSGLIRTNVCAEPGD-----
Pm. sukumoe               (41)  STVCRSGSTTGWHCGTIQAFNASVTYAEGTVSGLIRTNVCAEPGD-----
69B4 (ASP) mature         (92)  SAVCRSGSTTGWHCGTITALNSSVTYPEGTVRGLIRTTVCAEPGDSGGSL
Consensus                (301)  ASVCRSGSTTGWRCGTI AYNASV YAEGTVSGLIRTNVCAEPGDSGGSL 351                                               400
69B4(ASP)complete        (340)  LAGNQAQGVTSGGSGNCRTGGTTFFQPVNPILQAYGLRMITT-DSGSSPA
Cellulomonas gelida        (1)  LAGNQAQGVTSGGSGNCSSGGTTYFQPVNEALRVYGLTLVTS-DGGGTE-
Cellulomonas flavigena   (142)  VAGTQAQGVTSGGSGNCRYGGTTYFQPVNEILQDQPGPSTTR-AL-----
Cellulomonas biazotea    (226)  IAGNQAQGLTSGGSGNCTTGGTTYFQPVNEALSAYGLTLVTSSGGGGGGG
Cellulomonas fimi        (142)  VAG-----------------------------------------------
Cellulomonas iranensis    (86)  --------------------------------------------------
Cellulomonas cellasea    (240)  VAGTQAQGVTSGGSGNCRYGGTTYFQPVNEILQAYGLRLVLG-HARGGPS
C. xylanilytica          (127)  IAGTQARGVTSGGSGNC---------------------------------
Oerskovia turbata        (341)  LAGNQAQGVTSGGSGNCSSGGTTYFQPVNEALGGYGLTLVTSDGGGPSRR
Oerskovia jenensis       (127)  LAGNQAQGLTSGGSGNCSSGGTTYFQPVNEALSAYGLTLVTSGGRGNC--
Cm. cellulans            (269)  ISGNQAQGVTSGRINDCSNGGKFLYQPDRRPVARDHGRRVGQRARRARGQ
Pm. citrea                (86)  --------------------------------------------------
Pm. sukumoe               (86)  --------------------------------------------------
69B4 (ASP) mature        (142)  LAGNQAQGVTSGGSGNCRTGGTTFFQPVNPILQAYGLRMITTDSGSSP--
Consensus                (351)  LAGNQAQGVTSGGSGNC  GGTTYFQPVN  L  YGL LV 69B4(ASP)complete        (389)  -PAPTSCTGYARTFTGTLAAGRAAAQPNGSYVQVNRSGTHSVCLNGPSGA
Cellulomonas gelida       (49)  -PPPTGCQGYARTYQGSVSAGTSVAQPNGSYVTTG-GGTHRVCLSGPAGT
Cellulomonas flavigena   (186)  --------------------------------------------------
Cellulomonas biazotea    (276)  ----TTCTGYARTYTGSLASRQSAVQPSGSYVTVGSSGTIRVCLDGPSGT
Cellulomonas fimi        (145)  --------------------------------------------------
Cellulomonas iranensis    (86)  --------------------------------------------------
Cellulomonas cellasea    (289)  -PARRAPAPPARA-------------------------------------
C. xylanilytica          (144)  --------------------------------------------------
Oerskovia turbata        (391)  RPGARAMRGPTRAASRPGRRSRSERFVRHDRGRATGCA------------
Oerskovia jenensis       (175)  --------------------------------------------------
Cm. cellulans            (319)  VHRRPRVRLQ----------------------------------------
Pm. citrea                (86)  --------------------------------------------------
Pm. sukumoe               (86)  --------------------------------------------------
```

```
-continued

69B4 (ASP) mature       (190) ------------------------------------------------
Consensus               (401)

451                                           500
69B4(ASP)complete       (438) DFDLYVQRWNGSSWVTVAQSTSPGSNETITYRGNAGYYRYVVNAASGSGA
Cellulomonas gelida      (97) DLDLYLQKWNGYSWASVAQSTSPGATEAVTYTGTAGYYRYVVHAYAGSGA
Cellulomonas flavigena  (186) ------------------------------------------------
Cellulomonas biazotea   (322) DFDLYLQKWNGSAW----------------------------------
Cellulomonas fimi       (145) ------------------------------------------------
Cellulomonas iranensis   (86) ------------------------------------------------
Cellulomonas cellasea   (301) ------------------------------------------------
C. xylanilytica         (144) ------------------------------------------------
Oerskovia turbata       (429) ------------------------------------------------
Oerskovia jenensis      (175) ------------------------------------------------
Cm. cellulans           (329) ------------------------------------------------
Pm. citrea               (86) ------------------------------------------------
Pm. sukumoe              (86) ------------------------------------------------
69B4 (ASP) mature       (190) ------------------------------------------------
Consensus               (451)

501
69B4(ASP)complete       (488) YTMGLTLP (SEQ ID NO: 6)
Cellulomonas gelida     (147) YTLGATTP (SEQ ID NO: 60)
Cellulomonas flavigena  (186) -------- (SEQ ID NO: 54)
Cellulomonas biazotea   (336) -------- (SEQ ID NO: 56)
Cellulomonas fimi       (145) -------- (SEQ ID NO: 58)
Cellulomonas iranensis   (86) -------- (SEQ ID NO: 62)
Cellulomonas cellasea   (301) -------- (SEQ ID NO: 64)
C. xylanilytica         (144) -------- (SEQ ID NO: 66)
Oerskovia turbata       (429) -------- (SEQ ID NO: 68)
Oerskovia jenensis      (175) -------- (SEQ ID NO: 70)
Cm. cellulans           (329) -------- (SEQ ID NO: 72)
Pm. citrea               (86) -------- (SEQ ID NO: 74)
Pm. sukumoe              (86) -------- (SEQ ID NO: 76)
69B4 (ASP) mature       (190) -------- (SEQ ID NO: 8)
Consensus               (501)          (SEQ ID NO: 647)
```

Example 6
Detection of Novel Homologues of 69B4 Protease by Immunoblotting In this Example, immunoblotting experiments used to detect homologues of 6984 are described. The following organisms were used in these experiments:

1. *Cellulomonas biazotea* DSM 20112
2. *Cellulomonas flavigena* DSM 20109
3. *Cellulomonas fimi* DSM 20113
4. *Cellulomonas cellasea* DSM 20118
5. *Cellulomonas uda* DSM 20107
6. *Cellulomonas gelida* DSM 20111
7. *Cellulomonas xylanilytica* LMG 21723
8. *Cellulomonas iranensis* DSM 14785
9. *Oerskovia jenensis* DSM 46000
10. *Oerskovia turbata* DSM 20577
11. *Cellulosimicrobium cellulans* DSM 20424
12. *Xylanibacterium ulmi* LMG21721
13. *Isoptericola variabilis* DSM 10177
14. *Xylanimicrobium pachnodae* DSM 12657
15. *Promicromonospora citrea* DSM 43110
16. *Promicromonospora sukumoe* DSM 44121
17. *Agromyces ramosus* DSM 43045

The strains were first grown on Heart Infusion/skim milk agar plates (72 h, 30° C.) to confirm strain purity, protease reaction by clearing of the skim milk and to serve as inoculum. Bacterial strains were cultivated on Brain Heart Infusion broth supplemented with casein (0.8% w/v) in 100/500 Erlenmeyer flasks with baffles at 230 rpm, 30° C. for 5 days. Microbial growth was checked by microscopy. Supernatants were separated from cells by centrifugation for 30 min at 4766×g. Further solids were removed by centrifugation at 9500 rpm. Supernatants were concentrated using Vivaspin 20 ml concentrator (Vivascience), cutoff 10 kDa, by centrifugation at 4000×g. Concentrates were stored in aliquots of 0.5 mL at −20° C.

Primary Antibody

The primary antibody (EP034323) for the immunoblotting reaction, prepared by Eurogentec (Liege Science Park, Seraing, Belgium) was raised against 2 peptides consisting of amino acids 151-164 and 178-189 in the 69B4 mature protease (SEQ ID NO:8), namely:

TSGGSGNCRTGGTT (epitope 1; SEQ ID NO:51) and LRMITTDSGSSP (epitope 2; SEQ ID NO:52) as shown below in the amino acid sequence of 69B4 mature protease:

```
1    FDVIGGNAYT IGGRSRCSIG FAVNGGFITA GHCGRTGATT ANPTGTFAGS
51   SFPGNDYAFV RTGAGVNLLA QVNNYSGGRV QVAGHTAAPV GSAVCRSGST
101  TGWHCGTITA LNSSVTYPEG TVRGLIRTTV CAEPGDSGGS LLAGNQAQGV
151  TSGGSGNCRT GGTTFFQPVN PILQAYGLRM ITTDSGSSP   (SEQ ID NO:8)
```

Electrophoresis and Immunoblotting

Sample Preparation

1. Concentrated culture supernatant (50 μL)
2. PMSF (1 μL; 20 mg/ml)
3. 1M HCl (25 μL)
4. Nu PAGE LDS sample buffer (25 μL) (Invitrogen, Carlsbad, Calif., USA) Mixed and heated at 90° C. for 10 min.

Electrophoresis

SDS-PAGE was performed in duplicate using NuPAGE 10% Bis-Tris gels (Invitrogen) with MES-SDS running buffer at 100 v for 5 min. and 200 v constant. Where possible, 25 μL sample were loaded in each slot. One gel of each pair was stained with Coomassie Blue and the other gel was used for immunoblotting using the Boehringer Mannheim chromogenic Western blotting protocol (Roche).

Immunoblotting

The transfer buffer used was Transfer buffer: Tris (0.25M)-glycine (1.92M)-methanol (20% v/v). The PVDF membrane was pre-wetted by successive moistening in methanol, deionized water, and finally transfer buffer.

The PAGE gel was briefly washed in deionized water and transferred to blotting pads soaked in transfer buffer, covered with pre-wetted PVDF membrane and pre-soaked blotting pads. Blotting was performed in transfer buffer at 400 mA constant for 2.5-3 h. The membrane was briefly washed (2×) in Tris buffered saline (TBS) (0.5M Tris, 0.15M NaCl, pH7.5). Non-specific antibody binding was prevented by incubating the membrane in 1% v/v mouse/rabbit Blocking Reagent (Roche) in maleic acid solution (100 mM maleic acid, 150 mM NaCl, pH7.5) overnight at 4° C.

The primary antibody used in these reactions was EP034323 diluted 1:1000. The reaction was performed with the Ab diluted in 1% Blocking Solution with a 30 min. action time. The membrane was washed 4×10 min. in TBST (TSB+ 0.1% v/v Tween 20).

The secondary antibody consisted of anti-mouse/anti-rabbit IgG (Roche) 73 μL in 20 ml in 1% Blocking Solution with a reaction time of 30 min. The membrane was washed 4×15 min. in TBST and the substrate reaction (alkaline phosphatase) performed with BM Chromogenic Western Blotting Reagent (Roche) until staining occurred.

The results of the cross-reactivity with primary polyclonal antibody are shown in Table 6-1.

TABLE 6-1

Immunoblotting Results

| Strain | Immuno-Blot Result | Estimated Molecular Mass kDa | % Sequence Identity to 69B4 Mature Protease | Protease Activity On HI-Skim Milk Agar |
|---|---|---|---|---|
| C. flavigena DSM 20109 | positive | 21 | 66 | positive |
| C. biazotea DSM 20112 | negative | | 65 | positive |
| C. fimi DSM 20112 | negative | | 72 | weak + |
| C. gelida DSM 20111 | positive | 20 | 69 | weak + |

TABLE 6-1-continued

Immunoblotting Results

| Strain | Immuno-Blot Result | Estimated Molecular Mass kDa | % Sequence Identity to 69B4 Mature Protease | Protease Activity On HI-Skim Milk Agar |
|---|---|---|---|---|
| C. uda DSM 20107 | negative | | | weak + |
| C. iranensis DSM 14785 | negative | | 33 | weak + |
| C. cellasea DSM 20118 | positive | 27 | 61 | positive |
| C. xylanilytica LMG 21723 | negative | | 69 | positive |
| O. turbata DSM 20577 | positive | 18 | 73 | positive |
| O. jenensis DSM 46000 | positive | 35 | 78 | positive |
| C. cellulans DSM 20424 | negative | | 48 | positive |
| P. citrea DSM 43110 | negative | | 28 | positive |
| P. sukumoe DSM 44121 | negative | | 69 | positive |
| X. ulmi LMG21721 | negative | | 72 | negative |
| I. variabilis DSM 10177 | negative | | | positive |
| X. pachnodae DSM 12657 | negative | | | weak + |
| A. ramosus DSM 43045 | negative | | | weak + |

Based on these results, it is clear that the antibody used in these experiments is highly specific at detecting homologues with a very high percentage of amino acid sequence identity to 69B4 protease. Furthermore, these results indicate that the C-terminal portion of the 69B4 mature protease chain is fairly variable especially in the region of the 2-peptide epitopes. In these experiments, it was determined that in cases where there were more than 2 amino acid differences in this region a negative Western blotting reaction resulted.

Example 7

Inverse PCR and Genome Walking

In this Example, experiments conducted to elucidate polynucleotide sequences of ASP are described. The microorganisms utilized in these experiments were:
1. *Cellulomonas biazotea* DSM 20112
2. *Cellulomonas flavigena* DSM 20109
3. *Cellulomonas fimi* DSM 20113
4. *Cellulomonas cellasea* DSM 20118
5. *Cellulomonas gefida* DSM 20111
6. *Cellulomonas iranensis* (DSM 14785)
7. *Oerskovia jenensis* DSM 46000
8. *Oerskovia turbata* DSM 20577
9. *Cellulosimicrobium cellulans* DSM 20424
10. *Promicromonospora citrea* DSM 43110
11. *Promicromonospora sukumoe* DSM 44121

These bacterial strains were cultivated on Brain Heart Infusion broth or Tryptone Soya broth in 100/500 Erlenmeyer flasks with baffles at 230 rpm, 30° C. for 2 days: Cells were separated from the culture broth by centrifugation for 30 min at 4766×g.

Chromosomal DNA was obtained by standard phenol/chloroform extraction method known in the art from cells digested by lysozyme/EDTA (See e.g., Sambrook et al., supra). Chromosomal DNA was digested with the restriction enzymes selected from the following list: ApaI, BamHI, BssHII, KpnI, NarI, NcoI, NheI, PvuI, SalI or SstII.

The nucleotide and amino acid sequences of these organisms are provided below. In these listings, the mature protease is indicated in bold and the signal sequence is underlined.

```
C. flavigena (DSM 20109)
                                                      (SEQ ID NO: 53)
    1   GTCGACGTCA TCGGGGGCAA CGCGTACTAC ATCGGGTCGC GCTCGCGGTG
        CAGCTGCAGT AGCCCCCGTT GCGCATGATG TAGCCCAGCG CGAGCGCCAC 51   CTCGATCGGG TTCGCGGTCG AGGGCGGGTT CGTCACCGCG GGGCACTGCG
        GAGCTAGCCC AAGCGCCAGC TCCCGCCCAA GCAGTGGCGC CCCGTGACGC 101   GGCGCGCGGG CGCGAGCACG TCGTCACCGT CGGGGACCTT CCGCGGCTCG
        CCGCGCGCCC GCGCTCGTGC AGCAGTGGCA GCCCCTGGAA GGCGCCGAGC 151   TCGTTCCCCG GCAACGACTA CGCGTGGGTC CAGGTCGCCT CGGGCAACAC
        AGCAAGGGGC CGTTGCTGAT GCGCACCCAG GTCCAGCGGA GCCCGTTGTG 201   GCCGCGCGGG CTGGTGAACA ACCACTCGGG CGGCACGGTG CGCGTCACCG
        CGGCGCGCCC GACCACTTGT TGGTGAGCCC GCCGTGCCAC GCGCAGTGGC 251   GCTCGCAGCA GGCCGCGGTC GGCTCGTACG TGTGCCGATC GGGCAGCACG
        CGAGCGTCGT CCGGCGCCAG CCGAGCATGC ACACGGCTAG CCCGTCGTGC 301   ACGGGATGGC GGTGCGGCTA CGTCCGGGCG TACAACACGA CCGTGCGGTA
        TGCCCTACCG CCACGCCGAT GCAGGCCCGC ATGTTGTGCT GGCACGCCAT 351   CGCGGAGGGC TCGGTCTCGG GCCTCATCCG CACGAGCGTG TGCGCCGAGC
        GCGCCTCCCG AGCCAGAGCC GGAGTAGGC GTGCTCGCAC ACGCGGCTCG 401   CGGGCGACTC CGGCGGCTCG CTGGTCGCCG GCACGCAGGC CCAGGGCGTC
        GCCCGCTGAG GCCGCCGAGC GACCAGCGGC CGTGCGTCCG GGTCCCGCAG 451   ACGTCGGGCG GGTCCGGCAA CTGCCGCTAC GGGGGCACGA CGTACTTCCA
        TGCAGCCCGC CCAGGCCGTT GACGGCGATG CCCCCGTGCT GCATGAAGGT 501   GCCCGTGAAC GAGATCCTGC AGGACCAGCC CGGGCCGTCG ACCACGCGTG
        CGGGCACTTG CTCTAGGACG TCCTGGTCGG GCCCGGCAGC TGGTGCGCAC

551   CCCTA
        GGGAT

Cellulomonas flavigena (DSM 20109)
                                                      (SEQ ID NO: 54)
    1   VDVIGGNAYY IGSRSRCSIG FAVEGGFVTA GHCGRAGAST SSPSGTFRGS

51   SFPGNDYAWV QVASGNTPRG LVNNHSGGTV RVTGSQQAAV GSYVCRSGST

101   TGWRCGYVRA YNTTVRYAEG SVSGLIRTSV CAEPGDSGGS LVAGTQAQGV

151   TSGGSGNCRY GGTTYFQPVN EILQDQPGPS TTRAL

Cellulomonas biazotea (DSM 20112)
                                                      (SEQ ID NO: 55)
    1   TAAAACAGAC GGCCAGTGAA TTTGTAATAC GACTCACTAT AGGCGAATTG
        ATTTTGTCTG CCGGTCACTT AAACATTATG CTGAGTGATA TCCGCTTAAC 51   AATTTAGCGG CCGCGAATTC GCCCTTACCT ATAGGGCACG CGTGGTCGAC
        TTAAATCGCC GGCGCTTAAG CGGGAATGGA TATCCCGTGC GCACCAGCTG 101   GGCCCTGGGC TGGTACGTCG ACGTCACTAC CAACACGGTC GTCGTCAACG
        CCGGGACCCG ACCATGCAGC TGCAGTGATG GTTGTGCCAG CAGCAGTTGC
```

```
                                    -continued
151    CCACCGCCCT CGCCGTGGCC CAGGCGACCG AGATCGTCGC CGCCGCAACG
       GGTGGCGGGA GCGGCACCGG GTCCGCTGGC TCTAGCAGCG CGGCGTTGC 201    GTGCCCGCCG ACGCCGTCCG GGTCGTCGAG ACCACCGAGG CGCCCCGCAC
       CACGGGCGGC TGCGGCAGGC CCAGCAGCTC TGGTGGCTCC GCGGGGCGTG 251    GTTCATCGAC GTCATCGGCG GCAACCGTTA CCGGATCAAC AACACCTCGC
       CAAGTAGCTG CAGTAGCCGC CGTTGGCAAT GGCCTAGTTG TTGTGGAGCG 301    GCTGCTCGGT CGGCTTCGCC GTCAGCGGCG GCTTCGTCAC CGCCGGGCAC
       CGACGAGCCA GCCGAAGCGG CAGTCGCCGC CGAAGCAGTG GCGGCCCGTG 351    TGCGGCACGA CCGGCGCGAC CACGACGAAA CCGTCCGGCA CGTTCGCCGG
       ACGCCGTGCT GGCCGCGCTG GTGCTGCTTT GGCAGGCCGT GCAAGCGGCC 401    CTCGTCGTTC CCCGGCAACG ACTACGCGTG GGTGCGCGTC GCGTCCGGCA
       GAGCAGCAAG GGGCCGTTGC TGATGCGCAC CCACGCGCAG CGCAGGCCGT 451    ACACCCCGGT CGGCGCCGTG AACAACTACA GCGGCGGCAC CGTGGCCGTC
       TGTGGGGCCA GCCGCGGCAC TTGTTGATGT CGCCGCCGTG GCACCGGCAG 501    GCCGGCTCGA CGCAGGCGAC CGTCGGTGCG TCCGTCTGCC GCTCCGGCTC
       CGGCCGAGCT GCGTCCGCTG GCAGCCACGC AGGCAGACGG CGAGGCCGAG 551    CACCACGGGG TGGCGCTGCG GGACGATCCA GGCGTTCAAC TCCACCGTCA
       GTGGTGCCCC ACCGCGACGC CCTGCTAGGT CCGCAAGTTG AGGTGGCAGT 601    ACTACGCGCA GGGCAGCGTC TCCGGCCTCA TCCGCACGAA CGTGTGCGCC
       TGATGCGCGT CCCGTCGCAG AGGCCGGAGT AGGCGTGCTT GCACACGCGG 651    GAGCCCGGCG ACTCCGGCGG CTCGCTCATC GCCGGCAACC AGGCCCAGGG
       CTCGGGCCGC TGAGGCCGCC GAGCGAGTAG CGGCCGTTGG TCCGGGTCCC 701    CCTGACGTCC GGCGGGTCGG GCAACTGCAC CACCGGCGGG ACGACGTACT
       GGACTGCAGG CCGCCCAGCC CGTTGACGTG GTGGCCGCCC TGCTGCATGA 751    TCCAGCCCGT CAACGAGGCG CTCTCCGCCT ACGGCCTGAC GCTCGTCACG
       AGGTCGGGCA GTTGCTCCGC GAGAGGCGGA TGCCGGACTG CGAGCAGTGC 801    TCGTCCGGCG GCGGCGGTGG CGGCGGCACG ACCTGCACCG GGTACGCGCG
       AGCAGGCCGC CGCCGCCACC GCCGCCGTGC TGGACGTGGC CCATGCGCGC 851    GACCTACACC GGCTCGCTCG CCTCGCGGCA GTCCGCCGTC CAGCCGTCCG
       CTGGATGTGG CCGAGCGAGC GGAGCGCCGT CAGGCGGCAG GTCGGCAGGC 901    GCAGCTATGT GACCGTCGGG TCCAGCGGCA CCATCCGCGT CTGCCTCGAC
       CGTCGATACA CTGGCAGCCC AGGTCGCCGT GGTAGGCGCA GACGGAGCTG 951    GGCCCGAGCG GGACGGACTT CGACCTGTAC CTGCAGAAGT GGAACGGGTC
       CCGGGCTCGC CCTGCCTGAA GCTGGACATG GACGTCTTCA CCTTGCCCAG

1001   CGCGTGGGC
       GCGCACCCG

Cellulomonas biazotea (DSM 20112)
                                                          (SEQ ID NO: 56)
  1    KQTASEFVIR LTIGELNLAA ANSPLPIGHA WSTALGWYVD VTTNTVVVNA

51    TALAVAQATE IVAAATVPAD AVRVVETTEA PRTFIDVIGG NRYRINNTSR

101    CSVGFAVSGG FVTAGHCGTT GATTTKPSGT FAGSSFPGND YAWVRVASGN

151    TPVGAVNNYS GGTVAVAGST QATVGASVCR SGSTTGWRCG TIQAFNSTVN

201    YAQGSVSGLI RTNVCAEPGD SGGSLIAGNQ AQGLTSGGSG NCTTGGTTYF

251    QPVNEALSAY GLTLVTSSGG GGGGGTTCTG YARTYTGSLA SRQSAVQPSG

301    SYVTVGSSGT IRVCLDGPSG TDFDLYLQKW NGSAW

Cellulomonas fimi (DSM 20113)
                                                          (SEQ ID NO: 57)
  1    GTGGACGTGA TCGGCGGCGA CGCCTACTAC ATCGCGGCC GCAGCCGCTG
       CACCTGCACT AGCCGCCGCT GCGGATGATG TAGCCGCCGG CGTCGGCGAC 51    TTCGATCGGG TTCGCCGTCA CCGGGGGCTT CGTGACCGCC GGGCACTGCG
       AAGCTAGCCC AAGCGGCAGT GGCCCCCGAA GCACTGGCGG CCCGTGACGC 101    GCCGCACCGG CGCGGCCACG ACGAGCCCGT CGGGCACGTT CGCCGGCTCG
       CGGCGTGGCC GCGCCGGTGC TGCTCGGGCA GCCCGTGCAA GCGGCCGAGC
```

-continued

```
    151 AGCTTCCCGG GCAACGACTA CGCGTGGGTG CGGGTCGCGT CGGGCAACAC
        TCGAAGGGCC CGTTGCTGAT GCGCACCCAC GCCCAGCGCA GCCCGTTGTG

201 GCCCGTCGGC GCGGTGAACA ACTACAGCGG CGGCACGGTC GCCGTCGCCG
        CGGGCAGCCG CGCCACTTGT TGATGTCGCC GCCGTGCCAG CGGCAGCGGC

251 GCTCGACCCA GGCCGCCGTC GGTGCGACCG TGTGCCGCTC GGGCTCCACC
        CGAGCTGGGT CCGGCGGCAG CCACGCTGGC ACACGGCGAG CCCGAGGTGG

301 ACCGGCTGGC GGTGCGGCAC CATCCAGGCG TTCAACGCGA CCGTCAACTA
        TGGCCGACCG CCACGCCGTG GTAGGTCCGC AAGTTGCGCT GGCAGTTGAT

351 CGCCGAGGGC AGCGTCTCCG GCCTCATCCG CACGAACGTG TGCGCCGAGC
        GCGGCTCCCG TCGCAGAGGC CGGAGTAGGC GTGCTTGCAC ACGCGGCTCG

401 CCGGCGACTC GGGCGGCTCG CTCGTCGCCG GCAACCAGGC GCAGGGCATG
        GGCCGCTGAG CCCGCCGAGC GAGCAGCGGC CGTTGGTCCG CGTCCCGTAC

451 ACGTCCGGCG GCTCCGACAA CTGC
        TGCAGGCCGC CGAGGCTGTT GACG
```

Cellulomonas fimi (DSM 20113)

(SEQ ID NO: 58)

```
      1 VDVIGGDAYY IGGRSRCSIG FAVTGGFVTA GHCGRTGAAT TSPSGTFAGS

51 SFPGNDYAWV RVASGNTPVG AVNNYSGGTV AVAGSTQAAV GATVCRSGST

101 TGWRCGTIQA FNATVNYAEG SVSGLIRTNV CAEPGDSGGS LVAG
```

Cellulomonas gelida (DSM 20111)

(SEQ ID NO: 59)

```
      1 CTCGCGGGCA ACCAGGCGCA GGGCGTGACG TCGGGCGGGT CGGGCAACTG
        GAGCGCCCGT TGGTCCGCGT CCCGCACTGC AGCCCGCCCA GCCCGTTGAC

51 CTCGTCGGGC GGGACGACGT ACTTCCAGCC CGTCAACGAG GCCCTCCGGG
        GAGCAGCCCG CCCTGCTGCA TGAAGGTCGG GCAGTTGCTC CGGGAGGCCC

101 TGTACGGGCT CACGCTCGTG ACCTCTGACG GTGGGGGCAC CGAGCCGCCG
        ACATGCCCGA GTGCGAGCAC TGGAGACTGC CACCCCCGTG GCTCGGCGGC

151 CCGACCGGGT GCCAGGGCTA TGCGCGGACC TACCAGGGCA GCGTCTCGGC
        GGCTGGCCCA CGGTCCCGAT ACGCGCCTGG ATGGTCCCGT CGCAGAGCCG

201 CGGGACGTCG GTCGCGCAGC CGAACGGTTC GTACGTCACG ACCGGGGGCG
        GCCCTGCAGC CAGCGCGTCG GCTTGCCAAG CATGCAGTGC TGGCCCCCGC

251 GGACGCACCG GGTGTGCCTG AGCGGACCGG CGGGCACGGA CCTGGACCTG
        CCTGCGTGGC CCACACGGAC TCGCCTGGCC GCCCGTGCCT GGACCTGGAC

301 TACCTGCAGA AGTGGAACGG GTACTCGTGG GCCAGCGTCG CGCAGTCGAC
        ATGGACGTCT TCACCTTGCC CATGAGCACC CGGTCGCAGC GCGTCAGCTG

351 GTCGCCTGGT GCCACGGAGG CGGTCACGTA CACCGGGACC GCCGGCTACT
        CAGCGGACCA CGGTGCCTCC GCCAGTGCAT GTGGCCCTGG CGGCCGATGA

401 ACCGCTACGT GGTCCACGCG TACGCGGGTT CGGGGGCGTA CACCCTGGGG
        TGGCGATGCA CCAGGTGCGC ATGCGCCCAA GCCCCGCAT GTGGGACCCC

451 GCGACGACCC CG
        CGCTGCTGGG GC
```

Cellulomonas gelida (DSM 20111)

(SEQ ID NO: 60)

```
      1 LAGNQAQGVT SGGSGNCSSG GTTYFQPVNE ALRVYGLTLV TSDGGGTEPP

51 PTGCQGYART YQGSVSAGTS VAQPNGSYVT TGGGTHRVCL SGPAGTDLDL

101 YLQKWNGYSW ASVAQSTSPG ATEAVTYTGT AGYYRVVHA YAGSGAYTLG

151 ATTP
```

Cellulomonas iranensis (DSM 14785)

(SEQ ID NO: 61)

```
      1 TTCCCCGGCA ACGACTACGC GTGGGTCCAG GTCGGGTCGG GCGACACCCC
        AAGGGGCCGT TGCTGATGCG CACCCAGGTC CAGCCCAGCC CGCTGTGGGG

51 CCGCGGCCTG GTCAACAACT ACGCGGGCGG CACCGTGCGG GTCACCGGGT
        GGCGCCGGAC CAGTTGTTGA TGCGCCCGCC GTGGCACGCC CAGTGGCCCA
```

```
        -continued
101  CGCAGCAGGC CGCGGTCGGC GCGTACGTCT GCCGGTCGGG CAGCACGACG
     GCGTCGTCCG GCGCCAGCCG CGCATGCAGA CGGCCAGCCC GTCGTGCTGC 151  GGCTGGCGCT GCGGCACCGT GCAGGCCTAC AACGCGTCGG TCCGCTACGC
     CCGACCGCGA CGCCGTGGCA CGTCCGGATG TTGCGCAGCC AGGCGATGCG 201  CGAGGGCACC GTCTCGGGCC TCATCCGCAC CAACGTCTGC GCCGAGCCCG
     GCTCCCGTGG CAGAGCCCGG AGTAGGCGTG GTTGCAGACG CGGCTCGGGC

251  GCGACTC
     CGCTGAG
```

*Cellulomonas iranensis* (DSM 14785)
(SEQ ID NO: 62)
```
  1  FPGNDYAWVQ VGSGDTPRGL VNNYAGGTVR VTGSQQAAVG AYVCRSGSTT

51  GWRCGTVQAY NASVRYAEGT VSGLIRTNVC AEPGD
```

*Cellulomonas cellasea* (DSM 20118)
(SEQ ID NO: 63)
```
  1  GTCGGGCGGG TCCGGCAACT GCCGCTACGG GGGCACGACG TACTTCCAGC
     CAGCCCGCCC AGGCCGTTGA CGGCGATGCC CCCGTGCTGC ATGAAGGTCG 51  CCGTGAACGA GATCCTGCAG GCCTACGGTC TGCGTCTCGT CCTGGGCTGA
     GGCACTTGCT CTAGGACGTC CGGATGCCAG ACGCAGAGCA GGACCCGACT 101  CACGCTCGCG GCGGGCCCGG CTCGACGCGG CCGGCCCGTC GGCCCGGGTC
     GTGCGAGCGC CGCCCGGGCC GAGCTGCGCC GGCCGGGCAG CCGGGCCCAG 151  GCCGCCTGGT ACGTCGACGT GCCGACCAAC AAGCTCGTCG TCGAGTCGGT
     CGGCGGACCA TGCAGCTGCA CGGCTGGTTG TTCGAGCAGC AGCTCAGCCA 201  CGGCGACACC GCGGCGGCCG CCGACGCCGT CGCCGCCGCG GGCCTGCCTG
     GCCGCTGTGG CGCCGCCGGC GGCTGCGGCA GCGGCGGCGC CCGGACGGAC 251  CCGACGCCGT GACGCTCGCG ACCACCGAGG CGCCACGGAC GTTCGTCGAC
     GGCTGCGGCA CTGCGAGCGC TGGTGGCTCC GCGGTGCCTG CAAGCAGCTG 301  GTCATCGGCG GCAACGCGTA CTACATCAAC GCGAGCAGCC GCTGCTCGGT
     CAGTAGCCGC CGTTGCGCAT GATGTAGTTG CGCTCGTCGG CGACGAGCCA 351  CGGCTTCGCG GTCGAGGGCG GGTTCGTCAC CGCGGGCCAC TGCGGGCGCG
     GCCGAAGCGC CAGCTCCCGC CCAAGCAGTG GCGCCCGGTG ACGCCCGCGC 401  CGGGCGCGAG CACGTCGTCA CCGTCGGGGA CCTTCCGCGG CTCGTCGTTC
     GCCCGCGCTC GTGCAGCAGT GGCAGCCCCT GGAAGGCGCC GAGCAGCAAG 451  CCCGGCAACG ACTACGCGTG GGTCCAGGTC GCCTCGGGCA ACACGCCGCG
     GGGCCGTTGC TGATGCGCAC CCAGGTCCAG CGGAGCCCGT TGTGCGGCGC 501  CGGGCTGGTG AACAACCACT CGGGCGGCAC GGTGCGCGTC ACCGGCTCGC
     GCCCGACCAC TTGTTGGTGA GCCCGCCGTG CCACGCGCAG TGGCCGAGCG 551  AGCAGGCCGC GGTCGGCTCG TACGTGTGCC GATCGGGCAG CACGACGGGA
     TCGTCCGGCG CCAGCCGAGC ATGCACACGG CTAGCCCGTC GTGCTGCCCT 601  TGGCGGTGCG GCTACGTCCG GGCGTACAAC ACGACCGTGC GGTACGCGGA
     ACCGCCACGC CGATGCAGGC CCGCATGTTG TGCTGGCACG CCATGCGCCT 651  GGGCTCGGTC TCGGGCCTCA TCCGCACGAG CGTGTGCGCC GAGCCGGGCG
     CCCGAGCCAG AGCCCGGAGT AGGCGTGCTC GCACACGCGG CTCGGCCCGC 701  ACTCCGGCGG CTCGCTGGTC GCCGGCACGC AGGCCCAGGG CGTCACGTCG
     TGAGGCCGCC GAGCGACCAG CGGCCGTGCG TCCGGGTCCC GCAGTGCAGC 751  GGCGGGTCCG GCAACTGCCG CTACGGGGGC ACGACGTACT TCCAGCCCGT
     CCGCCCAGGC CGTTGACGGC GATGCCCCCG TGCTGCATGA AGGTCGGGCA 801  GAACGAGATC CTGCAGGCCT ACGGTCTGCG TCTCGTCCTG GGCTGACACG
     CTTGCTCTAG GACGTCCGGA TGCAGACGC AGAGCAGGAC CCGACTGTGC 851  CTCGCGGCGG GCCCTCCCCT GCCCGTCGCG CGCCGGCCCC ACCAGCCCGG
     GAGCGCCGCC CGGGAGGGGA CGGGCAGCGC GCGGCCGGGG TGGTCGGGCC

901  GCCG
     CGGC
```

-continued

Cellulomonas cellasea (DSM 20118)
(SEQ ID NO: 64)

```
  1 VGRVRQLPLR GHDVLPARER DPAGLRSASR PGLTRSRRAR LDAAGPSARV

51 AAWYVDVPTN KLVVESVGDT AAAADAVAAA GLPADAVTLA TTEAPRTFVD

101 VIGGNAYYIN ASSRCSVGFA VEGGFVTAGH CGRAGASTSS PSGTFRGSSF

151 PGNDYAWVQV ASGNTPRGLV NNHSGGTVRV TGSQQAAVGS YVCRSGSTTG

201 WRCGYVRAYN TTVRYAEGSV SGLIRTSVCA EPGDSGGSLV AGTQAQGVTS

251 GGSGNCRYGG TTYFQPVNEI LQAYGLRLVL G*HARGGPSP ARRAPAPPAR

301 A
```

Cellulomonas xylanilytica (LMG 21723)
(SEQ ID NO: 65)

```
  1 CGCTGCTCGA TCGGGTTCGC CGTGACGGGC GGCTTCGTGA CCGCCGGCCA
    CTGCGGACGG TCCGGCGCGA CGACGACGTC GCCGAGCGGC ACGTTCGCCG

GCGACGAGCT AGCCCAAGCG GCACTGCCCG CCGAAGCACT GGCGGCCGGT
    GACGCCTGCC AGGCCGCGCT GCTGCTGCAG CGGCTCGCCG TGCAAGCGGC

101 GGTCCAGCTT TCCCGGCAAC GACTACGCCT GGGTCCGCGC GGCCTCGGGC
    AACACGCCGG TCGGTGCGGT GAACCGCTAC GACGGCAGCC GGGTGACCGT

CCAGGTCGAA AGGGCCGTTG CTGATGCGGA CCCAGGCGCG CCGGAGCCCG
    TTGTGCGGCC AGCCACGCCA CTTGGCGATG CTGCCGTCGG CCCACTGGCA

201 GGCAGGGTCC ACCGACGCGG CCGTCGGTGC CGCGGTCTGC CGGTCGGGGT
    CGACGACCGC GTGGGGCTGC GGCACGATCC AGTCCCGCGG CGCGAGCGTC

CCGGCCCAGG TGGCTGCGCC GGCAGCCACG GCGCCAGACG GCCAGCCCCA
    GCTGCTGGCG CACCCCGACG CCGTGCTAGG TCAGGGCGCC GCGCTCGCAG

301 ACGTACGCCC AGGGCACCGT CAGCGGGCTC ATCCGCACCA ACGTGTGCGC
    CGAGCCGGGT GACTCCGGGG GGTCGCTGAT CGCGGGCACC CAGGCGCGGG

TGCATGCGGG TCCCGTGGCA GTCGCCCGAG TAGGCGTGGT TGCACACGCG
    GCTCGGCCCA CTGAGGCCCC CCAGCGACTA GCGCCCGTGG GTCCGCGCCC

401 GCGTGACGTC CGGCGGCTCC GGCAACTGC
    CGCACTGCAG GCCGCCGAGG CCGTTGACG
```

Cellulomonas xylanilytica (LMG 21723)
(SEQ ID NO: 66)

```
  1 RCSIGFAVTG GFVTAGHCGR SGATTTSPSG TFAGSSFPGN DYAWVRAASG

51 NTPVGAVNRY DGSRVTVAGS TDAAVGAAVC RSGSTTAWGC GTIQSRGASV

101 TYAQGTVSGL IRTNVCAEPG DSGGSLIAGT QARGVTSGGS GNC
```

Oerskovia turbata (DSM 20577)
(SEQ ID NO: 67)

```
  1 ATGGCACGAT CATTCTGGAG GACGCTCGCC ACGGCGTGCG CCGCGACGGC
    TACCGTGCTA GTAAGACCTC CTGCGAGCGG TGCCGCACGC GGCGCTGCCG

51 ACTGGTTGCC GGCCCCGCAG CGCTCACCGC GAACGCCGCG ACGCCCACCC
    TGACCAACGG CCGGGGCGTC GCGAGTGGCG CTTGCGGCGC TGCGGGTGGG

101 CCGACACCCC GACCGTTTCA CCCCAGACCT CCTCGAAGGT CTCGCCCGAG
    GGCTGTGGGG CTGGCAAAGT GGGGTCTGGA GGAGCTTCCA GAGCGGGCTC

151 GTGCTCCGCG CCCTCCAGCG GGACCTGGGG CTGAGCGCCA AGGACGCGAC
    CACGAGGCGC GGGAGGTCGC CCTGGACCCC GACTCGCGGT TCCTGCGCTG

201 GAAGCGTCTG GCGTTCCAGT CCGACGCGGC GAGCACCGAG GACGCTCTCG
    CTTCGCAGAC CGCAAGGTCA GGCTGCGCCG CTCGTGGCTC CTGCGAGAGC

251 CCGACAGCCT GGACGCCTAC GCGGGCGCCT GGGTCGACCC TGCGAGGAAC
    GGCTGTCGGA CCTGCGGATG CGCCCGCGGA CCCAGCTGGG ACGCTCCTTG

301 ACCCTGTACG TCGGCGTCGC CGACAGGGCC GAGGCCAAGG AGGTCCGTTC
    TGGGACATGC AGCCGCAGCG GCTGTCCCGG CTCCGGTTCC TCCAGGCAAG

351 GGCCGGAGCG ACCCCCGTGG TCGTCGACCA CACGCTCGCC GAGCTCGACA
    CCGGCCTCGC TGGGGGCACC AGCAGCTGGT GTGCGAGCGG CTCGAGCTGT
```

```
401  CGTGGAAGGC GGCGCTCGAC GGTGAGCTCA ACGACCCCGC GGGCGTCCCG
     GCACCTTCCG CCGCGAGCTG CCACTCGAGT TGCTGGGGCG CCCGCAGGGC

451  AGCTGGTTCG TCGACGTCAC GACCAACCAG GTCGTCGTCA ACGTGCACGA
     TCGACCAAGC AGCTGCAGTG CTGGTTGGTC CAGCAGCAGT TGCACGTGCT

501  CGGCGGACGC GCCCTCGCGG AGCTGGCTGC CGCGAGCGCG GGCGTGCCCG
     GCCGCCTGCG CGGGAGCGCC TCGACCGACG GCGCTCGCGC CCGCACGGGC

551  CCGACGCCAT CACCTACGTG ACGACGACCG AGGCTCCTCG TCCCCTCGTC
     GGCTGCGGTA GTGGATGCAC TGCTGCTGGC TCCGAGGAGC AGGGGAGCAG

601  GACGTGGTGG GCGGCAACGC GTACACCATG GGTTCGGGCG GCGCTGCTC
     CTGCACCACC CGCCGTTGCG CATGTGGTAC CCAAGCCCGC CGCGACGAG

651  GGTCGGCTTC GCGGTGAACG GGGGCTTCAT CACGGCCGGG CACTGCGGCT
     CCAGCCGAAG CGCCACTTGC CCCCGAAGTA GTGCCGGCCC GTGACGCCGA

701  CGGTCGGCAC CCGCACCTCG GGGCCGGGCG GCACGTTCCG GGGGTCGAAC
     GCCAGCCGTG GGCGTGGAGC CCCGGCCCGC CGTGCAAGGC CCCCAGCTTG

751  TTCCCCGGCA ACGACTACGC CTGGGTGCAG GTCGACGCGG GTAACACCCC
     AAGGGGCCGT TGCTGATGCG GACCCACGTC CAGCTGCGCC CATTGTGGGG

801  GGTCGGCGCG GTCAACAACT ACAGCGGTGG GCGCGTCGCG GTCGCAGGGT
     CCAGCCGCGC CAGTTGTTGA TGTCGCCACC CGCGCAGCGC CAGCGTCCCA

851  CGACGGCCGC GCCCGTGGGG GCCTCGGTCT GCCGGTCCGG TTCCACGACG
     GCTGCCGGCG CGGGCACCCC CGGAGCCAGA CGGCCAGGCC AAGGTGCTGC

901  GGCTGGCACT GCGGCACCAT CGGCGCGTAC AACACCTCGG TGACGTACCC
     CCGACCGTGA CGCCGTGGTA GCCGCGCATG TTGTGGAGCC ACTGCATGGG

951  GCAGGGCACC GTCTCGGGGC TCATCCGCAC GAACGTGTGC GCCGAGCCCG
     CGTCCCGTGG CAGAGCCCCG AGTAGGCGTG CTTGCACACG CGGCTCGGGC

1001 GCGACTCGGG CGGCTCGCTC CTCGCGGGCA ACCAGGCGCA GGGCGTGACC
     CGCTGAGCCC GCCGAGCGAG GAGCGCCCGT TGGTCCGCGT CCCGCACTGG

1051 TCGGGCGGGT CGGGCAACTG CTCGTCGGGC GGGACGACGT ACTTCCAGCC
     AGCCCGCCCA GCCCGTTGAC GAGCAGCCCG CCCTGCTGCA TGAAGGTCGG

1101 CGTCAACGAG GCCCTCGGGG GGTACGGGCT CACGCTCGTG ACCTCTGACG
     GCAGTTGCTC CGGGAGCCCC CCATGCCCGA GTGCGAGCAC TGGAGACTGC

1151 GTGGGGGCCC GAGCCGCCGC CGACCGGGTG CCAGGGCTAT GCGCGGACCT
     CACCCCCGGG CTCGGCGGCG GCTGGCCCAC GGTCCCGATA CGCGCCTGGA

1201 ACCAGGGCAG CGTCTCGGCC GGGACGTCGG TCGCGCAGCG AACGGTTCGT
     TGGTCCCGTC GCAGAGCCGG CCCTGCAGCC AGCGCGTCGC TTGCCAAGCA

1251 ACGTCACGAC CGGGGGCGGG CGACCGGGTG TGCC
     TGCAGTGCTG GCCCCCGCCC GCTGGCCCAC ACGG
```

*Oerskovia turbata* (DSM 20577)

(SEQ ID NO: 68)

```
  1  MARSFWRTLA TACAATALVA GPAALTANAA TPTPDTPTVS PQTSSKVSPE

51  VLRALQRDLG LSAKDATKRL AFQSDAASTE DALADSLDAY AGAWVDPARN

101  TLYVGVADRA EAKEVRSAGA TPVVVDHTLA ELDTWKAALD GELNDPAGVP

151  SWFVDVTTNQ VVVNVHDGGR ALAELAAASA GVPADAITYV TTTEAPRPLV

201  DVVGGNAYTM GSGGRCSVGF AVNGGFITAG HCGSVGTRTS GPGGTFRGSN

251  FPGNDYAWVQ VDAGNTPVGA VNNYSGGRVA VAGSTAAPVG ASVCRSGSTT

301  GWHCGTIGAY NTSVTYPQGT VSGLIRTNVC AEPGDSGGSL LAGNQAQGVT

351  SGGSGNCSSG GTTYFQPVNE ALGGYGLTLV TSDGGGPSRR RPGARAMRGP

401  TRAASRPGRR SRSERFVRHD RGRATGCA
```

*Oerskovia jenensis* (DSM 46000)

(SEQ ID NO: 69)

```
  1  GCCGCTGCTC GGTCGGCTTC GCGGTGAACG GCGGCTTCGT CACCGCAGGC
     CGGCGACGAG CCAGCCGAAG CGCCACTTGC CGCCGAAGCA GTGGCGTCCG
```

-continued

```
 51  CACTGCGGGA CGGTGGGCAC CCGCACCTCG GGGCCGGGCG GCACGTTCCG
     GTGACGCCCT GCCACCCGTG GGCGTGGAGC CCCGGCCCGC CGTGCAAGGC

101  CGGGTCGAGC TTCCCCGGCA ACGACTACGC CTGGGTGCAG GTCGACGCGG
     GCCCAGCTCG AAGGGGCCGT TGCTGATGCG GACCCACGTC CAGCTGCGCC

151  GGAACACCCC GGTCGGGGCC GTCAACAACT ACAGCGGTGG ACGCGTCGCG
     CCTTGTGGGG CCAGCCCCGG CAGTTGTTGA TGTCGCCACC TGCGCAGCGC

201  GTCGCGGGCT CGACGGCCGC ACCCGTGGGT TCCTCGGTCT GCCGGTCCGG
     CAGCGCCCGA GCTGCCGGCG TGGGCACCCA AGGAGCCAGA CGGCCAGGCC

251  TTCCACGACG GGCTGGCGCT GCGGCACGAT CGCGGCCTAC AACAGCTCGG
     AAGGTGCTGC CCGACCGCGA CGCCGTGCTA GCGCCGGATG TTGTCGAGCC

301  TGACGTACCC GCAGGGGACC GTCTCCGGGC TCATCCGCAC CAACGTGTGC
     ACTGCATGGG CGTCCCCTGG CAGAGGCCCG AGTAGGCGTG GTTGCACACG

351  GCCGAGCCGG GCGACTCGGG CGGCTCGCTC CTCGCGGGCA ACCAGGCACA
     CGGCTCGGCC CGCTGAGCCC GCCGAGCGAG GAGCGCCCGT TGGTCCGTGT

401  GGGCCTGACG TCGGGCGGGT CGGGCAACTG CTCGTCGGGC GGCACGACGT
     CCCGGACTGC AGCCCGCCCA GCCCGTTGAC GAGCAGCCCG CCGTGCTGCA

451  ACTTCCAGCC CGTCAACGAG GCGCTCTCGG CCTACGGCCT CACGCTCGTG
     TGAAGGTCGG GCAGTTGCTC CGCGAGAGCC GGATGCCGGA GTGCGAGCAC

501  ACCTCCGGCG GCAGGGGCAA CTGC
     TGGAGGCCGC CGTCCCCGTT GACG

Oerskovia jenensis (DSM 46000)
                                                      (SEQ ID NO: 70)
  1  RCSVGFAVNG GFVTAGHCGT VGTRTSGPGG TFRGSSFPGN DYAWVQVDAG

51  NTPVGAVNNY SGGRVAVAGS TAAPVGSSVC RSGSTTGWRC GTIAAYNSSV

101  TYPQGTVSGL IRTNVCAEPG DSGGSLLAGN QAQGLTSGGS GNCSSGGTTY

151  FQPVNEALSA YGLTLVTSGG RGNC

Cellulosimicrobium cellulans (DSM 20424)
                                                      (SEQ ID NO: 71)
  1  CCACGGGCGG CGGGTCGGGC AGCGCGCTCG TCGGGCTCGC GGGCAAGTGC
     GGTGCCCGCC GCCCAGCCCG TCGCGCGAGC AGCCCGAGCG CCCGTTCACG 51  ATCGACGTCC CCGGGTCCGA CTTCAGTGAC GGCAAGCGCC TCCAGCTGTG
     TAGCTGCAGG GGCCCAGGCT GAAGTCACTG CCGTTCGCGG AGGTCGACAC 101  GACGTGCAAC GGGTCGCAGG CAGCGCTGGA CGTTCGAAGC CGACGGCACC
     CTGCACGTTG CCCAGCGTCC GTCGCGACCT GCAAGCTTCG GCTGCCGTGG 151  GTACGCGCGG GCGGCAAGTG CATGGACGTC GCGTGGGCGC CGCGGCCGAC
     CATGCGCGCC CGCCGTTCAC GTACCTGCAG CGCACCCGCG GCGCCGGCTG 201  GGCACGGCGC TCCAGCTCGC GAACTGCACG GCAACGCGGC CCAGAAGTTC
     CCGTGCCGCG AGGTCGAGCG CTTGACGTGC CGTTGCGCCG GGTCTTCAAG 251  GTGCTCAACG GCGCGGGCGA CCTCGTGTCG GTGCTGGCGA ACAAAGTGCG
     CACGAGTTGC CGCGCCCGCT GGAGCACAGC CACGACCGCT TGTTTCACGC 301  TCGACGCCGC CGGGTGCGCA CCGAGGTACT CGCGGCGCCG TACGAGCTCA
     AGCTGCGGCG GCCCACGCGT GGCTCCATGA GCGCCGCGGC ATGCTCGAGT 351  CGGCGACGTG CGCGGCGGCG ACCGCTACAT CACACGGGAC CCGGGCGCGT
     GCCGCTGCAC GCGCCGCCGC TGGCGATGTA GTGTGCCCTG GGCCCGCGCA 401  CGTCGGGCTC GGCCTGCTCG ATCGGGTACG CCGTCCAGGG CGGCTTCGTC
     GCAGCCCGAG CCGGACGAGC TAGCCCATGC GGCAGGTCCC GCCGAAGCAG 451  ACGGCGGGGC ACTGCGGACG CGGCGGGACA AGGAGAGTGC TCACCGCGAG
     TGCCGCCCCG TGACGCCTGC GCCGCCCTGT TCCTCTCACG AGTGGCGCTC 501  CTGGGCGCGC ATGGGGACGG TCCAGGCGGC GTCGTTCCCC GGCCACGACT
     GACCCGCGCG TACCCCTGCC AGGTCCGCCG CAGCAAGGGG CCGGTGCTGA 551  ACGCGTGGGT GCGCGTCGAC GCCGGGTTCT CCCCCGTCCC GCGGGTGAAC
     TGCGCACCCA CGCGCAGCTG CGGCCCAAGA GGGGGCAGGG CGCCCACTTG 601  AACTACGCCG GCGGCACCGT CGACGTCGCC GGCTCGGCCG AGGCGCCCGT
     TTGATGCGGC CGCCGTGGCA GCTGCAGCGG CCGAGCCGGC TCCGCGGGCA
```

-continued

```
651  GGGTGCGTCG GTGTGCCGCT CGGGCGCCAC GACCGGCTGG CGCTGCGGCG
     CCCACGCAGC CACACGGCGA GCCCGCGGTG CTGGCCGACC GCGACGCCGC

701  TCATCGAGCA GAAGAACATC ACCGTCAACT ACGGCAACGG CGACGTTCCC
     AGTAGCTCGT CTTCTTGTAG TGGCAGTTGA TGCCGTTGCC GCTGCAAGGG

751  GGCCTCGTGC GCGGCAGCGC GTGCGCGGAG GGCGGCGACT CGGGCGGGTC
     CCGGAGCACG CGCCGTCGCG CACGCGCCTC CCGCCGCTGA GCCCGCCCAG

801  GGTGATCTCC GGCAACCAGG CGCAGGGCGT CACGTCGGGC AGGATCAACG
     CCACTAGAGG CCGTTGGTCC GCGTCCCGCA GTGCAGCCCG TCCTAGTTGC

851  ACTGCTCGAA CGGCGGCAAG TTCCTCTACC AGCCCGATCG ACGGCCTGTC
     TGACGAGCTT GCCGCCGTTC AAGGAGATGG TCGGGCTAGC TGCCGGACAG

901  GCTCGTGACC ACGGGCGGCG GGTCGGGCAG CGCGCTCGTC GGGCTCGCGG
     CGAGCACTGG TGCCCGCCGC CCAGCCCGTC GCGCGAGCAG CCCGAGCGCC

951  GCAAGTGCAT CGACGTCCCC GGGTCCGACT TCAG
     CGTTCACGTA GCTGCAGGGG CCCAGGCTGA AGTC
```

*Cellulosimicrobium cellulans* (DSM 20424)
(SEQ ID NO: 72)

```
  1  PRAAGRAARS SGSRASASTS PGPTSVTASA SSCGRATGRR QRWTFEADGT
 51  VRAGGKCMDV AWAPRPTARR SSSRTARQRG PEVRAQRRGR PRVGAGEQSA
101  STPPGAHRGT RGAVRAHGDV RGGDRYITRD PGASSGSACS IGYAVQGGFV
151  TAGHCGRGGT RRVLTASWAR MGTVQAASFP GHDYAWVRVD AGFSPVPRVN
201  NYAGGTVDVA GSAEAPVGAS VCRSGATTGW RCGVIEQKNI TVNYGNGDVP
251  GLVRGSACAE GGDSGGSVIS GNQAQGVTSG RINDCSNGGK FLYQPDRRPV
301  ARDHGRRVGQ RARRARGQVH RRPRVRLQ
```

*Promicromonospora citrea* (DSM 43110)
(SEQ ID NO: 73)

```
  1  TTCCCCGGCA ACGACTACGC GTGGGTGAAC ACGGGCACGG ACGACACCCT
     AAGGGGCCGT TGCTGATGCG CACCCACTTG TGCCCGTGCC TGCTGTGGGA

51  CGTCGGCGCC GTGAACAACT ACAGCGGCGG CACGGTCAAC GTCGCGGGCT
     GCAGCCGCGG CACTTGTTGA TGTCGCCGCC GTGCCAGTTG CAGCGCCCGA

101  CGACCCGTGC CGCCGTCGGC GCGACGGTCT GCCGCTCGGG CTCCACGACC
     GCTGGGCACG GCGGCAGCCG CGCTGCCAGA CGGCGAGCCC GAGGTGCTGG

151  GGCTGGCACT GCGGCACCAT CCAGGCGCTG AACGCGTCGG TCACCTACGC
     CCGACCGTGA CGCCGTGGTA GGTCCGCGAC TTGCGCAGCC AGTGGATGCG

201  CGAGGGCACC GTGAGCGGCC TCATCCGCAC CAACGTGTGC GCCGAGCCCG
     GCTCCCGTGG CACTCGCCGG AGTAGGCGTG GTTGCACACG CGGCTCGGGC

251  GCGACTC
     CGCTGAG
```

*Promicromonospora citrea* (DSM 43110)
(SEQ ID NO: 74)

```
  1  FPGNDYAWVN TGTDDTLVGA VNNYSGGTVN VAGSTRAAVG ATVCRSGSTT
 51  GWHCGTIQAL NASVTYAEGT VSGLIRTNVC AEPGD
```

*Promicromonospora sukumoe* (DSM 44121)
(SEQ ID NO: 75)

```
  1  TTCCCCGGCA ACGACTACGC GTGGGTGAAC GTCGGCTCCG ACGACACCCC
     AAGGGGCCGT TGCTGATGCG CACCCACTTG CAGCCGAGGC TGCTGTGGGG

51  GATCGGTGCG GTCAACAACT ACAGCGGCGG CACCGTGAAC GTCGCGGGCT
     CTAGCCACGC CAGTTGTTGA TGTCGCCGCC GTGGCACTTG CAGCGCCCGA

101  CGACCCAGGC CGCCGTCGGC TCCACCGTCT GCCGCTCCGG TTCCACGACC
     GCTGGGTCCG GCGGCAGCCG AGGTGGCAGA CGGCGAGGCC AAGGTGCTGG

151  GGCTGGCACT GCGGCACCAT CCAGGCCTTC AACGCGTCGG TCACCTACGC
     CCGACCGTGA CGCCGTGGTA GGTCCGGAAG TTGCGCAGCC AGTGGATGCG

201  CGAGGGCACC GTGTCCGGCC TGATCCGCAC CAACGTCTGC GCCGAGCCCG
     GCTCCCGTGG CACAGGCCGG ACTAGGCGTG GTTGCAGACG CGGCTCGGGC
```

-continued

```
251    GCGACTC
       CGCTGAG
```

*Promicromonospora sukumoe* (DSM 44121)

(SEQ ID NO: 76)
```
  1    FPGNDYAWVN VGSDDTPIGA VNNYSGGTVN VAGSTQAAVG STVCRSGSTT

51    GWHCGTIQAF NASVTYAEGT VSGLIRTNVC AEPGD
```

*Xylanibacterium ulmi* (LMG 21721)

(SEQ ID NO: 77)
```
  1    GCCGCTGCTC GATCGGGTTC GCCGTGACGG GCGGCTTCGT GACCGCCGGC
       CGGCGACGAG CTAGCCCAAG CGGCACTGCC CGCCGAAGCA CTGGCGGCCG

51    CACTGCGGAC GGTCCGGCGC GACGACGACG TCCGCGAGCG GCACGTTCGC
       GTGACGCCTG CCAGGCCGCG CTGCTGCTGC AGGCGCTCGC CGTGCAAGCG

101    CGGGTCCAGC TTTCCCGGCA ACGACTACGC CTGGGTCCGC GCGGCCTCGG
       GCCCAGGTCG AAAGGGCCGT TGCTGATGCG GACCCAGGCG CGCCGGAGCC

151    GAACACGCCG GTCGGTGCGG TGAACCGCTA CGACGGCAGC CGGGTGACCG
       CTTGTGCGGC CAGCCACGCC ACTTGGCGAT GCTGCCGTCG GCCCACTGGC

201    TGGCCGGGTC CACCGACGCG GCCGTCGGTG CCGCGGTCTG CCGGTCGGGG
       ACCGGCCCAG GTGGCTGCGC CGGCAGCCAC GGCGCCAGAC GGCCAGCCCC

251    TCGACGACCG CGTGGCGCTG CGGCACGATC CAGTCCCGCG GCGCGACGGT
       AGCTGCTGGC GCACCGCGAC GCCGTGCTAG GTCAGGGCGC CGCGCTGCCA

301    CACGTACGCC CAGGGCACCG TCAGCGGGCT CATCCGCACC AACGTGTGCG
       GTGCATGCGG GTCCCGTGGC AGTCGCCCGA GTAGGCGTGG TTGCACACGC

351    CCGAGCCGGG TGACTCCGGG GGGTCGCTGA TCGCGGGCAC CCAGGCGCAG
       GGCTCGGCCC ACTGAGGCCC CCCAGCGACT AGCGCCCGTG GGTCCGCGTC

401    GGCGTGACGT CCGGCGGCTC CGGCAACTGC
       CCGCACTGCA GGCCGCCGAG GCCGTTGACG
```

*Xylanibacterium ulmi*: (LMG 21721)

(SEQ ID NO: 78)
```
  1    RCSIGFAVTG GFVTAGHCGR SGATTTSASG TFAGSSFPGN DYAWVRAASG

51    NTPVGAVNRY DGSRVTVAGS TDAAVGAAVC RSGSTTAWRC GTIQSRGATV

101    TYAQGTVSGL IRTNVCAEPG DSGGSLIAGT QAQGVTSGGS G
```

Inverse PCR

Inverse PCR was used to determine the full-length serine protease genes from chromosomal DNA of bacterial strains of the suborder *Micrococcineae* shown by PCR or immuno-blotting to be novel homologues of the new *Cellulomonas* sp. 69B4 protease described herein.

Digested DNA was purified using the PCR purification kit (Qiagen, Catalogue #28106), and self-ligated with T4 DNA ligase (Invitrogen) according to the manufacturers' instructions. Ligation mixtures were purified with the PCR purification kit (Qiagen) and a PCR was performed with primers selected from the following list;

```
RV-1 Rest        5' - ACCCACGCGTAGTCGTTGCC - 3'         (SEQ ID NO: 79)

RV-1 Cellul      5' - ACCCACGCGTAGTCGTKGCCGGGG - 3'     (SEQ ID NO: 80)

RV-2 biaz-fimi   5' - TCGTCGTGGTCGCGCCGG - 3'           (SEQ ID NO: 81)

RV-2 cella-flavi 5' - CGACGTGCTCGCGCCCG - 3'            (SEQ ID NO: 82)

RV-2 cellul      5' - CGCGCCCAGCTCGCGGTG - 3'           (SEQ ID NO: 83)

RV-2 turb        5' - CGGCCCCGAGGTGCGGGTGCCG - 3'       (SEQ ID NO: 84)

Fw-1 biaz-fimi   5' - CAGCGTCTCCGGCCTCATCCGC - 3'       (SEQ ID NO: 85)

Fw-1 cella-flavi 5' - CTCGGTCTCGGGCCTCATCCGC - 3'       (SEQ ID NO: 86)

Fw-1 cellul      5' - CGACGTTCCCGGCCTCGTGCGC - 3'       (SEQ ID NO: 87)
```

```
Fw-1 turb        5' - CACCGTCTCGGGGCTCATCCGC - 3'       (SEQ ID NO: 88)

Fw-2 rest        5' - AGCARCGTGTGCGCCGAGCC - 3'         (SEQ ID NO: 89)

Fw-2 cellul      5' - GGCAGCGCGTGCGCGGAGGG - 3'         (SEQ ID NO: 90)

Fw-1 gelida      5' - GCCGCTGCTCGATCGGGTTC - 3'         (SEQ ID NO: 91)

Rv-1 gelida      5' - GCAGTTGCCGGAGCCGCCGGACGT - 3'.    (SEQ ID NO: 92)
```

The amplified PCR products were examined by agarose gel electrophoresis (0.8% agarose in TBE buffer (Invitrogen)). Distinct bands in the range 1.3-2.2 kbp for each organism were excised from the gel, purified using the Qiagen gel extraction kit and the sequence analyzed by BaseClear. Sequence analysis revealed that these DNA fragments covered some additional parts of protease gene homologues to the Cellulomonas 69B4 protease gene.

Genome Walking Using Rapid Amplification of Genomic Ends (RAGE)

A genome walking methodology (RAGE) known in the art was used to determine the full-length serine protease genes from chromosomal DNA of bacterial strains of the suborder *Micrococcineae* shown by PCR or immunoblotting to be novel homologues of the new *Cellulomonas* sp. 69B4 protease. RAGE was performed using the Universal GenomeWalker™ Kit (BD Biosciences Clontech), some with modifications to the manufacturer's protocol (BD Biosciences user manual PT3042-1, Version # PR03300). Modifications to the manufacturer's protocol included addition of DMSO (3 μL) to the reaction mixture in 50 μL total volume due to the high GC content of the template DNA and use of Advantage™—GC Genomic Polymerase Mix (BD Biosciences Clontech) for the PCR reactions which were performed as follows;

|  | PCR 1 | PCR 2 |
|---|---|---|
| 99° C. - 0.05 sec | | |
| 94° C. - 0.25 sec/72° C. - 3.00 min | 7 cycles | 4 cycles |
| 94° C. - 0.25 sec/67° C. - 4.00 min | 39 cycles | 24 cycles |
| 67° C. - 7.00 min | | |
| 15° C. - 1.00 min | | |

PCR was performed with primers (Invitrogen, Paisley, UK) selected from the following list (listed in 5' to 3' orientation);

```
RV-1 Rest          ACCCACGCGTAGTCGTTGCC              (SEQ ID NO: 79)

RV-1 Cellul        ACCCACGCGTAGTCGTKGCCGGGG          (SEQ ID NO: 80)

RV-2 biaz-fimi     TCGTCGTGGTCGCGCCGG                (SEQ ID NO: 81)

RV-2 cella-flavi   CGACGTGCTCGCGCCCG                 (SEQ ID NO: 82)

RV-2 cellul        CGCGCCCAGCTCGCGGTG                (SEQ ID NO: 83)

RV-2 turb          CGGCCCCGAGGTGCGGGTGCCG            (SEQ ID NO: 84)

Fw-1 biaz-fimi     CAGCGTCTCCGGCCTCATCCGC            (SEQ ID NO: 85)

Fw-1 cella-flavi   CTCGGTCTCGGGCCTCATCCGC            (SEQ ID NO: 86)

Fw-1 cellul        CGACGTTCCCGGCCTCGTGCGC            (SEQ ID NO: 87)

Fvv-1 turb         CACCGTCTCGGGGCTCATCCGC            (SEQ ID NO: 88)

Fw-2 rest          AGCARCGTGTGCGCCGAGCC              (SEQ ID NO: 89)

Fw-2 cellul        GGCAGCGCGTGCGCGGAGGG              (SEQ ID NO: 90)

Fw-1 gelida        GCCGCTGCTCGATCGGGTTC              (SEQ ID NO: 91)

Rv-1 gelida        GCAGTTGCCGGAGCCGCCGGACGT          (SEQ ID NO: 92)

Flavi FW1          TGCGCCGAGCCCGGCGACTCCGGC          (SEQ ID NO: 93)

Flavi FW2          GGCACGACGTACTTCCAGCCCGTGAAC       (SEQ ID NO: 94)

Flavi RV1          GACCCACGCGTAGTCGTTGCCGGGGAACGACGA (SEQ ID NO: 95)

Flavi RV2          GAAGGTCCCCGACGGTGACGACGTGCTCGCGCC (SEQ ID NO: 96)

Turb FW1           CAGGCGCAGGGCGTGACCTCGGGCGGGTCG    (SEQ ID NO: 97)

Turb FW2           GGCGGGACGACGTACTTCCAGCCCGTCAA     (SEQ ID NO: 98)

Cellu RV1          CACCCACGCGTAGTCGTGGCCGGGGAACGA    (SEQ ID NO: 99)

Cellu RV2          GAAGCCGCCCTGGACGGCGTACCCGATCGAGCA (SEQ ID NO: 100)
```

| | | |
|---|---|---|
| Cellu FW1 | TGCGCGGAGGGCGGCGACTCGGGCGGGTCG | (SEQ ID NO: 101) |
| Cellu FW2 | TTCCTCTACCAGCCCGTCAACCCGATCCTA | (SEQ ID NO: 102) |
| Cella RV2 | CGCCGCGGGACGAACCCGCCCTCGACCGCAA | (SEQ ID NO: 103) |
| Cella RV1 | CGCGTAGTCGTTGCCGGGGAACGACGAGCC | (SEQ ID NO: 104) |
| Cella FW1 | GGCCTCATCCGCACGAGCGTGTGCGCCGAG | (SEQ ID NO: 105) |
| Cella FW2 | ACGTCGGGCGGGTCCGGCAACTGCCGCTACGGGGGC | (SEQ ID NO: 106) |
| Gelida RV1 | GAGCCCGTACACCCGGAGGGCCTCGTTGACGGGCTGGAA | (SEQ ID NO: 107) |
| Gelida RV2 | CGTCACGCCCTGCGCCTGGTTGCCCGCGAG | (SEQ ID NO: 108) |
| Gelida FW1 | TCCAGCCCGTCAACGAGGCCCTCCGGGTGTACGGGCTC | (SEQ ID NO: 109) |
| Gelida FW2 | ACGTCGGTCGCGCAGCCGAACGGTTCGTACGTC | (SEQ ID NO: 110) |
| Biazot RV1 | CGTGGTCGCGCCGGTCGTGCCGCAGTGCCC | (SEQ ID NO: 111) |
| Biazot RV2 | GACGACGACCGTGTTGGTAGTGACGTCGACGTACCA | (SEQ ID NO: 112) |
| Biazot FW1 | TCCACCACGGGGTGGCGCTGCGGGACGATC | (SEQ ID NO: 113) |
| Biazot FW2 | GTGTGCGCCGAGCCCGGCGACTCCGGCGGC | (SEQ ID NO: 114) |
| Turb RV C-mature | GCTCGGGCCCCCACCGTCAGAGGTCACGAGCGTGAG | (SEQ ID NO: 115) |
| Turb FW signal | ATGGCACGATCATTCTGGAGGACGCTCGCCACGGCG | (SEQ ID NO: 116) |
| Cellu internal FW | TGCTCGATCGGGTACGCCGTCCAGGGCGGCTTC | (SEQ ID NO: 117) |
| Cellu internal RV | TAGGATCGGGTTGACGGGCTGGTAGAGGAA | (SEQ ID NO: 118) |
| Biazot Int Fw | TGGTACGTCGACGTCACTACCAACACGGTCGTCGTC | (SEQ ID NO: 119) |
| Biazot Int Rv | 5' - GCCGCCGGAGTCGCCGGGCTCGGCGCACAC | (SEQ ID NO: 120) |
| flavi Nterm | 5' - GTSGACGTSATCGGSGGSAACGCSTACTAC | (SEQ ID NO: 121) |
| flavi Cterm | 5' - SGCSGTSGCSGGNGANGA | (SEQ ID NO: 122) |
| fimi Nterm | 5' - GTSGAYGTSATCGGCGGCGAYGCSTAC | (SEQ ID NO: 123) |
| fimi Cterm | 5' - SGASGCGTANCCCTGNCC | (SEQ ID NO: 124) |

The PCR products were subcloned in the pCR4-TOPO TA cloning vector (Invitrogen) and transformed to E. coli Top10 one-shot electrocompetent cells (Invitrogen). The transformants were incubated (37° C., 260 rpm, 16 hours) in 2×TY medium with 100 µg/ml ampicillin. The isolated plasmid DNA (isolated using the Qiagen Qiaprep pDNA isolation kit) was sequenced by BaseClear.

Sequence Analysis

Full length polynucleotide sequences were assembled from PCR fragment sequences using the ContigExpress and AlignX programs in Vector NTI suite v. 9.0.0 (Invitrogen) using the original polynucleotide sequence obtained in Example 4 as template and the ASP mature protease and ASP full-length sequence for alignment. The results for the polynucleotide sequences are displayed in Table 7-1 and the translated amino acid sequences are displayed in Table 7-2. For each of the natural bacterial strains the polynucleotide sequences and translated amino acid sequences for each of the homologous proteases are provided above.

Table 7-1 provides comparison information between ASP protease and various other sequences obtained from other bacterial strains. Amino acid sequence information for Asp-mature-protease homologues is available from 13 species:
1. *Cellulomonas biazotea* DSM 20112
2. *Cellulomonas flavigena* DSM 20109
3. *Cellulomonas fimi* DSM 20113
4. *Cellulomonas cellasea* DSM 20118
5. *Cellulomonas gelida* DSM 20111
6. *Cellulomonas iranensis* DSM 14784
7. *Cellulomonas xylanilytica* LMG 21723
8. *Oerskovia jenensis* DSM 46000
9. *Oerskovia turbata* DSM 20577
9. *Oerskovia turbata* DSM 20577
10. *Cellulosimicrobium cellulans* DSM 20424
11. *Promicromonospora citrea* DSM 43110
12. *Promicromonospora sukumoe* DSM 44121
13. *Xylanibacterium ulmi* LMG 21721

Notably, the sequence from Cellulomonas gelida at 48 amino acids is too short for useful consensus alignment. Sequence alignment against Asp-mature for the remaining 12 species are provided herein. To date, complete mature sequence has been determined for *Oerskovia turbata, Cellulomonas cellasea, Cellulomonas biazotea* and *Cellulosimicrobium cellulans*. However, there are some problems and sequence fidelity is not guaranteed for the sequence information known to the public, *Cellulomonas cellasea* protease is clearly homologous to Asp (61.4% identity). However, the sequencing of 10 independent PCR fragments of the C-terminal region all gives a stop codon at position 184, suggesting that there is no C-terminal prosequence. In addition, *Cellulosimicrobium cellulans* is a close relative of Cellulomonas and clearly has an Asp homologous protease. However, the sequence identity is low, only 47.7%. It contains an insertion of 4 amino acids at position 43-44 and it is uncertain where the N-terminus of the protein begins. Nonetheless, the data provided here clearly show that there are enzymes homologous to the ASP protease described herein. Thus, it is intended that the present invention encompass the ASP protease isolated from Cellulomonas strain 69B4, as well as other homologous proteases.

In this Table, the nucleotide numbering is based on full-length gene of 69B4 protease (SEQ ID NO:2), where nt 1-84 encode the signal peptide, nt 85-594 encode the N-terminal prosequence, nt 595-1161 encode the mature 69B4 protease, and nt 1162-1485 encode the C-terminal prosequence.

TABLE 7-1

Percent Identity of Homologous Polynucleotide Sequences from Natural Isolate Strains Compared with ASP Mature Protease Gene Sequence

| Strain | Total Base Pairs | Overlap* | % Identity Overlap Mature Protease |
|---|---|---|---|
| 69B4 (ASP) Protease | 1485 | 1-1485 | |
| Cellulomonas flavigena DSM20109 | 555 | 595-1156 | 72.3 |
| Cellulomonas biazotea DSM 20112 | 627 | 332-1355 | 73.7 |
| Cellulomonas fimi DSM 20113 | 474 | 595-1068 | 78.7 |

TABLE 7-1-continued

Percent Identity of Homologous Polynucleotide Sequences from Natural Isolate Strains Compared with ASP Mature Protease Gene Sequence

| Strain | Total Base Pairs | Overlap* | % Identity Overlap Mature Protease |
|---|---|---|---|
| Cellulomonas gelida DSM 20118 | 462 | 1018-1485 | 72.2 |
| Cellulomonas iranensis DSM14784 | 257 | 748-1004 | 75.2 |
| Cellulomonas cellasea DSM 20118 | 904 | 294-1201 | 72.7 |
| Cellulomonas xylanilytica LMG 21723 | 429 | 640-1068 | 75.1 |
| Oerskovia turbata DSM 20577 | 1284 | 1-1291 | 73.1 |
| Oerskovia jenensis DSM 46000 | 387 | 638-1158 | 72.7 |
| Cellulosimicrobium cellulans DSM20424 | 984 | 251-1199 | 63.1 |
| Promicromonospora citrea DSM 43110 | 257 | 748-1004 | 75.9 |
| Promicromonospora sukumoe DSM 44121 | 257 | 748-1004 | 77.4 |
| Xylanibacterium ulmi LMG21721 | 430 | 638-1068 | 77.0 |

The following Table (Table 7-2) provides information regarding the translated amino acid sequence data in natural isolate strains compared with full-length ASP.

TABLE 7-2

Translated Amino Acid Sequence Data Comparisons

| Strain | Total amino acids | Signal peptide overlap: position | N-terminal pro overlap: position | Mature protease overlap: position | C-terminal pro overlap: position |
|---|---|---|---|---|---|
| 69B4 (ASP) Protease | 495 | 28 (1-28) | 170 (29-198) | 189 (199-387) | 108 (388-495) |
| Cellulomonas flavigena DSM20109 | 185 | | | 185 (199-383) id 68.6% | |
| Cellulomonas biazotea DSM 20112 | 335 | | 84 (104-198) id 35.8% | 189 (199-387) id 70.4% complete | 62 (388-451) id 64.1% |
| Cellulomonas fimi DSM 20113 | 144 | | | 144 (199-342) id 74.3% | |
| Cellulomonas gelida DSM 20118 | 154 | | | 48 (340-387) id 68.8% | 106 (388-495) id 63.9% complete |
| Cellulomonas iranensis DSM14784 | 85 | | | 85 (250-334) id 65.9% | |
| Cellulomonas cellasea DSM 20118 | 301 | | 98 (99-198) id 31.0% | 189 (199-387) id 68.3% complete | 13 (388-400) id 30.8% |
| Cellulomonas xylanilytica LMG 21723 | 143 | | | 143 (214-356) id 73.4% | |
| Oerskovia turbata DSM 20577 | 428 | 29 (2-30) id 43.3% | 171 (31-198) id 44.4% | 188 (201-389) id 73.0% complete | 40 (390-429) id 10.0% |
| Oerskovia jenensis DSM 46000 | 174 | | | 174 (214-334) id 73.6% | |
| Cellulosimicrobium cellulans DSM20424 | 328 | | 117 (82-198) id 6% | 199 (199-387) id 47.7% complete | 12 (388-399) |

TABLE 7-2-continued

Translated Amino Acid Sequence Data Comparisons

| Strain | Total amino acids | Signal peptide overlap: position | N-terminal pro overlap: position | Mature protease overlap: position | C-terminal pro overlap: position |
|---|---|---|---|---|---|
| *Promicromonospora citrea* DSM 43110 | 85 | | | 85 (250-334) id 75.3% | |
| *Promicromonospora sukumoe* DSM 44121 | 85 | | | 85 (250-334) id 64.7% | |
| *Xylanibacterium ulmi* LMG21721 | 141 | | | 141 (214-354) id 72.3% | |

These results clearly show that bacterial strains of the suborder *Micrococcineae*, including the families Cellulomonadaceae and Promicromonosporaceae posess genes that are homologous with the 69B4 protease. Over the region of the mature 69B protease, the gene sequence identities range from about 60%-80%. The amino acid sequences of these homologous sequences exhibit about 45%-80% identity with the mature 69B4 protease protein. In contrast to the majority of streptogrisin proteases derived from members of the suborder Streptomycineae, these 69B4 (Asp) protease homologues from the suborder *Micrococcineae* possess six cysteine residues, which form three disulfide bridges in the mature 69B4 protease protein.

Indeed, in spite of the incomplete sequences provided herein and questions regarding fidelity, the present invention provides essential elements of the Asp group of proteases and comparisons with streptogrisins. Asp is uniquely Asp is characterized, along with Streptogrisin C, as having 3 disulfide bridges. In the following sequence, the Asp amino acids are printed in bold and the fully conserved residues are underlined. The active site residues are marked with # and double underlined. The cysteine residues are marked with * and underlined. The disulfide bonds are located between C17 and C38, C95 and C105, and C131 and C158.

Table 7-3 (below) indicates the positions where ASP and Streptogrisin C differ:

TABLE 7-3

Positions At Which ASP and Streptogrisin C Differ

| ASP Position | ASP Amino Acid | ASP Homologs | Streptogrisin C Amino Acid |
|---|---|---|---|
| 22 | A | R? | S |
| 25 | G | G | N |
| 28 | I | V | A |
| 51 | S | N? | T |
| 55 | N | H? | R |
| 57 | Y | Y | I |
| 65 | G | D | N |
| 74 | N | R | G |
| 76 | S | D | G |
| 77 | G | G | R |
| 79 | R | T | D |
| 88 | A | A | S |
| 122 | V | V | I |
| 125 | L | L | V |
| 126 | I | V | T |
| 141 | L | V | Y |
| 145 | N | T | S |

```
                                                          (SEQ ID NO: 125)
1          5        8   17         20              25         30   32
X D V [I, V] G G [N, D] [X9] C* S [I, V] G [F, Y ] A V X G G F [I, V] T A G H#

33    35       40      45        50       55             60
C* G [X2] G [X2] TN [X4] G T F X G S S F P G N D# Y A [F, W] V [X4]

65               72         75                        80
[G, D] [X2] [L, P] [X3] V N [N, R] [Y, H] [S, D] G [G, S] [R, T] V X V [A, T] G 85            90            95            100            105
[H, S] [T, Q] X A X V G [S, A] X V C* R S G [S, A] T T [G, A] W [H, R] C* G 112          115            120                  125
[T, Y] [I, V] [X3] [N, G] X [S, T] V X Y [P, A] [E, Q] G [T, S, D] V [R, S] G L 130  131          135  137   140
[I, V] R [T, G] [T, N, S] [V, A] C* A E [P, G] G D S# G G S [L, V] [L, V, I] [A. S]

145           150            155           158
G [N, T] Q A [Q, R] G [V, L] T S G [G, R] [S, I] [G, N] [N, D] C* [X2] G 162   167 169   189
G [X4] Q P [X21]
```

Example 8

Mass Spectrometric Sequencing of ASP Homologues

In this Example, experiments conducted to confirm the DNA-derived sequence as well as verify/establish the N-terminal and C-terminal sequences of the mature ASP homologues are described. The microorganisms utilized in these experiments were the following:

1. *Cellulomonas biazotea* DSM 20112
2. *Cellulomonas flavigena* DSM 20109
3. *Cellulomonas fimi* DSM 20113
4. *Cellulomonas cellasea* DSM 20118
7. *Oerskovia jenensis* DSM 46000
8. *Oerskovia turbata* DSM 20577
9. *Cellulosimicrobium cellulans* DSM 20424

The micropurified ASP homologues were subjected to mass spectrometry-based protein sequencing procedures which consisted of these major steps: micropurification, gel electrophoresis, in-gel proteolytic digestion, capillary liquid chromatography electrospray tandem mass spectrometry (nanoLC-ESI-MS/MS), database searching of the mass spectrometric data, and de novo sequencing. Details of these steps are described what follows. As described previously in Example 6, concentrated culture sample (about 200 ml) was added to 500 ml 1M CaCl2 and centrifuged at 14,000 rpm (model 5415C Eppendorf) for min. The supernatant was cooled on ice and acidified with 200 ml 1N HCl. After 5 min, 200 ml 50% trichloroacetic acid were added and the sample was centrifuged for 4 min at 14,000 rpm (model 5415C Eppendorf). The supernatant was discarded and the pellet was washed first with water and then with 90% acetone. The pellet, after being dried in the speed vac, was dissolved in 2× Protein Preparation (Tris-Glycine Sample Buffer; Novex) buffer and diluted 1+1 with water before being applied to the SDS-PAGE gel. SDS-PAGE was run with NuPAGE MES SDS Running Buffer. SDS-PAGE gel (1 mm NuPAGE 10% Bis-Tris; Novex) was developed and stained using standard protocols known in the art. Following SDS-PAGE, bands corresponding to ASP homologues were excised and processed for mass spectrometric peptide sequencing using standard protocols in the art.

Peptide mapping and sequencing was performed using capillary liquid chromatography electrospray tandem mass spectrometry (nanoLC-ESI-MS/MS). This analysis systems consisted of capillary HPLC system (model COLO; Waters) and mass spectrometer (model Qtof Ultima API; Waters). Peptides were loaded on a pre-column (PepMap100 C18, 5 um, 100 A, 300 um ID×1 mm; Dionex) and chromatographed on capillary columns (Biobasic C18 75 um×10 cm; New Objectives) using a gradient from 0 to 100% solvent B in 45 min at a flow rate of 200nL/min (generated using a static split from a pump flow rate of 5uL/min). Solvent A consisted of 0.1% formic acid in water; and solvent B was 0.1% formic acid in acetonitrile. The mass spectrometer was operated with the following parameters: spray voltage of 3.1 kV, desolavation zone at 15° C., mass spectra acquired from 400 to 1900 m/z, resolution of 6000 in v-mode. Tandem MS spectra were acquired in data dependent mode with two most intense peaks selected and fragmented with mass dependent collision energy (as specified by vendor) and collision gas (argon) at 2.5×10-5 torr.

Figure 4:
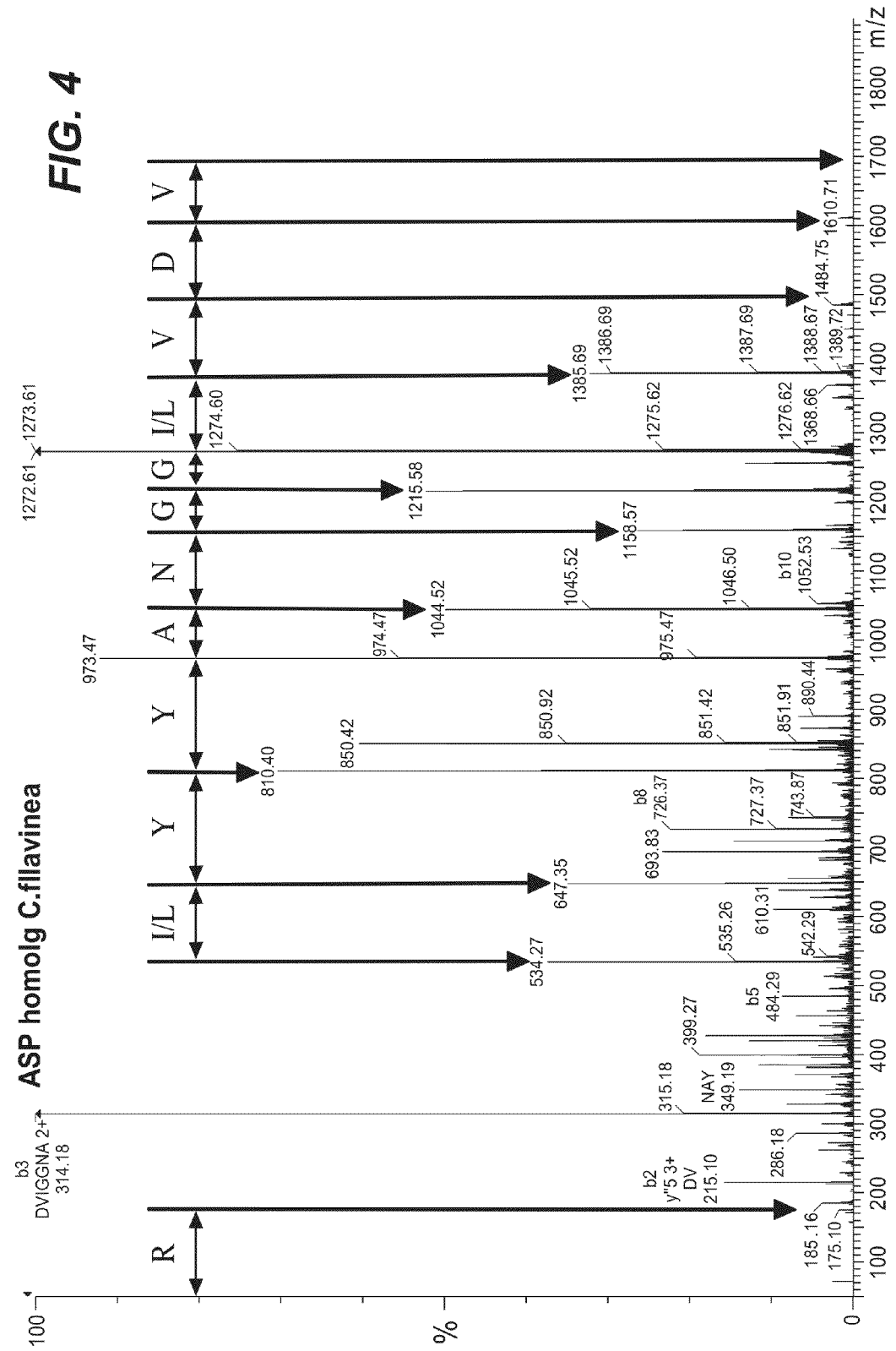
FIG. 4 shows the sequence of N-terminal most tryptic peptide from *C. flavigena*

The identities of the peptides were determined using a database search program (Mascot, Matrix Science) using a database containing ASP homologue DNA-obtained sequences. Database searches were performed with the following parameters: no enzyme selected, peptide error of 2.5Da, MS/MS ions error of 0.1Da, and variable modification of carboxyaminomethyl cysteine). For unmatched MS/MS spectra, manual de novo sequence assignments were performed. For example, FIG. 4 shows the sequence of N-terminal most tryptic peptide from *C. flavigena* determined from this tandem mass spectrum. In Table 8-1, the percentage of the sequence verified on the protein level for various homologues are reported along with N-terminal and C-terminal peptide sequences.

TABLE 8-1

Mass Spec. Sequencing of ASP Homologues

| ASP Homologue | Sequence Verified % Trypsin, Chymotrypsin Digests | N-terminal and C-terminal Sequences (Peptide Mass in Da) |
|---|---|---|
| *Cellulomonas cellasea* | 81, 81 | [IY]AWDAFAENVVDWSSR (SEQ ID NO:126)(2026.7) YGGTTYFQPVNEILQAY (SEQ ID NO:127)(1961.8) |
| *Cellulomonas flavigena* | 70, 50 | VDVI\LGGNAYYI/L[ . . . ]R (SEQ ID NO:128)(1697.7) |
| *Cellulomonas fimi* | 21, ND | VDVI/LGGDAY[ . . . ]R (SEQ ID NO:129)(1697.6) |

Notes:
ND: not determined
sequence not determined indicated in [..]
sequence order not determined indicated by [ ]
isobaric residues not distinguished indicated by I\L

Example 9

Protease Production in *Streptomyces lividans*

This Example describes experiments conductedto develop methods for production of protease by *S. lividans*. Thus, a plasmid comprising a polypeptide encoding a polypeptide having proteolytic activity was constructed and used such vector to transform *Streptomyces lividans* host cells The methods used for this transformation are more fully described in U.S. Pat. No. 6,287,839 and WO 02/50245, both of which are herein expressly incorporated by reference.

One plasmid developed during these experiments was designated as "pSEG69B4T." The construction of this plasmid made use of one pSEGCT plasmid vector (See, WO 02/50245). A glucose isomerase ("GI") promoter operably linked to the structural gene encoding the 69B4 protease was used to drive the expression of the protease. A fusion between the GI-promoter and the 69B4 signal-sequence, N-terminal prosequence and mature sequence was constructed by fusion-PCR techniques as a XbaI-BamHI fragment. The fragment was ligated into plasmid pSEGCT digested with XbaI and BamHI, resulting in plasmid pSEG69B4T (See, FIG. 6). Although the present Specification provides specific expression vectors, it is contemplated that additional vectors utilizing different promoters and/or signal sequences combined with various prosequences of the 69B4 protease will find use in the present invention.

Figure 7:
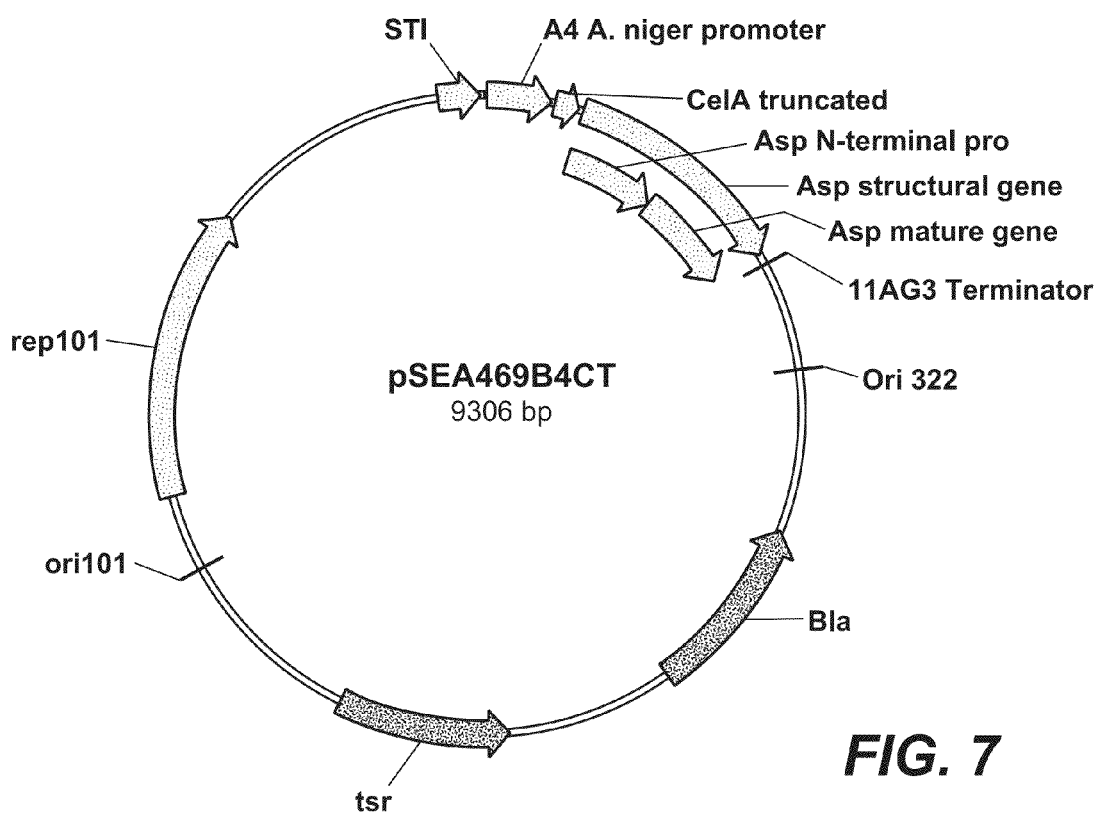
FIG. 7 provides the plasmid map of the pSEA469BCT vector.
Figure 8:
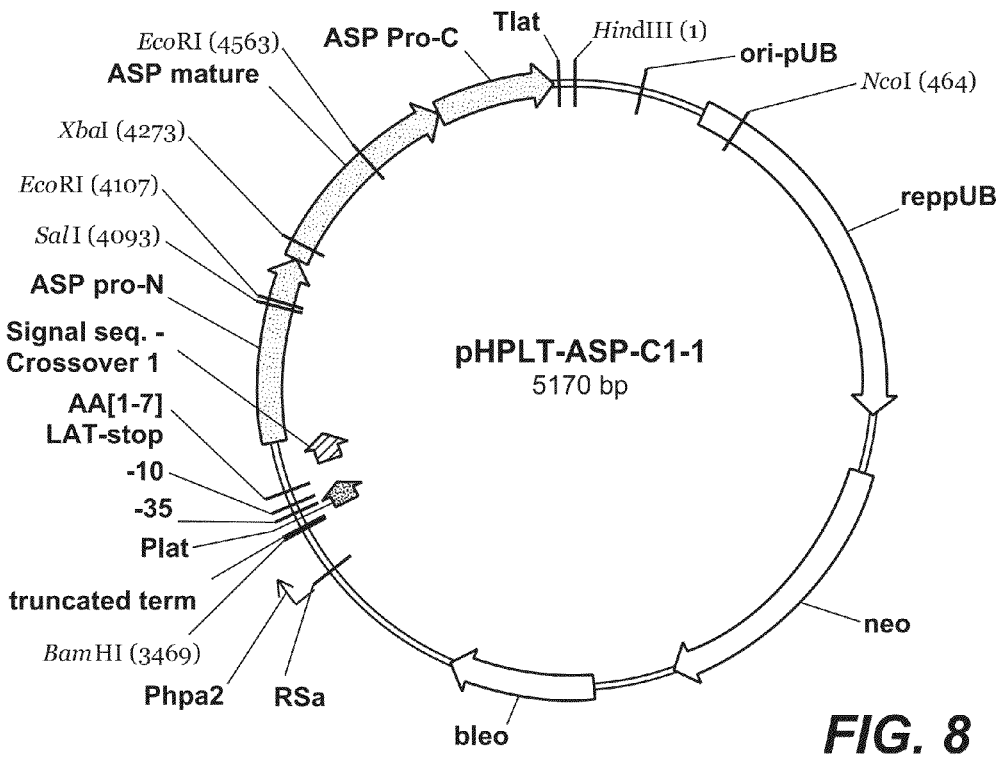
FIG. 8 provides the plasmid map of the pHPLT-Asp-C1-1 vector.

An additional plasmid developed during the experiments was designated as "pSEA469B4CT" (See, FIG. 7). As with the pSEG69B4T plasmid, one pSEGCT plasmid vector was used to construct this plasmid. To create the pSEA469B4CT, the *Aspergillus niger* (regulatory sequence) ("A4") promoter was operably linked to the structural gene encoding the 69B4 protease, and used to drive the expression of the protease. A fusion between the A4-promoter and the Cel A (from *Streptomyces coelicolor*) signal-sequence, the asp-N-terminal prosequence and the asp mature sequence was constructed by fusion-PCR techniques, as a XbaI-BamHI fragment. The fragment was ligated into plasmid pSEA4GCT digested with XbaI and BamHI, resulting in plasmid pSEA469B4CT (See, FIG. 7). The sequence of the A4 (*A. niger*) promoter region is:

```
                                                         (SEQ ID NO: 130)
  1       TCGAA CTTCAT GTTCGA GTTCTT GTTCAC GTAGAA GCCGGA GATGTG AGAGGT
          AGCTT GAAGTA CAAGCT CAAGAA CAAGTG CATCTT CGGCCT CTACAC TCTCCA

61   GATCTG GAACTG CTCACC CTCGTT GGTGGT GACCTG GAGGTA AAGCAA GTGACC CTTCTG
      CTAGAC CTTGAC GAGTGG GAGCAA CCACCA CTGGAC CTCCAT TTCGTT CACTGG GAAGAC

121   GCGGAG GTGGTA AGGAAC GGGGTT CCACGG GGAGAG AGAGAT GGCCTT GACGGT CTTGGG
      CGCCTC CACCAT TCCTTG CCCCAA GGTGCC CCTCTC TCTCTA CCGGAA CTGCCA GAACCC

181   AAGGGG AGCTTC NGCGCG GGGGAG GATGGT CTTGAG AGAGGG GGAGCT AGTAAT GTCGTA
      TTCCCC TCGAAG NCGCGC CCCCTC CTACCA GAACTC TCTCCC CCTCGA TCATTA CAGCAT

241   CTTGGA CAGGGA GTGCTC CTTCTC CGACGC ATCAGC CACCTC AGCGGA GATGGC ATCGTG
      GAACCT GTCCCT CACGAG GAAGAG GCTGCG TAGTCG GTGGAG TCGCCT CTACCG TAGCAC

301   CAGAGA CAGACC
      GTCTCT GTCTGG
```

In these experiments, the host *Streptomyces lividans* TK23 was transformed with either of the vectors described above using protoplast methods known in the art (See e.g., Hopwood, et al., *Genetic Manipulation of Streptomyces, A Laboratory Manual*, The John Innes Foundation, Norwich, United Kingdom [1985]).

The transformed culture was expanded to provide two fermentation cultures. At various time points, samples of the fermentation broths were removed for analysis. For the purposes of this experiment, a skimmed milk procedure was used to confirm successful cloning. In these methods, 30 µl of the shake flask supernatant was spotted in punched out holes in skim milk agar plates and incubated at 37° C. The incubated plates were visually reviewed after overnight incubation for the presence of halos. For purposes of this experiment, the same samples were also assayed for protease activity and for molecular weight (SDS-PAGE). At the end of the fermentation run, full length protease was observed by SDS-PAGE.

A sample of the fermentation broth was assayed as follows: 10 µl of the diluted 15 supernatant was taken and added to 190 µl AAPF substrate solution (conc. 1 mg/ml, in 0.1 M Tris/ 0.005% TWEEN, pH 8.6). The rate of increase in absorbance at 410 nm due to release of p-nitroaniline was monitored (25° C.). The assay results of the fermentation broth of 3 clones (X, Y, W) obtained using the pSEG69B4T and two clones using the pSEA469B4T indicated that Asp was expressed by both constructs.  able XXI. Results for Two Clones (pSEA469B4T). Indeed, the results obtained in these experiments showed that the polynucleotide encoding a polypeptide having proteolytic activity was expressed in *Streptomyces lividans*, using both of these expression vectors. Although two vectors are described in this Example, it is contemplated that additional expression vectors using different promoters and/or signal sequences combined with different combinations of 69B4 protease: +/–N terminal and C terminal prosequence in the pSEA4CT backbone (vector), as well as other constructs will find use in the present invention.

Example 10

Protease Production in *B. subtilis*

Figure 9:
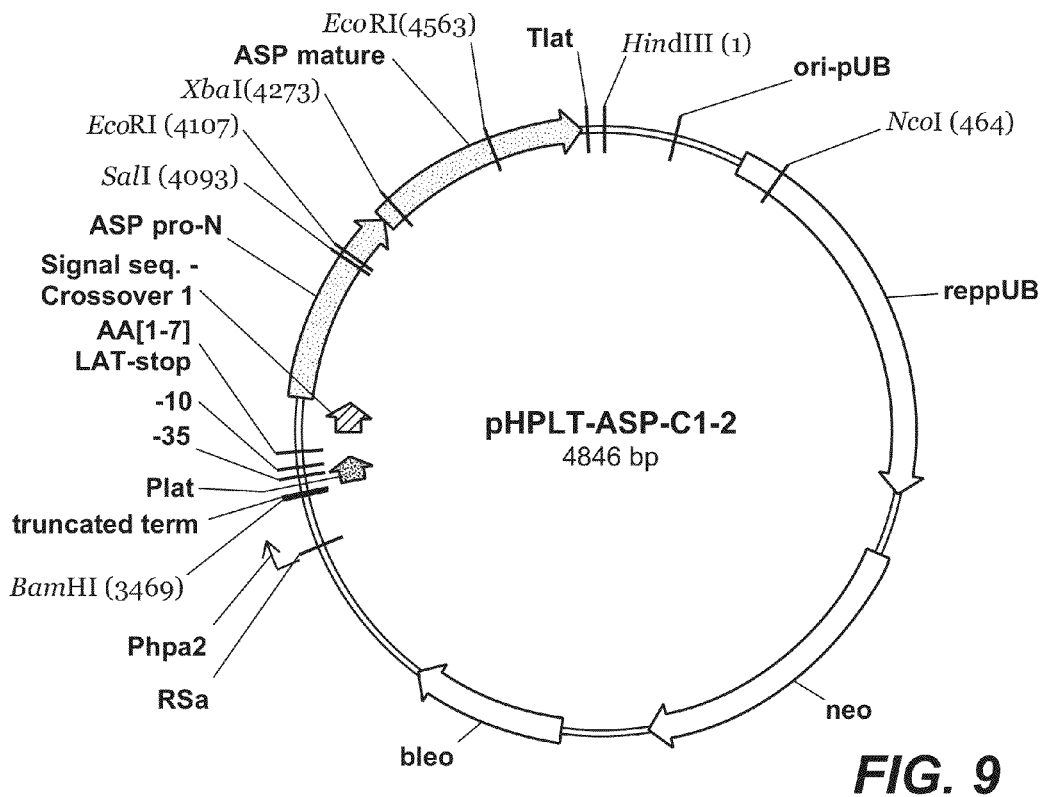
FIG. 9 provides the plasmid map of the pHPLT-Asp-C1-2 vector.
Figure 10:
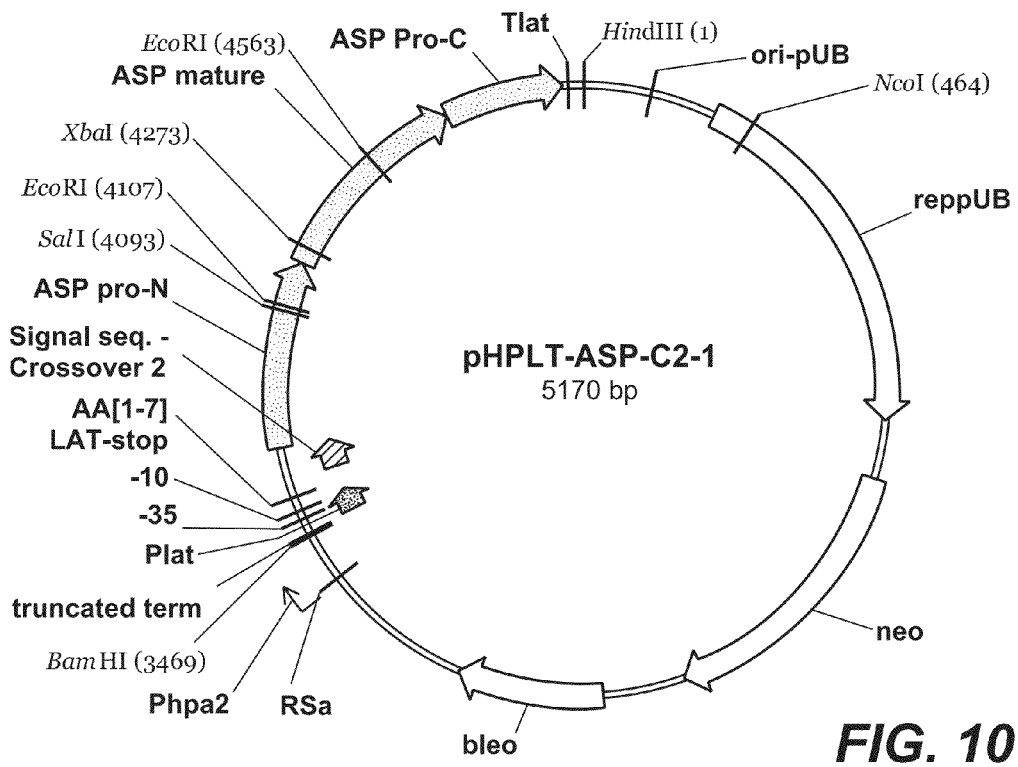
FIG. 10 provides the plasmid map of the pHPLT-Asp-C2-1 vector.
Figure 11:
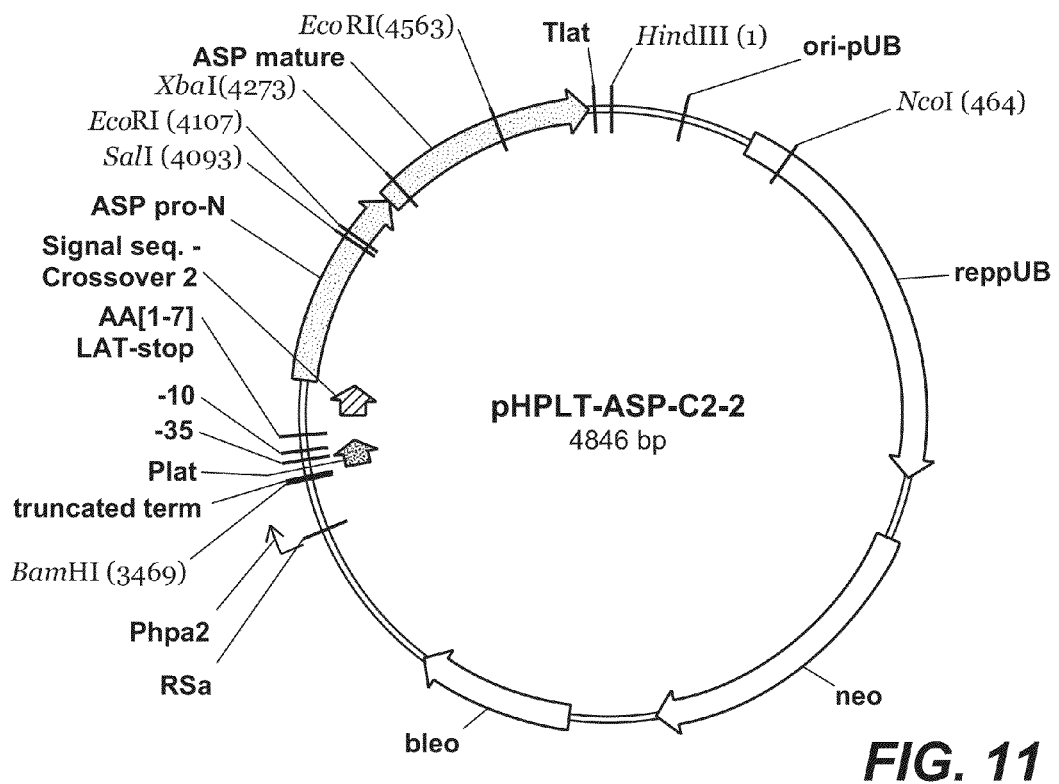
FIG. 11 provides the plasmid map of the pHPLT-Asp-C2-2 vector.
Figure 12:
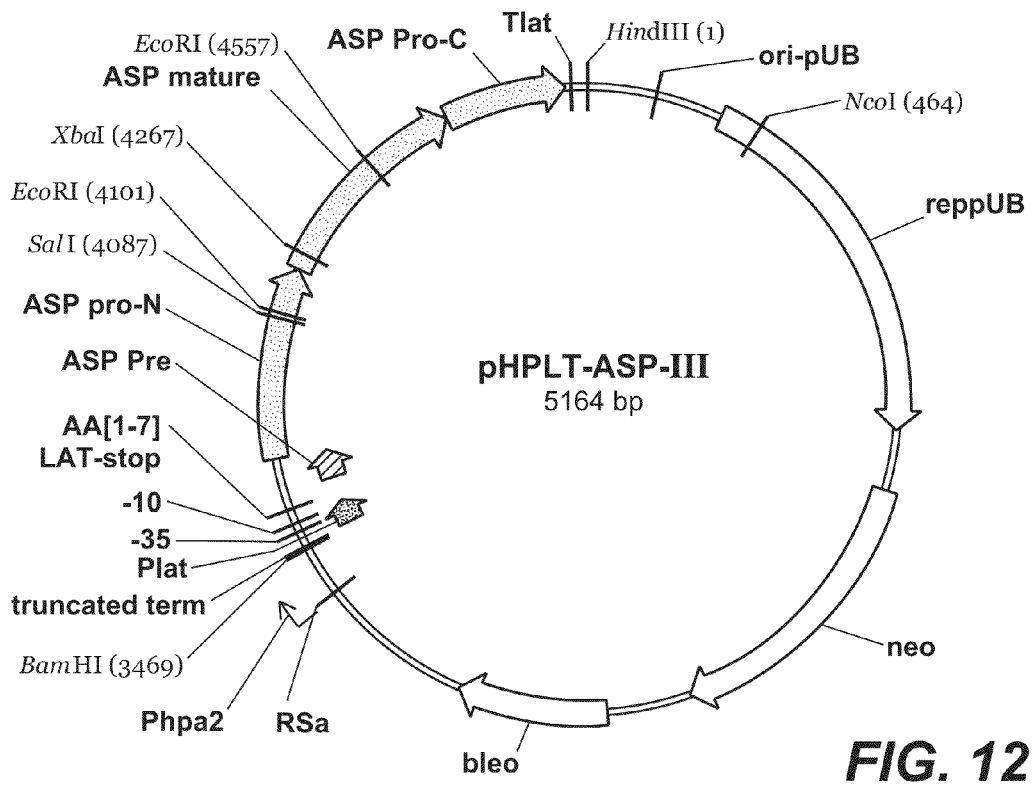
FIG. 12 provides the plasmid map of the pHPLT-ASP-III vector.

In this Example, experiments conducted to produce protease 69B4 (also referred to herein as "ASP," "Asp," and "ASP protease," and "Asp protease") in *B. subtilis* are described. In this Example, the transformation of plasmid pHPLT-ASP-C1-2 (See, Table 10-1; and FIG. 9), into *B. subtilis* is described. Transformation was performed as known in the art (See e.g., WO 02/14490, incorporated herein by reference. To optimize ASP expression in *B. subtilis* a synthetic DNA sequence was produced by DNA2.0, and utilized in these expression experiments. The DNA sequence (synthetic ASP DNA sequence) provided below, with codon usage adapted for *Bacillus* species, encodes the wild type ASP precursor protein:

(SEQ ID NO: 131)
ATGACACCACGAACTGTCACAAGAGCTCTGGCTGTGGCAACAGCAGCTGCTACACTCTTGGCTGGGGGTAT

GGCAGCACAAGCTAACGAACCGGCTCCTCCAGGATCTGCATCAGCCCCTCCACGATTAGCTGAAAAACTTGA

CCCTGACTTACTTGAAGCAATGGAACGCGATCTGGGGTTAGATGCAGAGGAAGCAGCTGCAACGTTAGCTTT

TCAGCATGACGCAGCTGAAACGGGAGAGGCTCTTGCTGAGGAACTCGACGAAGATTTCGCGGGCACGTGGG

TTGAAGATGATGTGCTGTATGTTGCAACCACTGATGAAGATGCTGTTGAAGAAGTCGAAGGCGAAGGAGCAA

CTGCTGTGACTGTTGAGCATTCTCTTGCTGATTTAGAGGCGTGGAAGACGGTTTTGGATGCTGCGCTGGAGG

GTCATGATGATGTGCCTACGTGGTACGTCGACGTGCCTACGAATTCGGTAGTCGTTGCTGTAAAGGCAGGAG

CGCAGGATGTAGCTGCAGGACTTGTGGAAGGCGCTGATGTGCCATCAGATGCGGTCACTTTTGTAGAAACG

GACGAAACGCCTAGAACGATGTTCGACGTAATTGGAGGCAACGCATATACTATTGGCGGCCGGTCTAGATG

TTCTATCGGATTCGCAGTAAACGGTGGCTTCATTACTGCCGGTCACTGCGGAAGAACAGGAGCCACTACTG

CCAATCCGACTGGCACATTTGCAGGTAGCTCGTTTCCGGGAAATGATTATGCATTCGTCCGAACAGGGGCA

GGAGTAAATTTGCTTGCCCAAGTCAATAACTACTCGGGCGGCAGAGTCCAAGTAGCAGGACATACGGCCG

-continued

CACCAGTTGGATCTGCTGTATGCCGCTCAGGTAGCACTACAGGTTGGCATTGCGGAACTATCACGGCGCT

GAATTCGTCTGTCACGTATCCAGAGGGAACAGTCCGAGGACTTATCCGCACGACGGTTTGTGCCGAACCA

GGTGATAGCGGAGGTAGCCTTTTAGCGGGAAATCAAGCCCAAGGTGTCACGTCAGGTGGTTCTGGAAATT

GTCGGACGGGGGAACAACATTCTTTCAACCAGTCAACCCGATTTTGCAGGCTTACGGCCTGAGAATGATT

ACGACTGACTCTGGAAGTTCCCCT<u>GCTCCAGCACCTACATCATGTACAGGCTACGCAAGAACGTTCACAGG</u>

<u>AACCCTCGCAGCAGGAAGAGCAGCAGCTCAACCGAACGGTAGCTATGTTCAGGTCAACCGGAGCGGTACAC</u>

<u>ATTCCGTCTGTCTCAATGGACCTAGCGGTGCGGACTTTGATTTGTATGTGCAGCGATGGAATGGCAGTAGCT</u>

<u>GGGTAACCGTCGCTCAATCGACATCGCCGGGAAGCAATGAAACCATTACGTACCGCGGAAATGCTGGATATT</u>

<u>ATCGCTACGTGGTTAACGCTGCGTCAGGATCAGGAGCTTACACAATGGGACTCACCCTCCCCTGA</u>

In the above sequence, bold indicates the DNA that encodes the mature protease, standard font indicates the leader sequence, and the underline indicates the N-terminal and so C-terminal prosequences.

Expression of the Synthetic ASP Gene

Figure 15:
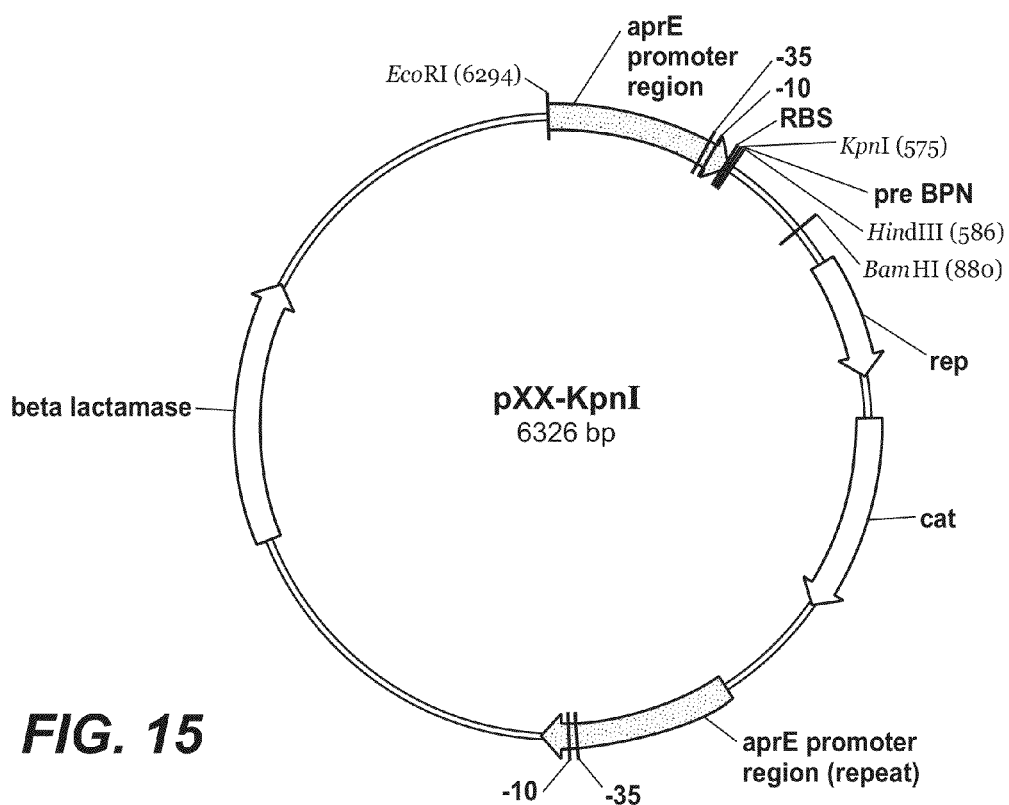
FIG. 15 provides the plasmid map of the pXX-KpnI vector.
Figure 16:
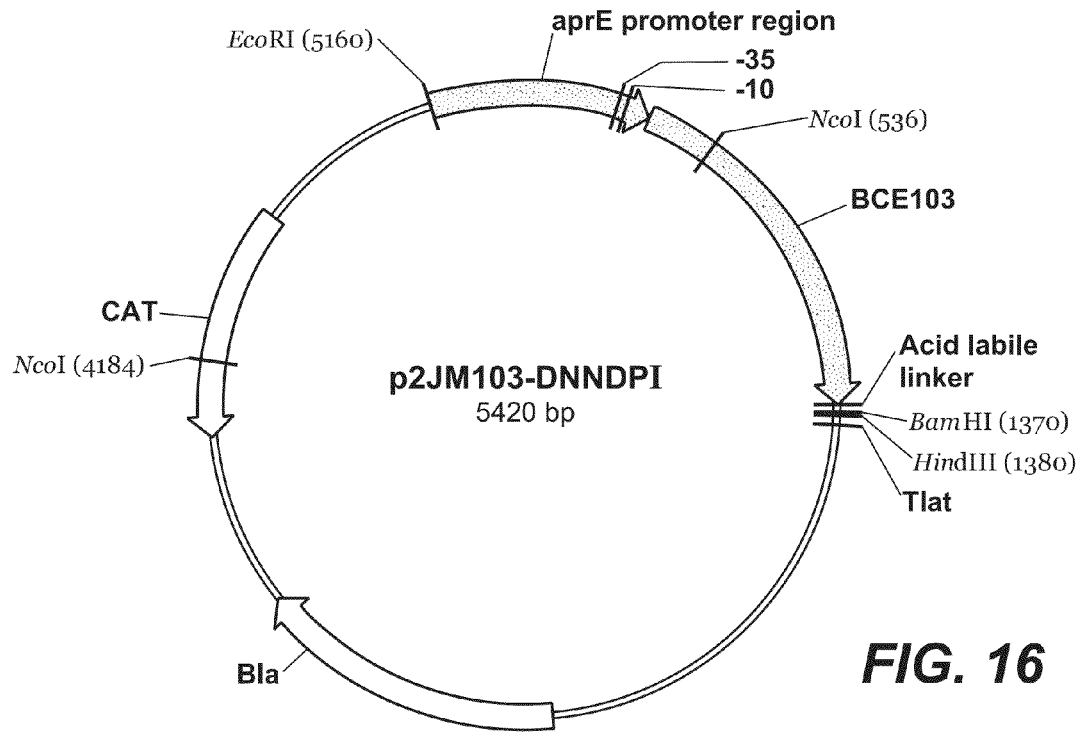
FIG. 16 provides the plasmid map of the p2JM103-DNNP1 vector.
Figure 17:
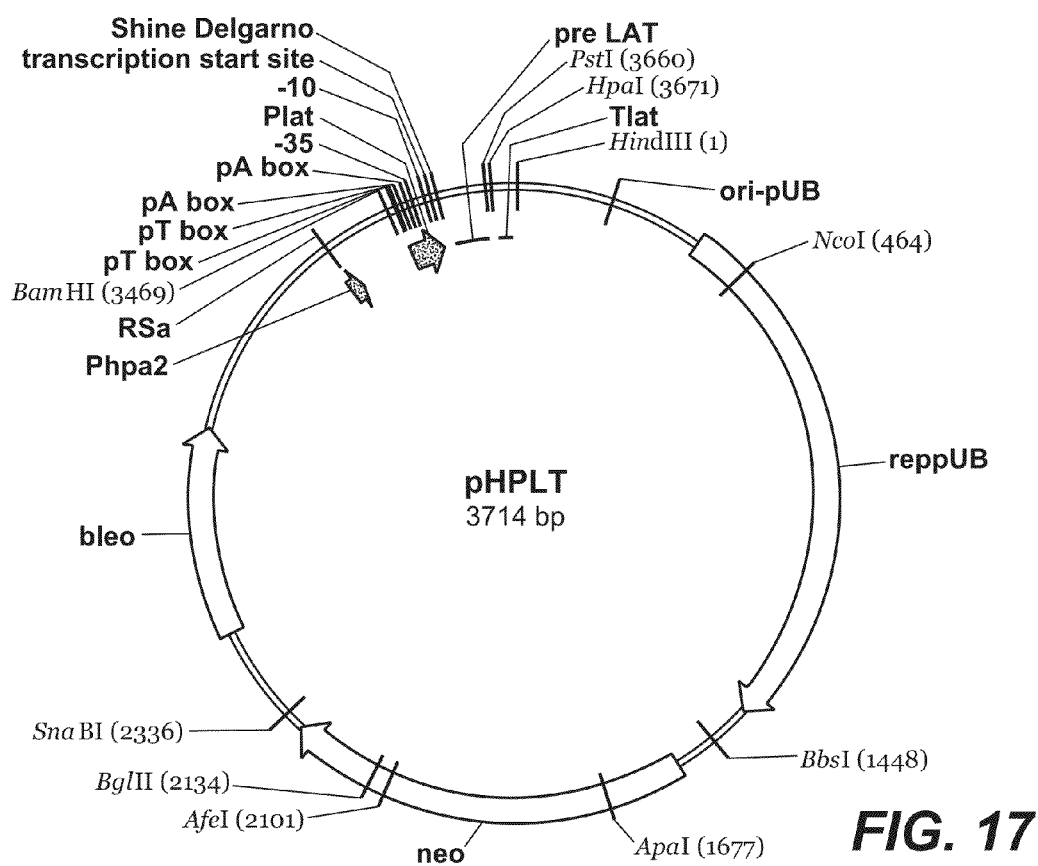
FIG. 17 provides the plasmid map of the pHPLT vector.
Figure 18:
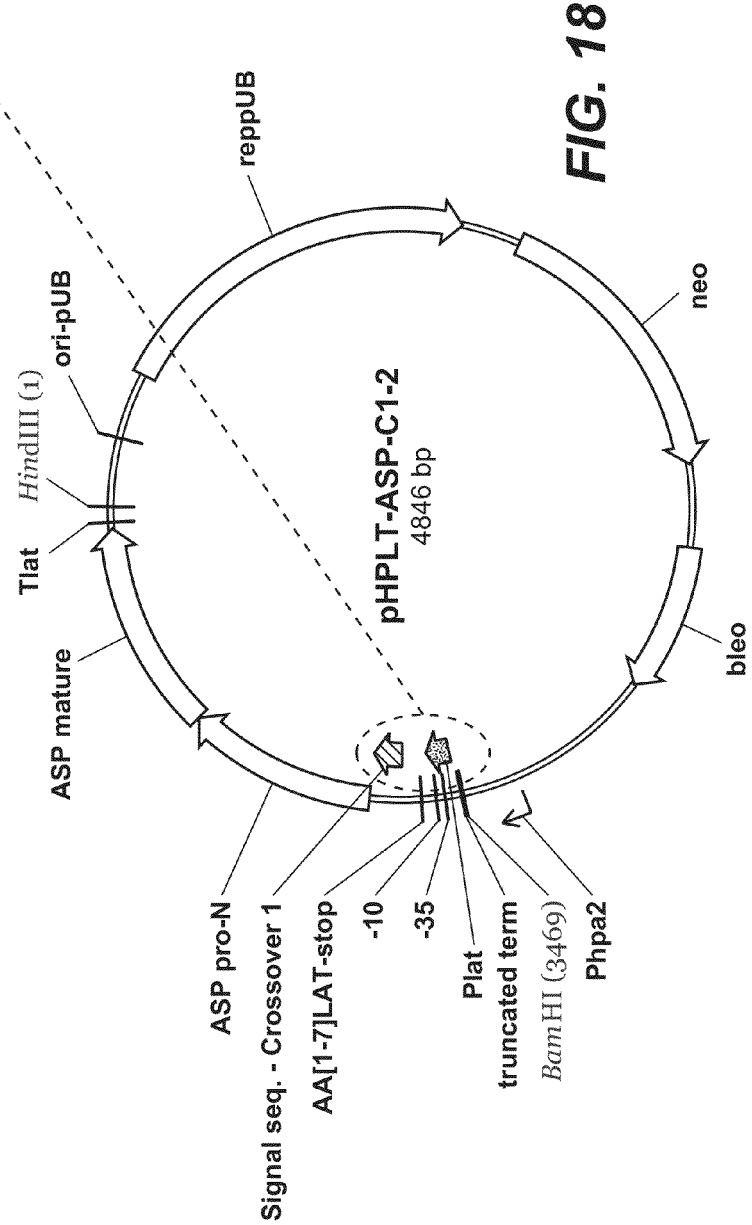
FIG. 18 provides the map and MXL-prom sequences for the opened pHPLT-ASP-C1-2.
Figure 19:
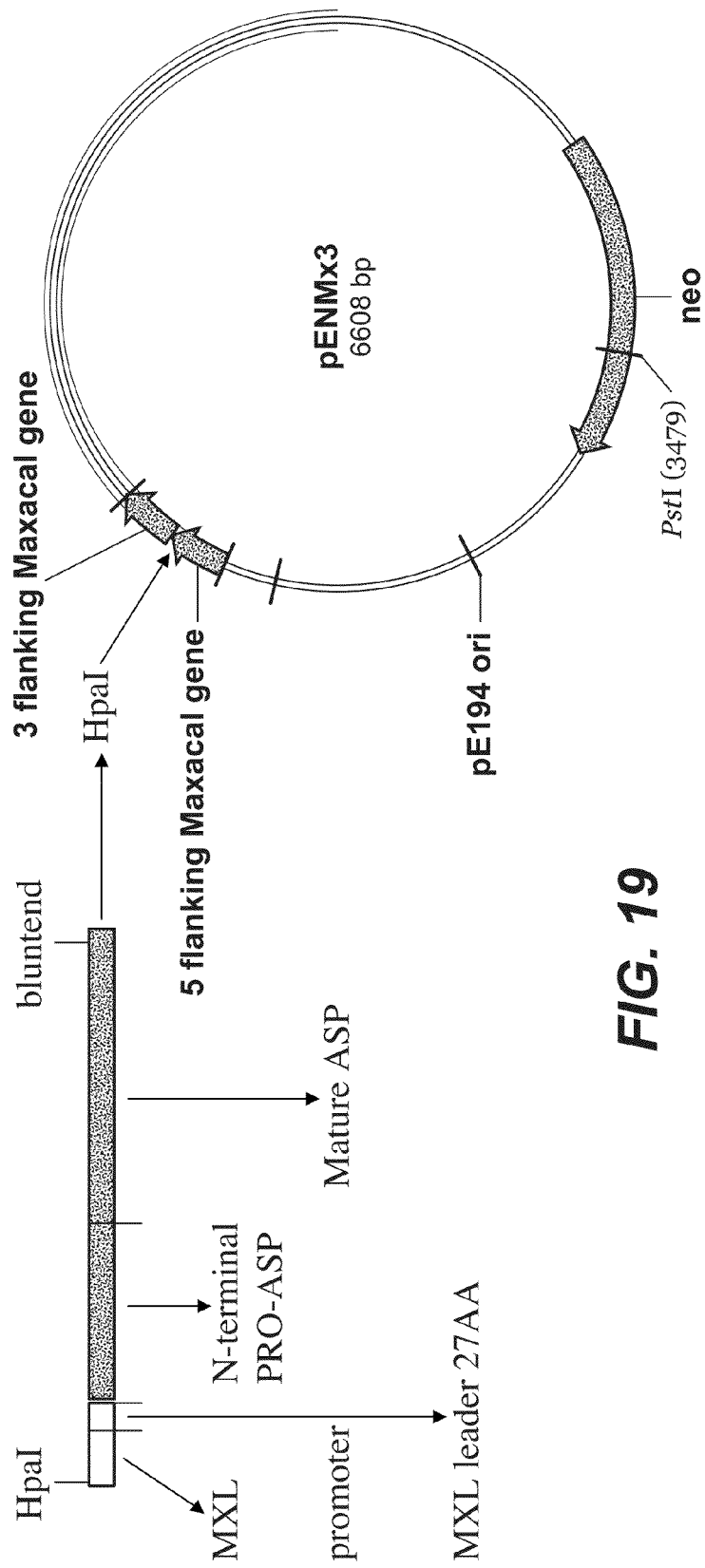
FIG. 19 provides the plasmid map of the pENMx3 vector.
Figure 20:
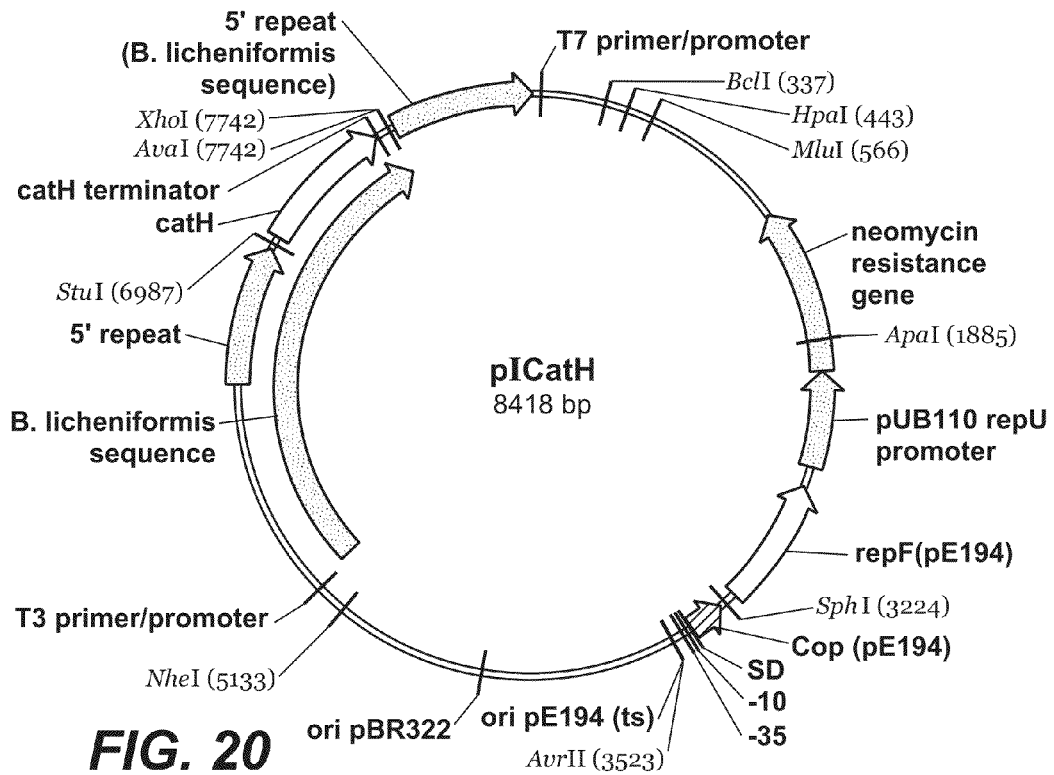
FIG. 20 provides the plasmid map of the pICatH vector.
Figure 21:
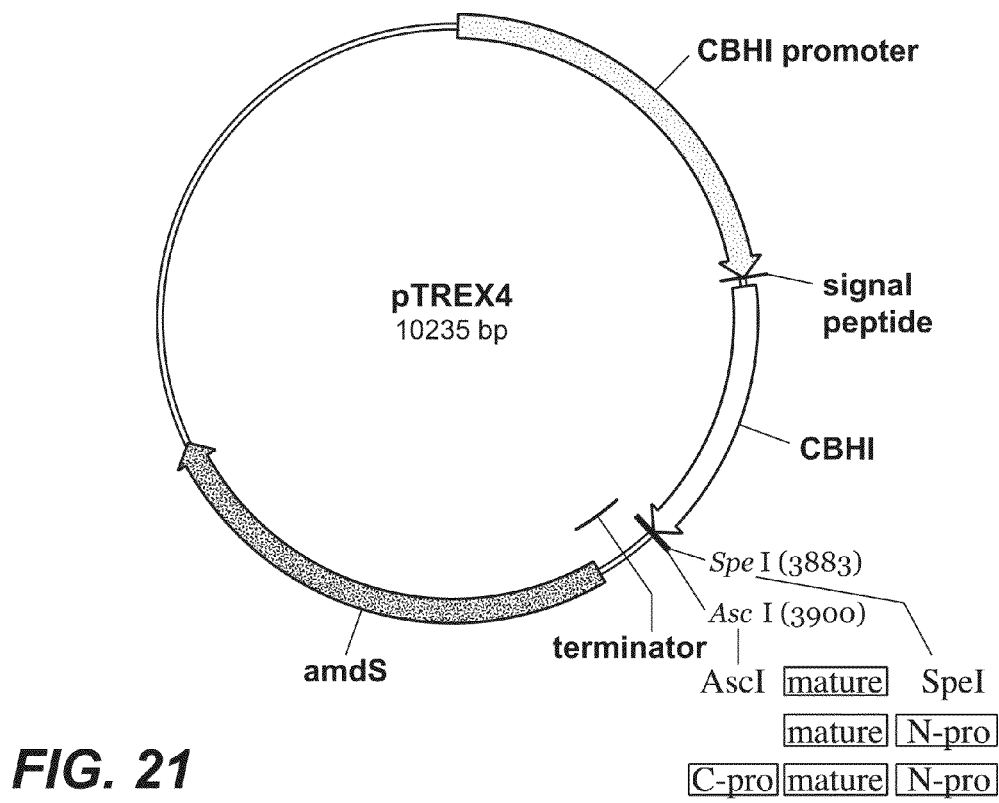
FIG. 21 provides the plasmid map of the pTREX4 vector.

Asp expression cassettes were constructed in the pXX-KpnI (See, FIG. 15) or p2JM103-DNNDPI (See, FIG. 16) vectors and subsequently cloned into the pHPLT vector ss (See, FIG. 17) for expression of ASP in *B. subtilis*. pXX-KpnI is a pUC based vector with the aprE promoter (*B. subtilis*) driving expression, a cat gene, and a duplicate aprE promoter for amplification of the copy number in *B. subtilis*. The bla gene allows selective growth in *E. coli*. The KpnI, introduced in the ribosomal binding site, downstream of the aprE promoter region, together with the HindIII site enables cloning of Asp expression cassettes in pXX-KpnI. The vector p2JM103-DNNDPI contains the aprE promoter (*B. subtilis*) to drive expression of the BCE103 cellulase core (endo-cellulase from an obligatory alkaliphilic *Bacillus*; See, Shaw et al., J. Mol. Biol., 320:303-309 [2002]), in frame with an acid labile linker (DDNDPI [SEQ ID NO:132]; See, Segalas et al., FEBS Lett., 371:171-175 [1995]). The ASP expression cassette (BamHI and HindIII) was fused to BCE103-DDNDPI fusion protein. When secreted, ASP is cleaved of the cellulase core to turn into the mature protease pHPLT (See, FIG. 17; and Solingen et al., Extremophiles 5:333-341 [2001]) contains the thermostable amylase LAT promoter ($P_{LAT}$) of *Bacillus licheniformis*, followed by XbaI and HpaI restriction sites for cloning ASP expression constructs. The following sequence is that of the BCE103 cellulase core with DNNDPI acid labile linker. In this sequence, the bold indicates the acid-labile linker, while the standard font indicates the BCE103 core.

```
                            (DNA; SEQ ID NO: 133) and (Amino Acid; SEQ ID NO: 134)
         V   R   S   K   K   L   W   I   S   L   L   F   A   L   T   L   I   F   T   M
    1    GTGAGA AGCAAA AAATTG TGGATC AGCTTG TTGTTT GCGTTA ACGTTA ATCTTT ACGATG
         CACTCT TCGTTT TTTAAC ACCTAG TCGAAC AACAAA CGCAAT TGCAAT TAGAAA TGCTAC A   F   S   N   M   S   A   Q   A   D   D   Y   S   V   V   E   H   G   Q
   61    GCGTTC AGCAAC ATGAGC GCGCAG GCTGAT GATTAT TCAGTT GTAGAG GAACAT GGCCAA
         CGCAAG TCGTTG TACTCG CGCGTC CGACTA CTAATA AGTCAA CATCTC CTTGTA CCGGTT L   S   I   S   N   G   E   L   V   N   E   R   G   E   Q   V   Q   L   K   G
  121    CTAAGT ATTAGT AACGGT GAATTA GTCAAT GAACGA GGCGAA CAAGTT CAGTTA AAAGGG
         GATTCA TAATCA TTGCCA CTTAAT CAGTTA CTTGCT CCGCTT GTTCAA GTCAAT TTTCCC M   S   S   H   G   L   Q   W   Y   G   Q   F   V   N   Y   E   S   M   K   W
  181    ATGAGT TCCCAT GGTTTG CAATGG TACGGT CAATTT GTAAAC TATGAA AGCATG AAATGG
         TACTCA AGGGTA CCAAAC GTTACC ATGCCA GTTAAA CATTTG ATACTT TCGTAC TTTACC L   R   D   D   W   G   I   T   V   F   R   A   A   M   Y   T   S   S   G   G
  241    CTAAGA GATGAT TGGGGA ATAACT GTATTC CGAGCA GCAATG TATACC TCTTCA GGAGGA
         GATTCT CTACTA ACCCCT TATTGA CATAAG GCTCGT CGTTAC ATATGG AGAAGT CCTCCT Y   I   D   D   P   S   V   K   E   K   V   K   E   T   V   E   A   A   I   D
  301    TATATT GACGAT CCATCA GTAAAG GAAAAA GTAAAA GAGACT GTTGAG GCTGCG ATAGAC
         ATATAA CTGCTA GGTAGT CATTTC CTTTTT CATTTT CTCTGA CAACTC CGACGC TATCTG L   G   I   Y   V   I   I   D   W   H   I   L   S   D   N   D   P   N   I   Y
  361    CTTGGC ATATAT GTGATC ATTGAT TGGCAT ATCCTT TCAGAC AATGAC CCGAAT ATATAT
         GAACCG TATATA CACTAG TAACTA ACCGTA TAGGAA AGTCTG TTACTG GGCTTA TATATA K   E   E   A   K   D   F   F   D   E   M   S   E   L   Y   G   D   Y   P   N
  421    AAAGAA GAAGCG AAGGAT TTCTTT GATGAA ATGTCA GAGTTG TATGGA GACTAT CCGAAT
         TTTCTT CTTCGC TTCCTA AAGAAA CTACTT TACAGT CTCAAC ATACCT CTGATA GGCTTA V   I   Y   E   I   A   N   E   P   N   G   S   D   V   T   W   D   N   Q   I
  481    GTGATA TACGAA ATTGCA AATGAA CCGAAT GGTAGT GATGTT ACGTGG GACAAT CAAATA
         CACTAT ATGCTT TAACGT TTACTT GGCTTA CCATCA CTACAA TGCACC CTGTTA GTTTAT
```

-continued

```
         K   P   Y   A   E   E   V   I   P   V   I   R   D   N   D   P   N   N   I   V
541    AAACCG TATGCA GAAGAA GTGATT CCGGTT ATTCGT GACAAT GACCCT AATAAC ATTGTT
       TTTGGC ATACGT CTTCTT CACTAA GGCCAA TAAGCA CTGTTA CTGGGA TTATTG TAACAA

I   V   G   T   G   T   W   S   Q   D   V   H   H   A   A   D   N   Q   L   A
601    ATTGTA GGTACA GGTACA TGGAGT CAGGAT GTCCAT CATGCA GCCGAT AATCAG CTTGTA
       TAACAT CCATGT CCATGT ACCTCA GTCCTA CAGGTA GTACGT CGGCTA TTAGTC GAACGT

D   P   N   V   M   Y   A   F   H   F   Y   A   G   T   H   G   Q   N   L   R
661    GATCCT AACGTC ATGTAT GCATTT CATTTT TATGCA GGAACA CATGGA CAAAAT TTACGA
       CTAGGA TTGCAG TACATA CGTAAA GTAAAA ATACGT CCTTGT GTACCT GTTTTA AATGCT

D   Q   V   D   Y   A   L   D   Q   G   A   A   I   F   V   S   E   W   G   T
721    GACCAA GTAGAT TATGCA TTAGAT CAAGGA GCAGCG ATATTT GTTAGT GAATGG GGGACA
       CTGGTT CATCTA ATACGT AATCTA GTTCCT CGTCGC TATAAA CAATCA CTTACC CCCTGT

S   A   A   T   G   D   G   G   V   F   L   D   E   A   Q   V   W   I   D   F
781    AGTGCA GCTACA GGTGAT GGTGGT GTGTTT TTAGAT GAAGCA CAAGTG TGGATT GACTTT
       TCACGT CGATGT CCACTA CCACCA CACAAA AATCTA CTTCGT GTTCAC ACCTAA CTGAAA

M   D   E   R   N   L   S   W   A   N   W   S   L   T   H   K   D   E   S   S
841    ATGGAT GAAAGA AATTTA AGCTGG GCCAAC TGGTCT CTAACG CATAAG GATGAG TCATCT
       TACCTA CTTTCT TTAAAT TCGACC CGGTTG ACCAGA GATTGC GTATTC CTACTC AGTAGA

A   A   L   M   P   G   A   N   P   T   G   G   W   T   E   A   E   L   S   P
901    GCAGCG TTAATG CCAGGT GCAAAT CCAACT GGTGGT TGGACA GAGGCT GAACTA TCTCCA
       CGTCGC AATTAC GGTCCA CGTTTA GGTTGA CCACCA ACCTGT CTCCGA CTTGAT AGAGGT

S   G   T   F   V   R   E   K   I   R   E   S   A   S   D   N   N   D   P   I
961    TCTGGT ACATTT GTGAGG GAAAGA ATAAGA GAATCA GCATCT GACAAC AATGAT CCCATA
       AGACCA TGTAAA CACTCC CTTTTT TATTCT CTTAGT CGTAGA CTGTTG TTACTA GGGTAT
```

The Asp expression cassettes were cloned in the pXX-KpnI vector containing DNA encoding the wild type Asp signal peptide, or a hybrid signal peptide constructed of 5 subtilisin AprE N-terminal signal peptide amino acids fused to the 25 Asp C-terminal signal peptide amino acids (MR-SKKRTVTRALAVATAAATLLAGGMAAQA (SEQ ID NO:135), or a hybrid signal peptide constructed of 11 subtilisin AprE N-terminal signal peptide amino acids fused to the 19 asp C-terminal signal peptide amino acids (MRSKKL-WISLLLAVATAAATLLAGGMAAQA (SEQ ID NO:136). These expression cassettes were also constructed with the asp C-terminal prosequence encoding DNA in frame. Another expression cassette, for cloning in the p2JM103-DNNDPI vector, encodes the ASP N-terminal pro- and mature sequence.

The Asp expression cassettes cloned in the pXX-KpnI or p2JM103-DNNDPI vector were transformed into E. coli (Electromax DH10B, Invitrogen, Cat. No. 12033-015). The primers and cloning strategy used are provided in Table 10-1. Subsequently, the expression cassettes were cloned from these vectors and introduced in the pHPLT expression vector for transformation into a B. subtilis (ΔaprE, ΔnprE, oppA, ΔspoIIE, degUHy32, ΔamyE::(xylR,pxylA-comK) strain. The primers and cloning strategy for ASP expression cassettes cloning in pHPLT are provided in Table 10-2. Transformation to B. subtilis was performed as described in WO 02/14490, incorporated herein by reference. FIGS. 12-21 provide plasmid maps for various plasmids described herein.

TABLE 10-1

ASP in pXX-KpnI and p2JM103-DNNDPI

| Vector Construct | Signal Peptide | ASP C-Terminal prosequence | Primers | DNA Template | Host vector | Restriction Sites Used for Cloning |
|---|---|---|---|---|---|---|
| pXX-ASP-1 | ASP | In frame | pXX-ASP-III/IV-Fw CTAGCTAGGTACCATGACA CCACGAACTGTCACAAGAG CT (SEQ ID NO: 137) ASP-syntc-ProC-RV GTGTGCAAGCTTTCAGGG GAGGGTGAGTCCCATTGT GTAA (SEQ ID NO: 138) | ASP synthetic gene G00222 | pXX-KpnI | KnpI and HindIII |
| pXX-ASP-2 | ASP | not incorporated | pXX-ASP-III/IV-Fw CTAGCTAGGTACCATGACA CCACGAACTGTCACAAGAG CT (SEQ ID NO: 139) ASP-syntc-mature-RV GTGTGCAAGCTTTCAGGG GAACTTCCAGAGTCAGTC (SEQ ID NO: 140) | ASP synthetic gene G00222 | pXX-KpnI | KnpI and HindIII |

TABLE 10-1-continued

ASP in pXX-KnpI and p2JM103-DNNDPI

| Vector Construct | Signal Peptide | ASP C-Terminal prosequence | Primers | DNA Template | Host vector | Restriction Sites Used for Cloning |
|---|---|---|---|---|---|---|
| pXX-ASP-3 | MRSKK RTVTR ALAVA TAAATL LAGGM AAQA (SEQ ID NO: 135) | In frame | ASP-PreCross-I-FW TCATGCAGGGTACCATGAG AAGCAAGAAGCGAACTGTC ACAAGAGCTCTGGCT (SEQ ID NO: 141) ASP-syntc-ProC-RV GTGTGCAAGCTTTCAGGG GAGGGTGAGTCCCATTGT GTAA (SEQ ID NO: 142) | ASP synthetic gene G00222 | pXX-KnpI | KnpI and HindIII |
| pXX-ASP-4 | MRSKK RTVTR ALAVA TAAATL LAGGM AAQA (SEQ ID NO: 135) | not incorporated | ASP-PreCross-I-FW TCATGCAGGGTACCATGAG AAGCAAGAAGCGAACTGTC ACAAGAGCTCTGGCT (SEQ ID NO: 143) ASP-syntc-mature-RV GTGTGCAAGCTTTCAAGGG GAACTTCCAGAGTCAGTC (SEQ ID NO: 144) | ASP synthetic gene G00222 | pXX-KnpI | KnpI and HindIII |
| pXX-ASP-5 | MRSKK LWISLL LAVAT AAATLL AGGMA AQA (SEQ ID NO: 136) | In frame | ASP-PreCross-II-FW TCATGCAGGGTACCATGAG AAGCAAGAAGTTGTGGATC AGTTTGCTGCTGGCTGTGG CAACAGCAGCTGCTACA (SEQ ID NO: 145) ASP-syntc-ProC-RV GTGTGCAAGCTTTCAGGG GAGGGTGAGTCCCATTGT GTAA (SEQ ID NO: 146) | ASP synthetic gene G00222 | pXX-KnpI | KnpI and HindIII |
| pXX-ASP-6 | MRSKK LWISLL LAVAT AAATLL AGGMA AQA (SEQ ID NO: 136) | not incorporated | ASP-PreCross-II-FW TCATGCAGGGTACCATGAG AAGCAAGAAGTTGTGGATC AGTTTGCTGCTGGCTGTGG CAACAGCAGCTGCTACA (SEQ ID NO: 147) ASP-syntc-mature-RV GTGTGCAAGCTTTCAAGGG GAACTTCCAGAGTCAGTC (SEQ ID NO: 148) | ASP synthetic gene G00222 | pXX-KnpI | KnpI and HindIII |
| p2JM-103 ASP | BCE103 cellulase core + acid labile linker | not incorporated | DPI-ASP-syntc-ProN-FW CCATACCCGGATCCAAACGA ACCGGCTCCTCCAGGATCT (SEQ ID NO: 149) DPI-ASP-syntc-Mature-RV CTCGAGTTAAGCTTTTAAG GGAACTTCCAGAGTCAGT C (SEQ ID NO: 150) | ASP synthetic gene G00222 | p2JM103-DNNDPI | BamHI and HindIII |

TABLE 10-2

ASP Expression Cassettes in pHPLT

| Vector construct | Primers | DNA template | Host vector | Restriction sites used for cloning |
|---|---|---|---|---|
| pHPLT-ASP-III | ASP-III&IV-FW TGAGCTGCTAGCAAAAGGAGAGGGTA AAGAATGACACCACGAACTGTC (SEQ ID NO: 151) pHPLT-ASPproC-RV CGTACATCCCGGTCAGGGGAGGGTG AGTCCCATTG (SEQ ID NO: 152) | pXX-ASP-1 | pHPLT (XbaI x NheI x SmaI HpaI) | |
| pHPLT-ASP-IV | ASP-III&IV-FW TGAGCTGCTAGCAAAAGGAGAGGGTA | pXX-ASP-2 | pHPLT (XbaI x NheI x SmaI HpaI) | |

TABLE 10-2-continued

ASP Expression Cassettes in pHPLT

| Vector construct | Primers | DNA template | Host vector | Restriction sites used for cloning |
|---|---|---|---|---|
| | AAGAATGACACCACGAACTGTC (SEQ ID NO: 153) pHPLT-ASPmat-RV CATGCATCCCGGGTTAAGGGGAACTT CCAGAGTCAGTC (SEQ ID NO: 154) | | | |
| pHPLT-ASP-C1-1 | ASP-Cross-1&2-FW TGAGCTGCTAGCAAAAGGAGAGGGTA AAGAATGAGAAGCAAGAAG (SEQ ID NO: 155) pHPLT-ASPproC-RV CGTACATCCCGGGTCAGGGGAGGGTG AGTCCCATTG (SEQ ID NO: 156) | pXX-ASP-3 | pHPLT (XbaI x HpaI) | NheI x SmaI |
| pHPLT-ASP-C1-2 | ASP-Cross-1&2-FW TGAGCTGCTAGCAAAAGGAGAGGGTA AAGAATGAGAAGCAAGAAG (SEQ ID NO: 157) pHPLT-ASPmat-RV CATGCATCCCGGGTTAAGGGGAACTT CCAGAGTCAGTC (SEQ ID NO: 158) | pXX-ASP-4 | pHPLT (XbaI x HpaI) | NheI x SmaI |
| pHPLT-ASP-C2-1 | ASP-Cross-1&2-FW TGAGCTGCTAGCAAAAGGAGAGGGTA AAGAATGAGAAGCAAGAAG (SEQ ID NO: 159) pHPLT-ASPproC-RV CGTACATCCCGGGTCAGGGGAGGGTG AGTCCCATTG (SEQ ID NO: 160) | pXX-ASP-5 | pHPLT (XbaI x HpaI) | NheI x SmaI |
| pHPLT-ASP-C2-2 | ASP-Cross-1&2-FW TGAGCTGCTAGCAAAAGGAGAGGGTA AAGAATGAGAAGCAAGAAG (SEQ ID NO: 161) pHPLT-ASPmat-RV CATGCATCCCGGGTTAAGGGGAACTT CCAGAGTCAGTC (SEQ ID NO: 162) | pXX-ASP-6 | pHPLT (XbaI x HpaI) | NheI x SmaI |
| pHPLT-ASP-VII | pHPLT-BCE/ASP-FW TGCAGTCTGCTAGCAAAAGGAGAGGG TAAAGAGTGAGAAG (SEQ ID NO: 163) pHPLT-ASPmat-RV CATGCATCCCGGGTTAAGGGGAACTT CCAGAGTCAGTC (SEQ ID NO: 164) | p2JM103-ASP | pHPLT | NheI x SmaI |

Primers were obtained from MWG and Invitrogen. Invitrogen Platinum Taq DNA polymerase High Fidelity (Cat. No. 11304-029) was used for PCR amplification (0.2 µM primers, up to 30 cycles) according to the Invitrogen's protocol. Ligase reactions of ASP expression cassettes and host vectors were completed by using Invitrogen T4 DNA Ligase (Cat. No. 15224-025), utilizing Invitrogen's protocol as recommended for general cloning of cohesive ends).

Selective growth of B. subtilis (ΔaprE, ΔnprE, oppA, ΔspoIIE, degUHy32, ΔamyE::(xyIR,pxyIA-comK) transformants harboring the p2JM103-ASP vector or one of the pHPLT-ASP vectors was performed in shake flasks containing 25 ml Synthetic Maxatase Medium (SMM), with 0.97 g/l CaCl$_2$.6H$_2$O instead of 0.5 g/l CaCl$_2$ (See, U.S. Pat. No. 5,324,653, herein incorporated by reference) with either 25 mg/L chloramphenicol or 20 mg/L neomycin. This growth resulted in the production of secreted ASP protease with proteolytic activity. However, gel analysis was performed using NuPage Novex 10% Bis-Tris gels (Invitrogen, Cat. No. NP0301 BOX). To prepare samples for analysis, 2 volumes of supernatant were mixed with 1 volume 1M HCl, 1 volume 4xLDS sample buffer (Invitrogen, Cat. No. NP0007), and 1% PMSF (20 mg/ml) and subsequently heated for 10 minutes at 70° C. Then, 25 µL of each sample was loaded onto the gel, together with 10 µL of SeeBlue plus 2 pre-stained protein standards (Invitrogen, Cat. No. LC5925). The results' clearly demonstrated that all asp cloning strategies described in this Example yield sufficent amounts of active Asp produced by B. subtilis.

In addition, samples of the same fermentation broths were assayed as follows: 10 µl of the diluted supernatant was taken and added to 190 µl AAPF substrate solution (conc. 1 mg/ml, in 0.1 M Tris/0.005% TWEEN®, pH 8.6). The rate of increase in absorbance at 410 nm due to release of p-nitroaniline was monitored (25° C.), as it provides a measure of the ASP concentration produced. These results indicated that all of the constructs resulted in the production of measurable ASP protease.

The impact of the synthetic asp gene was investigated in Bacillus subtilis comparing the expression levels of the pHPLT-ASP-c-1-2 construct with the synthetic and native asp gene in a B. subtilis (ΔaprE, ΔnprE, oppA, ΔspoIIE, degUHy32, ΔamyE::(xyIR,pxyIA-comK) strain. The native gene was amplified from plasmid containing the native asp gene, using platinum pfx polymerase (Invitrogen) with the following primers:

```
AK04-12.1: NheI thru RBS
                                  (SEQ ID NO: 165)
TTATGCGAGGCTAGCAAAAGGAGAGGGTAAAGAGTGAGAAGCAAAAAACG AK04-11: RBS thru
5 aa aprE for ASP native C1 fusion in pHPLT
                                  (SEQ ID NO: 166)
taaagagtgagaagcaaaaaacgcacagtcacgcgggccctg AK04-13: HpaI 3' of native ASP mature
                                  (SEQ ID NO: 167)
gtcctctgttaacttacgggctgctgcccgagtcc
```

The following conditions were used for these PCRs: 94° C. for 2 min.; followed by 25 cycles of 94° C. for 45 sec., 60° C. for 30 sec., and 68° C. for 2 min. for 30 sec.; followed by 68° C. for 5 min. The resulting PCR product was run on an E-gel (Invitrogen), excised, and purified with a gel extraction kit (Qiagen). Ligase reaction of this fragment containing the native ASP with the pHPLT vector was completed by using ligated (T4 DNA Ligase, NEB) and transformed directly into B. subtilis (ΔaprE, ΔnprE, oppA, ΔspoIIE, degUHy32, ΔamyE::(xylR,pxylA-comK). Transformation to B. subtilis was performed as described in WO 02/14490 A2, herein incorporated by reference.

The Asp protein was produced by growth in shake flasks at 37° C. in medium containing the following ingredients; 0.03 g/L MgSO4, 0.22 g/L K2HPO4, 21.3 g/L NA2HPO4*7H2O, 6.1 g/L NaH2PO4*H2O, 3.6 g/L Urea, 7 g/L soymeal, 70 g/L Maltrin M150, and 42 g/L glucose, with a final pH7.5. In these experiments, the production level of the host carrying the synthetic gene cassette was found to be 3-fold higher than the host carrying the native gene cassette.

In additional experiments, expression of ASP was investigated in Bacillus subtilis using the sacB promoter and aprE signal peptide. The gene was amplified from plasmid containing the synthetic asp gene using TGO polymerase (Roche) and the primers:

```
CF 520 (+) Fuse ASP (pro) to aprE ss
                                  (SEQ ID NO: 168)
GCAACATGTCTGCGCAGGCTAACGAACCGGCTCCTCCAGGA CF 525 (-) End of Asp gene HindIII
                                  (SEQ ID NO: 169)
GACATGACATAAGCTTAAGGGGAACTTCCAGAGTC
```

The sacB promoter (Bacillus subtilis), the start of the messenger RNA (+1) from aprE, and the aprE signal peptide were amplified from the plasmid pJHsacBJ2 using TGO polymerase (Roche) and the primers:

```
CF 161 (+) EcoRI at start of sacB promoter
                                  (SEQ ID NO: 170)
GAGCCGAATTCATATACCTGCCGTT CF 521 (-) Reverse complement of CF 520
                                  (SEQ ID NO: 171)
TCCTGGAGGAGCCGGTTCGTTAGCCTGCGCAGACATGTTGC
```

The following PCR conditions were used to amplify both pieces: 94° C. for 2 min.; followed by 30 cycles of 94° C. for 30 sec., 50° C. for 1 min., and 66° C. for 1 min.; followed by 72° C. for 7 min. The resulting PCR products were run on an E-gel (Invitrogen), excised, and purified with a gel extraction kit (Qiagen).

In addition, a PCR overlap extension fusion (Ho, Gene, 15:51-59 [1989]) was used to fuse the above gene fragment to the sacB promoter-aprE signal peptide fragment with PFX polymerase (Invitrogen) using the following primers:

```
CF 161 (+) EcoRI at start of sacB promoter
                                  (SEQ ID NO: 170)
GAGCCGAATTCATATACCTGCCGTT CF 525 (-) End of Asp gene HindIII
                                  (SEQ ID NO: 169)
GACATGACATAAGCTTAAGGGGAACTTCCAGAGTC
```

The following conditions were used for these PCRs: 94° C. for 2 min.; followed by 25 cycles of 94° C. for 45 sec., 60° C. for 30 sec., and 68° C. for 2 min. 30 sec.; followed 68° C. for 5 min. The resulting PCR fusion products were run on an E-gel (Invitrogen), excised, and purified with a gel extraction kit (Qiagen). The purified fusions were cut (EcoRI/HindIII) and ligated (T4 DNA Ligase, NEB) into an EcoRI/HindIII pJH101 (Ferrari et al., J. Bacteriol., 152:809-814 [1983]) vector containing a strong transcriptional terminator. The ligation mixture was transformed into competent E. coli cells (Top 10 chemically competent cells, Invitrogen) and plasmid preps were done to retrieve the plasmid (Qiagen spin-prep).

The plasmid, pJHsacB-ASP (1-96 sacB promoter; 97-395 aprE+1 through end of aprE ss; and 396-1472 pro+mature asp; See, sequence provided below) was transformed to B. subtilis. Transformation to B. subtilis (ΔaprE, ΔnprE, oppA, ΔspoIIE, degUHy32, ΔamyE::(xylR,pxylA-comK) strain was performed as described in WO 02/14490 A2, herein incorporated by reference. The chromosomal DNA was extracted from an overnight culture of the strain (grown in LB media) then transformed to strain BG 3594 and named "CF 202." This strain produced a clear halo on the indicator plate (LA+1.6% skim milk).

pJHsacB-ASP Sequence:

(SEQ ID NO: 172)

```
CATCACATATACCTGCCGTTCACTATTATTTAGTGAAATGAGATATTATGATATTTCTG

AATTGTGATTAAAAAGGCAACTTTATGCCCATGCAACAGAAACTATAAAAAATACAGAGA

ATGAAAAGAAACAGATAGATTTTTTAGTTCTTTAGGCCCGTAGTCTGCAAATCCTTTTAT

GATTTTCTATCAAACAAAAGAGGAAAATAGACCAGTTGCAATCCAAACGAGAGTCTAAT

AGAATGAGGTCacaGAATAGTCTTTTAAGTAAGTCTACTCTGAATTTTTTAAAAGGAGA

GGGTAAAGAgtgAGAAGCAAAAAATTGTGGATCAGCTTGTTGTTTGCGTTAACGTTAATC

TTTACGATGGCGTTCAGCAACATGTCTGCGCAGGCTaacgaaccggctcctccaggatctgcatcag cccctccacgattagctgaaaaacttgaccctgacttacttgaagcaatggaacgcgatctggggttagatgcagaggaagca
```

-continued gctgcaacgttagcttttcagcatgacgcagctgaaacgggagaggctcttgctgaggaactcgacgaagatttcgcgggcac gtgggttgaagatgatgtgctgtatgttgcaaccactgatgaagatgctgttgaagaagtcgaaggcgaaggagcaactgctgt gactgttgagcattctcttgctgatttagaggcgtggaagacggttttggatgctgcgctggagggtcatgatgatgtgcctacgtg gtacgtcgacgtgcctacgaattcggtagtcgttgctgtaaaggcaggagcgcaggatgtagctgcaggacttgtggaaggcg ctgatgtgccatcagatgcggtcacttttgtagaaacggacgaaacgcctagaacgatgttcgacgtaattggaggcaacgcat atactattggcggccggtctagatgttctatcggattcgcagtaaacggtggcttcattactgccggtcactgcggaagaacagg agccactactgccaatccgactggcacatttgcaggtagctcgtttccgggaaatgattatgcattcgtccgaacaggggcagg agtaaatttgcttgcccaagtcaataactactcgggcggcagagtccaagtagcaggacatacggccgcaccagttggatctg ctgtatgccgctcaggtagcactacaggttggcattgcggaactatcacggcgctgaattcgtctgtcacgtatccagagggaac agtccgaggacttatccgcacgacggtttgtgccgaaccaggtgatagcggaggtagccttttagcgggaaatcaagcccaag gtgtcacgtcaggtggttctggaaattgtcggacgggggaacaacattctttcaaccagtcaacccgattttgcaggcttacggc ctgagaatgattacgactgactctggaagttccccTAAGCTTAAAAAACCGGCCTTGGCCCCGCCGGTT

TTTTATTATTTTTCTTCCTCCGCATGTTCAATCCGCTCCATAATCGACGGATGGCTCCCT

CTGAAAATTTTAACGAGAAACGGCGGGTTGACCCGGCTCAGTCCCGTAACGGCCAAGT

CCTGAAACGTCTCAATCGCCGCTTCCCGGTTTCCGGTCAGCTCAATGCCGTAACGGTC

GGCGGCGTTTTCCTGATACCGGGAGACGGCATTCGTAATCGGATCCCGGACGCATCG

TGGCCGGCATCACCGGCGCCACAGGTGCGGTTGCTGGCGCCTATATCGCCGACATCA

CCGATGGGAAGATCGGGCTCGCCACTTCGGGCTCATGAGCGCTTGTTTCGGCGTGG

GTATGGTGGCAGGCCCCGTGGCCGGGGGACTGTTGGGCGCCATCTCCTTGCATGCAC

CATTCCTTGCGGCGGCGGTGCTCAACGGCCTCAACCTACTACTGGGCTGCTTCCTAAT

GCAGGAGTCGCATAAGGGAGAGCGTCGACCGATGCCCTTGAGAGCCTTCAACCCAGT

CAGCTCCTTCCGGTGGGCGCGGGGCATGACTATCGTCGCCGCACTTATGACTGTCTTC

TTTATCATGCAACTCGTAGGACAGGTGCCGGCAGCGCTCTGGGTCATTTTCGGCGAGG

ACCGCTTTCGCTGGAGCGCGACGATGATCGGCCTGTCGCTTGCGGTATTCGGAATCTT

GCACGCCCTCGCTCAAGCCTTCGTCACTGGTCCCGCCACCAAACGTTTCGGCGAGAA

GCAGGCCATTATCGCCGGCATGGCGGCCGACGCGCTGGGCTACGTCTTGCTGGCGTT

CGCGACGCGAGGCTGGATGGCCTTCCCCATTATGATTCTTCTCGCTTCCGGCGGCATC

GGGATGCCCGCGTTGCAGGCCATGCTGTCCAGGCAGGTAGATGACGACCATCAGGGA

CAGCTTCAAGGATCGCTCGCGGCTCTTACCAGCCTAACTTCGATCACTGGACCGCTGA

TCGTCACGGCGATTTATGCCGCCTCGGCGAGCACATGGAACGGGTTGGCATGGATTG

AGGCGCCGCCCTATACCTTATTTATGTTACAGTAATATTGACTTTTAAAAAAGGATTGAT

TCTAATGAAGAAAGCAGACAAGTAAGCCTCCTAAATTCACTTTAGATAAAAATTTAGGAG

GCATATCAAATGAACTTTAATAAAATTGATTTAGACAATTGGAAGAGAAAAGAGATATTT

AATCATTATTTGAACCAACAAACGACTTTTAGTATAACCACAGAAATTGATATTAGTGTTT

TATACCGAAACATAAAACAAGAAGGATATAAATTTTACCCTGCATTTATTTTCTTAGTGA

CAAGGGTGATAAACTCAAATACAGCTTTTAGAACTGGTTACAATAGCGACGGAGAGTTA

GGTTATTGGATAAGTTAGAGCCACTTTATACAATTTTTGATGGTGTATCTAAAACATTC

TCTGGTATTTGGACTCCTGTAAAGAATGACTTCAAAGAGTTTTATGATTTATACCTTTCT

GATGTAGAGAAATATAATGGTTCGGGGAAATTGTTTCCCAAAACACCTATACCTGAAAA

TGCTTTTTCTCTTTCTATTATTCCATGGACTTCATTTACTGGGTTTAACTTAAATATCAAT

-continued

```
AATAATAGTAATTACCTTCTACCCATTATTACAGCAGGAAAATTCATTAATAAAGGTAATT
CAATATATTTACCGCTATCTTTACAGGTACATCATTCTGTTTGTGATGGTTATCATGCAG
GATTGTTTATGAACTCTATTCAGGAATTGTCAGATAGGCCTAATGACTGGCTTTTATAAT
ATGAGATAATGCCGACTGTACTTTTTACAGTCGGTTTTCTAATGTCACTAACCTGCCCC
GTTAGTTGAAGAAGGTTTTTATATTACAGCTCCAGATCCTGCCTCGCGCGTTTCGGTGA
TGACGGTGAAAACCTCTGACACATGCAGCTCCCGGAGACGGTCACAGCTTGTCTGTAA
GCGGATGCCGGGAGCAGACAAGCCCGTCAGGGCGCGTCAGCGGGTGTTGGCGGGTG
TCGGGGCGCAGCCATGACCCAGTCACGTAGCGATAGCGGAGTGTATACTGGCTTAAC
TATGCGGCATCAGAGCAGATTGTACTGAGAGTGCACCATATGCGGTGTGAAATACCGC
ACAGATGCGTAAGGAGAAAATACCGCATCAGGCGCTCTTCCGCTTCCTCGCTCACTGA
CTCGCTGCGCTCGGTCGTTCGGCTGCGGCGAGCGGTATCAGCTCACTCAAAGGCGGT
AATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGA
CAGGACTATAAAGATACCAGGCGTTTCCCCCTGGAAGCTCCCTCGTGCGCTCTCCTGT
TCCGACCCTGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCGGTAACTA
TCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGG
CCTAACTACGGCTACACTAGAAGGACAGTATTTGGTATCTGCGCTCTGCTGAAGCCAG
TTACCTTCGGAAAAAGAGTTGGTAGCTCTTGATCCGGCAAACAAACCACCGCTGGTAG
CGGTGGTTTTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCACGTTAAGGG
ATTTTGGTCATGAGATTATCAAAAAGGATCTTCACCTAGATCCTTTTAAATTAAAAATGA
AGTTTTAAATCAATCTAAAGTATATATGAGTAAACTTGGTCTGACAGTTACCAATGCTTA
ATCAGTGAGGCACCTATCTCAGCGATCTGTCTATTTCGTTCATCCATAGTTGCCTGACT
CCCCGTCGTGTAGATAACTACGATACGGGAGGGCTTACCATCTGGCCCCAGTGCTGCA
ATGATACCGCGAGACCCACGCTCACCGGCTCCAGATTTATCAGCAATAAACCAGCCAG
CCGGAAGGGCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGCGCAACGTTG
TTGCCATTGCTGCAGGCATCGTGGTGTCACGCTCGTCGTTTGGTATGGCTTCATTCAG
CTCCGGTTCCCAACGATCAAGGCGAGTTACATGATCCCCCATGTTGTGCAAAAAAGCG
GTTAGCTCCTTCGGTCCTCCGATCGTTGTCAGAAGTAAGTTGGCCGCAGTGTTATCAC
TCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGA
GTTGCTCTTGCCCGGCGTCAACACGGGATAATACCGCGCCACATAGCAGAACTTTAAA
AGTGCTCATCATTGGAAAACGTTCTTCGGGGCGAAAACTCTCAAGGATCTTACCGCTG
TTGAGATCCAGTTCGATGTAACCCACTCGTGCACCCAACTGATCTTCAGCATCTTTTAC
TTTCACCAGCGTTTCTGGGTGAGCAAAAACAGGAAGGCAAAATGCCGCAAAAAAGGGA
ATAAGGGCGACACGGAAATGTTGAATACTCATACTCTTCCTTTTTCAATATTATTGAAGC
```

-continued

ATTTATCAGGGTTATTGTCTCATGAGCGGATACATATTTGAATGTATTTAGAAAAATAAA

CAAATAGGGGTTCCGCGCACATTTCCCCGAAAAGTGCCACCTGACGTCTAAGAAACCA

TTATTATCATGACATTAACCTATAAAAATAGGCGTATCACGAGGCCCTTTCGTCTTCAA

Expression of the asp gene was investigated in a nine-protease delete *Bacillus subtilis* host. The plasmid pHPLT-ASP-C1-2 (See, Table 10-2, and FIG. 9), was transformed into *B. subtilis* (ΔaprE, ΔnprE, Δepr, LispA, Δbpr, Δvpr, ΔwprA, Δmpr-ybfJ, ΔnprB) and (degU$^{Hy}$32, oppA, AspoIIE3501, amyE:(xyIRPxyIAcomK-ermC). Transformation was performed as known in the art (See e.g., WO 02/14490, incorporated herein by reference). The Asp protein was produced by growth in shake flasks at 37° C. in MBD medium, a MOPS based defined medium. MBD medium was made essentially as known in the art (See, Neidhardt et al., J. Bacteriol., 119: 736-747 [1974]), except NH4Cl2, FeSO4, and CaCl2 were left out of the base medium, 3 mM K2HPO4 was used, and the base medium was supplemented with 60 mM urea, 75 g/L glucose, and 1% soytone. Also, the micronutrients were made up as a 100× stock containing in one liter, 400 mg FeSO4 0.7H2O, 100 mg MnSO4.H2O, 100 mg ZnSO4.7H2O, 50 mg CuCl2.2H2O, 100 mg CoCl2.6H2O, 100 mg NaMoO4.2H2O, 100 mg Na2B4O7.10H2O, 10 ml of 1M CaCl2, and 10 ml of 0.5 M sodium citrate. The expression levels obtained in these experiments were found to be fairly high.

In additional embodiments, "consensus" promoters such as those developed through site-saturation mutagenesis to create promoters that more perfectly conform to the established consensus sequences for the "−10" and "−35" regions of the vegetative "sigma A-type" promoters for *B. subtilis* (See, Voskuil et al., Mol. Microbiol., 17:271-279 [1995]) find use in the present invention. However, it is not intended that the present invention be limited to any particular consensus promoter, as it is contemplated that other promoters that function in *Bacillus* cells will find use in the present invention.

Example 11

Protease Production in *Bacillus clausii*

In this Example, experiments conducted to produce protease 69B4 (also referred to as "Asp" herein) in *B. clausii* are described. In order to express the Asp protein in *Bacillus clausii*, it was necessary to use a promoter that works in this alkaliphilic microorganism due to its unique regulation systems. The production profile of the alkaline serine protease of *B. clausii* PB92 (MAXACAL® protease) has shown that it has to have a strong promoter (referred to as "MXL-prom." herein; SEQ ID NOS:173, 174, and 175, See, FIG. 18) with a delicate regulation. Besides the promoter region, also signal sequences (leader sequences) are known to be very important for secreting proteins in *B. clausii*. Therefore, 3 constructs were designed With the MAXACAL® protease promoter region and separate fusions of the MAXACAL® protease leader sequence and the Asp leader sequence in front of the N-terminal Pro and the mature Asp protein with 3, 6 and 27 amino acids of the MAXACAL® protease leader fused to 25, 25 and 0 amino acids of the Asp leader, respectively.

To make these constructs, amplification of DNA fragments needed to be done in order to enable the fusion. Therefore, PCRs were performed on both MAXACAL® protease and Asp template DNA with Phusion high fidelity polymerase (Finnzymes) according to the manufacturer's instructions.

PCR reactions were executed with the following primers (bold indicates the MAXACAL® protease part of the primer) synthesized at MWG-Biotech AG:

```
1: B. clau-3F:  agggaaccgaatgaagaaacgaactgtcacaagagctctg         (SEQ ID NO: 176)

2: B. clau-3R:  cagagctcttgtgacagttcgtttcttcattcggttccct         (SEQ ID NO: 177)

3: B. clau-6F:  aatgaagaaaccgttggggcgaactgtcacaagagctctg         (SEQ ID NO: 178)

4: B. clau-6R:  cagagctcttgtgacagttcgccccaacggtttcttcatt         (SEQ ID NO: 179)

5: B. clau-27F: agttcatcgatcgcatcggctaacgaaccggctcctccagga       (SEQ ID NO: 180)

6: B. clau-27R: tcctggaggagccggttcgttagccgatgcgatcgatgaact       (SEQ ID NO: 181)

7: B. clau-vector 5': tcagggggatcctagattctgttaacttaacgtt.         (SEQ ID NO: 182)
   This primer contains the HpaI-site (GTTAAC) from the
   promoter region and a BamHI-site (GGATCC) for cloning
   reasons (both underlined).

8: pHPLT-HindIII-R: gtgctgttttatcctttaccttgtctcc.               (SEQ ID NO: 183)
   The sequence of this primer lays just upstream of the
   HindIII-site of pHPLT-ASP-C1-2 (See, Table 10-2).
```

TABLE 11-1

PCR Setup to Create Fused MAXACAL ®
Protease-Asp Leader Fragments

| Template DNA | Primer 1 | Primer 2 | Fragment Name |
|---|---|---|---|
| pHPLT-ASP-C1-2 | 1 | 8 | 3F |
| pHPLT-ASP-C1-2 | 3 | 8 | 6F |
| pHPLT-ASP-C1-2 | 5 | 8 | 27F |
| pMAX4 | 2 | 7 | 3R |
| pMAX4 | 4 | 7 | 6R |
| pMAX4 | 6 | 7 | 27R |
| 3F + 3R | 7 | 8 | 3F3R |
| 6F + 6R | 7 | 8 | 6F6R |
| 27F + 27R | 7 | 8 | 27F27R |

In Table 11-1, "pMAX4" refers to the template described in WO 88/06623, herein incorporated by reference. PCR fragments 3F3R, 6F6R, 27F27R were digested with both BamHI and HindIII. The digested PCR fragments were ligated with T4 ligase (Invitrogen) into BamHIH+HindIII-opened plasmid pHPLT-ASP-C1-2 (See, FIG. 18). The ligation product was transformed to competent *B. subtilis* cells ((ΔaprE, ΔnprE, oppA, ΔspoIIE, degUHy32, ΔamyE::(xyIR,pxyIA-comk; See e.g., WO 02/14490, incorporated herein by reference) and selected on neomycin (20 mg/l). Heart Infusion-agar plates containing neomycin were used to identify neomycin resistant colonies. DNA of the *B. subtilis* transformants was isolated using Qiagen's plasmid isolation kit according to manufacture's instructions, and were tested on the appearance of the fused MAXACAL® protease-Asp fragment by their pattern after digestion with both NcoI+HpaI together in one tube. The restriction enzymes used in this Example (i.e., BamHI, HindIII, NcoI and HpaI) were all purchased from NEB, and used following the instructions of the supplier. DNA of *B. subtilis* transformants that showed 2 bands with restriction enzymes (NcoI+HpaI) was used to transform protease negative *B. clausii* strain PBT142 protoplast cells (these were derived from PB92).

The protoplast transformation of *B. clausii* strain PBT142 was performed according to the protocol mentioned for the protoplast transformation of *B. alkalophilus* (renamed *B. clausii*) strain PB92 in patent WO88/06623, herein incorporated by reference A modification to this protocol was the use of an alternative recipe for the regeneration plates, in that instead of 1.5% agar, 8.0 g/l Gelrite gellam gum (Kelco) was used. In addition, instead of 1000 mg/l neomycin, 20 mg/l neomycin was used as described by Van der Laan et al., (Van der Laan et al., Appl. Environ. Microbiol., 57:901-909 [1991]).

DNA from all 3 constructs isolated from *B. subtilis* (see above) was transformed into *B. clausii* PBT142 protoplasts using the same protocol as above. Transformants in *B. clausii* PBT142 were selected by replica-plating on Heart Infusion agar plates containing 20 mg/l neomycin. The *B. clausii* strains with the different construct were produced as indicated in Table 11-2.

TABLE 11-2

*B. clausii* Constructs

| Construct (length MAXACALI ® protease leader) | *B. clausii* Strain |
|---|---|
| 3 MXL/25ASP | PMAX-ASP3 |
| 6 MXL/25ASP | PMAX-ASP2 |
| 27 MXL/0ASP | PMAX-ASP1 |

These 3 strains were fermented in shake flasks containing 100 ml Synthetic Maxatase Medium (SMM) (See, U.S. Pat. No. 5,324,653, herein incorporated by reference). However, instead of 0.97 g/l CaCl$_2$.6H$_2$O, 0.5 g/l CaCl$_2$ was used. Also, instead of 0.5 ml/l antifoam 5693, 0.25 ml/l Basildon was used. The 100 ml SSM shake flasks were inoculated with 0.2 ml of a pre-culture of the 3 *B. clausii* strains containing the leader constructs in 10 ml TSB (Tryptone Soya Broth) with 20 mg/l neomycin. The protease production values were measured via the AAPF-assay (as described above) after growth in the shake flasks for 3 days. The results indicated that these constructs were able to express protease with proteolytic activity.

In an additional experiment, integration of the leader construct with the entire MAXACAL® protease leader length (27 amino acids) was investigated. However, it is not intended that the present invention be limited to any particular mechanism.

Stable integration of heterologous DNA in the *B. alcalophilus* (now, *B. clausii*) chromosome is described in several publications (See e.g., WO 88/06623, and Van der Laan et al., supra). The procedure described in patent WO 88/06623 for integration of 1 or 2 copies of the MAXACAL® protease gene in the chromosome of *B. alcalophilus* (now, *B. clausii*) was used to integrate at least 1 copy of the asp gene in the chromosome of *B. clausii* PBT142. However, a derivative of pE194-neo: pENM#3 (See, FIG. 19) was used instead of the integration vector pE194-neo (to make pMAX4 containing the MAXACAL® protease gene). In the integration vector pENM#3, the Asp leader PCR product 27F27R was cloned in the unique blunt end site HpaI in between the 5' and the 3' flanking regions of the MAXACAL® protease gene. Therefore, 27F27R was made blunt-ended as follows: it was first digested with HpaI (5' end), purified with the Qiagen PCR purification kit, and then digested with HindIII (3' end). This treated PCR fragment 27F27R was purified again after HindIII digestion (using the same Qiagen kit) and filled in with dNTP's using T4 polymerase (Invitrogen) and purified again with Qiagen kit. The HpaI-opened pENM#3 and the blunt-ended PCR product 27F27R were ligated with T4 ligase (Invitrogen). The ligation product was transformed directly to *B. clausii* PBT142 protoplasts and selected after replica-plating on HI agar plates with 20 mg/l neomycin. Two transformants with the correct orientation of the asp gene in the integration vector were identified and taken into the integration procedure as described in patent WO 88/06623. Selections were done at 2 mg/l and 20 mg/l neomycin for integration in the MAXACAL® protease locus and at an illegitimate locus, respectively. These results indicated that *B. clausii* is also suitable as an expression host for the Asp protease.

Example 12

Protease Production in *B. licheniformis*

In this Example, experiments conducted to produce protease 69B4 in *B. licheniformis* are described. During these experiments, various expression constructs were created to produce protease 69B4 protease (also referred to as "ASP protease") in *Bacillus licheniformis*. Constructs were cloned into expression plasmid pHPLT (replicating in *Bacillus*) and/or into integration vector pICatH. Plasmid pHPLT (See, FIG. 17; and U.S. Pat. No. 6,562,612 [herein incorporated by reference) is a pUB110 derivative, has a neomycin resistance marker for selection, and contains the *B. licheniformis* α-amylase (LAT) promoter (P$_{LAT}$), a sequence encoding the LAT signal peptide (preLAT), followed by PstI and HpaI restriction sites for cloning and the LAT transcription terminator. The pICatH vector (See, FIG. 20) contains a temperature sensitive origin of replication (ori pE194, for replication in *Bacillus*), ori pBR322 (for amplification in *E. coli*), a neomycin resistance gene for selection, and the native *B. licheniformis* chloramphenicol resistance gene (cat) with repeats for selection, chromosomal integration and cassette amplification.

Construct ASPc1 was created as a PstI-HpaI fragment by fusion PCR with High Fidelity Platinum Taq Polymerase (Invitrogen) according to the manufacturer's instructions, and with the following primers:

```
pHPLT-BgIII_FW
                                          (SEQ ID NO: 184)
AGTTAAGCAATCAGATCTTCTTCAGGTTA fusionC1_FW
                                          (SEQ ID NO: 185)
CATTGAAAGGGGAGGAGAATCATGAGAAGCAAGAAGCGAACTGTCAC fusionC1_RV
                                          (SEQ ID NO: 186)
GTGACAGTTCGCTTCTTGCTTCTCATGATTCTCCTCCCCTTTCAATG pHPLT-HindIII_RV
                                          (SEQ ID NO: 187)
CTTTACCTTGTCTCCAAGCTTAAAATAAAAAACGG
```

These primers were obtained from MWG Biotech. PCR reactions were typically performed on a thermocycler for 30 cycles with High Fidelity Platinum Taq polymerase (Invitrogen) according to the manufacturer's instructions, with annealing temperature of 55° C. PCR-I was performed with the primers pHPLT-BgIII_FW and fusionC1_RV on pHPLT as template DNA. PCR-II was performed with primers fusionC1_FW and pHPLTHindIII_RV on plasmid pHPLT-ASP-C1-2. The fragments from PCR-I and PCR-II were assembled in a fusion PCR with the primers pHPLT-BgII-I_FW and pHPLT-HindIII—RV. This final PCR fragment was purified using the Qiagen PCR purification kit, digested with BglII and HindIII, and ligated with T4 DNA ligase according to the manufacturers' instructions into BglII and HindIII digested pHPLT. The ligation mixture was transformed into B. subtilis strain OS14 as known in the art (See, U.S. Pat. Appl. No. US20020182734 and WO 02/14490, both of which are incorporated herein by reference). Correct transformants produced a halo on a skimmed milk plate and one of them was selected to isolate plasmid pHPLT-ASPc1. This plasmid was introduced into B. licheniformis host BML780 (BRA7 derivative, cat-, amyL-, spo-, aprL-, endoGluC-) by protoplast transformation as known in the art (See, Pragai et al., Microbiol., 140:305-310 [1994]). Neomycin resistant transformants formed halos on skim plates, whereas the parent strain without pHPLT-ASPc1 did not. This result shows that B. licheniformis is capable of expressing and secreting ASP protease when expression is driven by the LAT promoter and when it is fused to a hybrid signal peptide (MRSKKRTV-TRALAVATAAATLLAGGMAAQA; SEQ ID NO:135).

Construct ASPc3 was created as a PstI-HpaI fragment by fusion PCR (necessary to remove the internal PstI site in the synthetic asp gene) as described above with the following primers:

```
ASPdelPstI_FW
                                          (SEQ ID NO: 188)
GCGCAGGATGTAGCAGCTGGACTTGTGG ASPdelPstI_RV
                                          (SEQ ID NO: 189)
CCACAAGTCCAGCTGCTACATCCTGCGC AspPstI_FW
                                           SEQ ID NO: 190)
GCCTCATTCTGCAGCTTCAGCAAACGAACCGGCTCCTCCAGG AspHpaI_RV
                                          (SEQ ID NO: 191)
CGTCCTCTGTTAACTCAGTCGTCACTTCCAGAGTCAGTCGTAATC
```

After purification, the PCR product was digested with PstI-HpaI and ligated into PstI and HpaI digested pHPLT and then transformed into B. subtilis strain OS14. Plasmid pHPLT-ASPc3 was isolated from a neomycin resistant that formed a relatively (compared to other transformants) large halo on a skim milk plate. Plasmid DNA was isolated using the Qiagen plasmid purification kit and sequenced by BaseClear.

Sequencing confirmed that the ASPc3 construct encodes mature ASP that has two aspartic acid residues at the extreme C-terminal end (S188D, P189D). These mutations were deliberately introduced by PCR to make the C-terminus of ASP less susceptible against proteolytic degradation (See, WO 02055717). It also appeared that two mutations were introduced into the coding region of the N-terminal pro region by the PCR methods. These mutations caused two amino acid changes in the N-terminal pro-region: L42I and Q141P. Since this particular clone with these two pro(N) mutations gives a somewhat larger halo than other clones without these mutations, it was contemplated that expression and/or secretion of ASP protease in Bacillus is positively affected by these N-terminal pro mutations. However, it is not intended that the present invention be limited to these specific mutations, as it is also contemplated that further mutations will find use in the present invention.

Next, pHPLT-ASPc3 was transformed into BML780 as described above. In contrast to the parental strain without the plasmid, BML780(pHLPT-ASPc3) produced a halo on a skim milk plate indicating that also this ASPc3 construct leads to ASP expression in B. licheniformis. To make an integrated, amplified strain containing the ASPc3 expression cassette, the C3 construct was amplified from pHPLT-ASPc3 with the following primeis:

```
EBS2XhoI_FW
                                          (SEQ ID NO: 192)
ATCCTACTCGAGGCCTTTTGGAAGAAAATATAGGG

EBS2XhoI_RV
                                          (SEQ ID NO: 193)
TGGAATCTCGAGGTTTTATCCTTTACCTTGTCTCC
```

The PCR product was digested with XhoI, ligated into XhoI-digested plCatH (See, FIG. 20) and transformed into B. subtilis OS14 as described above. The plasmid from an ASP expressing clone (judged by halo formation on skim milk plates) was isolated and designated plCatH-ASPc3. DNA sequencing by BaseClear confirmed that no further mutations were introduced in the ASPc3 cassette in plCatH-ASPC3. The plasmid was then transformed into BML780 at the permissive temperature (37° C.) and one neomycin resistant (neoR) and chloramphenicol resistant (capR) transformant were selected and designated BML780(plCatH-ASPc3). The plasmid in BML780(plCatH-ASPc3) was integrated into the cat region on the B. licheniformis genome by growing the strain at a non-permissive temperature (50° C.) in medium with chloramphenicol. One capR resistant clone was selected and designated BML780-plCatH-ASPc3. BML780-plCatH-ASPc3 was grown again at the permissive temperature for several generations without antibiotics to loop-out vector sequences and then one neomycin sensitive (neoS), capR clone was selected. In this clone, vector sequences of plCatH on the chromosome were excised (including the neomycin resistance gene) and only the ASPc3-cat cassette was left. Note that the cat gene is a native B. licheniformis gene and that the asp gene is the only heterologous piece of DNA introduced into the host. Next, the ASPc3-cat cassette on the chromosome was amplified by growing the strain in/on media with increasing concentrations of chloramphenicol. After various rounds of amplification, one clone (resistant against 75 µg/ml chloramphenicol) was selected and designated "BML780-ASPc3." This clone produced a clear halo on a skim milk plate, whereas the parental strain BML780 did not, indicating that ASP protease is produced and secreted by the BML780-ASPc3 strain.

Construct ASPc4 is similar to ASPc3, but ASP protease expressed from ASPc4 does not have two aspartic acid residues at the C-terminal end of the mature chain. ASPc4 was created by amplification of the asp gene in pHPLT-ASPc3 with the following Hypur primers from MWG Biotech (Germany):

XhoPlatPRElat_FW
(SEQ ID NO: 194)
accccctcgaggcttttcttttggaagaaaatatagggaaaatggtact tgttaaaaattcggaatatttatacaatatcatatgtttcacattgaaag ggggaggagaatcatgaaacaacaaaaacggctttac ASPendTERMXhoI_RV
(SEQ ID NO: 195)
gtcgacctcgaggttttatccttaccttgtctccaagcttaaaataaaa aaacggatttccttcaggaaatccgtcctctgttaactcaaggggaactt ccagagtcagtcgtaatc The ASPc4 PCR product was purified and digested with XhoI, ligated into XhoI-digested plCatH, and transformed into B. subtilis OS14 as described above for ASPc3. Plasmid was isolated from a neoR, capR clone and designated plCatH-ASPc4. plCatH-ASPc4 was transformed into BML780, integrated in the genome, vector sequences were excised, and the cat-ASPc4 cassette was amplified as described above for the ASPc3 construct. Strains with the ASPc4 cassette did not produce smaller halos on skim milk plates than strains with the AspC3 cassette, suggesting that the polarity of the C-terminus of ASP mature is not a significant factor for ASP production, secretion and/or stability in Bacillus. However, it is not intended that the present invention be limited to any particular method.

To explore whether the native ASP signal peptide can drive export in Bacillus, ASPc5 was constructed. PCR was performed on the synthetic asp gene of DNA2.0 with primers ASPendTERMXhoI_RV (above) and XhoPlatPREasp_FW.

XhoPlatPREasp_FW
(SEQ ID NO: 196)
:accccctcgaggcttttcttttggaagaaaatatagggaaaatggtac ttgttaaaaattcggaatatttatacaatatcatatgtttcacattgaaa ggggaggagaatcatgacaccacgaactgtcacaag The ASPc5 PCR product was purified and digested with XhoI, ligated into XhoI digested plCatH, and transformed into B. subtilis OS14 as described above for ASPc3. Plasmid was isolated from a neoR, capR clone and designated "plCatH-ASPc5." DNA sequencing confirmed that no unwanted mutations were introduced into the asp gene by the PCR. plCatH-ASPc5 was transformed into BML780, integrated in the genome, vector sequences were excised, and the cat-ASPc5 cassette was amplified as described above for the ASPc3 construct. It was observed that B. licheniformis strains with the ASPc5 construct also form halos on skim milk plates, confirming that the native signal peptide of ASP functions as a secretion signal in Bacillus species.

Finally, construct ASPc6 was created. It has the B. licheniformis subtilisin (aprL) promoter, RBS and signal peptide sequence fused in-frame to the DNA sequence encoding mature ASP from the optimized DNA2.0 gene. It was created by a fusion PCR with primer ASPendTERMXhoI_RV and the following primers:

AprLupXhoI_FW
(SEQ ID NO: 197)
attagtctcgaggatcgaccggaccgcaacctcc

AprLAsp_FW
(SEQ ID NO: 198)
cgatggcattcagcgattccgcttctgctaacgaaccggctcctccagga tctgc AprLAsp_RV
(SEQ ID NO: 199)
gcagatcctggaggagccggttcgttagcagaagcggaatcgctgaatgc catcg PCR-I was performed with the primers AprLupXhoI_FW and AprLAsp_RV on chromosomal DNA of BRAT as template DNA. PCR-II was performed with primers AprLAsp_FW and ASPendTERMXhoI_RV on the synthetic asp gene of DNA2.0. The fragments from PCR-I and PCR-II were assembled in a fusion PCR with the primers so ASPendTERMXhoI_RV and AprLupXhoI_FW. This final PCR fragment was purified using Qiagen's PCR purification kit (according to the manufacturers instructions), digested with XhoI, ligated into plCatH, and transformed into B. subtilis OS14, as described above for ASPc3. Plasmid was isolated from a neoR, capR clone and designated "plCatH-ASPc6." DNA sequencing confirmed that no unwanted mutations were introduced into the asp gene or aprL region by the PCRs. plCatH-ASPc6 was transformed into BML780, integrated in the genome, vector sequences were excised, and the cat-ASPc6 cassette was amplified as described above for the ASPc3 construct. B. licheniformis strains with the ASPc6 construct also formed halos on skim milk plates, indicating that the aprL promoter in combination with the AprL signal peptide drives expression/secretion of ASP protease in B. licheniformis.

Example 13

Protease Production in T. reesei

In this Example, experiments conducted to produce protease 69B4 in T. reesei are described. In these experiments, three different fungal constructs (fungal expression vectors comprising cbhl fusions) were developed. One contained the ASP 5' pro region, mature gene, and 3' pro region; the second contained the ASP 5' pro region and the mature gene; and the third contained only the ASP mature gene.

The following primer pairs were used to PCR (in the presence of 10% DMSO), the different fragments from the chromosomal DNA K25.10, carrying the ASP gene and introduced SpeI-AscI sites to clone the fragments into the vector pTREX4 (See, FIG. 21) digested with SpeI and AscI restriction enzymes.

1. CBHI fusion with the ASP 5' pro region, mature gene, and 3' pro region:

```
AspproF
forward primer (SpeI-Kexin site-ATG-pro sequence):
                                          (SEQ ID NO: 200)
5'-ACTAGTAAGCGGATGAACGAGCCCGCACCACCCGGGAGCGCGAGC AspproR reverse primer
(AscI site; C-term pro region
from the TAA stop codon to the end of the gene):
                                          (SEQ ID NO: 201)
5'- GGCGCGCC TTA GGGGAGGGTGAGCCCCATGGTGTAGGCACCG
```

2. The ASP 5' pro region and mature gene:

```
AspproF
forward primer (SpeI-Kexin site-ATG-pro sequence):
                                          (SEQ ID NO: 202)
5'-ACTAGTAAGCGGATGAACGAGCCCGCACCACCCGGGAGCGCGAGC AspmatR reverse primer (AscI site: TAA
stop to the end of the mature sequence)
                                          (SEQ ID NO: 203)
5'- GGCGCGCC TTA CGGGCTGCTGCCCGAGTCCGTGGTGATCA-3'
```

3. The ASP mature gene only:

```
AspmatF forward primer SpeI-Kexin site-ATG-mature:
                                          (SEQ ID NO: 204)
5'-ACTAGT AAGCGG ATG TTCGACGTGATCGGCGGCAACGCCTACAC
CAT AspmatR Reverse Primer
(AscI site: TAA stop to end of mature sequence)
                                          (SEQ ID NO: 205)
5'-GGCGCGCC TTA CGGGCTGCTGCCCGAGTCCGTGGTGATCA-3'
```

After construction, the different plasmids were transformed into a *Trichoderma reesei* strain with disruptions in the cbh1, cbh2, egl1, and egl2 genes, using biolistic transformation methods known in the art. Stable transformants were screened, based on morphology. Ten stable transformants for each construct were screened in shake flasks. The initial inoculum media used contained 30 g/L α-lactose, 6.5 g/L $(NH_4)_2SO_4$, 2 g/L $KH_2PO_4$, 0.3 g/L $MgSO_4*7H_2O$, 0.2 g/L $CACl_2$, 1 ml/L 1000× *T. reesei* Trace Salts, 2 mL/L 10% TWEEN®-80, 22.5 g/L Proflo, and 0.72 g/L $CaCO_3$, in which the transformants were grown for approximately 48 hr. After this incubation period, 10% of the culture was transferred into flasks containing minimal medium known in the art (See, Foreman et al., J. Biol. Chem., 278:31988-31997 [2003]), with 16 g/L of lactose to induce expression. The flasks were placed in a 28° C. shaker. Four-day samples were run on NuPAGE 4-12% gels, and stained with Coomassie Blue. After five-days the protease activity was measured by adding 10 µl of the supernatant to 190 µl AAPF substrate solution (conc. 1 mg/ml, in 0.1 M Tris/0.005% TWEEN, pH 8.6). The rate of increase in absorbance at 410 nm due to release of p-nitroaniline was monitored (25° C.)

The activity data showed that there was a 5× higher production over the control strain (i.e., the parent strain), indicating that *T. reesei* is suitable for the expression of ASP protease.

Example 14

Protease Production in *A. niger*

In this Example, experiments conducted to produce protease 69B4 in *Aspergillus niger* var. *awamori* (PCT WO90/00192) are described. In these experiments, four different fungal constructs (fungal expression vectors comprising glaA fusions) were developed. One contained the ASP pre-region, 5' pro-region, mature gene, and the 3' pro-region: the second contained the ASP pre-region, 5' pro-region, and the mature gene; the third contained the ASP 5' pro-region, mature gene, and the 3' pro-region; the fourth contained the ASP 5' pro-region, and the mature gene.

Figure 22:
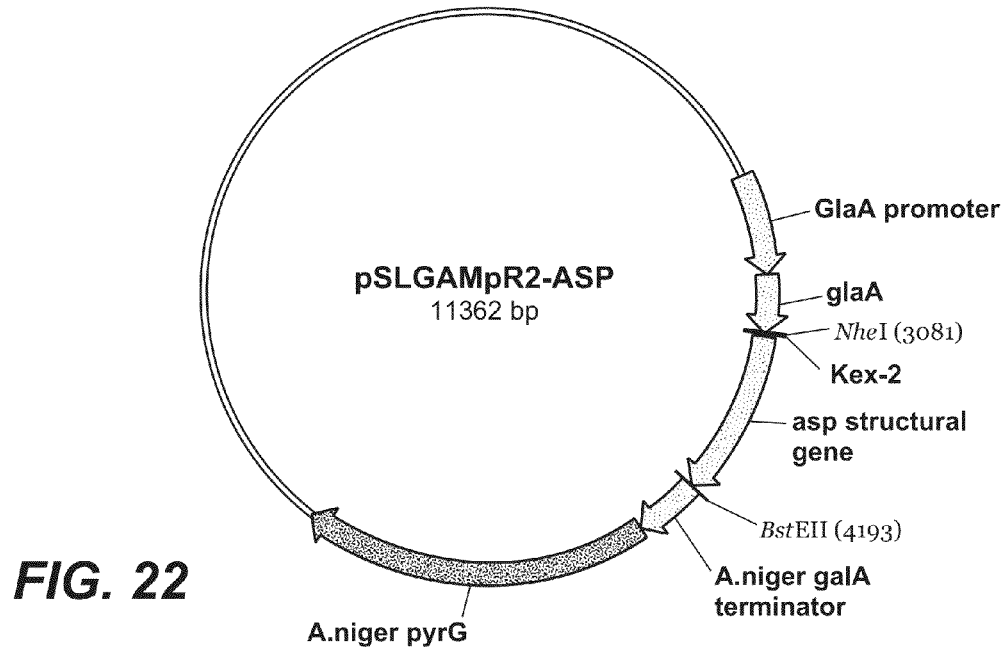
FIG. 22 provides the plasmid map of the pSLGAMpR2 vector.

Selected from the following primer pairs, primers were used to PCR (in the presence of 10% DMSO) the different fragments from the chromosomal DNA 69B4 carrying the asp gene and introduced the Nhe 1-BstEII sites to clone the fragments into the vector pSLGAMpR2 (See, FIG. 22) digested with Nhe1 and BstEII restriction enzymes.

Primers Anforward 01 and Anforward 02 contained attB1 Gateway cloning sequences (Invitrogen) at the 5' end of the primer. Primers Anreversed 01 and Anreversed 02 contained attB2 Gateway cloning sequences (Invitrogen) at the 5' end of the primer. These primers were used to PCR (in the presence of 10% DMSO) the different fragments from the chromosomal DNA 69B4 carrying the ASP genes.

Figure 23:
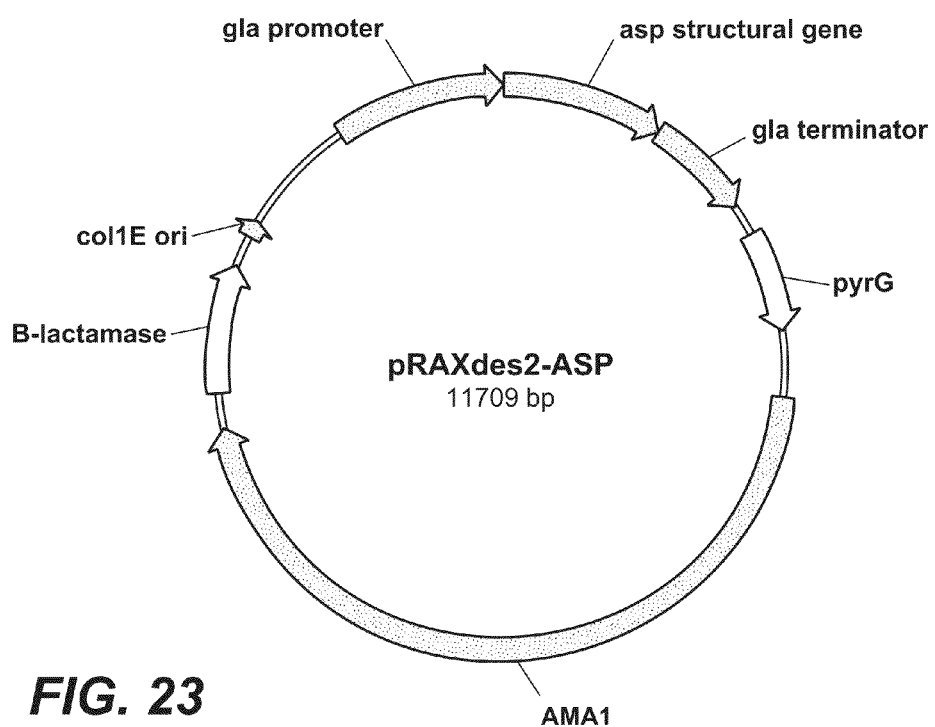
FIG. 23 provides the plasmid map of the pRAXdes2-ASP vector.
Figure 24:
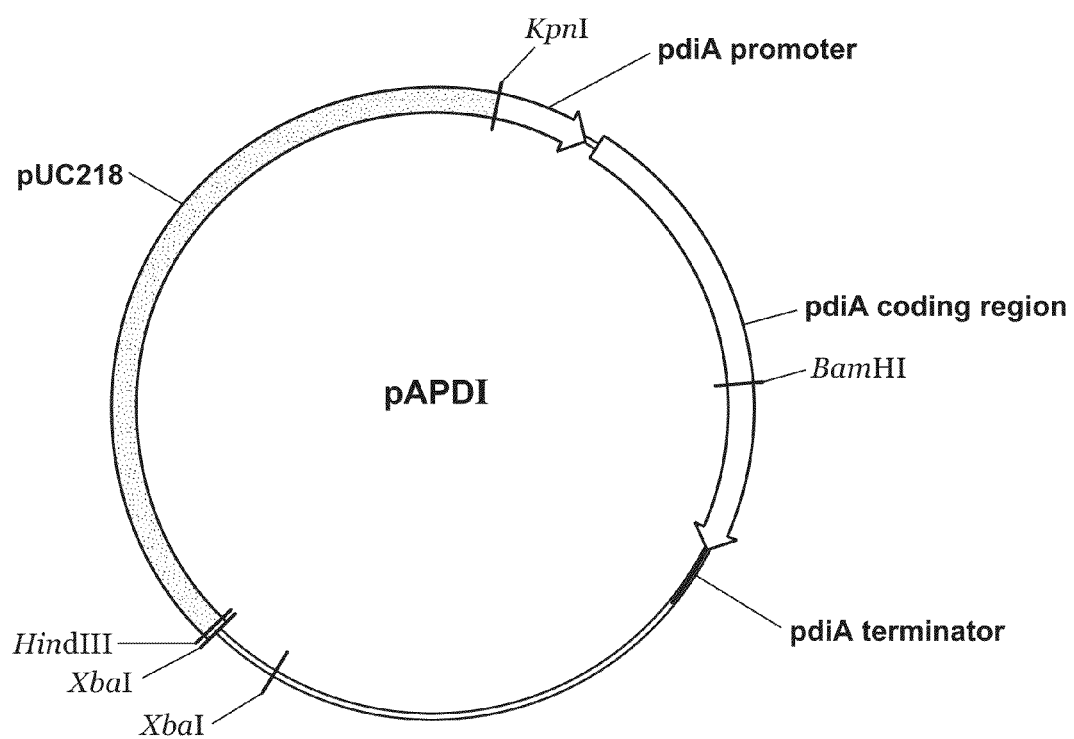
FIG. 24 provides the plasmid map of the pAPDI vector.
Figure 25A:
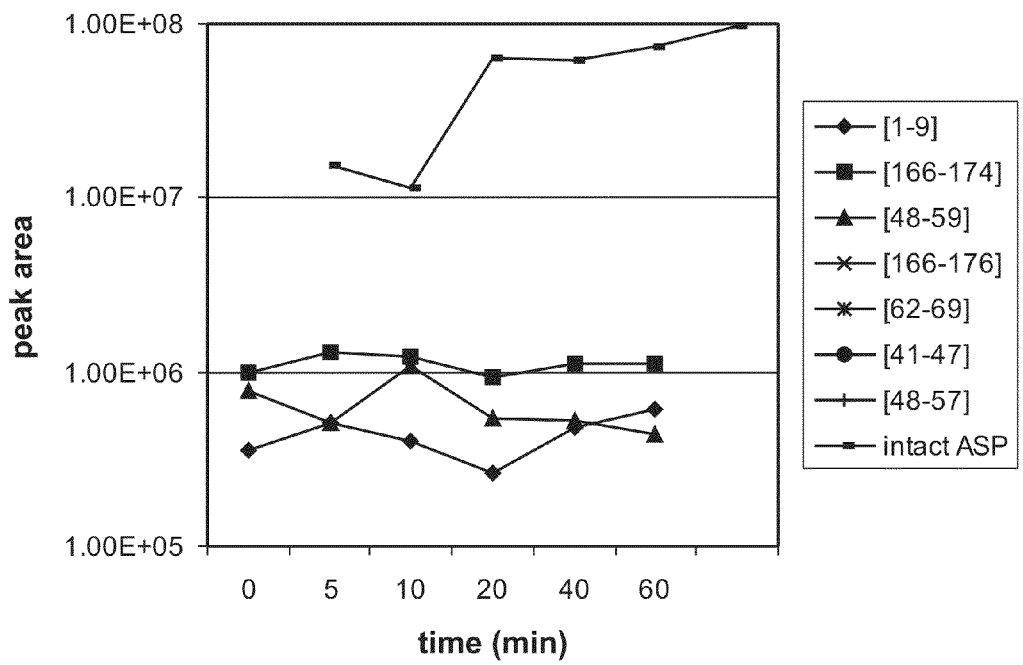
FIG. 25 provides graphs showing ASP autolysis. Panel A provides a graph showing the ASP autolysis peptides observed in a buffer without LAS. Panel B provides a graph showing the ASP autolysis peptides observed in a buffer with 0.1% LAS.
Figure 25B:
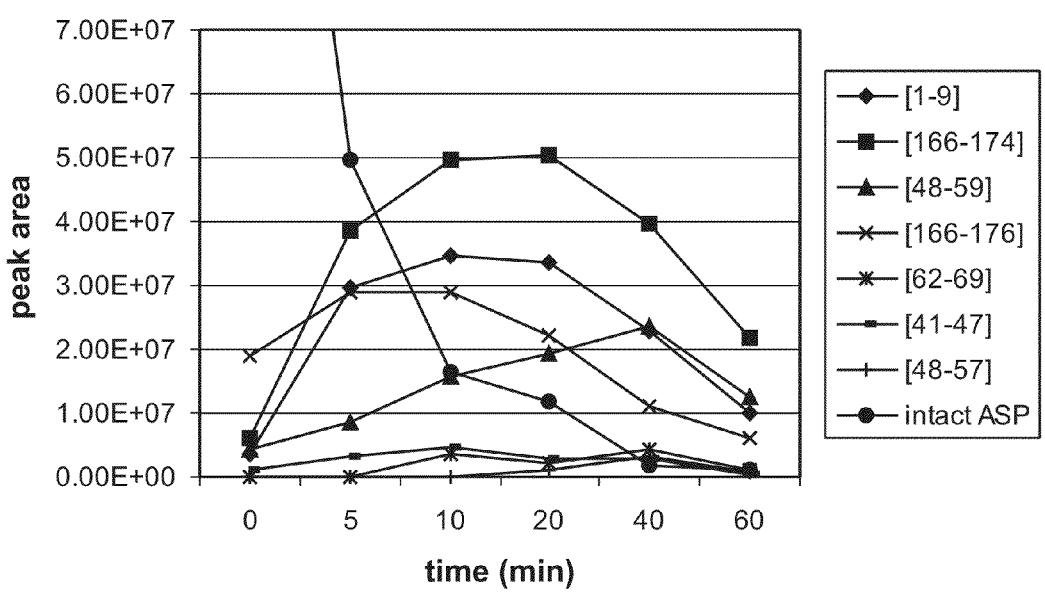

The different constructs were transferred to a *A. niger* Gateway compatible destination vector pRAXdes2 (See, FIG. 23; See also, U.S. patent application Ser. No. 10/804,785, and PCT Appln. No. US04/08520, both of which are incorporated herein by reference).

```
Anforward 01 (without the attB1 sequence)
                                          (SEQ ID NO: 206)
5'-ATGACACCACGAACTGTCACAAGAGCTCTG-3'

Anforward 02 (without the attB1 sequence)
                                          (SEQ ID NO: 207)
5'-AACGAACCGGCTCCTCCAGGATCTGCATCA-3'

Anreversed 01 (without the attB2 sequence)
                                          (SEQ ID NO: 208)
5'-AGGGGAACTTCCAGAGTCAGTCGTAATCATTCTCAGGCC-3'

Anreversed 02 (without the attB1 sequence)
                                          (SEQ ID NO: 209)
5'-GGGGAGGGTGAGTCCCATTGTGTAAGCTCCTGA-3' pSLGAM-NT_FW
                                          (SEQ ID NO: 210)
5'-ACCGCGACTGCTAGCAACGTCATCTCCAAGCGCGGCGGTGGCAACGA
ACCGGCTCCTCCAGGATCt-3' pSLGAM-MAT_FW
                                          (SEQ ID NO: 211)
5'-ACCGCGACTGCTAGCAACGTCATCTCCAAGCGCGGCGGTGGCAACGA
ACCGGCTCCTCCAGGATCT-3' pSLGAM-MAT_RV
                                          (SEQ ID NO: 212)
5'-CCGCCAGGTGTCGGTCACCTAAGGGGAACTTCCAGAGTCAGTCGTAA
TCATTCT-3'
```

PCR conditions were as follows: 5 µL of 10×PCR reaction buffer (Invitrogen); 20 mM $MgSO_4$; 0.2 mM each of dATP, dTTP, dGTP, dCTP (final concentration), 1 µL of 10 ng/µL genomic DNA, 1 µL of High Fidelity Taq polymerase (Invitrogen) at 1 unit per µL, 0.2 µM of each primer (final concentration), 5 µl DMSO and water to 50 µL. The PCR protocol was: 94° C. for 5 min.; followed by 30 cycles of 94° C. for 30 sec., 55° C. for 30 sec., and 68° C. for 3 min; followed by 68° C. for 10 min., and 15° C. for 1 min.

After construction, the different plasmids and a helper plasmid (HM 396 pAPDI) were transformed into *Aspergillus niger* var *awamori* (Delta Ap4 strain), using protoplast transformation methods known in the art. Stable transformants were screened, based on morphology. Ten stable transformants for each construct were screened in shake flasks. After this period, a piece of agar containing the strain was transferred into flasks containing RoboSoy medium or the formula 12 g/l Tryptone, 8 g/l Soytone, 15 g/l Ammonium sulfate, 12.1 g/l NaH$_2$PO$_4$.H$_2$O, 2.19 g/l Na$_2$HPO$_4$, 5 ml 20% MgSO4.7H2O, 10 ml 10% Tween 80, 500 ml 30% Maltose and 50 ml 1M phosphate buffer pH 5.8 and 2 g/l uridine to induce expression. The flasks were placed in a 28° C. shaker. Four-day samples were run on NuPAGE 10% Bis Tris protein gels, and stained with Coomassie Blue. Five-day samples were assayed for protease activity using the AAPF method.

The amount of ASP expressed was found to be low, such that it could not be detected in the Coomassie stained gel. Colonies on plates however showed a clear halo formation on skim milk plate agar plates that were significantly larger than the control strain. Thus, although the expression was low, these results clearly indicate that *A. niger* is suitable for the expression of ASP protease.

Example 15

Generation of Asp Site-Saturated Mutagenesis (SSM) Libraries

In this Example, experiments conducted to develop site-saturation mutagenesis libraries of asp are described. Site saturated Asp libraries each contained 96 *B. subtilis* (ΔaprE, ΔnprE, oppA, ΔspoIIE, degUHy32, ΔamyE::(xylR,pxylA-comK) clones harboring the pHPLT-ASP-c1-2 expression vector. This vector, containing the Asp expression cassette composed of the synthetic DNA sequence (See, Example 10) encoding the Asp hybrid Signal peptide and the Asp N-terminal pro and mature protein were found to enable expression of the protein indicated below (the signal peptide and precursor protease) and secretion of the mature Asp protease.

DNA Sequence encoding synthetic Asp hybrid signal peptide:

(SEQ ID NO: 213)
ATGAGAAGCAAGAAGCGAACTGTCACAAGAGCTCTGGCTGTGGCAACAGC

AGCTGCTACACTCTTGGCTGGGGGTATGGCAGCACAAGCT

The signal peptide and precursor protease are provided in the following sequence (SEQ ID NO:214) (in this sequence, bold indicates the mature protease, underlining indicates the N-terminal prosequence, and the standard font indicates the signal peptide):

(SEQ ID NO: 214)
MRSKKRTVTRALAVATAAATLLAGGMAAQA<u>NEPAPPGSASAPPRLAEKLD

PDLLEAMERDLGLDAEEAAATLAFQHDAAETGEALAEELDEDFAGTWVED

DVLYVATTDEDAVEEVEGEGATAVTVEHSLADLEAWKTVLDAALEGHDDV

PTWYVDVPTNSVVVAVKAGAQDVAAGLVEGADVPSDAVTFVETDETPRTM</u>

FDVIGGNAYTIGGRSRCSIGFAVNGGFITAGHCGRTGATTANPTGTFAGS

SFPGNDYAFVRTGAGVNLLAQVNNYSGGRVQVAGHTAAPVGSAVCRSGST

TGWHCGTITALNSSVTYPEGTVRGLIRTTVCAEPGDSGGSLLAGNQAQGV

TSGGSGNCRTGGTTFFQPVNPILQAYGLRMITTDSGSSP

Construction of the 189 asp site saturated mutagenesis libraries was completed by using the pHPLT-ASP-C1-2 expression vector as template and primers listed in Table 15-1. The mutagenesis primers used in these experiments all contain the triple DNA sequence code NNS (N=A, C, T or G and S=C or G) at the position that corresponds with the codon of the Asp mature sequence to be mutated and guaranteed random incorporation of nucleotides at that position. Construction of each SSM library started with two PCR amplifications using pHPLT-BgIII-FW primer and a specific Reverse mutagenesis primer, and pHPLT-BgIII-RV primer and a specific Forward mutagenesis primer (equal positions for the mutagenesis primers). Platinum Taq DNA polymerase High Fidelity (Cat. No. 11304-029; Invitrogen) was used for PCR amplification (0.2 μM primers, 20 up to 30 cycles) according to protocol provided by Invitrogen. Briefly, 1 μL amplified DNA fragment of both specific PCR mixes, both targeted the same codon, was added to 48 μL of fresh PCR reaction solution together with primers pHPLT-BgIII-FW and pHPLT-BgIII-RV. This fusion PCR amplification (22 cycles) resulted in a linear pHPLT-ASP-c1-2 DNA fragment with a specific Asp mature codon randomly mutated and a unique BgIII restriction site on both ends. Purification of this DNA fragment (Qiagen PCR purification kit, Cat. No. 28106), digesting it with BgIII, performing an additional purification step and a ligation reaction (Invitrogen T4 DNA Ligase (Cat. No. 15224-025) generated circular and multimeric DNA that was subsequently transformed into *B. subtilis* (ΔaprE, ΔnprE, oppA, ΔspoIIE, degUHy32, ΔamyE:(xylR,pxylA-comK). For each library, after overnight incubation at 37° C., 96 single colonies were picked from Heart Infusion agar plates with 20 mg/L neomycin and grown for 4 days at 37° C. in MOPS media with 20 mg/ml neomycin and 1.25 g/L yeast extract (See, WO 03/062380, incorporated herein by reference, for the exact medium formulation used herein) for sequence analysis (BaseClear) and protease expression for screening purposes. The library numbers ranged from 1 up to 189, with each number representing the codon of the mature asp sequence that is randomly mutated. After selection, each library included a maximum of 20 Asp protease variants.

TABLE 15-1

Primers Used to Generate Synthetic ASP SSM Libraries

| | |
|---|---|
| pHPLT-BgIII-FW | GCAATCAGATCTTCCTTCAGGTTATGACC (SEQ ID NO: 215) |
| pHPLT-BgIII-RV | GCATCGAAGATCTGATTGCTTAACTGCTTC (SEQ ID NO: 216) |
| Forward Mutagenesis Primer | DNA sequence, 5' to 3' |
| asp1F | GAAACGCCTAGAACGATGNNSGACGTAATTGGAGGCAAC (SEQ ID NO: 217) |

TABLE 15-1-continued

Primers Used to Generate Synthetic ASP SSM Libraries

| | |
|---|---|
| asp2F | ACGCCTAGAACGATGTTCNNSGTAATTGGAGGCAACGCA (SEQ ID NO: 218) |
| asp3F | CCTAGAACGATGTTCGACNNSATTGGAGGCAACGCATAT (SEQ ID NO: 219) |
| asp4F | AGAACGATGTTCGACGTANNSGGAGGCAACGCATATACT (SEQ ID NO: 220) |
| asp5F | ACGATGTTCGACGTAATTNNSGGCAACGCATATACTATT (SEQ ID NO: 221) |
| asp6F | ATGTTCGACGTAATTGGANNSAACGCATATACTATTGGC (SEQ ID NO: 222) |
| asp7F | TTCGACGTAATTGGAGGCNNSGCATATACTATTGGCGGC (SEQ ID NO: 223) |
| asp8F | GACGTAATTGGAGGCAACNNSTATACTATTGGCGGCCGG (SEQ ID NO: 224) |
| asp9F | GTAATTGGAGGCAACGCANNSACTATTGGCGGCCGGTCT (SEQ ID NO: 225) |
| asp10F | ATTGGAGGCAACGCATATNNSATTGGCGGCCGGTCTAGA (SEQ ID NO: 226) |
| asp11F | GGAGGCAACGCATATACTNNSGGCGGCCGGTCTAGATGT (SEQ ID NO: 227) |
| asp12F | GGCAACGCATATACTATTNNSGGCCGGTCTAGATGTTCT (SEQ ID NO: 228) |
| asp13F | AACGCATATACTATTGGCNNSCGGTCTAGATGTTCTATC (SEQ ID NO: 229) |
| asp14F | GCATATACTATTGGCGGCNNSTCTAGATGTTCTATCGGA (SEQ ID NO: 230) |
| asp15F | TATACTATTGGCGGCCGGNNSAGATGTTCTATCGGATTC (SEQ ID NO: 231) |
| asp16F | ACTATTGGCGGCCGGTCTNNSTGTTCTATCGGATTCGCA (SEQ ID NO: 232) |
| asp17F | ATTGGCGGCCGGTCTAGANNSTCTATCGGATTCGCAGTA (SEQ ID NO: 233) |
| asp18F | GGCGGCCGGTCTAGATGTNNSATCGGATTCGCAGTAAAC (SEQ ID NO: 234) |
| asp19F | GGCCGGTCTAGATGTTCTNNSGGATTCGCAGTAAACGGT (SEQ ID NO: 235) |
| asp20F | CGGTCTAGATGTTCTATCNNSTTCGCAGTAAACGGTGGC (SEQ ID NO: 236) |
| asp21F | TCTAGATGTTCTATCGGANNSGCAGTAAACGGTGGCTTC (SEQ ID NO: 237) |
| asp22F | AGATGTTCTATCGGATTCNNSGTAAACGGTGGCTTCATT (SEQ ID NO: 238) |
| asp23F | TGTTCTATCGGATTCGCANNSAACGGTGGCTTCATTACT (SEQ ID NO: 239) |
| asp24F | TCTATCGGATTCGCAGTANNSGGTGGCTTCATTACTGCC (SEQ ID NO: 240) |
| asp25F | ATCGGATTCGCAGTAAACNNSGGCTTCATTACTGCCGGT (SEQ ID NO: 241) |
| asp26F | GGATTCGCAGTAAACGGTNNSTTCATTACTGCCGGTCAC (SEQ ID NO: 242) |
| asp27F | TTCGCAGTAAACGGTGGCNNSATTACTGCCGGTCACTGC (SEQ ID NO: 243) |

TABLE 15-1-continued

Primers Used to Generate Synthetic ASP SSM Libraries

| | |
|---|---|
| asp28F | GCAGTAAACGGTGGCTTCNNSACTGCCGGTCACTGCGGA (SEQ ID NO: 244) |
| asp29F | GTAAACGGTGGCTTCATTNNSGCCGGTCACTGCGGAAGA (SEQ ID NO: 245) |
| asp30F | AACGGTGGCTTCATTACTNNSGGTCACTGCGGAAGAACA (SEQ ID NO: 246) |
| asp31F | GGTGGCTTCATTACTGCCNNSCACTGCGGAAGAACAGGA (SEQ ID NO: 247) |
| asp32F | GGCTTCATTACTGCCGGTNNSTGCGGAAGAACAGGAGCC (SEQ ID NO: 248) |
| asp33F | TTCATTACTGCCGGTCACNNSGGAAGAACAGGAGCCACT (SEQ ID NO: 249) |
| asp34F | ATTACTGCCGGTCACTGCNNSAGAACAGGAGCCACTACT (SEQ ID NO: 250) |
| asp35F | ACTGCCGGTCACTGCGGANNSACAGGAGCCACTACTGCC (SEQ ID NO: 251) |
| asp36F | GCCGGTCACTGCGGAAGANNSGGAGCCACTACTGCCAAT (SEQ ID NO: 252) |
| asp37F | GGTCACTGCGGAAGAACANNSGCCACTACTGCCAATCCG (SEQ ID NO: 253) |
| asp38F | CACTGCGGAAGAACAGGANNSACTACTGCCAATCCGACT (SEQ ID NO: 254) |
| asp39F | TGCGGAAGAACAGGAGCCNNSACTGCCAATCCGACTGGC (SEQ ID NO: 255) |
| asp40F | GGAAGAACAGGAGCCACTNNSGCCAATCCGACTGGCACA (SEQ ID NO: 256) |
| asp41F | AGAACAGGAGCCACTACTNNSAATCCGACTGGCACATTT (SEQ ID NO: 257) |
| asp42F | ACAGGAGCCACTACTGCCNNSCCGACTGGCACATTTGCA (SEQ ID NO: 258) |
| asp43F | GGAGCCACTACTGCCAATNNSACTGGCACATTTGCAGGT (SEQ ID NO: 259) |
| asp44F | GCCACTACTGCCAATCCGNNSGGCACATTTGCAGGTAGC (SEQ ID NO: 260) |
| asp45F | ACTACTGCCAATCCGACTNNSACATTTGCAGGTAGCTCG (SEQ ID NO: 261) |
| asp46F | ACTGCCAATCCGACTGGCNNSTTTGCAGGTAGCTCGTTT (SEQ ID NO: 262) |
| asp47F | GCCAATCCGACTGGCACANNSGCAGGTAGCTCGTTTCCG (SEQ ID NO: 263) |
| asp48F | AATCCGACTGGCACATTTNNSGGTAGCTCGTTTCCGGGA (SEQ ID NO: 264) |
| asp49F | CCGACTGGCACATTTGCANNSAGCTCGTTTCCGGGAAAT (SEQ ID NO: 265) |
| asp50F | ACTGGCACATTTGCAGGTNNSTCGTTTCCGGGAAATGAT (SEQ ID NO: 266) |
| asp51F | GGCACATTTGCAGGTAGCNNSTTTCCGGGAAATGATTAT (SEQ ID NO: 267) |
| asp52F | ACATTTGCAGGTAGCTCGNNSCCGGGAAATGATTATGCA (SEQ ID NO: 268) |
| asp53F | TTTGCAGGTAGCTCGTTTNNSGGAAATGATTATGCATTC (SEQ ID NO: 269) |

TABLE 15-1-continued

Primers Used to Generate Synthetic ASP SSM Libraries

| | |
|---|---|
| asp54F | GCAGGTAGCTCGTTTCCGNNSAATGATTATGCATTCGTC (SEQ ID NO: 270) |
| asp55F | GGTAGCTCGTTTCCGGGANNSGATTATGCATTCGTCCGA (SEQ ID NO: 271) |
| asp56F | AGCTCGTTTCCGGGAAATNNSTATGCATTCGTCCGAACA (SEQ ID NO: 272) |
| asp57F | TCGTTTCCGGGAAATGATNNSGCATTCGTCCGAACAGGG (SEQ ID NO: 273) |
| asp58F | TTTCCGGGAAATGATTATNNSTTCGTCCGAACAGGGGCA (SEQ ID NO: 274) |
| asp59F | CCGGGAAATGATTATGCANNSGTCCGAACAGGGGCAGGA (SEQ ID NO: 275) |
| asp60F | GGAAATGATTATGCATTCNNSCGAACAGGGGCAGGAGTA (SEQ ID NO: 276) |
| asp61F | AATGATTATGCATTCGTCNNSACAGGGGCAGGAGTAAAT (SEQ ID NO: 277) |
| asp62F | GATTATGCATTCGTCCGANNSGGGGCAGGAGTAAATTTG (SEQ ID NO: 278) |
| asp63F | TATGCATTCGTCCGAACANNSGCAGGAGTAAATTTGCTT (SEQ ID NO: 279) |
| asp64F | GCATTCGTCCGAACAGGGNNSGGAGTAAATTTGCTTGCC (SEQ ID NO: 280) |
| asp65F | TTCGTCCGAACAGGGGCANNSGTAAATTTGCTTGCCCAA (SEQ ID NO: 281) |
| asp66F | GTCCGAACAGGGGCAGGANNSAATTTGCTTGCCCAAGTC (SEQ ID NO: 282) |
| asp67F | CGAACAGGGGCAGGAGTANNSTTGCTTGCCCAAGTCAAT (SEQ ID NO: 283) |
| asp68F | ACAGGGGCAGGAGTAAATNNSCTTGCCCAAGTCAATAAC (SEQ ID NO: 284) |
| asp69F | GGGGCAGGAGTAAATTTGNNSGCCCAAGTCAATAACTAC (SEQ ID NO: 285) |
| asp70F | GCAGGAGTAAATTTGCTTNNSCAAGTCAATAACTACTCG (SEQ ID NO: 286) |
| asp71F | GGAGTAAATTTGCTTGCCNNSGTCAATAACTACTCGGGC (SEQ ID NO: 287) |
| asp72F | GTAAATTTGCTTGCCCAANNSAATAACTACTCGGGCGGC (SEQ ID NO: 288) |
| asp73F | AATTTGCTTGCCCAAGTCNNSAACTACTCGGGCGGCAGA (SEQ ID NO: 289) |
| asp74F | TTGCTTGCCCAAGTCAATNNSTACTCGGGCGGCAGAGTC (SEQ ID NO: 290) |
| asp75F | CTTGCCCAAGTCAATAACNNSTCGGGCGGCAGAGTCCAA (SEQ ID NO: 291) |
| asp76F | GCCCAAGTCAATAACTACNNSGGCGGCAGAGTCCAAGTA (SEQ ID NO: 292) |
| asp77F | CAAGTCAATAACTACTCGNNSGGCAGAGTCCAAGTAGCA (SEQ ID NO: 293) |
| asp78F | GTCAATAACTACTCGGGCNNSAGAGTCCAAGTAGCAGGA (SEQ ID NO: 294) |
| asp79F | AATAACTACTCGGGCGGCNNSGTCCAAGTAGCAGGACAT (SEQ ID NO: 295) |

TABLE 15-1-continued

Primers Used to Generate Synthetic ASP SSM Libraries

| | |
|---|---|
| asp80F | AACTACTCGGGCGGCAGANNSCAAGTAGCAGGACATACG (SEQ ID NO: 296) |
| asp81F | TACTCGGGCGGCAGAGTCNNSGTAGCAGGACATACGGCC (SEQ ID NO: 297) |
| asp82F | TCGGGCGGCAGAGTCCAANNSGCAGGACATACGGCCGCA (SEQ ID NO: 298) |
| asp83F | GGCGGCAGAGTCCAAGTANNSGGACATACGGCCGCACCA (SEQ ID NO: 299) |
| asp84F | GGCAGAGTCCAAGTAGCANNSCATACGGCCGCACCAGTT (SEQ ID NO: 300) |
| asp85F | AGAGTCCAAGTAGCAGGANNSACGGCCGCACCAGTTGGA (SEQ ID NO: 301) |
| asp86F | GTCCAAGTAGCAGGACATNNSGCCGCACCAGTTGGATCT (SEQ ID NO: 302) |
| asp87F | CAAGTAGCAGGACATACGNNSGCACCAGTTGGATCTGCT (SEQ ID NO: 303) |
| asp88F | GTAGCAGGACATACGGCCNNSCCAGTTGGATCTGCTGTA (SEQ ID NO: 304) |
| asp89F | GCAGGACATACGGCCGCANNSGTTGGATCTGCTGTATGC (SEQ ID NO: 305) |
| asp90F | GGACATACGGCCGCACCANNSGGATCTGCTGTATGCCGC (SEQ ID NO: 306) |
| asp91F | CATACGGCCGCACCAGTTNNSTCTGCTGTATGCCGCTCA (SEQ ID NO: 307) |
| asp92F | ACGGCCGCACCAGTTGGANNSGCTGTATGCCGCTCAGGT (SEQ ID NO: 308) |
| asp93F | GCCGCACCAGTTGGATCTNNSGTATGCCGCTCAGGTAGC (SEQ ID NO: 309) |
| asp94F | GCACCAGTTGGATCTGCTNNSTGCCGCTCAGGTAGCACT (SEQ ID NO: 310) |
| asp95F | CCAGTTGGATCTGCTGTANNSCGCTCAGGTAGCACTACA (SEQ ID NO: 311) |
| asp96F | GTTGGATCTGCTGTATGCNNSTCAGGTAGCACTACAGGT (SEQ ID NO: 312) |
| asp97F | GGATCTGCTGTATGCCGCNNSGGTAGCACTACAGGTTGG (SEQ ID NO: 313) |
| asp98F | TCTGCTGTATGCCGCTCANNSAGCACTACAGGTTGGCAT (SEQ ID NO: 314) |
| asp99F | GCTGTATGCCGCTCAGGTNNSACTACAGGTTGGCATTGC (SEQ ID NO: 315) |
| asp100F | GTATGCCGCTCAGGTAGCNNSACAGGTTGGCATTGCGGA (SEQ ID NO: 316) |
| asp101F | TGCCGCTCAGGTAGCACTNNSGGTTGGCATTGCGGAACT (SEQ ID NO: 317) |
| asp102F | CGCTCAGGTAGCACTACANNSTGGCATTGCGGAACTATC (SEQ ID NO: 318) |
| asp103F | TCAGGTAGCACTACAGGTNNSCATTGCGGAACTATCACG (SEQ ID NO: 319) |
| asp104F | GGTAGCACTACAGGTTGGNNSTGCGGAACTATCACGGCG (SEQ ID NO: 320) |
| asp105F | AGCACTACAGGTTGGCATNNSGGAACTATCACGGCGCTG (SEQ ID NO: 321) |

TABLE 15-1-continued

Primers Used to Generate Synthetic ASP SSM Libraries

| | |
|---|---|
| asp106F | ACTACAGGTTGGCATTGCNNSACTATCACGGCGCTGAAT (SEQ ID NO: 322) |
| asp107F | ACAGGTTGGCATTGCGGANNSATCACGGCGCTGAATTCG (SEQ ID NO: 323) |
| asp108F | GGTTGGCATTGCGGAACTNNSACGGCGCTGAATTCGTCT (SEQ ID NO: 324) |
| asp109F | TGGCATTGCGGAACTATCNNSGCGCTGAATTCGTCTGTC (SEQ ID NO: 325) |
| asp110F | CATTGCGGAACTATCACGNNSCTGAATTCGTCTGTCACG (SEQ ID NO: 326) |
| asp111F | TGCGGAACTATCACGGCGNNSAATTCGTCTGTCACGTAT (SEQ ID NO: 327) |
| asp112F | GGAACTATCACGGCGCTGNNSTCGTCTGTCACGTATCCA (SEQ ID NO: 328) |
| asp113F | ACTATCACGGCGCTGAATNNSTCTGTCACGTATCCAGAG (SEQ ID NO: 329) |
| asp114F | ATCACGGCGCTGAATTCGNNSGTCACGTATCCAGAGGGA (SEQ ID NO: 330) |
| asp115F | ACGGCGCTGAATTCGTCTNNSACGTATCCAGAGGGAACA (SEQ ID NO: 331) |
| asp116F | GCGCTGAATTCGTCTGTCNNSTATCCAGAGGGAACAGTC (SEQ ID NO: 332) |
| asp117F | CTGAATTCGTCTGTCACGNNSCCAGAGGGAACAGTCCGA (SEQ ID NO: 333) |
| asp118F | AATTCGTCTGTCACGTATNNSGAGGGAACAGTCCGAGGA (SEQ ID NO: 334) |
| asp119F | TCGTCTGTCACGTATCCANNSGGAACAGTCCGAGGACTT (SEQ ID NO: 335) |
| asp120F | TCTGTCACGTATCCAGAGNNSACAGTCCGAGGACTTATC (SEQ ID NO: 336) |
| asp121F | GTCACGTATCCAGAGGGANNSGTCCGAGGACTTATCCGC (SEQ ID NO: 337) |
| asp122F | ACGTATCCAGAGGGAACANNSCGAGGACTTATCCGCACG (SEQ ID NO: 338) |
| asp123F | TATCCAGAGGGAACAGTCNNSGGACTTATCCGCACGACG (SEQ ID NO: 339) |
| asp124F | CCAGAGGGAACAGTCCGANNSCTTATCCGCACGACGGTT (SEQ ID NO: 340) |
| asp125F | GAGGGAACAGTCCGAGGANNSATCCGCACGACGGTTTGT (SEQ ID NO: 341) |
| asp126F | GGAACAGTCCGAGGACTTNNSCGCACGACGGTTTGTGCC (SEQ ID NO: 342) |
| asp127F | ACAGTCCGAGGACTTATCNNSACGACGGTTTGTGCCGAA (SEQ ID NO: 343) |
| asp128F | GTCCGAGGACTTATCCGCNNSACGGTTTGTGCCGAACCA (SEQ ID NO: 344) |
| asp129F | CGAGGACTTATCCGCACGNNSGTTTGTGCCGAACCAGGT (SEQ ID NO: 345) |
| asp130F | GGACTTATCCGCACGACGNNSTGTGCCGAACCAGGTGAT (SEQ ID NO: 346) |
| asp131F | CTTATCCGCACGACGGTTNNSGCCGAACCAGGTGATAGC (SEQ ID NO: 347) |

TABLE 15-1-continued

Primers Used to Generate Synthetic ASP SSM Libraries

| Primer | Sequence |
|---|---|
| asp132F | ATCCGCACGACGGTTTGTNNSGAACCAGGTGATAGCGGA (SEQ ID NO: 348) |
| asp133F | CGCACGACGGTTTGTGCCNNSCCAGGTGATAGCGGAGGT (SEQ ID NO: 349) |
| asp134F | ACGACGGTTTGTGCCGAANNSGGTGATAGCGGAGGTAGC (SEQ ID NO: 350) |
| asp135F | ACGGTTTGTGCCGAACCANNSGATAGCGGAGGTAGCCTT (SEQ ID NO: 351) |
| asp136F | GTTTGTGCCGAACCAGGTNNSAGCGGAGGTAGCCTTTTA (SEQ ID NO: 352) |
| asp137F | TGTGCCGAACCAGGTGATNNSGGAGGTAGCCTTTTAGCG (SEQ ID NO: 353) |
| asp138F | GCCGAACCAGGTGATAGCNNSGGTAGCCTTTTAGCGGGA (SEQ ID NO: 354) |
| asp139F | GAACCAGGTGATAGCGGANNSAGCCTTTTAGCGGGAAAT (SEQ ID NO: 355) |
| asp140F | CCAGGTGATAGCGGAGGTNNSCTTTTAGCGGGAAATCAA (SEQ ID NO: 356) |
| asp141F | GGTGATAGCGGAGGTAGCNNSTTAGCGGGAAATCAAGCC (SEQ ID NO: 357) |
| asp142F | GATAGCGGAGGTAGCCTTNNSGCGGGAAATCAAGCCCAA (SEQ ID NO: 358) |
| asp143F | AGCGGAGGTAGCCTTTTANNSGGAAATCAAGCCCAAGGT (SEQ ID NO: 359) |
| asp144F | GGAGGTAGCCTTTTAGCGNNSAATCAAGCCCAAGGTGTC (SEQ ID NO: 360) |
| asp145F | GGTAGCCTTTTAGCGGGANNSCAAGCCCAAGGTGTCACG (SEQ ID NO: 361) |
| asp146F | AGCCTTTTAGCGGGAAATNNSGCCCAAGGTGTCACGTCA (SEQ ID NO: 362) |
| asp147F | CTTTTAGCGGGAAATCAANNSCAAGGTGTCACGTCAGGT (SEQ ID NO: 363) |
| asp148F | TTAGCGGGAAATCAAGCCNNSGGTGTCACGTCAGGTGGT (SEQ ID NO: 364) |
| asp149F | GCGGGAAATCAAGCCCAANNSGTCACGTCAGGTGGTTCT (SEQ ID NO: 365) |
| asp150F | GGAAATCAAGCCCAAGGTNNSACGTCAGGTGGTTCTGGA (SEQ ID NO: 366) |
| asp151F | AATCAAGCCCAAGGTGTCNNSTCAGGTGGTTCTGGAAAT (SEQ ID NO: 367) |
| asp152F | CAAGCCCAAGGTGTCACGNNSGGTGGTTCTGGAAATTGT (SEQ ID NO: 368) |
| asp153F | GCCCAAGGTGTCACGTCANNSGGTTCTGGAAATTGTCGG (SEQ ID NO: 369) |
| asp154F | CAAGGTGTCACGTCAGGTNNSTCTGGAAATTGTCGGACG (SEQ ID NO: 370) |
| asp155F | GGTGTCACGTCAGGTGGTNNSGGAAATTGTCGGACGGGG (SEQ ID NO: 371) |
| asp156F | GTCACGTCAGGTGGTTCTNNSAATTGTCGGACGGGGGGA (SEQ ID NO: 372) |
| asp157F | ACGTCAGGTGGTTCTGGANNSTGTCGGACGGGGGGAACA (SEQ ID NO: 373) |

TABLE 15-1-continued

Primers Used to Generate Synthetic ASP SSM Libraries

| Primer | Sequence |
|---|---|
| asp158F | TCAGGTGGTTCTGGAAATNNSCGGACGGGGGGAACAACA (SEQ ID NO: 374) |
| asp159F | GGTGGTTCTGGAAATTGTNNSACGGGGGGAACAACATTC (SEQ ID NO: 375) |
| asp160F | GGTTCTGGAAATTGTCGGNNSGGGGGAACAACATTCTTT (SEQ ID NO: 376) |
| asp161F | TCTGGAAATTGTCGGACGNNSGGAACAACATTCTTTCAA (SEQ ID NO: 377) |
| asp162F | GGAAATTGTCGGACGGGGNNSACAACATTCTTTCAACCA (SEQ ID NO: 378) |
| asp163F | AATTGTCGGACGGGGGGANNSACATTCTTTCAACCAGTC (SEQ ID NO: 379) |
| asp164F | TGTCGGACGGGGGGAACANNSTTCTTTCAACCAGTCAAC (SEQ ID NO: 380) |
| asp165F | CGGACGGGGGGAACAACANNSTTTCAACCAGTCAACCCG (SEQ ID NO: 381) |
| asp166F | ACGGGGGGAACAACATTCNNSCAACCAGTCAACCCGATT (SEQ ID NO: 382) |
| asp167F | GGGGGAACAACATTCTTTNNSCCAGTCAACCCGATTTTG (SEQ ID NO: 383) |
| asp168F | GGAACAACATTCTTTCAANNSGTCAACCCGATTTTGCAG (SEQ ID NO: 384) |
| asp169F | ACAACATTCTTTCAACCANNSAACCCGATTTTGCAGGCT (SEQ ID NO: 385) |
| asp170F | ACATTCTTTCAACCAGTCNNSCCGATTTTGCAGGCTTAC (SEQ ID NO: 386) |
| asp171F | TTCTTTCAACCAGTCAACNNSATTTTGCAGGCTTACGGC (SEQ ID NO: 387) |
| asp172F | TTTCAACCAGTCAACCCGNNSTTGCAGGCTTACGGCCTG (SEQ ID NO: 388) |
| asp173F | CAACCAGTCAACCCGATTNNSCAGGCTTACGGCCTGAGA (SEQ ID NO: 389) |
| asp174F | CCAGTCAACCCGATTTTGNNSGCTTACGGCCTGAGAATG (SEQ ID NO: 390) |
| asp175F | GTCAACCCGATTTTGCAGNNSTACGGCCTGAGAATGATT (SEQ ID NO: 391) |
| asp176F | AACCCGATTTTGCAGGCTNNSGGCCTGAGAATGATTACG (SEQ ID NO: 392) |
| asp177F | CCGATTTTGCAGGCTTACNNSCTGAGAATGATTACGACT (SEQ ID NO: 393) |
| asp178F | ATTTTGCAGGCTTACGGCNNSAGAATGATTACGACTGAC (SEQ ID NO: 394) |
| asp179F | TTGCAGGCTTACGGCCTGNNSATGATTACGACTGACTCT (SEQ ID NO: 395) |
| asp180F | CAGGCTTACGGCCTGAGANNSATTACGACTGACTCTGGA (SEQ ID NO: 396) |
| asp181F | GCTTACGGCCTGAGAATGNNSACGACTGACTCTGGAAGT (SEQ ID NO: 397) |
| asp182F | TACGGCCTGAGAATGATTNNSACTGACTCTGGAAGTTCC (SEQ ID NO: 398) |
| asp183F | GGCCTGAGAATGATTACGNNSGACTCTGGAAGTTCCCCT (SEQ ID NO: 399) |

TABLE 15-1-continued

Primers Used to Generate Synthetic ASP SSM Libraries

| | |
|---|---|
| asp184F | CTGAGAATGATTACGACTNNSTCTGGAAGTTCCCCTTAA<br>(SEQ ID NO: 400) |
| asp185F | AGAATGATTACGACTGACNNSGGAAGTTCCCCTTAACCC<br>(SEQ ID NO: 401) |
| asp186F | ATGATTACGACTGACTCTNNSAGTTCCCCTTAACCCAAC<br>(SEQ ID NO: 402) |
| asp187F | ATTACGACTGACTCTGGANNSTCCCCTTAACCCAACAGA<br>(SEQ ID NO: 403) |
| asp188F | ACGACTGACTCTGGAAGTNNSCCTTAACCCAACAGAGGA<br>(SEQ ID NO: 404) |
| asp189F | ACTGACTCTGGAAGTTCCNNSTAACCCAACAGAGGACGG<br>(SEQ ID NO: 405) |

| Reverse mutagenesis primer | DNA sequence, 5'-3' |
|---|---|
| asp1R | GTTGCCTCCAATTACGTCSNNCATCGTTCTAGGCGTTTC<br>(SEQ ID NO: 406) |
| asp2R | TGCGTTGCCTCCAATTACSNNGAACATCGTTCTAGGCGT<br>(SEQ ID NO: 407) |
| asp3R | ATATGCGTTGCCTCCAATSNNGTCGAACATCGTTCTAGG<br>(SEQ ID NO: 408) |
| asp4R | AGTATATGCGTTGCCTCCSNNTACGTCGAACATCGTTCT<br>(SEQ ID NO: 409) |
| asp5R | AATAGTATATGCGTTGCCSNNAATTACGTCGAACATCGT<br>(SEQ ID NO: 410) |
| asp6R | GCCAATAGTATATGCGTTSNNTCCAATTACGTCGAACAT<br>(SEQ ID NO: 411) |
| asp7R | GCCGCCAATAGTATATGCSNNGCCTCCAATTACGTCGAA<br>(SEQ ID NO: 412) |
| asp8R | CCGGCCGCCAATAGTATASNNGTTGCCTCCAATTACGTC<br>(SEQ ID NO: 413) |
| asp9R | AGACCGGCCGCCAATAGTSNNTGCGTTGCCTCCAATTAC<br>(SEQ ID NO: 414) |
| asp10R | TCTAGACCGGCCGCCAATSNNATATGCGTTGCCTCCAAT<br>(SEQ ID NO: 415) |
| asp11R | ACATCTAGACCGGCCGCCSNNAGTATATGCGTTGCCTCC<br>(SEQ ID NO: 416) |
| asp12R | AGAACATCTAGACCGGCCSNNAATAGTATATGCGTTGCC<br>(SEQ ID NO: 417) |
| asp13R | GATAGAACATCTAGACCGSNNGCCAATAGTATATGCGTT<br>(SEQ ID NO: 418) |
| asp14R | TCCGATAGAACATCTAGASNNGCCGCCAATAGTATATGC<br>(SEQ ID NO: 419) |
| asp15R | GAATCCGATAGAACATCTSNNCCGGCCGCCAATAGTATA<br>(SEQ ID NO: 420) |
| asp16R | TGCGAATCCGATAGAACASNNAGACCGGCCGCCAATAGT<br>(SEQ ID NO: 421) |
| asp17R | TACTGCGAATCCGATAGASNNTCTAGACCGGCCGCCAAT<br>(SEQ ID NO: 422) |
| asp18R | GTTTACTGCGAATCCGATSNNACATCTAGACCGGCCGCC<br>(SEQ ID NO: 423) |
| asp19R | ACCGTTTACTGCGAATCCSNNAGAACATCTAGACCGGCC<br>(SEQ ID NO: 424) |

TABLE 15-1-continued

Primers Used to Generate Synthetic ASP SSM Libraries

| | |
|---|---|
| asp20R | GCCACCGTTTACTGCGAASNNGATAGAACATCTAGACCG (SEQ ID NO: 425) |
| asp21R | GAAGCCACCGTTTACTGCSNNTCCGATAGAACATCTAGA (SEQ ID NO: 426) |
| asp22R | AATGAAGCCACCGTTTACSNNGAATCCGATAGAACATCT (SEQ ID NO: 427) |
| asp23R | AGTAATGAAGCCACCGTTSNNTGCGAATCCGATAGAACA (SEQ ID NO: 428) |
| asp24R | GGCAGTAATGAAGCCACCSNNTACTGCGAATCCGATAGA (SEQ ID NO: 429) |
| asp25R | ACCGGCAGTAATGAAGCCSNNGTTTACTGCGAATCCGAT (SEQ ID NO: 430) |
| asp26R | GTGACCGGCAGTAATGAASNNACCGTTTACTGCGAATCC (SEQ ID NO: 431) |
| asp27R | GCAGTGACCGGCAGTAATSNNGCCACCGTTTACTGCGAA (SEQ ID NO: 432) |
| asp28R | TCCGCAGTGACCGGCAGTSNNGAAGCCACCGTTTACTGC (SEQ ID NO: 433) |
| asp29R | TCTTCCGCAGTGACCGGCSNNAATGAAGCCACCGTTTAC (SEQ ID NO: 434) |
| asp30R | TGTTCTTCCGCAGTGACCSNNAGTAATGAAGCCACCGTT (SEQ ID NO: 435) |
| asp31R | TCCTGTTCTTCCGCAGTGSNNGGCAGTAATGAAGCCACC (SEQ ID NO: 436) |
| asp32R | GGCTCCTGTTCTTCCGCASNNACCGGCAGTAATGAAGCC (SEQ ID NO: 437) |
| asp33R | AGTGGCTCCTGTTCTTCCSNNGTGACCGGCAGTAATGAA (SEQ ID NO: 438) |
| asp34R | AGTAGTGGCTCCTGTTCTSNNGCAGTGACCGGCAGTAAT (SEQ ID NO: 439) |
| asp35R | GGCAGTAGTGGCTCCTGTSNNTCCGCAGTGACCGGCAGT (SEQ ID NO: 440) |
| asp36R | ATTGGCAGTAGTGGCTCCSNNTCTTCCGCAGTGACCGGC (SEQ ID NO: 441) |
| asp37R | CGGATTGGCAGTAGTGGCSNNTGTTCTTCCGCAGTGACC (SEQ ID NO: 442) |
| asp38R | AGTCGGATTGGCAGTAGTSNNTCCTGTTCTTCCGCAGTG (SEQ ID NO: 443) |
| asp39R | GCCAGTCGGATTGGCAGTSNNGGCTCCTGTTCTTCCGCA (SEQ ID NO: 444) |
| asp40R | TGTGCCAGTCGGATTGGCSNNAGTGGCTCCTGTTCTTCC (SEQ ID NO: 445) |
| asp41R | AAATGTGCCAGTCGGATTSNNAGTAGTGGCTCCTGTTCT (SEQ ID NO: 446) |
| asp42R | TGCAAATGTGCCAGTCGGSNNGGCAGTAGTGGCTCCTGT (SEQ ID NO: 447) |
| asp43R | ACCTGCAAATGTGCCAGTSNNATTGGCAGTAGTGGCTCC (SEQ ID NO: 448) |
| asp44R | GCTACCTGCAAATGTGCCSNNCGGATTGGCAGTAGTGGC (SEQ ID NO: 449) |
| asp45R | CGAGCTACCTGCAAATGTSNNAGTCGGATTGGCAGTAGT (SEQ ID NO: 450) |

TABLE 15-1-continued

Primers Used to Generate Synthetic ASP SSM Libraries

| | |
|---|---|
| asp46R | AAACGAGCTACCTGCAAASNNGCCAGTCGGATTGGCAGT (SEQ ID NO: 451) |
| asp47R | CGGAAACGAGCTACCTGCSNNTGTGCCAGTCGGATTGGC (SEQ ID NO: 452) |
| asp48R | TCCCGGAAACGAGCTACCSNNAAATGTGCCAGTCGGATT (SEQ ID NO: 453) |
| asp49R | ATTTCCCGGAAACGAGCTSNNTGCAAATGTGCCAGTCGG (SEQ ID NO: 454) |
| asp50R | ATCATTTCCCGGAAACGASNNACCTGCAAATGTGCCAGT (SEQ ID NO: 455) |
| asp51R | ATAATCATTTCCCGGAAASNNGCTACCTGCAAATGTGCC (SEQ ID NO: 456) |
| asp52R | TGCATAATCATTTCCCGGSNNCGAGCTACCTGCAAATGT (SEQ ID NO: 457) |
| asp53R | GAATGCATAATCATTTCCSNNAAACGAGCTACCTGCAAA (SEQ ID NO: 458) |
| asp54R | GACGAATGCATAATCATTSNNCGGAAACGAGCTACCTGC (SEQ ID NO: 459) |
| asp55R | TCGGACGAATGCATAATCSNNTCCCGGAAACGAGCTACC (SEQ ID NO: 460) |
| asp56R | TGTTCGGACGAATGCATASNNATTTCCCGGAAACGAGCT (SEQ ID NO: 461) |
| asp57R | CCCTGTTCGGACGAATGCSNNATCATTTCCCGGAAACGA (SEQ ID NO: 462) |
| asp58R | TGCCCCTGTTCGGACGAASNNATAATCATTTCCCGGAAA (SEQ ID NO: 463) |
| asp59R | TCCTGCCCCTGTTCGGACSNNTGCATAATCATTTCCCGG (SEQ ID NO: 464) |
| asp60R | TACTCCTGCCCCTGTTCGSNNGAATGCATAATCATTTCC (SEQ ID NO: 465) |
| asp61R | ATTTACTCCTGCCCCTGTSNNGACGAATGCATAATCATT (SEQ ID NO: 466) |
| asp62R | CAAATTTACTCCTGCCCCSNNTCGGACGAATGCATAATC (SEQ ID NO: 467) |
| asp63R | AAGCAAATTTACTCCTGCSNNTGTTCGGACGAATGCATA (SEQ ID NO: 468) |
| asp64R | GGCAAGCAAATTTACTCCSNNCCCTGTTCGGACGAATGC (SEQ ID NO: 469) |
| asp65R | TTGGGCAAGCAAATTTACSNNTGCCCCTGTTCGGACGAA (SEQ ID NO: 470) |
| asp66R | GACTTGGGCAAGCAAATTSNNTCCTGCCCCTGTTCGGAC (SEQ ID NO: 471) |
| asp67R | ATTGACTTGGGCAAGCAASNNTACTCCTGCCCCTGTTCG (SEQ ID NO: 472) |
| asp68R | GTTATTGACTTGGGCAAGSNNATTACTCCTGCCCCTGT (SEQ ID NO: 473) |
| asp69R | GTAGTTATTGACTTGGGCSNNCAAATTTACTCCTGCCCC (SEQ ID NO: 474) |
| asp70R | CGAGTAGTTATTGACTTGSNNAAGCAAATTTACTCCTGC (SEQ ID NO: 475) |
| asp71R | GCCCGAGTAGTTATTGACSNNGGCAAGCAAATTTACTCC (SEQ ID NO: 476) |

TABLE 15-1-continued

Primers Used to Generate Synthetic ASP SSM Libraries

| | |
|---|---|
| asp72R | GCCGCCCGAGTAGTTATTSNNTTGGGCAAGCAAATTTAC (SEQ ID NO: 477) |
| asp73R | TCTGCCGCCCGAGTAGTTSNNGACTTGGGCAAGCAAATT (SEQ ID NO: 478) |
| asp74R | GACTCTGCCGCCCGAGTASNNATTGACTTGGGCAAGCAA (SEQ ID NO: 479) |
| asp75R | TTGGACTCTGCCGCCCGASNNGTTATTGACTTGGGCAAG (SEQ ID NO: 480) |
| asp76R | TACTTGGACTCTGCCGCCSNNGTAGTTATTGACTTGGGC (SEQ ID NO: 481) |
| asp77R | TGCTACTTGGACTCTGCCSNNCGAGTAGTTATTGACTTG (SEQ ID NO: 482) |
| asp78R | TCCTGCTACTTGGACTCTSNNGCCCGAGTAGTTATTGAC (SEQ ID NO: 483) |
| asp79R | ATGTCCTGCTACTTGGACSNNGCCGCCCGAGTAGTTATT (SEQ ID NO: 484) |
| asp80R | CGTATGTCCTGCTACTTGSNNTCTGCCGCCCGAGTAGTT (SEQ ID NO: 485) |
| asp81R | GGCCGTATGTCCTGCTACSNNGACTCTGCCGCCCGAGTA (SEQ ID NO: 486) |
| asp82R | TGCGGCCGTATGTCCTGCSNNTTGGACTCTGCCGCCCGA (SEQ ID NO: 487) |
| asp83R | TGGTGCGGCCGTATGTCCSNNTACTTGGACTCTGCCGCC (SEQ ID NO: 488) |
| asp84R | AACTGGTGCGGCCGTATGSNNTGCTACTTGGACTCTGCC (SEQ ID NO: 489) |
| asp85R | TCCAACTGGTGCGGCCGTSNNTCCTGCTACTTGGACTCT (SEQ ID NO: 490) |
| asp86R | AGATCCAACTGGTGCGGCSNNATGTCCTGCTACTTGGAC (SEQ ID NO: 491) |
| asp87R | AGCAGATCCAACTGGTGCSNNCGTATGTCCTGCTACTTG (SEQ ID NO: 492) |
| asp88R | TACAGCAGATCCAACTGGSNNGGCCGTATGTCCTGCTAC (SEQ ID NO: 493) |
| asp89R | GCATACAGCAGATCCAACSNNTGCGGCCGTATGTCCTGC (SEQ ID NO: 494) |
| asp90R | GCGGCATACAGCAGATCCSNNTGGTGCGGCCGTATGTCC (SEQ ID NO: 495) |
| asp91R | TGAGCGGCATACAGCAGASNNAACTGGTGCGGCCGTATG (SEQ ID NO: 496) |
| asp92R | ACCTGAGCGGCATACAGCSNNTCCAACTGGTGCGGCCGT (SEQ ID NO: 497) |
| asp93R | GCTACCTGAGCGGCATACSNNAGATCCAACTGGTGCGGC (SEQ ID NO: 498) |
| asp94R | AGTGCTACCTGAGCGGCASNNAGCAGATCCAACTGGTGC (SEQ ID NO: 499) |
| asp95R | TGTAGTGCTACCTGAGCGSNNTACAGCAGATCCAACTGG (SEQ ID NO: 500) |
| asp96R | ACCTGTAGTGCTACCTGASNNGCATACAGCAGATCCAAC (SEQ ID NO: 501) |
| asp97R | CCAACCTGTAGTGCTACCSNNGCGGCATACAGCAGATCC (SEQ ID NO: 502) |

TABLE 15-1-continued

Primers Used to Generate Synthetic ASP SSM Libraries

| | |
|---|---|
| asp98R | ATGCCAACCTGTAGTGCTSNNTGAGCGGCATACAGCAGA (SEQ ID NO: 503) |
| asp99R | GCAATGCCAACCTGTAGTSNNACCTGAGCGGCATACAGC (SEQ ID NO: 504) |
| asp100R | TCCGCAATGCCAACCTGTSNNGCTACCTGAGCGGCATAC (SEQ ID NO: 505) |
| asp101R | AGTTCCGCAATGCCAACCSNNAGTGCTACCTGAGCGGCA (SEQ ID NO: 506) |
| asp102R | GATAGTTCCGCAATGCCASNNTGTAGTGCTACCTGAGCG (SEQ ID NO: 507) |
| asp103R | CGTGATAGTTCCGCAATGSNNACCTGTAGTGCTACCTGA (SEQ ID NO: 508) |
| asp104R | CGCCGTGATAGTTCCGCASNNCCAACCTGTAGTGCTACC (SEQ ID NO: 509) |
| asp105R | CAGCGCCGTGATAGTTCCSNNATGCCAACCTGTAGTGCT (SEQ ID NO: 510) |
| asp106R | ATTCAGCGCCGTGATAGTSNNGCAATGCCAACCTGTAGT (SEQ ID NO: 511) |
| asp107R | CGAATTCAGCGCCGTGATSNNTCCGCAATGCCAACCTGT (SEQ ID NO: 512) |
| asp108R | AGACGAATTCAGCGCCGTSNNAGTTCCGCAATGCCAACC (SEQ ID NO: 513) |
| asp109R | GACAGACGAATTCAGCGCSNNGATAGTTCCGCAATGCCA (SEQ ID NO: 514) |
| asp110R | CGTGACAGACGAATTCAGSNNCGTGATAGTTCCGCAATG (SEQ ID NO: 515) |
| asp111R | ATACGTGACAGACGAATTSNNCGCCGTGATAGTTCCGCA (SEQ ID NO: 516) |
| asp112R | TGGATACGTGACAGACGASNNCAGCGCCGTGATAGTTCC (SEQ ID NO: 517) |
| asp113R | CTCTGGATACGTGACAGASNNATTCAGCGCCGTGATAGT (SEQ ID NO: 518) |
| asp114R | TCCCTCTGGATACGTGACSNNCGAATTCAGCGCCGTGAT (SEQ ID NO: 519) |
| asp115R | TGTTCCCTCTGGATACGTSNNAGACGAATTCAGCGCCGT (SEQ ID NO: 520) |
| asp116R | GACTGTTCCCTCTGGATASNNGACAGACGAATTCAGCGC (SEQ ID NO: 521) |
| asp117R | TCGGACTGTTCCCTCTGGSNNCGTGACAGACGAATTCAG (SEQ ID NO: 522) |
| asp118R | TCCTCGGACTGTTCCCTCSNNATACGTGACAGACGAATT (SEQ ID NO: 523) |
| asp119R | AAGTCCTCGGACTGTTCCSNNTGGATACGTGACAGACGA (SEQ ID NO: 524) |
| asp120R | GATAAGTCCTCGGACTGTSNNCTCTGGATACGTGACAGA (SEQ ID NO: 525) |
| asp121R | GCGGATAAGTCCTCGGACSNNTCCCTCTGGATACGTGAC (SEQ ID NO: 526) |
| asp122R | CGTGCGGATAAGTCCTCGSNNTGTTCCCTCTGGATACGT (SEQ ID NO: 527) |
| asp123R | CGTCGTGCGGATAAGTCCSNNGACTGTTCCCTCTGGATA (SEQ ID NO: 528) |

TABLE 15-1-continued

Primers Used to Generate Synthetic ASP SSM Libraries

| | |
|---|---|
| asp124R | AACCGTCGTGCGGATAAGSNNTCGGACTGTTCCCTCTGG (SEQ ID NO: 529) |
| asp125R | ACAAACCGTCGTGCGGATSNNTCCTCGGACTGTTCCCTC (SEQ ID NO: 530) |
| asp126R | GGCACAAACCGTCGTGCGSNNAAGTCCTCGGACTGTTCC (SEQ ID NO: 531) |
| asp127R | TTCGGCACAAACCGTCGTSNNGATAAGTCCTCGGACTGT (SEQ ID NO: 532) |
| asp128R | TGGTTCGGCACAAACCGTSNNGCGGATAAGTCCTCGGAC (SEQ ID NO: 533) |
| asp129R | ACCTGGTTCGGCACAAACSNNCGTGCGGATAAGTCCTCG (SEQ ID NO: 534) |
| asp130R | ATCACCTGGTTCGGCACASNNCGTCGTGCGGATAAGTCC (SEQ ID NO: 535) |
| asp131R | GCTATCACCTGGTTCGGCSNNAACCGTCGTGCGGATAAG (SEQ ID NO: 536) |
| asp132R | TCCGCTATCACCTGGTTCSNNACAAACCGTCGTGCGGAT (SEQ ID NO: 537) |
| asp133R | ACCTCCGCTATCACCTGGSNNGGCACAAACCGTCGTGCG (SEQ ID NO: 538) |
| asp134R | GCTACCTCCGCTATCACCSNNTTCGGCACAAACCGTCGT (SEQ ID NO: 539) |
| asp135R | AAGGCTACCTCCGCTATCSNNTGGTTCGGCACAAACCGT (SEQ ID NO: 540) |
| asp136R | TAAAAGGCTACCTCCGCTSNNACCTGGTTCGGCACAAAC (SEQ ID NO: 541) |
| asp137R | CGCTAAAAGGCTACCTCCSNNATCACCTGGTTCGGCACA (SEQ ID NO: 542) |
| asp138R | TCCCGCTAAAAGGCTACCSNNGCTATCACCTGGTTCGGC (SEQ ID NO: 543) |
| asp139R | ATTTCCCGCTAAAAGGCTSNNTCCGCTATCACCTGGTTC (SEQ ID NO: 544) |
| asp140R | TTGATTTCCCGCTAAAAGSNNACCTCCGCTATCACCTGG (SEQ ID NO: 545) |
| asp141R | GGCTTGATTTCCCGCTAASNNGCTACCTCCGCTATCACC (SEQ ID NO: 546) |
| asp142R | TTGGGCTTGATTTCCCGCSNNAAGGCTACCTCCGCTATC (SEQ ID NO: 547) |
| asp143R | ACCTTGGGCTTGATTTCCSNNTAAAAGGCTACCTCCGCT (SEQ ID NO: 548) |
| asp144R | GACACCTTGGGCTTGATTSNNCGCTAAAAGGCTACCTCC (SEQ ID NO: 549) |
| asp145R | CGTGACACCTTGGGCTTGSNNTCCCGCTAAAAGGCTACC (SEQ ID NO: 550) |
| asp146R | TGACGTGACACCTTGGGCSNNATTTCCCGCTAAAAGGCT (SEQ ID NO: 551) |
| asp147R | ACCTGACGTGACACCTTGSNNTTGATTTCCCGCTAAAAG (SEQ ID NO: 552) |
| asp148R | ACCACCTGACGTGACACCSNNGGCTTGATTTCCCGCTAA (SEQ ID NO: 553) |
| asp149R | AGAACCACCTGACGTGACSNNTTGGGCTTGATTTCCCGC (SEQ ID NO: 554) |

TABLE 15-1-continued

Primers Used to Generate Synthetic ASP SSM Libraries

| | |
|---|---|
| asp150R | TCCAGAACCACCTGACGTSNNACCTTGGGCTTGATTTCC (SEQ ID NO: 555) |
| asp151R | ATTTCCAGAACCACCTGASNNGACACCTTGGGCTTGATT (SEQ ID NO: 556) |
| asp152R | ACAATTTCCAGAACCACCSNNCGTGACACCTTGGGCTTG (SEQ ID NO: 557) |
| asp153R | CCGACAATTTCCAGAACCSNNTGACGTGACACCTTGGGC (SEQ ID NO: 558) |
| asp154R | CGTCCGACAATTTCCAGASNNACCTGACGTGACACCTTG (SEQ ID NO: 559) |
| asp155R | CCCCGTCCGACAATTTCCSNNACCACCTGACGTGACACC (SEQ ID NO: 560) |
| asp156R | TCCCCCCGTCCGACAATTSNNAGAACCACCTGACGTGAC (SEQ ID NO: 561) |
| asp157R | TGTTCCCCCGTCCGACASNNTCCAGAACCACCTGACGT (SEQ ID NO: 562) |
| asp158R | TGTTGTTCCCCCGTCCGSNNATTTCCAGAACCACCTGA (SEQ ID NO: 563) |
| asp159R | GAATGTTGTTCCCCCGTSNNACAATTTCCAGAACCACC (SEQ ID NO: 564) |
| asp160R | AAAGAATGTTGTTCCCCCSNNCCGACAATTTCCAGAACC (SEQ ID NO: 565) |
| asp161R | TTGAAAGAATGTTGTTCCSNNCGTCCGACAATTTCCAGA (SEQ ID NO: 566) |
| asp162R | TGGTTGAAAGAATGTTGTSNNCCCCGTCCGACAATTTCC (SEQ ID NO: 567) |
| asp163R | GACTGGTTGAAAGAATGTSNNTCCCCCGTCCGACAATT (SEQ ID NO: 568) |
| asp164R | GTTGACTGGTTGAAAGAASNNTGTTCCCCCGTCCGACA (SEQ ID NO: 569) |
| asp165R | CGGGTTGACTGGTTGAAASNNTGTTGTTCCCCCGTCCG (SEQ ID NO: 570) |
| asp166R | AATCGGGTTGACTGGTTGSNNGAATGTTGTTCCCCCGT (SEQ ID NO: 571) |
| asp167R | CAAAATCGGGTTGACTGGSNNAAAGAATGTTGTTCCCCC (SEQ ID NO: 572) |
| asp168R | CTGCAAAATCGGGTTGACSNNTTGAAAGAATGTTGTTCC (SEQ ID NO: 573) |
| asp169R | AGCCTGCAAAATCGGGTTSNNTGGTTGAAAGAATGTTGT (SEQ ID NO: 574) |
| asp170R | GTAAGCCTGCAAAATCGGSNNGACTGGTTGAAAGAATGT (SEQ ID NO: 575) |
| asp171R | GCCGTAAGCCTGCAAAATSNNGTTGACTGGTTGAAAGAA (SEQ ID NO: 576) |
| asp172R | CAGGCCGTAAGCCTGCAASNNCGGGTTGACTGGTTGAAA (SEQ ID NO: 577) |
| asp173R | TCTCAGGCCGTAAGCCTGSNNAATCGGGTTGACTGGTTG (SEQ ID NO: 578) |
| asp174R | CATTCTCAGGCCGTAAGCSNNCAAAATCGGGTTGACTGG (SEQ ID NO: 579) |
| asp175R | AATCATTCTCAGGCCGTASNNCTGCAAAATCGGGTTGAC (SEQ ID NO: 580) |

TABLE 15-1-continued

Primers Used to Generate Synthetic ASP SSM Libraries

| | |
|---|---|
| asp176R | CGTAATCATTCTCAGGCCSNNAGCCTGCAAAATCGGGTT (SEQ ID NO: 581) |
| asp177R | AGTCGTAATCATTCTCAGSNNGTAAGCCTGCAAAATCGG (SEQ ID NO: 582) |
| asp178R | GTCAGTCGTAATCATTCTSNNGCCGTAAGCCTGCAAAAT (SEQ ID NO: 583) |
| asp179R | AGAGTCAGTCGTAATCATSNNCAGGCCGTAAGCCTGCAA (SEQ ID NO: 584) |
| asp180R | TCCAGAGTCAGTCGTAATSNNTCTCAGGCCGTAAGCCTG (SEQ ID NO: 585) |
| asp181R | ACTTCCAGAGTCAGTCGTSNNCATTCTCAGGCCGTAAGC (SEQ ID NO: 586) |
| asp182R | GGAACTTCCAGAGTCAGTSNNAATCATTCTCAGGCCGTA (SEQ ID NO: 587) |
| asp183R | AGGGGAACTTCCAGAGTCSNNCGTAATCATTCTCAGGCC (SEQ ID NO: 588) |
| asp184R | TTAAGGGGAACTTCCAGASNNAGTCGTAATCATTCTCAG (SEQ ID NO: 589) |
| asp185R | GGGTTAAGGGGAACTTCCSNNGTCAGTCGTAATCATTCT (SEQ ID NO: 590) |
| asp186R | GTTGGGTTAAGGGGAACTSNNAGAGTCAGTCGTAATCAT (SEQ ID NO: 591) |
| asp187R | TCTGTTGGGTTAAGGGGASNNTCCAGAGTCAGTCGTAAT (SEQ ID NO: 592) |
| asp188R | TCCTCTGTTGGGTTAAGGSNNACTTCCAGAGTCAGTCGT (SEQ ID NO: 593) |
| asp189R | CCGTCCTCTGTTGGGTTASNNGGAACTTCCAGAGTCAGT (SEQ ID NO: 594) |

Example 16

Construction of Arginine and Cysteine Combinatorial Mutants

In this Example, the construction of multiple arginine and cysteine mutants of ASP is described. These experiments were conducted in order to determine whether the use of surface arginine and cysteine combinatorial libraries would lead to mutants with increased expression at the protein level.

The QuikChange® multi site-directed mutagenesis (QCMS) kit (Stratagene) was used to construct the two libraries. The 5' phosphorylated primers used to create the two libraries are shown in Table 16-1. It was noted that HPLC, PAGE or any other type of purified primers gave far better results in terms of incorporation of full length primers as well as significant reduction in primer-containing errors. However, in these experiments, purified primers were not used, probably resulting in the production of 12% of clones had undesired mutations.

TABLE 16-1

Primers and Sequences

| Primer name | Primer sequence |
|---|---|
| ASPR14L | gcatatactattggcggcctgtctagatgttctatcgga (SEQ ID NO: 595) |
| ASPR16Q | actattggcggccggtctcagtgttctatcggattcgc (SEQ ID NO: 596) |
| ASPR35F | ctgccggtcactgcggatttacaggagccactactgc (SEQ ID NO: 597) |
| ASPR61S | atgattatgcattcgtctcaacaggggcaggagtaaat (SEQ ID NO: 598) |
| ASPR79T | ataactactcgggcggcacagtccaagtagcaggacatac (SEQ ID NO: 599) |
| ASPR123L | atccagagggaacagtcctgggacttatccgcacgac (SEQ ID NO: 600) |
| ASPR127Q | cagtccgaggacttatccagacgacggtttgtgccgaac (SEQ ID NO: 601) |
| ASPR159Q | gtggttctggaaattgtcagacgggggaacaacattc (SEQ ID NO: 602) |
| ASPR179Q | tgcaggcttacggcctgcagatgattacgactgactc (SEQ ID NO: 603) |

TABLE 16-1-continued

Primers and Sequences

| Primer name | Primer sequence |
|---|---|
| ASPC17S | ttggcggccggtctagatcatctatcggattcgcagta (SEQ ID NO: 604) |
| ASPC33S | tcattactgccggtcactcaggaagaacaggagccact (SEQ ID NO: 605) |
| ASPC95S | cagttggatctgctgtatctcgctcaggtagcactac (SEQ ID NO: 606) |
| ASPC105S | cactacaggttggcattcaggaactatcacggcgctg (SEQ ID NO: 607) |
| ASPC131S | cttatccgcacgacggtttcagccgaaccaggtgatag (SEQ ID NO: 608) |
| ASPC158S | caggtggttctggaaattcacggacgggggaacaac (SEQ ID NO: 609) |
| ASPSEQF1 | tgcctcacatttgtgccac (SEQ ID NO: 610) |
| ASPSEQF4 | caggatgtagctgcaggac (SEQ ID NO: 611) |
| ASPSEQR4 | ctcggttatgagttagttc (SEQ ID NO: 612) | pHPLT-ASP-C1-2 Plasmid Preparation and In Vitro Methylation

To construct the cysteine and arginine libraries using the QCMS kit, the template plasmid pHPLT-ASP-C1-2 was first methylated in vitro since it was derived from a *Bacillus* strain that does not methylate DNA at GATC sites. This method was used because the more common approach of ensuring methylation in plasmid used in the QCMS protocol involving deriving DNA from dam+*E. coli* strains was not an option here, because the plasmid pHPLT-ASP-C1-2 does not grown in *E. coli*.

Miniprep DNA was prepared from *Bacillus* cells harboring the pHPLT-ASP-C1-2 plasmid. Specifically, the strain was grown overnight in 5 mL of LB with 10 ppm of neomycin, after which the cells were spun down. The Qiagen spin miniprep DNA kit was used for preparing the plasmid DNA with an additional step wherein 100 uL of 10 mg/mL lysozyme was added after the addition of 250 uL of P1 buffer from the kit. The sample was incubated at 37° C. for 15 min with shaking, after which the remaining steps outlined in the Qiagen miniprep kit manual were carried out. The miniprep DNA was eluted with 30 uL of Qiagen buffer EB provided in the kit.

Next, the pHPLT-ASP-C1-2 plasmid DNA was methylated in vitro using a dam methylase kit from NEB (NEB catalog #MO222S). Briefly, 25 µL of the miniprep DNA (about 1-2 µg) was incubated with 20 µL of the 10×NEB dam methylase buffer, 0.5 µL of S-adenosylmethionine (80 µM), 4 µL of the dam methylase and 150.5 µL of sterile distilled water. The reaction was incubated at 37° C. for 4 hours, after which the DNA was purified using a Qiagen PCR purification kit. The methylated DNA was eluted with 40 µL of buffer EB provided in the kit. To confirm methylation of the DNA, 4 µL of the purified, methylated DNA was digested with MboI (NEB; this enzyme cuts unmethylated GATC sites) or DpnI (Roche; this enzyme cuts methylated GATC sites) in a 20 µL reaction using 2 µL of each enzyme. The reactions were incubated at 37° C. for 2 hours and they were analyzed on a 1.2% E-gel (Invitrogen). A small molecular weight DNA smear/ladder was observed for the DpnI digest, whereas the MboI digest showed intact DNA, which indicated that the pHPLT-ASP-C1-2 plasmid was successfully methylated.

Library Construction

The cysteine (cys) and arginine (arg) combinatorial libraries were constructed as outlined in the Stratagene QCMS kit, with the exception of the primer concentration used in the reactions. Specifically, 4 µL of the methylated, purified pHPLT-ASP-C1-2 plasmid (about 25 to 50 ng) was mixed with 15 µL of sterile distilled water, 1.5 µL of dNTP, 2.5 µL of 10× buffer, 1 µL of the enzyme blend and 1.0 µL arginine or cysteine mutant primer mix (i.e., for a total of 100 ng of primers). The primer mix was prepared using 10 µL of each of the nine arginine primers (100 ng/µL) or each of the six cysteine primers (100 ng/µL); adding 50 ng of each primer for both the arg and cys libraries as recommended in the Stratagene manual resulted in less than 50% of the clones containing mutations in a previous round of mutagenesis. Thus, the protocol was modified in the present round of mutagenesis to include a total of 100 ng of primers in each reaction. The cycling conditions were 95° C. for 1 min, followed by 30 cycles of 95° C. for 1 min, 55° C. for 1 min, and 65° C. for 9 min, in an MJ Research thermocycler using thin-walled 0.2 mL PCR tubes. The reaction product was digested with 1 µL of DpnI from the QCMS kit by incubating at 37° C. overnight. An additional 0.5 µL of DpnI was added, and the reaction was incubated for 1 hour.

To transform the library DNA directly into *Bacillus* cells with out going through *E. coli*, the library DNA (single-stranded QCMS product) was amplified using the TempliPhi kit (Amersham cat. #25-6400), because *Bacillus* requires double-stranded multimeric DNA for transformation. For this purpose, 1 µL of the arginine or cysteine QCMS reaction was mixed with 5 µL of sample buffer from the TempliPhi kit and heated for 3 minutes at 95° C. to denature the DNA. The reaction was placed on ice to cool for 2 minutes and then spun down briefly. Next, 5 µL of reaction buffer and 0.2 µL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine.

For transformation of the libraries into *Bacillus*, 0.5 µL of the TempliPhi amplification reaction product was mixed with 100 µL of comK competent cells followed by vigorous shaking at 37° C. for 1 hour. The transformation was serially diluted up to $10^5$ fold, and 50 µL of each dilution was plated on LA plates containing 10 ppm neomycin and 1.6% skim milk. Twenty-four clones from each library were picked for sequencing. Briefly, the colonies were resuspended in 20 µL of sterile distilled water and 2 µL was then used for PCR with ReadyTaq beads (Amersham) in a total volume of 25 µL. Primers ASPF1 and ASPR4 were added at a concentration of 0.5 µM. Cycling conditions were 94° C. for 4 min once, followed by 30 cycles of 94° C. for 1 min, 55° C. for 1 min, and 72° C. for 1 min, followed by one round at 72° C. for 7 min. A 1.5 kb fragment was obtained in each case and the product was purified using a Qiagen PCR purification kit. The purified PCR products were sequenced with ASPF4 and ASPR4 primers.

A total of 48 clones were sequenced (24 from each library). The mutagenesis worked quite well in that only about 15% of the clones were WT. But 20% of the clones had mixed sequences because the plate was crowded with colonies or the TempliPhi amplification resulted in very concentrated DNA for transformation. Also, as indicated above, about 12% of clones had extra mutations. The remaining clones were all mutant, and of these about 60-80% were unique mutants. The sequencing results for the arginine and cysteine libraries are provided below in Tables 16-2, and 16-3.

TABLE 16-2

Arginine Library Sequencing and Skim Milk Plate Results

| Colony | Halo | R14L | R16O | R35F | R61S | R79T | R123L | R127Q | R159Q | R179O |
|---|---|---|---|---|---|---|---|---|---|---|
| R1 | medium | | X | X | | | | | X | |
| R2 | yes | | | | | | | | X | |
| R3 | yes | | X | | | | X | | | |
| R4 | yes | | X | | | | X | | | |
| R5 | yes | | X | | | | X | | | |
| R6 | yes | | X | | | | X | | | |
| R7 | yes | X | | | | | | X | X | |
| R8 | yes | | X | | | | X | | | |
| R9 | yes | | | | | | | | | |
| R10 | yes | X | | | | | | | | X |
| R11 | yes | | | | | | | | | |
| R12 | medium | | X | X | | | | X | | |
| R13 | yes | | | | | X | | | | |
| R14 | yes | | | | | | | | | |
| R15 | yes | | | | | | | | | |
| R16 | medium | | | | | | | | | |
| R17 | no | | | | X | | X | X | | |
| R18 | medium | | | | | | X | X | | X |
| R19 | medium | | | | | | | | | |
| R20 | yes | X | | | | | | X | X | |
| R21 | medium | | X | | | X | | X | | |
| R22 | small | | | | | | | | | |
| R23 | yes | | X | | | X | | | | |
| R24 | yes | | | | | | | | | |

TABLE 16-3

Cysteine Library Sequencing and Skim Milk Plate Results

| Colony | Halo? | C17S | C33S | C95S | C105S | C131S | C158S |
|---|---|---|---|---|---|---|---|
| C1 | no | X | X | | | | |
| C2 | no | | | | | | |
| C3 | yes | | | | | | |
| C4 | yes | | | | | | |
| C5 | no | X | | X | | | |
| C6 | small | X | | | X | | |
| C7 | no | | | X | X | X | |
| C8 | yes | | | | | | |
| C9 | no | | | | | | |
| C10 | no | | | | | | |
| C11 | small | | | | | | |
| C12 | no | | | | | | |
| C13 | no | X | | X | | | |
| C14 | no | X | X | X | | | X |
| C15 | no | | | | | | |
| C16 | no | | | | | | X |
| C17 | no | | | | | | X |
| C18 | no | X | | X | X | | X |
| C19 | yes | | | | | | |
| C20 | no | | | | | | |
| C21 | no | | | | | | |
| C22 | no | | | X | | | |
| C23 | no | X | | X | | | |
| C24 | yes | | | | | | |

Of the mutants identified in sequencing, the following mutants from the arginine library (See, Table 16-4) were found to be of interest. See the Examples below for additional data regarding the properties of these mutants.

TABLE 16-4

Arginine Mutants of Interest

| MUTANT | SEQUENCE |
|---|---|
| R1 | R16Q R35F R159Q |
| R2 | R159Q |
| R3 | R16Q R123L |
| R7 | R14L R127Q R159Q |

TABLE 16-4-continued

Arginine Mutants of Interest

| MUTANT | SEQUENCE |
|---|---|
| R10B | R14L R179Q |
| R18 | R123L R127Q R179Q |
| R21 | R16Q R79T R127Q |
| R23 | R16Q R79T |
| R10 | R14L R79T |

Importantly, the activity results indicated that mutations in the cysteine residues produced ASP proteases with very low or no activity, suggesting that the disulfide bridges play an important role in the stability of the molecule. However, it is not intended that the present invention be limited to any particular mechanism(s).

Example 17

Expression of Homologous *O. turbata* Protease in *S. lividans*

In this Example, expression of protease produced by *O. turbata* that is homologous to the protease 69B4 in *S. lividans* is described. Thus, this Example describes plasmids comprising polynucleotides encoding a polypeptide having proteolytic activity and used such vectors to transform a *Streptomyces lividans* host cell. The transformation methods used herein are known in the art (See e.g., U.S. Pat. No. 6,287,839; and WO 02/50245, herein incorporated by reference).

The vector (i.e., plasmid) used in these experiments comprised a polynucleotide encoding a protease of the present invention obtained from *Oerskovia turbata* DSM 20577. This plasmid was used to transform *Streptomyces lividans*. The final plasmid vector is referred to herein as "pSEA4CT-*O. turbata*."

As with previous vectors, the construction of pSEA4CT-*O. turbata* made use of the pSEGCT plasmid vector (See, above).

An *Aspergillus niger* ("A4") regulatory sequence operably linked to the structural gene encoding the *Oerskovia turbata* protease (Otp) was used to drive the expression of the protease. A fusion between the A4-regulatory sequence and the *Oerskovia turbata* signal; sequence, N-terminal prosequence and mature protease sequence (i.e., without the C-terminal prosequence) was constructed by fusion-PCR techniques known in the art, as an XbaI-BamHI fragment. The polynucleotide primers for the cloning of *Oerskovia turbata* protease (Otp) in pSEA4CT were based on SEQ ID NO:67. The primer sequences used were:

```
A4-turb Fw
                                           (SEQ ID NO: 613)
5'-CAGAGACAGACCCCCGGAGGTAACCATGGCACGATCATTCTGGAGGA

CGC-3'

A4-turb RV
                                           (SEQ ID NO: 614)
5'-GCGTCCTCCAGAATGATCGTGCCATGGTTACCTCCGGGGTCTGTCT

CTG-3'

A4-turb Bam Rv
                                           (SEQ ID NO: 615)
5'-ATCCGCTCGCGGATCCCCATTGTCAGCTCGGGCCCCCACCGTCAGAG

GTCACGAG-3'

A4-XbaI-FW
                                           (SEQ ID NO: 616)
5'-GCAGCCTGAACTAGTTGCGATCCTCTAGAGATCGAACTTCAT-3'
```

The fragment was ligated into plasmid pSEA4CT digested with XbaI and BamHI, resulting in plasmid pSEA4CT-*O. turbata*.

The host *Streptomyces lividans* TK23 was transformed with plasmid vector pSEA4CT-*O. turbata* using the protoplast method described in the previous Example (i.e., using the method of Hopwood et al., supra).

The transformed culture was expanded to provide two fermentation cultures in TS* medium. The composition of TS* medium was (g/L) tryptone (Difco) 16, soytone (Difco) 4, casein hydrolysate (Merck) 20, K$_2$HPO$_4$ 10, glucose 15, Basildon antifoam 0.6, pH 7.0. At various time points, samples of the fermentation broths were removed for analysis. For the purposes of this experiment, a skim milk procedure was used to confirm successful cloning. 30 µL of the shake flask supernatant was pipetted in punched out holes in skim milk agar plates and incubated at 37° C.

The incubated plates were visually reviewed after overnight incubation for the presence of clearing zones (halos) indicating the expression of proteolytic enzyme. For purposes of this experiment, the samples were also assayed for protease activity and for molecular weight (SDS-PAGE). At the end of the fermentation, full length protease was observed by SDS-PAGE.

A sample of the fermentation broth was assayed as follows: 10 µL of the diluted supernatant was collected and analyzed using the Dimethylcasein Hydrolysis Assay described in Example 1. The assay results of the fermentation broth of 2 clones clearly show that the polynucleotide from *Oerskovia turbata* encoding a polypeptide having proteolytic activity was expressed in *Streptomyces*

Example 18

Expression of Homologous Cellulomonas and Cellulosimicrobium Proteases in *S. lividans*

In this Example, expression of proteases produced by *Cellulomonas cellasea* DSM 20118 and *Cellulosimicrobium cellulans* DSM 204244 that are homologous to the protease 69B4 in *S. lividans* is described. Thus, this Example describes plasmids comprising polynucleotides encoding a polypeptide having proteolytic activity and used such vectors to transform a *Streptomyces lividans* host cell. The transformation methods used herein are known in the art (See e.g., U.S. Pat. No. 6,287,839; and WO 02/50245, herein incorporated by reference).

The final plasmid vectors are referred to as pSEA4CT-*C. cellasea* and pSEA4CT-Cm.cellulans. The construction of pSEA4CT-C.cellasea and pSEA4CT-Cm.cellulans made use of the pSEGCT plasmid vector described above.

An *Aspergillus niger* ("A4") regulatory sequence operably linked to the structural gene encoding the *Cellulomonas cellasea* mature protease (Ccp) or alternatively, the structural gene encoding the *Cellulosimicrobium cellulans* mature protease (Cmcp) was used to drive the expression of the protease. A fusion between the A4-regulatory sequence and the 69B4 protease signal-sequence, N-terminal prosequence of the 69B4 protease gene and mature sequence of the native protease gene obtained from genomic DNA of a strain of *Micrococcineae* (herein, *Cellulomonas cellasea* or *Cellulosimicrobium cellulans*) was constructed by fusion-PCR techniques, as a XbaI-BamHI fragment. The polynucleotide primers for the cloning of *Cellulomonas cellasea* protease (Ccp) in pSEA4CT were based on SEQ ID NO:63, and are as follows:

```
Asp-npro fw-cell
5'-AGACCGACGAGACCCCGCGGACCATGGTCGACGTCATCGGCGGCAACGCGTACTAC-3'   (SEQ ID NO: 617)

Cell-BH1-rv
5'-TCAGCCGATCCGCTCGCGGATCCCCATTGTCAGCCCAGGACGAGACGCAGACCGTA-3'   (SEQ ID NO: 618)

Asp-npro rv-cell
5'-GTAGTACGCGTTGCCGCCGATGACGTCGACCATGGTCCGCGGGGTCTCGTCGGTCT-3'   (SEQ ID NO: 619)

Xba-1 fw A4
5'-GCAGCCTGAACTAGTTGCGATCCTCTAGAGATCGAACTTCATGTTCGA-3'           (SEQ ID NO: 620)
```

The polynucleotide primers for the cloning of *Cellulosimicrobium cellulans* protease (Cmcp) in pSEA4CT were based on SEQ ID NO: 71, and are as follows,

```
ASP-npro fw cellu
5'-ACCGACGAGACCCCGCGGACCATGCACGGCGACGTGCGCGGCGGCGACCGCTA-3'           (SEQ ID NO: 621)

ASP-npro rv cellu
5'-TAGCGGTCGCCGCCGCGCACGTCGCCGTGCATGGTCCGCGGGGTCTCGTCGGT-3'           (SEQ ID NO: 622)

Cellu-BH1-rv
5'-TCAGCCGATCCGCTCGCGGATCCCCATTGTCAGCGAGCCCGACGAGCGCGCTGCCCGAC-3'     (SEQ ID NO: 623)

Xba-1 fw A4
5'-GCAGCCTGAACTAGTTGCGATCCTCTAGAGATCGAACTTCATGTTCGA-3'                (SEQ ID NO: 620)
```

The host *Streptomyces lividans* TK23 was transformed with plasmid vector pSEA4CT using the protoplast method described above (i.e., Hopwood et al., supra). The transformed culture was expanded to provide two fermentation cultures in TS* medium. The composition of TS* medium was (g/L) tryptone (Difco) 16, soytone (Difco) 4, casein hydrolysate (Merck) 20, $K_2HPO_4$ 10, glucose 15, Basildon antifoam 0.6, pH 7.0. At various time points, samples of the fermentation broths were removed for analysis. For the purposes of this experiment, a skim milk procedure was used to confirm successful cloning. 30 µL of the shake flask supernatant was pipetted in punched out holes in skim milk agar plates and incubated at 37° C.

The incubated plates were visually reviewed after overnight incubation for the presence of clearing zones (halos) indicating the expression of proteolytic enzyme. For purposes of this experiment, the samples were also assayed for protease activity and for molecular weight (SDS-PAGE). At the end of the fermentation full length protease was observed by SDS-PAGE.

A sample of the fermentation broth was assayed as follows: 10 µL of the diluted supernatant was taken and added to 190 µL AAPF substrate solution (conc. 1 mg/ml, in 0.1 M Tris/0.005% Tween 80, pH 8.6). The rate of increase in absorbance at 410 nm due to release of p-nitroaniline was monitored (25° C.).

As in previous Examples, the results obtained clearly indicated that the polynucleotide from *Cellulomonas cellasea* or from *Cellulosimicrobium cellulans*, both encoding polypeptides having proteolytic activity were expressed in *Streptomyces lividans*.

Example 19

Determination of the Crystal Structure of ASP Protease

In this Example, methods used to determine the crystal structure of ASP protease are described. Indeed, high quality single crystals were obtained from purified ASP protease. The crystallization conditions were as follows: 25% PEG 8000, 0.2M ammonium sulphate, and 15% glycerol. These crystallization conditions are cryo-protective, so transfer to a cryo-protectant was not required. The crystals were frozen in liquid nitrogen, and kept frozen during data collection using an Xstream (Molecular Structure). Data were collected with a R-axis IV (Molecular Structure), equipped with focusing mirrors. X-ray reflection data were obtained to 1.9 Å resolution. The space group was $P2_12_12_1$, with cell dimensions a=35.65 Å, b=51.82 Å and c=76.86 Å. There was one molecule per asymmetric unit.

The crystal structure was solved using the molecular replacement method. The program used was X-MR (Accelrys Inc.). The starting model for the molecular replacement calculations was Streptogrisin. It is clear from the electron density map obtained from X-MR that the molecular replacement solution is correct. Thus, 98% of the model was built correctly, with some minor errors that were fixed manually. The R-factor for data to 1.9 Å was 0.23.

The structure was found to largely consist of β-sheets, with 2 very short α-helices, and a longer helix toward the C-terminal end. There are two sets of β-sheets, with a considerable interface between them. The active-site is found in a cleft formed at this interface. The catalytic triad is formed by His 32, Asp 56, and Ser 137. Table 19-1 provides the atomic coordinates identified for ASP.

TABLE 19-1

Atomic Coordinates of ASP with the Modeled Octapeptide Substrate

| CRYST1 | | 35.770 | | 51.730 | 76.650 | 90.00 | 90.00 | 90.00 | P212121 | | |
|---|---|---|---|---|---|---|---|---|---|---|---|
| ATOM | 1 | N | PHE | A | 1 | 2.421 | 18.349 | 15.176 | 1.00 | 16.78 | N |
| ATOM | 2 | CA | PHE | A | 1 | 3.695 | 18.087 | 15.905 | 1.00 | 18.18 | C |
| ATOM | 3 | CB | PHE | A | 1 | 4.875 | 18.550 | 15.048 | 1.00 | 16.73 | C |
| ATOM | 4 | C | PHE | A | 1 | 3.700 | 18.810 | 17.249 | 1.00 | 16.36 | C |
| ATOM | 5 | O | PHE | A | 1 | 3.443 | 20.011 | 17.315 | 1.00 | 17.91 | O |
| ATOM | 6 | CG | PHE | A | 1 | 6.214 | 18.292 | 15.664 | 1.00 | 17.42 | C |
| ATOM | 7 | CD2 | PHE | A | 1 | 6.955 | 17.180 | 15.296 | 1.00 | 19.42 | C |
| ATOM | 8 | CD1 | PHE | A | 1 | 6.736 | 19.160 | 16.611 | 1.00 | 16.13 | C |
| ATOM | 9 | CE2 | PHE | A | 1 | 8.200 | 16.933 | 15.863 | 1.00 | 18.08 | C |
| ATOM | 10 | CE1 | PHE | A | 1 | 7.977 | 18.922 | 17.180 | 1.00 | 18.34 | C |
| ATOM | 11 | CZ | PHE | A | 1 | 8.710 | 17.807 | 16.806 | 1.00 | 19.32 | C |
| ATOM | 12 | N | ASP | A | 2 | 3.984 | 18.076 | 18.321 | 1.00 | 13.94 | N |
| ATOM | 13 | CA | ASP | A | 2 | 4.015 | 18.670 | 19.654 | 1.00 | 15.04 | C |
| ATOM | 14 | CB | ASP | A | 2 | 3.527 | 17.677 | 20.714 | 1.00 | 15.13 | C |
| ATOM | 15 | C | ASP | A | 2 | 5.403 | 19.149 | 20.063 | 1.00 | 14.43 | C |
| ATOM | 16 | O | ASP | A | 2 | 6.381 | 18.408 | 19.966 | 1.00 | 11.44 | O |
| ATOM | 17 | CG | ASP | A | 2 | 2.088 | 17.243 | 20.502 | 1.00 | 18.25 | C |
| ATOM | 18 | OD2 | ASP | A | 2 | 1.721 | 16.150 | 20.986 | 1.00 | 19.05 | O |
| ATOM | 19 | OD1 | ASP | A | 2 | 1.320 | 17.996 | 19.874 | 1.00 | 15.33 | O |
| ATOM | 20 | N | VAL | A | 3 | 5.479 | 20.393 | 20.523 | 1.00 | 12.30 | N |
| ATOM | 21 | CA | VAL | A | 3 | 6.740 | 20.979 | 20.959 | 1.00 | 11.83 | C |

TABLE 19-1-continued

Atomic Coordinates of ASP with the Modeled Octapeptide Substrate

| ATOM | 22 | CB | VAL | A | 3 | 6.812 | 22.480 | 20.603 | 1.00 | 11.52 | C |
|------|----|----|-----|---|---|-------|--------|--------|------|-------|---|
| ATOM | 23 | C | VAL | A | 3 | 6.766 | 20.795 | 22.470 | 1.00 | 13.77 | C |
| ATOM | 24 | O | VAL | A | 3 | 5.912 | 21.321 | 23.183 | 1.00 | 11.14 | O |
| ATOM | 25 | CG1 | VAL | A | 3 | 7.987 | 23.133 | 21.309 | 1.00 | 15.13 | C |
| ATOM | 26 | CG2 | VAL | A | 3 | 6.968 | 22.637 | 19.101 | 1.00 | 14.21 | C |
| ATOM | 27 | CB | ILE | A | 4 | 7.561 | 18.267 | 24.642 | 1.00 | 14.73 | C |
| ATOM | 28 | CG2 | ILE | A | 4 | 7.799 | 17.929 | 26.099 | 1.00 | 14.20 | C |
| ATOM | 29 | CG1 | ILE | A | 4 | 6.103 | 17.995 | 24.267 | 1.00 | 16.79 | C |
| ATOM | 30 | CD1 | ILE | A | 4 | 5.774 | 16.518 | 24.166 | 1.00 | 19.32 | C |
| ATOM | 31 | C | ILE | A | 4 | 9.334 | 20.031 | 24.816 | 1.00 | 14.04 | C |
| ATOM | 32 | O | ILE | A | 4 | 10.289 | 19.660 | 24.140 | 1.00 | 11.09 | O |
| ATOM | 33 | N | ILE | A | 4 | 7.745 | 20.033 | 22.945 | 1.00 | 10.83 | N |
| ATOM | 34 | CA | ILE | A | 4 | 7.903 | 19.750 | 24.365 | 1.00 | 13.46 | C |
| ATOM | 35 | N | GLY | A | 5 | 9.475 | 20.681 | 25.965 | 1.00 | 11.82 | N |
| ATOM | 36 | CA | GLY | A | 5 | 10.800 | 20.995 | 26.467 | 1.00 | 9.81 | C |
| ATOM | 37 | C | GLY | A | 5 | 11.700 | 19.785 | 26.644 | 1.00 | 11.77 | C |
| ATOM | 38 | O | GLY | A | 5 | 11.256 | 18.737 | 27.114 | 1.00 | 9.20 | O |
| ATOM | 39 | N | GLY | A | 6 | 12.966 | 19.927 | 26.255 | 1.00 | 10.03 | N |
| ATOM | 40 | CA | GLY | A | 6 | 13.917 | 18.836 | 26.397 | 1.00 | 8.54 | C |
| ATOM | 41 | C | GLY | A | 6 | 14.070 | 17.979 | 25.156 | 1.00 | 9.57 | C |
| ATOM | 42 | O | GLY | A | 6 | 15.020 | 17.200 | 25.042 | 1.00 | 7.69 | O |
| ATOM | 43 | N | ASN | A | 7 | 13.131 | 18.119 | 24.224 | 1.00 | 9.01 | N |
| ATOM | 44 | CA | ASN | A | 7 | 13.168 | 17.359 | 22.985 | 1.00 | 10.51 | C |
| ATOM | 45 | CB | ASN | A | 7 | 11.780 | 17.293 | 22.349 | 1.00 | 14.65 | C |
| ATOM | 46 | CG | ASN | A | 7 | 10.897 | 16.250 | 22.981 | 1.00 | 10.35 | C |
| ATOM | 47 | OD1 | ASN | A | 7 | 9.715 | 16.144 | 22.644 | 1.00 | 13.61 | O |
| ATOM | 48 | ND2 | ASN | A | 7 | 11.456 | 15.470 | 23.896 | 1.00 | 6.66 | N |
| ATOM | 49 | C | ASN | A | 7 | 14.130 | 17.952 | 21.976 | 1.00 | 12.30 | C |
| ATOM | 50 | O | ASN | A | 7 | 14.424 | 19.146 | 21.991 | 1.00 | 15.93 | O |
| ATOM | 51 | N | ALA | A | 8 | 14.608 | 17.107 | 21.079 | 1.00 | 11.08 | N |
| ATOM | 52 | CA | ALA | A | 8 | 15.532 | 17.564 | 20.063 | 1.00 | 14.32 | C |
| ATOM | 53 | CB | ALA | A | 8 | 16.336 | 16.392 | 19.541 | 1.00 | 14.61 | C |
| ATOM | 54 | C | ALA | A | 8 | 14.766 | 18.202 | 18.914 | 1.00 | 11.23 | C |
| ATOM | 55 | O | ALA | A | 8 | 13.567 | 17.987 | 18.747 | 1.00 | 12.54 | O |
| ATOM | 56 | N | TYR | A | 9 | 15.468 | 19.021 | 18.145 | 1.00 | 9.75 | N |
| ATOM | 57 | CA | TYR | A | 9 | 14.899 | 19.691 | 16.988 | 1.00 | 12.42 | C |
| ATOM | 58 | CB | TYR | A | 9 | 14.279 | 21.059 | 17.334 | 1.00 | 12.79 | C |
| ATOM | 59 | CG | TYR | A | 9 | 15.216 | 22.150 | 17.790 | 1.00 | 14.12 | C |
| ATOM | 60 | CD2 | TYR | A | 9 | 15.485 | 22.333 | 19.139 | 1.00 | 10.17 | C |
| ATOM | 61 | CE2 | TYR | A | 9 | 16.302 | 23.366 | 19.572 | 1.00 | 12.49 | C |
| ATOM | 62 | CD1 | TYR | A | 9 | 15.791 | 23.029 | 16.877 | 1.00 | 9.02 | C |
| ATOM | 63 | CE1 | TYR | A | 9 | 16.604 | 24.066 | 17.294 | 1.00 | 10.92 | C |
| ATOM | 64 | CZ | TYR | A | 9 | 16.857 | 24.230 | 18.644 | 1.00 | 13.93 | C |
| ATOM | 65 | OH | TYR | A | 9 | 17.661 | 25.261 | 19.070 | 1.00 | 12.50 | O |
| ATOM | 66 | C | TYR | A | 9 | 16.127 | 19.792 | 16.101 | 1.00 | 12.21 | C |
| ATOM | 67 | O | TYR | A | 9 | 17.247 | 19.589 | 16.583 | 1.00 | 11.38 | O |
| ATOM | 68 | N | THR | A | 10 | 15.946 | 20.055 | 14.816 | 1.00 | 11.44 | N |
| ATOM | 69 | CA | THR | A | 10 | 17.105 | 20.144 | 13.946 | 1.00 | 13.35 | C |
| ATOM | 70 | CB | THR | A | 10 | 17.114 | 18.998 | 12.916 | 1.00 | 14.07 | C |
| ATOM | 71 | OG1 | THR | A | 10 | 15.952 | 19.098 | 12.086 | 1.00 | 13.63 | O |
| ATOM | 72 | CG2 | THR | A | 10 | 17.121 | 17.648 | 13.620 | 1.00 | 12.60 | C |
| ATOM | 73 | C | THR | A | 10 | 17.267 | 21.452 | 13.194 | 1.00 | 14.66 | C |
| ATOM | 74 | O | THR | A | 10 | 16.299 | 22.161 | 12.907 | 1.00 | 12.64 | O |
| ATOM | 75 | N | ILE | A | 11 | 18.520 | 21.749 | 12.881 | 1.00 | 14.05 | N |
| ATOM | 76 | CA | ILE | A | 11 | 18.889 | 22.954 | 12.157 | 1.00 | 18.00 | C |
| ATOM | 77 | CB | ILE | A | 11 | 19.649 | 23.931 | 13.068 | 1.00 | 17.58 | C |
| ATOM | 78 | CG2 | ILE | A | 11 | 19.919 | 25.230 | 12.323 | 1.00 | 20.00 | C |
| ATOM | 79 | CG1 | ILE | A | 11 | 18.825 | 24.212 | 14.327 | 1.00 | 21.47 | C |
| ATOM | 80 | CD1 | ILE | A | 11 | 19.560 | 25.031 | 15.377 | 1.00 | 23.61 | C |
| ATOM | 81 | C | ILE | A | 11 | 19.802 | 22.485 | 11.030 | 1.00 | 16.40 | C |
| ATOM | 82 | O | ILE | A | 11 | 20.913 | 22.014 | 11.278 | 1.00 | 17.72 | O |
| ATOM | 83 | N | GLY | A | 12 | 19.330 | 22.603 | 9.794 | 1.00 | 18.83 | N |
| ATOM | 84 | CA | GLY | A | 12 | 20.132 | 22.155 | 8.673 | 1.00 | 17.69 | C |
| ATOM | 85 | C | GLY | A | 12 | 20.359 | 20.659 | 8.791 | 1.00 | 18.86 | C |
| ATOM | 86 | O | GLY | A | 12 | 21.395 | 20.141 | 8.376 | 1.00 | 19.71 | O |
| ATOM | 87 | N | GLY | A | 13 | 19.391 | 19.964 | 9.380 | 1.00 | 17.62 | N |
| ATOM | 88 | CA | GLY | A | 13 | 19.509 | 18.525 | 9.529 | 1.00 | 16.37 | C |
| ATOM | 89 | C | GLY | A | 13 | 20.352 | 18.060 | 10.703 | 1.00 | 17.10 | C |
| ATOM | 90 | O | GLY | A | 13 | 20.470 | 16.861 | 10.946 | 1.00 | 15.94 | O |
| ATOM | 91 | N | ARG | A | 14 | 20.931 | 19.002 | 11.438 | 1.00 | 17.27 | N |
| ATOM | 92 | CA | ARG | A | 14 | 21.772 | 18.667 | 12.585 | 1.00 | 15.15 | C |
| ATOM | 93 | CB | ARG | A | 14 | 23.017 | 19.558 | 12.586 | 1.00 | 19.68 | C |
| ATOM | 94 | C | ARG | A | 14 | 21.030 | 18.842 | 13.908 | 1.00 | 16.27 | C |
| ATOM | 95 | O | ARG | A | 14 | 20.423 | 19.882 | 14.159 | 1.00 | 12.16 | O |
| ATOM | 96 | CG | ARG | A | 14 | 24.009 | 19.273 | 13.699 | 1.00 | 25.94 | C |
| ATOM | 97 | CD | ARG | A | 14 | 24.879 | 18.069 | 13.393 | 1.00 | 31.69 | C |
| ATOM | 98 | NE | ARG | A | 14 | 25.964 | 17.928 | 14.360 | 1.00 | 40.26 | N |
| ATOM | 99 | CZ | ARG | A | 14 | 25.802 | 17.572 | 15.630 | 1.00 | 42.65 | C |

TABLE 19-1-continued

Atomic Coordinates of ASP with the Modeled Octapeptide Substrate

| ATOM | 100 | NH1 | ARG | A | 14 | 26.852 | 17.483 | 16.435 | 1.00 | 45.09 | N |
|------|-----|-----|-----|---|----|--------|--------|--------|------|-------|---|
| ATOM | 101 | NH2 | ARG | A | 14 | 24.592 | 17.302 | 16.091 | 1.00 | 41.89 | N |
| ATOM | 102 | N | SER | A | 15 | 21.075 | 17.821 | 14.756 | 1.00 | 14.36 | N |
| ATOM | 103 | CA | SER | A | 15 | 20.407 | 17.892 | 16.047 | 1.00 | 18.05 | C |
| ATOM | 104 | CB | SER | A | 15 | 20.033 | 16.488 | 16.524 | 1.00 | 19.52 | C |
| ATOM | 105 | C | SER | A | 15 | 21.402 | 18.533 | 17.011 | 1.00 | 18.51 | C |
| ATOM | 106 | O | SER | A | 15 | 21.966 | 17.870 | 17.882 | 1.00 | 16.89 | O |
| ATOM | 107 | OG | SER | A | 15 | 19.311 | 16.542 | 17.742 | 1.00 | 24.25 | O |
| ATOM | 108 | N | ARG | A | 16 | 21.625 | 19.829 | 16.842 | 1.00 | 15.76 | N |
| ATOM | 109 | CA | ARG | A | 16 | 22.560 | 20.544 | 17.695 | 1.00 | 18.30 | C |
| ATOM | 110 | CB | ARG | A | 16 | 23.077 | 21.795 | 16.976 | 1.00 | 22.82 | C |
| ATOM | 111 | C | ARG | A | 16 | 22.006 | 20.952 | 19.050 | 1.00 | 17.05 | C |
| ATOM | 112 | O | ARG | A | 16 | 22.760 | 21.064 | 20.015 | 1.00 | 11.60 | O |
| ATOM | 113 | CG | ARG | A | 16 | 23.892 | 21.498 | 15.729 | 1.00 | 30.78 | C |
| ATOM | 114 | CD | ARG | A | 16 | 24.503 | 22.758 | 15.131 | 1.00 | 36.12 | C |
| ATOM | 115 | NE | ARG | A | 16 | 23.494 | 23.756 | 14.789 | 1.00 | 41.88 | N |
| ATOM | 116 | CZ | ARG | A | 16 | 23.737 | 24.839 | 14.058 | 1.00 | 44.68 | C |
| ATOM | 117 | NH2 | ARG | A | 16 | 24.954 | 25.057 | 13.579 | 1.00 | 46.43 | N |
| ATOM | 118 | NH1 | ARG | A | 16 | 22.762 | 25.698 | 13.796 | 1.00 | 44.09 | N |
| ATOM | 119 | N | CYS | A | 17 | 20.695 | 21.152 | 19.130 | 1.00 | 12.26 | N |
| ATOM | 120 | CA | CYS | A | 17 | 20.085 | 21.562 | 20.388 | 1.00 | 11.02 | C |
| ATOM | 121 | CB | CYS | A | 17 | 19.949 | 23.079 | 20.394 | 1.00 | 11.05 | C |
| ATOM | 122 | C | CYS | A | 17 | 18.744 | 20.946 | 20.756 | 1.00 | 8.62 | C |
| ATOM | 123 | O | CYS | A | 17 | 18.178 | 20.154 | 20.008 | 1.00 | 10.24 | O |
| ATOM | 124 | SG | CYS | A | 17 | 21.542 | 23.945 | 20.503 | 1.00 | 10.83 | S |
| ATOM | 125 | N | SER | A | 18 | 18.246 | 21.338 | 21.926 | 1.00 | 9.44 | N |
| ATOM | 126 | CA | SER | A | 18 | 16.976 | 20.849 | 22.441 | 1.00 | 10.14 | C |
| ATOM | 127 | CB | SER | A | 18 | 17.226 | 20.053 | 23.726 | 1.00 | 11.06 | C |
| ATOM | 128 | OG | SER | A | 18 | 18.198 | 19.042 | 23.516 | 1.00 | 11.13 | O |
| ATOM | 129 | C | SER | A | 18 | 16.019 | 22.004 | 22.736 | 1.00 | 10.28 | C |
| ATOM | 130 | O | SER | A | 18 | 16.439 | 23.152 | 22.882 | 1.00 | 12.80 | O |
| ATOM | 131 | N | ILE | A | 19 | 14.731 | 21.689 | 22.806 | 1.00 | 8.87 | N |
| ATOM | 132 | CA | ILE | A | 19 | 13.698 | 22.676 | 23.087 | 1.00 | 9.04 | C |
| ATOM | 133 | CB | ILE | A | 19 | 12.278 | 22.070 | 22.951 | 1.00 | 9.94 | C |
| ATOM | 134 | CG2 | ILE | A | 19 | 11.236 | 23.126 | 23.287 | 1.00 | 10.60 | C |
| ATOM | 135 | CG1 | ILE | A | 19 | 12.053 | 21.514 | 21.543 | 1.00 | 12.49 | C |
| ATOM | 136 | CD1 | ILE | A | 19 | 12.083 | 22.554 | 20.439 | 1.00 | 10.46 | C |
| ATOM | 137 | C | ILE | A | 19 | 13.840 | 23.154 | 24.530 | 1.00 | 9.36 | C |
| ATOM | 138 | O | ILE | A | 19 | 14.039 | 22.346 | 25.442 | 1.00 | 7.81 | O |
| ATOM | 139 | N | GLY | A | 20 | 13.748 | 24.466 | 24.729 | 1.00 | 6.59 | N |
| ATOM | 140 | CA | GLY | A | 20 | 13.827 | 25.024 | 26.067 | 1.00 | 7.48 | C |
| ATOM | 141 | C | GLY | A | 20 | 12.424 | 25.027 | 26.649 | 1.00 | 10.12 | C |
| ATOM | 142 | O | GLY | A | 20 | 12.047 | 24.128 | 27.400 | 1.00 | 9.28 | O |
| ATOM | 143 | N | PHE | A | 21 | 11.636 | 26.037 | 26.293 | 1.00 | 11.70 | N |
| ATOM | 144 | CA | PHE | A | 21 | 10.262 | 26.132 | 26.770 | 1.00 | 9.99 | C |
| ATOM | 145 | CB | PHE | A | 21 | 10.182 | 27.019 | 28.009 | 1.00 | 12.23 | C |
| ATOM | 146 | CG | PHE | A | 21 | 10.891 | 26.455 | 29.197 | 1.00 | 12.14 | C |
| ATOM | 147 | CD1 | PHE | A | 21 | 10.282 | 25.493 | 29.985 | 1.00 | 10.45 | C |
| ATOM | 148 | CD2 | PHE | A | 21 | 12.174 | 26.873 | 29.517 | 1.00 | 11.10 | C |
| ATOM | 149 | CE1 | PHE | A | 21 | 10.943 | 24.953 | 31.078 | 1.00 | 9.63 | C |
| ATOM | 150 | CE2 | PHE | A | 21 | 12.841 | 26.339 | 30.606 | 1.00 | 10.44 | C |
| ATOM | 151 | CZ | PHE | A | 21 | 12.225 | 25.377 | 31.390 | 1.00 | 5.44 | C |
| ATOM | 152 | C | PHE | A | 21 | 9.378 | 26.721 | 25.692 | 1.00 | 11.93 | C |
| ATOM | 153 | O | PHE | A | 21 | 9.838 | 27.500 | 24.861 | 1.00 | 11.86 | O |
| ATOM | 154 | N | ALA | A | 22 | 8.105 | 26.346 | 25.709 | 1.00 | 8.59 | N |
| ATOM | 155 | CA | ALA | A | 22 | 7.171 | 26.861 | 24.722 | 1.00 | 10.98 | C |
| ATOM | 156 | CB | ALA | A | 22 | 5.978 | 25.920 | 24.580 | 1.00 | 9.33 | C |
| ATOM | 157 | C | ALA | A | 22 | 6.708 | 28.233 | 25.200 | 1.00 | 9.72 | C |
| ATOM | 158 | O | ALA | A | 22 | 6.452 | 28.431 | 26.390 | 1.00 | 10.20 | O |
| ATOM | 159 | N | VAL | A | 23 | 6.621 | 29.178 | 24.270 | 1.00 | 9.39 | N |
| ATOM | 160 | CA | VAL | A | 23 | 6.186 | 30.542 | 24.579 | 1.00 | 11.79 | C |
| ATOM | 161 | CB | VAL | A | 23 | 7.369 | 31.545 | 24.567 | 1.00 | 8.77 | C |
| ATOM | 162 | CG1 | VAL | A | 23 | 8.373 | 31.176 | 25.644 | 1.00 | 12.30 | C |
| ATOM | 163 | CG2 | VAL | A | 23 | 8.034 | 31.557 | 23.195 | 1.00 | 9.56 | C |
| ATOM | 164 | C | VAL | A | 23 | 5.197 | 30.943 | 23.496 | 1.00 | 12.96 | C |
| ATOM | 165 | O | VAL | A | 23 | 5.047 | 30.234 | 22.507 | 1.00 | 15.51 | O |
| ATOM | 166 | N | ASN | A | 24 | 4.509 | 32.066 | 23.668 | 1.00 | 15.64 | N |
| ATOM | 167 | CA | ASN | A | 24 | 3.559 | 32.472 | 22.642 | 1.00 | 18.48 | C |
| ATOM | 168 | CB | ASN | A | 24 | 2.848 | 33.772 | 23.048 | 1.00 | 23.96 | C |
| ATOM | 169 | C | ASN | A | 24 | 4.304 | 32.661 | 21.319 | 1.00 | 18.42 | C |
| ATOM | 170 | O | ASN | A | 24 | 5.277 | 33.410 | 21.251 | 1.00 | 16.60 | O |
| ATOM | 171 | CG | ASN | A | 24 | 3.800 | 34.949 | 23.182 | 1.00 | 23.94 | C |
| ATOM | 172 | OD1 | ASN | A | 24 | 4.697 | 34.951 | 24.025 | 1.00 | 23.82 | O |
| ATOM | 173 | ND2 | ASN | A | 24 | 3.602 | 35.964 | 22.345 | 1.00 | 25.51 | N |
| ATOM | 174 | N | GLY | A | 25 | 3.868 | 31.956 | 20.278 | 1.00 | 19.39 | N |
| ATOM | 175 | CA | GLY | A | 25 | 4.509 | 32.086 | 18.978 | 1.00 | 18.25 | C |
| ATOM | 176 | C | GLY | A | 25 | 5.628 | 31.106 | 18.649 | 1.00 | 18.73 | C |
| ATOM | 177 | O | GLY | A | 25 | 6.103 | 31.065 | 17.515 | 1.00 | 18.70 | O |

TABLE 19-1-continued

Atomic Coordinates of ASP with the Modeled Octapeptide Substrate

| ATOM | 178 | N | GLY | A | 26 | 6.064 | 30.318 | 19.624 | 1.00 | 14.44 | N |
|---|---|---|---|---|---|---|---|---|---|---|---|
| ATOM | 179 | CA | GLY | A | 26 | 7.123 | 29.362 | 19.348 | 1.00 | 15.00 | C |
| ATOM | 180 | C | GLY | A | 26 | 7.779 | 28.822 | 20.602 | 1.00 | 11.05 | C |
| ATOM | 181 | O | GLY | A | 26 | 7.095 | 28.457 | 21.554 | 1.00 | 10.68 | O |
| ATOM | 182 | N | PHE | A | 27 | 9.107 | 28.759 | 20.599 | 1.00 | 11.66 | N |
| ATOM | 183 | CA | PHE | A | 27 | 9.832 | 28.268 | 21.761 | 1.00 | 11.72 | C |
| ATOM | 184 | CB | PHE | A | 27 | 10.056 | 26.748 | 21.679 | 1.00 | 10.14 | C |
| ATOM | 185 | C | PHE | A | 27 | 11.169 | 28.960 | 21.934 | 1.00 | 10.62 | C |
| ATOM | 186 | O | PHE | A | 27 | 11.727 | 29.509 | 20.985 | 1.00 | 12.74 | O |
| ATOM | 187 | CG | PHE | A | 27 | 11.000 | 26.309 | 20.580 | 1.00 | 9.74 | C |
| ATOM | 188 | CD1 | PHE | A | 27 | 10.524 | 26.006 | 19.308 | 1.00 | 12.75 | C |
| ATOM | 189 | CD2 | PHE | A | 27 | 12.361 | 26.158 | 20.832 | 1.00 | 11.98 | C |
| ATOM | 190 | CE1 | PHE | A | 27 | 11.384 | 25.555 | 18.312 | 1.00 | 8.90 | C |
| ATOM | 191 | CE2 | PHE | A | 27 | 13.228 | 25.707 | 19.837 | 1.00 | 10.80 | C |
| ATOM | 192 | CZ | PHE | A | 27 | 12.740 | 25.406 | 18.580 | 1.00 | 9.83 | C |
| ATOM | 193 | N | ILE | A | 28 | 11.675 | 28.948 | 23.162 | 1.00 | 12.44 | N |
| ATOM | 194 | CA | ILE | A | 28 | 12.956 | 29.573 | 23.442 | 1.00 | 10.82 | C |
| ATOM | 195 | CB | ILE | A | 28 | 12.903 | 30.454 | 24.707 | 1.00 | 10.35 | C |
| ATOM | 196 | C | ILE | A | 28 | 13.992 | 28.469 | 23.590 | 1.00 | 12.26 | C |
| ATOM | 197 | O | ILE | A | 28 | 13.667 | 27.335 | 23.960 | 1.00 | 11.25 | O |
| ATOM | 198 | CG2 | ILE | A | 28 | 12.081 | 31.701 | 24.434 | 1.00 | 7.92 | C |
| ATOM | 199 | CG1 | ILE | A | 28 | 12.278 | 29.690 | 25.873 | 1.00 | 12.08 | C |
| ATOM | 200 | CD1 | ILE | A | 28 | 12.175 | 30.526 | 27.129 | 1.00 | 10.36 | C |
| ATOM | 201 | N | THR | A | 29 | 15.238 | 28.804 | 23.283 | 1.00 | 11.02 | N |
| ATOM | 202 | CA | THR | A | 29 | 16.327 | 27.845 | 23.364 | 1.00 | 11.15 | C |
| ATOM | 203 | CB | THR | A | 29 | 16.348 | 26.988 | 22.052 | 1.00 | 13.72 | C |
| ATOM | 204 | OG1 | THR | A | 29 | 17.364 | 25.981 | 22.124 | 1.00 | 11.80 | O |
| ATOM | 205 | CG2 | THR | A | 29 | 16.594 | 27.875 | 20.841 | 1.00 | 9.32 | C |
| ATOM | 206 | C | THR | A | 29 | 17.630 | 28.628 | 23.555 | 1.00 | 10.10 | C |
| ATOM | 207 | O | THR | A | 29 | 17.595 | 29.818 | 23.888 | 1.00 | 8.90 | O |
| ATOM | 208 | N | ALA | A | 30 | 18.771 | 27.974 | 23.353 | 1.00 | 8.93 | N |
| ATOM | 209 | CA | ALA | A | 30 | 20.069 | 28.630 | 23.511 | 1.00 | 8.72 | C |
| ATOM | 210 | CB | ALA | A | 30 | 21.135 | 27.602 | 23.862 | 1.00 | 9.30 | C |
| ATOM | 211 | C | ALA | A | 30 | 20.476 | 29.388 | 22.252 | 1.00 | 8.30 | C |
| ATOM | 212 | O | ALA | A | 30 | 20.243 | 28.925 | 21.133 | 1.00 | 11.59 | O |
| ATOM | 213 | N | GLY | A | 31 | 21.097 | 30.547 | 22.448 | 1.00 | 10.82 | N |
| ATOM | 214 | CA | GLY | A | 31 | 21.527 | 31.366 | 21.330 | 1.00 | 10.68 | C |
| ATOM | 215 | C | GLY | A | 31 | 22.626 | 30.770 | 20.469 | 1.00 | 12.90 | C |
| ATOM | 216 | O | GLY | A | 31 | 22.656 | 31.014 | 19.259 | 1.00 | 12.57 | O |
| ATOM' | 217 | N | HIS | A | 32 | 23.529 | 29.991 | 21.065 | 1.00 | 9.76 | N |
| ATOM | 218 | CA | HIS | A | 32 | 24.615 | 29.409 | 20.285 | 1.00 | 9.96 | C |
| ATOM | 219 | CB | HIS | A | 32 | 25.747 | 28.891 | 21.194 | 1.00 | 11.85 | C |
| ATOM | 220 | CG | HIS | A | 32 | 25.442 | 27.602 | 21.896 | 1.00 | 9.52 | C |
| ATOM | 221 | CD2 | HIS | A | 32 | 25.495 | 26.319 | 21.464 | 1.00 | 11.42 | C |
| ATOM | 222 | ND1 | HIS | A | 32 | 25.093 | 27.545 | 23.226 | 1.00 | 12.01 | N |
| ATOM | 223 | CE1 | HIS | A | 32 | 24.945 | 26.281 | 23.588 | 1.00 | 12.23 | C |
| ATOM | 224 | NE2 | HIS | A | 32 | 25.185 | 25.518 | 22.538 | 1.00 | 12.81 | N |
| ATOM | 225 | C | HIS | A | 32 | 24.138 | 28.301 | 19.355 | 1.00 | 8.20 | C |
| ATOM | 226 | O | HIS | A | 32 | 24.917 | 27.768 | 18.569 | 1.00 | 10.19 | O |
| ATOM | 227 | N | CYS | A | 33 | 22.850 | 27.977 | 19.430 | 1.00 | 8.42 | N |
| ATOM | 228 | CA | CYS | A | 33 | 22.270 | 26.933 | 18.589 | 1.00 | 9.80 | C |
| ATOM | 229 | CB | CYS | A | 33 | 20.894 | 26.536 | 19.117 | 1.00 | 11.66 | C |
| ATOM | 230 | SG | CYS | A | 33 | 20.964 | 25.864 | 20.798 | 1.00 | 13.22 | S |
| ATOM | 231 | C | CYS | A | 33 | 22.131 | 27.410 | 17.152 | 1.00 | 14.10 | C |
| ATOM | 232 | O | CYS | A | 33 | 22.338 | 26.649 | 16.212 | 1.00 | 14.43 | O |
| ATOM | 233 | N | GLY | A | 34 | 21.775 | 28.676 | 16.982 | 1.00 | 14.60 | N |
| ATOM | 234 | CA | GLY | A | 34 | 21.622 | 29.202 | 15.643 | 1.00 | 13.42 | C |
| ATOM | 235 | C | GLY | A | 34 | 21.365 | 30.690 | 15.632 | 1.00 | 13.64 | C |
| ATOM | 236 | O | GLY | A | 34 | 20.989 | 31.278 | 16.652 | 1.00 | 12.12 | O |
| ATOM | 237 | N | ARG | A | 35 | 21.565 | 31.299 | 14.467 | 1.00 | 12.90 | N |
| ATOM | 238 | CA | ARG | A | 35 | 21.360 | 32.728 | 14.301 | 1.00 | 15.08 | C |
| ATOM | 239 | CB | ARG | A | 35 | 22.458 | 33.322 | 13.416 | 1.00 | 14.13 | C |
| ATOM | 240 | C | ARG | A | 35 | 20.003 | 33.020 | 13.673 | 1.00 | 11.11 | C |
| ATOM | 241 | O | ARG | A | 35 | 19.367 | 32.144 | 13.084 | 1.00 | 14.43 | O |
| ATOM | 242 | CG | ARG | A | 35 | 22.408 | 32.854 | 11.971 | 1.00 | 19.31 | C |
| ATOM | 243 | CD | ARG | A | 35 | 23.430 | 33.597 | 11.123 | 1.00 | 21.41 | C |
| ATOM | 244 | NE | ARG | A | 35 | 24.800 | 33.232 | 11.469 | 1.00 | 22.20 | N |
| ATOM | 245 | CZ | ARG | A | 35 | 25.410 | 32.135 | 11.032 | 1.00 | 22.78 | C |
| ATOM | 246 | NH1 | ARG | A | 35 | 26.658 | 31.875 | 11.400 | 1.00 | 21.47 | N |
| ATOM | 247 | NH2 | ARG | A | 35 | 24.779 | 31.305 | 10.215 | 1.00 | 23.65 | N |
| ATOM | 248 | N | THR | A | 36 | 19.566 | 34.265 | 13.803 | 1.00 | 12.06 | N |
| ATOM | 249 | CA | THR | A | 36 | 18.291 | 34.688 | 13.251 | 1.00 | 10.87 | C |
| ATOM | 250 | CB | THR | A | 36 | 18.123 | 36.212 | 13.411 | 1.00 | 14.79 | C |
| ATOM | 251 | C | THR | A | 36 | 18.212 | 34.305 | 11.774 | 1.00 | 11.54 | C |
| ATOM | 252 | O | THR | A | 36 | 19.195 | 34.414 | 11.043 | 1.00 | 10.69 | O |
| ATOM | 253 | OG1 | THR | A | 36 | 18.002 | 36.552 | 14.802 | 1.00 | 19.95 | O |
| ATOM | 254 | CG2 | THR | A | 36 | 16.889 | 36.705 | 12.679 | 1.00 | 17.55 | C |
| ATOM | 255 | N | GLY | A | 37 | 17.047 | 33.839 | 11.339 | 1.00 | 11.25 | N |

TABLE 19-1-continued

Atomic Coordinates of ASP with the Modeled Octapeptide Substrate

| ATOM | 256 | CA | GLY | A | 37 | 16.896 | 33.446 | 9.950 | 1.00 | 10.63 | C |
|---|---|---|---|---|---|---|---|---|---|---|---|
| ATOM | 257 | C | GLY | A | 37 | 17.140 | 31.965 | 9.705 | 1.00 | 16.44 | C |
| ATOM | 258 | O | GLY | A | 37 | 16.711 | 31.421 | 8.688 | 1.00 | 13.24 | O |
| ATOM | 259 | N | ALA | A | 38 | 17.837 | 31.306 | 10.624 | 1.00 | 16.27 | N |
| ATOM | 260 | CA | ALA | A | 38 | 18.101 | 29.877 | 10.481 | 1.00 | 17.14 | C |
| ATOM | 261 | C | ALA | A | 38 | 16.781 | 29.118 | 10.602 | 1.00 | 15.01 | C |
| ATOM | 262 | O | ALA | A | 38 | 15.943 | 29.447 | 11.442 | 1.00 | 14.04 | O |
| ATOM | 263 | CB | ALA | A | 38 | 19.074 | 29.416 | 11.559 | 1.00 | 16.54 | C |
| ATOM | 264 | N | THR | A | 39 | 16.588 | 28.107 | 9.764 | 1.00 | 15.44 | N |
| ATOM | 265 | CA | THR | A | 39 | 15.355 | 27.329 | 9.811 | 1.00 | 16.44 | C |
| ATOM | 266 | CB | THR | A | 39 | 14.867 | 26.956 | 8.397 | 1.00 | 16.50 | C |
| ATOM | 267 | OG1 | THR | A | 39 | 15.848 | 26.146 | 7.746 | 1.00 | 22.08 | O |
| ATOM | 268 | CG2 | THR | A | 39 | 14.615 | 28.209 | 7.578 | 1.00 | 17.88 | C |
| ATOM | 269 | C | THR | A | 39 | 15.522 | 26.052 | 10.622 | 1.00 | 14.04 | C |
| ATOM | 270 | O | THR | A | 39 | 16.603 | 25.467 | 10.669 | 1.00 | 13.48 | O |
| ATOM | 271 | N | THR | A | 40 | 14.437 | 25.626 | 11.256 | 1.00 | 14.41 | N |
| ATOM | 272 | CA | THR | A | 40 | 14.445 | 24.421 | 12.072 | 1.00 | 12.76 | C |
| ATOM | 273 | CB | THR | A | 40 | 14.081 | 24.735 | 13.536 | 1.00 | 13.70 | C |
| ATOM | 274 | OG1 | THR | A | 40 | 12.745 | 25.260 | 13.601 | 1.00 | 11.68 | O |
| ATOM | 275 | CG2 | THR | A | 40 | 15.043 | 25.752 | 14.118 | 1.00 | 10.97 | C |
| ATOM | 276 | C | THR | A | 40 | 13.437 | 23.399 | 11.566 | 1.00 | 12.70 | C |
| ATOM | 277 | O | THR | A | 40 | 12.554 | 23.717 | 10.773 | 1.00 | 15.30 | O |
| ATOM | 278 | N | ALA | A | 41 | 13.592 | 22.164 | 12.033 | 1.00 | 12.69 | N |
| ATOM | 279 | CA | ALA | A | 41 | 12.713 | 21.062 | 11.667 | 1.00 | 13.39 | C |
| ATOM | 280 | C | ALA | A | 41 | 12.425 | 20.346 | 12.986 | 1.00 | 13.08 | C |
| ATOM | 281 | O | ALA | A | 41 | 13.234 | 20.403 | 13.912 | 1.00 | 13.32 | O |
| ATOM | 282 | CB | ALA | A | 41 | 13.403 | 20.121 | 10.682 | 1.00 | 12.91 | C |
| ATOM | 283 | N | ASN | A | 42 | 11.280 | 19.680 | 13.075 | 1.00 | 13.98 | N |
| ATOM | 284 | CA | ASN | A | 42 | 10.909 | 18.966 | 14.296 | 1.00 | 15.22 | C |
| ATOM | 285 | C | ASN | A | 42 | 11.074 | 19.886 | 15.507 | 1.00 | 15.41 | C |
| ATOM | 286 | O | ASN | A | 42 | 11.835 | 19.580 | 16.426 | 1.00 | 14.69 | O |
| ATOM | 287 | CB | ASN | A | 42 | 11.792 | 17.727 | 14.507 | 1.00 | 18.61 | C |
| ATOM | 288 | CG | ASN | A | 42 | 11.862 | 16.826 | 13.282 | 1.00 | 22.16 | C |
| ATOM | 289 | OD1 | ASN | A | 42 | 10.893 | 16.685 | 12.536 | 1.00 | 20.39 | O |
| ATOM | 290 | ND1 | ASN | A | 42 | 13.017 | 16.192 | 13.085 | 1.00 | 21.80 | N |
| ATOM | 291 | NA | PRO | A | 43 | 10.319 | 20.994 | 15.558 | 1.00 | 12.16 | N |
| ATOM | 292 | CA | PRO | A | 43 | 9.329 | 21.449 | 14.579 | 1.00 | 13.99 | C |
| ATOM | 293 | CB | PRO | A | 43 | 8.328 | 22.178 | 15.454 | 1.00 | 14.60 | C |
| ATOM | 294 | C | PRO | A | 43 | 9.863 | 22.387 | 13.508 | 1.00 | 14.85 | C |
| ATOM | 295 | O | PRO | A | 43 | 10.949 | 22.950 | 13.633 | 1.00 | 12.84 | O |
| ATOM | 296 | CD | PRO | A | 43 | 10.287 | 21.862 | 16.751 | 1.00 | 11.35 | C |
| ATOM | 297 | CG | PRO | A | 43 | 9.259 | 22.940 | 16.356 | 1.00 | 12.54 | C |
| ATOM | 298 | N | THR | A | 44 | 9.074 | 22.556 | 12.454 | 1.00 | 12.78 | N |
| ATOM | 299 | CA | THR | A | 44 | 9.454 | 23.436 | 11.370 | 1.00 | 13.48 | C |
| ATOM | 300 | CB | THR | A | 44 | 8.441 | 23.349 | 10.217 | 1.00 | 15.07 | C |
| ATOM | 301 | C | THR | A | 44 | 9.387 | 24.818 | 12.010 | 1.00 | 13.36 | C |
| ATOM | 302 | O | THR | A | 44 | 8.430 | 25.127 | 12.721 | 1.00 | 12.32 | O |
| ATOM | 303 | OG1 | THR | A | 44 | 8.582 | 22.082 | 9.565 | 1.00 | 17.67 | O |
| ATOM | 304 | OG2 | THR | A | 44 | 8.660 | 24.473 | 9.216 | 1.00 | 14.97 | C |
| ATOM | 305 | N | GLY | A | 45 | 10.412 | 25.631 | 11.787 | 1.00 | 12.10 | N |
| ATOM | 306 | CA | GLY | A | 45 | 10.423 | 26.958 | 12.369 | 1.00 | 13.77 | C |
| ATOM | 307 | C | GLY | A | 45 | 11.557 | 27.824 | 11.865 | 1.00 | 12.84 | C |
| ATOM | 308 | O | GLY | A | 45 | 12.340 | 27.412 | 11.006 | 1.00 | 14.31 | O |
| ATOM | 309 | N | THR | A | 46 | 11.648 | 29.033 | 12.404 | 1.00 | 12.18 | N |
| ATOM | 310 | CA | THR | A | 46 | 12.686 | 29.970 | 12.001 | 1.00 | 15.03 | C |
| ATOM | 311 | CB | THR | A | 46 | 12.141 | 30.953 | 10.952 | 1.00 | 15.90 | C |
| ATOM | 312 | OG1 | THR | A | 46 | 11.528 | 30.219 | 9.884 | 1.00 | 20.72 | O |
| ATOM | 313 | CG2 | THR | A | 46 | 13.257 | 31.821 | 10.392 | 1.00 | 18.41 | C |
| ATOM | 314 | C | THR | A | 46 | 13.167 | 30.777 | 13.203 | 1.00 | 13.19 | C |
| ATOM | 315 | O | THR | A | 46 | 12.352 | 31.331 | 13.944 | 1.00 | 10.72 | O |
| ATOM | 316 | N | PHE | A | 47 | 14.480 | 30.835 | 13.407 | 1.00 | 11.27 | N |
| ATOM | 317 | CA | PHE | A | 47 | 15.009 | 31.596 | 14.527 | 1.00 | 10.95 | C |
| ATOM | 318 | CB | PHE | A | 47 | 16.541 | 31.508 | 14.596 | 1.00 | 11.26 | C |
| ATOM | 319 | CG | PHE | A | 47 | 17.054 | 30.306 | 15.346 | 1.00 | 12.89 | C |
| ATOM | 320 | CD2 | PHE | A | 47 | 17.559 | 30.442 | 16.633 | 1.00 | 8.64 | C |
| ATOM | 321 | CD1 | PHE | A | 47 | 17.036 | 29.046 | 14.767 | 1.00 | 12.80 | C |
| ATOM | 322 | CE2 | PHE | A | 47 | 18.040 | 29.342 | 17.331 | 1.00 | 12.73 | C |
| ATOM | 323 | CE1 | PHE | A | 47 | 17.514 | 27.941 | 15.457 | 1.00 | 12.73 | C |
| ATOM | 324 | CZ | PHE | A | 47 | 18.017 | 28.088 | 16.740 | 1.00 | 14.16 | C |
| ATOM | 325 | C | PHE | A | 47 | 14.590 | 33.041 | 14.291 | 1.00 | 12.22 | C |
| ATOM | 326 | O | PHE | A | 47 | 14.737 | 33.563 | 13.182 | 1.00 | 13.19 | O |
| ATOM | 327 | N | ALA | A | 48 | 14.058 | 33.673 | 15.330 | 1.00 | 11.62 | N |
| ATOM | 328 | CA | ALA | A | 48 | 13.613 | 35.059 | 15.240 | 1.00 | 12.91 | C |
| ATOM | 329 | CB | ALA | A | 48 | 12.092 | 35.126 | 15.261 | 1.00 | 13.93 | C |
| ATOM | 330 | C | ALA | A | 48 | 14.184 | 35.856 | 16.400 | 1.00 | 15.66 | C |
| ATOM | 331 | O | ALA | A | 48 | 13.470 | 36.598 | 17.072 | 1.00 | 21.12 | O |
| ATOM | 332 | N | GLY | A | 49 | 15.482 | 35.700 | 16.622 | 1.00 | 15.68 | N |
| ATOM | 333 | CA | GLY | A | 49 | 16.139 | 36.407 | 17.701 | 1.00 | 16.25 | C |

TABLE 19-1-continued

Atomic Coordinates of ASP with the Modeled Octapeptide Substrate

| ATOM | 334 | C | GLY | A | 49 | 17.156 | 35.500 | 18.352 | 1.00 | 15.88 | C |
|---|---|---|---|---|---|---|---|---|---|---|---|
| ATOM | 335 | O | GLY | A | 49 | 16.820 | 34.403 | 18.799 | 1.00 | 13.45 | O |
| ATOM' | 336 | N | SER | A | 49 | 18.404 | 35.947 | 18.405 | 1.00 | 13.85 | N |
| ATOM | 337 | CA | SER | A | 50 | 19.454 | 35.144 | 19.012 | 1.00 | 13.96 | C |
| ATOM | 338 | CB | SER | A | 50 | 20.014 | 34.156 | 17.984 | 1.00 | 17.08 | C |
| ATOM | 339 | OG | SER | A | 50 | 21.045 | 33.365 | 18.541 | 1.00 | 14.72 | O |
| ATOM | 340 | C | SER | A | 50 | 20.574 | 36.026 | 19.543 | 1.00 | 16.90 | C |
| ATOM | 341 | O | SER | A | 50 | 21.082 | 36.894 | 18.835 | 1.00 | 16.85 | O |
| ATOM | 342 | N | SER | A | 51 | 20.941 | 35.802 | 20.801 | 1.00 | 15.23 | N |
| ATOM | 343 | CA | SER | A | 51 | 22.003 | 36.561 | 21.447 | 1.00 | 14.67 | C |
| ATOM | 344 | CB | SER | A | 51 | 21.440 | 37.431 | 22.570 | 1.00 | 15.96 | C |
| ATOM | 345 | OG | SER | A | 51 | 22.474 | 38.172 | 23.187 | 1.00 | 18.34 | O |
| ATOM | 346 | C | SER | A | 51 | 23.062 | 35.622 | 22.017 | 1.00 | 11.74 | C |
| ATOM | 347 | O | SER | A | 51 | 22.809 | 34.888 | 22.969 | 1.00 | 12.45 | O |
| ATOM | 348 | N | PHE | A | 52 | 24.247 | 35.655 | 21.419 | 1.00 | 8.44 | N |
| ATOM | 349 | CA | PHE | A | 52 | 25.367 | 34.822 | 21.842 | 1.00 | 11.84 | C |
| ATOM | 350 | CB | PHE | A | 52 | 25.090 | 33.344 | 21.557 | 1.00 | 9.85 | C |
| ATOM | 351 | CG | PHE | A | 52 | 26.264 | 32.450 | 21.837 | 1.00 | 14.45 | C |
| ATOM | 352 | CD1 | PHE | A | 52 | 26.561 | 32.056 | 23.133 | 1.00 | 14.77 | C |
| ATOM | 353 | CD2 | PHE | A | 52 | 27.095 | 32.037 | 20.808 | 1.00 | 14.93 | C |
| ATOM | 354 | CE1 | PHE | A | 52 | 27.665 | 31.267 | 23.400 | 1.00 | 12.39 | C |
| ATOM | 355 | CE2 | PHE | A | 52 | 28.203 | 31.250 | 21.067 | 1.00 | 13.03 | C |
| ATOM | 356 | CZ | PHE | A | 52 | 28.489 | 30.864 | 22.364 | 1.00 | 15.39 | C |
| ATOM | 357 | C | PHE | A | 52 | 26.595 | 35.245 | 21.051 | 1.00 | 11.09 | C |
| ATOM | 358 | O | PHE | A | 52 | 26.523 | 35.416 | 19.830 | 1.00 | 10.06 | O |
| ATOM | 359 | N | PRO | A | 53 | 27.737 | 35.427 | 21.732 | 1.00 | 13.84 | N |
| ATOM | 360 | CD | PRO | A | 53 | 29.034 | 35.610 | 21.055 | 1.00 | 13.82 | C |
| ATOM | 361 | CA | PRO | A | 53 | 27.919 | 35.257 | 23.177 | 1.00 | 11.97 | C |
| ATOM | 362 | CB | PRO | A | 53 | 29.433 | 35.114 | 23.319 | 1.00 | 15.91 | C |
| ATOM | 363 | CG | PRO | A | 53 | 29.953 | 35.957 | 22.201 | 1.00 | 16.14 | C |
| ATOM | 364 | C | PRO | A | 53 | 27.345 | 36.429 | 23.972 | 1.00 | 13.65 | C |
| ATOM | 365 | O | PRO | A | 53 | 26.411 | 37.085 | 23.516 | 1.00 | 12.98 | O |
| ATOM | 366 | N | GLY | A | 54 | 27.909 | 36.706 | 25.144 | 1.00 | 13.22 | N |
| ATOM | 367 | CA | GLY | A | 54 | 27.385 | 37.778 | 25.975 | 1.00 | 13.41 | C |
| ATOM | 368 | C | GLY | A | 54 | 26.291 | 37.112 | 26.781 | 1.00 | 13.11 | C |
| ATOM | 369 | O | GLY | A | 54 | 26.403 | 36.931 | 27.995 | 1.00 | 12.76 | O |
| ATOM | 370 | N | ASN | A | 55 | 25.223 | 36.740 | 26.083 | 1.00 | 13.05 | N |
| ATOM | 371 | CA | ASN | A | 55 | 24.110 | 36.013 | 26.681 | 1.00 | 14.39 | C |
| ATOM | 372 | CB | ASN | A | 55 | 22.761 | 36.681 | 26.396 | 1.00 | 12.65 | C |
| ATOM | 373 | CG | ASN | A | 55 | 22.758 | 38.153 | 26.682 | 1.00 | 11.23 | C |
| ATOM | 374 | OD1 | ASN | A | 55 | 22.521 | 38.967 | 25.784 | 1.00 | 16.09 | O |
| ATOM | 375 | ND2 | ASN | A | 55 | 23.001 | 38.516 | 27.933 | 1.00 | 11.47 | N |
| ATOM | 376 | C | ASN | A | 55 | 24.141 | 34.721 | 25.888 | 1.00 | 15.51 | C |
| ATOM | 377 | O | ASN | A | 55 | 25.076 | 34.485 | 25.123 | 1.00 | 11.36 | O |
| ATOM | 378 | N | ASP | A | 56 | 23.124 | 33.890 | 26.072 | 1.00 | 14.13 | N |
| ATOM | 379 | CA | ASP | A | 56 | 23.039 | 32.631 | 25.346 | 1.00 | 11.90 | C |
| ATOM | 380 | CB | ASP | A | 56 | 23.881 | 31.522 | 25.993 | 1.00 | 9.70 | C |
| ATOM | 381 | CG | ASP | A | 56 | 24.053 | 30.320 | 25.070 | 1.00 | 9.97 | C |
| ATOM | 382 | OD1 | ASP | A | 56 | 24.712 | 29.330 | 25.459 | 1.00 | 12.57 | O |
| ATOM | 383 | OD2 | ASP | A | 56 | 23.526 | 30.365 | 23.938 | 1.00 | 8.45 | O |
| ATOM | 384 | C | ASP | A | 56 | 21.578 | 32.216 | 25.279 | 1.00 | 9.86 | C |
| ATOM | 385 | O | ASP | A | 56 | 21.158 | 31.254 | 25.920 | 1.00 | 11.82 | O |
| ATOM | 386 | N | TYR | A | 57 | 20.798 | 32.969 | 24.509 | 1.00 | 8.71 | N |
| ATOM | 387 | CA | TYR | A | 57 | 19.379 | 32.677 | 24.351 | 1.00 | 10.51 | C |
| ATOM | 388 | CB | TYR | A | 57 | 18.523 | 33.480 | 25.348 | 1.00 | 12.30 | C |
| ATOM | 389 | CG | TYR | A | 57 | 18.650 | 34.992 | 25.271 | 1.00 | 12.51 | C |
| ATOM | 390 | CD1 | TYR | A | 57 | 19.275 | 35.708 | 26.291 | 1.00 | 11.12 | C |
| ATOM | 391 | CE1 | TYR | A | 57 | 19.366 | 37.094 | 26.244 | 1.00 | 11.36 | C |
| ATOM | 392 | CD2 | TYR | A | 57 | 18.121 | 35.706 | 24.197 | 1.00 | 13.29 | C |
| ATOM | 393 | CE2 | TYR | A | 57 | 18.209 | 37.096 | 24.144 | 1.00 | 10.62 | C |
| ATOM | 394 | CZ | TYR | A | 57 | 18.832 | 37.783 | 25.169 | 1.00 | 13.60 | C |
| ATOM | 395 | OH | TYR | A | 57 | 18.921 | 39.162 | 25.122 | 1.00 | 12.04 | O |
| ATOM | 396 | C | TYR | A | 57 | 18.912 | 32.963 | 22.933 | 1.00 | 10.26 | C |
| ATOM | 397 | O | TYR | A | 57 | 19.573 | 33.674 | 22.172 | 1.00 | 10.59 | O |
| ATOM | 398 | N | ALA | A | 58 | 17.767 | 32.393 | 22.578 | 1.00 | 9.32 | N |
| ATOM | 399 | CA | ALA | A | 58 | 17.200 | 32.583 | 21.254 | 1.00 | 7.41 | C |
| ATOM | 400 | CB | ALA | A | 58 | 17.943 | 31.732 | 20.241 | 1.00 | 7.89 | C |
| ATOM | 401 | C | ALA | A | 58 | 15.727 | 32.207 | 21.271 | 1.00 | 10.96 | C |
| ATOM | 402 | O | ALA | A | 58 | 15.260 | 31.510 | 22.175 | 1.00 | 11.10 | O |
| ATOM | 403 | N | PHE | A | 59 | 15.002 | 32.702 | 20.277 | 1.00 | 11.71 | N |
| ATOM | 404 | CA | PHE | A | 59 | 13.578 | 32.435 | 20.136 | 1.00 | 12.26 | C |
| ATOM | 405 | CB | PHE | A | 59 | 12.748 | 33.707 | 20.333 | 1.00 | 10.18 | C |
| ATOM | 406 | CG | PHE | A | 59 | 11.321 | 33.576 | 19.859 | 1.00 | 11.71 | C |
| ATOM | 407 | CD2 | PHE | A | 59 | 10.871 | 34.297 | 18.764 | 1.00 | 11.51 | C |
| ATOM | 408 | CD1 | PHE | A | 59 | 10.441 | 32.709 | 20.490 | 1.00 | 10.35 | C |
| ATOM | 409 | CE2 | PHE | A | 59 | 9.566 | 34.156 | 18.307 | 1.00 | 15.38 | C |
| ATOM | 410 | CE1 | PHE | A | 59 | 9.140 | 32.563 | 20.044 | 1.00 | 14.84 | C |
| ATOM | 411 | CZ | PHE | A | 59 | 8.700 | 33.286 | 18.949 | 1.00 | 13.16 | C |

TABLE 19-1-continued

Atomic Coordinates of ASP with the Modeled Octapeptide Substrate

| ATOM | 412 | C | PHE | A | 59 | 13.361 | 31.931 | 18.722 | 1.00 | 11.77 | C |
| ATOM | 413 | O | PHE | A | 59 | 13.887 | 32.507 | 17.771 | 1.00 | 13.80 | O |
| ATOM | 414 | N | VAL | A | 60 | 12.600 | 30.852 | 18.590 | 1.00 | 10.53 | N |
| ATOM | 415 | CA | VAL | A | 60 | 12.310 | 30.278 | 17.285 | 1.00 | 11.14 | C |
| ATOM | 416 | CB | VAL | A | 60 | 12.738 | 28.796 | 17.209 | 1.00 | 15.19 | C |
| ATOM | 417 | CG1 | VAL | A | 60 | 12.337 | 28.212 | 15.856 | 1.00 | 10.78 | C |
| ATOM | 418 | CG2 | VAL | A | 60 | 14.248 | 28.670 | 17.421 | 1.00 | 11.44 | C |
| ATOM | 419 | C | VAL | A | 60 | 10.801 | 30.363 | 17.082 | 1.00 | 11.30 | C |
| ATOM | 420 | O | VAL | A | 60 | 10.034 | 29.905 | 17.924 | 1.00 | 8.90 | O |
| ATOM | 421 | N | ARG | A | 61 | 10.372 | 30.964 | 15.979 | 1.00 | 12.67 | N |
| ATOM | 422 | CA | ARG | A | 61 | 8.944 | 31.083 | 15.716 | 1.00 | 11.18 | C |
| ATOM | 423 | CB | ARG | A | 61 | 8.655 | 32.314 | 14.844 | 1.00 | 12.63 | C |
| ATOM | 424 | CG | ARG | A | 61 | 7.194 | 32.398 | 14.379 | 1.00 | 17.12 | C |
| ATOM | 425 | CD | ARG | A | 61 | 6.967 | 33.527 | 13.376 | 1.00 | 20.85 | C |
| ATOM | 426 | NE | ARG | A | 61 | 5.563 | 33.614 | 12.971 | 1.00 | 24.18 | N |
| ATOM | 427 | CZ | ARG | A | 61 | 4.949 | 32.744 | 12.171 | 1.00 | 24.05 | C |
| ATOM | 428 | NH2 | ARG | A | 61 | 3.665 | 32.904 | 11.884 | 1.00 | 25.34 | N |
| ATOM | 429 | NH1 | ARG | A | 61 | 5.609 | 31.708 | 11.670 | 1.00 | 25.91 | N |
| ATOM | 430 | C | ARG | A | 61 | 8.424 | 29.831 | 15.011 | 1.00 | 12.67 | C |
| ATOM | 431 | O | ARG | A | 61 | 9.070 | 29.316 | 14.096 | 1.00 | 11.46 | O |
| ATOM | 432 | N | THR | A | 62 | 7.274 | 29.333 | 15.461 | 1.00 | 13.58 | N |
| ATOM | 433 | CA | THR | A | 62 | 6.666 | 28.147 | 14.865 | 1.00 | 13.24 | C |
| ATOM | 434 | CB | THR | A | 62 | 6.495 | 26.995 | 15.884 | 1.00 | 11.66 | C |
| ATOM | 435 | OG1 | THR | A | 62 | 5.729 | 27.450 | 17.007 | 1.00 | 13.55 | O |
| ATOM | 436 | CG2 | THR | A | 62 | 7.853 | 26.485 | 16.349 | 1.00 | 13.26 | C |
| ATOM | 437 | C | THR | A | 62 | 5.289 | 28.558 | 14.335 | 1.00 | 13.42 | C |
| ATOM | 438 | O | THR | A | 62 | 4.727 | 29.568 | 14.770 | 1.00 | 16.80 | O |
| ATOM | 439 | N | GLY | A | 63 | 4.748 | 27.778 | 13.406 | 1.00 | 16.51 | N |
| ATOM | 440 | CA | GLY | A | 63 | 3.455 | 28.108 | 12.834 | 1.00 | 15.85 | C |
| ATOM | 441 | C | GLY | A | 63 | 2.387 | 27.033 | 12.894 | 1.00 | 16.64 | C |
| ATOM | 442 | O | GLY | A | 63 | 2.137 | 26.432 | 13.938 | 1.00 | 12.21 | O |
| ATOM | 443 | N | ALA | A | 64 | 1.753 | 26.788 | 11.753 | 1.00 | 15.51 | N |
| ATOM | 444 | CA | ALA | A | 64 | 0.678 | 25.810 | 11.663 | 1.00 | 15.84 | C |
| ATOM | 445 | C | ALA | A | 64 | 1.090 | 24.378 | 11.977 | 1.00 | 15.00 | C |
| ATOM | 446 | O | ALA | A | 64 | 2.228 | 23.977 | 11.742 | 1.00 | 15.60 | O |
| ATOM | 447 | CB | ALA | A | 64 | 0.052 | 25.866 | 10.279 | 1.00 | 16.27 | C |
| ATOM | 448 | N | GLY | A | 65 | 0.144 | 23.614 | 12.510 | 1.00 | 17.17 | N |
| ATOM | 449 | CA | GLY | A | 65 | 0.390 | 22.217 | 12.828 | 1.00 | 19.42 | C |
| ATOM | 450 | C | GLY | A | 65 | 1.369 | 21.946 | 13.953 | 1.00 | 19.21 | C |
| ATOM | 451 | O | GLY | A | 65 | 1.691 | 20.790 | 14.234 | 1.00 | 22.10 | O |
| ATOM | 452 | N | VAL | A | 66 | 1.842 | 23.001 | 14.603 | 1.00 | 15.20 | N |
| ATOM | 453 | CA | VAL | A | 66 | 2.788 | 22.844 | 15.697 | 1.00 | 15.99 | C |
| ATOM | 454 | CB | VAL | A | 66 | 4.018 | 23.746 | 15.501 | 1.00 | 15.02 | C |
| ATOM | 455 | C | VAL | A | 66 | 2.116 | 23.195 | 17.016 | 1.00 | 18.46 | C |
| ATOM | 456 | O | VAL | A | 66 | 1.769 | 24.349 | 17.257 | 1.00 | 16.96 | O |
| ATOM | 457 | CG1 | VAL | A | 66 | 4.961 | 23.602 | 16.688 | 1.00 | 13.36 | C |
| ATOM | 458 | CG2 | VAL | A | 66 | 4.725 | 23.375 | 14.195 | 1.00 | 11.46 | C |
| ATOM | 459 | N | ASN | A | 67 | 1.931 | 22.193 | 17.866 | 1.00 | 15.34 | N |
| ATOM | 460 | CA | ASN | A | 67 | 1.294 | 22.407 | 19.158 | 1.00 | 16.12 | C |
| ATOM | 461 | CB | ASN | A | 67 | 0.474 | 21.177 | 19.539 | 1.00 | 21.01 | C |
| ATOM | 462 | C | ASN | A | 67 | 2.332 | 22.704 | 20.228 | 1.00 | 17.24 | C |
| ATOM | 463 | O | ASN | A | 67 | 3.172 | 21.862 | 20.554 | 1.00 | 17.97 | O |
| ATOM | 464 | CG | ASN | A | 67 | −0.465 | 20.748 | 18.431 | 1.00 | 29.21 | C |
| ATOM | 465 | OD1 | ASN | A | 67 | −1.308 | 21.527 | 17.976 | 1.00 | 33.32 | O |
| ATOM | 466 | ND2 | ASN | A | 67 | −0.323 | 19.505 | 17.982 | 1.00 | 33.03 | N |
| ATOM | 467 | N | LEU | A | 68 | 2.260 | 23.915 | 20.767 | 1.00 | 13.94 | N |
| ATOM | 468 | CA | LEU | A | 68 | 3.175 | 24.378 | 21.807 | 1.00 | 14.43 | C |
| ATOM | 469 | CB | LEU | A | 68 | 3.317 | 25.896 | 21.707 | 1.00 | 13.70 | C |
| ATOM | 470 | C | LEU | A | 68 | 2.638 | 23.985 | 23.178 | 1.00 | 15.01 | C |
| ATOM | 471 | O | LEU | A | 68 | 1.670 | 24.568 | 23.664 | 1.00 | 16.08 | O |
| ATOM | 472 | CG | LEU | A | 68 | 3.835 | 26.395 | 20.358 | 1.00 | 8.95 | C |
| ATOM | 473 | CD1 | LEU | A | 68 | 3.736 | 27.910 | 20.284 | 1.00 | 8.47 | C |
| ATOM | 474 | CD2 | LEU | A | 68 | 5.270 | 25.931 | 20.179 | 1.00 | 12.27 | C |
| ATOM | 475 | N | LEU | A | 69 | 3.284 | 23.005 | 23.805 | 1.00 | 12.99 | N |
| ATOM | 476 | CA | LEU | A | 69 | 2.861 | 22.529 | 25.119 | 1.00 | 12.18 | C |
| ATOM | 477 | CB | LEU | A | 69 | 2.88 | 20.997 | 25.134 | 1.00 | 12.27 | C |
| ATOM | 478 | CG | LEU | A | 69 | 2.075 | 20.310 | 24.029 | 1.00 | 16.54 | C |
| ATOM | 479 | CD1 | LEU | A | 69 | 2.251 | 18.802 | 24.113 | 1.00 | 17.85 | C |
| ATOM | 480 | CD2 | LEU | A | 69 | 0.611 | 20.679 | 24.170 | 1.00 | 19.65 | C |
| ATOM | 481 | C | LEU | A | 69 | 3.665 | 23.050 | 26.307 | 1.00 | 14.39 | C |
| ATOM | 482 | O | LEU | A | 69 | 4.879 | 23.239 | 26.228 | 1.00 | 14.53 | O |
| ATOM | 483 | N | ALA | A | 70 | 2.969 | 23.271 | 27.416 | 1.00 | 12.89 | N |
| ATOM | 484 | CA | ALA | A | 70 | 3.594 | 23.761 | 28.635 | 1.00 | 14.83 | C |
| ATOM | 485 | CB | ALA | A | 70 | 2.585 | 24.547 | 29.457 | 1.00 | 18.71 | C |
| ATOM | 486 | C | ALA | A | 70 | 4.042 | 22.519 | 29.391 | 1.00 | 12.67 | C |
| ATOM | 487 | O | ALA | A | 70 | 3.638 | 22.293 | 30.523 | 1.00 | 11.15 | O |
| ATOM | 488 | N | GLN | A | 71 | 4.876 | 21.711 | 28.742 | 1.00 | 13.59 | N |
| ATOM | 489 | CA | GLN | A | 71 | 5.382 | 20.483 | 29.334 | 1.00 | 14.04 | C |

TABLE 19-1-continued

Atomic Coordinates of ASP with the Modeled Octapeptide Substrate

| ATOM | 490 | CB | GLN | A | 71 | 4.591 | 19.282 | 28.809 | 1.00 | 14.08 | C |
|---|---|---|---|---|---|---|---|---|---|---|---|
| ATOM | 491 | CG | GLN | A | 71 | 3.114 | 19.283 | 29.157 | 1.00 | 17.65 | C |
| ATOM | 492 | CD | GLN | A | 71 | 2.378 | 18.099 | 28.560 | 1.00 | 19.50 | C |
| ATOM | 493 | OE1 | GLN | A | 71 | 1.421 | 17.592 | 29.143 | 1.00 | 24.87 | O |
| ATOM | 494 | NE2 | GLN | A | 71 | 2.815 | 17.658 | 27.386 | 1.00 | 17.48 | N |
| ATOM | 495 | C | GLN | A | 71 | 6.849 | 20.255 | 29.011 | 1.00 | 16.23 | C |
| ATOM | 496 | O | GLN | A | 71 | 7.375 | 20.786 | 28.035 | 1.00 | 15.48 | O |
| ATOM | 497 | N | VAL | A | 72 | 7.501 | 19.451 | 29.840 | 1.00 | 13.56 | N |
| ATOM | 498 | CA | VAL | A | 72 | 8.907 | 19.133 | 29.648 | 1.00 | 12.57 | C |
| ATOM | 499 | CB | VAL | A | 72 | 9.792 | 19.754 | 30.748 | 1.00 | 10.81 | C |
| ATOM | 500 | CG1 | VAL | A | 72 | 11.193 | 19.162 | 30.677 | 1.00 | 12.46 | C |
| ATOM | 501 | CG2 | VAL | A | 72 | 9.862 | 21.271 | 30.563 | 1.00 | 10.56 | C |
| ATOM | 502 | C | VAL | A | 72 | 9.007 | 17.610 | 29.695 | 1.00 | 10.65 | C |
| ATOM | 503 | O | VAL | A | 72 | 8.415 | 16.968 | 30.565 | 1.00 | 11.44 | O |
| ATOM | 504 | N | ASN | A | 73 | 9.736 | 17.036 | 28.746 | 1.00 | 11.79 | N |
| ATOM | 505 | CA | ASN | A | 73 | 9.913 | 15.586 | 28.673 | 1.00 | 10.87 | C |
| ATOM | 506 | CB | ASN | A | 73 | 10.633 | 15.229 | 27.369 | 1.00 | 12.22 | C |
| ATOM | 507 | CG | ASN | A | 73 | 10.598 | 13.743 | 27.065 | 1.00 | 12.04 | C |
| ATOM | 508 | OD1 | ASN | A | 73 | 10.411 | 12.916 | 27.959 | 1.00 | 11.92 | O |
| ATOM | 509 | ND2 | ASN | A | 73 | 10.790 | 13.397 | 25.798 | 1.00 | 10.15 | N |
| ATOM | 510 | C | ASN | A | 73 | 10.751 | 15.098 | 29.863 | 1.00 | 11.93 | C |
| ATOM | 511 | O | ASN | A | 73 | 11.854 | 15.597 | 30.092 | 1.00 | 11.67 | O |
| ATOM | 512 | N | ASN | A | 74 | 10.239 | 14.137 | 30.631 | 1.00 | 12.17 | N |
| ATOM | 513 | CA | ASN | A | 74 | 11.010 | 13.640 | 31.766 | 1.00 | 9.29 | C |
| ATOM | 514 | CB | ASN | A | 74 | 10.109 | 13.275 | 32.958 | 1.00 | 13.70 | C |
| ATOM | 515 | CG | ASN | A | 74 | 9.162 | 12.126 | 32.662 | 1.00 | 16.27 | C |
| ATOM | 516 | OD1 | ASN | A | 74 | 9.432 | 11.274 | 31.815 | 1.00 | 14.62 | O |
| ATOM | 517 | ND2 | ASN | A | 74 | 8.048 | 12.088 | 33.384 | 1.00 | 18.77 | N |
| ATOM | 518 | C | ASN | A | 74 | 11.853 | 12.435 | 31.359 | 1.00 | 11.15 | C |
| ATOM | 519 | O | ASN | A | 74 | 12.528 | 11.823 | 32.189 | 1.00 | 10.62 | O |
| ATOM | 520 | N | TYR | A | 75 | 11.813 | 12.115 | 30.069 | 1.00 | 13.30 | N |
| ATOM | 521 | CA | TYR | A | 75 | 12.556 | 10.998 | 29.495 | 1.00 | 13.21 | C |
| ATOM | 522 | CB | TYR | A | 75 | 14.039 | 11.363 | 29.386 | 1.00 | 10.04 | C |
| ATOM | 523 | CG | TYR | A | 75 | 14.313 | 12.223 | 28.170 | 1.00 | 11.82 | C |
| ATOM | 524 | CD1 | TYR | A | 75 | 14.424 | 11.652 | 26.907 | 1.00 | 10.82 | C |
| ATOM | 525 | CE1 | TYR | A | 75 | 14.591 | 12.435 | 25.775 | 1.00 | 12.83 | C |
| ATOM | 526 | CD2 | TYR | A | 75 | 14.381 | 13.608 | 28.271 | 1.00 | 10.15 | C |
| ATOM | 527 | CE2 | TYR | A | 75 | 14.545 | 14.402 | 27.142 | 1.00 | 10.33 | C |
| ATOM | 528 | CZ | TYR | A | 75 | 14.648 | 13.805 | 25.898 | 1.00 | 9.45 | C |
| ATOM | 529 | OH | TYR | A | 75 | 14.793 | 14.579 | 24.770 | 1.00 | 10.77 | O |
| ATOM | 530 | C | TYR | A | 75 | 12.380 | 9.652 | 30.188 | 1.00 | 16.68 | C |
| ATOM | 531 | O | TYR | A | 75 | 13.298 | 8.835 | 30.228 | 1.00 | 18.39 | O |
| ATOM | 532 | N | SER | A | 76 | 11.185 | 9.433 | 30.723 | 1.00 | 18.33 | N |
| ATOM | 533 | CA | SER | A | 76 | 10.846 | 8.193 | 31.411 | 1.00 | 20.49 | C |
| ATOM | 534 | CB | SER | A | 76 | 10.811 | 8.390 | 32.926 | 1.00 | 21.53 | C |
| ATOM | 535 | OG | SER | A | 76 | 12.121 | 8.424 | 33.457 | 1.00 | 25.72 | O |
| ATOM | 536 | C | SER | A | 76 | 9.470 | 7.775 | 30.919 | 1.00 | 21.06 | C |
| ATOM | 537 | O | SER | A | 76 | 8.843 | 6.868 | 31.473 | 1.00 | 20.62 | O |
| ATOM | 538 | N | GLY | A | 77 | 9.013 | 8.452 | 29.870 | 1.00 | 17.80 | N |
| ATOM | 539 | CA | GLY | A | 77 | 7.715 | 8.156 | 29.295 | 1.00 | 18.95 | C |
| ATOM | 540 | C | GLY | A | 77 | 6.649 | 9.128 | 29.752 | 1.00 | 17.33 | C |
| ATOM | 541 | O | GLY | A | 77 | 5.464 | 8.942 | 29.470 | 1.00 | 16.27 | O |
| ATOM | 542 | N | GLY | A | 78 | 7.059 | 10.173 | 30.462 | 1.00 | 15.79 | N |
| ATOM | 543 | CA | GLY | A | 78 | 6.088 | 11.142 | 30.939 | 1.00 | 16.07 | C |
| ATOM | 544 | C | GLY | A | 78 | 6.499 | 12.585 | 30.734 | 1.00 | 17.80 | C |
| ATOM | 545 | O | GLY | A | 78 | 7.481 | 12.876 | 30.041 | 1.00 | 15.22 | O |
| ATOM | 546 | N | ARG | A | 79 | 5.742 | 13.492 | 31.342 | 1.00 | 17.07 | N |
| ATOM | 547 | CA | ARG | A | 79 | 6.025 | 14.914 | 31.226 | 1.00 | 19.85 | C |
| ATOM | 548 | CB | ARG | A | 79 | 5.199 | 15.528 | 30.090 | 1.00 | 23.00 | C |
| ATOM | 549 | CG | ARG | A | 79 | 5.711 | 15.176 | 28.701 | 1.00 | 29.54 | C |
| ATOM | 550 | CD | ARG | A | 79 | 4.683 | 14.404 | 27.910 | 1.00 | 35.50 | C |
| ATOM | 551 | NE | ARG | A | 79 | 5.207 | 13.941 | 26.626 | 1.00 | 39.02 | N |
| ATOM | 552 | CZ | ARG | A | 79 | 6.223 | 13.094 | 26.493 | 1.00 | 41.51 | C |
| ATOM | 553 | NH1 | ARG | A | 79 | 6.838 | 12.611 | 27.566 | 1.00 | 38.71 | N |
| ATOM | 554 | NH2 | ARG | A | 79 | 6.620 | 12.716 | 25.285 | 1.00 | 43.02 | N |
| ATOM | 555 | C | ARG | A | 79 | 5.784 | 15.695 | 32.510 | 1.00 | 18.62 | C |
| ATOM | 556 | O | ARG | A | 79 | 4.968 | 15.313 | 33.353 | 1.00 | 16.21 | O |
| ATOM | 557 | N | VAL | A | 80 | 6.517 | 16.793 | 32.646 | 1.00 | 15.48 | N |
| ATOM | 558 | CA | VAL | A | 80 | 6.412 | 17.660 | 33.810 | 1.00 | 14.56 | C |
| ATOM | 559 | CB | VAL | A | 80 | 7.806 | 18.040 | 34.349 | 1.00 | 14.30 | C |
| ATOM | 560 | CG1 | VAL | A | 80 | 7.666 | 18.967 | 35.542 | 1.00 | 16.79 | C |
| ATOM | 561 | CG2 | VAL | A | 80 | 8.580 | 16.787 | 34.729 | 1.00 | 18.13 | C |
| ATOM | 562 | C | VAL | A | 80 | 5.690 | 18.930 | 33.375 | 1.00 | 15.88 | C |
| ATOM | 563 | O | VAL | A | 80 | 6.106 | 19.588 | 32.421 | 1.00 | 14.01 | O |
| ATOM | 564 | N | GLN | A | 81 | 4.602 | 19.270 | 34.057 | 1.00 | 15.03 | N |
| ATOM | 565 | CA | GLN | A | 81 | 3.863 | 20.472 | 33.698 | 1.00 | 18.02 | C |
| ATOM | 566 | CB | GLN | A | 81 | 2.503 | 20.512 | 34.403 | 1.00 | 21.88 | C |
| ATOM | 567 | CG | GLN | A | 81 | 1.422 | 19.659 | 33.760 | 1.00 | 29.23 | C |

TABLE 19-1-continued

Atomic Coordinates of ASP with the Modeled Octapeptide Substrate

| ATOM | 568 | CD | GLN | A | 81 | 1.161 | 20.030 | 32.311 | 1.00 | 29.08 | C |
|---|---|---|---|---|---|---|---|---|---|---|---|
| ATOM | 569 | OE1 | GLN | A | 81 | 0.928 | 21.194 | 31.984 | 1.00 | 31.12 | O |
| ATOM | 570 | NE2 | GLN | A | 81 | 1.192 | 19.034 | 31.434 | 1.00 | 32.61 | N |
| ATOM | 571 | C | GLN | A | 81 | 4.654 | 21.722 | 34.067 | 1.00 | 17.67 | C |
| ATOM | 572 | O | GLN | A | 81 | 5.278 | 21.786 | 35.128 | 1.00 | 18.79 | O |
| ATOM | 573 | N | VAL | A | 82 | 4.636 | 22.709 | 33.179 | 1.00 | 15.10 | N |
| ATOM | 574 | CA | VAL | A | 82 | 5.345 | 23.960 | 33.411 | 1.00 | 17.88 | C |
| ATOM | 575 | CB | VAL | A | 82 | 5.973 | 24.494 | 32.107 | 1.00 | 16.36 | C |
| ATOM | 576 | CG1 | VAL | A | 82 | 6.710 | 25.792 | 32.374 | 1.00 | 19.17 | C |
| ATOM | 577 | CG2 | VAL | A | 82 | 6.927 | 23.454 | 31.534 | 1.00 | 15.85 | C |
| ATOM | 578 | C | VAL | A | 82 | 4.309 | 24.952 | 33.930 | 1.00 | 18.78 | C |
| ATOM | 579 | O | VAL | A | 82 | 3.512 | 25.494 | 33.163 | 1.00 | 19.15 | O |
| ATOM | 580 | N | ALA | A | 83 | 4.321 | 25.175 | 35.240 | 1.00 | 20.30 | N |
| ATOM | 581 | CA | ALA | A | 83 | 3.382 | 26.091 | 35.879 | 1.00 | 20.84 | C |
| ATOM | 582 | CB | ALA | A | 83 | 3.230 | 25.725 | 37.348 | 1.00 | 20.26 | C |
| ATOM | 583 | C | ALA | A | 83 | 3.734 | 27.568 | 35.751 | 1.00 | 20.34 | C |
| ATOM | 584 | O | ALA | A | 83 | 2.849 | 28.405 | 35.594 | 1.00 | 21.44 | O |
| ATOM | 585 | N | GLY | A | 84 | 5.021 | 27.886 | 35.826 | 1.00 | 18.33 | N |
| ATOM | 586 | CA | GLY | A | 84 | 5.445 | 29.267 | 35.721 | 1.00 | 15.96 | C |
| ATOM | 587 | C | GLY | A | 84 | 6.946 | 29.381 | 35.558 | 1.00 | 18.35 | C |
| ATOM | 588 | O | GLY | A | 84 | 7.599 | 28.433 | 35.117 | 1.00 | 16.24 | O |
| ATOM | 589 | N | HIS | A | 85 | 7.495 | 30.534 | 35.924 | 1.00 | 16.53 | N |
| ATOM | 590 | CA | HIS | A | 85 | 8.931 | 30.767 | 35.798 | 1.00 | 14.08 | C |
| ATOM | 591 | CB | HIS | A | 85 | 9.219 | 31.528 | 34.498 | 1.00 | 14.33 | C |
| ATOM | 592 | C | HIS | A | 85 | 9.534 | 31.510 | 36.988 | 1.00 | 14.07 | C |
| ATOM | 593 | O | HIS | A | 85 | 10.349 | 32.413 | 36.818 | 1.00 | 15.60 | O |
| ATOM | 594 | CG | HIS | A | 85 | 8.399 | 32.770 | 34.323 | 1.00 | 18.31 | C |
| ATOM | 595 | ND1 | HIS | A | 85 | 8.937 | 34.035 | 34.404 | 1.00 | 21.61 | N |
| ATOM | 596 | CD2 | HIS | A | 85 | 7.079 | 32.936 | 34.064 | 1.00 | 19.95 | C |
| ATOM | 597 | NE2 | HIS | A | 85 | 6.848 | 34.289 | 33.994 | 1.00 | 18.84 | N |
| ATOM | 598 | CE1 | HIS | A | 85 | 7.983 | 34.929 | 34.202 | 1.00 | 22.08 | C |
| ATOM | 599 | N | THR | A | 86 | 9.128 | 31.124 | 38.193 | 1.00 | 14.33 | N |
| ATOM | 600 | CA | THR | A | 86 | 9.640 | 31.758 | 39.405 | 1.00 | 13.94 | C |
| ATOM | 601 | CB | THR | A | 86 | 8.754 | 31.449 | 40.612 | 1.00 | 15.26 | C |
| ATOM | 602 | C | THR | A | 86 | 11.044 | 31.243 | 39.690 | 1.00 | 14.65 | C |
| ATOM | 603 | O | THR | A | 86 | 11.249 | 30.042 | 39.855 | 1.00 | 11.10 | O |
| ATOM | 604 | OG1 | THR | A | 86 | 7.424 | 31.904 | 40.347 | 1.00 | 16.89 | O |
| ATOM | 605 | CG2 | THR | A | 86 | 9.289 | 32.147 | 41.854 | 1.00 | 16.68 | C |
| ATOM | 606 | N | ALA | A | 87 | 12.005 | 32.157 | 39.756 | 1.00 | 15.86 | N |
| ATOM | 607 | CA | ALA | A | 87 | 13.396 | 31.801 | 40.016 | 1.00 | 17.16 | C |
| ATOM | 608 | C | ALA | A | 87 | 13.633 | 31.152 | 41.375 | 1.00 | 19.39 | C |
| ATOM | 609 | O | ALA | A | 87 | 13.113 | 31.608 | 42.395 | 1.00 | 18.84 | O |
| ATOM | 610 | CB | ALA | A | 87 | 14.272 | 33.034 | 39.877 | 1.00 | 17.44 | C |
| ATOM | 611 | N | ALA | A | 88 | 14.431 | 30.088 | 41.373 | 1.00 | 16.82 | N |
| ATOM | 612 | CA | ALA | A | 88 | 14.766 | 29.352 | 42.584 | 1.00 | 14.95 | C |
| ATOM | 613 | C | ALA | A | 88 | 16.112 | 29.832 | 43.119 | 1.00 | 15.66 | C |
| ATOM | 614 | O | ALA | A | 88 | 17.004 | 30.204 | 42.355 | 1.00 | 15.62 | O |
| ATOM | 615 | CB | ALA | A | 88 | 14.827 | 27.861 | 42.291 | 1.00 | 10.05 | C |
| ATOM | 616 | N | PRO | A | 89 | 16.275 | 29.822 | 44.447 | 1.00 | 15.05 | N |
| ATOM | 617 | CA | PRO | A | 89 | 17.510 | 30.259 | 45.100 | 1.00 | 16.15 | C |
| ATOM | 618 | CB | PRO | A | 89 | 17.060 | 30.498 | 46.535 | 1.00 | 16.59 | C |
| ATOM | 619 | C | PRO | A | 89 | 18.661 | 29.260 | 45.022 | 1.00 | 17.33 | C |
| ATOM | 620 | O | PRO | A | 89 | 18.461 | 28.076 | 44.741 | 1.00 | 14.79 | O |
| ATOM | 621 | CD | PRO | A | 89 | 15.236 | 29.522 | 45.448 | 1.00 | 17.98 | C |
| ATOM | 622 | CG | PRO | A | 89 | 16.040 | 29.425 | 46.728 | 1.00 | 15.94 | C |
| ATOM | 623 | N | VAL | A | 90 | 19.873 | 29.751 | 45.257 | 1.00 | 18.24 | N |
| ATOM | 624 | CA | VAL | A | 90 | 21.046 | 28.894 | 45.221 | 1.00 | 17.32 | C |
| ATOM | 625 | CB | VAL | A | 90 | 22.312 | 29.658 | 45.672 | 1.00 | 16.39 | C |
| ATOM | 626 | CG1 | VAL | A | 90 | 23.449 | 28.678 | 45.932 | 1.00 | 19.70 | C |
| ATOM | 627 | CG2 | VAL | A | 90 | 22.711 | 30.665 | 44.609 | 1.00 | 18.18 | C |
| ATOM | 628 | C | VAL | A | 90 | 20.764 | 27.770 | 46.211 | 1.00 | 17.15 | C |
| ATOM | 629 | O | VAL | A | 90 | 20.153 | 28.005 | 47.254 | 1.00 | 17.16 | O |
| ATOM | 630 | N | GLY | A | 91 | 21.192 | 26.556 | 45.878 | 1.00 | 13.56 | N |
| ATOM | 631 | CA | GLY | A | 91 | 20.971 | 25.420 | 46.755 | 1.00 | 13.61 | C |
| ATOM | 632 | C | GLY | A | 91 | 19.787 | 24.583 | 46.314 | 1.00 | 14.54 | C |
| ATOM | 633 | O | GLY | A | 91 | 19.652 | 23.422 | 46.695 | 1.00 | 13.48 | O |
| ATOM | 634 | N | SER | A | 92 | 18.928 | 25.175 | 45.497 | 1.00 | 12.12 | N |
| ATOM | 635 | CA | SER | A | 92 | 17.741 | 24.486 | 45.014 | 1.00 | 13.41 | C |
| ATOM | 636 | CB | SER | A | 92 | 16.846 | 25.457 | 44.239 | 1.00 | 10.87 | C |
| ATOM | 637 | OG | SER | A | 92 | 16.334 | 26.463 | 45.090 | 1.00 | 12.36 | O |
| ATOM | 638 | C | SER | A | 92 | 18.040 | 23.284 | 44.134 | 1.00 | 13.34 | C |
| ATOM | 639 | O | SER | A | 92 | 19.015 | 23.268 | 43.383 | 1.00 | 9.90 | O |
| ATOM | 640 | N | ALA | A | 93 | 17.189 | 22.274 | 44.252 | 1.00 | 11.16 | N |
| ATOM | 641 | CA | ALA | A | 93 | 17.324 | 21.057 | 43.475 | 1.00 | 14.34 | C |
| ATOM | 642 | CB | ALA | A | 93 | 16.554 | 19.925 | 44.136 | 1.00 | 14.73 | C |
| ATOM | 643 | C | ALA | A | 93 | 16.713 | 21.389 | 42.119 | 1.00 | 14.46 | C |
| ATOM | 644 | O | ALA | A | 93 | 15.605 | 21.920 | 42.047 | 1.00 | 13.83 | O |
| ATOM | 645 | N | VAL | A | 94 | 17.440 | 21.092 | 41.048 | 1.00 | 14.27 | N |

TABLE 19-1-continued

Atomic Coordinates of ASP with the Modeled Octapeptide Substrate

| ATOM | 646 | CA | VAL | A | 94 | 16.946 | 21.370 | 39.707 | 1.00 | 9.84 | O |
|---|---|---|---|---|---|---|---|---|---|---|---|
| ATOM | 647 | CB | VAL | A | 94 | 17.617 | 22.629 | 39.113 | 1.00 | 11.32 | C |
| ATOM | 648 | CG1 | VAL | A | 94 | 17.204 | 23.859 | 39.904 | 1.00 | 9.34 | C |
| ATOM | 649 | CG2 | VAL | A | 94 | 19.140 | 22.467 | 39.126 | 1.00 | 10.97 | C |
| ATOM | 650 | C | VAL | A | 94 | 17.216 | 20.209 | 38.763 | 1.00 | 9.69 | C |
| ATOM | 651 | O | VAL | A | 94 | 18.139 | 19.421 | 38.976 | 1.00 | 10.59 | O |
| ATOM | 652 | N | CYS | A | 95 | 16.398 | 20.094 | 37.727 | 1.00 | 10.10 | N |
| ATOM | 653 | CA | CYS | A | 95 | 16.573 | 19.027 | 36.752 | 1.00 | 9.94 | C |
| ATOM | 654 | CB | CYS | A | 95 | 15.468 | 17.983 | 36.845 | 1.00 | 11.63 | C |
| ATOM | 655 | SG | CYS | A | 95 | 15.412 | 17.059 | 38.410 | 1.00 | 13.27 | S |
| ATOM | 656 | C | CYS | A | 95 | 16.566 | 19.624 | 35.359 | 1.00 | 10.91 | C |
| ATOM | 657 | O | CYS | A | 95 | 15.808 | 20.551 | 35.061 | 1.00 | 11.33 | O |
| ATOM | 658 | N | ARG | A | 96 | 17.424 | 19.070 | 34.515 | 1.00 | 9.30 | N |
| ATOM | 659 | CA | ARG | A | 96 | 17.570 | 19.496 | 33.135 | 1.00 | 7.08 | C |
| ATOM | 660 | CB | ARG | A | 96 | 19.050 | 19.767 | 32.827 | 1.00 | 9.79 | C |
| ATOM | 661 | CG | ARG | A | 96 | 19.326 | 20.069 | 31.353 | 1.00 | 10.80 | C |
| ATOM | 662 | CD | ARG | A | 96 | 20.808 | 19.966 | 31.011 | 1.00 | 10.58 | C |
| ATOM | 663 | NE | ARG | A | 96 | 21.355 | 18.643 | 31.312 | 1.00 | 11.86 | N |
| ATOM | 664 | CZ | ARG | A | 96 | 20.957 | 17.506 | 30.747 | 1.00 | 10.78 | C |
| ATOM | 665 | NH1 | ARG | A | 96 | 19.995 | 17.500 | 29.831 | 1.00 | 10.18 | N |
| ATOM | 666 | NH2 | ARG | A | 96 | 21.529 | 16.365 | 31.103 | 1.00 | 12.39 | N |
| ATOM | 667 | C | ARG | A | 96 | 17.068 | 18.397 | 32.211 | 1.00 | 9.14 | C |
| ATOM | 668 | O | ARG | A | 96 | 17.237 | 17.214 | 32.499 | 1.00 | 10.81 | O |
| ATOM | 669 | N | SER | A | 97 | 16.442 | 18.792 | 31.104 | 1.00 | 8.35 | N |
| ATOM | 670 | CA | SER | A | 97 | 15.925 | 17.841 | 30.134 | 1.00 | 8.67 | C |
| ATOM | 671 | CB | SER | A | 97 | 14.406 | 17.976 | 29.984 | 1.00 | 10.18 | C |
| ATOM | 672 | OG | SER | A | 97 | 13.893 | 16.991 | 29.094 | 1.00 | 10.36 | O |
| ATOM | 673 | C | SER | A | 97 | 16.607 | 18.169 | 28.810 | 1.00 | 9.06 | C |
| ATOM | 674 | O | SER | A | 97 | 16.564 | 19.313 | 28.353 | 1.00 | 10.38 | O |
| ATOM | 675 | N | GLY | A | 98 | 17.243 | 17.168 | 28.209 | 1.00 | 9.45 | N |
| ATOM | 676 | CA | GLY | A | 98 | 17.939 | 17.365 | 26.947 | 1.00 | 8.70 | C |
| ATOM | 677 | C | GLY | A | 98 | 17.853 | 16.131 | 26.070 | 1.00 | 11.12 | C |
| ATOM | 678 | O | GLY | A | 98 | 17.689 | 15.021 | 26.569 | 1.00 | 9.32 | O |
| ATOM | 679 | N | SER | A | 99 | 17.993 | 16.320 | 24.762 | 1.00 | 13.12 | N |
| ATOM | 680 | CA | SER | A | 99 | 17.884 | 15.222 | 23.805 | 1.00 | 13.49 | C |
| ATOM | 681 | CB | SER | A | 99 | 17.628 | 15.784 | 22.414 | 1.00 | 16.87 | C |
| ATOM | 682 | OG | SER | A | 99 | 18.805 | 16.381 | 21.906 | 1.00 | 16.57 | O |
| ATOM | 683 | C | SER | A | 99 | 19.073 | 14.272 | 23.709 | 1.00 | 13.85 | C |
| ATOM | 684 | O | SER | A | 99 | 18.972 | 13.230 | 23.060 | 1.00 | 10.18 | O |
| ATOM | 685 | N | THR | A | 100 | 20.195 | 14.617 | 24.331 | 1.00 | 9.80 | N |
| ATOM | 686 | CA | THR | A | 100 | 21.365 | 13.749 | 24.266 | 1.00 | 12.00 | C |
| ATOM | 687 | CB | THR | A | 100 | 22.645 | 14.572 | 24.075 | 1.00 | 13.43 | C |
| ATOM | 688 | OG1 | THR | A | 100 | 22.564 | 15.297 | 22.844 | 1.00 | 15.69 | O |
| ATOM | 689 | CG2 | THR | A | 100 | 23.860 | 13.667 | 24.044 | 1.00 | 13.71 | C |
| ATOM | 690 | C | THR | A | 100 | 21.547 | 12.845 | 25.477 | 1.00 | 13.37 | C |
| ATOM | 691 | O | THR | A | 100 | 21.888 | 11.667 | 25.332 | 1.00 | 9.57 | O |
| ATOM | 692 | N | THR | A | 101 | 21.319 | 13.389 | 26.668 | 1.00 | 11.47 | N |
| ATOM | 693 | CA | THR | A | 101 | 21.468 | 12.613 | 27.893 | 1.00 | 10.42 | C |
| ATOM | 694 | CB | THR | A | 101 | 22.469 | 13.277 | 28.851 | 1.00 | 12.08 | C |
| ATOM | 695 | OG1 | THR | A | 101 | 22.031 | 14.607 | 29.151 | 1.00 | 10.91 | O |
| ATOM | 696 | CG2 | THR | A | 101 | 23.847 | 13.334 | 28.216 | 1.00 | 11.99 | C |
| ATOM | 697 | C | THR | A | 101 | 20.153 | 12.410 | 28.633 | 1.00 | 13.44 | C |
| ATOM | 698 | O | THR | A | 101 | 20.078 | 11.617 | 29.566 | 1.00 | 12.54 | O |
| ATOM | 699 | N | GLY | A | 102 | 19.119 | 13.128 | 28.217 | 1.00 | 10.42 | N |
| ATOM | 700 | CA | GLY | A | 102 | 17.829 | 12.979 | 28.860 | 1.00 | 9.53 | C |
| ATOM | 701 | C | GLY | A | 102 | 17.578 | 13.835 | 30.087 | 1.00 | 10.82 | C |
| ATOM | 702 | O | GLY | A | 102 | 17.846 | 15.041 | 30.096 | 1.00 | 8.61 | O |
| ATOM | 703 | N | TRP | A | 103 | 17.067 | 13.190 | 31.132 | 1.00 | 9.62 | N |
| ATOM | 704 | CA | TRP | A | 103 | 16.716 | 13.845 | 32.383 | 1.00 | 11.61 | C |
| ATOM | 705 | CB | TRP | A | 103 | 15.370 | 13.289 | 32.865 | 1.00 | 11.52 | C |
| ATOM | 706 | CG | TRP | A | 103 | 14.837 | 13.868 | 34.145 | 1.00 | 13.15 | C |
| ATOM | 707 | CD2 | TRP | A | 103 | 13.964 | 14.998 | 34.282 | 1.00 | 12.58 | C |
| ATOM | 708 | CE2 | TRP | A | 103 | 13.680 | 15.147 | 35.655 | 1.00 | 15.29 | C |
| ATOM | 709 | CE3 | TRP | A | 103 | 13.387 | 15.896 | 33.375 | 1.00 | 11.72 | C |
| ATOM | 710 | CD1 | TRP | A | 103 | 15.050 | 13.397 | 35.404 | 1.00 | 16.94 | C |
| ATOM | 711 | NE1 | TRP | A | 103 | 14.357 | 14.156 | 36.320 | 1.00 | 16.85 | N |
| ATOM | 712 | CZ2 | TRP | A | 103 | 12.852 | 16.155 | 36.147 | 1.00 | 11.23 | C |
| ATOM | 713 | CZ3 | TRP | A | 103 | 12.561 | 16.900 | 33.865 | 1.00 | 12.19 | C |
| ATOM | 714 | CH2 | TRP | A | 103 | 12.303 | 17.019 | 35.240 | 1.00 | 13.20 | C |
| ATOM | 715 | C | TRP | A | 103 | 17.790 | 13.659 | 33.448 | 1.00 | 12.90 | C |
| ATOM | 716 | O | TRP | A | 103 | 18.082 | 12.539 | 33.872 | 1.00 | 9.69 | O |
| ATOM | 717 | N | HIS | A | 104 | 18.386 | 14.768 | 33.872 | 1.00 | 10.38 | N |
| ATOM | 718 | CA | HIS | A | 104 | 19.434 | 14.724 | 34.890 | 1.00 | 12.11 | C |
| ATOM | 719 | CB | HIS | A | 104 | 20.806 | 14.734 | 34.226 | 1.00 | 12.14 | C |
| ATOM | 720 | CG | HIS | A | 104 | 21.106 | 13.474 | 33.477 | 1.00 | 12.45 | C |
| ATOM | 721 | CD2 | HIS | A | 104 | 20.822 | 13.110 | 32.204 | 1.00 | 14.29 | C |
| ATOM | 722 | ND1 | HIS | A | 104 | 21.684 | 12.375 | 34.072 | 1.00 | 13.64 | N |
| ATOM | 723 | CE1 | HIS | A | 104 | 21.740 | 11.384 | 33.197 | 1.00 | 14.53 | C |

TABLE 19-1-continued

Atomic Coordinates of ASP with the Modeled Octapeptide Substrate

| ATOM | 724 | NE2 | HIS | A | 104 | 21.222 | 11.804 | 32.058 | 1.00 | 12.11 | N |
|---|---|---|---|---|---|---|---|---|---|---|---|
| ATOM | 725 | C | HIS | A | 104 | 19.283 | 15.898 | 35.839 | 1.00 | 12.75 | C |
| ATOM | 726 | O | HIS | A | 104 | 18.959 | 17.014 | 35.426 | 1.00 | 10.16 | O |
| ATOM | 727 | N | CYS | A | 105 | 19.545 | 15.650 | 37.114 | 1.00 | 10.52 | N |
| 1'TOM | 728 | CA | CYS | A | 105 | 19.408 | 16.703 | 38.102 | 1.00 | 13.24 | C |
| ATOM | 729 | CB | CYS | A | 105 | 18.278 | 16.318 | 39.049 | 1.00 | 13.49 | C |
| ATOM | 730 | SG | CYS | A | 105 | 16.817 | 15.612 | 38.216 | 1.00 | 14.12 | S |
| ATOM | 731 | C | CYS | A | 105 | 20.657 | 17.057 | 38.896 | 1.00 | 13.65 | C |
| ATOM | 732 | O | CYS | A | 105 | 21.720 | 16.465 | 38.720 | 1.00 | 13.71 | O |
| ATOM | 733 | N | GLY | A | 106 | 20.511 | 18.042 | 39.770 | 1.00 | 11.96 | N |
| ATOM | 734 | CA | GLY | A | 106 | 21.619 | 18.499 | 40.583 | 1.00 | 8.39 | C |
| ATOM | 735 | C | GLY | A | 106 | 21.112 | 19.662 | 41.404 | 1.00 | 8.29 | C |
| ATOM | 736 | O | GLY | A | 106 | 19.919 | 19.720 | 41.723 | 1.00 | 9.88 | O |
| ATOM | 737 | N | THR | A | 107 | 21.997 | 20.587 | 41.748 | 1.00 | 10.00 | N |
| ATOM | 738 | CA | THR | A | 107 | 21.593 | 21.749 | 42.529 | 1.00 | 10.90 | C |
| ATOM | 739 | CB | THR | A | 107 | 21.979 | 21.607 | 44.021 | 1.00 | 15.03 | C |
| ATOM | 740 | OG1 | THR | A | 107 | 23.401 | 21.490 | 44.138 | 1.00 | 19.34 | O |
| ATOM | 741 | CG2 | THR | A | 107 | 21.324 | 20.379 | 44.630 | 1.00 | 19.07 | C |
| ATOM | 742 | C | THR | A | 107 | 22.230 | 23.021 | 42.003 | 1.00 | 11.41 | C |
| ATOM | 743 | O | THR | A | 107 | 23.274 | 22.986 | 41.349 | 1.00 | 10.42 | O |
| ATOM | 744 | N | ILE | A | 108 | 21.590 | 24.150 | 42.282 | 1.00 | 9.46 | N |
| ATOM | 745 | CA | ILE | A | 108 | 22.116 | 25.430 | 41.835 | 1.00 | 8.75 | C |
| ATOM | 746 | CB | ILE | A | 108 | 21.050 | 26.533 | 41.895 | 1.00 | 10.61 | C |
| ATOM | 747 | CG2 | ILE | A | 108 | 21.696 | 27.892 | 41.613 | 1.00 | 8.96 | C |
| ATOM | 748 | CG1 | ILE | A | 108 | 19.926 | 26.214 | 40.905 | 1.00 | 11.64 | C |
| ATOM | 749 | CD1 | ILE | A | 108 | 18.797 | 27.223 | 40.898 | 1.00 | 10.98 | C |
| ATOM | 750 | C | ILE | A | 108 | 23.240 | 25.788 | 42.798 | 1.00 | 12.89 | C |
| ATOM | 751 | O | ILE | A | 108 | 23.030 | 25.842 | 44.010 | 1.00 | 12.63 | O |
| ATOM | 752 | N | THR | A | 109 | 24.432 | 26.026 | 42.263 | 1.00 | 12.30 | N |
| ATOM | 753 | CA | THR | A | 109 | 25.570 | 26.372 | 43.109 | 1.00 | 12.21 | C |
| ATOM | 754 | CB | THR | A | 109 | 26.814 | 25.557 | 42.714 | 1.00 | 16.03 | C |
| ATOM | 755 | OG1 | THR | A | 109 | 27.027 | 25.662 | 41.304 | 1.00 | 16.72 | O |
| ATOM | 756 | CG2 | THR | A | 109 | 26.623 | 24.097 | 43.079 | 1.00 | 19.29 | C |
| ATOM | 757 | C | THR | A | 109 | 25.916 | 27.855 | 43.094 | 1.00 | 14.26 | C |
| ATOM | 758 | O | THR | A | 109 | 26.590 | 28.353 | 43.994 | 1.00 | 15.02 | O |
| ATOM | 759 | N | ALA | A | 110 | 25.440 | 28.563 | 42.078 | 1.00 | 13.73 | N |
| ATOM | 760 | CA | ALA | A | 110 | 25.708 | 29.985 | 41.967 | 1.00 | 14.67 | C |
| ATOM | 761 | CB | ALA | A | 110 | 27.186 | 30.215 | 41.668 | 1.00 | 15.41 | C |
| ATOM | 762 | C | ALA | A | 110 | 24.853 | 30.611 | 40.879 | 1.00 | 12.70 | C |
| ATOM | 763 | O | ALA | A | 110 | 24.367 | 29.924 | 39.982 | 1.00 | 13.13 | O |
| ATOM | 764 | N | LEU | A | 111 | 24.664 | 31.921 | 40.982 | 1.00 | 13.52 | N |
| ATOM | 765 | CA | LEU | A | 111 | 23.876 | 32.680 | 40.019 | 1.00 | 11.96 | C |
| ATOM | 766 | CB | LEU | A | 111 | 22.639 | 33.286 | 40.689 | 1.00 | 15.77 | C |
| ATOM | 767 | CG | LEU | A | 111 | 21.638 | 32.338 | 41.357 | 1.00 | 19.65 | C |
| ATOM | 768 | CD1 | LEU | A | 111 | 20.593 | 33.151 | 42.113 | 1.00 | 17.73 | C |
| ATOM | 769 | CD2 | LEU | A | 111 | 20.970 | 31.462 | 40.313 | 1.00 | 14.60 | C |
| ATOM | 770 | C | LEU | A | 111 | 24.775 | 33.798 | 39.501 | 1.00 | 15.77 | C |
| ATOM | 771 | O | LEU | A | 111 | 25.753 | 34.169 | 40.151 | 1.00 | 15.15 | O |
| ATOM | 772 | N | ASN | A | 112 | 24.443 | 34.330 | 38.332 | 1.00 | 12.74 | N |
| ATOM | 773 | CA | ASN | A | 112 | 25.219 | 35.409 | 37.729 | 1.00 | 17.38 | C |
| ATOM | 774 | CB | ASN | A | 112 | 25.168 | 36.663 | 38.605 | 1.00 | 24.14 | C |
| ATOM | 775 | CG | ASN | A | 112 | 23.756 | 37.053 | 38.980 | 1.00 | 26.37 | C |
| ATOM | 776 | OD1 | ASN | A | 112 | 23.279 | 36.726 | 40.067 | 1.00 | 33.64 | O |
| ATOM | 777 | ND2 | ASN | A | 112 | 23.072 | 37.744 | 38.076 | 1.00 | 34.88 | N |
| ATOM | 778 | C | ASN | A | 112 | 26.672 | 35.023 | 37.495 | 1.00 | 16.99 | C |
| ATOM | 779 | O | ASN | A | 112 | 27.572 | 35.850 | 37.643 | 1.00 | 14.78 | O |
| ATOM | 780 | N | SER | A | 113 | 26.896 | 33.766 | 37.131 | 1.00 | 16.31 | N |
| ATOM | 781 | CA | SER | A | 113 | 28.245 | 33.280 | 36.872 | 1.00 | 19.39 | C |
| ATOM | 782 | CB | SER | A | 113 | 28.315 | 31.757 | 37.020 | 1.00 | 18.03 | C |
| ATOM | 783 | OG | SER | A | 113 | 28.262 | 31.349 | 38.374 | 1.00 | 21.23 | O |
| ATOM | 784 | C | SER | A | 113 | 28.637 | 33.650 | 35.450 | 1.00 | 19.59 | C |
| ATOM | 785 | O | SER | A | 113 | 27.780 | 33.946 | 34.620 | 1.00 | 20.53 | O |
| ATOM | 786 | N | SER | A | 114 | 29.938 | 33.634 | 35.180 | 1.00 | 20.43 | N |
| ATOM | 787 | CA | SER | A | 114 | 30.454 | 33.957 | 33.857 | 1.00 | 21.50 | C |
| ATOM | 788 | CB | SER | A | 114 | 31.256 | 35.259 | 33.878 | 1.00 | 23.57 | C |
| ATOM | 789 | OG | SER | A | 114 | 30.407 | 36.384 | 34.009 | 1.00 | 27.72 | O |
| ATOM | 790 | C | SER | A | 114 | 31.356 | 32.824 | 33.406 | 1.00 | 21.25 | C |
| ATOM | 791 | O | SER | A | 114 | 32.019 | 32.181 | 34.222 | 1.00 | 21.50 | O |
| ATOM | 792 | N | VAL | A | 115 | 31.364 | 32.569 | 32.106 | 1.00 | 19.94 | N |
| ATOM | 793 | CA | VAL | A | 115 | 32.188 | 31.515 | 31.542 | 1.00 | 19.21 | C |
| ATOM | 794 | CB | VAL | A | 115 | 31.394 | 30.203 | 31.350 | 1.00 | 20.02 | C |
| ATOM | 795 | CG1 | VAL | A | 115 | 30.768 | 29.782 | 32.663 | 1.00 | 23.26 | C |
| ATOM | 796 | CG2 | VAL | A | 115 | 30.335 | 30.380 | 30.276 | 1.00 | 19.81 | C |
| ATOM | 797 | C | VAL | A | 115 | 32.675 | 31.986 | 30.183 | 1.00 | 17.61 | C |
| ATOM | 798 | O | VAL | A | 115 | 32.065 | 32.857 | 29.561 | 1.00 | 16.06 | O |
| ATOM | 799 | N | THR | A | 116 | 33.783 | 31.419 | 29.729 | 1.00 | 15.49 | N |
| ATOM | 800 | CA | THR | A | 116 | 34.330 | 31.791 | 28.441 | 1.00 | 15.82 | C |
| ATOM | 801 | CB | THR | A | 116 | 35.750 | 32.380 | 28.569 | 1.00 | 16.00 | C |

TABLE 19-1-continued

Atomic Coordinates of ASP with the Modeled Octapeptide Substrate

| ATOM | 802 | OG1 | THR | A | 116 | 35.697 | 33.577 | 29.355 | 1.00 | 19.34 | O |
|---|---|---|---|---|---|---|---|---|---|---|---|
| ATOM | 803 | CG2 | THR | A | 116 | 36.312 | 32.721 | 27.189 | 1.00 | 13.81 | C |
| ATOM | 804 | C | THR | A | 116 | 34.364 | 30.572 | 27.535 | 1.00 | 16.67 | C |
| ATOM | 805 | O | THR | A | 116 | 35.031 | 29.576 | 27.828 | 1.00 | 15.27 | O |
| ATOM | 806 | N | TYR | A | 117 | 33.604 | 30.663 | 26.451 | 1.00 | 14.40 | N |
| ATOM | 807 | CA | TYR | A | 117 | 33.500 | 29.609 | 25.453 | 1.00 | 18.79 | C |
| ATOM | 808 | CB | TYR | A | 117 | 32.077 | 29.553 | 24.886 | 1.00 | 16.32 | C |
| ATOM | 809 | CG | TYR | A | 117 | 30.993 | 29.168 | 25.871 | 1.00 | 19.43 | C |
| ATOM | 810 | CD1 | TYR | A | 117 | 29.875 | 29.977 | 26.057 | 1.00 | 17.65 | C |
| ATOM | 811 | CE1 | TYR | A | 117 | 28.844 | 29.594 | 26.911 | 1.00 | 19.53 | C |
| ATOM | 812 | CD2 | TYR | A | 117 | 31.053 | 27.967 | 26.569 | 1.00 | 19.30 | C |
| ATOM | 813 | CE2 | TYR | A | 117 | 30.029 | 27.577 | 27.421 | 1.00 | 23.56 | C |
| ATOM | 814 | CZ | TYR | A | 117 | 28.926 | 28.392 | 27.588 | 1.00 | 21.66 | C |
| ATOM | 815 | OH | TYR | A | 117 | 27.898 | 27.991 | 28.417 | 1.00 | 18.29 | O |
| ATOM | 816 | C | TYR | A | 117 | 34.462 | 29.985 | 24.330 | 1.00 | 16.91 | C |
| ATOM | 817 | O | TYR | A | 117 | 34.968 | 31.107 | 24.288 | 1.00 | 18.67 | O |
| ATOM | 818 | N | PRO | A | 118 | 34.727 | 29.058 | 23.400 | 1.00 | 17.80 | N |
| ATOM | 819 | CA | PRO | A | 118 | 35.644 | 29.417 | 22.317 | 1.00 | 18.47 | C |
| ATOM | 820 | CB | PRO | A | 118 | 35.655 | 28.165 | 21.434 | 1.00 | 19.17 | C |
| ATOM | 821 | C | PRO | A | 118 | 35.210 | 30.679 | 21.567 | 1.00 | 22.88 | C |
| ATOM | 822 | O | PRO | A | 118 | 36.052 | 31.426 | 21.064 | 1.00 | 22.73 | O |
| ATOM | 823 | CD | PRO | A | 118 | 34.280 | 27.663 | 23.277 | 1.00 | 19.00 | C |
| ATOM | 824 | CG | PRO | A | 118 | 34.390 | 27.442 | 21.799 | 1.00 | 22.37 | C |
| ATOM | 825 | N | GLU | A | 119 | 33.900 | 30.923 | 21.509 | 1.00 | 21.24 | N |
| ATOM | 826 | CA | GLU | A | 119 | 33.375 | 32.101 | 20.819 | 1.00 | 22.24 | C |
| ATOM | 827 | CB | GLU | A | 119 | 31.888 | 31.930 | 20.495 | 1.00 | 23.42 | C |
| ATOM | 828 | C | GLU | A | 119 | 33.539 | 33.356 | 21.665 | 1.00 | 24.28 | C |
| ATOM | 829 | O | GLU | A | 119 | 33.672 | 34.464 | 21.142 | 1.00 | 24.95 | O |
| ATOM | 830 | CG | GLU | A | 119 | 31.561 | 30.815 | 19.522 | 1.00 | 25.42 | C |
| ATOM | 831 | CD | GLU | A | 119 | 31.812 | 29.443 | 20.104 | 1.00 | 29.77 | C |
| ATOM | 832 | OE1 | GLU | A | 119 | 31.546 | 29.252 | 21.310 | 1.00 | 28.43 | O |
| ATOM | 833 | OE2 | GLU | A | 119 | 32.260 | 28.552 | 19.350 | 1.00 | 28.50 | O |
| ATOM | 834 | N | GLY | A | 120 | 33.517 | 33.181 | 22.979 | 1.00 | 21.77 | N |
| ATOM | 835 | CA | GLY | A | 120 | 33.658 | 34.323 | 23.857 | 1.00 | 21.24 | C |
| ATOM | 836 | C | GLY | A | 120 | 33.028 | 34.099 | 25.215 | 1.00 | 18.48 | C |
| ATOM | 837 | O | GLY | A | 120 | 32.613 | 32.991 | 25.549 | 1.00 | 16.77 | O |
| ATOM | 838 | N | THR | A | 121 | 32.944 | 35.169 | 25.994 | 1.00 | 15.75 | N |
| ATOM | 839 | CA | THR | A | 121 | 32.388 | 35.098 | 27.332 | 1.00 | 15.58 | C |
| ATOM | 840 | CB | THR | A | 121 | 33.050 | 36.151 | 28.242 | 1.00 | 20.73 | C |
| ATOM | 841 | OG1 | THR | A | 121 | 34.472 | 35.973 | 28.215 | 1.00 | 22.66 | O |
| ATOM | 842 | CG1 | THR | A | 121 | 32.548 | 36.020 | 29.675 | 1.00 | 19.40 | C |
| ATOM | 843 | C | THR | A | 121 | 30.876 | 35.292 | 27.393 | 1.00 | 13.13 | C |
| ATOM | 844 | O | THR | A | 121 | 30.307 | 36.105 | 26.665 | 1.00 | 12.67 | O |
| ATOM | 845 | N | VAL | A | 122 | 30.235 | 34.523 | 28.263 | 1.00 | 10.86 | N |
| ATOM | 846 | CA | VAL | A | 122 | 28.789 | 34.591 | 28.460 | 1.00 | 11.99 | C |
| ATOM | 847 | CB | VAL | A | 122 | 28.095 | 33.263 | 28.093 | 1.00 | 10.42 | C |
| ATOM | 848 | CG1 | VAL | A | 122 | 26.641 | 33.290 | 28.534 | 1.00 | 11.35 | C |
| ATOM | 849 | CG2 | VAL | A | 122 | 28.176 | 33.044 | 26.587 | 1.00 | 7.40 | C |
| ATOM | 850 | C | VAL | A | 122 | 28.616 | 34.875 | 29.951 | 1.00 | 13.37 | C |
| ATOM | 851 | O | VAL | A | 122 | 29.219 | 34.199 | 30.786 | 1.00 | 13.64 | O |
| ATOM | 852 | N | ARG | A | 123 | 27.801 | 35.870 | 30.288 | 1.00 | 14.96 | N |
| ATOM | 853 | CA | ARG | A | 123 | 27.581 | 36.221 | 31.691 | 1.00 | 17.69 | C |
| ATOM | 854 | CB | ARG | A | 123 | 27.936 | 37.693 | 31.903 | 1.00 | 19.72 | C |
| ATOM | 855 | CG | ARG | A | 123 | 29.309 | 38.079 | 31.374 | 1.00 | 28.94 | C |
| ATOM | 856 | CD | ARG | A | 123 | 29.620 | 39.545 | 31.642 | 1.00 | 34.45 | C |
| ATOM | 857 | NE | ARG | A | 123 | 30.913 | 39.934 | 31.084 | 1.00 | 34.81 | N |
| ATOM | 858 | CZ | ARG | A | 123 | 31.148 | 40.109 | 29.787 | 1.00 | 37.65 | C |
| ATOM | 859 | NH1 | ARG | A | 123 | 30.175 | 39.936 | 28.901 | 1.00 | 40.89 | N |
| ATOM | 860 | NH2 | ARG | A | 123 | 32.362 | 40.450 | 29.373 | 1.00 | 35.27 | N |
| ATOM | 861 | C | ARG | A | 123 | 26.160 | 35.970 | 32.188 | 1.00 | 15.87 | C |
| ATOM | 862 | O | ARG | A | 123 | 25.297 | 35.538 | 31.430 | 1.00 | 14.52 | O |
| ATOM | 863 | N | GLY | A | 124 | 25.942 | 36.231 | 33.477 | 1.00 | 14.67 | N |
| ATOM | 864 | CA | GLY | A | 124 | 24.629 | 36.064 | 34.084 | 1.00 | 12.41 | C |
| ATOM | 865 | C | GLY | A | 124 | 24.058 | 34.659 | 34.085 | 1.00 | 13.04 | C |
| ATOM | 866 | O | GLY | A | 124 | 22.841 | 34.477 | 34.106 | 1.00 | 11.06 | O |
| ATOM | 867 | N | LEU | A | 125 | 24.937 | 33.666 | 34.092 | 1.00 | 10.63 | N |
| ATOM | 868 | CA | LEU | A | 125 | 24.520 | 32.270 | 34.063 | 1.00 | 11.37 | C |
| ATOM | 869 | CB | LEU | A | 125 | 25.556 | 31.455 | 33.293 | 1.00 | 10.04 | C |
| ATOM | 870 | CG | LEU | A | 125 | 25.729 | 31.810 | 31.820 | 1.00 | 8.76 | C |
| ATOM | 871 | CD1 | LEU | A | 125 | 26.853 | 30.973 | 31.236 | 1.00 | 12.07 | C |
| ATOM | 872 | CD2 | LEU | A | 125 | 24.430 | 31.559 | 31.072 | 1.00 | 10.99 | C |
| ATOM | 873 | C | LEU | A | 125 | 24.290 | 31.595 | 35.413 | 1.00 | 11.50 | C |
| ATOM | 874 | O | LEU | A | 125 | 24.887 | 31.958 | 36.424 | 1.00 | 13.58 | O |
| ATOM | 875 | N | ILE | A | 126 | 23.412 | 30.595 | 35.398 | 1.00 | 9.91 | N |
| ATOM | 876 | CA | ILE | A | 126 | 23.078 | 29.829 | 36.586 | 1.00 | 10.95 | C |
| ATOM | 877 | CB | ILE | A | 126 | 21.649 | 29.253 | 36.502 | 1.00 | 12.17 | C |
| ATOM | 878 | CG2 | ILE | A | 126 | 21.379 | 28.348 | 37.704 | 1.00 | 11.45 | C |
| ATOM | 879 | CG1 | ILE | A | 126 | 20.631 | 30.394 | 36.417 | 1.00 | 12.38 | C |

TABLE 19-1-continued

Atomic Coordinates of ASP with the Modeled Octapeptide Substrate

| ATOM | 880 | CD1 | ILE | A | 126 | 19.207 | 29.931 | 36.143 | 1.00 | 11.96 | C |
|---|---|---|---|---|---|---|---|---|---|---|---|
| ATOM | 881 | C | ILE | A | 126 | 24.066 | 28.668 | 36.579 | 1.00 | 11.47 | C |
| ATOM | 882 | O | ILE | A | 126 | 24.109 | 27.898 | 35.620 | 1.00 | 11.84 | O |
| ATOM | 883 | N | ARG | A | 127 | 24.874 | 28.557 | 37.627 | 1.00 | 12.21 | N |
| ATOM | 884 | CA | ARG | A | 127 | 25.854 | 27.478 | 37.716 | 1.00 | 14.56 | C |
| ATOM | 885 | CB | ARG | A | 127 | 27.106 | 27.969 | 38.444 | 1.00 | 14.59 | C |
| ATOM | 886 | CG | ARG | A | 127 | 28.195 | 26.921 | 38.616 | 1.00 | 23.58 | C |
| ATOM | 887 | CD | ARG | A | 127 | 29.308 | 27.473 | 39.493 | 1.00 | 26.48 | C |
| ATOM | 888 | NE | ARG | A | 127 | 30.349 | 26.489 | 39.769 | 1.00 | 36.15 | N |
| ATOM | 889 | CZ | ARG | A | 127 | 31.209 | 26.033 | 38.865 | 1.00 | 38.33 | C |
| ATOM | 890 | NH2 | ARG | A | 127 | 32.127 | 25.139 | 39.211 | 1.00 | 41.31 | N |
| ATOM | 891 | NH1 | ARG | A | 127 | 31.156 | 26.472 | 37.616 | 1.00 | 41.25 | N |
| ATOM | 892 | C | ARG | A | 127 | 25.221 | 26.324 | 38.485 | 1.00 | 12.51 | C |
| ATOM | 893 | O | ARG | A | 127 | 24.554 | 26.548 | 39.495 | 1.00 | 10.73 | O |
| ATOM | 894 | N | THR | A | 128 | 25.434 | 25.098 | 38.011 | 1.00 | 11.75 | N |
| ATOM | 895 | CA | THR | A | 128 | 24.867 | 23.924 | 38.667 | 1.00 | 11.43 | C |
| ATOM | 896 | CB | THR | A | 128 | 23.547 | 23.501 | 37.998 | 1.00 | 12.42 | C |
| ATOM | 897 | OG1 | THR | A | 128 | 23.835 | 22.848 | 36.751 | 1.00 | 11.64 | O |
| ATOM | 898 | CG2 | THR | A | 128 | 22.668 | 24.719 | 37.728 | 1.00 | 8.69 | C |
| ATOM | 899 | C | THR | A | 128 | 25.778 | 22.698 | 38.622 | 1.00 | 13.02 | C |
| ATOM | 900 | O | THR | A | 128 | 26.790 | 22.680 | 37.914 | 1.00 | 12.78 | O |
| ATOM | 901 | N | THR | A | 129 | 25.391 | 21.674 | 39.381 | 1.00 | 11.69 | N |
| ATOM | 902 | CA | THR | A | 129 | 26.132 | 20.419 | 39.456 | 1.00 | 12.47 | C |
| ATOM | 903 | CB | THR | A | 129 | 26.099 | 19.827 | 40.878 | 1.00 | 12.66 | C |
| ATOM | 904 | OG1 | THR | A | 129 | 24.737 | 19.612 | 41.277 | 1.00 | 11.15 | O |
| ATOM | 905 | CG2 | THR | A | 129 | 26.782 | 20.766 | 41.859 | 1.00 | 12.84 | C |
| ATOM | 906 | C | THR | A | 129 | 25.503 | 19.399 | 38.506 | 1.00 | 15.23 | C |
| ATOM | 907 | O | THR | A | 129 | 25.820 | 18.211 | 38.564 | 1.00 | 10.87 | O |
| ATOM | 908 | N | VAL | A | 130 | 24.601 | 19.870 | 37.646 | 1.00 | 14.09 | N |
| ATOM | 909 | CA | VAL | A | 130 | 23.923 | 19.006 | 36.680 | 1.00 | 12.55 | C |
| ATOM | 910 | CB | VAL | A | 130 | 22.662 | 19.694 | 36.103 | 1.00 | 13.46 | C |
| ATOM | 911 | CG1 | VAL | A | 130 | 21.913 | 18.730 | 35.195 | 1.00 | 15.05 | C |
| ATOM | 912 | CG2 | VAL | A | 130 | 21.755 | 20.178 | 37.234 | 1.00 | 10.45 | C |
| ATOM | 913 | C | VAL | A | 130 | 24.872 | 18.692 | 35.521 | 1.00 | 13.62 | C |
| ATOM | 914 | O | VAL | A | 130 | 25.655 | 19.546 | 35.120 | 1.00 | 17.44 | O |
| ATOM | 915 | N | CYS | A | 131 | 24.804 | 17.468 | 34.997 | 1.00 | 10.87 | N |
| ATOM | 916 | CA | CYS | A | 131 | 25.658 | 17.047 | 33.886 | 1.00 | 12.09 | C |
| ATOM | 917 | CB | CYS | A | 131 | 25.939 | 15.541 | 33.966 | 1.00 | 12.10 | C |
| ATOM | 918 | SG | CYS | A | 131 | 24.447 | 14.512 | 33.745 | 1.00 | 14.96 | S |
| ATOM | 919 | C | CYS | A | 131 | 24.957 | 17.343 | 32.568 | 1.00 | 12.93 | C |
| ATOM | 920 | O | CYS | A | 131 | 23.739 | 17.506 | 32.532 | 1.00 | 11.56 | O |
| ATOM | 921 | N | ALA | A | 132 | 25.723 | 17.403 | 31.486 | 1.00 | 13.76 | N |
| ATOM | 922 | CA | ALA | A | 132 | 25.141 | 17.676 | 30.181 | 1.00 | 14.09 | C |
| ATOM | 923 | CB | ALA | A | 132 | 24.724 | 19.141 | 30.089 | 1.00 | 13.62 | C |
| ATOM | 924 | C | ALA | A | 132 | 26.086 | 17.337 | 29.042 | 1.00 | 17.97 | C |
| ATOM | 925 | O | ALA | A | 132 | 27.294 | 17.179 | 29.237 | 1.00 | 15.14 | O |
| ATOM | 926 | N | GLU | A | 133 | 25.508 | 17.215 | 27.853 | 1.00 | 13.21 | N |
| ATOM | 927 | CA | GLU | A | 133 | 26.243 | 16.900 | 26.639 | 1.00 | 18.49 | C |
| ATOM | 928 | CB | GLU | A | 133 | 25.732 | 15.592 | 26.039 | 1.00 | 21.95 | C |
| ATOM | 929 | CG | GLU | A | 133 | 26.808 | 14.614 | 25.652 | 1.00 | 27.91 | C |
| ATOM | 930 | CD | GLU | A | 133 | 27.336 | 13.850 | 26.840 | 1.00 | 31.31 | C |
| ATOM | 931 | OE1 | GLU | A | 133 | 27.870 | 14.494 | 27.767 | 1.00 | 28.79 | O |
| ATOM | 932 | OE2 | GLU | A | 133 | 27.214 | 12.606 | 26.846 | 1.00 | 28.57 | O |
| ATOM | 933 | C | GLU | A | 133 | 25.919 | 18.051 | 25.693 | 1.00 | 15.23 | C |
| ATOM | 934 | O | GLU | A | 133 | 24.915 | 18.738 | 25.866 | 1.00 | 16.37 | O |
| ATOM | 935 | N | PRO | A | 134 | 26.762 | 18.276 | 24.680 | 1.00 | 16.75 | N |
| ATOM | 936 | CA | PRO | A | 134 | 26.527 | 19.366 | 23.725 | 1.00 | 17.31 | C |
| ATOM | 937 | CB | PRO | A | 134 | 27.558 | 19.082 | 22.638 | 1.00 | 17.01 | C |
| ATOM | 938 | C | PRO | A | 134 | 25.093 | 19.449 | 23.177 | 1.00 | 18.87 | C |
| ATOM | 939 | O | PRO | A | 134 | 24.468 | 20.515 | 23.204 | 1.00 | 21.16 | O |
| ATOM | 940 | CD | PRO | A | 134 | 28.022 | 17.572 | 24.385 | 1.00 | 14.41 | C |
| ATOM | 941 | CG | PRO | A | 134 | 28.708 | 18.528 | 23.429 | 1.00 | 15.96 | C |
| ATOM | 942 | N | GLY | A | 135 | 24.577 | 18.329 | 22.683 | 1.00 | 13.73 | N |
| ATOM | 943 | CA | GLY | A | 135 | 23.228 | 18.315 | 22.138 | 1.00 | 11.51 | C |
| ATOM | 944 | C | GLY | A | 135 | 22.114 | 18.674 | 23.112 | 1.00 | 12.22 | C |
| ATOM | 945 | O | GLY | A | 135 | 20.982 | 18.933 | 22.696 | 1.00 | 10.70 | O |
| ATOM | 946 | N | ASP | A | 136 | 22.425 | 18.676 | 24.405 | 1.00 | 9.59 | N |
| ATOM | 947 | CA | ASP | A | 136 | 21.451 | 19.019 | 25.441 | 1.00 | 10.66 | C |
| ATOM | 948 | CB | ASP | A | 136 | 21.957 | 18.550 | 26.808 | 1.00 | 9.43 | C |
| ATOM | 949 | C | ASP | A | 136 | 21.239 | 20.533 | 25.485 | 1.00 | 9.56 | C |
| ATOM | 950 | O | ASP | A | 136 | 20.270 | 21.018 | 26.076 | 1.00 | 7.80 | O |
| ATOM | 951 | CG | ASP | A | 136 | 21.907 | 17.044 | 26.969 | 1.00 | 12.00 | C |
| ATOM | 952 | OD2 | ASP | A | 136 | 21.038 | 16.399 | 26.348 | 1.00 | 14.65 | O |
| ATOM | 953 | OD1 | ASP | A | 136 | 22.732 | 16.510 | 27.737 | 1.00 | 11.73 | O |
| ATOM | 954 | N | SER | A | 137 | 22.159 | 21.270 | 24.867 | 1.00 | 11.68 | N |
| ATOM | 955 | CA | SER | A | 137 | 22.089 | 22.728 | 24.831 | 1.00 | 9.45 | C |
| ATOM | 956 | CB | SER | A | 137 | 23.167 | 23.298 | 23.902 | 1.00 | 12.71 | C |
| ATOM | 957 | C | SER | A | 137 | 20.723 | 23.231 | 24.381 | 1.00 | 12.56 | C |

TABLE 19-1-continued

Atomic Coordinates of ASP with the Modeled Octapeptide Substrate

| ATOM | 958 | O | SER | A | 137 | 20.110 | 22.671 | 23.470 | 1.00 | 9.42 | O |
| --- | --- | --- | --- | --- | --- | --- | --- | --- | --- | --- | --- |
| ATOM | 959 | OG | SER | A | 137 | 24.460 | 23.160 | 24.466 | 1.00 | 11.89 | O |
| ATOM | 960 | N | GLY | A | 138 | 20.264 | 24.298 | 25.027 | 1.00 | 12.50 | N |
| ATOM | 961 | CA | GLY | A | 138 | 18.974 | 24.873 | 24.698 | 1.00 | 10.84 | C |
| ATOM | 962 | C | GLY | A | 138 | 17.863 | 24.228 | 25.497 | 1.00 | 11.17 | C |
| ATOM | 963 | O | GLY | A | 138 | 16.759 | 24.774 | 25.583 | 1.00 | 10.27 | O |
| ATOM | 964 | N | GLY | A | 139 | 18.171 | 23.075 | 26.090 | 1.00 | 9.62 | N |
| ATOM | 965 | CA | GLY | A | 139 | 17.202 | 22.326 | 26.877 | 1.00 | 11.99 | C |
| ATOM | 966 | C | GLY | A | 139 | 16.675 | 22.997 | 28.135 | 1.00 | 9.04 | C |
| ATOM | 967 | O | GLY | A | 139 | 17.243 | 23.698 | 28.632 | 1.00 | 11.52 | O |
| ATOM | 968 | N | SER | A | 140 | 15.588 | 22.444 | 28.668 | 1.00 | 9.88 | N |
| ATOM | 969 | CA | SER | A | 140 | 14.942 | 22.990 | 29.858 | 1.00 | 10.08 | C |
| ATOM | 970 | CB | SER | A | 140 | 13.507 | 22.456 | 29.977 | 1.00 | 9.88 | C |
| ATOM | 971 | OG | SER | A | 140 | 12.972 | 22.057 | 28.729 | 1.00 | 11.61 | O |
| ATOM | 972 | C | SER | A | 140 | 15.628 | 22.710 | 31.187 | 1.00 | 9.54 | C |
| ATOM | 973 | O | SER | A | 140 | 16.253 | 21.670 | 31.369 | 1.00 | 8.61 | O |
| ATOM | 974 | N | LEU | A | 141 | 15.492 | 23.660 | 32.108 | 1.00 | 11.67 | N |
| ATOM | 975 | CA | LEU | A | 141 | 16.057 | 23.559 | 33.453 | 1.00 | 10.92 | C |
| ATOM | 976 | CB | LEU | A | 141 | 17.184 | 24.554 | 33.718 | 1.00 | 10.21 | C |
| ATOM | 977 | CG | LEU | A | 141 | 17.665 | 24.342 | 35.164 | 1.00 | 9.58 | C |
| ATOM | 978 | CD1 | LEU | A | 141 | 18.252 | 22.936 | 35.290 | 1.00 | 7.62 | C |
| ATOM | 979 | CD2 | LEU | A | 141 | 18.682 | 25.407 | 35.575 | 1.00 | 8.11 | C |
| ATOM | 980 | C | LEU | A | 141 | 14.867 | 23.916 | 34.330 | 1.00 | 10.82 | C |
| ATOM | 981 | O | LEU | A | 141 | 14.325 | 25.021 | 34.240 | 1.00 | 10.91 | O |
| ATOM | 982 | N | LEU | A | 142 | 14.455 | 22.972 | 35.161 | 1.00 | 7.99 | N |
| ATOM | 983 | CA | LEU | A | 142 | 13.327 | 23.175 | 36.046 | 1.00 | 11.41 | C |
| ATOM | 984 | CB | LEU | A | 142 | 12.234 | 22.140 | 35.741 | 1.00 | 12.37 | C |
| ATOM | 985 | CG | LEU | A | 142 | 11.432 | 22.235 | 34.449 | 1.00 | 13.83 | C |
| ATOM | 986 | CD1 | LEU | A | 142 | 10.710 | 20.914 | 34.195 | 1.00 | 16.69 | C |
| ATOM | 987 | CD2 | LEU | A | 142 | 10.443 | 23.391 | 34.562 | 1.00 | 13.02 | C |
| ATOM | 988 | C | LEU | A | 142 | 13.675 | 23.050 | 37.518 | 1.00 | 10.11 | C |
| ATOM | 989 | O | LEU | A | 142 | 14.631 | 22.377 | 37.904 | 1.00 | 13.30 | O |
| ATOM | 990 | N | ALA | A | 143 | 12.875 | 23.731 | 38.326 | 1.00 | 10.55 | N |
| ATOM | 991 | CA | ALA | A | 143 | 12.992 | 23.746 | 39.775 | 1.00 | 12.59 | C |
| ATOM | 992 | CB | ALA | A | 143 | 13.306 | 25.141 | 40.284 | 1.00 | 14.58 | C |
| ATOM | 993 | C | ALA | A | 143 | 11.539 | 23.388 | 40.061 | 1.00 | 13.64 | C |
| ATOM | 994 | O | ALA | A | 143 | 10.677 | 24.258 | 40.124 | 1.00 | 15.86 | O |
| ATOM | 995 | N | GLY | A | 144 | 11.260 | 22.098 | 40.178 | 1.00 | 14.54 | N |
| ATOM | 996 | CA | GLY | A | 144 | 9.890 | 21.681 | 40.396 | 1.00 | 18.53 | C |
| ATOM | 997 | C | GLY | A | 144 | 9.156 | 21.932 | 39.092 | 1.00 | 18.05 | C |
| ATOM | 998 | O | GLY | A | 144 | 9.570 | 21.445 | 38.040 | 1.00 | 18.26 | O |
| ATOM | 999 | N | ASN | A | 145 | 8.071 | 22.695 | 39.144 | 1.00 | 17.01 | N |
| ATOM | 1000 | CA | ASN | A | 145 | 7.316 | 23.001 | 37.940 | 1.00 | 17.28 | C |
| ATOM | 1001 | CB | ASN | A | 145 | 5.821 | 22.829 | 38.199 | 1.00 | 24.24 | C |
| ATOM | 1002 | CG | ASN | A | 145 | 5.380 | 23.471 | 39.497 | 1.00 | 34.66 | C |
| ATOM | 1003 | OD1 | ASN | A | 145 | 5.502 | 24.685 | 39.682 | 1.00 | 36.73 | O |
| ATOM | 1004 | ND2 | ASN | A | 145 | 4.868 | 22.655 | 40.413 | 1.00 | 41.73 | N |
| ATOM | 1005 | C | ASN | A | 145 | 7.589 | 24.425 | 37.477 | 1.00 | 16.30 | C |
| ATOM | 1006 | O | ASN | A | 145 | 6.844 | 24.966 | 36.671 | 1.00 | 13.74 | O |
| ATOM | 1007 | N | GLN | A | 146 | 8.667 | 25.022 | 37.976 | 1.00 | 13.23 | N |
| ATOM | 1008 | CA | GLN | A | 146 | 9.022 | 26.388 | 37.609 | 1.00 | 13.97 | C |
| ATOM | 1009 | CB | GLN | A | 146 | 9.283 | 27.205 | 38.786 | 1.00 | 17.49 | C |
| ATOM | 1010 | CG | GLN | A | 146 | 8.116 | 27.191 | 39.850 | 1.00 | 17.44 | C |
| ATOM | 1011 | CD | GLN | A | 146 | 6.920 | 27.948 | 39.324 | 1.00 | 19.58 | C |
| ATOM | 1012 | OE1 | GLN | A | 146 | 5.781 | 27.478 | 39.412 | 1.00 | 18.02 | O |
| ATOM | 1013 | NE2 | GLN | A | 146 | 7.166 | 29.135 | 38.781 | 1.00 | 13.47 | N |
| ATOM | 1014 | C | GLN | A | 146 | 10.238 | 26.469 | 36.692 | 1.00 | 13.36 | C |
| ATOM | 1015 | O | GLN | A | 146 | 11.332 | 26.026 | 37.052 | 1.00 | 9.49 | O |
| ATOM | 1016 | N | ALA | A | 147 | 10.036 | 27.038 | 35.508 | 1.00 | 10.85 | N |
| ATOM | 1017 | CA | ALA | A | 147 | 11.107 | 27.187 | 34.527 | 1.00 | 11.86 | C |
| ATOM | 1018 | CB | ALA | A | 147 | 10.560 | 27.790 | 33.231 | 1.00 | 9.60 | C |
| ATOM | 1019 | C | ALA | A | 147 | 12.212 | 28.077 | 35.079 | 1.00 | 12.02 | C |
| ATOM | 1020 | O | ALA | A | 147 | 11.947 | 29.181 | 35.559 | 1.00 | 11.92 | O |
| ATOM | 1021 | N | GLN | A | 148 | 13.450 | 27.595 | 34.990 | 1.00 | 9.31 | N |
| ATOM | 1022 | CA | GLN | A | 148 | 14.608 | 28.334 | 35.478 | 1.00 | 8.96 | C |
| ATOM | 1023 | CB | GLN | A | 148 | 15.502 | 27.426 | 36.317 | 1.00 | 9.82 | C |
| ATOM | 1024 | CG | GLN | A | 148 | 14.814 | 26.838 | 37.532 | 1.00 | 9.18 | C |
| ATOM | 1025 | CD | GLN | A | 148 | 14.193 | 27.914 | 38.392 | 1.00 | 8.87 | C |
| ATOM | 1026 | OE1 | GLN | A | 148 | 12.974 | 27.953 | 38.581 | 1.00 | 13.35 | O |
| ATOM | 1027 | NE2 | GLN | A | 148 | 15.024 | 28.797 | 38.916 | 1.00 | 6.09 | N |
| ATOM | 1028 | C | GLN | A | 148 | 15.449 | 28.925 | 34.353 | 1.00 | 9.54 | C |
| ATOM | 1029 | O | GLN | A | 148 | 15.874 | 30.073 | 34.424 | 1.00 | 10.41 | O |
| ATOM | 1030 | N | GLY | A | 149 | 15.707 | 28.130 | 33.322 | 1.00 | 9.02 | N |
| ATOM | 1031 | CA | GLY | A | 149 | 16.522 | 28.620 | 32.226 | 1.00 | 11.94 | C |
| ATOM | 1032 | C | GLY | A | 149 | 16.762 | 27.559 | 31.172 | 1.00 | 10.03 | C |
| ATOM | 1033 | O | GLY | A | 149 | 16.130 | 26.505 | 31.198 | 1.00 | 11.61 | O |
| ATOM | 1034 | N | VAL | A | 150 | 17.670 | 27.840 | 30.241 | 1.00 | 8.37 | N |
| ATOM | 1035 | CA | VAL | A | 150 | 17.977 | 26.885 | 29.185 | 1.00 | 10.02 | C |

TABLE 19-1-continued

Atomic Coordinates of ASP with the Modeled Octapeptide Substrate

| ATOM | 1036 | CB  | VAL | A | 150 | 17.557 | 27.428 | 27.796 | 1.00 | 8.22  | C |
| ATOM | 1037 | CG1 | VAL | A | 150 | 16.058 | 27.733 | 27.799 | 1.00 | 9.61  | C |
| ATOM | 1038 | CG2 | VAL | A | 150 | 18.343 | 28.682 | 27.452 | 1.00 | 6.21  | C |
| ATOM | 1039 | C   | VAL | A | 150 | 19.465 | 26.542 | 29.211 | 1.00 | 11.57 | C |
| ATOM | 1040 | O   | VAL | A | 150 | 20.309 | 27.391 | 29.504 | 1.00 | 9.64  | O |
| ATOM | 1041 | N   | THR | A | 151 | 19.773 | 25.283 | 28.925 | 1.00 | 11.95 | N |
| ATOM | 1042 | CA  | THR | A | 151 | 21.153 | 24.805 | 28.923 | 1.00 | 11.13 | C |
| ATOM | 1043 | CB  | THR | A | 151 | 21.195 | 23.325 | 28.552 | 1.00 | 9.19  | C |
| ATOM | 1044 | OG1 | THR | A | 151 | 20.223 | 22.622 | 29.340 | 1.00 | 6.16  | O |
| ATOM | 1045 | CG2 | THR | A | 151 | 22.578 | 22.748 | 28.828 | 1.00 | 8.56  | C |
| ATOM | 1046 | C   | THR | A | 151 | 22.086 | 25.577 | 27.999 | 1.00 | 11.68 | C |
| ATOM | 1047 | O   | THR | A | 151 | 21.838 | 25.677 | 26.801 | 1.00 | 8.62  | O |
| ATOM | 1048 | N   | SER | A | 152 | 23.172 | 26.107 | 28.560 | 1.00 | 11.36 | N |
| ATOM | 1049 | CA  | SER | A | 152 | 24.133 | 26.869 | 27.771 | 1.00 | 10.56 | C |
| ATOM | 1050 | CB  | SER | A | 152 | 24.480 | 28.183 | 28.479 | 1.00 | 13.70 | C |
| ATOM | 1051 | OG  | SER | A | 152 | 25.434 | 28.928 | 27.735 | 1.00 | 11.67 | O |
| ATOM | 1052 | C   | SER | A | 152 | 25.407 | 26.080 | 27.503 | 1.00 | 12.67 | C |
| ATOM | 1053 | O   | SER | A | 152 | 25.873 | 26.005 | 26.369 | 1.00 | 11.22 | O |
| ATOM | 1054 | N   | GLY | A | 153 | 25.967 | 25.485 | 28.547 | 1.00 | 11.74 | N |
| ATOM | 1055 | CA  | GLY | A | 153 | 27.185 | 24.719 | 28.374 | 1.00 | 13.59 | C |
| ATOM | 1056 | C   | GLY | A | 153 | 27.807 | 24.348 | 29.699 | 1.00 | 13.34 | C |
| ATOM | 1057 | O   | GLY | A | 153 | 27.226 | 24.590 | 30.758 | 1.00 | 11.10 | O |
| ATOM | 1058 | N   | GLY | A | 154 | 29.001 | 23.769 | 29.644 | 1.00 | 12.77 | N |
| ATOM | 1059 | CA  | GLY | A | 154 | 29.669 | 23.370 | 30.862 | 1.00 | 14.55 | C |
| ATOM | 1060 | C   | GLY | A | 154 | 30.763 | 22.360 | 30.583 | 1.00 | 16.81 | C |
| ATOM | 1061 | O   | GLY | A | 154 | 31.228 | 22.235 | 29.452 | 1.00 | 15.66 | O |
| ATOM | 1062 | N   | SER | A | 155 | 31.171 | 21.631 | 31.615 | 1.00 | 16.15 | N |
| ATOM | 1063 | CA  | SER | A | 155 | 32.230 | 20.641 | 31.472 | 1.00 | 16.05 | C |
| ATOM | 1064 | CB  | SER | A | 155 | 33.475 | 21.113 | 32.214 | 1.00 | 16.89 | C |
| ATOM | 1065 | OG  | SER | A | 155 | 33.181 | 21.338 | 33.582 | 1.00 | 23.41 | O |
| ATOM | 1066 | C   | SER | A | 155 | 31.799 | 19.291 | 32.026 | 1.00 | 16.84 | C |
| ATOM | 1067 | O   | SER | A | 155 | 30.783 | 19.187 | 32.714 | 1.00 | 14.62 | O |
| ATOM | 1068 | N   | GLY | A | 156 | 32.588 | 18.262 | 31.731 | 1.00 | 15.26 | N |
| ATOM | 1069 | CA  | GLY | A | 156 | 32.279 | 16.928 | 32.211 | 1.00 | 13.85 | C |
| ATOM | 1070 | C   | GLY | A | 156 | 31.211 | 16.256 | 31.376 | 1.00 | 14.91 | C |
| ATOM | 1071 | O   | GLY | A | 156 | 30.935 | 16.667 | 30.251 | 1.00 | 17.56 | O |
| ATOM | 1072 | N   | ASN | A | 157 | 30.613 | 15.213 | 31.931 | 1.00 | 14.60 | N |
| ATOM | 1073 | CA  | ASN | A | 157 | 29.566 | 14.471 | 31.248 | 1.00 | 16.61 | C |
| ATOM | 1074 | CB  | ASN | A | 157 | 30.179 | 13.445 | 30.289 | 1.00 | 16.79 | C |
| ATOM | 1075 | CG  | ASN | A | 157 | 31.168 | 12.525 | 30.974 | 1.00 | 16.85 | C |
| ATOM | 1076 | OD1 | ASN | A | 157 | 30.808 | 11.768 | 31.876 | 1.00 | 17.38 | O |
| ATOM | 1077 | ND2 | ASN | A | 157 | 32.429 | 12.585 | 30.545 | 1.00 | 19.44 | N |
| ATOM | 1078 | C   | ASN | A | 157 | 28.694 | 13.773 | 32.283 | 1.00 | 16.81 | C |
| ATOM | 1079 | O   | ASN | A | 157 | 28.936 | 13.888 | 33.487 | 1.00 | 14.11 | O |
| ATOM | 1080 | N   | CYS | A | 158 | 27.679 | 13.057 | 31.812 | 1.00 | 16.33 | N |
| ATOM | 1081 | CA  | CYS | A | 158 | 26.773 | 12.348 | 32.704 | 1.00 | 17.79 | C |
| ATOM | 1082 | CB  | CYS | A | 158 | 25.406 | 12.202 | 32.048 | 1.00 | 19.95 | C |
| ATOM | 1083 | SG  | CYS | A | 158 | 24.578 | 13.802 | 31.845 | 1.00 | 17.50 | S |
| ATOM | 1084 | C   | CYS | A | 158 | 27.257 | 10.989 | 33.174 | 1.00 | 19.67 | C |
| ATOM | 1085 | O   | CYS | A | 158 | 26.591 | 10.333 | 33.971 | 1.00 | 21.67 | O |
| ATOM | 1086 | N   | ARG | A | 159 | 28.403 | 10.554 | 32.672 | 1.00 | 18.94 | N |
| ATOM | 1087 | CA  | ARG | A | 159 | 28.948 | 9.267  | 33.070 | 1.00 | 19.35 | C |
| ATOM | 1088 | CB  | ARG | A | 159 | 29.835 | 8.700  | 31.953 | 1.00 | 19.37 | C |
| ATOM | 1089 | CG  | ARG | A | 159 | 29.074 | 8.300  | 30.702 | 1.00 | 24.85 | C |
| ATOM | 1090 | CD  | ARG | A | 159 | 30.003 | 7.779  | 29.615 | 1.00 | 25.44 | C |
| ATOM | 1091 | NE  | ARG | A | 159 | 30.852 | 8.831  | 29.068 | 1.00 | 26.55 | N |
| ATOM | 1092 | CZ  | ARG | A | 159 | 30.414 | 9.821  | 28.296 | 1.00 | 28.60 | C |
| ATOM | 1093 | NH1 | ARG | A | 159 | 29.130 | 9.901  | 27.971 | 1.00 | 28.12 | N |
| ATOM | 1094 | NH2 | ARG | A | 159 | 31.264 | 10.734 | 27.848 | 1.00 | 25.81 | N |
| ATOM | 1095 | C   | ARG | A | 159 | 29.775 | 9.461  | 34.345 | 1.00 | 19.70 | C |
| ATOM | 1096 | O   | ARG | A | 159 | 29.653 | 8.704  | 35.309 | 1.00 | 20.82 | O |
| ATOM | 1097 | N   | THR | A | 160 | 30.608 | 10.494 | 34.355 | 1.00 | 16.93 | N |
| ATOM | 1098 | CA  | THR | A | 160 | 31.445 | 10.762 | 35.517 | 1.00 | 18.57 | C |
| ATOM | 1099 | CB  | THR | A | 160 | 32.937 | 10.775 | 35.109 | 1.00 | 18.72 | C |
| ATOM | 1100 | OG1 | THR | A | 160 | 33.136 | 11.696 | 34.028 | 1.00 | 19.41 | O |
| ATOM | 1101 | CG2 | THR | A | 160 | 33.372 | 9.387  | 34.654 | 1.00 | 23.02 | C |
| ATOM | 1102 | C   | THR | A | 160 | 31.097 | 12.055 | 36.267 | 1.00 | 17.76 | C |
| ATOM | 1103 | O   | THR | A | 160 | 31.730 | 12.391 | 37.269 | 1.00 | 14.64 | O |
| ATOM | 1104 | N   | GLY | A | 161 | 30.079 | 12.767 | 35.792 | 1.00 | 15.51 | N |
| ATOM | 1105 | CA  | GLY | A | 161 | 29.666 | 14.000 | 36.444 | 1.00 | 18.63 | C |
| ATOM | 1106 | C   | GLY | A | 161 | 30.199 | 15.264 | 35.791 | 1.00 | 17.91 | C |
| ATOM | 1107 | O   | GLY | A | 161 | 31.178 | 15.231 | 35.047 | 1.00 | 17.74 | O |
| ATOM | 1108 | N   | GLY | A | 162 | 29.556 | 16.392 | 36.070 | 1.00 | 17.00 | N |
| ATOM | 1109 | CA  | GLY | A | 162 | 30.008 | 17.633 | 35.475 | 1.00 | 15.39 | C |
| ATOM | 1110 | C   | GLY | A | 162 | 29.373 | 18.881 | 36.048 | 1.00 | 14.86 | C |
| ATOM | 1111 | O   | GLY | A | 162 | 28.607 | 18.824 | 37.013 | 1.00 | 12.41 | O |
| ATOM | 1112 | N   | THR | A | 163 | 29.716 | 20.014 | 35.445 | 1.00 | 11.47 | N |
| ATOM | 1113 | CA  | THR | A | 163 | 29.203 | 21.318 | 35.847 | 1.00 | 12.96 | C |

TABLE 19-1-continued

Atomic Coordinates of ASP with the Modeled Octapeptide Substrate

| ATOM | 1114 | CB  | THR | A | 163 | 30.343 | 22.255 | 36.285 | 1.00 | 15.39 | C |
| ATOM | 1115 | OG1 | THR | A | 163 | 31.024 | 21.685 | 37.409 | 1.00 | 15.28 | O |
| ATOM | 1116 | CG2 | THR | A | 163 | 29.793 | 23.622 | 36.664 | 1.00 | 11.49 | C |
| ATOM | 1117 | C   | THR | A | 163 | 28.532 | 21.921 | 34.619 | 1.00 | 13.39 | C |
| ATOM | 1118 | O   | THR | A | 163 | 29.168 | 22.081 | 33.577 | 1.00 | 15.12 | O |
| ATOM | 1119 | N   | THR | A | 164 | 27.252 | 22.253 | 34.741 | 1.00 | 10.11 | N |
| ATOM | 1120 | CA  | THR | A | 164 | 26.518 | 22.833 | 33.624 | 1.00 | 10.81 | C |
| ATOM | 1121 | CB  | THR | A | 164 | 25.362 | 21.914 | 33.192 | 1.00 | 8.40  | C |
| ATOM | 1122 | OG1 | THR | A | 164 | 25.878 | 20.612 | 32.891 | 1.00 | 6.91  | O |
| ATOM | 1123 | CG2 | THR | A | 164 | 24.675 | 22.471 | 31.955 | 1.00 | 6.07  | C |
| ATOM | 1124 | C   | THR | A | 164 | 25.950 | 24.203 | 33.967 | 1.00 | 10.82 | C |
| ATOM | 1125 | O   | THR | A | 164 | 25.401 | 24.402 | 35.053 | 1.00 | 9.66  | O |
| ATOM | 1126 | N   | PHE | A | 165 | 26.092 | 25.139 | 33.034 | 1.00 | 9.84  | N |
| ATOM | 1127 | CA  | PHE | A | 165 | 25.600 | 26.502 | 33.210 | 1.00 | 10.47 | C |
| ATOM | 1128 | CB  | PHE | A | 165 | 26.669 | 27.513 | 32.796 | 1.00 | 11.30 | C |
| ATOM | 1129 | CG  | PHE | A | 165 | 27.940 | 27.419 | 33.597 | 1.00 | 14.89 | C |
| ATOM | 1130 | CD1 | PHE | A | 165 | 28.871 | 26.429 | 33.335 | 1.00 | 15.07 | C |
| ATOM | 1131 | CD2 | PHE | A | 165 | 28.188 | 28.311 | 34.626 | 1.00 | 16.48 | C |
| ATOM | 1132 | CE1 | PHE | A | 165 | 30.030 | 26.330 | 34.085 | 1.00 | 16.20 | C |
| ATOM | 1133 | CE2 | PHE | A | 165 | 29.341 | 28.219 | 35.379 | 1.00 | 16.91 | C |
| ATOM | 1134 | CZ  | PHE | A | 165 | 30.264 | 27.223 | 35.108 | 1.00 | 16.17 | C |
| ATOM | 1135 | C   | PHE | A | 165 | 24.344 | 26.725 | 32.373 | 1.00 | 11.04 | C |
| ATOM | 1136 | O   | PHE | A | 165 | 24.224 | 26.204 | 31.263 | 1.00 | 9.74  | O |
| ATOM | 1137 | N   | PHE | A | 166 | 23.417 | 27.517 | 32.901 | 1.00 | 7.30  | N |
| ATOM | 1138 | CA  | PHE | A | 166 | 22.177 | 27.796 | 32.195 | 1.00 | 8.16  | C |
| ATOM | 1139 | CB  | PHE | A | 166 | 20.990 | 27.127 | 32.901 | 1.00 | 7.36  | C |
| ATOM | 1140 | CG  | PHE | A | 166 | 21.148 | 25.650 | 33.093 | 1.00 | 7.82  | C |
| ATOM | 1141 | CD2 | PHE | A | 166 | 20.436 | 24.758 | 32.302 | 1.00 | 10.08 | C |
| ATOM | 1142 | CD1 | PHE | A | 166 | 22.018 | 25.148 | 34.050 | 1.00 | 10.99 | C |
| ATOM | 1143 | CE2 | PHE | A | 166 | 20.591 | 23.383 | 32.463 | 1.00 | 9.63  | C |
| ATOM | 1144 | CE1 | PHE | A | 166 | 22.179 | 23.777 | 34.218 | 1.00 | 7.63  | C |
| ATOM | 1145 | CZ  | PHE | A | 166 | 21.464 | 22.894 | 33.422 | 1.00 | 9.75  | C |
| ATOM | 1146 | C   | PHE | A | 166 | 21.871 | 29.277 | 32.077 | 1.00 | 9.41  | C |
| ATOM | 1147 | O   | PHE | A | 166 | 22.183 | 30.070 | 32.967 | 1.00 | 9.92  | O |
| ATOM | 1148 | N   | GLN | A | 167 | 21.247 | 29.634 | 30.963 | 1.00 | 9.95  | N |
| ATOM | 1149 | CA  | GLN | A | 167 | 20.866 | 31.010 | 30.690 | 1.00 | 9.14  | C |
| ATOM | 1150 | CB  | GLN | A | 167 | 20.777 | 31.231 | 29.176 | 1.00 | 8.25  | C |
| ATOM | 1151 | CG  | GLN | A | 167 | 19.911 | 32.403 | 28.738 | 1.00 | 11.98 | C |
| ATOM | 1152 | CD  | GLN | A | 167 | 20.487 | 33.751 | 29.110 | 1.00 | 13.09 | C |
| ATOM | 1153 | OE1 | GLN | A | 167 | 21.590 | 34.111 | 28.690 | 1.00 | 12.87 | O |
| ATOM | 1154 | NE2 | GLN | A | 167 | 19.746 | 34.505 | 29.905 | 1.00 | 10.51 | N |
| ATOM | 1155 | C   | GLN | A | 167 | 19.492 | 31.178 | 31.337 | 1.00 | 10.77 | C |
| ATOM | 1156 | O   | GLN | A | 167 | 18.542 | 30.483 | 30.977 | 1.00 | 7.43  | O |
| ATOM | 1157 | N   | PRO | A | 168 | 19.375 | 32.085 | 32.318 | 1.00 | 10.69 | N |
| ATOM | 1158 | CD  | PRO | A | 168 | 20.431 | 32.933 | 32.897 | 1.00 | 11.76 | C |
| ATOM | 1159 | CA  | PRO | A | 168 | 18.092 | 32.310 | 32.996 | 1.00 | 11.69 | C |
| ATOM | 1160 | CB  | PRO | A | 168 | 18.392 | 33.482 | 33.924 | 1.00 | 12.25 | C |
| ATOM | 1161 | CG  | PRO | A | 168 | 19.837 | 33.296 | 34.241 | 1.00 | 14.30 | C |
| ATOM | 1162 | C   | PRO | A | 168 | 16.988 | 32.628 | 31.994 | 1.00 | 11.80 | C |
| ATOM | 1163 | O   | PRO | A | 168 | 17.222 | 33.317 | 31.006 | 1.00 | 9.94  | O |
| ATOM | 1164 | N   | VAL | A | 169 | 15.784 | 32.133 | 32.261 | 1.00 | 10.31 | N |
| ATOM | 1165 | CA  | VAL | A | 169 | 14.650 | 32.358 | 31.373 | 1.00 | 12.92 | C |
| ATOM | 1166 | CB  | VAL | A | 169 | 13.528 | 31.331 | 31.662 | 1.00 | 17.07 | C |
| ATOM | 1167 | CG1 | VAL | A | 169 | 13.026 | 31.491 | 33.088 | 1.00 | 15.81 | C |
| ATOM | 1168 | CG2 | VAL | A | 169 | 12.394 | 31.505 | 30.678 | 1.00 | 19.48 | C |
| ATOM | 1169 | C   | VAL | A | 169 | 14.028 | 33.757 | 31.358 | 1.00 | 12.62 | C |
| ATOM | 1170 | O   | VAL | A | 169 | 13.648 | 34.253 | 30.302 | 1.00 | 11.62 | O |
| ATOM | 1171 | N   | ASN | A | 170 | 13.927 | 34.405 | 32.510 | 1.00 | 12.76 | N |
| ATOM | 1172 | CA  | ASN | A | 170 | 13.328 | 35.736 | 32.537 | 1.00 | 15.21 | C |
| ATOM | 1173 | CB  | ASN | A | 170 | 13.268 | 36.249 | 33.976 | 1.00 | 13.89 | C |
| ATOM | 1174 | CG  | ASN | A | 170 | 12.353 | 35.396 | 34.841 | 1.00 | 19.50 | C |
| ATOM | 1175 | OD1 | ASN | A | 170 | 11.367 | 34.848 | 34.347 | 1.00 | 19.07 | O |
| ATOM | 1176 | ND2 | ASN | A | 170 | 12.667 | 35.283 | 36.128 | 1.00 | 18.85 | N |
| ATOM | 1177 | C   | ASN | A | 170 | 13.948 | 36.764 | 31.591 | 1.00 | 12.70 | C |
| ATOM | 1178 | O   | ASN | A | 170 | 13.235 | 37.554 | 30.977 | 1.00 | 14.77 | O |
| ATOM | 1179 | N   | PRO | A | 171 | 15.278 | 36.778 | 31.458 | 1.00 | 15.34 | N |
| ATOM | 1180 | CD  | PRO | A | 171 | 16.339 | 36.181 | 32.282 | 1.00 | 16.10 | C |
| ATOM | 1181 | CA  | PRO | A | 171 | 15.826 | 37.772 | 30.530 | 1.00 | 16.08 | C |
| ATOM | 1182 | CB  | PRO | A | 171 | 17.336 | 37.710 | 30.790 | 1.00 | 17.98 | C |
| ATOM | 1183 | CG  | PRO | A | 171 | 17.539 | 36.351 | 31.399 | 1.00 | 23.99 | C |
| ATOM | 1184 | C   | PRO | A | 171 | 15.457 | 37.465 | 29.077 | 1.00 | 15.20 | C |
| ATOM | 1185 | O   | PRO | A | 171 | 15.464 | 38.355 | 28.228 | 1.00 | 10.27 | O |
| ATOM | 1186 | N   | ILE | A | 172 | 15.139 | 36.203 | 28.794 | 1.00 | 11.01 | N |
| ATOM | 1187 | CA  | ILE | A | 172 | 14.769 | 35.813 | 27.437 | 1.00 | 10.79 | C |
| ATOM | 1188 | CB  | ILE | A | 172 | 14.784 | 34.282 | 27.247 | 1.00 | 8.59  | C |
| ATOM | 1189 | CG2 | ILE | A | 172 | 14.453 | 33.943 | 25.792 | 1.00 | 10.32 | C |
| ATOM | 1190 | CG1 | ILE | A | 172 | 16.152 | 33.712 | 27.617 | 1.00 | 7.68  | C |
| ATOM | 1191 | CD1 | ILE | A | 172 | 16.184 | 32.189 | 27.604 | 1.00 | 6.34  | C |

TABLE 19-1-continued

Atomic Coordinates of ASP with the Modeled Octapeptide Substrate

| ATOM | 1192 | C   | ILE | A | 172 | 13.355 | 36.310 | 27.145 | 1.00 | 9.04  | O |
|------|------|-----|-----|---|-----|--------|--------|--------|------|-------|---|
| ATOM | 1193 | O   | ILE | A | 172 | 13.074 | 36.849 | 26.070 | 1.00 | 9.00  | O |
| ATOM | 1194 | N   | LEU | A | 173 | 12.461 | 36.112 | 28.107 | 1.00 | 10.13 | N |
| ATOM | 1195 | CA  | LEU | A | 173 | 11.080 | 36.544 | 27.951 | 1.00 | 12.20 | C |
| ATOM | 1196 | CB  | LEU | A | 173 | 10.249 | 36.103 | 29.157 | 1.00 | 9.16  | C |
| ATOM | 1197 | CG  | LEU | A | 173 | 10.233 | 34.595 | 29.436 | 1.00 | 10.30 | C |
| ATOM | 1198 | CD1 | LEU | A | 173 | 9.469  | 34.304 | 30.717 | 1.00 | 9.41  | C |
| ATOM | 1199 | CD2 | LEU | A | 173 | 9.598  | 33.873 | 28.268 | 1.00 | 11.50 | C |
| ATOM | 1200 | C   | LEU | A | 173 | 11.049 | 38.061 | 27.824 | 1.00 | 13.01 | C |
| ATOM | 1201 | O   | LEU | A | 173 | 10.295 | 38.608 | 27.026 | 1.00 | 17.74 | O |
| ATOM | 1202 | N   | GLN | A | 174 | 11.885 | 38.733 | 28.608 | 1.00 | 16.26 | N |
| ATOM | 1203 | CA  | GLN | A | 174 | 11.962 | 40.190 | 28.592 | 1.00 | 14.31 | C |
| ATOM | 1204 | CB  | GLN | A | 174 | 12.817 | 40.681 | 29.769 | 1.00 | 19.36 | C |
| ATOM | 1205 | CG  | GLN | A | 174 | 12.968 | 42.198 | 29.866 | 1.00 | 25.15 | C |
| ATOM | 1206 | CD  | GLN | A | 174 | 11.695 | 42.891 | 30.315 | 1.00 | 30.84 | C |
| ATOM | 1207 | OE1 | GLN | A | 174 | 10.628 | 42.684 | 29.743 | 1.00 | 30.46 | O |
| ATOM | 1208 | NE2 | GLN | A | 174 | 11.805 | 43.723 | 31.348 | 1.00 | 34.53 | N |
| ATOM | 1209 | C   | GLN | A | 174 | 12.556 | 40.694 | 27.282 | 1.00 | 15.28 | C |
| ATOM | 1210 | O   | GLN | A | 174 | 12.104 | 41.694 | 26.722 | 1.00 | 10.15 | O |
| ATOM | 1211 | N   | ALA | A | 175 | 13.567 | 39.994 | 26.786 | 1.00 | 13.61 | N |
| ATOM | 1212 | CA  | ALA | A | 175 | 14.210 | 40.393 | 25.544 | 1.00 | 16.01 | C |
| ATOM | 1213 | CB  | ALA | A | 175 | 15.372 | 39.453 | 25.234 | 1.00 | 14.76 | C |
| ATOM | 1214 | C   | ALA | A | 175 | 13.245 | 40.427 | 24.363 | 1.00 | 17.13 | C |
| ATOM | 1215 | O   | ALA | A | 175 | 13.221 | 41.387 | 23.598 | 1.00 | 14.51 | O |
| ATOM | 1216 | N   | TYR | A | 176 | 12.426 | 39.391 | 24.229 | 1.00 | 16.19 | N |
| ATOM | 1217 | CA  | TYR | A | 176 | 11.481 | 39.329 | 23.124 | 1.00 | 17.75 | C |
| ATOM | 1218 | CB  | TYR | A | 176 | 11.595 | 37.947 | 22.476 | 1.00 | 15.30 | C |
| ATOM | 1219 | CG  | TYR | A | 176 | 13.033 | 37.599 | 22.138 | 1.00 | 15.11 | C |
| ATOM | 1220 | CD1 | TYR | A | 176 | 13.818 | 38.482 | 21.415 | 1.00 | 16.28 | C |
| ATOM | 1221 | CE1 | TYR | A | 176 | 15.134 | 38.186 | 21.101 | 1.00 | 13.92 | C |
| ATOM | 1222 | CD2 | TYR | A | 176 | 13.605 | 36.395 | 22.548 | 1.00 | 12.95 | C |
| ATOM | 1223 | CE2 | TYR | A | 176 | 14.925 | 36.086 | 22.238 | 1.00 | 12.38 | C |
| ATOM | 1224 | CZ  | TYR | A | 176 | 15.682 | 36.990 | 21.512 | 1.00 | 13.61 | C |
| ATOM | 1225 | OH  | TYR | A | 176 | 16.983 | 36.705 | 21.184 | 1.00 | 13.98 | O |
| ATOM | 1226 | C   | TYR | A | 176 | 10.303 | 39.653 | 23.461 | 1.00 | 14.14 | C |
| ATOM | 1227 | O   | TYR | A | 176 | 9.155  | 39.546 | 22.604 | 1.00 | 16.16 | O |
| ATOM | 1228 | N   | GLY | A | 177 | 9.780  | 40.057 | 24.701 | 1.00 | 14.82 | N |
| ATOM | 1229 | CA  | GLY | A | 177 | 8.424  | 40.392 | 25.105 | 1.00 | 16.43 | C |
| ATOM | 1230 | C   | GLY | A | 177 | 7.500  | 39.207 | 24.933 | 1.00 | 16.44 | C |
| ATOM | 1231 | O   | GLY | A | 177 | 6.376  | 39.340 | 24.439 | 1.00 | 17.81 | O |
| ATOM | 1232 | N   | LEU | A | 178 | 7.987  | 38.046 | 25.361 | 1.00 | 14.56 | N |
| ATOM | 1233 | CA  | LEU | A | 178 | 7.261  | 36.789 | 25.258 | 1.00 | 15.86 | C |
| ATOM | 1234 | CB  | LEU | A | 178 | 8.209  | 35.656 | 24.778 | 1.00 | 15.44 | C |
| ATOM | 1235 | CG  | LEU | A | 178 | 8.886  | 35.807 | 23.415 | 1.00 | 19.21 | C |
| ATOM | 1236 | CD1 | LEU | A | 178 | 10.030 | 34.805 | 23.331 | 1.00 | 18.33 | C |
| ATOM | 1237 | CD2 | LEU | A | 178 | 7.870  | 35.553 | 22.311 | 1.00 | 21.44 | C |
| ATOM | 1238 | C   | LEU | A | 178 | 6.670  | 36.350 | 26.586 | 1.00 | 16.50 | C |
| ATOM | 1239 | O   | LEU | A | 178 | 7.086  | 36.808 | 27.650 | 1.00 | 16.26 | O |
| ATOM | 1240 | N   | ARG | A | 179 | 5.700  | 35.447 | 26.504 | 1.00 | 17.69 | N |
| ATOM | 1241 | CA  | ARG | A | 179 | 5.040  | 34.911 | 27.684 | 1.00 | 15.79 | C |
| ATOM | 1242 | CB  | ARG | A | 179 | 3.565  | 35.312 | 27.729 | 1.00 | 21.75 | C |
| ATOM | 1243 | CG  | ARG | A | 179 | 3.321  | 36.700 | 28.298 | 1.00 | 30.60 | C |
| ATOM | 1244 | CD  | ARG | A | 179 | 1.837  | 36.960 | 28.493 | 1.00 | 37.51 | C |
| ATOM | 1245 | NE  | ARG | A | 179 | 1.586  | 38.213 | 29.199 | 1.00 | 47.17 | N |
| ATOM | 1246 | CZ  | ARG | A | 179 | 2.011  | 39.405 | 28.790 | 1.00 | 49.75 | C |
| ATOM | 1247 | NH1 | ARG | A | 179 | 2.715  | 39.516 | 27.672 | 1.00 | 52.12 | N |
| ATOM | 1248 | NH2 | ARG | A | 179 | 1.731  | 40.488 | 29.500 | 1.00 | 50.23 | N |
| ATOM | 1249 | C   | ARG | A | 179 | 5.153  | 33.398 | 27.640 | 1.00 | 15.02 | C |
| ATOM | 1250 | O   | ARG | A | 179 | 5.039  | 32.787 | 26.574 | 1.00 | 14.80 | O |
| ATOM | 1251 | N   | MET | A | 180 | 5.401  | 32.800 | 28.799 | 1.00 | 13.59 | N |
| ATOM | 1252 | CA  | MET | A | 180 | 5.529  | 31.356 | 28.909 | 1.00 | 16.64 | C |
| ATOM | 1253 | CB  | MET | A | 180 | 5.991  | 30.969 | 30.316 | 1.00 | 17.26 | C |
| ATOM | 1254 | CG  | MET | A | 180 | 7.358  | 31.449 | 30.714 | 1.00 | 22.61 | C |
| ATOM | 1255 | SD  | MET | A | 180 | 8.603  | 30.324 | 30.120 | 1.00 | 24.38 | S |
| ATOM | 1256 | CE  | MET | A | 180 | 8.143  | 28.828 | 30.998 | 1.00 | 21.48 | C |
| ATOM | 1257 | C   | MET | A | 180 | 4.156  | 30.739 | 28.706 | 1.00 | 16.31 | C |
| ATOM | 1258 | O   | MET | A | 180 | 3.167  | 31.255 | 29.225 | 1.00 | 17.83 | O |
| ATOM | 1259 | N   | ILE | A | 181 | 4.076  | 29.656 | 27.942 | 1.00 | 14.71 | N |
| ATOM | 1260 | CA  | ILE | A | 181 | 2.778  | 29.019 | 27.740 | 1.00 | 13.74 | C |
| ATOM | 1261 | CB  | ILE | A | 181 | 2.794  | 28.044 | 26.559 | 1.00 | 16.62 | C |
| ATOM | 1262 | CG2 | ILE | A | 181 | 1.570  | 27.130 | 26.622 | 1.00 | 15.86 | C |
| ATOM | 1263 | CG1 | ILE | A | 181 | 2.829  | 28.835 | 25.247 | 1.00 | 17.95 | C |
| ATOM | 1264 | CD1 | ILE | A | 181 | 2.732  | 27.982 | 24.009 | 1.00 | 26.87 | C |
| ATOM | 1265 | C   | ILE | A | 181 | 2.589  | 28.256 | 29.049 | 1.00 | 15.69 | C |
| ATOM | 1266 | O   | ILE | A | 181 | 3.452  | 27.469 | 29.438 | 1.00 | 13.45 | O |
| ATOM | 1267 | N   | THR | A | 182 | 1.468  | 28.483 | 29.727 | 1.00 | 17.74 | N |
| ATOM | 1268 | CA  | THR | A | 182 | 1.210  | 27.812 | 30.998 | 1.00 | 23.56 | C |
| ATOM | 1269 | C   | THR | A | 182 | 0.141  | 26.728 | 31.019 | 1.00 | 26.44 | C |

TABLE 19-1-continued

Atomic Coordinates of ASP with the Modeled Octapeptide Substrate

| ATOM | 1270 | O   | THR | A | 182 | −0.071 | 26.088 | 32.052 | 1.00 | 29.65 | O    |   |
|------|------|-----|-----|---|-----|--------|--------|--------|------|-------|------|---|
| ATOM | 1271 | CB  | THR | A | 182 | 0.841  | 28.841 | 32.073 | 1.00 | 24.55 | C    |   |
| ATOM | 1272 | OG1 | THR | A | 182 | −0.378 | 29.497 | 31.701 | 1.00 | 27.19 | O    |   |
| ATOM | 1273 | CG2 | THR | A | 182 | 1.940  | 29.877 | 32.211 | 1.00 | 28.36 | C    |   |
| ATOM | 1274 | N   | THR | A | 183 | −0.540 | 26.517 | 29.901 | 1.00 | 27.09 | N    |   |
| ATOM | 1275 | CA  | THR | A | 183 | −1.573 | 25.494 | 29.866 | 1.00 | 33.19 | C    |   |
| ATOM | 1276 | C   | THR | A | 183 | −1.835 | 25.008 | 28.447 | 1.00 | 33.29 | C    |   |
| ATOM | 1277 | O   | THR | A | 183 | −1.707 | 25.765 | 27.484 | 1.00 | 34.57 | O    |   |
| ATOM | 1278 | CB  | THR | A | 183 | −2.888 | 26.020 | 30.477 | 1.00 | 33.38 | C    |   |
| ATOM | 1279 | OG1 | THR | A | 183 | −3.822 | 24.942 | 30.602 | 1.00 | 39.37 | O    |   |
| ATOM | 1280 | CG2 | THR | A | 183 | −3.486 | 27.105 | 29.600 | 1.00 | 36.39 | C    |   |
| ATOM | 1281 | N   | ASP | A | 184 | −2.210 | 23.739 | 28.330 | 1.00 | 33.90 | N    |   |
| ATOM | 1282 | CA  | ASP | A | 184 | −2.489 | 23.133 | 27.035 | 1.00 | 36.90 | C    |   |
| ATOM | 1283 | C   | ASP | A | 184 | −3.988 | 23.017 | 26.769 | 1.00 | 36.93 | C    |   |
| ATOM | 1284 | O   | ASP | A | 184 | −4.744 | 23.965 | 26.985 | 1.00 | 38.19 | O    |   |
| ATOM | 1285 | CB  | ASP | A | 184 | −1.841 | 21.749 | 26.980 | 1.00 | 36.49 | C    |   |
| ATOM | 1286 | CG  | ASP | A | 184 | −0.497 | 21.713 | 27.682 | 1.00 | 39.84 | C    |   |
| ATOM | 1287 | OD1 | ASP | A | 184 | 0.341  | 22.597 | 27.400 | 1.00 | 40.10 | O    |   |
| ATOM | 1288 | OD2 | ASP | A | 184 | −0.279 | 20.804 | 28.515 | 1.00 | 34.43 | O    |   |
| TER  | 1289 | O   | ASP | A | 184 |        |        |        |      |       |      |   |
| ATOM | 1290 | O   | *1  |   | 1   | 13.322 | 21.904 | 47.897 | 1.00 | 25.15 | LIGA | O |
| ATOM | 1291 | H   | *1  |   | 1   | 12.748 | 22.438 | 47.362 | 1.00 | 20.00 | LIGA | H |
| ATOM | 1292 | S   | *1  |   | 1   | 14.827 | 22.185 | 47.500 | 1.00 | 22.18 | LIGA | S |
| ATOM | 1293 | O   | *1  |   | 1   | 15.755 | 21.317 | 48.284 | 1.00 | 26.48 | LIGA | O |
| ATOM | 1294 | O   | *1  |   | 1   | 15.030 | 21.926 | 46.041 | 1.00 | 26.21 | LIGA | O |
| ATOM | 1295 | O   | *1  |   | 1   | 15.058 | 23.692 | 47.860 | 1.00 | 25.81 | LIGA | O |
| ATOM | 1296 | H   | *1  |   | 1   | 15.899 | 23.969 | 47.521 | 1.00 | 20.00 | LIGA | H |
| TER  | 1297 |     | *1  |   | 1   |        |        |        |      |       |      |   |
| ATOM | 1298 | O   | *1  |   | 1   | 8.257  | 10.233 | 23.934 | 1.00 | 51.93 | LIGA | O |
| ATOM | 1299 | H   | *1  |   | 1   | 8.965  | 10.771 | 24.260 | 1.00 | 20.00 | LIGA | H |
| ATOM | 1300 | S   | *1  |   | 1   | 7.968  | 9.064  | 24.968 | 1.00 | 52.38 | LIGA | S |
| ATOM | 1301 | O   | *1  |   | 1   | 6.699  | 8.342  | 24.628 | 1.00 | 53.41 | LIGA | O |
| ATOM | 1302 | O   | *1  |   | 1   | 9.106  | 8.094  | 25.015 | 1.00 | 51.29 | LIGA | O |
| ATOM | 1303 | O   | *1  |   | 1   | 7.802  | 9.828  | 26.339 | 1.00 | 52.66 | LIGA | O |
| ATOM | 1304 | H   | *1  |   | 1   | 7.532  | 9.218  | 27.014 | 1.00 | 20.00 | LIGA | H |
| TER  | 1305 |     | *1  |   | 1   |        |        |        |      |       |      |   |
| ATOM | 1306 | O   | *1  |   | 1   | 31.870 | 41.807 | 26.377 | 1.00 | 77.97 | LIGA | O |
| ATOM | 1307 | H   | *1  |   | 1   | 32.101 | 42.067 | 27.259 | 1.00 | 20.00 | LIGA | H |
| ATOM | 1308 | S   | *1  |   | 1   | 33.167 | 41.279 | 25.641 | 1.00 | 81.24 | LIGA | S |
| ATOM | 1309 | O   | *1  |   | 1   | 33.774 | 40.123 | 26.382 | 1.00 | 80.04 | LIGA | O |
| ATOM | 1310 | O   | *1  |   | 1   | 32.867 | 40.862 | 24.230 | 1.00 | 80.50 | LIGA | O |
| ATOM | 1311 | O   | *1  |   | 1   | 34.119 | 42.548 | 25.670 | 1.00 | 79.65 | LIGA | O |
| ATOM | 1312 | H   | *1  |   | 1   | 34.951 | 42.330 | 25.269 | 1.00 | 20.00 | LIGA | H |
| TER  | 1313 |     | *1  |   | 1   |        |        |        |      |       |      |   |
| ATOM | 1314 | O   | HOH | W | 1   | 19.154 | 20.019 | 28.345 | 1.00 | 14.14 | S    | O |
| ATOM | 1315 | O   | HON | W | 2   | 23.228 | 15.643 | 36.576 | 1.00 | 16.94 | S    | O |
| ATOM | 1316 | O   | HOH | W | 3   | 9.851  | 19.721 | 10.708 | 1.00 | 13.00 | S    | O |
| ATOM | 1317 | O   | HOH | W | 4   | 8.807  | 18.269 | 21.008 | 1.00 | 14.72 | S    | O |
| ATOM | 1318 | O   | HOH | W | 5   | 4.955  | 20.914 | 9.889  | 1.00 | 26.47 | S    | O |
| ATOM | 1319 | O   | HOH | W | 6   | 17.303 | 10.248 | 31.329 | 1.00 | 20.21 | S    | O |
| ATOM | 1320 | O   | HOH | W | 7   | 21.419 | 36.535 | 33.815 | 1.00 | 20.37 | S    | O |
| ATOM | 1321 | O   | HOH | W | 8   | 17.558 | 29.940 | 39.867 | 1.00 | 20.33 | S    | O |
| ATOM | 1322 | O   | HOH | W | 9   | 6.195  | 26.062 | 12.062 | 1.00 | 15.73 | S    | O |
| ATOM | 1323 | O   | HOH | W | 10  | 27.195 | 16.076 | 37.425 | 1.00 | 23.27 | S    | O |
| ATOM | 1324 | O   | HOH | W | 11  | 7.569  | 24.195 | 27.699 | 1.00 | 15.49 | S    | O |
| ATOM | 1325 | O   | HOH | W | 12  | 9.918  | 10.244 | 27.897 | 1.00 | 14.73 | S    | O |
| ATOM | 1326 | O   | HOH | W | 13  | 18.578 | 40.541 | 22.823 | 1.00 | 17.35 | S    | O |
| ATOM | 1327 | O   | HOH | W | 14  | 12.929 | 31.417 | 36.841 | 1.00 | 14.91 | S    | O |
| ATOM | 1328 | O   | HOH | W | 15  | 18.919 | 21.848 | 17.030 | 1.00 | 16.90 | S    | O |
| ATOM | 1329 | O   | HOH | W | 16  | 16.648 | 20.485 | 10.072 | 1.00 | 19.27 | S    | O |
| ATOM | 1330 | O   | HOH | W | 17  | 22.460 | 33.500 | 36.980 | 1.00 | 16.01 | S    | O |
| ATOM | 1331 | O   | HOH | W | 18  | 3.488  | 17.715 | 36.292 | 1.00 | 27.12 | S    | O |
| ATOM | 1332 | O   | HOH | W | 19  | 19.370 | 14.862 | 9.712  | 1.00 | 13.10 | S    | O |
| ATOM | 1333 | O   | HOH | W | 20  | 19.355 | 40.188 | 27.351 | 1.00 | 20.79 | S    | O |
| ATOM | 1334 | O   | HOH | W | 21  | 16.874 | 12.423 | 21.691 | 1.00 | 24.23 | S    | O |
| ATOM | 1335 | O   | HOH | W | 22  | 18.521 | 38.452 | 20.251 | 1.00 | 22.43 | S    | O |
| ATOM | 1336 | O   | HOH | W | 23  | 10.797 | 19.540 | 36.865 | 1.00 | 27.07 | S    | O |
| ATOM | 1337 | O   | HOH | W | 24  | 11.234 | 19.209 | 19.064 | 1.00 | 21.16 | S    | O |
| ATOM | 1338 | O   | HOH | W | 25  | 11.110 | 10.795 | 24.566 | 1.00 | 21.70 | S    | O |
| ATOM | 1339 | O   | HOH | W | 26  | 10.089 | 25.686 | 42.195 | 1.00 | 27.30 | S    | O |
| ATOM | 1340 | O   | HOH | W | 27  | 5.885  | 26.924 | 28.544 | 1.00 | 17.14 | S    | O |
| ATOM | 1341 | O   | HOH | W | 28  | 22.189 | 13.924 | 20.647 | 1.00 | 19.65 | S    | O |
| ATOM | 1342 | O   | HOH | W | 29  | 2.839  | 15.407 | 25.779 | 1.00 | 24.76 | S    | O |
| ATOM | 1343 | O   | HOH | W | 30  | 20.416 | 36.872 | 30.702 | 1.00 | 22.38 | S    | O |
| ATOM | 1344 | O   | HOH | W | 31  | 14.010 | 25.569 | 46.267 | 1.00 | 20.18 | S    | O |
| ATOM | 1345 | O   | HOH | W | 32  | 19.103 | 14.781 | 19.716 | 1.00 | 25.71 | S    | O |
| ATOM | 1346 | O   | HOH | W | 33  | 14.999 | 33.688 | 35.037 | 1.00 | 17.93 | S    | O |
| ATOM | 1347 | O   | HOH | W | 35  | 23.578 | 36.561 | 29.922 | 1.00 | 21.76 | S    | O |

TABLE 19-1-continued

Atomic Coordinates of ASP with the Modeled Octapeptide Substrate

| ATOM | 1348 | O | HOH | W | 36 | 20.341 | 32.322 | 45.950 | 1.00 | 21.47 | S | O |
|---|---|---|---|---|---|---|---|---|---|---|---|---|
| ATOM | 1349 | O | HOH | W | 37 | 0.497 | 25.775 | 19.401 | 1.00 | 26.47 | S | O |
| ATOM | 1350 | O | HOH | W | 38 | 11.741 | 34.995 | 39.424 | 1.00 | 22.41 | S | O |
| ATOM | 1351 | O | HOH | W | 39 | 22.467 | 9.409 | 26.630 | 1.00 | 15.84 | S | O |
| ATOM | 1352 | O | HOH | W | 40 | 22.662 | 11.866 | 36.367 | 1.00 | 45.41 | S | O |
| ATOM | 1353 | O | HOH | W | 41 | 3.122 | 26.816 | 16.542 | 1.00 | 23.85 | S | O |
| ATOM | 1354 | O | HOH | W | 42 | 6.805 | 20.983 | 12.758 | 1.00 | 24.18 | S | O |
| ATOM | 1355 | O | HOH | W | 43 | 29.143 | 24.285 | 40.975 | 1.00 | 26.61 | S | O |
| ATOM | 1356 | O | HOH | W | 44 | 24.253 | 18.985 | 43.742 | 1.00 | 21.24 | S | O |
| ATOM | 1357 | O | HOH | W | 45 | 16.923 | 33.119 | 42.439 | 1.00 | 24.24 | S | O |
| ATOM | 1358 | O | HOH | W | 46 | −0.710 | 24.821 | 24.871 | 1.00 | 22.41 | S | O |
| ATOM | 1359 | O | HOH | W | 47 | 28.123 | 37.039 | 34.996 | 1.00 | 23.29 | S | O |
| ATOM | 1360 | O | HOH | W | 48 | 22.509 | 29.264 | 12.288 | 1.00 | 22.20 | S | O |
| ATOM | 1361 | O | HOH | W | 49 | 18.268 | 20.963 | 47.186 | 1.00 | 27.23 | S | O |
| ATOM | 1362 | O | HOH | W | 50 | 25.603 | 33.211 | 43.598 | 1.00 | 26.97 | S | O |
| ATOM | 1363 | O | HOH | W | 51 | 20.065 | 33.475 | 8.796 | 1.00 | 27.50 | S | O |
| ATOM | 1364 | O | HOH | W | 52 | 27.258 | 11.820 | 29.311 | 1.00 | 24.08 | S | O |
| ATOM | 1365 | O | HOH | W | 53 | 10.875 | 28.986 | 41.865 | 1.00 | 23.77 | S | O |
| ATOM | 1366 | O | HOH | W | 54 | 5.763 | 34.393 | 31.210 | 1.00 | 25.54 | S | O |
| ATOM | 1367 | O | HOH | W | 55 | 13.975 | 14.195 | 21.784 | 1.00 | 27.82 | S | O |
| ATOM | 1368 | O | HOH | W | 56 | 12.541 | 23.538 | 8.045 | 1.00 | 22.43 | S | O |
| ATOM | 1369 | O | HOH | W | 57 | 24.567 | 16.480 | 39.993 | 1.00 | 26.58 | S | O |
| ATOM | 1370 | O | HOH | W | 58 | 24.532 | 38.285 | 35.829 | 1.00 | 57.74 | S | O |
| ATOM | 1371 | O | HOH | W | 59 | 25.710 | 22.863 | 22.059 | 1.00 | 31.50 | S | O |
| ATOM | 1372 | O | HOH | W | 60 | 12.323 | 34.306 | 43.203 | 1.00 | 31.10 | S | O |
| ATOM | 1373 | O | HOH | W | 61 | 4.395 | 14.949 | 17.739 | 1.00 | 29.65 | S | O |
| ATOM | 1374 | O | HOH | W | 62 | 6.745 | 20.043 | 6.966 | 1.00 | 84.14 | S | O |
| ATOM | 1375 | O | HOH | W | 63 | 5.532 | 20.170 | 37.794 | 1.00 | 41.49 | S | O |
| ATOM | 1376 | O | HOH | W | 64 | 26.003 | 16.001 | 22.248 | 1.00 | 29.03 | S | O |
| ATOM | 1377 | O | HOH | W | 65 | 5.525 | 35.401 | 19.570 | 1.00 | 33.21 | S | O |
| ATOM | 1378 | O | HOH | W | 66 | 31.845 | 33.895 | 37.644 | 1.00 | 34.28 | S | O |
| ATOM | 1379 | O | HOH | W | 67 | 20.183 | 13.414 | 38.159 | 1.00 | 27.70 | S | O |
| ATOM | 1380 | O | HOH | W | 68 | 20.038 | 18.219 | 20.060 | 1.00 | 50.13 | S | O |
| ATOM | 1381 | O | HOH | W | 70 | 0.763 | 17.179 | 17.010 | 1.00 | 37.46 | S | O |
| ATOM | 1382 | O | HOH | W | 71 | 24.671 | 21.255 | 26.579 | 1.00 | 25.15 | S | O |
| ATOM | 1383 | O | HOH | W | 72 | 8.061 | 13.765 | 23.048 | 1.00 | 31.32 | S | O |
| ATOM | 1384 | O | HOH | W | 73 | 21.384 | 36.182 | 15.238 | 1.00 | 25.91 | S | O |
| ATOM | 1385 | O | HOH | W | 74 | 32.543 | 19.236 | 37.104 | 1.00 | 32.62 | S | O |
| ATOM | 1386 | O | HOH | W | 75 | 3.201 | 29.276 | 38.786 | 1.00 | 44.04 | S | O |
| ATOM | 1387 | O | HOH | W | 76 | 2.482 | 32.835 | 31.391 | 1.00 | 47.33 | S | O |
| ATOM | 1388 | O | HOH | W | 77 | 22.558 | 9.563 | 30.212 | 1.00 | 60.39 | S | O |
| ATOM | 1389 | O | HOH | W | 78 | 24.502 | 25.394 | 46.538 | 1.00 | 35.15 | S | O |
| ATOM | 1390 | O | HOH | W | 79 | 7.028 | 39.862 | 28.058 | 1.00 | 31.57 | S | O |
| ATOM | 1391 | O | HOH | W | 80 | 33.571 | 14.425 | 35.307 | 1.00 | 26.04 | S | O |
| ATOM | 1392 | O | HOH | W | 81 | 2.732 | 10.198 | 34.775 | 1.00 | 30.67 | S | O |
| ATOM | 1393 | O | HOH | W | 82 | 34.746 | 11.362 | 31.655 | 1.00 | 34.37 | S | O |
| ATOM | 1394 | O | HOH | W | 83 | 27.003 | 10.835 | 24.556 | 1.00 | 34.40 | S | O |
| ATOM | 1395 | O | HOH | W | 84 | 11.607 | 15.263 | 18.090 | 1.00 | 53.18 | S | O |
| ATOM | 1396 | O | HOH | W | 85 | 18.961 | 26.409 | 8.948 | 1.00 | 30.64 | S | O |
| ATOM | 1397 | O | HOH | W | 86 | 8.329 | 30.456 | 11.682 | 1.00 | 24.79 | S | O |
| ATOM | 1398 | O | HOH | W | 87 | 28.267 | 25.545 | 24.816 | 1.00 | 34.18 | S | O |
| ATOM | 1399 | O | HOH | W | 88 | 27.826 | 26.788 | 46.520 | 1.00 | 45.31 | S | O |
| ATOM | 1400 | O | HOH | W | 89 | 13.822 | 23.152 | 43.665 | 1.00 | 23.81 | S | O |
| ATOM | 1401 | O | HOH | W | 90 | 15.013 | 32.301 | 6.825 | 1.00 | 36.86 | S | O |
| ATOM | 1402 | O | HOH | W | 91 | 7.321 | 15.444 | 19.576 | 1.00 | 38.03 | S | O |
| ATOM | 1403 | O | HOH | W | 92 | 9.274 | 4.160 | 30.626 | 1.00 | 34.25 | S | O |
| ATOM | 1404 | O | HOH | W | 93 | 1.045 | 23.765 | 33.021 | 1.00 | 29.72 | S | O |
| ATOM | 1405 | O | HOH | W | 94 | 0.274 | 28.435 | 36.491 | 1.00 | 39.40 | S | O |
| ATOM | 1406 | O | HOH | W | 95 | 26.351 | 23.628 | 18.493 | 1.00 | 37.43 | S | O |
| ATOM | 1407 | O | HOH | W | 96 | 34.940 | 15.280 | 30.014 | 1.00 | 38.02 | S | O |
| ATOM | 1408 | O | HOH | W | 97 | 20.426 | 30.014 | 49.201 | 1.00 | 33.87 | S | O |
| ATOM | 1409 | O | HOH | W | 98 | 13.509 | 20.866 | 41.132 | 1.00 | 41.63 | S | O |
| ATOM | 1410 | O | HOH | W | 99 | 28.366 | 18.133 | 31.889 | 1.00 | 32.04 | S | O |
| ATOM | 1411 | O | HOH | W | 100 | 0.422 | 36.030 | 31.986 | 1.00 | 42.04 | S | O |
| ATOM | 1412 | O | HOH | W | 103 | 13.872 | 24.846 | 4.468 | 1.00 | 45.22 | S | O |
| ATOM | 1413 | O | HOH | W | 104 | 25.742 | 19.925 | 19.691 | 1.00 | 41.00 | S | O |
| ATOM | 1414 | O | HOH | W | 105 | 5.894 | 32.368 | 37.453 | 1.00 | 28.07 | S | O |
| ATOM | 1415 | O | HOH | W | 108 | 27.692 | 30.529 | 45.176 | 1.00 | 36.94 | S | O |
| ATOM | 1416 | O | HOH | W | 109 | 30.999 | 38.392 | 25.165 | 1.00 | 26.39 | S | O |
| ATOM | 1417 | O | HOH | W | 111 | 13.400 | 10.503 | 34.273 | 1.00 | 29.92 | S | O |
| ATOM | 1418 | O | HOH | W | 112 | 20.748 | 36.914 | 39.970 | 1.00 | 40.16 | S | O |
| ATOM | 1419 | O | HOH | W | 113 | 24.634 | 31.190 | 17.336 | 1.00 | 36.87 | S | O |
| ATOM | 1420 | O | HOH | W | 114 | 5.642 | 30.898 | 42.120 | 1.00 | 38.57 | S | O |
| ATOM | 1421 | O | HOH | W | 115 | 8.972 | 40.592 | 30.979 | 1.00 | 32.13 | S | O |
| ATOM | 1422 | O | HOH | W | 116 | 2.047 | 31.605 | 35.777 | 1.00 | 62.75 | S | O |
| ATOM | 1423 | O | HOH | W | 117 | 27.060 | 7.939 | 28.519 | 1.00 | 31.51 | S | O |
| ATOM | 1424 | O | HOH | W | 118 | 4.134 | 24.143 | 10.395 | 1.00 | 19.77 | S | O |
| ATOM | 1425 | O | HOH | W | 119 | 17.406 | 32.729 | 38.273 | 1.00 | 19.77 | S | O |

TABLE 19-1-continued

Atomic Coordinates of ASP with the Modeled Octapeptide Substrate

| ATOM | 1426 | O | HOH | W | 120 | 21.370 | 42.268 | 22.477 | 1.00 | 19.75 | S | O |
|---|---|---|---|---|---|---|---|---|---|---|---|---|
| ATOM | 1427 | O | HOH | W | 121 | 23.854 | 15.724 | 43.136 | 1.00 | 19.76 | S | O |
| ATOM | 1428 | O | HOH | W | 122 | 19.654 | 34.836 | 37.602 | 1.00 | 19.76 | S | O |
| ATOM | 1429 | O | HOH | W | 123 | 21.170 | 42.930 | 27.470 | 1.00 | 19.75 | S | O |
| ATOM | 1430 | O | HOH | W | 124 | 25.304 | 8.005 | 25.551 | 1.00 | 19.75 | S | O |
| ATOM | 1431 | O | HOH | W | 125 | 20.739 | 40.152 | 30.476 | 1.00 | 19.73 | S | O |
| ATOM | 1432 | O | HOH | W | 126 | 19.238 | 15.779 | 6.587 | 1.00 | 19.76 | S | O |
| ATOM | 1433 | O | HOH | W | 127 | 7.151 | 28.097 | 9.617 | 1.00 | 19.75 | S | O |
| ATOM | 1434 | O | HOH | W | 128 | 7.122 | 17.869 | 11.543 | 1.00 | 19.75 | S | O |
| ATOM | 1435 | O | HOH | W | 129 | 9.467 | 35.418 | 37.012 | 1.00 | 19.76 | S | O |
| ATOM | 1436 | O | HOH | W | 130 | 5.720 | 23.417 | 6.558 | 1.00 | 19.76 | S | O |
| ATOM | 1437 | O | HOH | W | 131 | 3.123 | 12.568 | 32.283 | 1.00 | 19.76 | S | O |
| ATOM | 1438 | O | HOH | W | 132 | 12.909 | 18.142 | 39.232 | 1.00 | 19.75 | S | O |
| ATOM | 1439 | O | HOH | W | 133 | 18.190 | 34.668 | 45.077 | 1.00 | 19.77 | S | O |
| ATOM | 1440 | O | HOH | W | 134 | 16.371 | 23.490 | 8.743 | 1.00 | 19.77 | S | O |
| ATOM | 1441 | O | HOH | W | 135 | 25.889 | 26.341 | 15.721 | 1.00 | 19.77 | S | O |
| ATOM | 1442 | O | HOH | W | 138 | 18.831 | 37.368 | 35.694 | 1.00 | 19.75 | S | O |
| ATOM | 1443 | O | HOH | W | 139 | -1.837 | 27.004 | 34.243 | 1.00 | 19.78 | S | O |
| ATOM | 1444 | O | HOH | W | 140 | 29.965 | 21.328 | 39.814 | 1.00 | 19.75 | S | O |
| ATOM | 1445 | O | HOH | W | 141 | 29.084 | 22.512 | 22.380 | 1.00 | 19.74 | S | O |
| ATOM | 1446 | O | HOH | W | 144 | 26.825 | 34.183 | 16.982 | 1.00 | 19.75 | S | O |
| ATOM | 1447 | O | HOH | W | 146 | 28.060 | 21.125 | 26.874 | 1.00 | 19.76 | S | O |
| ATOM | 1448 | O | HOH | W | 147 | 7.953 | 28.465 | 43.320 | 1.00 | 19.76 | S | O |
| ATOM | 1449 | O | HOH | W | 148 | 25.139 | 13.555 | 38.510 | 1.00 | 19.76 | S | O |
| ATOM | 1450 | O | HOH | W | 154 | 27.898 | 15.263 | 40.931 | 1.00 | 19.75 | S | O |
| ATOM | 1451 | O | HOH | W | 157 | 29.305 | 18.029 | 39.665 | 1.00 | 19.76 | S | O |
| ATOM | 1452 | O | HOH | W | 158 | 22.038 | 30.753 | 9.108 | 1.00 | 19.76 | S | O |
| ATOM | 1453 | O | HOH | W | 159 | 18.399 | 11.163 | 36.207 | 1.00 | 19.76 | S | O |
| ATOM | 1454 | O | HOH | W | 164 | 26.335 | 11.937 | 35.945 | 1.00 | 19.75 | S | O |
| ATOM | 1455 | O | HOH | W | 165 | 1.758 | 29.855 | 17.357 | 1.00 | 19.75 | S | O |
| ATOM | 1456 | O | HOH | W | 166 | 24.163 | 39.471 | 32.170 | 1.00 | 19.76 | S | O |
| ATOM | 1457 | O | HOH | W | 170 | 16.077 | 17.918 | 7.749 | 1.00 | 19.75 | S | O |
| ATOM | 1458 | O | HOH | W | 172 | 32.921 | 14.044 | 27.295 | 1.00 | 19.76 | S | O |
| ATOM | 1459 | O | HOH | W | 177 | 32.795 | 38.969 | 32.954 | 1.00 | 19.77 | S | O |
| ATOM | 1460 | O | HOH | W | 179 | 4.059 | 6.708 | 28.892 | 1.00 | 19.75 | S | O |
| ATOM | 1461 | O | HOH | W | 180 | 25.397 | 29.865 | 14.090 | 1.00 | 19.76 | S | O |
| ATOM | 1462 | O | HOH | W | 182 | 11.078 | 20.731 | 43.859 | 1.00 | 19.77 | S | O |
| ATOM | 1463 | O | HOH | W | 184 | 30.825 | 30.779 | 39.402 | 1.00 | 19.77 | S | O |
| ATOM | 1464 | O | HOH | W | 187 | 10.289 | 21.108 | 7.474 | 1.00 | 19.75 | S | O |
| ATOM | 1465 | O | HOH | W | 189 | 27.314 | 38.906 | 38.135 | 1.00 | 19.76 | S | O |
| ATOM | 1466 | O | HOH | W | 197 | 25.884 | 26.959 | 11.320 | 1.00 | 19.70 | S | O |
| ATOM | 1467 | O | HOH | W | 209 | 9.364 | 16.866 | 38.731 | 1.00 | 19.73 | S | O |
| ATOM | 1468 | O | HOH | W | 219 | 32.352 | 16.134 | 38.786 | 1.00 | 19.73 | S | O |
| ATOM | 1469 | O | HOH | W | 221 | 15.972 | 35.898 | 37.609 | 1.00 | 19.69 | S | O |
| ATOM | 1470 | O | HOH | W | 223 | 3.319 | 35.758 | 13.483 | 1.00 | 19.71 | S | O |
| TER | 1471 | | HOH | W | 223 | | | | | | | |
| END | | | | | | | | | | | | |

The surface accessible residues of ASP were determined from the crystallographic coordinates provided above, using the program DS Modeling (Accelrys), using the default settings. The total surface accessibility (SA) for ASP was found to be 8044.777 Angstroms. Table 19-2 provides the total SA, side chain SA, and percent SAS is the percentage of an amino acid's total surface that is accessible to solvent.

TABLE 19-2

Total Surface Accessibility of ASP

| Residue | Total SA ang$^2$ | SideChain SA ang$^2$ | Percent SAS |
|---|---|---|---|
| asp 1: Phe | 89.992 | 66.420 | 36.954 |
| asp 2: Asp | 85.970 | 68.625 | 48.199 |
| asp 4: Ile | 17.921 | 12.076 | 9.714 |
| asp 7: Asn | 40.541 | 40.541 | 21.246 |
| asp 8: Ala | 41.497 | 24.153 | 35.259 |
| asp 10: Thr | 35.846 | 35.846 | 21.190 |
| asp 11: Ile | 29.424 | 18.114 | 17.028 |
| asp 12: Gly | 81.658 | 30.191 | 73.513 |
| asp 13: Gly | 75.236 | 18.114 | 67.615 |
| asp 14: Arg | 124.289 | 124.289 | 55.664 |
| asp 15: Ser | 29.424 | 29.424 | 19.554 |
| asp 16: Arg | 105.411 | 88.447 | 38.127 |
| asp 22: Ala | 11.690 | 0.000 | 9.932 |
| asp 24: Asn | 71.105 | 65.067 | 47.079 |
| asp 25: Gly | 53.190 | 30.191 | 43.325 |
| asp 32: His | 34.693 | 17.728 | 19.568 |
| asp 34: Gly | 18.114 | 12.076 | 20.656 |
| asp 35: Arg | 177.087 | 171.242 | 69.918 |
| asp 36: Thr | 87.506 | 64.886 | 45.401 |
| asp 37: Gly | 58.465 | 24.153 | 55.659 |
| asp 38: Ala | 18.114 | 12.076 | 16.195 |
| asp 39: Thr | 99.579 | 87.889 | 55.002 |
| asp 40: Thr | 11.310 | 0.000 | 6.469 |
| asp 41: Ala | 36.229 | 36.229 | 38.182 |
| asp 42: Asn | 86.537 | 74.844 | 43.919 |
| asp 43: Pro | 6.038 | 0.000 | 4.599 |
| asp 44: Thr | 111.082 | 99.582 | 59.375 |
| asp 45: Gly | 6.038 | 6.038 | 5.436 |
| asp 46: Thr | 52.427 | 52.427 | 28.958 |
| asp 47: Phe | 5.655 | 0.000 | 2.715 |
| asp 48: Ala | 58.848 | 30.191 | 52.705 |
| asp 49: Gly | 12.076 | 12.076 | 12.937 |
| asp 50: Ser | 51.274 | 0.000 | 37.049 |

TABLE 19-2-continued

Total Surface Accessibility of ASP

| Residue | Total SA ang² | SideChain SA ang² | Percent SAS |
|---|---|---|---|
| asp 51: Ser | 17.348 | 17.348 | 11.573 |
| asp 52: Phe | 52.040 | 12.076 | 25.034 |
| asp 53: Pro | 53.193 | 36.229 | 40.511 |
| asp 54: Gly | 30.191 | 30.191 | 27.274 |
| asp 55: Asn | 34.499 | 34.499 | 18.613 |
| asp 57: Tyr | 28.658 | 28.658 | 11.861 |
| asp 59: Phe | 18.114 | 18.114 | 9.808 |
| asp 61: Arg | 146.706 | 141.051 | 59.429 |
| asp 62: Thr | 22.619 | 5.655 | 12.939 |
| asp 63: Gly | 17.538 | 6.038 | 17.646 |
| asp 64: Ala | 112.229 | 60.381 | 90.564 |
| asp 65: Gly | 70.535 | 30.191 | 60.226 |
| asp 66: Val | 16.965 | 0.000 | 10.907 |
| asp 67: Asn | 69.002 | 62.964 | 39.692 |
| asp 68: Leu | 34.503 | 6.038 | 16.536 |
| asp 69: Leu | 42.267 | 42.267 | 20.295 |
| asp 71: Gln | 39.774 | 39.774 | 18.552 |
| asp 73: Asn | 17.345 | 17.345 | 8.760 |
| asp 74: Asn | 41.301 | 41.301 | 25.351 |
| asp 75: Tyr | 93.544 | 47.922 | 37.830 |
| asp 76: Ser | 97.666 | 52.044 | 76.965 |
| asp 77: Gly | 81.275 | 24.153 | 73.294 |
| asp 78: Gly | 17.921 | 12.076 | 18.067 |
| asp 79: Arg | 139.911 | 94.292 | 56.632 |
| asp 80: Val | 36.229 | 30.191 | 22.621 |
| asp 81: Gln | 82.421 | 70.921 | 37.295 |
| asp 83: Ala | 41.117 | 24.153 | 33.386 |
| asp 84: Gly | 12.076 | 12.076 | 12.151 |
| asp 85: His | 71.298 | 65.454 | 36.451 |
| asp 86: Thr | 111.082 | 93.544 | 65.517 |
| asp 87: Ala | 64.886 | 42.267 | 52.523 |
| asp 88: Ala | 12.076 | 6.038 | 10.760 |
| asp 89: Pro | 90.572 | 78.496 | 58.405 |
| asp 90: Val | 94.694 | 66.420 | 53.062 |
| asp 91: Gly | 58.082 | 18.114 | 49.593 |
| asp 92: Ser | 34.886 | 23.003 | 27.450 |
| asp 93: Ala | 83.381 | 60.381 | 70.846 |
| asp 95: Cys | 26.565 | 26.565 | 15.773 |
| asp 99: Ser | 39.584 | 0.000 | 29.907 |
| asp 100: Thr | 87.123 | 47.155 | 48.121 |
| asp 101: Thr | 34.696 | 6.038 | 22.060 |
| asp 102: Gly | 12.076 | 12.076 | 13.771 |
| asp 103: Trp | 70.728 | 47.919 | 27.630 |
| asp 104: His | 47.726 | 41.687 | 23.152 |
| asp 105: Cys | 54.609 | 31.799 | 33.796 |
| asp 106: Gly | 23.386 | 12.076 | 23.531 |
| asp 107: Thr | 47.155 | 47.155 | 29.873 |
| asp 108: Ile | 5.655 | 0.000 | 2.888 |
| asp 109: Thr | 64.503 | 30.191 | 35.741 |
| asp 110: Ala | 24.153 | 24.153 | 21.668 |
| asp 111: Leu | 71.115 | 48.305 | 36.142 |
| asp 112: Asn | 138.770 | 104.841 | 66.301 |
| asp 113: Ser | 17.731 | 11.693 | 12.794 |
| asp 114: Ser | 92.391 | 52.427 | 63.967 |
| asp 115: Val | 30.191 | 24.153 | 18.166 |
| asp 116: Thr | 128.237 | 82.618 | 66.534 |
| asp 117: Tyr | 35.846 | 24.153 | 15.603 |
| asp 118: Pro | 159.964 | 102.648 | 93.188 |
| asp 119: Glu | 132.745 | 87.123 | 63.766 |
| asp 120: Gly | 18.114 | 18.114 | 20.611 |
| asp 121: Thr | 93.924 | 76.579 | 48.828 |
| asp 123: Arg | 129.748 | 129.748 | 59.619 |
| asp 124: Gly | 29.231 | 12.076 | 26.315 |
| asp 126: Ile | 6.038 | 6.038 | 3.084 |
| asp 127: Arg | 99.943 | 99.943 | 36.957 |
| asp 128: Thr | 5.655 | 0.000 | 3.450 |
| asp 129: Thr | 76.579 | 59.615 | 45.219 |
| asp 130: Val | 0.000 | 0.000 | 0.000 |
| asp 131: Cys | 25.568 | 19.723 | 18.583 |
| asp 132: Ala | 11.693 | 6.038 | 9.495 |
| asp 133: Glu | 40.734 | 29.041 | 20.057 |
| asp 134: Pro | 114.531 | 102.648 | 68.994 |
| asp 135: Gly | 11.883 | 6.038 | 11.979 |
| asp 137: Ser | 5.655 | 5.655 | 3.915 |
| asp 143: Ala | 17.731 | 6.038 | 18.763 |
| asp 144: Gly | 59.612 | 36.229 | 63.599 |
| asp 145: Asn | 81.832 | 70.142 | 44.061 |
| asp 146: Gln | 52.810 | 52.810 | 27.510 |
| asp 147: Ala | 5.655 | 0.000 | 4.797 |
| asp 148: Gln | 11.500 | 5.845 | 5.335 |
| asp 152: Ser | 5.655 | 0.000 | 4.092 |
| asp 153: Gly | 24.153 | 18.114 | 25.819 |
| asp 154: Gly | 63.927 | 12.076 | 64.322 |
| asp 155: Ser | 88.656 | 70.541 | 69.864 |
| asp 156: Gly | 52.807 | 18.114 | 50.090 |
| asp 157: Asn | 35.263 | 35.263 | 20.195 |
| asp 158: Cys | 34.312 | 6.038 | 21.893 |
| asp 159: Arg | 199.716 | 154.094 | 79.090 |
| asp 160: Thr | 135.044 | 89.422 | 85.862 |
| asp 161: Gly | 35.462 | 24.153 | 33.699 |
| asp 162: Gly | 23.576 | 6.038 | 21.225 |
| asp 163: Thr | 46.005 | 46.005 | 25.438 |
| asp 164: Thr | 5.655 | 5.655 | 3.127 |
| asp 165: Phe | 24.153 | 24.153 | 10.669 |
| asp 167: Gln | 5.845 | 5.845 | 3.042 |
| asp 168: Pro | 48.305 | 48.305 | 31.227 |
| asp 170: Asn | 59.032 | 53.377 | 31.882 |
| asp 171: Pro | 59.615 | 42.267 | 42.027 |
| asp 173: Leu | 17.731 | 12.076 | 8.274 |
| asp 174: Gln | 145.572 | 122.569 | 80.497 |
| asp 175: Ala | 52.044 | 6.038 | 44.291 |
| asp 176: Tyr | 64.886 | 36.229 | 29.811 |
| asp 177: Gly | 69.775 | 24.153 | 70.340 |
| asp 178: Leu | 11.693 | 6.038 | 5.788 |
| asp 179: Arg | 182.932 | 182.932 | 72.390 |
| asp 180: Met | 34.886 | 12.076 | 17.253 |
| asp 181: Ile | 36.229 | 30.191 | 19.053 |
| asp 182: Thr | 99.389 | 76.579 | 60.785 |
| asp 183: Thr | 104.854 | 93.544 | 68.979 |
| asp 184: Asp | 122.008 | 23.386 | 52.822 |

The ASP co-ordinates, and those of homologous structures were loaded into MOE (Chemical Computing Group). Co-ordinates for waters and ligands were removed. Using MOE align, the structures were aligned using actual secondary structure, with structural alignment enabled and superpose chains enabled. This resulted in the following structural alignment. The numbers indicated refer to the mature ASP protease amino-acid sequence.

```
PDB ID
              1         10        20        30        40
ASP    FDVIGGNAYTIG-GRSRCSIGFAVN-----GGFITAGHCGRTGATTAN------PTGTFA
1HPG   --VLGGGAIYGG-GSR-CSAAFNVTK-GGARYFVTAGHCTNISANWSASS-GGSVVGVRE
1SGP   --ISGGDAIYSS-TGR-CSLGFNVRS-GSTYYFLTAGHCTDGATTWWANSARTTVLGTTS
1TAL   ANIVGGIEYSINNASL-CSVGFSVTR-GATKGFVTAGHCGTVNATARIG---GAVVGTFA
2SFA   --IAGGEAIYAAGGGR-CSLGFNVRSSSGATYALTAGHCTEIASTWYTNSGQTSLLGTRA
2SGA   --IAGGEAITT-GGSR-CSLGFNVSV-NGVAHALTAGHCTNISASWS--------IGTRT
```

-continued

PDB ID

```
           50         60         70         80         90        100
ASP    GSSFPGNDYAFVRTGAG-VNLLAQVNNYSGGRVQVAGHTAAPVGSAVCRSGSTTGWHCGT
1HPG   GTSFPTNDYGIVRYTDG-SSPAGTVDLYNGSTQDISSAANAVVGQAIKKSGSTTKVTSGT
1SGP   GSSFPNNDYGIVRYTNTTIPKDGTVG-----GQDITSAANATVGMAVTRRGSTTGTHSGS
1TAL   ARVFPGNDRAWVSLTSA-QTLLPRVANG-SSFVTVRGSTEAAVGAAVCRSGRTTGYQCGT
2SFA   GTSFPGNDYGLIRHSNA-SAADGRVYLYNGSYRDITGAGNAYVGQTVQRSGSTTGLHSGR
2SGA   GTSFPNNDYGIIRHSNP-AAADGRVYLYNGSYQDITTAGNAFVGQAVQRSGSTTGLRSGS 110        120        130        140        150        160
ASP    ITALNSSVTYPE-GTVRGLIRTTVCAEPGDSGGSLLA-GNQAQGVTSGGSG-----NCRT
1HPG   VTAVNVTVNYGD-GPVYNMVRTTACSAGGDSGGAHFA-GSVALGIHSGSSG------CSG
1SGP   VTALNATVNYGGGDVVYGMIRTNVCAEPGDSGGPLYS-GTRAIGLTSGGSG-----NCSS
1TAL   ITAKNVTANYAE-GAVRGLTQGNACMGRGDSGGSWITSAGQAQGVMSGGNVQSNGNNCGI
2SFA   VTGLNATVNYGGGDIVSGLIQTNVCAEPGDSGGALFA-GSTALGLTSGGSG-----NCRT
2SGA   VTGLNATVNYGSSGIVYGMIQTNVCAQPGDSGGSLFA-GSTALGLTSGGSG-----NCRT 170        180
ASP    G---GTTFFQPVNPILQAYGLRMITTD   (SEQ ID NO: 624)
1HPG   TA--GSAIHQPVTEALSAYGVTVY---   (SEQ ID NO: 625)
1SGP   G---GTTFFQPVTEALVAYGVSVY---   (SEQ ID NO: 626)
1TAL   PASQRSSLFERLQPILSQYGLSLVTG-   (SEQ ID NO: 627)
2SFA   G---GTTFFQPVTEALSAYGVSIL---   (SEQ ID NO: 628)
2SGA   G---GTTFYQPVTEALSAYGATVL---   (SEQ ID NO: 629)
```

In the above alignment, the codes are as follows:
1HPG = *Streptomyces griseus* glutamic acid specific protease.
1SGP = *Streptomyces griseus* proteinase B
1SGT = *Streptomyces griseus* strain K1 trypsin
1TAL = *Lysobacter enzymogenes* alpha-lytic protease
2SFA = *Streptomyces fradiae* serine proteinase
2SGA = *Streptomyces griseus* protease A Example 20

Enzyme Substrate Modeling and Mapping of the ASP Active-Site

In this Example, enzyme-substrate modeling and mapping of the ASP active site methods are described. Preliminary inspection of the active-site revealed a large P1 binding pocket that is large enough to accommodate large hydrophobic groups such as the side-chains of Trp, Tyr, and Phe.

The crystal structure of Streptogrisin A with the turkey third domain of the ovomucoid inhibitor (pdb code 2SGB) was been determined. 2SGB was structurally aligned to ASP, using MOE (Chemical Computing Corp), which places the inhibitor in the active-site of ASP. All of the 2SGB co-ordinates were removed, except for those which define a hexa-peptide bound in the ASP active-site, corresponding to binding at the S4 to S2' binding sites. The Pro-ASP protein self-cleaves the pro domain-mature domain junction, to release the mature protease enzyme. The last four residues of the pro domain are expected to occupy the S1-S4 sites, and the first two residues of the mature protease occupy the S1' and S2' sites. Therefore the hexapeptide in the active-site was in-silico mutated to sequence PRTMFD (SEQ ID NO:630).

From inspection of the structure of the initial substrate bound model, the backbone amide of Gly135 and Asp136 would be expected to form the oxy-anion hole. However, the amide nitrogen of Gly135 appears to point in the wrong direction. Comparison with streptogrisin A confirms this. Thus, it is presumed that a conformational change in ASP is required to form the oxy-anion hole. However, it is not intended that the present invention be limited by any particular mechanism nor hypothesis. The peptide backbone between residues 134 and 135 was altered to that of a similar orientation to that of structurally equivalent atoms in the streptogrisin A structure. The enzyme substrate model was then energy minimized.

Residues within 6 Å of the modeled substrate were determined using the proximity tools within the program QUANTA. These residues were identified as: Arg14, Ser15, Arg16, Cys17, His32, Cys33, Phe52, Asp56, Thr100, Val115, Thr116, Tyr117, Pro118, Glu119, Ala132, Glu133, Pro134, Gly135, Asp136, Ser137, Thr151, Ser152, Gly153, Gly154, Ser155, Gly156, Asn157, Thr164, Phe165. Of these, His 32, Asp56, and Ser137 form the catalytic triad.

The P1 pocket is formed by Cys131, Ala132, Glu133, Pro134, Gly135, Thr151, Ser152, Gly153, Gly154, Ser155, Gly156, Asn157 and Gly 162, Thr 163, Thr164. The P2 pocket is defined by Phe52, Tyr117, Pro118 and Glu119. The P3 pocket has main-chain to main chain hydrogen bonding from Gly 154 to the substrate main-chain. The P1' pocket is defined by Arg16, and His32. The P2' pocket is defined by Thr100, and Pro134. The atomic coordinates of ASP with the modeled octapeptide substrate are provided in Table 20-1 below.

Table 20-1

Atomic Coordinates of ASP with the Modeled Octapeptide Substrate

| ATOM | 1 | N  | PHE | A | 1 | 2.452 | 18.495 | 15.165 | 0.00 | N1+ |
|------|---|----|-----|---|---|-------|--------|--------|------|-----|
| ATOM | 2 | CA | PHE | A | 1 | 3.712 | 18.208 | 15.901 | 0.00 | C   |
| ATOM | 3 | CB | PHE | A | 1 | 4.906 | 18.646 | 15.055 | 0.00 | C   |
| ATOM | 4 | C  | PHE | A | 1 | 3.743 | 18.914 | 17.254 | 0.00 | C   |
| ATOM | 5 | O  | PHE | A | 1 | 3.539 | 20.133 | 17.340 | 0.00 | O   |

Table 20-1-continued

Atomic Coordinates of ASP with the Modeled Octapeptide Substrate

| ATOM | 6 | CG | PHE | A | 1 | 6.232 | 18.405 | 15.707 | 0.00 | C |
|---|---|---|---|---|---|---|---|---|---|---|
| ATOM | 7 | CD2 | PHE | A | 1 | 6.963 | 17.268 | 15.411 | 0.00 | C |
| ATOM | 8 | CD1 | PHE | A | 1 | 6.750 | 19.312 | 16.618 | 0.00 | C |
| ATOM | 9 | CE2 | PHE | A | 1 | 8.192 | 17.035 | 16.010 | 0.00 | C |
| ATOM | 10 | CE1 | PHE | A | 1 | 7.981 | 19.086 | 17.222 | 0.00 | C |
| ATOM | 11 | CZ | PHE | A | 1 | 8.702 | 17.946 | 16.917 | 0.00 | C |
| ATOM | 12 | N | ASP | A | 2 | 4.000 | 18.148 | 18.311 | 0.00 | N |
| ATOM | 13 | CA | ASP | A | 2 | 4.052 | 18.708 | 19.659 | 0.00 | C |
| ATOM | 14 | CB | ASP | A | 2 | 3.584 | 17.678 | 20.688 | 0.00 | C |
| ATOM | 15 | C | ASP | A | 2 | 5.422 | 19.210 | 20.066 | 0.00 | C |
| ATOM | 16 | O | ASP | A | 2 | 6.415 | 18.508 | 19.925 | 0.00 | O |
| ATOM | 17 | CG | ASP | A | 2 | 2.109 | 17.354 | 20.560 | 0.00 | C |
| ATOM | 18 | OD2 | ASP | A | 2 | 1.597 | 16.558 | 21.379 | 0.00 | O1− |
| ATOM | 19 | OD1 | ASP | A | 2 | 1.459 | 17.889 | 19.638 | 0.00 | O |
| ATOM | 20 | N | VAL | A | 3 | 5.464 | 20.440 | 20.562 | 0.00 | N |
| ATOM | 21 | CA | VAL | A | 3 | 6.707 | 21.057 | 21.009 | 0.00 | C |
| ATOM | 22 | CB | VAL | A | 3 | 6.736 | 22.574 | 20.718 | 0.00 | C |
| ATOM | 23 | C | VAL | A | 3 | 6.737 | 20.837 | 22.513 | 0.00 | C |
| ATOM | 24 | O | VAL | A | 3 | 5.806 | 21.233 | 23.216 | 0.00 | O |
| ATOM | 25 | CG1 | VAL | A | 3 | 7.921 | 23.222 | 21.425 | 0.00 | C |
| ATOM | 26 | CG2 | VAL | A | 3 | 6.840 | 22.810 | 19.220 | 0.00 | C |
| ATOM | 27 | CB | ILE | A | 4 | 7.602 | 18.448 | 24.730 | 0.00 | C |
| ATOM | 28 | CG2 | ILE | A | 4 | 7.684 | 18.189 | 26.227 | 0.00 | C |
| ATOM | 29 | CG1 | ILE | A | 4 | 6.196 | 18.137 | 24.220 | 0.00 | C |
| ATOM | 30 | CD1 | ILE | A | 4 | 5.768 | 16.711 | 24.456 | 0.00 | C |
| ATOM | 31 | C | ILE | A | 4 | 9.379 | 20.168 | 24.911 | 0.00 | C |
| ATOM | 32 | O | ILE | A | 4 | 10.346 | 19.836 | 24.229 | 0.00 | C |
| ATOM | 33 | N | ILE | A | 4 | 7.801 | 20.200 | 22.997 | 0.00 | N |
| ATOM | 34 | CA | ILE | A | 4 | 7.955 | 19.916 | 24.423 | 0.00 | C |
| ATOM | 35 | N | GLY | A | 5 | 9.499 | 20.743 | 26.103 | 0.00 | N |
| ATOM | 36 | CA | GLY | A | 5 | 10.807 | 21.030 | 26.653 | 0.00 | C |
| ATOM | 37 | C | GLY | A | 5 | 11.655 | 19.787 | 26.819 | 0.00 | C |
| ATOM | 36 | O | GLY | A | 5 | 11.171 | 18.750 | 27.277 | 0.00 | O |
| ATOM | 39 | N | GLY | A | 6 | 12.927 | 19.885 | 26.443 | 0.00 | N |
| ATOM | 40 | CA | GLY | A | 6 | 13.817 | 18.747 | 26.572 | 0.00 | C |
| ATOM | 41 | C | GLY | A | 6 | 14.007 | 17.948 | 25.294 | 0.00 | C |
| ATOM | 42 | O | GLY | A | 6 | 14.990 | 17.217 | 25.157 | 0.00 | O |
| ATOM | 43 | N | ASN | A | 7 | 13.069 | 18.082 | 24.359 | 0.00 | N |
| ATOM | 44 | CA | ASN | A | 7 | 13.155 | 17.351 | 23.100 | 0.00 | C |
| ATOM | 45 | CB | ASN | A | 7 | 11.784 | 17.247 | 22.450 | 0.00 | C |
| ATOM | 46 | CG | ASN | A | 7 | 10.918 | 16.210 | 23.102 | 0.00 | C |
| ATOM | 47 | OD1 | ASN | A | 7 | 9.741 | 16.069 | 22.760 | 0.00 | O |
| ATOM | 40 | ND2 | ASN | A | 7 | 11.492 | 15.464 | 24.049 | 0.00 | N |
| ATOM | 49 | C | ASN | A | 7 | 14.124 | 17.933 | 22.086 | 0.00 | C |
| ATOM | 50 | O | ASN | A | 7 | 14.466 | 19.114 | 22.119 | 0.00 | C |
| ATOM | 51 | N | ALA | A | 8 | 14.561 | 17.077 | 21.176 | 0.00 | N |
| ATOM | 52 | CA | ALA | A | 8 | 15.486 | 17.487 | 20.138 | 0.00 | C |
| ATOM | 53 | CB | ALA | A | 8 | 16.212 | 16.271 | 19.577 | 0.00 | C |
| ATOM | 54 | C | ALA | A | 8 | 14.716 | 18.174 | 19.023 | 0.00 | C |
| ATOM | 55 | O | ALA | A | 8 | 13.509 | 17.988 | 18.874 | 0.00 | O |
| ATOM | 56 | N | TYR | A | 9 | 15.423 | 18.993 | 18.262 | 0.00 | N |
| ATOM | 57 | CA | TYR | A | 9 | 14.847 | 19.714 | 17.143 | 0.00 | C |
| ATOM | 58 | CB | TYR | A | 9 | 14.253 | 21.064 | 17.580 | 0.00 | C |
| ATOM | 59 | CG | TYR | A | 9 | 15.221 | 22.148 | 17.963 | 0.00 | C |
| ATOM | 60 | CD2 | TYR | A | 9 | 15.517 | 22.398 | 19.301 | 0.00 | C |
| ATOM | 61 | CE2 | TYR | A | 9 | 16.341 | 23.443 | 19.663 | 0.00 | C |
| ATOM | 62 | CD1 | TYR | A | 9 | 15.785 | 22.972 | 16.993 | 0.00 | C |
| ATOM | 63 | CE1 | TYR | A | 9 | 16.609 | 24.021 | 17.343 | 0.00 | C |
| ATOM | 64 | CZ | TYR | A | 9 | 16.883 | 24.255 | 18.678 | 0.00 | C |
| ATOM | 65 | OH | TYR | A | 9 | 17.688 | 25.309 | 19.029 | 0.00 | O |
| ATOM | 66 | C | TYR | A | 9 | 16.072 | 19.837 | 16.262 | 0.00 | C |
| ATOM | 67 | O | TYR | A | 9 | 17.188 | 19.678 | 16.753 | 0.00 | O |
| ATOM | 68 | N | THR | A | 10 | 15.886 | 20.077 | 14.970 | 0.00 | N |
| ATOM | 69 | CA | THR | A | 10 | 17.034 | 20.183 | 14.082 | 0.00 | C |
| ATOM | 70 | CB | THR | A | 10 | 17.031 | 19.031 | 13.041 | 0.00 | C |
| ATOM | 71 | OG1 | THR | A | 10 | 15.822 | 19.082 | 12.269 | 0.00 | O |
| ATOM | 72 | CG2 | THR | A | 10 | 17.129 | 17.676 | 13.741 | 0.00 | C |
| ATOM | 73 | C | THR | A | 10 | 17.205 | 21.486 | 13.329 | 0.00 | C |
| ATOM | 74 | O | THR | A | 10 | 16.249 | 22.243 | 13.104 | 0.00 | O |
| ATOM | 75 | N | ILE | A | 11 | 18.453 | 21.734 | 12.936 | 0.00 | N |
| ATOM | 76 | CA | ILE | A | 11 | 18.828 | 22.930 | 12.197 | 0.00 | C |
| ATOM | 77 | CB | ILE | A | 11 | 19.609 | 23.914 | 13.093 | 0.00 | C |
| ATOM | 78 | CG | ILE | A | 11 | 19.855 | 25.221 | 12.343 | 0.00 | C |
| ATOM | 79 | CG1 | ILE | A | 11 | 18.811 | 24.187 | 14.369 | 0.00 | C |
| ATOM | 80 | CD1 | ILE | A | 11 | 19.546 | 25.036 | 15.385 | 0.00 | C |
| ATOM | 81 | C | ILE | A | 11 | 19.712 | 22.442 | 11.054 | 0.00 | C |
| ATOM | 82 | O | ILE | A | 11 | 20.772 | 21.856 | 11.284 | 0.00 | O |
| ATOM | 83 | N | GLY | A | 12 | 19.274 | 22.668 | 9.821 | 0.00 | N |

Table 20-1-continued

Atomic Coordinates of ASP with the Modeled Octapeptide Substrate

| ATOM | 84 | CA | GLY | A | 12 | 20.048 | 22.193 | 8.689 | 0.00 | C |
|---|---|---|---|---|---|---|---|---|---|---|
| ATOM | 85 | C | GLY | A | 12 | 20.344 | 20.705 | 8.845 | 0.00 | C |
| ATOM | 86 | O | GLY | A | 12 | 21.439 | 20.239 | 8.523 | 0.00 | O |
| ATOM | 87 | N | GLY | A | 13 | 19.373 | 19.957 | 9.361 | 0.00 | N |
| ATOM | 88 | CA | GLY | A | 13 | 19.564 | 18.531 | 9.545 | 0.00 | C |
| ATOM | 89 | C | GLY | A | 13 | 20.373 | 18.127 | 10.769 | 0.00 | C |
| ATOM | 90 | O | GLY | A | 13 | 20.438 | 16.945 | 11.103 | 0.00 | O |
| ATOM | 91 | N | ARG | A | 14 | 20.984 | 19.091 | 11.449 | 0.00 | N |
| ATOM | 92 | CA | ARG | A | 14 | 21.787 | 18.782 | 12.627 | 0.00 | C |
| ATOM | 93 | CB | ARG | A | 14 | 23.036 | 19.670 | 12.669 | 0.00 | C |
| ATOM | 94 | C | ARG | A | 14 | 21.018 | 18.938 | 13.935 | 0.00 | C |
| ATOM | 95 | O | ARG | A | 14 | 20.441 | 19.982 | 14.212 | 0.00 | O |
| ATOM | 96 | CG | ARG | A | 14 | 24.251 | 19.072 | 11.964 | 0.00 | C |
| ATOM | 97 | CD | ARG | A | 14 | 24.065 | 19.084 | 10.450 | 0.00 | C |
| ATOM | 98 | NE | ARG | A | 14 | 24.173 | 17.752 | 9.858 | 0.00 | N1+ |
| ATOM | 99 | CZ | ARG | A | 14 | 25.316 | 17.100 | 9.660 | 0.00 | C |
| ATOM | 100 | NH1 | ARG | A | 14 | 26.474 | 17.655 | 10.004 | 0.00 | N |
| ATOM | 101 | NH2 | ARG | A | 14 | 25.302 | 15.886 | 9.120 | 0.00 | N |
| ATOM | 102 | N | SER | A | 15 | 21.016 | 17.878 | 14.733 | 0.00 | N |
| ATOM | 103 | CA | SER | A | 15 | 20.335 | 17.870 | 16.017 | 0.00 | C |
| ATOM | 104 | CB | SER | A | 15 | 20.062 | 16.429 | 16.454 | 0.00 | C |
| ATOM | 105 | C | SER | A | 15 | 21.312 | 18.525 | 16.983 | 0.00 | C |
| ATOM | 106 | O | SER | A | 15 | 21.933 | 17.849 | 17.803 | 0.00 | O |
| ATOM | 107 | OG | SER | A | 15 | 19.396 | 16.382 | 17.701 | 0.00 | O |
| ATOM | 108 | N | ARG | A | 16 | 21.454 | 19.841 | 16.867 | 0.00 | N |
| ATOM | 109 | CA | ARG | A | 16 | 22.362 | 20.594 | 17.724 | 0.00 | C |
| ATOM | 110 | CB | ARG | A | 16 | 22.741 | 21.927 | 17.073 | 0.00 | C |
| ATOM | 111 | C | ARG | A | 16 | 21.815 | 20.907 | 19.104 | 0.00 | C |
| ATOM | 112 | O | ARG | A | 16 | 22.550 | 20.867 | 20.088 | 0.00 | O |
| ATOM | 113 | CG | ARG | A | 16 | 23.719 | 21.851 | 15.915 | 0.00 | C |
| ATOM | 114 | CD | ARG | A | 16 | 24.200 | 23.253 | 15.549 | 0.00 | C |
| ATOM | 115 | NE | ARG | A | 16 | 24.625 | 23.984 | 16.745 | 0.00 | N1+ |
| ATOM | 116 | CZ | ARG | A | 16 | 25.242 | 25.166 | 16.739 | 0.00 | C |
| ATOM | 117 | NH2 | ARG | A | 16 | 25.581 | 25.735 | 17.888 | 0.00 | N |
| ATOM | 118 | NH1 | ARG | A | 16 | 25.528 | 25.781 | 15.597 | 0.00 | N |
| ATOM | 119 | N | CYS | A | 17 | 20.526 | 21.215 | 19.178 | 0.00 | N |
| ATOM | 120 | CA | CYS | A | 17 | 19.928 | 21.546 | 20.455 | 0.00 | C |
| ATOM | 121 | CB | CYS | A | 17 | 19.800 | 23.068 | 20.553 | 0.00 | C |
| ATOM | 122 | C | CYS | A | 17 | 10.539 | 20.911 | 20.003 | 0.00 | C |
| ATOM | 123 | O | CYS | A | 17 | 18.071 | 20.077 | 20.071 | 0.00 | O |
| ATOM | 124 | SG | CYS | A | 17 | 21.393 | 23.932 | 20.696 | 0.00 | S |
| ATOM | 125 | N | SER | A | 18 | 18.066 | 21.348 | 21.942 | 0.00 | N |
| ATOM | 126 | CA | SER | A | 18 | 16.799 | 20.865 | 22.455 | 0.00 | C |
| ATOM | 127 | CB | SER | A | 18 | 17.042 | 20.053 | 23.723 | 0.00 | C |
| ATOM | 128 | CG | SER | A | 18 | 18.081 | 19.111 | 23.521 | 0.00 | O |
| ATOM | 129 | C | SER | A | 18 | 15.871 | 22.030 | 22.769 | 0.00 | C |
| ATOM | 130 | O | SER | A | 18 | 16.312 | 23.175 | 22.890 | 0.00 | O |
| ATOM | 131 | N | ILE | A | 19 | 14.584 | 21.728 | 22.892 | 0.00 | N |
| ATOM | 132 | CA | ILE | A | 19 | 13.582 | 22.737 | 23.195 | 0.00 | C |
| ATOM | 133 | CB | ILE | A | 19 | 12.150 | 22.152 | 23.125 | 0.00 | C |
| ATOM | 134 | CG2 | ILE | A | 19 | 11.133 | 23.215 | 23.532 | 0.00 | C |
| ATOM | 135 | CG1 | ILE | A | 19 | 11.852 | 21.634 | 21.715 | 0.00 | C |
| ATOM | 136 | CD1 | ILE | A | 19 | 11.832 | 22.709 | 20.655 | 0.00 | C |
| ATOM | 137 | C | ILE | A | 19 | 13.794 | 23.273 | 24.614 | 0.00 | C |
| ATOM | 138 | O | ILE | A | 19 | 14.070 | 22.505 | 25.545 | 0.00 | O |
| ATOM | 139 | N | GLY | A | 20 | 13.670 | 24.589 | 24.774 | 0.00 | N |
| ATOM | 140 | CA | GLY | A | 20 | 13.818 | 25.185 | 26.088 | 0.00 | C |
| ATOM | 141 | C | GLY | A | 20 | 12.443 | 25.203 | 26.722 | 0.00 | C |
| ATOM | 142 | O | GLY | A | 20 | 12.122 | 24.389 | 27.585 | 0.00 | O |
| ATOM | 143 | N | PHE | A | 21 | 11.616 | 26.137 | 26.274 | 0.00 | N |
| ATOM | 144 | CA | PHE | A | 21 | 10.253 | 26.258 | 26.763 | 0.00 | C |
| ATOM | 145 | CB | PHE | A | 21 | 10.196 | 27.160 | 27.992 | 0.00 | C |
| ATOM | 146 | CG | PHE | A | 21 | 10.855 | 26.559 | 29.195 | 0.00 | C |
| ATOM | 147 | CD1 | PHE | A | 21 | 10.269 | 25.491 | 29.857 | 0.00 | C |
| ATOM | 148 | CD2 | PHE | A | 21 | 12.086 | 27.025 | 29.638 | 0.00 | C |
| ATOM | 149 | CE1 | PHE | A | 21 | 10.898 | 24.898 | 30.936 | 0.00 | C |
| ATOM | 150 | CE2 | PHE | A | 21 | 12.713 | 26.435 | 30.715 | 0.00 | C |
| ATOM | 151 | CZ | PHE | A | 21 | 12.122 | 25.370 | 31.366 | 0.00 | C |
| ATOM | 152 | C | PHE | A | 21 | 9.391 | 26.825 | 25.664 | 0.00 | C |
| ATOM | 153 | O | PHE | A | 21 | 9.865 | 27.597 | 24.830 | 0.00 | O |
| ATOM | 154 | N | ALA | A | 22 | 8.131 | 26.413 | 25.646 | 0.00 | N |
| ATOM | 155 | CA | ALA | A | 22 | 7.194 | 26.882 | 24.647 | 0.00 | C |
| ATOM | 156 | CB | ALA | A | 22 | 6.014 | 25.915 | 24.533 | 0.00 | C |
| AT CM | 157 | C | ALA | A | 22 | 6.719 | 28.230 | 25.138 | 0.00 | C |
| ATOM | 158 | O | ALA | A | 22 | 6.416 | 28.388 | 26.320 | 0.00 | O |
| ATOM | 159 | N | VAL | A | 23 | 6.677 | 29.202 | 24.239 | 0.00 | N |
| ATOM | 160 | CA | VAL | A | 23 | 6.233 | 30.546 | 24.582 | 0.00 | C |
| ATOM | 161 | CB | VAL | A | 23 | 7.402 | 31.570 | 24.551 | 0.00 | C |

TABLE 20-1-continued

Atomic Coordinates of ASP with the Modeled Octapeptide Substrate

| ATOM | 162 | CG1 | VAL | A | 23 | 8.328 | 31.338 | 25.728 | 0.00 | C |
|---|---|---|---|---|---|---|---|---|---|---|
| ATOM | 163 | CG2 | VAL | A | 23 | 8.182 | 31.442 | 23.248 | 0.00 | C |
| ATOM | 164 | C | VAL | A | 23 | 5.206 | 30.945 | 23.545 | 0.00 | C |
| ATOM | 165 | O | VAL | A | 23 | 5.053 | 30.267 | 22.526 | 0.00 | O |
| ATOM | 166 | N | ASN | A | 24 | 4.495 | 32.036 | 23.791 | 0.00 | N |
| ATOM | 167 | CA | ASN | A | 24 | 3.492 | 32.476 | 22.832 | 0.00 | C |
| ATOM | 168 | CB | ASN | A | 24 | 2.807 | 33.759 | 23.328 | 0.00 | C |
| ATOM | 169 | C | ASN | A | 24 | 4.177 | 32.715 | 21.484 | 0.00 | C |
| ATOM | 170 | O | ASN | A | 24 | 5.050 | 33.576 | 21.365 | 0.00 | O |
| ATOM | 171 | CG | ASN | A | 24 | 3.737 | 34.963 | 23.334 | 0.00 | C |
| ATOM | 172 | OD1 | ASN | A | 24 | 4.697 | 35.029 | 24.107 | 0.00 | O |
| ATOM | 173 | ND2 | ASN | A | 24 | 3.451 | 35.927 | 22.462 | 0.00 | N |
| ATOM | 174 | N | GLY | A | 25 | 3.801 | 31.929 | 20.477 | 0.00 | N |
| ATOM | 175 | CA | GLY | A | 25 | 4.396 | 32.084 | 19.158 | 0.00 | C |
| ATOM | 176 | C | GLY | A | 25 | 5.503 | 31.104 | 18.788 | 0.00 | C |
| ATOM | 177 | O | GLY | A | 25 | 5.925 | 31.054 | 17.635 | 0.00 | O |
| ATOM | 178 | N | GLY | A | 26 | 5.989 | 30.327 | 19.748 | 0.00 | N |
| ATOM | 179 | CA | GLY | A | 26 | 7.043 | 29.377 | 19.433 | 0.00 | C |
| ATOM | 180 | C | GLY | A | 26 | 7.702 | 28.795 | 20.666 | 0.00 | C |
| ATOM | 181 | O | GLY | A | 26 | 7.028 | 28.328 | 21.582 | 0.00 | O |
| ATOM | 182 | N | PHE | A | 27 | 9.028 | 28.813 | 20.688 | 0.00 | N |
| ATOM | 183 | CA | PHE | A | 27 | 9.757 | 28.294 | 21.832 | 0.00 | C |
| ATOM | 184 | CB | PHE | A | 27 | 9.973 | 26.783 | 21.710 | 0.00 | C |
| ATOM | 185 | C | PHE | A | 27 | 11.103 | 28.975 | 21.954 | 0.00 | C |
| ATOM | 186 | O | PHE | A | 27 | 11.660 | 29.459 | 20.963 | 0.00 | O |
| ATOM | 187 | CG | PHE | A | 27 | 10.949 | 26.376 | 20.624 | 0.00 | C |
| ATOM | 188 | CD1 | PHE | A | 27 | 10.504 | 26.078 | 19.336 | 0.00 | C |
| ATOM | 189 | CD2 | PHE | A | 27 | 12.306 | 26.246 | 20.905 | 0.00 | C |
| ATOM | 190 | CE1 | PHE | A | 27 | 11.391 | 25.650 | 18.352 | 0.00 | C |
| ATOM | 191 | CE2 | PHE | A | 27 | 13.202 | 25.819 | 19.926 | 0.00 | C |
| ATOM | 192 | CZ | PHE | A | 27 | 12.742 | 25.518 | 18.648 | 0.00 | C |
| ATOM | 193 | H | ILE | A | 28 | 11.615 | 29.020 | 23.180 | 0.00 | N |
| ATOM | 194 | CA | ILE | A | 28 | 12.904 | 29.640 | 23.445 | 0.00 | C |
| ATOM | 195 | CB | ILE | A | 28 | 12.843 | 30.524 | 24.704 | 0.00 | C |
| ATOM | 196 | C | ILE | A | 28 | 13.953 | 28.542 | 23.603 | 0.00 | C |
| ATOM | 197 | O | ILE | A | 2R | 13.640 | 27.426 | 24.011 | 0.00 | O |
| ATOM | 198 | CG2 | ILE | A | 28 | 11.915 | 31.688 | 24.450 | 0.00 | C |
| ATOM | 199 | CG1 | ILE | A | 28 | 12.350 | 29.718 | 25.904 | 0.00 | C |
| ATOM | 200 | CD1 | ILE | A | 28 | 12.270 | 30.524 | 27.176 | 0.00 | C |
| ATOM | 201 | N | THR | A | 29 | 15.195 | 28.866 | 23.265 | 0.00 | N |
| ATOM | 202 | CA | THR | A | 29 | 16.293 | 27.916 | 23.353 | 0.00 | C |
| ATOM | 203 | CB | THR | A | 29 | 16.329 | 27.054 | 22.052 | 0.00 | C |
| ATOM | 204 | OG1 | THR | A | 29 | 17.423 | 26.126 | 22.095 | 0.00 | O |
| ATOM | 205 | CG2 | THR | A | 29 | 16.459 | 27.950 | 20.831 | 0.00 | C |
| ATOM | 206 | C | THR | A | 29 | 17.601 | 28.695 | 23.538 | 0.00 | C |
| ATOM | 207 | O | THR | A | 29 | 17.565 | 29.881 | 23.842 | 0.00 | O |
| ATOM | 208 | N | ALA | A | 30 | 18.743 | 28.029 | 23.362 | 0.00 | N |
| ATOM | 209 | CA | ALA | A | 30 | 20.059 | 28.662 | 23.510 | 0.00 | C |
| ATOM | 210 | CB | ALA | A | 30 | 21.121 | 27.601 | 23.765 | 0.00 | C |
| ATOM | 211 | C | ALA | A | 30 | 20.447 | 29.486 | 22.282 | 0.00 | C |
| ATOM | 212 | O | ALA | A | 30 | 20.232 | 29.061 | 21.141 | 0.00 | O |
| ATOM | 213 | N | GLY | A | 31 | 21.028 | 30.659 | 22.520 | 0.00 | N |
| ATOM | 214 | CA | GLY | A | 31 | 21.427 | 31.522 | 21.423 | 0.00 | C |
| ATOM | 215 | C | GLY | A | 31 | 22.508 | 30.942 | 20.528 | 0.00 | C |
| ATOM | 216 | O | GLY | A | 31 | 22.527 | 31.212 | 19.322 | 0.00 | O |
| ATOM | 217 | N | HIS | A | 32 | 23.410 | 30.143 | 21.099 | 0.00 | N |
| ATOM | 218 | CA | HIS | A | 32 | 24.490 | 29.558 | 20.310 | 0.00 | C |
| ATOM | 219 | CB | HIS | A | 32 | 25.648 | 29.091 | 21.215 | 0.00 | C |
| ATOM | 220 | CG | HIS | A | 32 | 25.412 | 27.772 | 21.885 | 0.00 | C |
| ATOM | 221 | CD2 | HIS | A | 32 | 24.715 | 27.451 | 23.001 | 0.00 | C |
| ATOM | 222 | ND1 | HIS | A | 32 | 25.946 | 26.589 | 21.419 | 0.00 | N |
| ATOM | 223 | CE1 | HIS | A | 32 | 25.590 | 25.601 | 22.216 | 0.00 | C |
| ATOM | 224 | NE2 | HIS | A | 32 | 24.842 | 26.098 | 23.188 | 0.00 | N |
| ATOM | 225 | C | HIS | A | 32 | 24.029 | 28.401 | 19.413 | 0.00 | C |
| ATOM | 226 | O | HIS | A | 32 | 24.805 | 27.870 | 18.630 | 0.00 | O |
| ATOM | 227 | N | CYS | A | 33 | 22.762 | 28.025 | 19.525 | 0.00 | N |
| ATOM | 228 | CA | CYS | A | 33 | 22.210 | 26.940 | 18.723 | 0.00 | C |
| ATOM | 229 | CB | CYS | A | 33 | 20.836 | 26.522 | 19.251 | 0.00 | C |
| ATOM | 230 | SG | CYS | A | 33 | 20.853 | 25.876 | 20.942 | 0.00 | S |
| ATOM | 231 | C | CYS | A | 33 | 22.062 | 27.395 | 17.283 | 0.00 | C |
| ATOM | 232 | O | CYS | A | 33 | 22.149 | 26.603 | 16.356 | 0.00 | O |
| ATOM | 233 | N | GLY | A | 34 | 21.822 | 28.680 | 17.095 | 0.00 | N |
| ATOM | 234 | CA | GLY | A | 34 | 21.664 | 29.181 | 15.749 | 0.00 | C |
| ATOM | 235 | C | GLY | A | 34 | 21.360 | 30.656 | 15.763 | 0.00 | C |
| ATOM | 236 | O | GLY | A | 34 | 20.984 | 31.213 | 16.794 | 0.00 | O |
| ATOM | 237 | N | ARG | A | 35 | 21.523 | 31.288 | 14.608 | 0.00 | N |
| ATOM | 238 | CA | ARG | A | 35 | 21.284 | 32.716 | 14.478 | 0.00 | C |
| ATOM | 239 | CB | ARG | A | 35 | 22.417 | 33.355 | 13.680 | 0.00 | C |

Table 20-1-continued

Atomic Coordinates of ASP with the Modeled Octapeptide Substrate

| | | | | | | | | | | |
|---|---|---|---|---|---|---|---|---|---|---|
| ATOM | 240 | C | ARG | A | 35 | 19.951 | 33.012 | 13.798 | 0.00 | C |
| ATOM | 241 | O | ARG | A | 35 | 19.348 | 32.138 | 13.173 | 0.00 | O |
| ATOM | 242 | CG | ARG | A | 35 | 22.437 | 32.937 | 12.219 | 0.00 | C |
| ATOM | 243 | CD | ARG | A | 35 | 23.488 | 33.715 | 11.458 | 0.00 | C |
| ATOM | 244 | NE | ARG | A | 35 | 24.832 | 33.237 | 11.755 | 0.00 | N1+ |
| ATOM | 245 | CZ | ARG | A | 35 | 25.406 | 32.207 | 11.139 | 0.00 | C |
| ATOM | 246 | NH1 | ARG | A | 35 | 26.634 | 31.832 | 11.471 | 0.00 | N |
| ATOM | 247 | NH2 | ARG | A | 35 | 24.759 | 31.559 | 10.178 | 0.00 | N |
| ATOM | 248 | N | THR | A | 36 | 19.513 | 34.258 | 13.918 | 0.00 | N |
| ATOM | 249 | CA | THR | A | 36 | 18.259 | 34.714 | 13.335 | 0.00 | C |
| ATOM | 250 | CB | THR | A | 36 | 18.124 | 36.242 | 13.522 | 0.00 | C |
| ATOM | 251 | C | THR | A | 36 | 18.161 | 34.353 | 11.856 | 0.00 | C |
| ATOM | 252 | O | THR | A | 36 | 19.123 | 34.512 | 11.099 | 0.00 | O |
| ATOM | 253 | OG1 | THR | A | 36 | 18.120 | 36.536 | 14.923 | 0.00 | O |
| ATOM | 254 | CG2 | THR | A | 36 | 16.844 | 36.773 | 12.880 | 0.00 | C |
| ATOM | 255 | N | GLY | A | 37 | 16.999 | 33.855 | 11.449 | 0.00 | N |
| ATOM | 256 | CA | GLY | A | 37 | 16.813 | 33.479 | 10.059 | 0.00 | C |
| ATOM | 257 | C | GLY | A | 37 | 17.046 | 32.001 | 9.799 | 0.00 | C |
| ATOM | 258 | O | GLY | A | 37 | 16.521 | 31.451 | 8.839 | 0.00 | O |
| ATOM | 259 | N | ALA | A | 38 | 17.842 | 31.349 | 10.640 | 0.00 | N |
| ATOM | 260 | CA | ALA | A | 38 | 18.095 | 29.924 | 10.470 | 0.00 | C |
| ATOM | 261 | C | ALA | A | 38 | 16.745 | 29.222 | 10.565 | 0.00 | C |
| ATOM | 262 | O | ALA | A | 38 | 15.881 | 29.657 | 11.324 | 0.00 | O |
| ATOM | 263 | CB | ALA | A | 38 | 19.026 | 29.426 | 11.566 | 0.00 | C |
| ATOM | 264 | N | THR | A | 39 | 16.553 | 28.151 | 9.800 | 0.00 | N |
| ATOM | 265 | CA | THR | A | 39 | 15.281 | 27.432 | 9.842 | 0.00 | C |
| ATOM | 266 | CB | THR | A | 39 | 14.779 | 27.066 | 8.425 | 0.00 | C |
| ATOM | 267 | OG1 | THR | A | 39 | 15.582 | 26.012 | 7.887 | 0.00 | O |
| ATOM | 268 | CG2 | THR | A | 39 | 14.857 | 28.277 | 7.504 | 0.00 | C |
| ATOM | 269 | C | THR | A | 39 | 15.433 | 26.157 | 10.664 | 0.00 | C |
| ATOM | 270 | O | THR | A | 39 | 16.533 | 25.637 | 10.821 | 0.00 | O |
| ATOM | 271 | N | THR | A | 40 | 14.328 | 25.649 | 11.186 | 0.00 | N |
| ATOM | 272 | CA | THR | A | 40 | 14.382 | 24.437 | 11.990 | 0.00 | C |
| ATOM | 273 | CB | THR | A | 40 | 14.143 | 24.753 | 13.473 | 0.00 | C |
| ATOM | 274 | OG1 | THR | A | 40 | 12.807 | 25.242 | 13.636 | 0.00 | O |
| ATOM | 275 | CG2 | THR | A | 40 | 15.124 | 25.799 | 13.962 | 0.00 | C |
| ATOM | 276 | C | THR | A | 40 | 13.332 | 23.421 | 11.581 | 0.00 | C |
| ATOM | 277 | O | THR | A | 40 | 12.345 | 23.760 | 10.927 | 0.00 | O |
| ATOM | 278 | N | ALA | A | 41 | 13.546 | 22.178 | 11.994 | 0.00 | N |
| ATOM | 279 | CA | ALA | A | 41 | 12.629 | 21.084 | 11.698 | 0.00 | C |
| ATOM | 280 | C | ALA | A | 41 | 12.368 | 20.368 | 13.030 | 0.00 | C |
| ATOM | 281 | O | ALA | A | 41 | 13.211 | 20.394 | 13.936 | 0.00 | O |
| ATOM | 282 | CB | ALA | A | 41 | 13.247 | 20.133 | 10.684 | 0.00 | C |
| ATOM | 283 | N | ASN | A | 42 | 11.206 | 19.734 | 13.149 | 0.00 | N |
| ATOM | 284 | CA | ASN | A | 42 | 10.839 | 19.022 | 14.370 | 0.00 | C |
| ATOM | 285 | C | ASN | A | 42 | 11.037 | 19.959 | 15.555 | 0.00 | C |
| ATOM | 286 | O | ASN | A | 42 | 11.861 | 19.693 | 16.424 | 0.00 | O |
| ATOM | 287 | CB | ASN | A | 42 | 11.720 | 17.780 | 14.584 | 0.00 | C |
| ATOM | 288 | CG | ASN | A | 42 | 11.686 | 16.812 | 13.408 | 0.00 | C |
| ATOM | 289 | OD1 | ASN | A | 42 | 10.687 | 16.713 | 12.695 | 0.00 | O |
| ATOM | 290 | ND2 | ASN | A | 42 | 12.779 | 16.076 | 13.217 | 0.00 | N |
| ATOM | 291 | N | PRO | A | 43 | 10.258 | 21.046 | 15.635 | 0.00 | N |
| ATOM | 292 | CA | PRO | A | 43 | 9.206 | 21.493 | 14.718 | 0.00 | C |
| ATOM | 293 | CB | PRO | A | 43 | 8.274 | 22.244 | 15.649 | 0.00 | C |
| ATOM | 294 | C | PRO | A | 43 | 9.697 | 22.416 | 13.612 | 0.00 | C |
| ATOM | 295 | O | PRO | A | 43 | 10.816 | 22.920 | 13.660 | 0.00 | O |
| ATOM | 296 | CD | PRO | A | 43 | 10.319 | 21.934 | 16.809 | 0.00 | C |
| ATOM | 297 | CG | PRO | A | 43 | 9.278 | 23.008 | 16.480 | 0.00 | C |
| ATOM | 298 | N | THR | A | 44 | 8.841 | 22.652 | 12.621 | 0.00 | N |
| ATOM | 299 | CA | THR | A | 44 | 9.208 | 23.533 | 11.522 | 0.00 | C |
| ATOM | 300 | CB | THR | A | 44 | 8.225 | 23.421 | 10.345 | 0.00 | C |
| ATOM | 301 | C | THR | A | 44 | 9.142 | 24.934 | 12.110 | 0.00 | C |
| ATOM | 302 | O | THR | A | 44 | 8.162 | 25.293 | 12.772 | 0.00 | O |
| ATOM | 303 | OG1 | THR | A | 44 | 8.437 | 22.176 | 9.671 | 0.00 | O |
| ATOM | 304 | CG2 | THR | A | 44 | 8.423 | 24.566 | 9.366 | 0.00 | C |
| ATOM | 305 | N | GLY | A | 45 | 10.196 | 25.710 | 11.893 | 0.00 | N |
| ATOM | 306 | CA | GLY | A | 45 | 10.233 | 27.057 | 12.425 | 0.00 | C |
| ATOM | 307 | C | GLY | A | 45 | 11.421 | 27.851 | 11.920 | 0.00 | C |
| ATOM | 308 | O | GLY | A | 45 | 12.226 | 27.355 | 11.120 | 0.00 | O |
| ATOM | 309 | N | THR | A | 46 | 11.537 | 29.084 | 12.401 | 0.00 | N |
| ATOM | 310 | CA | THR | A | 46 | 12.615 | 29.979 | 11.998 | 0.00 | C |
| ATOM | 311 | CB | THR | A | 46 | 12.134 | 30.919 | 10.867 | 0.00 | C |
| ATOM | 312 | OG1 | THR | A | 46 | 11.720 | 30.132 | 9.741 | 0.00 | O |
| ATOM | 313 | CG2 | THR | A | 46 | 13.246 | 31.872 | 10.438 | 0.00 | C |
| ATOM | 314 | C | THR | A | 46 | 13.097 | 30.831 | 13.171 | 0.00 | C |
| ATOM | 315 | O | THR | A | 46 | 12.287 | 31.407 | 13.909 | 0.00 | O |
| ATOM | 316 | N | PHE | A | 47 | 14.412 | 30.903 | 13.358 | 0.00 | N |
| ATOM | 317 | CA | PHE | A | 47 | 14.954 | 31.702 | 14.451 | 0.00 | C |

Table 20-1-continued

Atomic Coordinates of ASP with the Modeled Octapeptide Substrate

| ATOM | 318 | CB | PHE | A | 47 | 16.478 | 31.585 | 14.530 | 0.00 | C |
|---|---|---|---|---|---|---|---|---|---|---|
| ATOM | 319 | CG | PHE | A | 47 | 16.959 | 30.410 | 15.339 | 0.00 | C |
| ATOM | 320 | CD2 | PHE | A | 47 | 17.538 | 30.606 | 16.590 | 0.00 | C |
| ATOM | 321 | CD1 | PHE | A | 47 | 16.843 | 29.115 | 14.857 | 0.00 | C |
| ATOM | 322 | CE2 | PHE | A | 47 | 17.996 | 29.532 | 17.345 | 0.00 | C |
| ATOM | 323 | CE1 | PHE | A | 47 | 17.300 | 28.030 | 15.608 | 0.00 | C |
| ATOM | 324 | CZ | PHE | A | 47 | 17.878 | 26.241 | 16.855 | 0.00 | C |
| ATOM | 325 | C | PHE | A | 47 | 14.567 | 33.160 | 14.226 | 0.00 | C |
| ATOM | 326 | O | PHE | A | 47 | 14.665 | 33.686 | 13.111 | 0.00 | O |
| ATOM | 327 | N | ALA | A | 46 | 14.102 | 33.795 | 15.291 | 0.00 | N |
| ATOM | 328 | CA | ALA | A | 48 | 13.690 | 35.184 | 15.245 | 0.00 | C |
| ATOM | 329 | CB | ALA | A | 48 | 12.161 | 35.280 | 15.133 | 0.00 | C |
| ATOM | 330 | C | ALA | A | 48 | 14.174 | 35.828 | 16.532 | 0.00 | C |
| ATOM | 331 | O | ALA | A | 48 | 13.389 | 36.116 | 17.433 | 0.00 | O |
| ATOM | 332 | N | GLY | A | 49 | 15.481 | 36.038 | 16.609 | 0.00 | N |
| ATOM | 333 | CA | GLY | A | 49 | 16.072 | 36.635 | 17.791 | 0.00 | C |
| ATOM | 334 | C | GLY | A | 49 | 17.068 | 35.674 | 18.415 | 0.00 | C |
| ATOM | 335 | O | GLY | A | 49 | 16.698 | 34.589 | 18.867 | 0.00 | O |
| ATOM | 336 | N | SER | A | 50 | 18.333 | 36.073 | 18.438 | 0.00 | N |
| ATOM | 337 | CA | SER | A | 50 | 19.387 | 35.248 | 18.999 | 0.00 | C |
| ATOM | 338 | CB | SER | A | 50 | 19.976 | 34.360 | 17.899 | 0.00 | C |
| ATOM | 339 | OG | SER | A | 50 | 21.019 | 33.552 | 18.406 | 0.00 | O |
| ATOM | 340 | C | SER | A | 50 | 20.484 | 36.112 | 19.633 | 0.00 | C |
| ATOM | 341 | O | SER | A | 50 | 20.999 | 37.045 | 19.012 | 0.00 | O |
| ATOM | 342 | N | SER | A | 51 | 20.832 | 35.794 | 20.877 | 0.00 | N |
| ATOM | 343 | CA | SER | A | 51 | 21.860 | 36.529 | 21.603 | 0.00 | C |
| ATOM | 344 | CB | SER | A | 51 | 21.228 | 37.337 | 22.741 | 0.00 | C |
| ATOM | 345 | OG | SER | A | 51 | 22.179 | 38.189 | 23.359 | 0.00 | O |
| ATOM | 346 | C | SER | A | 53 | 22.938 | 35.596 | 22.162 | 0.00 | C |
| ATOM | 347 | O | SER | A | 51 | 22.700 | 34.819 | 22.089 | 0.00 | O |
| ATOM | 348 | N | PHE | A | 52 | 24.127 | 35.692 | 21.579 | 0.00 | N |
| ATOM | 349 | CA | PHE | A | 52 | 25.277 | 34.869 | 21.970 | 0.00 | C |
| ATOM | 350 | CB | PHE | A | 52 | 25.031 | 33.414 | 21.643 | 0.00 | C |
| ATOM | 351 | CG | PHE | A | 52 | 26.204 | 32.518 | 21.941 | 0.00 | C |
| ATOM | 352 | CD1 | PHE | A | 52 | 26.485 | 32.124 | 23.238 | 0.00 | C |
| ATOM | 353 | CD2 | PHE | A | 52 | 27.034 | 32.081 | 20.922 | 0.00 | C |
| ATOM | 354 | CE1 | PHE | A | 52 | 27.575 | 31.312 | 23.516 | 0.00 | C |
| ATOM | 355 | CE2 | PHE | A | 52 | 28.131 | 31.266 | 21.193 | 0.00 | C |
| ATOM | 356 | CZ | PHE | A | 52 | 28.400 | 30.883 | 27.492 | 0.00 | C |
| ATOM | 357 | C | PHE | A | 52 | 26.468 | 35.390 | 21.167 | 0.00 | C |
| ATOM | 358 | O | PHE | A | 52 | 26.370 | 35.589 | 19.960 | 0.00 | C |
| ATOM | 359 | N | PRO | A | 53 | 27.612 | 35.603 | 21.827 | 0.00 | N |
| ATOM | 360 | CD | PRO | A | 53 | 28.893 | 35.756 | 21.110 | 0.00 | C |
| ATOM | 361 | CA | PRO | A | 53 | 27.831 | 35.405 | 23.266 | 0.00 | C |
| ATOM | 362 | CB | PRO | A | 53 | 29.351 | 35.249 | 23.361 | 0.00 | C |
| ATOM | 363 | CG | PRO | A | 53 | 29.851 | 36.088 | 22.223 | 0.00 | C |
| ATOM | 364 | C | PRO | A | 53 | 27.268 | 36.543 | 24.132 | 0.00 | C |
| ATOM | 365 | O | PRO | A | 53 | 26.346 | 37.235 | 23.713 | 0.00 | O |
| ATOM | 366 | N | GLY | A | 54 | 27.814 | 36.744 | 25.328 | 0.00 | N |
| ATOM | 367 | CA | GLY | A | 54 | 27.288 | 37.777 | 26.211 | 0.00 | C |
| ATOM | 368 | C | GLY | A | 54 | 26.143 | 37.138 | 26.980 | 0.00 | C |
| ATOM | 369 | O | GLY | A | 54 | 26.210 | 36.964 | 28.197 | 0.00 | O |
| ATOM | 370 | N | ASN | A | 55 | 25.079 | 36.806 | 26.254 | 0.00 | N |
| ATOM | 371 | CA | ASN | A | 55 | 23.922 | 36.103 | 26.810 | 0.00 | C |
| ATOM | 372 | CB | ASN | A | 55 | 22.579 | 36.740 | 26.404 | 0.00 | C |
| ATOM | 373 | CG | ASN | A | 55 | 22.516 | 38.240 | 26.641 | 0.00 | C |
| ATOM | 374 | OD1 | ASN | A | 55 | 22.161 | 39.005 | 25.734 | 0.00 | O |
| ATOM | 375 | ND2 | ASN | A | 55 | 22.833 | 38.667 | 27.857 | 0.00 | N |
| ATOM | 376 | C | ASN | A | 55 | 24.011 | 34.788 | 26.037 | 0.00 | C |
| ATOM | 377 | O | ASN | A | 55 | 24.998 | 34.538 | 25.333 | 0.00 | O |
| ATOM | 378 | N | ASP | A | 56 | 22.980 | 33.958 | 26.171 | 0.00 | N |
| ATOM | 379 | CA | ASP | A | 56 | 22.917 | 32.682 | 25.473 | 0.00 | C |
| ATOM | 380 | CB | ASP | A | 56 | 23.774 | 31.595 | 26.119 | 0.00 | C |
| ATOM | 381 | CG | ASP | A | 56 | 23.987 | 30.395 | 25.179 | 0.00 | C |
| ATOM | 382 | OD1 | ASP | A | 56 | 24.631 | 29.408 | 25.585 | 0.00 | O |
| ATOM | 383 | OD2 | ASP | A | 56 | 23.504 | 30.443 | 24.024 | 0.00 | O1− |
| ATOM | 384 | C | ASP | A | 56 | 21.470 | 32.221 | 25.379 | 0.00 | C |
| ATOM | 385 | O | ASP | A | 56 | 21.078 | 31.195 | 25.930 | 0.00 | O |
| ATOM | 386 | N | TYR | A | 57 | 20.672 | 33.008 | 24.671 | 0.00 | N |
| ATOM | 387 | CA | TYR | A | 57 | 19.266 | 32.693 | 24.485 | 0.00 | C |
| ATOM | 388 | CB | TYR | A | 57 | 18.396 | 33.484 | 25.463 | 0.00 | C |
| ATOM | 389 | CG | TYR | A | 57 | 18.527 | 34.993 | 25.374 | 0.00 | C |
| ATOM | 390 | CD1 | TYR | A | 57 | 19.153 | 35.711 | 26.390 | 0.00 | C |
| ATOM | 391 | CE1 | TYR | A | 57 | 19.231 | 37.092 | 26.352 | 0.00 | C |
| ATOM | 392 | CD2 | TYR | A | 57 | 17.986 | 35.706 | 24.303 | 0.00 | C |
| ATOM | 393 | CE2 | TYR | A | 57 | 18.060 | 37.093 | 24.255 | 0.00 | C |
| ATOM | 394 | CZ | TYR | A | 57 | 18.682 | 37.781 | 25.289 | 0.00 | C |
| ATOM | 395 | OH | TYR | A | 57 | 18.732 | 39.165 | 25.286 | 0.00 | O |

Table 20-1-continued

Atomic Coordinates of ASP with the Modeled Octapeptide Substrate

| ATOM | 396 | C | TYR | A | 57 | 18.820 | 32.998 | 23.062 | 0.00 | C |
|---|---|---|---|---|---|---|---|---|---|---|
| ATOM | 397 | O | TYR | A | 57 | 19.438 | 33.800 | 22.355 | 0.00 | O |
| ATOM | 398 | N | ALA | A | 58 | 17.742 | 32.344 | 22.652 | 0.00 | N |
| ATOM | 399 | CA | ALA | A | 58 | 17.187 | 32.532 | 21.323 | 0.00 | C |
| ATOM | 400 | CB | ALA | A | 58 | 17.899 | 31.645 | 20.312 | 0.00 | C |
| ATOM | 401 | C | ALA | A | 58 | 15.706 | 32.191 | 21.360 | 0.00 | C |
| ATOM | 402 | O | ALA | A | 58 | 15.228 | 31.521 | 22.284 | 0.00 | O |
| ATOM | 403 | N | PHE | A | 59 | 14.989 | 32.683 | 20.359 | 0.00 | N |
| ATOM | 404 | CA | PHE | A | 59 | 13.564 | 32.453 | 20.225 | 0.00 | C |
| ATOM | 405 | CB | PHE | A | 59 | 12.762 | 33.735 | 20.438 | 0.00 | C |
| ATOM | 406 | CO | PHE | A | 59 | 11.333 | 33.629 | 19.970 | 0.00 | C |
| ATOM | 407 | CD2 | PHE | A | 59 | 10.859 | 34.437 | 18.947 | 0.00 | C |
| ATOM | 408 | CD1 | PHE | A | 59 | 10.475 | 32.698 | 20.531 | 0.00 | C |
| ATOM | 409 | CE2 | PHE | A | 59 | 9.553 | 34.316 | 18.491 | 0.00 | C |
| ATOM | 410 | CE1 | PHE | A | 59 | 9.175 | 32.573 | 20.084 | 0.00 | C |
| ATOM | 411 | CZ | PHE | A | 59 | 8.712 | 33.382 | 19.063 | 0.00 | C |
| ATOM | 412 | C | PHE | A | 59 | 13.294 | 31.942 | 18.816 | 0.00 | C |
| ATOM | 413 | O | PHE | A | 59 | 13.693 | 32.562 | 17.820 | 0.00 | O |
| ATOM | 414 | N | VAL | A | 60 | 12.616 | 30.809 | 18.731 | 0.00 | N |
| ATOM | 415 | CA | VAL | A | 60 | 12.308 | 30.253 | 17.434 | 0.00 | C |
| ATOM | 416 | CB | VAL | A | 60 | 12.702 | 28.776 | 17.340 | 0.00 | C |
| ATOM | 417 | CG1 | VAL | A | 60 | 12.503 | 28.279 | 15.908 | 0.00 | C |
| ATOM | 418 | CG2 | VAL | A | 60 | 14.147 | 28.593 | 17.796 | 0.00 | C |
| ATOM | 419 | C | VAL | A | 60 | 10.816 | 30.361 | 17.236 | 0.00 | C |
| ATOM | 420 | O | VAL | A | 60 | 10.043 | 29.927 | 18.087 | 0.00 | O |
| ATOM | 421 | N | ARG | A | 61 | 10.406 | 30.960 | 16.126 | 0.00 | N |
| ATOM | 422 | CA | APR | A | 61 | 8.987 | 31.098 | 15.851 | 0.00 | C |
| ATOM | 423 | CB | ARG | A | 61 | 8.704 | 32.313 | 14.962 | 0.00 | C |
| ATOM | 424 | CG | ARG | A | 61 | 7.255 | 32.374 | 14.430 | 0.00 | C |
| ATOM | 425 | CD | ARG | A | 61 | 7.019 | 33.543 | 13.521 | 0.00 | C |
| ATOM | 426 | NE | ARG | A | 61 | 5.615 | 33.660 | 13.118 | 0.00 | N1+ |
| ATOM | 427 | CZ | ARG | A | 61 | 4.989 | 32.815 | 12.303 | 0.00 | C |
| ATOM | 428 | NH2 | ARG | A | 61 | 3.711 | 33.007 | 12.004 | 0.00 | N |
| ATOM | 429 | NH1 | ARG | A | 61 | 5.636 | 31.777 | 11.787 | 0.00 | N |
| ATOM | 430 | C | ARG | A | 61 | 8.509 | 29.847 | 15.128 | 0.00 | C |
| ATOM | 431 | O | ARG | A | 61 | 9.193 | 29.338 | 14.238 | 0.00 | O |
| ATOM | 432 | N | THR | A | 62 | 7.338 | 29.357 | 15.527 | 0.00 | N |
| ATOM | 433 | CA | THR | A | 62 | 6.740 | 28.170 | 14.923 | 0.00 | C |
| ATOM | 434 | CB | THR | A | 62 | 6.514 | 27.046 | 15.956 | 0.00 | C |
| ATOM | 435 | OG1 | THR | A | 62 | 5.808 | 27.570 | 17.089 | 0.00 | O |
| ATOM | 436 | CG2 | THR | A | 62 | 7.845 | 26.460 | 16.396 | 0.00 | C |
| ATOM | 437 | C | THR | A | 62 | 5.391 | 28.597 | 14.352 | 0.00 | C |
| ATOM | 438 | O | THR | A | 62 | 4.857 | 29.645 | 14.724 | 0.00 | O |
| ATOM | 439 | N | GLY | A | 63 | 4.837 | 27.791 | 13.455 | 0.00 | N |
| ATOM | 440 | CA | GLY | A | 63 | 3.562 | 28.146 | 12.859 | 0.00 | C |
| ATOM | 441 | C | GLY | A | 63 | 2.522 | 27.046 | 12.880 | 0.00 | C |
| ATOM | 442 | O | GLY | A | 63 | 2.375 | 26.326 | 13.873 | 0.00 | O |
| ATOM | 443 | N | ALA | A | 64 | 1.806 | 26.909 | 11.767 | 0.00 | N |
| ATOM | 444 | CA | ALA | A | 64 | 0.744 | 25.916 | 11.643 | 0.00 | C |
| ATOM | 445 | C | ALA | A | 64 | 1.213 | 24.496 | 11.895 | 0.00 | C |
| ATOM | 446 | O | ALA | A | 64 | 2.370 | 24.154 | 11.651 | 0.00 | O |
| ATOM | 447 | CB | ALA | A | 64 | 0.111 | 26.009 | 10.268 | 0.00 | C |
| ATOM | 448 | N | GLY | A | 65 | 0.291 | 23.672 | 12.381 | 0.00 | N |
| ATOM | 449 | CA | GLY | A | 65 | 0.596 | 22.281 | 12.657 | 0.00 | C |
| ATOM | 450 | C | GLY | A | 65 | 1.469 | 22.050 | 13.877 | 0.00 | C |
| ATOM | 451 | O | GLY | A | 65 | 1.797 | 20.908 | 14.199 | 0.00 | O |
| ATOM | 452 | N | VAL | A | 66 | 1.837 | 23.119 | 14.572 | 0.00 | N |
| ATOM | 453 | CA | VAL | A | 66 | 2.699 | 22.976 | 15.736 | 0.00 | C |
| ATOM | 454 | CB | VAL | A | 66 | 3.946 | 23.854 | 15.595 | 0.00 | C |
| ATOM | 455 | C | VAL | A | 66 | 2.031 | 23.307 | 17.063 | 0.00 | C |
| ATOM | 456 | O | VAL | A | 66 | 1.737 | 24.467 | 17.337 | 0.00 | O |
| ATOM | 457 | CGI | VAL | A | 66 | 4.832 | 23.683 | 16.818 | 0.00 | C |
| ATOM | 458 | CG2 | VAL | A | 66 | 4.698 | 23.482 | 14.324 | 0.00 | C |
| ATOM | 459 | N | ASN | A | 67 | 1.806 | 22.283 | 17.882 | 0.00 | N |
| ATOM | 460 | CA | ASN | A | 67 | 1.176 | 22.454 | 19.185 | 0.00 | C |
| ATOM | 461 | CB | ASN | A | 67 | 0.403 | 21.188 | 19.564 | 0.00 | C |
| ATOM | 462 | C | ASN | A | 67 | 2.240 | 22.745 | 20.237 | 0.00 | C |
| ATOM | 463 | O | ASN | A | 67 | 3.120 | 21.920 | 20.491 | 0.00 | O |
| ATOM | 464 | CG | ASN | A | 67 | −0.405 | 20.634 | 18.404 | 0.00 | C |
| ATOM | 465 | OD1 | ASN | A | 67 | −1.160 | 21.361 | 17.750 | 0.00 | O |
| ATOM | 466 | ND2 | ASN | A | 67 | −0.253 | 19.340 | 18.140 | 0.00 | N |
| ATOM | 467 | N | LEU | A | 68 | 2.148 | 23.923 | 20.845 | 0.00 | N |
| ATOM | 468 | CA | LEU | A | 68 | 3.087 | 24.366 | 21.876 | 0.00 | C |
| ATOM | 469 | CB | LEU | A | 68 | 3.279 | 25.883 | 21.759 | 0.00 | C |
| ATOM | 470 | C | LEU | A | 68 | 2.571 | 23.996 | 23.273 | 0.00 | C |
| ATOM | 471 | O | LEU | A | 68 | 1.620 | 24.597 | 23.770 | 0.00 | O |
| ATOM | 472 | CG | LEU | A | 68 | 3.688 | 26.430 | 20.380 | 0.00 | C |
| ATOM | 473 | CD1 | LEU | A | 68 | 3.724 | 27.950 | 20.406 | 0.00 | C |

Table 20-1-continued

Atomic Coordinates of ASP with the Modeled Octapeptide Substrate

| ATOM | 474 | CD2 | LEU | A | 68 | 5.051 | 25.888 | 19.987 | 0.00 | C |
|---|---|---|---|---|---|---|---|---|---|---|
| ATOM | 475 | N | LEU | A | 69 | 3.218 | 23.027 | 23.917 | 0.00 | N |
| ATOM | 476 | CA | LEU | A | 69 | 2.803 | 22.584 | 25.250 | 0.00 | C |
| ATOM | 477 | CB | LEU | A | 69 | 2.769 | 21.052 | 25.286 | 0.00 | C |
| ATOM | 478 | CG | LEU | A | 69 | 2.045 | 20.369 | 24.116 | 0.00 | C |
| ATOM | 479 | CD1 | LEU | A | 69 | 2.109 | 18.857 | 24.274 | 0.00 | C |
| ATOM | 460 | CD2 | LEU | A | 69 | 0.604 | 20.841 | 24.050 | 0.00 | C |
| ATOM | 481 | C | LEU | A | 69 | 3.612 | 23.078 | 26.449 | 0.00 | C |
| ATOM | 482 | O | LEU | A | 69 | 4.635 | 23.216 | 26.394 | 0.00 | O |
| ATOM | 483 | N | ALA | A | 70 | 2.907 | 23.332 | 27.544 | 0.00 | N |
| ATOM | 484 | CA | ALA | A | 70 | 3.534 | 23.796 | 28.773 | 0.00 | C |
| ATOM | 485 | CB | ALA | A | 70 | 2.507 | 24.496 | 29.646 | 0.00 | C |
| ATOM | 486 | C | ALA | A | 70 | 4.048 | 22.539 | 29.473 | 0.00 | C |
| ATOM | 487 | O | ALA | A | 70 | 3.712 | 22.273 | 30.618 | 0.00 | O |
| ATOM | 488 | N | GLN | A | 71 | 4.862 | 21.763 | 28.770 | 0.00 | N |
| ATOM | 489 | CA | GLN | A | 71 | 5.408 | 20.536 | 29.325 | 0.00 | C |
| ATOM | 490 | CB | GLN | A | 71 | 4.618 | 19.333 | 28.808 | 0.00 | C |
| ATOM | 491 | CG | GLN | A | 71 | 3.169 | 19.299 | 29.255 | 0.00 | C |
| ATOM | 492 | CD | GLN | A | 71 | 2.407 | 18.116 | 28.692 | 0.00 | C |
| ATOM | 493 | OE1 | GLN | A | 71 | 1.460 | 17.634 | 29.308 | 0.00 | O |
| ATOM | 494 | NE2 | GLN | A | 71 | 2.809 | 17.646 | 27.515 | 0.00 | N |
| ATOM | 495 | C | GLN | A | 71 | 6.869 | 20.310 | 28.998 | 0.00 | C |
| ATOM | 496 | O | GLN | A | 71 | 7.395 | 20.825 | 28.009 | 0.00 | O |
| ATOM | 497 | N | VAL | A | 72 | 7.520 | 19.529 | 29.850 | 0.00 | N |
| ATOM | 498 | CA | VAL | A | 12 | 8.924 | 19.199 | 29.676 | 0.00 | C |
| ATOM | 499 | CB | VAL | A | 12 | 9.809 | 19.799 | 30.777 | 0.00 | C |
| ATOM | 500 | CG1 | VAL | A | 72 | 11.240 | 19.342 | 30.580 | 0.00 | C |
| ATOM | 501 | CG2 | VAL | A | 72 | 9.726 | 21.309 | 30.758 | 0.00 | C |
| ATOM | 502 | C | VAL | A | 72 | 8.997 | 17.685 | 29.772 | 0.00 | C |
| ATOM | 503 | O | VAL | A | 72 | 8.419 | 17.086 | 30.680 | 0.00 | O |
| ATOM | 504 | N | ASN | A | 73 | 9.699 | 17.075 | 28.824 | 0.00 | N |
| ATOM | 505 | CA | ASN | A | 73 | 9.867 | 15.629 | 28.771 | 0.00 | C |
| ATOM | 506 | CB | ASN | A | 73 | 10.543 | 15.250 | 27.452 | 0.00 | C |
| ATOM | 507 | CG | ASN | A | 73 | 10.513 | 13.756 | 27.182 | 0.00 | C |
| ATOM | 508 | OD1 | ASN | A | 73 | 10.470 | 12.947 | 28.106 | 0.00 | O |
| ATOM | 509 | ND2 | ASN | A | 73 | 10.551 | 13.387 | 25.906 | 0.00 | N |
| ATOM | 510 | C | ASN | A | 73 | 10.735 | 15.146 | 29.931 | 0.00 | C |
| ATOM | 511 | O | ASN | A | 73 | 11.843 | 15.651 | 30.123 | 0.00 | O |
| ATOM | 512 | N | ASN | A | 74 | 10.244 | 14.175 | 30.703 | 0.00 | N |
| ATOM | 513 | CA | ASN | A | 74 | 11.028 | 13.663 | 31.823 | 0.00 | C |
| ATOM | 514 | CB | ASN | A | 74 | 10.151 | 13.368 | 33.049 | 0.00 | C |
| ATOM | 515 | CG | ASN | A | 74 | 9.191 | 12.217 | 32.830 | 0.00 | C |
| ATOM | 516 | OD1 | ASN | A | 74 | 9.486 | 11.265 | 32.108 | 0.00 | O |
| ATOM | 517 | ND2 | ASN | A | 74 | 8.032 | 12.291 | 33.477 | 0.00 | N |
| ATOM | 518 | C | ASN | A | 74 | 11.791 | 12.408 | 31.417 | 0.00 | C |
| ATOM | 519 | O | ASN | A | 74 | 12.332 | 11.695 | 32.266 | 0.00 | O |
| ATOM | 520 | N | TYR | A | 75 | 11.830 | 12.156 | 30.112 | 0.00 | N |
| ATOM | 521 | CA | TYR | A | 75 | 12.514 | 11.005 | 29.528 | 0.00 | C |
| ATOM | 522 | CB | TYR | A | 75 | 14.008 | 11.321 | 29.354 | 0.00 | C |
| ATOM | 523 | CG | TYR | A | 75 | 14.268 | 12.239 | 28.181 | 0.00 | C |
| ATOM | 524 | CD1 | TYR | A | 75 | 14.228 | 11.756 | 26.873 | 0.00 | C |
| ATOM | 525 | CE1 | TYR | A | 75 | 14.371 | 12.597 | 25.792 | 0.00 | C |
| ATOM | 526 | CD2 | TYR | A | 75 | 14.466 | 13.599 | 28.370 | 0.00 | C |
| ATOM | 527 | CE2 | TYR | A | 75 | 14.608 | 14.451 | 27.290 | 0.00 | C |
| ATOM | 528 | CZ | TYR | A | 75 | 14.557 | 13.945 | 26.005 | 0.00 | C |
| ATOM | 529 | OH | TYR | A | 75 | 14.679 | 14.796 | 24.931 | 0.00 | O |
| ATOM | 530 | C | TYR | A | 75 | 12.326 | 9.680 | 30.260 | 0.00 | C |
| ATOM | 531 | O | TYR | A | 75 | 13.253 | 8.875 | 30.378 | 0.00 | O |
| ATOM | 532 | N | SER | A | 76 | 11.112 | 9.464 | 30.747 | 0.00 | N |
| ATOM | 533 | CA | SER | A | 76 | 10.773 | 8.244 | 31.458 | 0.00 | C |
| ATOM | 534 | CB | SER | A | 76 | 10.737 | 8.471 | 32.968 | 0.00 | C |
| ATOM | 535 | OG | SER | A | 76 | 12.053 | 8.566 | 33.47S | 0.00 | O |
| ATOM | 536 | C | SER | A | 76 | 9.407 | 7.816 | 30.963 | 0.00 | C |
| ATOM | 537 | O | SER | A | 76 | 8.784 | 6.905 | 31.512 | 0.00 | O |
| ATOM | 538 | N | GLY | A | 77 | 8.960 | 8.483 | 29.905 | 0.00 | N |
| ATOM | 539 | CA | GLY | A | 77 | 7.671 | 8.180 | 29.320 | 0.00 | C |
| ATOM | 540 | C | GLY | A | 77 | 6.610 | 9.168 | 29.755 | 0.00 | C |
| ATOM | 541 | O | GLY | A | 77 | 5.464 | 9.090 | 29.311 | 0.00 | O |
| ATOM | 542 | N | GLY | A | 78 | 6.992 | 10.102 | 30.622 | 0.00 | N |
| ATOM | 543 | CA | GLY | A | 78 | 6.043 | 11.087 | 31.101 | 0.00 | C |
| ATOM | 544 | C | GLY | A | 78 | 6.492 | 12.522 | 30.887 | 0.00 | C |
| ATOM | 545 | O | GLY | A | 78 | 7.545 | 12.775 | 30.293 | 0.00 | O |
| ATOM | 546 | N | ARG | A | 79 | 5.681 | 13.462 | 31.315 | 0.00 | N |
| ATOM | 547 | CA | ARG | A | 79 | 5.986 | 14.879 | 31.240 | 0.00 | C |
| ATOM | 548 | CB | ARG | A | 79 | 5.099 | 15.537 | 30.166 | 0.00 | C |
| ATOM | 549 | CG | ARG | A | 75 | 5.356 | 15.117 | 20.732 | 0.00 | C |
| ATOM | 550 | CD | ARG | A | 79 | 4.770 | 13.772 | 28.432 | 0.00 | C |
| ATOM | 551 | NE | ARG | A | 79 | 4.975 | 13.348 | 27.048 | 0.00 | N1+ |

Table 20-1-continued

Atomic Coordinates of ASP with the Modeled Octapeptide Substrate

| ATOM | 552 | CZ | ARG | A | 79 | 6.081 | 12.764 | 26.593 | 0.00 | C |
|---|---|---|---|---|---|---|---|---|---|---|
| ATOM | 553 | NH1 | ARG | A | 79 | 7.095 | 12.529 | 27.412 | 0.00 | N |
| ATOM | 554 | NH2 | ARG | A | 79 | 6.165 | 12.399 | 25.319 | 0.00 | N |
| ATOM | 555 | C | ARG | A | 79 | 5.797 | 15.627 | 32.550 | 0.00 | C |
| ATOM | 556 | O | ARG | A | 79 | 5.129 | 15.149 | 33.466 | 0.00 | O |
| ATOM | 557 | N | VAL | A | 80 | 6.398 | 16.809 | 32.620 | 0.00 | N |
| ATOM | 558 | CA | VAL | A | 80 | 6.317 | 17.656 | 33.794 | 0.00 | C |
| ATOM | 559 | CB | VAL | A | 80 | 7.714 | 17.891 | 34.389 | 0.00 | C |
| ATOM | 560 | CG1 | VAL | A | 80 | 7.630 | 18.858 | 35.546 | 0.00 | C |
| ATOM | 561 | CG2 | VAL | A | 80 | 8.300 | 16.566 | 34.853 | 0.00 | C |
| ATOM | 562 | C | VAL | A | 80 | 5.682 | 18.989 | 33.398 | 0.00 | C |
| ATOM | 563 | O | VAL | A | 80 | 6.182 | 19.701 | 32.517 | 0.00 | O |
| ATOM | 564 | N | GLN | A | 81 | 4.561 | 19.307 | 34.036 | 0.00 | N |
| ATOM | 565 | CA | GLN | A | 81 | 3.846 | 20.546 | 33.760 | 0.00 | C |
| ATOM | 566 | CB | GLN | A | 81 | 2.516 | 20.579 | 34.527 | 0.00 | C |
| ATOM | 567 | CG | GLN | A | 81 | 1.415 | 19.722 | 33.930 | 0.00 | C |
| ATOM | 568 | CD | GLN | A | 81 | 1.138 | 20.067 | 32.473 | 0.00 | C |
| ATOM | 569 | OE1 | GLN | A | 81 | 1.086 | 21.239 | 32.101 | 0.00 | O |
| ATOM | 570 | NE2 | GLN | A | 81 | 0.950 | 19.044 | 31.644 | 0.00 | N |
| ATOM | 571 | C | GLN | A | 81 | 4.650 | 21.785 | 34.126 | 0.00 | C |
| ATOM | 572 | O | GLN | A | 81 | 5.333 | 21.817 | 35.154 | 0.00 | O |
| ATOM | 573 | N | VAL | A | 82 | 4.578 | 22.798 | 33.272 | 0.00 | N |
| ATOM | 574 | CA | VAL | A | 82 | 5.288 | 24.047 | 33.510 | 0.00 | C |
| ATOM | 575 | CB | VAL | A | 82 | 5.925 | 24.610 | 32.219 | 0.00 | C |
| ATOM | 576 | CG1 | VAL | A | 82 | 6.695 | 25.885 | 32.535 | 0.00 | C |
| ATOM | 577 | CG2 | VAL | A | 82 | 6.841 | 23.580 | 31.605 | 0.00 | C |
| ATOM | 578 | C | VAL | A | 82 | 4.222 | 25.022 | 34.003 | 0.00 | C |
| ATOM | 579 | O | VAL | A | 82 | 3.399 | 25.500 | 33.221 | 0.00 | O |
| ATOM | 580 | N | ALA | A | 83 | 4.242 | 25.305 | 35.302 | 0.00 | N |
| ATOM | 581 | CA | ALA | A | 83 | 3.277 | 26.213 | 35.919 | 0.00 | C |
| ATOM | 582 | CB | ALA | A | 83 | 3.009 | 25.768 | 37.342 | 0.00 | C |
| ATOM | 583 | C | ALA | A | 83 | 3.677 | 27.688 | 35.909 | 0.00 | C |
| ATOM | 584 | O | ALA | A | 83 | 2.820 | 28.571 | 35.886 | 0.00 | O |
| ATOM | 585 | N | GLY | A | 84 | 4.975 | 27.960 | 35.934 | 0.00 | N |
| ATOM | 586 | CA | GLY | A | 84 | 5.413 | 29.339 | 35.930 | 0.00 | C |
| ATOM | 587 | C | GLY | A | 84 | 6.913 | 29.458 | 35.790 | 0.00 | C |
| ATOM | 588 | O | GLY | A | 84 | 7.601 | 28.463 | 35.536 | 0.00 | O |
| ATOM | 589 | N | HIS | A | 85 | 7.426 | 30.673 | 35.960 | 0.00 | N |
| ATOM | 590 | CA | HIS | A | 85 | 8.856 | 30.903 | 35.841 | 0.00 | C |
| ATOM | 591 | CB | HIS | A | 85 | 9.154 | 31.684 | 34.557 | 0.00 | C |
| ATOM | 592 | C | HIS | A | 85 | 9.476 | 31.610 | 37.037 | 0.00 | C |
| ATOM | 593 | O | HIS | A | 85 | 10.275 | 32.530 | 36.866 | 0.00 | O |
| ATOM | 594 | CG | HIS | A | 85 | 8.328 | 32.920 | 34.391 | 0.00 | C |
| ATOM | 595 | ND1 | HIS | A | 85 | 6.864 | 34.188 | 34.455 | 0.00 | N |
| ATOM | 596 | CD2 | HIS | A | 85 | 7.006 | 33.083 | 34.147 | 0.00 | C |
| ATOM | 597 | NE2 | HIS | A | 85 | 6.772 | 34.434 | 34.067 | 0.00 | N |
| ATOM | 598 | CE1 | HIS | A | 85 | 7.909 | 35.078 | 34.256 | 0.00 | C |
| ATOM | 599 | N | THR | A | 86 | 9.115 | 31.163 | 38.243 | 0.00 | N |
| ATOM | 600 | CA | THR | A | 86 | 9.631 | 31.738 | 39.491 | 0.00 | C |
| ATOM | 601 | CB | THR | A | 86 | 8.743 | 31.356 | 40.683 | 0.00 | C |
| ATOM | 602 | C | THR | A | 86 | 11.055 | 31.244 | 39.779 | 0.00 | C |
| ATOM | 603 | O | THR | A | 86 | 11.289 | 30.047 | 39.908 | 0.00 | O |
| ATOM | 604 | OG1 | THR | A | 86 | 7.417 | 31.837 | 40.456 | 0.00 | O |
| ATOM | 605 | CG2 | THR | A | 86 | 9.283 | 31.957 | 41.971 | 0.00 | C |
| ATOM | 606 | N | ALA | A | 87 | 11.996 | 32.175 | 39.894 | 0.00 | N |
| ATOM | 607 | CA | ALA | A | 87 | 13.391 | 31.830 | 40.160 | 0.00 | C |
| ATOM | 608 | C | ALA | A | 87 | 13.621 | 31.173 | 41.519 | 0.00 | C |
| ATOM | 609 | O | ALA | A | 87 | 13.145 | 31.649 | 42.546 | 0.00 | O |
| ATOM | 610 | CB | ALA | A | 87 | 14.265 | 33.077 | 40.032 | 0.00 | C |
| ATOM | 611 | N | ALA | A | 88 | 14.360 | 30.074 | 41.517 | 0.00 | N |
| ATOM | 612 | CA | ALA | A | 88 | 14.653 | 29.360 | 42.747 | 0.00 | C |
| ATOM | 613 | C | ALA | A | 88 | 16.009 | 29.831 | 43.263 | 0.00 | C |
| ATOM | 614 | O | ALA | A | 88 | 16.904 | 27.855 | 42.490 | 0.00 | C |
| ATOM | 615 | CB | ALA | A | 88 | 14.662 | 30.156 | 42.482 | 0.00 | O |
| ATOM | 616 | N | PRO | A | 89 | 16.173 | 29.877 | 44.592 | 0.00 | N |
| ATOM | 617 | CA | PRO | A | 89 | 17.404 | 30.310 | 45.260 | 0.00 | C |
| ATOM | 618 | CB | PRO | A | 89 | 16.939 | 30.560 | 46.690 | 0.00 | C |
| ATOM | 619 | C | PRO | A | 89 | 18.545 | 29.304 | 45.204 | 0.00 | C |
| ATOM | 620 | O | PRO | A | 89 | 18.323 | 28.106 | 45.007 | 0.00 | O |
| ATOM | 621 | CD | PRO | A | 89 | 15.136 | 29.511 | 45.576 | 0.00 | C |
| ATOM | 622 | CG | PRO | A | 89 | 15.917 | 29.473 | 46.866 | 0.00 | C |
| ATOM | 623 | N | VAL | A | 90 | 19.767 | 29.809 | 45.361 | 0.00 | N |
| ATOM | 624 | CA | VAL | A | 90 | 20.960 | 28.973 | 45.343 | 0.00 | C |
| ATOM | 625 | CB | VAL | A | 90 | 22.197 | 29.747 | 45.873 | 0.00 | C |
| ATOM | 626 | CG1 | VAL | A | 90 | 23.347 | 28.779 | 46.162 | 0.00 | C |
| ATOM | 627 | CG2 | VAL | A | 90 | 22.623 | 30.803 | 44.858 | 0.00 | C |
| ATOM | 628 | C | VAL | A | 90 | 20.680 | 21.810 | 46.279 | 0.00 | C |
| ATOM | 629 | O | VAL | A | 90 | 19.988 | 27.976 | 47.287 | 0.00 | O |

Table 20-1-continued

Atomic Coordinates of ASP with the Modeled Octapeptide Substrate

| ATOM | 630 | N   | GLY | A | 91  | 21.205 | 26.635 | 45.954 | 0.00 | N   |
|------|-----|-----|-----|---|-----|--------|--------|--------|------|-----|
| ATOM | 631 | CA  | GLY | A | 91  | 20.976 | 25.482 | 46.806 | 0.00 | C   |
| ATOM | 632 | C   | GLY | A | 91  | 19.734 | 24.699 | 46.425 | 0.00 | C   |
| ATOM | 633 | O   | GLY | A | 91  | 19.576 | 23.550 | 46.836 | 0.00 | O   |
| ATOM | 634 | N   | SER | A | 92  | 18.853 | 25.314 | 45.642 | 0.00 | N   |
| ATOM | 635 | CA  | SER | A | 92  | 17.620 | 24.659 | 45.210 | 0.00 | C   |
| ATOM | 636 | CB  | SER | A | 92  | 16.720 | 25.634 | 44.438 | 0.00 | C   |
| ATOM | 637 | OG  | SER | A | 92  | 16.414 | 26.792 | 45.196 | 0.00 | O   |
| ATOM | 638 | C   | SER | A | 92  | 17.929 | 23.479 | 44.306 | 0.00 | C   |
| ATOM | 639 | O   | SER | A | 92  | 18.881 | 23.512 | 43.521 | 0.00 | O   |
| ATOM | 640 | N   | ALA | A | 93  | 17.117 | 22.435 | 44.417 | 0.00 | N   |
| ATOM | 641 | CA  | ALA | A | 93  | 17.301 | 21.247 | 43.600 | 0.00 | C   |
| ATOM | 642 | CB  | ALA | A | 93  | 16.576 | 20.054 | 44.231 | 0.00 | C   |
| ATOM | 643 | C   | ALA | A | 93  | 16.715 | 21.559 | 42.226 | 0.00 | C   |
| ATOM | 644 | O   | ALA | A | 93  | 15.669 | 22.202 | 42.126 | 0.00 | O   |
| ATOM | 645 | N   | VAL | A | 94  | 17.396 | 21.125 | 41.170 | 0.00 | N   |
| ATOM | 646 | CA  | VAL | A | 94  | 16.916 | 21.371 | 39.814 | 0.00 | C   |
| ATOM | 647 | CB  | VAL | A | 94  | 17.544 | 22.639 | 39.212 | 0.00 | C   |
| ATOM | 648 | CG1 | VAL | A | 91  | 17.072 | 23.872 | 39.971 | 0.00 | C   |
| ATOM | 649 | CG2 | VAL | A | 94  | 19.050 | 22.534 | 39.241 | 0.00 | C   |
| ATOM | 650 | C   | VAL | A | 94  | 17.204 | 20.211 | 38.867 | 0.00 | C   |
| ATOM | 651 | O   | VAL | A | 94  | 18.143 | 19.432 | 39.071 | 0.00 | O   |
| ATOM | 652 | N   | CYS | A | 95  | 16.378 | 20.090 | 37.834 | 0.00 | N   |
| ATOM | 653 | CA  | CYS | A | 95  | 16.548 | 19.030 | 36.851 | 0.00 | C   |
| ATOM | 654 | CB  | CYS | A | 95  | 15.428 | 17.983 | 36.942 | 0.00 | C   |
| ATOM | 655 | SG  | CYS | A | 95  | 15.344 | 17.009 | 38.470 | 0.00 | S   |
| ATOM | 656 | C   | CYS | A | 95  | 16.552 | 19.647 | 35.464 | 0.00 | C   |
| ATOM | 657 | O   | CYS | A | 95  | 15.820 | 20.598 | 35.194 | 0.00 | O   |
| ATOM | 658 | N   | ARG | A | 96  | 17.391 | 19.092 | 34.598 | 0.00 | N   |
| ATOM | 659 | CA  | ARG | A | 96  | 17.531 | 19.551 | 33.228 | 0.00 | C   |
| ATOM | 660 | CB  | ARG | A | 96  | 19.003 | 19.840 | 32.935 | 0.00 | C   |
| ATOM | 661 | CG  | ARG | A | 96  | 19.300 | 20.110 | 31.465 | 0.00 | C   |
| ATOM | 662 | CD  | ARG | A | 96  | 20.778 | 19.955 | 31.151 | 0.00 | C   |
| ATOM | 663 | NE  | ARG | A | 96  | 21.272 | 18.625 | 31.499 | 0.00 | N1+ |
| ATOM | 664 | CZ  | ARG | A | 96  | 20.875 | 17.493 | 30.927 | 0.00 | C   |
| ATOM | 665 | NH1 | ARG | A | 96  | 19.967 | 17.507 | 29.960 | 0.00 | N   |
| ATOM | 666 | NH2 | ARG | A | 96  | 21.377 | 16.341 | 31.341 | 0.00 | N   |
| ATOM | 667 | C   | ARG | A | 96  | 17.027 | 18.487 | 32.258 | 0.00 | C   |
| ATOM | 668 | O   | ARG | A | 96  | 17.160 | 17.288 | 32.509 | 0.00 | O   |
| ATOM | 669 | N   | SER | A | 97  | 16.458 | 18.924 | 31.142 | 0.00 | N   |
| ATOM | 670 | CA  | SER | A | 97  | 15.950 | 17.983 | 30.157 | 0.00 | C   |
| ATOM | 671 | CB  | SER | A | 97  | 14.418 | 18.054 | 30.082 | 0.00 | C   |
| ATOM | 672 | OG  | SER | A | 97  | 13.913 | 17.133 | 29.134 | 0.00 | O   |
| ATOM | 673 | C   | SER | A | 97  | 16.564 | 18.272 | 28.797 | 0.00 | C   |
| ATOM | 674 | O   | SER | A | 97  | 16.429 | 19.378 | 26.267 | 0.00 | O   |
| ATOM | 675 | N   | GLY | A | 98  | 17.246 | 17.265 | 28.251 | 0.00 | N   |
| ATOM | 676 | CA  | GLY | A | 98  | 17.900 | 17.390 | 26.960 | 0.00 | C   |
| ATOM | 677 | C   | GLY | A | 98  | 17.767 | 16.133 | 26.115 | 0.00 | C   |
| ATOM | 678 | O   | GLY | A | 98  | 17.481 | 15.042 | 26.624 | 0.00 | O   |
| ATOM | 679 | N   | SER | A | 99  | 17.997 | 16.290 | 24.814 | 0.00 | N   |
| ATOM | 680 | CA  | SER | A | 99  | 17.865 | 15.196 | 23.864 | 0.00 | C   |
| ATOM | 681 | CB  | SER | A | 99  | 17.547 | 15.749 | 22.478 | 0.00 | C   |
| ATOM | 682 | OG  | SER | A | 99  | 18.663 | 16.457 | 21.968 | 0.00 | O   |
| ATOM | 683 | C   | SER | A | 99  | 19.067 | 14.279 | 23.740 | 0.00 | C   |
| ATOM | 684 | O   | SER | A | 99  | 18.992 | 13.275 | 23.039 | 0.00 | O   |
| ATOM | 685 | N   | THR | A | 100 | 20.174 | 14.612 | 24.396 | 0.00 | N   |
| ATOM | 686 | CA  | THR | A | 100 | 21.358 | 13.766 | 24.307 | 0.00 | C   |
| ATOM | 687 | CB  | THR | A | 100 | 22.641 | 14.602 | 24.125 | 0.00 | C   |
| ATOM | 688 | OG1 | THR | A | 100 | 22.516 | 15.417 | 22.953 | 0.00 | O   |
| ATOM | 689 | CG2 | THR | A | 100 | 23.860 | 13.690 | 23.967 | 0.00 | C   |
| ATOM | 690 | C   | THR | A | 100 | 21.531 | 12.872 | 25.524 | 0.00 | C   |
| ATOM | 691 | O   | THR | A | 100 | 21.890 | 11.697 | 25.368 | 0.00 | O   |
| ATOM | 692 | N   | THR | A | 101 | 21.269 | 13.422 | 26.707 | 0.00 | N   |
| ATOM | 693 | CA  | THR | A | 101 | 21.401 | 12.662 | 27.950 | 0.00 | C   |
| ATOM | 694 | CB  | THR | A | 101 | 22.375 | 13.340 | 28.936 | 0.00 | C   |
| ATOM | 695 | OG1 | THR | A | 101 | 21.791 | 14.549 | 29.441 | 0.00 | O   |
| ATOM | 696 | CG2 | THR | A | 101 | 23.692 | 13.642 | 28.244 | 0.00 | C   |
| ATOM | 697 | C   | THR | A | 101 | 20.083 | 12.442 | 28.677 | 0.00 | C   |
| ATOM | 698 | O   | THR | A | 101 | 19.990 | 11.581 | 29.548 | 0.00 | O   |
| ATOM | 699 | N   | GLY | A | 102 | 19.068 | 13.227 | 28.342 | 0.00 | N   |
| ATOM | 700 | CA  | GLY | A | 102 | 17.784 | 13.044 | 28.985 | 0.00 | C   |
| ATOM | 701 | C   | GLY | A | 102 | 17.522 | 13.868 | 30.231 | 0.00 | C   |
| ATOM | 702 | O   | GLY | A | 102 | 17.759 | 15.075 | 30.245 | 0.00 | O   |
| ATOM | 703 | N   | TRP | A | 103 | 17.023 | 13.207 | 31.274 | 0.00 | N   |
| ATOM | 704 | CA  | TRP | A | 103 | 16.681 | 13.847 | 32.540 | 0.00 | C   |
| ATOM | 705 | CB  | TRP | A | 103 | 15.339 | 13.286 | 33.027 | 0.00 | C   |
| ATOM | 706 | CG  | TRP | A | 103 | 14.790 | 13.876 | 34.311 | 0.00 | C   |
| ATOM | 707 | CD2 | TRP | A | 103 | 13.889 | 14.989 | 34.434 | 0.00 | C   |

Table 20-1-continued

Atomic Coordinates of ASP with the Modeled Octapeptide Substrate

| ATOM | 708 | CE2 | TRP | A | 103 | 13.601 | 15.141 | 35.807 | 0.00 | C |
|---|---|---|---|---|---|---|---|---|---|---|
| ATOM | 709 | CE3 | TRP | A | 103 | 13.293 | 15.858 | 33.517 | 0.00 | C |
| ATOM | 710 | CD1 | TRP | A | 103 | 15.010 | 13.424 | 35.581 | 0.00 | C |
| ATOM | 711 | NE1 | TRP | A | 103 | 14.295 | 14.179 | 36.483 | 0.00 | N |
| ATOM | 712 | CZ2 | TRP | A | 103 | 12.749 | 16.138 | 36.284 | 0.00 | C |
| ATOM | 713 | CZ3 | TRP | A | 103 | 12.444 | 16.848 | 33.991 | 0.00 | C |
| ATOM | 714 | CH2 | TRP | A | 103 | 12.178 | 16.977 | 35.363 | 0.00 | C |
| ATOM | 715 | C | TRP | A | 103 | 17.776 | 13.652 | 33.593 | 0.00 | C |
| ATOM | 716 | O | TRP | A | 103 | 18.112 | 12.526 | 33.955 | 0.00 | C |
| ATOM | 717 | N | HIS | A | 104 | 18.333 | 14.762 | 34.074 | 0.00 | N |
| ATOM | 718 | CA | HIS | A | 104 | 19.391 | 14.731 | 35.081 | 0.00 | C |
| ATOM | 719 | CB | HIS | A | 104 | 20.755 | 14.780 | 34.405 | 0.00 | C |
| ATOM | 720 | CG | HIS | A | 104 | 21.064 | 13.554 | 33.619 | 0.00 | C |
| ATOM | 721 | CD2 | HIS | A | 104 | 20.741 | 13.202 | 32.352 | 0.00 | C |
| ATOM | 722 | ND1 | HIS | A | 104 | 21.704 | 12.465 | 34.167 | 0.00 | N |
| ATOM | 723 | CE1 | HIS | A | 104 | 21.759 | 11.496 | 33.273 | 0.00 | C |
| ATOM | 724 | NE2 | HIS | A | 104 | 21.181 | 11.917 | 32.162 | 0.00 | N |
| ATOM | 725 | C | HIS | A | 104 | 19.229 | 15.894 | 36.038 | 0.00 | C |
| ATOM | 726 | O | HIS | A | 104 | 18.859 | 16.995 | 35.636 | 0.00 | O |
| ATOM | 111 | N | CYS | A | 105 | 19.512 | 15.647 | 37.309 | 0.00 | N |
| ATOM | 728 | CA | CYS | A | 105 | 19.373 | 16.692 | 38.303 | 0.00 | C |
| ATOM | 729 | CB | CYS | A | 105 | 18.223 | 16.317 | 39.234 | 0.00 | C |
| ATOM | 730 | SG | CYS | A | 105 | 16.804 | 15.602 | 38.342 | 0.00 | S |
| ATOM | 731 | C | CYS | A | 105 | 20.635 | 17.014 | 39.099 | 0.00 | C |
| ATOM | 732 | O | CYS | A | 105 | 21.665 | 16.361 | 38.964 | 0.00 | O |
| ATOM | 733 | N | GLY | A | 106 | 20.533 | 18.046 | 39.923 | 0.00 | N |
| ATOM | 734 | CA | GLY | A | 106 | 21.642 | 18.487 | 40.739 | 0.00 | C |
| ATOM | 735 | C | GLY | A | 106 | 21.125 | 19.693 | 41.490 | 0.00 | C |
| ATOM | 736 | O | GLY | A | 106 | 19.916 | 19.805 | 41.707 | 0.00 | O |
| ATOM | 737 | N | THR | A | 107 | 22.011 | 20.598 | 41.888 | 0.00 | N |
| ATOM | 738 | CA | THR | A | 107 | 21.572 | 21.784 | 42.603 | 0.00 | C |
| ATOM | 739 | CB | THR | A | 107 | 21.865 | 21.681 | 44.117 | 0.00 | C |
| ATOM | 740 | OG1 | THR | A | 107 | 23.250 | 21.386 | 44.328 | 0.00 | O |
| ATOM | 741 | CG2 | THR | A | 107 | 21.021 | 20.583 | 44.746 | 0.00 | C |
| ATOM | 742 | C | THR | A | 107 | 22.215 | 23.046 | 42.058 | 0.00 | C |
| ATOM | 743 | O | THR | A | 107 | 23.238 | 23.001 | 41.372 | 0.00 | O |
| ATOM | 744 | N | ILE | A | 108 | 21.588 | 24.178 | 42.344 | 0.00 | N |
| ATOM | 745 | CA | ILE | A | 108 | 22.103 | 25.452 | 41.886 | 0.00 | C |
| ATOM | 746 | CB | ILE | A | 108 | 21.039 | 26.550 | 41.982 | 0.00 | C |
| ATOM | 747 | CG2 | ILE | A | 108 | 21.651 | 27.904 | 41.614 | 0.00 | C |
| ATOM | 748 | CG1 | ILE | A | 108 | 19.850 | 26.200 | 41.091 | 0.00 | C |
| ATOM | 749 | CD1 | ILE | A | 108 | 18.691 | 27.166 | 41.228 | 0.00 | C |
| ATOM | 750 | C | ILE | A | 108 | 23.216 | 25.803 | 42.852 | 0.00 | C |
| ATOM | 751 | O | ILE | A | 108 | 23.001 | 25.774 | 44.065 | 0.00 | O |
| ATOM | 752 | N | THR | A | 109 | 24.399 | 26.118 | 42.331 | 0.00 | N |
| ATOM | 753 | CA | THR | A | 109 | 25.516 | 26.472 | 43.197 | 0.00 | C |
| ATOM | 754 | CB | THR | A | 109 | 26.787 | 25.662 | 42.849 | 0.00 | C |
| ATOM | 755 | OG1 | THR | A | 109 | 27.055 | 25.748 | 41.443 | 0.00 | O |
| ATOM | 756 | CG2 | THR | A | 109 | 26.599 | 24.201 | 43.244 | 0.00 | C |
| ATOM | 757 | C | THR | A | 109 | 25.827 | 27.965 | 43.128 | 0.00 | C |
| ATOM | 758 | O | THR | A | 109 | 26.599 | 28.481 | 43.928 | 0.00 | O |
| ATOM | 759 | N | ALA | A | 110 | 25.214 | 28.664 | 42.181 | 0.00 | N |
| ATOM | 760 | CA | ALA | A | 110 | 25.457 | 30.090 | 42.053 | 0.00 | C |
| ATOM | 761 | CB | ALA | A | 110 | 26.949 | 30.348 | 41.846 | 0.00 | C |
| ATOM | 762 | C | ALA | A | 110 | 24.650 | 30.767 | 40.946 | 0.00 | C |
| ATOM | 763 | O | ALA | A | 110 | 24.191 | 30.132 | 40.001 | 0.00 | O |
| ATOM | 764 | N | LEU | A | 111 | 24.491 | 32.078 | 41.092 | 0.00 | N |
| ATOM | 765 | CA | LEU | A | 111 | 23.755 | 32.893 | 40.145 | 0.00 | C |
| ATOM | 766 | CB | LEU | A | 111 | 22.550 | 33.530 | 40.844 | 0.00 | C |
| ATOM | 767 | CG | LEU | A | 111 | 21.547 | 32.545 | 41.465 | 0.00 | C |
| ATOM | 768 | CD1 | LEU | A | 111 | 20.462 | 33.315 | 42.227 | 0.00 | C |
| ATOM | 769 | CD2 | LEU | A | 111 | 20.925 | 31.681 | 40.371 | 0.00 | C |
| ATOM | 770 | C | LEU | A | 111 | 24.688 | 33.970 | 39.593 | 0.00 | C |
| ATOM | 771 | O | LEU | A | 111 | 25.661 | 34.363 | 40.243 | 0.00 | O |
| ATOM | 772 | N | ASN | A | 112 | 24.380 | 34.439 | 38.390 | 0.00 | N |
| ATOM | 773 | CA | ASN | A | 112 | 25.171 | 35.468 | 37.719 | 0.00 | C |
| ATOM | 774 | CB | ASN | A | 112 | 25.123 | 36.788 | 38.490 | 0.00 | C |
| ATOM | 775 | CG | ASN | A | 112 | 23.725 | 37.149 | 38.930 | 0.00 | C |
| ATOM | 776 | OD1 | ASN | A | 112 | 23.244 | 36.663 | 39.950 | 0.00 | O |
| ATOM | 777 | ND2 | ASN | A | 112 | 23.057 | 37.994 | 38.155 | 0.00 | N |
| ATOM | 778 | C | ASN | A | 112 | 26.629 | 35.074 | 37.507 | 0.00 | C |
| ATOM | 779 | O | ASN | A | 112 | 27.526 | 35.891 | 37.680 | 0.00 | O |
| ATOM | 780 | N | SER | A | 113 | 26.870 | 33.820 | 37.144 | 0.00 | N |
| ATOM | 781 | CA | SER | A | 113 | 28.237 | 33.383 | 36.916 | 0.00 | C |
| ATOM | 782 | CB | SER | A | 113 | 28.375 | 31.875 | 37.126 | 0.00 | C |
| ATOM | 783 | OG | SER | A | 113 | 28.149 | 31.522 | 38.479 | 0.00 | O |
| ATOM | 784 | C | SER | A | 113 | 28.604 | 33.726 | 35.480 | 0.00 | C |
| ATOM | 785 | O | SER | A | 113 | 27.733 | 34.045 | 34.663 | 0.00 | O |

Table 20-1-continued

Atomic Coordinates of ASP with the Modeled Octapeptide Substrate

| ATOM | 786 | N   | SER | A | 114 | 29.899 | 33.691 | 35.192 | 0.00 | N   |
|------|-----|-----|-----|---|-----|--------|--------|--------|------|-----|
| ATOM | 787 | CA  | SER | A | 114 | 30.403 | 33.985 | 33.859 | 0.00 | C   |
| ATOM | 788 | CB  | SER | A | 114 | 31.288 | 35.234 | 33.847 | 0.00 | C   |
| ATOM | 789 | OG  | SER | A | 114 | 30.524 | 36.417 | 33.962 | 0.00 | O   |
| ATOM | 790 | C   | SER | A | 114 | 31.237 | 32.795 | 33.440 | 0.00 | C   |
| ATOM | 791 | O   | SER | A | 114 | 31.708 | 32.027 | 34.277 | 0.00 | O   |
| ATOM | 792 | N   | VAL | A | 115 | 31.400 | 32.631 | 32.138 | 0.00 | N   |
| ATOM | 793 | CA  | VAL | A | 115 | 32.185 | 31.535 | 31.611 | 0.00 | C   |
| ATOM | 794 | CB  | VAL | A | 115 | 31.342 | 30.241 | 31.427 | 0.00 | C   |
| ATOM | 795 | CG1 | VAL | A | 115 | 30.850 | 29.751 | 32.772 | 0.00 | C   |
| ATOM | 796 | CG2 | VAL | A | 115 | 30.174 | 30.492 | 30.485 | 0.00 | C   |
| ATOM | 797 | C   | VAL | A | 115 | 32.678 | 32.010 | 30.266 | 0.00 | C   |
| ATOM | 798 | O   | VAL | A | 115 | 32.121 | 32.945 | 29.691 | 0.00 | O   |
| ATOM | 799 | N   | THR | A | 116 | 33.735 | 31.387 | 29.768 | 0.00 | N   |
| ATOM | 800 | CA  | THR | A | 116 | 34.268 | 31.779 | 28.482 | 0.00 | C   |
| ATOM | 801 | CB  | THR | A | 116 | 35.671 | 32.359 | 28.634 | 0.00 | C   |
| ATOM | 802 | OG1 | THR | A | 116 | 35.602 | 33.538 | 29.446 | 0.00 | O   |
| ATOM | 803 | CG2 | THR | A | 116 | 36.247 | 32.726 | 27.277 | 0.00 | C   |
| ATOM | 804 | C   | THR | A | 116 | 34.278 | 30.589 | 27.535 | 0.00 | C   |
| ATOM | 805 | O   | THR | A | 116 | 34.931 | 29.573 | 27.787 | 0.00 | O   |
| ATOM | 806 | N   | TYR | A | 117 | 33.512 | 30.721 | 26.459 | 0.00 | N   |
| ATOM | 807 | CA  | TYR | A | 117 | 33.397 | 29.691 | 25.443 | 0.00 | C   |
| ATOM | 808 | CB  | TYR | A | 117 | 31.972 | 29.664 | 24.885 | 0.00 | C   |
| ATOM | 809 | CG  | TYR | A | 117 | 30.892 | 29.244 | 25.874 | 0.00 | C   |
| ATOM | 810 | CD1 | TYR | A | 117 | 29.803 | 30.072 | 26.134 | 0.00 | C   |
| ATOM | 811 | CE1 | TYR | A | 117 | 28.780 | 29.675 | 26.981 | 0.00 | C   |
| ATOM | 812 | CD2 | TYR | A | 117 | 30.930 | 27.998 | 26.499 | 0.00 | C   |
| ATOM | 813 | CE2 | TYR | A | 117 | 29.908 | 27.589 | 27.353 | 0.00 | C   |
| ATOM | 814 | CZ  | TYR | A | 117 | 28.834 | 28.432 | 27.590 | 0.00 | C   |
| ATOM | 815 | OH  | TYR | A | 117 | 27.814 | 28.036 | 28.431 | 0.00 | O   |
| ATOM | 816 | C   | TYR | A | 117 | 34.368 | 30.064 | 24.333 | 0.00 | C   |
| ATOM | 817 | O   | TYR | A | 117 | 34.922 | 31.161 | 24.329 | 0.00 | O   |
| ATOM | 818 | N   | PRO | A | 118 | 34.609 | 29.151 | 23.384 | 0.00 | N   |
| ATOM | 819 | CA  | PRO | A | 118 | 35.541 | 29.528 | 22.318 | 0.00 | C   |
| ATOM | 820 | CB  | PRO | A | 118 | 35.655 | 28.249 | 21.472 | 0.00 | C   |
| ATOM | 821 | C   | PRO | A | 118 | 35.080 | 30.751 | 21.520 | 0.00 | C   |
| ATOM | 822 | O   | PRO | A | 118 | 35.875 | 31.369 | 20.805 | 0.00 | O   |
| ATOM | 823 | CD  | PRO | A | 118 | 34.313 | 27.711 | 23.347 | 0.00 | C   |
| ATOM | 824 | CG  | PRO | A | 118 | 34.472 | 27.405 | 21.890 | 0.00 | C   |
| ATOM | 825 | N   | GLU | A | 119 | 33.804 | 31.109 | 21.651 | 0.00 | N   |
| ATOM | 826 | CA  | GLU | A | 119 | 33.266 | 32.265 | 20.935 | 0.00 | C   |
| ATOM | 827 | CB  | GLU | A | 119 | 31.785 | 32.079 | 20.612 | 0.00 | C   |
| ATOM | 828 | C   | GLU | A | 119 | 33.416 | 33.514 | 21.789 | 0.00 | C   |
| ATOM | 829 | O   | GLU | A | 119 | 33.498 | 34.634 | 21.275 | 0.00 | O   |
| ATOM | 830 | CG  | GLU | A | 119 | 31.470 | 30.965 | 19.611 | 0.00 | C   |
| ATOM | 831 | CD  | GLU | A | 119 | 31.686 | 29.606 | 20.179 | 0.00 | C   |
| ATOM | 832 | OE1 | GLU | A | 119 | 31.593 | 29.460 | 21.415 | 0.00 | O1− |
| ATOM | 833 | OE2 | GLU | A | 119 | 31.932 | 28.667 | 19.393 | 0.00 | O   |
| ATOM | 834 | N   | GLY | A | 120 | 33.437 | 33.315 | 23.102 | 0.00 | N   |
| ATOM | 835 | CA  | GLY | A | 120 | 33.575 | 34.438 | 24.002 | 0.00 | C   |
| ATOM | 836 | C   | GLY | A | 120 | 32.984 | 34.167 | 25.368 | 0.00 | C   |
| ATOM | 837 | O   | GLY | A | 120 | 32.714 | 33.020 | 25.727 | 0.00 | O   |
| ATOM | 838 | N   | THR | A | 121 | 32.782 | 35.233 | 26.133 | 0.00 | N   |
| ATOM | 839 | CA  | THR | A | 121 | 32.233 | 35.110 | 27.471 | 0.00 | C   |
| ATOM | 840 | CB  | THR | A | 121 | 32.932 | 36.084 | 28.435 | 0.00 | C   |
| ATOM | 841 | OG1 | THR | A | 121 | 34.319 | 35.733 | 28.527 | 0.00 | O   |
| ATOM | 842 | CG2 | THR | A | 121 | 32.293 | 36.026 | 29.831 | 0.00 | C   |
| ATOM | 843 | C   | THR | A | 121 | 30.739 | 35.358 | 27.526 | 0.00 | C   |
| ATOM | 844 | O   | THR | A | 121 | 30.198 | 36.160 | 26.771 | 0.00 | O   |
| ATOM | 845 | N   | VAL | A | 122 | 30.075 | 34.632 | 28.417 | 0.00 | N   |
| ATOM | 846 | CA  | VAL | A | 122 | 28.635 | 34.754 | 28.607 | 0.00 | C   |
| ATOM | 847 | CB  | VAL | A | 122 | 27.899 | 33.451 | 28.196 | 0.00 | C   |
| ATOM | 848 | CG1 | VAL | A | 122 | 26.412 | 33.553 | 28.519 | 0.00 | C   |
| ATOM | 849 | CG2 | VAL | A | 122 | 28.091 | 33.207 | 26.695 | 0.00 | C   |
| ATOM | 850 | C   | VAL | A | 122 | 28.515 | 35.016 | 30.103 | 0.00 | C   |
| ATOM | 851 | O   | VAL | A | 122 | 29.182 | 34.363 | 30.902 | 0.00 | O   |
| ATOM | 852 | N   | ARG | A | 123 | 27.689 | 35.978 | 30.493 | 0.00 | N   |
| ATOM | 853 | CA  | ARG | A | 123 | 27.546 | 36.282 | 31.915 | 0.00 | C   |
| ATOM | 854 | CB  | ARG | A | 123 | 27.917 | 37.748 | 32.153 | 0.00 | C   |
| ATOM | 855 | CG  | ARG | A | 123 | 26.856 | 38.724 | 31.655 | 0.00 | C   |
| ATOM | 856 | CD  | ARG | A | 123 | 25.712 | 38.852 | 32.671 | 0.00 | C   |
| ATOM | 857 | NE  | ARG | A | 123 | 24.459 | 39.336 | 32.089 | 0.00 | N1+ |
| ATOM | 858 | CZ  | ARG | A | 123 | 24.345 | 40.426 | 31.336 | 0.00 | C   |
| ATOM | 859 | NH1 | ARG | A | 123 | 25.414 | 41.162 | 31.054 | 0.00 | N   |
| ATOM | 860 | NH2 | ARG | A | 123 | 23.156 | 40.796 | 30.877 | 0.00 | N   |
| ATOM | 861 | C   | ARG | A | 123 | 26.151 | 36.018 | 32.468 | 0.00 | C   |
| ATOM | 862 | O   | ARG | A | 123 | 25.252 | 35.605 | 31.739 | 0.00 | O   |
| ATOM | 863 | N   | GLY | A | 124 | 25.991 | 36.272 | 33.767 | 0.00 | N   |

TABLE 20-1-continued

Atomic Coordinates of ASP with the Modeled Octapeptide Substrate

| ATOM | 864 | CA | GLY | A | 124 | 24.714 | 36.080 | 34.438 | 0.00 | C |
|---|---|---|---|---|---|---|---|---|---|---|
| ATOM | 865 | C | GLY | A | 124 | 24.094 | 34.712 | 34.238 | 0.00 | C |
| ATOM | 866 | O | GLY | A | 124 | 22.910 | 34.603 | 33.936 | 0.00 | O |
| ATOM | 867 | N | LEU | A | 125 | 24.891 | 33.666 | 34.415 | 0.00 | N |
| ATOM | 868 | CA | LEU | A | 125 | 24.412 | 32.304 | 34.238 | 0.00 | C |
| ATOM | 869 | CB | LEU | A | 125 | 25.411 | 31.495 | 33.406 | 0.00 | C |
| ATOM | 870 | CG | LEU | A | 125 | 25.597 | 31.779 | 31.913 | 0.00 | C |
| ATOM | 871 | CD1 | LEU | A | 125 | 26.780 | 30.977 | 31.383 | 0.00 | C |
| ATOM | 872 | CD2 | LEU | A | 125 | 24.333 | 31.411 | 31.152 | 0.00 | C |
| ATOM | 873 | C | LEU | A | 125 | 24.189 | 31.574 | 35.554 | 0.00 | C |
| ATOM | 874 | O | LEU | A | 125 | 24.828 | 31.869 | 36.573 | 0.00 | O |
| ATOM | 875 | N | ILE | A | 126 | 23.270 | 30.615 | 35.516 | 0.00 | N |
| ATOM | 876 | CA | ILE | A | 126 | 22.949 | 29.813 | 36.665 | 0.00 | C |
| ATOM | 877 | CB | ILE | A | 126 | 21.506 | 29.276 | 36.600 | 0.00 | C |
| ATOM | 878 | CG2 | ILE | A | 126 | 21.268 | 28.230 | 37.672 | 0.00 | C |
| ATOM | 879 | CG1 | ILE | A | 126 | 20.517 | 30.441 | 36.754 | 0.00 | C |
| ATOM | 880 | CD1 | ILE | A | 126 | 19.074 | 30.045 | 36.578 | 0.00 | C |
| ATOM | 881 | C | ILE | A | 126 | 23.947 | 28.646 | 36.668 | 0.00 | C |
| ATOM | 882 | O | ILE | A | 126 | 24.009 | 27.881 | 35.701 | 0.00 | O |
| ATOM | 883 | N | ARG | A | 127 | 24.746 | 28.536 | 37.723 | 0.00 | N |
| ATOM | 884 | CA | ARG | A | 127 | 25.738 | 27.473 | 37.831 | 0.00 | C |
| ATOM | 885 | CB | ARG | A | 127 | 26.989 | 28.007 | 38.528 | 0.00 | C |
| ATOM | 886 | CG | ARG | A | 127 | 28.129 | 27.015 | 38.679 | 0.00 | C |
| ATOM | 887 | CD | ARG | A | 127 | 29.261 | 27.678 | 39.441 | 0.00 | C |
| ATOM | 888 | NE | ARG | A | 127 | 30.312 | 26.748 | 39.830 | 0.00 | N1+ |
| ATOM | 889 | CZ | ARG | A | 127 | 31.098 | 26.112 | 36.971 | 0.00 | C |
| ATOM | 890 | NH2 | ARG | A | 127 | 32.033 | 25.279 | 39.417 | 0.00 | N |
| ATOM | 891 | NH1 | ARG | A | 127 | 30.949 | 26.310 | 37.669 | 0.00 | N |
| ATOM | 892 | C | ARG | A | 127 | 25.132 | 26.328 | 36.633 | 0.00 | C |
| ATOM | 893 | O | ARG | A | 127 | 24.507 | 26.553 | 39.676 | 0.00 | O |
| ATOM | 894 | N | THR | A | 128 | 25.325 | 25.103 | 38.151 | 0.00 | N |
| ATOM | 895 | CA | THR | A | 128 | 24.784 | 23.929 | 38.628 | 0.00 | C |
| ATOM | 896 | CB | THR | A | 128 | 23.447 | 23.475 | 38.189 | 0.00 | C |
| ATOM | 897 | OG1 | THR | A | 128 | 23.718 | 22.755 | 36.977 | 0.00 | O |
| ATOM | 896 | CG2 | THR | A | 128 | 22.568 | 24.674 | 37.863 | 0.00 | C |
| ATOM | 899 | C | THR | A | 128 | 25.720 | 22.729 | 38.782 | 0.00 | C |
| ATOM | 900 | O | THR | A | 128 | 26.763 | 22.759 | 38.135 | 0.00 | O |
| ATOM | 901 | N | THR | A | 129 | 25.317 | 21.667 | 39.472 | 0.00 | N |
| ATOM | 902 | CA | THR | A | 129 | 26.084 | 20.429 | 39.533 | 0.00 | C |
| ATOM | 903 | CB | THR | A | 129 | 26.055 | 19.838 | 40.946 | 0.00 | C |
| ATOM | 904 | OG1 | THR | A | 129 | 24.691 | 19.639 | 41.355 | 0.00 | O |
| ATOM | 905 | CG2 | THR | A | 129 | 26.758 | 20.779 | 41.924 | 0.00 | C |
| ATOM | 906 | C | THR | A | 129 | 25.474 | 19.411 | 38.565 | 0.00 | C |
| ATOM | 907 | O | THR | A | 129 | 25.792 | 18.227 | 38.607 | 0.00 | O |
| ATOM | 908 | N | VAL | A | 130 | 24.589 | 19.886 | 37.696 | 0.00 | N |
| ATOM | 909 | CA | VAL | A | 130 | 23.930 | 19.027 | 36.722 | 0.00 | C |
| ATOM | 910 | CB | VAL | A | 130 | 22.663 | 19.707 | 36.164 | 0.00 | C |
| ATOM | 911 | CG1 | VAL | A | 130 | 21.972 | 18.790 | 35.162 | 0.00 | C |
| ATOM | 912 | CG2 | VAL | A | 130 | 21.715 | 20.054 | 37.308 | 0.00 | C |
| ATOM | 913 | C | VAL | A | 130 | 24.857 | 18.691 | 35.561 | 0.00 | C |
| ATOM | 914 | O | VAL | A | 130 | 25.623 | 19.536 | 35.109 | 0.00 | O |
| ATOM | 915 | N | CYS | A | 131 | 24.790 | 17.449 | 35.086 | 0.00 | N |
| ATOM | 916 | CA | CYS | A | 131 | 25.626 | 17.016 | 33.975 | 0.00 | C |
| ATOM | 917 | CB | CYS | A | 131 | 25.889 | 15.507 | 34.034 | 0.00 | C |
| ATOM | 918 | SG | CYS | A | 131 | 24.399 | 14.468 | 33.874 | 0.00 | S |
| ATOM | 919 | C | CYS | A | 131 | 24.893 | 17.340 | 32.690 | 0.00 | C |
| ATOM | 920 | O | CYS | A | 131 | 23.670 | 17.436 | 32.678 | 0.00 | O |
| ATOM | 921 | N | ALA | A | 132 | 25.636 | 17.514 | 31.607 | 0.00 | N |
| ATOM | 922 | CA | ALA | A | 132 | 25.020 | 17.821 | 30.329 | 0.00 | C |
| ATOM | 923 | CB | ALA | A | 132 | 24.707 | 19.313 | 30.237 | 0.00 | C |
| ATOM | 924 | C | ALA | A | 132 | 25.920 | 17.404 | 29.176 | 0.00 | C |
| ATOM | 925 | O | ALA | A | 132 | 27.113 | 17.139 | 29.356 | 0.00 | O |
| ATOM | 926 | N | GLU | A | 133 | 25.323 | 17.353 | 27.992 | 0.00 | N |
| ATOM | 927 | CA | GLU | A | 133 | 26.017 | 16.981 | 26.774 | 0.00 | C |
| ATOM | 928 | CB | GLU | A | 133 | 25.434 | 15.686 | 26.219 | 0.00 | C |
| ATOM | 929 | CG | GLU | A | 133 | 26.457 | 14.695 | 25.730 | 0.00 | C |
| ATOM | 930 | CD | GLU | A | 133 | 27.077 | 13.909 | 26.862 | 0.oo | C |
| ATOM | 931 | OE1 | GLU | A | 133 | 27.702 | 14.533 | 27.741 | 0.00 | O1− |
| ATOM | 932 | OE2 | GLU | A | 133 | 26.937 | 12.667 | 26.871 | 0.00 | O |
| ATOM | 933 | C | GLU | A | 133 | 25.750 | 18.114 | 25.792 | 0.00 | C |
| ATOM | 934 | O | GLU | A | 133 | 24.778 | 18.851 | 25.946 | 0.00 | O |
| ATOM | 935 | N | PRO | A | 134 | 26.602 | 18.268 | 24.769 | 0.00 | N |
| ATOM | 936 | CA | PRO | A | 134 | 26.395 | 19.343 | 23.789 | 0.00 | C |
| ATOM | 937 | CB | PRO | A | 134 | 27.471 | 19.059 | 22.742 | 0.00 | C |
| ATOM | 938 | C | PRO | A | 134 | 24.975 | 19.390 | 23.185 | 0.00 | C |
| ATOM | 939 | O | PRO | A | 134 | 24.331 | 20.446 | 23.159 | 0.00 | O |
| ATOM | 940 | CD | PRO | A | 134 | 27.856 | 17.539 | 24.501 | 0.00 | C |
| ATOM | 941 | CG | PRO | A | 134 | 28.586 | 16.478 | 23.572 | 0.00 | C |

Table 20-1-continued

Atomic Coordinates of ASP with the Modeled Octapeptide Substrate

| ATOM | 942 | N | GLY | A | 135 | 24.490 | 16.250 | 22.708 | 0.00 | N |
|---|---|---|---|---|---|---|---|---|---|---|
| ATOM | 943 | CA | GLY | A | 135 | 23.167 | 18.218 | 22.117 | 0.00 | C |
| ATOM | 944 | C | GLY | A | 135 | 22.074 | 18.675 | 23.063 | 0.00 | C |
| ATOM | 945 | O | GLY | A | 135 | 20.979 | 19.053 | 22.631 | 0.00 | O |
| ATOM | 946 | N | ASP | A | 136 | 22.369 | 18.638 | 24.359 | 0.00 | N |
| ATOM | 947 | CA | ASP | A | 136 | 21.414 | 19.046 | 25.387 | 0.00 | C |
| ATOM | 946 | CB | ASP | A | 136 | 21.914 | 18.588 | 26.770 | 0.00 | C |
| ATOM | 949 | C | ASP | A | 136 | 21.162 | 20.564 | 25.400 | 0.00 | C |
| ATOM | 950 | O | ASP | A | 136 | 20.124 | 21.024 | 25.886 | 0.00 | O |
| ATOM | 951 | CG | ASP | A | 136 | 21.783 | 17.075 | 26.982 | 0.00 | C |
| ATOM | 952 | OD2 | ASP | A | 136 | 20.834 | 16.471 | 26.436 | 0.00 | O1− |
| ATOM | 953 | OD1 | ASP | A | 136 | 22.618 | 16.492 | 27.714 | 0.00 | O |
| ATOM | 954 | N | SER | A | 137 | 22.109 | 21.332 | 24.868 | 0.00 | N |
| ATOM | 955 | CA | SER | A | 137 | 21.989 | 22.791 | 24.823 | 0.00 | C |
| ATOM | 956 | CB | SER | A | 137 | 23.048 | 23.390 | 23.896 | 0.00 | C |
| ATOM | 957 | C | SER | A | 137 | 20.610 | 23.287 | 24.388 | 0.00 | C |
| ATOM | 956 | O | SER | A | 137 | 19.993 | 22.752 | 23.456 | 0.00 | O |
| ATOM | 959 | OG | SER | A | 137 | 24.352 | 23.234 | 24.427 | 0.00 | O |
| ATOM | 960 | N | GLY | A | 138 | 20.148 | 24.332 | 25.070 | 0.00 | N |
| ATOM | 961 | CA | GLY | A | 138 | 18.854 | 24.904 | 24.782 | 0.00 | C |
| ATOM | 962 | C | GLY | A | 138 | 17.803 | 24.224 | 25.629 | 0.00 | C |
| ATOM | 963 | O | GLY | A | 138 | 16.706 | 24.748 | 25.609 | 0.00 | O |
| ATOM | 964 | N | GLY | A | 139 | 18.150 | 23.057 | 26.160 | 0.00 | N |
| ATOM | 965 | CA | GLY | A | 139 | 17.222 | 22.297 | 26.982 | 0.00 | C |
| ATOM | 966 | C | GLY | A | 139 | 16.617 | 23.021 | 28.176 | 0.00 | C |
| ATOM | 967 | O | GLY | A | 139 | 17.104 | 24.070 | 28.604 | 0.00 | O |
| ATOM | 968 | N | SER | A | 140 | 15.555 | 22.438 | 28.729 | 0.00 | N |
| ATOM | 969 | CA | SER | A | 140 | 14.858 | 23.024 | 29.870 | 0.00 | C |
| ATOM | 970 | CB | SER | A | 140 | 13.423 | 22.500 | 29.948 | 0.00 | C |
| ATOM | 971 | OG | SER | A | 140 | 12.971 | 22.037 | 28.691 | 0.00 | O |
| ATOM | 972 | C | SER | A | 140 | 15.532 | 22.736 | 31.198 | 0.00 | C |
| ATOM | 973 | O | SER | A | 140 | 16.162 | 21.691 | 31.389 | 0.00 | O |
| ATOM | 974 | N | LEU | A | 141 | 15.393 | 23.683 | 32.115 | 0.00 | N |
| ATOM | 975 | CA | LEU | A | 141 | 15.967 | 23.558 | 33.448 | 0.00 | C |
| ATOM | 976 | CB | LEU | A | 141 | 17.175 | 24.482 | 33.639 | 0.00 | C |
| ATOM | 977 | CG | LEU | A | 141 | 17.722 | 24.420 | 35.073 | 0.00 | C |
| ATOM | 978 | CD1 | LEU | A | 141 | 18.323 | 23.047 | 35.334 | 0.00 | C |
| ATOM | 979 | CD2 | LEU | A | 141 | 18.749 | 25.518 | 35.297 | 0.00 | C |
| ATOM | 980 | C | LEU | A | 141 | 14.851 | 23.945 | 34.405 | 0.00 | C |
| ATOM | 981 | O | LEU | A | 141 | 14.398 | 25.081 | 34.422 | 0.00 | O |
| ATOM | 982 | N | LEU | A | 142 | 14.409 | 22.987 | 35.199 | 0.00 | N |
| ATOM | 983 | CA | LEU | A | 142 | 13.341 | 23.220 | 36.150 | 0.00 | C |
| ATOM | 984 | CB | LEU | A | 142 | 12.230 | 22.198 | 35.913 | 0.00 | C |
| ATOM | 985 | CG | LEU | A | 142 | 11.289 | 22.306 | 34.719 | 0.00 | C |
| ATOM | 986 | CD1 | LEU | A | 142 | 10.674 | 20.933 | 34.463 | 0.00 | C |
| ATOM | 987 | CD2 | LEU | A | 142 | 10.219 | 23.350 | 34.996 | 0.00 | C |
| ATOM | 988 | C | LEU | A | 142 | 13.702 | 23.168 | 37.629 | 0.00 | C |
| ATOM | 989 | O | LEU | A | 142 | 14.745 | 22.671 | 38.029 | 0.00 | O |
| ATOM | 990 | N | ALA | A | 143 | 12.788 | 23.701 | 38.424 | 0.00 | N |
| ATOM | 991 | CA | ALA | A | 143 | 12.880 | 23.759 | 39.875 | 0.00 | C |
| ATOM | 992 | CB | ALA | A | 143 | 13.159 | 25.178 | 40.345 | 0.00 | C |
| ATOM | 993 | C | ALA | A | 143 | 11.434 | 23.368 | 40.165 | 0.00 | C |
| ATOM | 994 | O | ALA | A | 143 | 10.557 | 24.221 | 40.225 | 0.00 | O |
| ATOM | 995 | N | GLY | A | 144 | 11.175 | 22.072 | 40.287 | 0.00 | N |
| ATOM | 996 | CA | GLY | A | 144 | 9.610 | 21.642 | 40.513 | 0.00 | C |
| ATOM | 997 | C | GLY | A | 144 | 9.058 | 21.945 | 39.232 | 0.00 | C |
| ATOM | 998 | O | GLY | A | 144 | 9.457 | 21.487 | 38.154 | 0.00 | O |
| ATOM | 999 | N | ASN | A | 145 | 7.984 | 22.723 | 39.322 | 0.00 | N |
| ATOM | 1000 | CA | ASN | A | 145 | 7.241 | 23.066 | 38.122 | 0.00 | C |
| ATOM | 1001 | CB | ASN | A | 145 | 5.736 | 22.846 | 38.321 | 0.00 | C |
| ATOM | 1002 | CG | ASN | A | 145 | 5.144 | 23.751 | 39.384 | 0.00 | C |
| ATOM | 1003 | OD1 | ASN | A | 145 | 5.382 | 24.962 | 39.396 | 0.00 | O |
| ATOM | 1004 | ND2 | ASN | A | 145 | 4.351 | 23.166 | 40.281 | 0.00 | N |
| ATOM | 1005 | C | ASN | A | 145 | 7.503 | 24.496 | 37.650 | 0.00 | C |
| ATOM | 1006 | O | ASN | A | 145 | 6.716 | 25.049 | 36.886 | 0.00 | O |
| ATOM | 1007 | N | GLN | A | 146 | 8.613 | 25.086 | 38.093 | 0.00 | N |
| ATOM | 1006 | CA | GLN | A | 146 | 8.968 | 26.455 | 37.702 | 0.00 | C |
| ATOM | 1009 | CB | GLN | A | 146 | 9.234 | 27.314 | 38.942 | 0.00 | C |
| ATOM | 1010 | CG | GLN | A | 146 | 8.080 | 27.367 | 39.916 | 0.00 | C |
| ATOM | 1011 | CD | GLN | A | 146 | 6.875 | 28.097 | 39.363 | 0.00 | C |
| ATOM | 1012 | OE1 | GLN | A | 146 | 5.735 | 27.705 | 39.615 | 0.00 | O |
| ATOM | 1013 | NE2 | GLN | A | 146 | 7.117 | 29.172 | 38.617 | 0.00 | N |
| ATOM | 1014 | C | GLN | A | 146 | 10.205 | 26.492 | 36.798 | 0.00 | C |
| ATOM | 1015 | O | GLN | A | 146 | 11.277 | 25.999 | 37.169 | 0.00 | O |
| ATOM | 1016 | N | ALA | A | 147 | 10.055 | 27.084 | 35.618 | 0.00 | N |
| ATOM | 1017 | CA | ALA | A | 147 | 11.160 | 27.188 | 34.660 | 0.00 | C |
| ATOM | 1018 | CB | ALA | A | 147 | 10.642 | 27.698 | 33.309 | 0.00 | C |
| ATOM | 1019 | C | ALA | A | 147 | 12.253 | 28.124 | 35.163 | 0.00 | C |

Table 20-1-continued

Atomic Coordinates of ASP with the Modeled Octapeptide Substrate

| ATOM | 1020 | O   | ALA | A | 147 | 11.958 | 29.233 | 35.625 | 0.00 | O |
|------|------|-----|-----|---|-----|--------|--------|--------|------|---|
| ATOM | 1021 | N   | GLN | A | 148 | 13.506 | 27.679 | 35.124 | 0.00 | N |
| ATOM | 1022 | CA  | GLN | A | 148 | 14.637 | 28.481 | 35.593 | 0.00 | C |
| ATOM | 1023 | CB  | GLN | A | 148 | 15.576 | 27.627 | 36.435 | 0.00 | C |
| ATOM | 1024 | CG  | GLN | A | 148 | 14.939 | 27.023 | 37.667 | 0.00 | C |
| ATOM | 1025 | CD  | GLN | A | 148 | 14.283 | 28.062 | 38.553 | 0.00 | C |
| ATOM | 1026 | OE1 | GLN | A | 148 | 13.074 | 28.016 | 38.797 | 0.00 | O |
| ATOM | 1027 | NE2 | GLN | A | 148 | 15.075 | 29.005 | 39.040 | 0.00 | N |
| ATOM | 1028 | C   | GLN | A | 148 | 15.440 | 29.128 | 34.466 | 0.00 | C |
| ATOM | 1029 | O   | GLN | A | 148 | 15.723 | 30.325 | 34.501 | 0.00 | O |
| ATOM | 1030 | N   | GLY | A | 149 | 15.818 | 28.330 | 33.472 | 0.00 | N |
| ATOM | 1031 | CA  | GLY | A | 149 | 16.578 | 28.852 | 32.349 | 0.00 | C |
| ATOM | 1032 | C   | GLY | A | 149 | 16.762 | 27.783 | 31.290 | 0.00 | C |
| ATOM | 1033 | O   | GLY | A | 149 | 16.104 | 26.742 | 31.348 | 0.00 | O |
| ATOM | 1034 | N   | VAL | A | 150 | 17.628 | 28.041 | 30.311 | 0.00 | N |
| ATOM | 1035 | CA  | VAL | A | 150 | 17.896 | 27.061 | 29.261 | 0.00 | C |
| ATOM | 1036 | CB  | VAL | A | 150 | 17.568 | 27.604 | 27.848 | 0.00 | C |
| ATOM | 1037 | CG1 | VAL | A | 150 | 16.053 | 27.737 | 27.694 | 0.00 | C |
| ATOM | 1038 | CG2 | VAL | A | 150 | 18.256 | 28.936 | 27.611 | 0.00 | C |
| ATOM | 1039 | C   | VAL | A | 150 | 19.351 | 26.630 | 29.329 | 0.00 | C |
| ATOM | 1040 | O   | VAL | A | 150 | 20.210 | 27.368 | 29.809 | 0.00 | O |
| ATOM | 1041 | N   | THR | A | 151 | 19.630 | 25.431 | 28.844 | 0.00 | N |
| ATOM | 1042 | CA  | THR | A | 151 | 20.985 | 24.914 | 28.873 | 0.00 | C |
| ATOM | 1043 | CB  | THR | A | 151 | 20.980 | 23.429 | 28.536 | 0.00 | C |
| ATOM | 1044 | OG1 | THR | A | 151 | 20.057 | 22.771 | 29.412 | 0.00 | O |
| ATOM | 1045 | CG2 | THR | A | 151 | 22.361 | 22.828 | 28.748 | 0.00 | C |
| ATOM | 1046 | C   | THR | A | 151 | 21.954 | 25.675 | 27.984 | 0.00 | C |
| ATOM | 1047 | O   | THR | A | 151 | 21.756 | 25.796 | 26.779 | 0.00 | O |
| ATOM | 1048 | N   | SER | A | 152 | 23.007 | 26.192 | 28.607 | 0.00 | N |
| ATOM | 1049 | CA  | SER | A | 152 | 24.020 | 26.956 | 27.898 | 0.00 | C |
| ATOM | 1050 | CB  | SER | A | 152 | 24.382 | 28.193 | 28.723 | 0.00 | C |
| ATOM | 1051 | OG  | SER | A | 152 | 25.262 | 29.047 | 28.021 | 0.00 | O |
| ATOM | 1052 | C   | SER | A | 152 | 25.264 | 26.127 | 27.603 | 0.00 | C |
| ATOM | 1053 | O   | SER | A | 152 | 25.673 | 26.005 | 26.450 | 0.00 | O |
| ATOM | 1054 | N   | GLY | A | 153 | 25.859 | 25.561 | 28.648 | 0.00 | N |
| ATOM | 1055 | CA  | GLY | A | 153 | 27.047 | 24.740 | 28.483 | 0.00 | C |
| ATOM | 1056 | C   | GLY | A | 153 | 27.702 | 24.415 | 29.817 | 0.00 | C |
| ATOM | 1057 | O   | GLY | A | 153 | 27.151 | 24.724 | 30.872 | 0.00 | O |
| ATOM | 1058 | N   | GLY | A | 154 | 28.876 | 23.794 | 29.771 | 0.00 | N |
| ATOM | 1059 | CA  | GLY | A | 154 | 29.589 | 23.443 | 30.984 | 0.00 | C |
| ATOM | 1060 | C   | GLY | A | 154 | 30.688 | 22.439 | 30.708 | 0.00 | C |
| ATOM | 1061 | O   | GLY | A | 154 | 31.161 | 22.322 | 29.579 | 0.00 | O |
| ATOM | 1062 | N   | SER | A | 155 | 31.101 | 21.703 | 31.736 | 0.00 | N |
| ATOM | 1063 | CA  | SER | A | 155 | 32.149 | 20.701 | 31.572 | 0.00 | C |
| ATOM | 1064 | CB  | SER | A | 155 | 33.416 | 21.148 | 32.296 | 0.00 | C |
| ATOM | 1065 | OG  | SER | A | 155 | 33.180 | 21.231 | 33.688 | 0.00 | O |
| ATOM | 1066 | C   | SER | A | 155 | 31.700 | 19.354 | 32.128 | 0.00 | C |
| ATOM | 1067 | O   | SER | A | 155 | 30.690 | 19.268 | 32.836 | 0.00 | O |
| ATOM | 1068 | N   | GLY | A | 156 | 32.460 | 18.307 | 31.805 | 0.00 | N |
| ATOM | 1069 | CA  | GLY | A | 156 | 32.142 | 16.970 | 32.283 | 0.00 | C |
| ATOM | 1070 | C   | GLY | A | 156 | 31.101 | 16.231 | 31.458 | 0.00 | C |
| ATOM | 1071 | O   | GLY | A | 156 | 30.856 | 16.564 | 30.302 | 0.00 | O |
| ATOM | 1072 | N   | ASN | A | 157 | 30.495 | 15.211 | 32.051 | 0.00 | N |
| ATOM | 1073 | CA  | ASN | A | 157 | 29.470 | 14.434 | 31.369 | 0.00 | C |
| ATOM | 1074 | CB  | ASN | A | 157 | 30.115 | 13.390 | 30.450 | 0.00 | C |
| ATOM | 1075 | CG  | ASN | A | 157 | 31.077 | 12.472 | 31.188 | 0.00 | C |
| ATOM | 1076 | OD1 | ASN | A | 157 | 30.669 | 11.681 | 32.038 | 0.00 | O |
| ATOM | 1077 | ND2 | ASN | A | 157 | 32.365 | 12.575 | 30.863 | 0.00 | N |
| ATOM | 1078 | C   | ASN | A | 157 | 28.578 | 13.766 | 32.410 | 0.00 | C |
| ATOM | 1079 | O   | ASN | A | 157 | 28.788 | 13.932 | 33.610 | 0.00 | O |
| ATOM | 1080 | N   | CYS | A | 158 | 27.580 | 13.021 | 31.948 | 0.00 | N |
| ATOM | 1081 | CA  | CYS | A | 158 | 26.661 | 12.337 | 32.840 | 0.00 | C |
| ATOM | 1082 | CB  | CYS | A | 158 | 25.304 | 12.169 | 32.155 | 0.00 | C |
| ATOM | 1083 | SG  | CYS | A | 158 | 24.426 | 13.754 | 31.973 | 0.00 | S |
| ATOM | 1084 | C   | CYS | A | 158 | 27.181 | 11.000 | 33.350 | 0.00 | C |
| ATOM | 1085 | O   | CYS | A | 158 | 26.592 | 10.393 | 34.244 | 0.00 | O |
| ATOM | 1086 | N   | ARG | A | 159 | 28.288 | 10.538 | 32.784 | 0.00 | N |
| ATOM | 1087 | CA  | ARG | A | 159 | 28.862 | 9.271  | 33.215 | 0.00 | C |
| ATOM | 1088 | CB  | ARG | A | 159 | 29.714 | 6.662  | 32.099 | 0.00 | C |
| ATOM | 1089 | CG  | ARG | A | 159 | 28.922 | 8.198  | 30.890 | 0.00 | C |
| ATOM | 1090 | CD  | ARG | A | 159 | 29.852 | 7.660  | 29.817 | 0.00 | C |
| ATOM | 1091 | NE  | ARG | A | 159 | 30.711 | 8.703  | 29.260 | 0.00 | N1+ |
| ATOM | 1092 | CZ  | ARG | A | 159 | 30.273 | 9.714  | 28.517 | 0.00 | C |
| ATOM | 1093 | NH1 | ARG | A | 159 | 28.980 | 9.826  | 28.237 | 0.00 | N |
| ATOM | 1094 | NH2 | ARG | A | 159 | 31.128 | 10.610 | 28.049 | 0.00 | N |
| ATOM | 1095 | C   | ARG | A | 159 | 29.716 | 9.462  | 34.467 | 0.00 | C |
| ATOM | 1096 | O   | ARG | A | 159 | 29.634 | 8.675  | 35.405 | 0.00 | O |
| ATOM | 1097 | N   | THR | A | 160 | 30.533 | 10.510 | 34.481 | 0.00 | N |

Table 20-1-continued

Atomic Coordinates of ASP with the Modeled Octapeptide Substrate

| ATOM | 1098 | CA | THR | A | 160 | 31.400 | 10.785 | 35.628 | 0.00 | C |
|---|---|---|---|---|---|---|---|---|---|---|
| ATOM | 1099 | CB | THR | A | 160 | 32.874 | 10.925 | 35.185 | 0.00 | C |
| ATOM | 1100 | OG1 | THR | A | 160 | 32.966 | 11.897 | 34.138 | 0.00 | O |
| ATOM | 1101 | CG2 | THR | A | 160 | 33.404 | 9.605 | 34.676 | 0.00 | C |
| ATOM | 1102 | C | THR | A | 160 | 31.000 | 12.048 | 36.396 | 0.00 | C |
| ATOM | 1103 | O | THR | A | 160 | 31.525 | 12.320 | 37.475 | 0.00 | O |
| ATOM | 1104 | N | GLY | A | 161 | 30.068 | 12.812 | 35.836 | 0.00 | N |
| ATOM | 1105 | CA | GLY | A | 161 | 29.622 | 14.028 | 36.490 | 0.00 | C |
| ATOM | 1106 | C | GLY | A | 161 | 30.200 | 15.295 | 35.878 | 0.00 | C |
| ATOM | 1107 | O | GLY | A | 161 | 31.194 | 15.262 | 35.150 | 0.00 | O |
| ATOM | 1108 | N | GLY | A | 162 | 29.577 | 16.426 | 36.180 | 0.00 | N |
| ATOM | 1109 | CA | GLY | A | 162 | 30.061 | 17.681 | 35.646 | 0.00 | C |
| ATOM | 1110 | C | GLY | A | 162 | 29.414 | 18.909 | 36.250 | 0.00 | C |
| ATOM | 1111 | O | GLY | A | 162 | 28.785 | 18.856 | 37.318 | 0.00 | O |
| ATOM | 1112 | N | THR | A | 163 | 29.592 | 20.023 | 35.547 | 0.00 | N |
| ATOM | 1113 | CA | THR | A | 163 | 29.057 | 21.322 | 35.934 | 0.00 | C |
| ATOM | 1114 | CB | THR | A | 163 | 30.179 | 22.248 | 36.440 | 0.00 | C |
| ATOM | 1115 | OG1 | THR | A | 163 | 30.861 | 21.621 | 37.535 | 0.00 | O |
| ATOM | 1116 | CG2 | THR | A | 163 | 29.604 | 23.576 | 36.896 | 0.00 | C |
| ATOM | 1117 | C | THR | A | 163 | 28.414 | 21.948 | 34.695 | 0.00 | C |
| ATOM | 1118 | O | THR | A | 163 | 29.052 | 22.077 | 33.650 | 0.00 | O |
| ATOM | 1119 | N | THR | A | 164 | 27.152 | 22.342 | 34.810 | 0.00 | N |
| ATOM | 1120 | CA | THR | A | 164 | 26.452 | 22.945 | 33.680 | 0.00 | C |
| ATOM | 1121 | CB | THR | A | 164 | 25.290 | 22.053 | 33.208 | 0.00 | C |
| ATOM | 1122 | OG1 | THR | A | 164 | 25.744 | 20.700 | 33.075 | 0.00 | C |
| ATOM | 1123 | CG2 | THR | A | 164 | 24.768 | 22.536 | 31.869 | 0.00 | C |
| ATOM | 1124 | C | THR | A | 164 | 25.878 | 24.298 | 34.060 | 0.00 | C |
| ATOM | 1125 | O | THR | A | 164 | 25.354 | 24.466 | 35.167 | 0.00 | O |
| ATOM | 1126 | N | PHE | A | 165 | 25.981 | 25.256 | 33.139 | 0.00 | N |
| ATOM | 1127 | CA | PHE | A | 165 | 25.470 | 26.607 | 33.369 | 0.00 | C |
| ATOM | 1128 | CB | PHE | A | 165 | 26.521 | 27.662 | 33.021 | 0.00 | C |
| ATOM | 1129 | CG | PHE | A | 165 | 27.818 | 27.507 | 33.769 | 0.00 | C |
| ATOM | 1130 | CD1 | PHE | A | 165 | 28.758 | 26.554 | 33.380 | 0.00 | C |
| ATOM | 1131 | CD2 | PHE | A | 165 | 28.107 | 28.319 | 34.858 | 0.00 | C |
| ATOM | 1132 | CE1 | PHE | A | 165 | 29.957 | 26.427 | 34.071 | 0.00 | C |
| ATOM | 1133 | CE2 | PHE | A | 165 | 29.302 | 28.187 | 35.541 | 0.00 | C |
| ATOM | 1134 | CZ | PHE | A | 165 | 30.224 | 27.242 | 35.146 | 0.00 | C |
| ATOM | 1135 | C | PHE | A | 165 | 24.242 | 26.834 | 32.505 | 0.00 | C |
| ATOM | 1136 | O | PHE | A | 165 | 24.170 | 26.334 | 31.386 | 0.00 | O |
| ATOM | 1137 | N | PHE | A | 166 | 23.276 | 27.586 | 33.020 | 0.00 | N |
| ATOM | 1138 | CA | PHE | A | 166 | 22.067 | 27.854 | 32.262 | 0.00 | C |
| ATOM | 1139 | CB | PHE | A | 166 | 20.860 | 27.130 | 32.880 | 0.00 | C |
| ATOM | 1140 | CG | PHE | A | 166 | 21.062 | 25.643 | 33.076 | 0.00 | C |
| ATOM | 1141 | CD2 | PHE | A | 166 | 20.371 | 24.721 | 32.295 | 0.00 | C |
| ATOM | 1142 | CD1 | PHE | A | 166 | 21.936 | 25.165 | 34.050 | 0.00 | C |
| ATOM | 1143 | CE2 | PHE | A | 166 | 20.549 | 23.339 | 32.484 | 0.00 | C |
| ATOM | 1144 | CE1 | PHE | A | 166 | 22.117 | 23.788 | 34.243 | 0.00 | C |
| ATOM | 1145 | CZ | PHE | A | 166 | 21.423 | 22.879 | 33.460 | 0.00 | C |
| ATOM | 1146 | C | PHE | A | 166 | 21.765 | 29.344 | 32.173 | 0.00 | C |
| ATOM | 1147 | O | PHE | A | 166 | 22.066 | 30.122 | 33.086 | 0.00 | O |
| ATOM | 1148 | N | GLN | A | 167 | 21.187 | 29.736 | 31.046 | 0.00 | N |
| ATOM | 1149 | CA | GLN | A | 167 | 20.822 | 31.122 | 30.802 | 0.00 | C |
| ATOM | 1150 | CB | GLN | A | 167 | 20.737 | 31.366 | 29.291 | 0.00 | C |
| ATOM | 1151 | CG | GLN | A | 167 | 19.786 | 32.464 | 28.875 | 0.00 | C |
| ATOM | 1152 | CD | GLN | A | 167 | 20.300 | 33.840 | 29.234 | 0.00 | C |
| ATOM | 1153 | OE1 | GLN | A | 167 | 21.329 | 34.282 | 28.722 | 0.00 | O |
| ATOM | 1154 | NE2 | GLN | A | 167 | 19.589 | 34.525 | 30.126 | 0.00 | N |
| ATOM | 1155 | C | GLN | A | 167 | 19.449 | 31.262 | 31.442 | 0.00 | C |
| ATOM | 1156 | O | GLN | A | 167 | 18.500 | 30.600 | 31.020 | 0.00 | O |
| ATOM | 1157 | N | PRO | A | 168 | 19.322 | 32.107 | 32.481 | 0.00 | N |
| ATOM | 1158 | CD | PRO | A | 168 | 20.334 | 32.973 | 33.113 | 0.00 | C |
| ATOM | 1159 | CA | PRO | A | 168 | 18.013 | 32.270 | 33.132 | 0.00 | C |
| ATOM | 1160 | CB | PRO | A | 168 | 18.261 | 33.395 | 34.138 | 0.00 | C |
| ATOM | 1161 | CG | PRO | A | 168 | 19.716 | 33.237 | 34.470 | 0.00 | C |
| ATOM | 1162 | C | PRO | A | 168 | 16.926 | 32.611 | 32.108 | 0.00 | C |
| ATOM | 1163 | O | PRO | A | 168 | 17.180 | 33.288 | 31.116 | 0.00 | O |
| ATOM | 1164 | N | VAL | A | 169 | 15.711 | 32.149 | 32.373 | 0.00 | N |
| ATOM | 1165 | CA | VAL | A | 169 | 14.578 | 32.379 | 31.487 | 0.00 | C |
| ATOM | 1166 | CB | VAL | A | 169 | 13.465 | 31.328 | 31.802 | 0.00 | C |
| ATOM | 1167 | CG1 | VAL | A | 169 | 12.914 | 31.542 | 33.204 | 0.00 | C |
| ATOM | 1168 | CG2 | VAL | A | 169 | 12.370 | 31.401 | 30.786 | 0.00 | C |
| ATOM | 1169 | C | VAL | A | 169 | 13.962 | 33.788 | 31.427 | 0.00 | C |
| ATOM | 1170 | O | VAL | A | 169 | 13.638 | 34.273 | 30.358 | 0.00 | O |
| ATOM | 1171 | N | ASN | A | 170 | 13.802 | 34.455 | 32.560 | 0.00 | N |
| ATOM | 1172 | CA | ASN | A | 170 | 13.213 | 35.793 | 32.554 | 0.00 | C |
| ATOM | 1173 | CB | ASN | A | 170 | 13.128 | 36.329 | 33.979 | 0.00 | C |
| ATOM | 1174 | CG | ASN | A | 170 | 12.215 | 35.486 | 34.843 | 0.00 | C |
| ATOM | 1175 | OD1 | ASN | A | 170 | 11.177 | 35.008 | 34.373 | 0.00 | O |

Table 20-1-continued

Atomic Coordinates of ASP with the Modeled Octapeptide Substrate

| ATOM | 1176 | ND2 | ASN | A | 170 | 12.587 | 35.298 | 36.107 | 0.00 | N |
|---|---|---|---|---|---|---|---|---|---|---|
| ATOM | 1177 | C | ASN | A | 170 | 13.859 | 36.822 | 31.635 | 0.00 | C |
| ATOM | 1178 | O | ASN | A | 170 | 13.166 | 37.586 | 30.975 | 0.00 | O |
| ATOM | 1179 | N | PRO | A | 171 | 15.192 | 36.873 | 31.590 | 0.00 | N |
| ATOM | 1180 | CD | PRO | A | 171 | 16.217 | 36.299 | 32.476 | 0.00 | C |
| ATOM | 1181 | CA | PRO | A | 171 | 15.768 | 37.872 | 30.684 | 0.00 | C |
| ATOM | 1182 | CB | PRO | A | 171 | 17.258 | 37.857 | 31.043 | 0.00 | C |
| ATOM | 1183 | CG | PRO | A | 171 | 17.466 | 36.517 | 31.673 | 0.00 | C |
| ATOM | 1184 | C | PRO | A | 171 | 15.484 | 37.551 | 29.209 | 0.00 | C |
| ATOM | 1185 | O | PRO | A | 171 | 15.601 | 38.418 | 28.338 | 0.00 | O |
| ATOM | 1186 | N | ILE | A | 172 | 15.101 | 36.307 | 28.935 | 0.00 | N |
| ATOM | 1187 | CA | ILE | A | 172 | 14.798 | 35.896 | 27.570 | 0.00 | C |
| ATOM | 1188 | CB | ILE | A | 172 | 14.811 | 34.374 | 27.403 | 0.00 | C |
| ATOM | 1189 | CG2 | ILE | A | 172 | 14.516 | 34.018 | 25.947 | 0.00 | C |
| ATOM | 1190 | CG1 | ILE | A | 172 | 16.164 | 33.801 | 27.813 | 0.00 | C |
| ATOM | 1191 | CD1 | ILE | A | 172 | 16.196 | 32.269 | 27.764 | 0.00 | C |
| ATOM | 1192 | C | ILE | A | 172 | 13.386 | 36.369 | 27.251 | 0.00 | C |
| ATOM | 1193 | O | ILE | A | 172 | 13.113 | 36.885 | 26.166 | 0.00 | O |
| ATOM | 1194 | N | LEU | A | 173 | 12.488 | 36.179 | 28.210 | 0.00 | N |
| ATOM | 1195 | CA | LEU | A | 173 | 11.102 | 36.587 | 28.038 | 0.00 | C |
| ATOM | 1196 | CB | LEU | A | 173 | 10.279 | 36.158 | 29.252 | 0.00 | C |
| ATOM | 1197 | CG | LEU | A | 173 | 10.263 | 34.645 | 29.486 | 0.00 | C |
| ATOM | 1198 | CD1 | LEU | A | 173 | 9.465 | 34.308 | 30.759 | 0.00 | C |
| ATOM | 1199 | CD2 | LEU | A | 173 | 9.671 | 33.965 | 28.251 | 0.00 | C |
| ATOM | 1200 | C | LEU | A | 173 | 11.031 | 38.105 | 27.869 | 0.00 | C |
| ATOM | 1201 | O | LEU | A | 173 | 10.287 | 38.617 | 27.037 | 0.00 | O |
| ATOM | 1202 | N | GLN | A | 174 | 11.831 | 38.807 | 28.662 | 0.00 | N |
| ATOM | 1203 | CA | GLN | A | 174 | 11.896 | 40.259 | 28.641 | 0.00 | C |
| ATOM | 1204 | CB | GLN | A | 174 | 12.665 | 40.752 | 29.870 | 0.00 | C |
| ATOM | 1205 | CG | GLN | A | 174 | 12.868 | 42.259 | 29.923 | 0.00 | C |
| ATOM | 1206 | CD | GLN | A | 174 | 11.664 | 43.006 | 30.461 | 0.00 | C |
| ATOM | 1207 | OE1 | GLN | A | 174 | 10.532 | 42.811 | 30.003 | 0.00 | O |
| ATOM | 1208 | NE2 | GLN | A | 174 | 11.904 | 43.876 | 31.438 | 0.00 | N |
| ATOM | 1209 | C | GLN | A | 174 | 12.555 | 40.817 | 27.381 | 0.00 | C |
| ATOM | 1210 | O | GLN | A | 174 | 12.219 | 41.909 | 26.933 | 0.00 | O |
| ATOM | 1211 | N | ALA | A | 175 | 13.493 | 40.078 | 26.808 | 0.00 | N |
| ATOM | 1212 | CA | ALA | A | 175 | 14.164 | 40.552 | 25.604 | 0.00 | C |
| ATOM | 1213 | CB | ALA | A | 175 | 15.378 | 39.681 | 25.306 | 0.00 | C |
| ATOM | 1214 | C | ALA | A | 175 | 13.238 | 40.580 | 24.394 | 0.00 | C |
| ATOM | 1215 | O | ALA | A | 175 | 13.276 | 41.512 | 23.595 | 0.00 | O |
| ATOM | 1216 | N | TYR | A | 176 | 12.396 | 39.561 | 24.276 | 0.00 | N |
| ATOM | 1217 | CA | TYP | A | 176 | 11.462 | 39.458 | 23.161 | 0.00 | C |
| ATOM | 1218 | CB | TYP | A | 176 | 11.571 | 38.063 | 22.535 | 0.00 | C |
| ATOM | 1219 | CG | TYR | A | 176 | 12.990 | 37.700 | 22.173 | 0.00 | C |
| ATOM | 1220 | CD1 | TYR | A | 176 | 13.761 | 38.551 | 21.381 | 0.00 | C |
| ATOM | 1221 | CE1 | TYP | A | 176 | 15.075 | 38.249 | 21.073 | 0.00 | C |
| ATOM | 1222 | CD2 | TYR | A | 176 | 13.574 | 36.528 | 22.643 | 0.00 | C |
| ATOM | 1223 | CE2 | TYR | A | 176 | 14.890 | 36.213 | 22.335 | 0.00 | C |
| ATOM | 1224 | CZ | TYP | A | 176 | 15.636 | 37.083 | 21.553 | 0.00 | C |
| ATOM | 1225 | OH | TYR | A | 176 | 16.959 | 36.817 | 21.285 | 0.00 | O |
| ATOM | 1226 | C | TYP | A | 176 | 10.004 | 39.742 | 23.500 | 0.00 | C |
| ATOM | 1227 | O | TYP | A | 176 | 9.135 | 39.574 | 22.646 | 0.00 | O |
| ATOM | 1228 | N | GLY | A | 177 | 9.736 | 40.165 | 24.733 | 0.00 | N |
| ATOM | 1229 | CA | GLY | A | 177 | 8.366 | 40.457 | 25.131 | 0.00 | C |
| ATOM | 1230 | C | GLY | A | 177 | 7.469 | 39.232 | 25.065 | 0.00 | C |
| ATOM | 1231 | O | GLY | A | 177 | 6.295 | 39.326 | 24.711 | 0.00 | O |
| ATOM | 1232 | N | LEU | A | 178 | 8.033 | 38.080 | 25.421 | 0.00 | N |
| ATOM | 1233 | CA | LEU | A | 178 | 7.323 | 36.807 | 25.390 | 0.00 | C |
| ATOM | 1234 | CB | LEU | A | 178 | 8.275 | 35.694 | 24.937 | 0.00 | C |
| ATOM | 1235 | CG | LEU | A | 178 | 8.981 | 35.724 | 23.591 | 0.00 | C |
| ATOM | 1236 | CD1 | LEU | A | 178 | 10.077 | 34.688 | 23.584 | 0.00 | C |
| ATOM | 1237 | CD2 | LEU | A | 178 | 8.006 | 35.441 | 22.454 | 0.00 | C |
| ATOM | 1238 | C | LEU | A | 178 | 6.737 | 36.403 | 26.741 | 0.00 | C |
| ATOM | 1239 | O | LEU | A | 178 | 7.221 | 36.821 | 27.794 | 0.00 | O |
| ATOM | 1240 | N | ARG | A | 179 | 5.698 | 35.573 | 26.668 | 0.00 | N |
| ATOM | 1241 | CA | ARG | A | 179 | 5.008 | 35.060 | 27.875 | 0.00 | C |
| ATOM | 1242 | CB | ARG | A | 179 | 3.519 | 35.439 | 27.872 | 0.00 | C |
| ATOM | 1243 | CG | ARG | A | 179 | 3.193 | 36.849 | 28.356 | 0.00 | C |
| ATOM | 1244 | CD | ARG | A | 179 | 1.760 | 37.239 | 27.989 | 0.00 | C |
| ATOM | 1245 | NE | ARG | A | 179 | 1.401 | 38.565 | 28.490 | 0.00 | N1+ |
| ATOM | 1246 | CZ | ARG | A | 179 | 1.070 | 38.825 | 29.751 | 0.00 | C |
| ATOM | 1247 | NH1 | ARG | A | 179 | 1.044 | 37.844 | 30.646 | 0.00 | N |
| ATOM | 1248 | NH2 | ARG | A | 179 | 0.773 | 40.066 | 30.117 | 0.00 | N |
| ATOM | 1249 | C | ARG | A | 179 | 5.118 | 33.541 | 27.794 | 0.00 | C |
| ATOM | 1250 | O | ARG | A | 179 | 5.043 | 32.978 | 26.707 | 0.00 | O |
| ATOM | 1251 | N | MET | A | 180 | 5.313 | 32.882 | 28.931 | 0.00 | N |
| ATOM | 1252 | CA | MET | A | 180 | 5.422 | 31.428 | 28.955 | 0.00 | C |
| ATOM | 1253 | CB | MET | A | 180 | 5.866 | 30.936 | 30.329 | 0.00 | C |

Table 20-1-continued

Atomic Coordinates of ASP with the Modeled Octapeptide Substrate

| ATOM | 1254 | CG | MET | A | 180 | 7.257 | 31.311 | 30.768 | 0.00 | C |
|---|---|---|---|---|---|---|---|---|---|---|
| ATOM | 1255 | SD | MET | A | 180 | 8.400 | 30.052 | 30.227 | 0.00 | S |
| ATOM | 1256 | CE | MET | A | 180 | 7.622 | 28.610 | 30.892 | 0.00 | C |
| ATOM | 1257 | C | MET | A | 180 | 4.034 | 30.856 | 28.712 | 0.00 | C |
| ATOM | 12S8 | O | MET | A | 180 | 3.034 | 31.444 | 29.118 | 0.00 | O |
| ATOM | 1259 | N | ILE | A | 181 | 3.967 | 29.715 | 28.042 | 0.00 | N |
| ATOM | 1260 | CA | ILE | A | 181 | 2.690 | 29.085 | 27.781 | 0.00 | C |
| ATOM | 1261 | CB | ILE | A | 181 | 2.726 | 28.266 | 26.464 | 0.00 | C |
| ATOM | 1262 | CG2 | ILE | A | 181 | 1.534 | 27.294 | 26.399 | 0.00 | C |
| ATOM | 1263 | CG1 | ILE | A | 181 | 2.711 | 29.237 | 25.270 | 0.00 | C |
| ATOM | 1264 | CD1 | ILE | A | 181 | 2.740 | 28.556 | 23.910 | 0.00 | C |
| ATOM | 1265 | C | ILE | A | 181 | 2.613 | 28.211 | 29.023 | 0.00 | C |
| ATOM | 1266 | O | ILE | A | 181 | 3.458 | 27.357 | 29.238 | 0.00 | O |
| ATOM | 1267 | N | THR | A | 182 | 1.598 | 28.457 | 29.845 | 0.00 | N |
| ATOM | 1268 | CA | THR | A | 182 | 1.398 | 27.724 | 31.090 | 0.00 | C |
| ATOM | 1269 | C | THR | A | 182 | 0.212 | 26.770 | 31.163 | 0.00 | C |
| ATOM | 1270 | O | THR | A | 182 | −0.098 | 26.231 | 32.241 | 0.00 | O |
| ATOM | 1271 | CB | THR | A | 182 | 1.315 | 28.733 | 32.273 | 0.00 | C |
| ATOM | 1272 | OG1 | THR | A | 182 | 0.199 | 28.407 | 33.111 | 0.00 | O |
| ATOM | 1273 | CG2 | THR | A | 182 | 1.137 | 30.133 | 31.739 | 0.00 | C |
| ATOM | 1274 | N | THR | A | 183 | −0.448 | 26.534 | 30.036 | 0.00 | N |
| ATOM | 1275 | CA | THR | A | 183 | −1.593 | 25.623 | 30.045 | 0.00 | C |
| ATOM | 1276 | C | THR | A | 183 | −1.754 | 25.043 | 28.647 | 0.00 | C |
| ATOM | 1277 | O | THR | A | 183 | −1.274 | 25.608 | 27.675 | 0.00 | O |
| ATOM | 1278 | CB | THR | A | 183 | −2.909 | 26.342 | 30.433 | 0.00 | C |
| ATOM | 1279 | OG1 | THR | A | 183 | −3.716 | 25.460 | 31.228 | 0.00 | O |
| ATOM | 1280 | CG2 | THR | A | 183 | −3.690 | 26.738 | 29.184 | 0.00 | C |
| ATOM | 1281 | N | ASP | A | 184 | −2.402 | 23.896 | 28.532 | 0.00 | N |
| ATOM | 1282 | CA | ASP | A | 184 | −2.573 | 23.318 | 27.213 | 0.00 | C |
| ATOM | 1283 | C | ASP | A | 184 | −4.035 | 23.091 | 26.918 | 0.00 | C |
| ATOM | 1284 | O | ASP | A | 184 | −4.380 | 22.208 | 26.174 | 0.00 | O |
| ATOM | 1285 | CB | ASP | A | 184 | −1.810 | 22.005 | 27.113 | 0.00 | C |
| ATOM | 1286 | CG | ASP | A | 184 | −0.464 | 22.056 | 27.794 | 0.00 | C |
| ATOM | 1287 | OD1 | ASP | A | 184 | 0.296 | 23.029 | 27.577 | 0.00 | O |
| ATOM | 1288 | OD2 | ASP | A | 184 | −0.152 | 21.080 | 28.527 | 0.00 | O1− |
| TER | 1289 | | ASP | A | 184 | | | | | |
| ATOM | 1290 | N | ALA | B | 14 | 37.553 | 22.457 | 29.194 | 0.00 | N1+ |
| ATOM | 1291 | H | ALA | B | 14 | 36.582 | 22.364 | 28.935 | 0.00 | H |
| ATOM | 1292 | H | ALA | B | 14 | 37.991 | 23.157 | 28.614 | 0.00 | H |
| ATOM | 1293 | H | ALA | B | 14 | 38.021 | 21.572 | 29.065 | 0.00 | H |
| ATOM | 1294 | CA | ALA | B | 14 | 37.649 | 22.863 | 30.616 | 0.00 | C |
| ATOM | 1295 | C | ALA | B | 14 | 36.345 | 22.665 | 31.400 | 0.00 | C |
| ATOM | 1296 | O | ALA | B | 14 | 36.364 | 21.816 | 32.304 | 0.00 | O |
| ATOM | 1297 | CB | ALA | B | 14 | 38.235 | 24.270 | 30.658 | 0.00 | C |
| ATOM | 1298 | N | ALA | B | 15 | 35.261 | 23.393 | 31.094 | 0.00 | N |
| ATOM | 1299 | CA | ALA | B | 15 | 35.165 | 24.394 | 30.026 | 0.00 | C |
| ATOM | 1300 | C | ALA | B | 15 | 34.368 | 23.941 | 28.790 | 0.00 | C |
| ATOM | 1301 | O | ALA | B | 15 | 34.957 | 23.330 | 27.892 | 0.00 | O |
| ATOM | 1302 | CB | ALA | B | 15 | 34.779 | 25.773 | 30.573 | 0.00 | C |
| ATOM | 1303 | N | ALA | B | 16 | 33.028 | 24.069 | 28.763 | 0.00 | N |
| ATOM | 1304 | CA | ALA | B | 15 | 52.304 | 23.388 | 27.683 | 0.00 | C |
| ATOM | 1305 | C | ALA | B | 16 | 31.144 | 24.054 | 26.918 | 0.00 | C |
| ATOM | 1306 | O | ALA | B | 16 | 30.114 | 24.490 | 27.453 | 0.00 | O |
| ATOM | 1307 | CB | ALA | B | 16 | 32.420 | 21.850 | 27.713 | 0.00 | C |
| ATOM | 1308 | H | ALA | B | 16 | 32.544 | 24.608 | 29.452 | 0.00 | H |
| ATOM | 1309 | N | HIS | B | 17 | 31.370 | 24.111 | 25.600 | 0.00 | N |
| ATOM | 1310 | CA | HIS | B | 17 | 30.508 | 24.676 | 24.521 | 0.00 | C |
| ATOM | 1311 | C | HIS | B | 17 | 29.820 | 23.558 | 23.756 | 0.00 | C |
| ATOM | 1312 | O | HIS | B | 17 | 30.487 | 22.621 | 23.291 | 0.00 | O |
| ATOM | 1313 | CB | HIS | B | 17 | 31.473 | 25.545 | 23.683 | 0.00 | C |
| ATOM | 1314 | CG | HIS | B | 17 | 30.806 | 26.351 | 22.601 | 0.00 | C |
| ATOM | 1315 | ND1 | HIS | B | 17 | 30.728 | 26.028 | 21.264 | 0.00 | N |
| ATOM | 1316 | CD2 | HIS | B | 17 | 30.170 | 27.551 | 22.772 | 0.00 | C |
| ATOM | 1317 | CE1 | HIS | B | 17 | 30.054 | 27.014 | 20.648 | 0.00 | C |
| ATOM | 1318 | NE2 | HIS | B | 17 | 29.694 | 27.965 | 21.525 | 0.00 | N |
| ATOM | 1319 | H | HIS | B | 17 | 32.233 | 23.710 | 25.292 | 0.00 | H |
| ATOM | 1320 | N | TYR | B | 18 | 28.491 | 23.661 | 23.613 | 0.00 | N |
| ATOM | 1321 | CA | TYR | B | 18 | 27.651 | 22.538 | 23.244 | 0.00 | C |
| ATOM | 1322 | C | TYR | B | 18 | 26.791 | 22.741 | 21.978 | 0.00 | C |
| ATOM | 1323 | O | TYR | B | 18 | 25.936 | 21.904 | 21.762 | 0.00 | O |
| ATOM | 1324 | CB | TYR | B | 18 | 26.869 | 22.044 | 24.476 | 0.00 | C |
| ATOM | 1325 | CG | TYR | B | 18 | 27.638 | 21.257 | 25.527 | 0.00 | C |
| ATOM | 1326 | CD1 | TYR | B | 18 | 27.073 | 20.996 | 26.793 | 0.00 | C |
| ATOM | 1327 | CD2 | TYR | B | 18 | 28.818 | 20.596 | 25.160 | 0.00 | C |
| ATOM | 1328 | CE1 | TYR | B | 18 | 27.702 | 20.099 | 27.685 | 0.00 | C |
| ATOM | 1329 | CE2 | TYR | B | 18 | 29.420 | 19.668 | 26.020 | 0.00 | C |
| ATOM | 1330 | CZ | TYR | B | 18 | 28.855 | 19.410 | 27.276 | 0.00 | C |
| ATOM | 1331 | OH | TYR | B | 18 | 29.519 | 18.595 | 28.139 | 0.00 | O |

Table 20-1-continued

Atomic Coordinates of ASP with the Modeled Octapeptide Substrate

| | | | | | | | | | |
|---|---|---|---|---|---|---|---|---|---|
| ATOM | 1332 | H | TYR | B | 18 | 28.022 | 24.521 | 23.872 | 0.00 H |
| ATOM | 1333 | N | ASP | B | 19 | 27.328 | 23.446 | 20.986 | 0.00 N |
| ATOM | 1334 | CA | ASP | B | 19 | 27.252 | 23.065 | 19.573 | 0.00 C |
| ATOM | 1335 | C | ASP | B | 19 | 25.957 | 22.335 | 19.178 | 0.00 C |
| ATOM | 1336 | O | ASP | B | 19 | 24.855 | 22.851 | 19.367 | 0.00 O |
| ATOM | 1337 | CB | ASP | B | 19 | 27.381 | 24.271 | 18.655 | 0.00 C |
| ATOM | 1338 | CG | ASP | B | 19 | 28.399 | 25.369 | 18.926 | 0.00 C |
| ATOM | 1339 | OD1 | ASP | B | 19 | 28.777 | 25.568 | 20.105 | 0.00 O |
| ATOM | 1340 | OD2 | ASP | B | 19 | 28.588 | 26.117 | 17.941 | 0.00 O1− |
| ATOM | 1341 | H | ASP | B | 19 | 28.092 | 24.050 | 21.252 | 0.00 H |
| ATOM | 1342 | N | GLU | B | 20 | 26.024 | 21.140 | 18.622 | 0.00 N |
| ATOM | 1343 | CA | GLU | B | 20 | 27.219 | 20.341 | 18.451 | 0.00 C |
| ATOM | 1344 | C | GLU | B | 20 | 27.848 | 20.634 | 17.079 | 0.00 C |
| ATOM | 1345 | O | GLU | B | 20 | 27.311 | 20.147 | 16.091 | 0.00 O |
| ATOM | 1346 | CB | GLU | B | 20 | 26.641 | 18.934 | 18.532 | 0.00 C |
| ATOM | 1347 | CG | GLU | B | 20 | 26.790 | 18.174 | 19.836 | 0.00 C |
| ATOM | 1348 | CD | GLU | B | 20 | 26.391 | 16.720 | 19.643 | 0.00 C |
| ATOM | 1349 | OE1 | GLU | B | 20 | 26.614 | 16.043 | 20.673 | 0.00 O1− |
| ATOM | 1350 | OE2 | GLU | B | 20 | 26.569 | 16.221 | 18.501 | 0.00 O |
| ATOM | 1351 | H | GLU | B | 20 | 25.129 | 20.696 | 16.442 | 0.00 H |
| ATOM | 1352 | N | ALA | B | 21 | 29.122 | 21.069 | 17.024 | 0.00 N |
| ATOM | 1353 | CA | ALA | 3 | 21 | 29.859 | 21.221 | 15.768 | 0.00 C |
| ATOM | 1354 | C | ALA | 3 | 21 | 30.422 | 19.894 | 15.208 | 0.00 C |
| ATOM | 1355 | O | ALA | B | 21 | 31.618 | 19.821 | 14.879 | 0.00 O |
| ATOM | 1356 | CB | ALA | B | 21 | 30.954 | 22.295 | 15.900 | 0.00 C |
| ATOM | 1357 | OXT | ALA | B | 21 | 29.677 | 18.897 | 15.088 | 0.00 O1− |
| ATOM | 1358 | H | ALA | B | 21 | 29.585 | 21.298 | 17.880 | 0.00 H |
| TER | 1359 | | ALA | B | 21 | | | | |

Example 21

Oxidative Stability of ASP

This Example describes experiments conducted to determine the oxidative stability of the ASP protease and mutant proteases. The resistance to oxidation of *Cellulomonas* 69B4 protease was compared to that of: a BPN'-variant protease (BPN'-variant 1; Genencor; See, U.S. Pat. No. RE 34,606 [incorporated herein by reference], for a description of this enzyme); a GG36 variant protease (GG36-variant 1; Genencor; See e.g., U.S. Pat. Nos. 5,955,340 and 5,700,676, herein incorporated by reference); and PURAFECT protease (Genencor).

The assay was conducted by incubating a sample of the protease with 0.1 M $H_2O_2$. A 2.0 ml volume of 0.1 M Borate buffer (45.4 gm $NaB_4O_7 10H_2O$), pH 9.45 containing 0.1 M $H_2O_2$ and 100 ppm protease was incubated at 25° C. for 20 minutes and assayed for enzyme activity.

Figure 31:
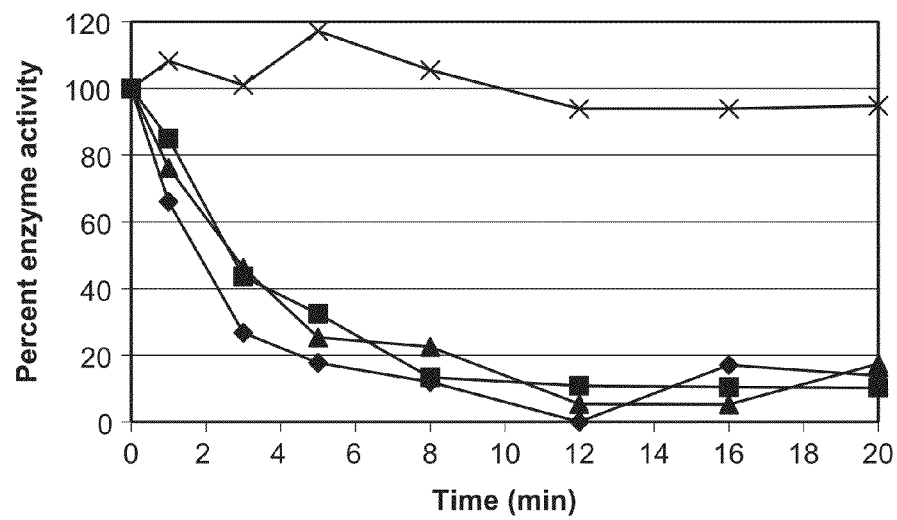
FIG. 31 provides a graph that shows comparative oxidative inactivation of various serine proteases (100 ppm) as a measure of percent enzyme activity over time (minutes) (69B4 [-x-]; BPN' variant 1 [-♦-]; PURAFECT® [-▲-]; and GG36-variant 1 [-■-]) with 0.1 M $H_2O_2$ at pH 9.45, 25° C.

The enzyme activity was determined as follows: 50 µl of the incubation mixture was combined with 950 µl 0.1 M Tris buffer, pH 8.6 and a sample from 10 µl was taken and added to 990 µl AAPF substrate solution, conc. 1 mg/ml, in 0.1 M Tris/0.005% TWEEN®, pH 8.6. The rate of increase in absorbance at 410 nm due to release of p-nitroaniline was monitored. The results obtained for these proteases are provided in FIG. 31. As indicated in this graph, protease 69B4 showed greatly enhanced stability under oxidative conditions relative to the subtilisin proteases.

Example 22

Chelate Stability of ASP

In this Example, experiments to determine the chelate stability of ASP are described. The resistance to the presence of a chelator of 69B4 protease was assayed by incubating an aliquot of the enzyme with 10 mM EDTA in 50 mM Tris, pH 8.2. The same enzyme preparations as used in Example 21 were used in these experiments.

In specific, a volume of 2.0 ml 50 mM Tris buffer, pH 8.2, containing 10 mM EDTA and 100 ppm protease was incubated at 45° C. for 100 minutes and assayed for enzyme activity as follows: 50 µl of the incubation mixture was combined with 950 µl 0.1 M Tris buffer, pH 8.6 and a sample from 10 µl was taken and added to 990 µl AAPF substrate solution, conc. 1 mg/ml, in 0.1 M Tris/0.005% TWEEN®, pH 8.6

Figure 32:
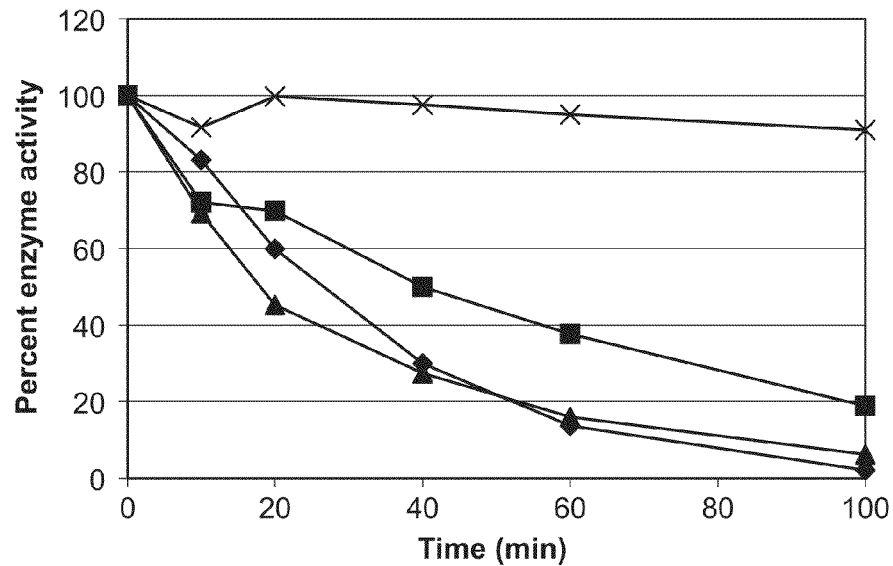
FIG. 32 provides a graph that shows comparative chelator inactivation of various serine proteases (100 ppm) as a measure of percent enzyme activity over time (minutes) (69B4 [-x-]; BPN'-variant 1 [-♦-]; PURAFECT® [-▲-]; and GG36-variant 1 [-■-] with 10 mM EDTA at pH 8.20, 45° C.

The rate of increase in absorbance at 410 nm due to release of p-nitroaniline was monitored. The results obtained for these four proteases are shown in FIG. 32. As indicated by these results, protease 69B4 showed greatly enhanced stability in the presence of a chelator than BPN' variant-1, PURAFECT®, or GG36 variant-1.

Example 23

Thermal Stability of ASP

In this Example, experiments conducted to determine the thermostability of ASP protease are described. In one set of experiments, 69B4 protease was tested for resistance to thermal inactivation in solution. As in Examples 21 and 22, a BPN' variant (BPN'-variant-1), PURAFECT®, and a GG36 variant (GG36-variant-1) were also tested and compared with ASP.

Figure 33:
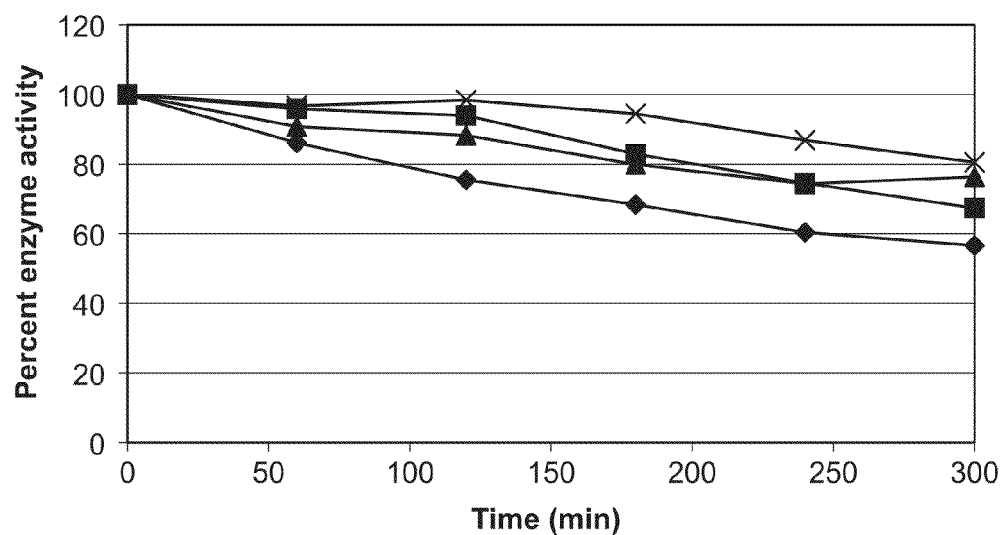
FIG. 33 provides a graph that shows comparative thermal inactivation of various serine proteases (100 ppm) as a measure of percent enzyme activity over time (minutes) (69B4 [-x-]; BPN'-variant [-♦-]; PURAFECT® [-▲-]; and GG36-variant 1 [-■-] with 50 mM Tris at pH 8.0, 45° C.

The thermal inactivation was performed by incubating a volume of 2.0 ml 50 mM Tris buffer, pH 8.0, containing 100 ppm protease at 45° C. for 300 minutes and assayed for enzyme activity as follows: 50 µl of the incubation mixture was combined with 950 µl 0.1 M Tris buffer, pH 8.6 and a sample from 10 µl was taken and added to 990 µl AAPF substrate solution, conc. 1 mg/ml, in 0.1 M Tris/0.005% TWEEN®, pH 8.6. The rate of increase in absorbance at 410 nm due to release of p-nitroaniline was monitored. The results of these four proteases are shown in FIG. 33. As shown by these results, protease 6984 showed enhanced or comparative thermal stability at 45 degrees centigrade than the BPN' variant, PURAFECT®, or the GG36 variant.

Figure 34:
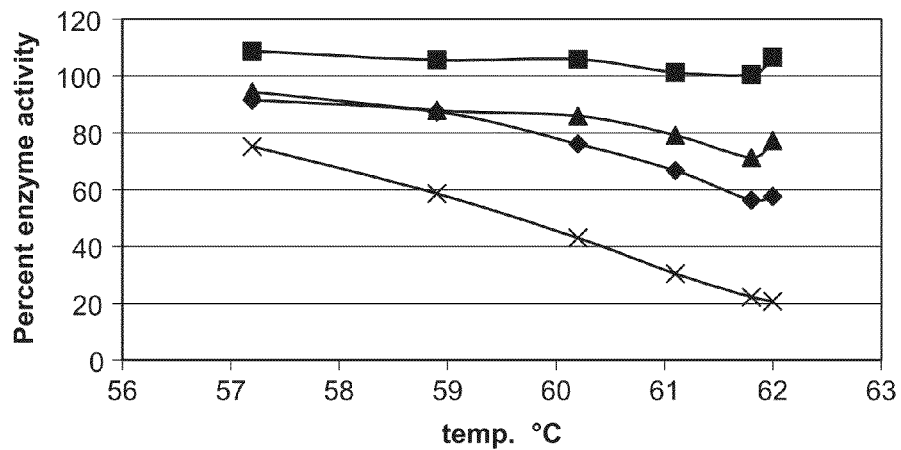
FIG. 34 provides a graph that shows comparative thermal inactivation of certain serine proteases (69B4 [-x-]; BPN'-variant [-♦]; PURAFECT® [-▲-]; and GG36-variant-1 [■-] at pH 8.60, over a temperature gradient of 57° C. to 62° C.

In addition to the above experiments, an alternative method for determining the thermostability of ASP was also tested. In these experiments, a temperature gradient between 57°-62° C. was used. The thermal inactivation (using a Thermocycler-MTP plate DNA Engine Tetad; MJ Research) was performed by incubating a volume of 180 µl 100 mM Tris buffer, pH 8.6, containing 1 mM $CaCl_2$ and 5 ppm protease for 60 minutes and assayed for enzyme activity as follows: 10 µl was taken and added to 190 µl AAPF substrate solution, conc. 1 mg/ml, in 0.1 M Tris/0.005% TWEEN®, pH 8.6. The rate of increase in absorbance at 410 nm due to release of p-nitroaniline was monitored (at 25° C.). The results of 4 proteases are shown in FIG. 34.

Example 24 pH Profile of ASP Protease on DMC Substrate

In this Example, experiments conducted to determine the pH profile of the ASP protease are described. The *Cellulomonas* 69B4 protease of the present invention, isolated and purified by methods described herein and three currently used subtilisin proteases (PURAFECT®, BPN'-variant 1, GG36-variant-1) described in Examples 21-23, were analyzed for their ability to hydrolyze a commercial synthetic substrate, di-methyl casein ("DMC"/Sigma C-9801) in the pH range from 4 to 12.

The DMC method described at the beginning of the Experimental section was used, with modifications, as indicated below. Briefly, a 5 mg/ml DMC substrate solution was prepared in the appropriate buffer (5 mg/ml DMC, 0.005% (w/w) TWEEN-80® (polyoxyethylene sorbitan mono-oleate, Sigma P-1754)). The appropriate DMC buffers were composed as follows: 40 mM MES for pH 4 and 5; 40 mM HEPES for pH 6 and 7, 40 mM TRIS for pH 8 and 9; and 40 mM Carbonate for pH 10, 11 and 12.

For the determination, 180 µl of each pH-substrate solution was transferred into 96 well microtiter plate and were pre-incubated at 37° C. for twenty minutes prior to enzyme addition. The respective enzyme solutions (BPN'-variant-1; GG36-variant-1; PURAFECT®; and 69B4 protease) were prepared, containing about 25 ppm and 20 µl of these enzyme solutions. These enzyme solutions were pipetted into the substrate containing wells in order to achieve a 2.5 ppm final enzyme concentration in each well. The 96 well plate containing enzyme-substrate mixtures was incubated at 37° C. and 300 rpm for one hour in an IKS-Multitron incubator/shaker.

A 2,4,6-trinitrobenzene sulfonate ("TNBS") color reaction method was used to determine the amount of peptides and amino acids release from DMC substrate. The free amino groups (of the peptides and amino acids) react with 2,4,6-trinitro-benzene sulfonic acid to form a yellow colored complex. The absorbance was measured at 405 nm in a Spectra-Max 250 MTP Reader.

The TNBS assay was conducted as follows. A 1 mg/ml solution of TNBS (5% 2,4,6 trinitrobenzene sulfonic acid/Sigma-P2297) was prepared in reagent buffer A (2.4 g NaOH, 45.4 g $Na_2B_4O_7.10H_2O$ dissolved by heating in 1000 ml). Then, 60 µl per well were aliquoted into a 96-well plate and 10 µl of the incubation mixture described above were added to each well and mixed for 20 minutes at room temperature. Then, 200 µl of reagent B (70.4 g $NaH_2PO_4.H_2O$ and 1.2 g $Na_2SO_3$ in 2000 ml) were added to each well and mixed to stop the reaction. The absorbance at 405 nm was measured in a SpectraMax 250 MTP Reader. The absorbance value was corrected for a blank (without enzyme).

The data in Table 24-1 show the comparative ability of the 69B4 protease to hydrolyze such substrate versus proteases from a known mutant variants (BPN' variant-1 and GG36 variant-1).

Figure 35:
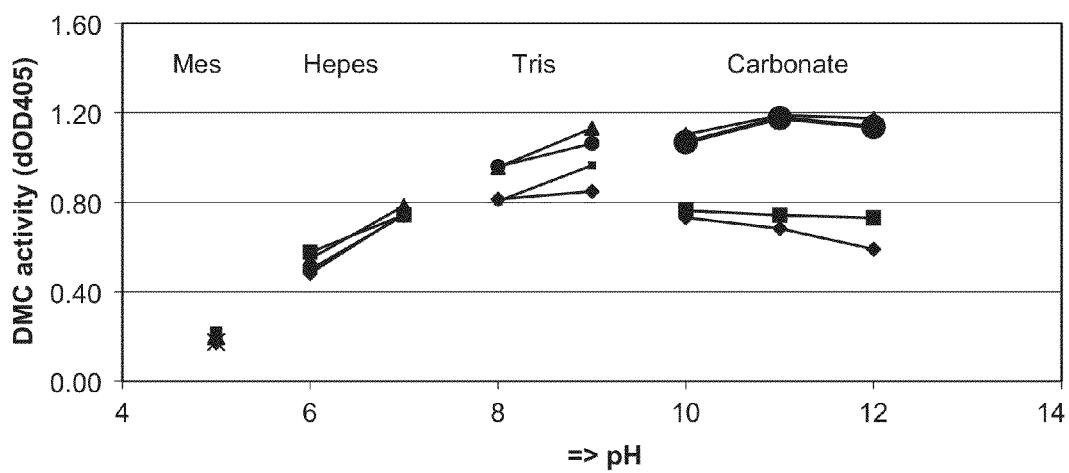
FIG. 35 provides a graph that shows enzyme activity (hydrolysis of di-methyl casein measured by absorbance at 405 nm) of certain serine proteases (2.5 ppm) (69B4 [■-]; BPN'-variant [-♦-PURAFECT® [-▲-]; and GG36-variant 1[-●-] at pH's ranging from 5 to 12 at 37° C.
Figure 36:
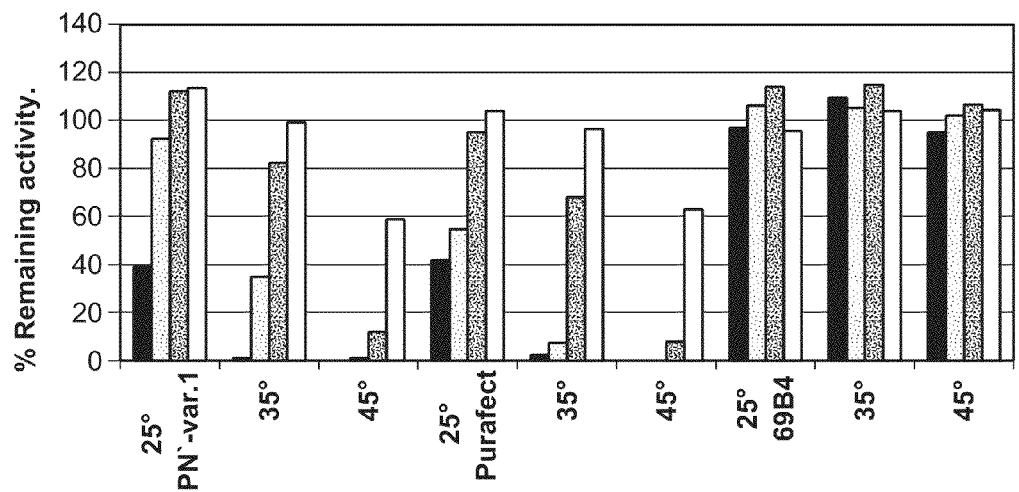
FIG. 36 provides a bar graph that shows enzyme stability as indicated by % remaining activity (hydrolysis of di-methyl casein measured by absorbance at 405 nm) of certain serine proteases (2.5 ppm) (69B4, BPN'-variant; PURAFECT® and GG36-variant 1 at pHs ranging from 3 (■), 4 (▨), 5 (▤) to 6 (▧) at 25°, 35°, and 45° C., respectively.
Figure 37:
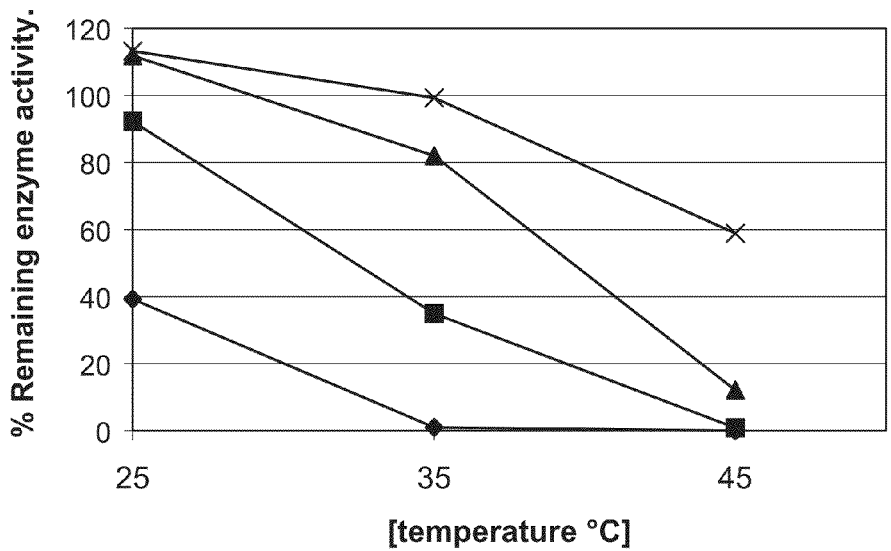
FIG. 37 provides a graph that shows enzyme stability as indicated by % remaining activity of a BPN'-variant at pH ranges from 3 (-▼-), 4 (--■--), 5 (--▲--) to 6 (--X--) at 25°, 35°, and 45° C., respectively FIG. 38 provides a graph that shows enzyme stability as indicated by % remaining activity of PURAFECT® TM protease at pH ranges from 3 (-♦-), 4 (--■--), 5 (--▲--) to 6 (--X--) at 25°, 35°, and 45° C., respectively FIG. 39 provides a graph that shows enzyme stability as indicated by % remaining activity of 69B4 protease at pH ranges from 3 (-♦-), 4 (--■--), 5 (--▲--) to 6 (--X--) at 25°, 35° and 45° C., respectively
Figure 38:
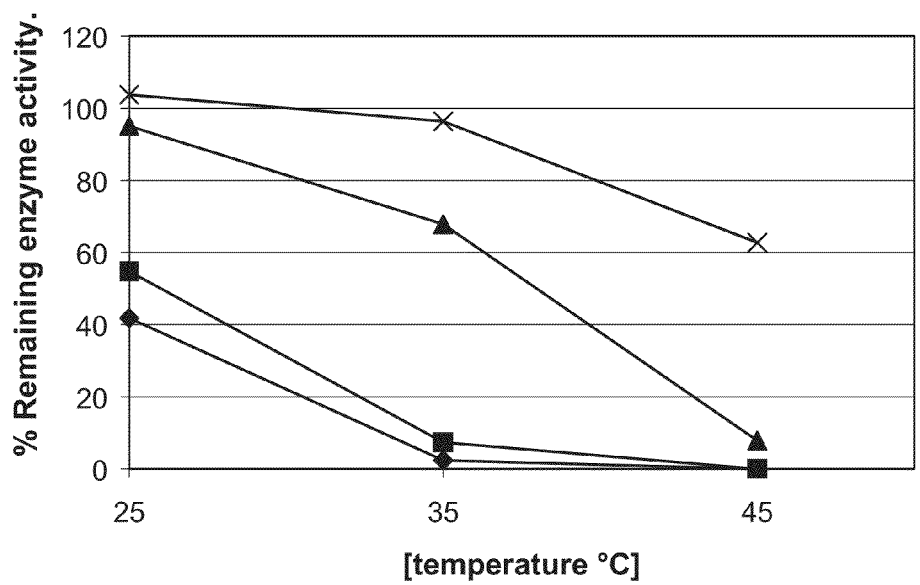
Figure 39:
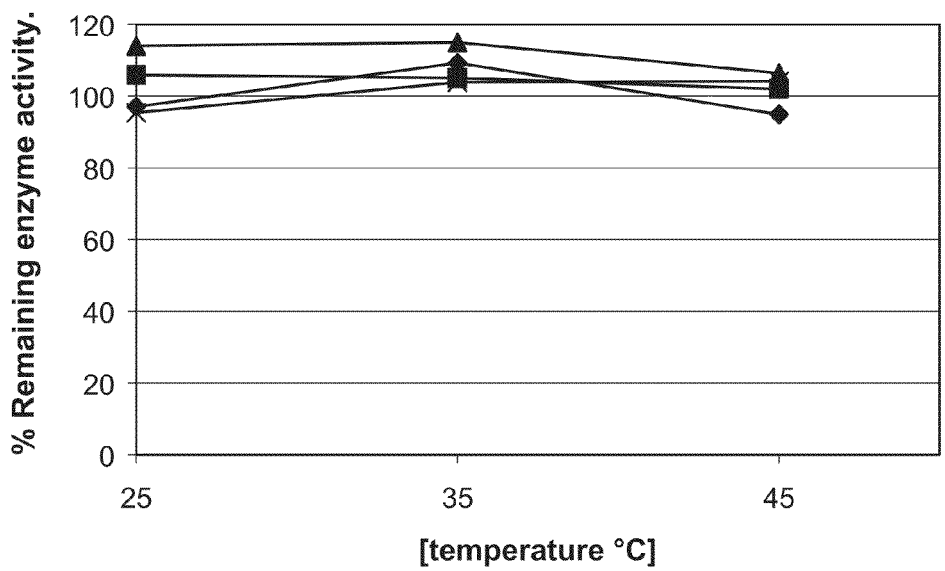

Also, as shown in FIG. 35, the serine protease of the present invention showed comparative or increased hydrolysis of DMC substrate with an optimal DMC-hydrolysis activity over a broad pH range from 7 to 12.

TABLE 24-1

| | TNBS Response | | | | | | | | |
|---|---|---|---|---|---|---|---|---|---|
| | TNBS response (OD405 nm) | | | | | | | | |
| Enzyme | pH4 | pH5 | pH6 | pH7 | pH8 | pH9 | pH10 | pH11 | pH12 |
| BPN' variant-1 | 0.095 | 0.174 | 0.482 | 0.749 | 0.813 | 0.847 | 0.730 | 0.683 | 0.590 |
| GG36 variant-1 | 0.228 | 0.172 | 0.499 | 0.740 | 0.958 | 1.062 | 1.068 | 1.175 | 1.136 |
| Purafect ® | 0.042 | 0.202 | 0.545 | 0.783 | 0.956 | 1.130 | 1.102 | 1.188 | 1.174 |
| 69B4 | 0.252 | 0.218 | 0.575 | 0.742 | 0.803 | 0.965 | 0.762 | 0.741 | 0.729 |

Example 25 pH Stability of ASP Protease

In this Example, experiments conducted to determine the pH stability of the ASP protease are described. As in Examples 21-24, two currently used subtilisin proteases (PURAFECT® and BPN'-variant-1) were also tested.

The respective enzyme solutions (i.e., BPN'-variant-1, PURAFECT®, and 69B4 protease) were prepared containing 90 ppm protease in 0.1 M Citrate buffer, pH 3, 4, 5 and 6. Then, 10 ml tubes containing 1 ml of buffered enzyme solutions were placed in a GFL 1083 water bath set at 25° C., 35° C. and 45° C. respectively, for 60 minutes. AAPF activity was determined for each enzyme sample at time 0 and 60 minutes as described above. The remaining enzyme activity was calculated and the results are provided in Table 25-1 below, and are shown in FIGS. 25-28).

As indicated by the data in Table 25-1, the ASP protease is exceptional stable at pH 3, 4, 5, and 6, at temperatures between 25° C. and 45° C., as compared to the BPN' variant-1 and PURAFECT®.

TABLE 25-1 pH Stability Data

| pH | BPN' Variant-1 | | | PURAFECT ® | | | ASP | | |
|---|---|---|---|---|---|---|---|---|---|
|  | 25° | 35° | 45° | 25° | 35° | 45° | 25° | 35° | 45° |
| pH 3 | 39 | 1 | 0 | 42 | 2 | 0 | 97 | 109 | 95 |
| pH 4 | 92 | 35 | 1 | 55 | 7 | 0 | 106 | 105 | 102 |
| pH 5 | 112 | 82 | 12 | 95 | 68 | 8 | 114 | 115 | 106 |
| pH 6 | 113 | 99 | 59 | 104 | 96 | 63 | 95 | 104 | 104 |

Example 26

Stability and Specificity of ASP

In this Example, experiments conducted to determine the stability and specificity differences between ASP, ASP mutants, and FNA are described. These experiments were performed by formulating liquid TIDE® detergent (Procter & Gamble) with calcium formate (an anionic surfactant titrant), borate (a P1 binder/inhibitor), and glycerol (water ordering), either independently of or in combination with each other. The enzyme was tested under these conditions and the residual enzyme activity was determined over time at a fixed temperature.

The experiments are described in greater detail below. Unformulated liquid TIDE® detergent (i.e., without added enzyme stabilizing chemicals) was divided into eleven aliquots. Then, glycerol, borax, or calcium formate were added to the detergent aliquots in the proportions shown in Table 26-1.

TABLE 26-1

Detergent Additives (%)

| Aliquot # | % Glycerol | % Borax | % Calcium Formate |
|---|---|---|---|
| 1 | 5 | 0 | .1 |
| 2 | 2.5 | 1.5 | .05 |
| 3 | 5 | 3 | 0 |
| 4 | 0 | 3 | 0 |
| 5 | 2.5 | 1.5 | .05 |
| 6 | 0 | 0 | .1 |
| 7 | 0 | 3 | .1 |
| 8 | 0 | 0 | 0 |
| 9 | 5 | 0 | 0 |
| 10 | 2.5 | 1.5 | .05 |
| 11 | 5 | 3 | .1 |

Each aliquot was pre-warmed to 90° F., and either FNA, ASP (wild-type) or an ASP R18 variant was added to approximately one gram per liter protease. After thorough mixing, a portion was removed and assayed for activity with synthetic AAPF-pNA substrate, as described above. After the assay, each aliquot was placed back into a 90° F. oven. The assay process was repeated over time, and the decline in activity at T0 was plotted as a % T0 activity remaining.

Surprisingly, it was found that ASP did not have the same calcium formate or glycerol dependency as FNA. Furthermore, it was determined that borate (alone) had the most dramatic effect on stabilizing ASP. It was also found that the addition of stabilizing chemicals provided significant benefits to the wild-type ASP, as well as the ASP R18 variant, indicating that the variant site is independent of the borate-activated site.

Example 27

LAS Stability of ASP

In this Example, experiments conducted to determine the stability of ASP to anionic surfactants are described. LAS (linear alkyl sulfonate), an anionic surfactant, is a component of HDL detergents known to inactivate enzymes. The methods used are described above.

It was determined that wild-type ASP incubated in LAS dissolved in Tris HCl pH 8.6 is inactivated (See, Table 27-1, below). Further study revealed that inactivation is rapid (See, Table 27-2). As LAS is a negatively charged molecule, the hypothesis that electrostatic attraction of LAS with positively charged amino-acid side chains of ASP was the cause of the LAS sensitivity, was developed. To test this hypothesis, arginine residues (wild-type ASP contains no lysine residues), were mutated to other amino-acids.

Incubation of these mutants in 0.05% (w/v) LAS in Tris HCl pH8.6, for one hour revealed that all arginine replacement mutants were more stable than wild-type ASP. In contrast, non-arginine replacement mutations that were also tested for LAS stability were generally not improved compared to wild-type (See, Table 27-3). Subsequent multiple arginine replacement mutations revealed that the enzyme is substantially more stable than the wild-type enzyme, and more stable that single arginine replacement mutations (See, Table 27-4).

Another anionic surfactant that is used in HDL detergents is AES. Wild-type ASP was found to be unstable in high concentrations of AES (See, Table 27-5). The mutant ASP R18 was found to be more stable than wild-type in AES (See, Table 27-5). Also, the rate of inactivation of activity by 5% AES was found to be higher for the wild-type than the ASP R18 mutant (See, Table 27-6). These results confirm that replacement of arginine residues of ASP improves the stability of ASP in anionic detergents in general. It is not intended that the present invention be limited to any specific anionic detergents or mutations. Indeed, it is contemplated that various anionic detergents (as well as other detergents) will find use in the present invention, as will various ASP mutants.

TABLE 27-1

Inactivation of ASP by LAS in Tris HCl pH 8.6

| % LAS (w/v) | % Activity of Control |
|---|---|
| Control (0 LAS) | 100 |
| 0.01 | 87 |
| 0.03 | 77 |
| 0.06 | 59 |
| 0.10 | 47 |
| 0.30 | 31 |
| 0.60 | 20 |
| 1.00 | 12 |

TABLE 27-2

Time-course of ASP Inactivation by 0.1% LAS

| Time (secs) | % Remaining Activity |
|---|---|
| 0 | 100 |
| 60 | 45 |
| 120 | 26 |
| 240 | 20 |
| 600 | 11 |

TABLE 27-3

Stability of ASP and Single Mutants
(Incubated 0.05% LAS in Tris HCl, pH 8.6, for 60 mins.)

| Mutant | % Remaining Activity of 0 LAS Control |
| --- | --- |
| Wild-type | 18 |
| R14L | 47 |
| R16I | 49 |
| R16L | 56 |
| R16Q | 51 |
| R35F | 43 |
| R127A | 59 |
| R127K | 31 |
| R127Q | 52 |
| R159K | 25 |
| T36S | 11 |
| G65Q | 22 |
| Y75G | 7 |
| N76L | 17 |
| S76V | 17 |

TABLE 27-4

Stability of ASP and Multiple Arginine Replacements
(Incubated 0.05% LAS in Tris HCl, pH 8.6, for 60 mins)

| Mutant | % Remaining Activity of 0 LAS Control |
| --- | --- |
| Wild-type | 27.5 |
| ASP R-1 | 98.8 |
| ASP R-2 | 69.6 |
| ASP R-3 | 100.2 |
| ASP R-7 | 103.9 |
| ASP R-10B | 98.9 |
| ASP R-18 | 100.9 |
| ASP R23 | 79.4 |

In this Table,
R-1 = R16Q/R35F/R159Q
R-2 = R159Q
R-3 = R16Q/R123L
R-7 = R14L/R127Q/R159Q
R-10B = R14L/R179Q
R-18 = R123L/R127Q/R179Q.
R-21 = R16Q/R79T/R127Q
R-23 = R16Q/R79T

TABLE 27-5

Inactivation of ASP and ASP Mutant R-18 by AES in Tris HCl pH 8.6

| | % Remaining activity of 0% AES control | |
| --- | --- | --- |
| % AES (v/w) | Wild-type ASP | ASP R-18 |
| 0 | 100 | 100 |
| 1 | 70 | 94 |
| 5 | 32 | 57 |

TABLE 27-6

Time-course of ASP and Mutant R-18 Inactivation
by 5% AES in Tris HCl, pH 8.6

| | % Remaining Activity of 0% AES Control | |
| --- | --- | --- |
| Time (Mins) | Wild-type ASP | ASP R-128 |
| 0 | 100 | 100 |
| 90 | 99 | 105 |
| 4020 | 15 | 83 |

Example 28

Determination of ASP Autolysis Sites in the
Presence and Absence of LAS Detergent In this Example, experiments conducted to determine the ASP autolysis sites in the presence and absence of LAS are described. ASP autolysis was evaluated in a buffer with and without LAS (dodecylbenzene-sulfonic acid). Autolysis peptide assignments were made based on molecular weight and sequence of each peptide (from MS and MS/MS data, respectively).

ASP (at concentration of 0.35 ug/uL) was incubated (at 4° C.) in a 100 mM Tris pH 8.6 with and without 0.1% LAS (dodecylbenzene-sulfonic acid). Aliquots were taken at time periods from 0 to 30 min of incubation and autolysis was terminated by an addition of TFA (final concentration 1%). Aliquots (10 μL) were analyzed by liquid chromatography coupled with electrospray tandem mass spectrometry (LC-ESI-MS/MS). Peptides were resolved using an HPLC system (model 1100, Agilent Technologies) using a reversed-phase column (Vydac C4, 0.3 mmID×150 mm), and a gradient from 0 to 100% solvent B (0.1% formic acid in acetonitrile) in 60 min at a flow rate of 5 μL/min (generated using a static split from a pump flow rate of 250uL/min). Solvent A consisted of 0.1% formic acid in water; and solvent B was 0.1% formic acid in acetonitrile.

Mass spectra were acquired using ion trap mass spectrometer (model LCQ Classic, Thermo). The mass spectrometer was tuned for optimum detection of m/z of 785 and operated with spray voltage of 2.5 kV, and a heated capillary at 250° C. Mass spectra were acquired with injection time of 500 msec and 5 microscans. Tandem MS spectra were acquired in data-dependent mode, with the most intense peak selected and fragmented with a normalized collision energy of 35%. For relative peptide quantitation, peak areas were determined using vendor software. The identity of the autolysis peptides was determined using a database search program (TurboSequest, Thermo) run on a database containing ASP sequence. Database searches were performed with no enzyme selected, threshold of 10000, dta file parameters (peptide m/z error of 1.7, group 11, minimum ion count 15), and database parameters (peptide error of 2.2, MS/MS ions error of 0.0, both B,Y ions).

Without LAS in the sample buffer, ASP cleavages were primarily observed at the termini and in the middle of the molecule (positions Y9, F47, Y59, F165, Q174, Y176; See Table 28-1, below). Relative quantitative data for observed peptides and intact ASP was plotted over the course of the experiment (See, FIG. 25, Panel A). The majority of the ASP remained intact and only 1% was in the form of cleaved peptides (protein:peptide ratio of 99:1) These data indicated that the majority of ASP remains intact, folded, and resistant to further autolytic cleavage.

With 0.1% LAS in the sample buffer, ASP cleavages were observed throughout the protein (positions Y9, T40, F47, Y57, F59, R61, L69, F165, Q174, Y176). The majority of the ASP was in the peptide form after 10 min (See, FIG. 25, Panel B). After 60 min, the protein:peptide ratio was <1:99. These data indicate that ASP is totally unfolded in the presence of LAS detergent, thus extensive cleavage throughout the sequence was observed. The observed autolysis cleavage sites under the two conditions are summarized in the following Table. In this Table, the amino acids preceding and following the periods are the amino acids that immediately precede and follow the autolysis peptide. The sequence between the periods indicates the sequence of the autolysis peptides observed.

TABLE 28-1

ASP Autolysis Peptides Observed With and Without 0.1% LAS

| Peptide Sequence | Start-End | Calculated Mass (Da) | Measured Mass (Da) | Observed in 0.1% LAS | Observed in 0% LAS |
|---|---|---|---|---|---|
| -.FDVIGGNAY.T (SEQ ID NO: 631) | [1-9] | 954.5 | 954.4 | Y | Y |
| T.ANPTGTF.A (SEQ ID NO: 632) | [41-47] | 706.3 | 706.3 | Y | N |
| F.AGSSFPGNDY.A (SEQ ID NO: 633) | [48-57] | 1013.4 | 1013.3 | Y | N |
| F.AGSSFPGNDYAF.V (SEQ ID NO: 634) | [48-59] | 1231.5 | 1231.4 | Y | Y |
| R.TGAGVNLL.A (SEQ ID NO: 635) | [62-69] | 743.3 | 743.4 | Y | N |
| F.FQPVNPI.L (SEQ ID NO: 636) | [166-172] | 813.4 | | N | N |
| F.FQPVNPILQ.A (SEQ ID NO: 637) | [166-174] | 1054.6 | 1054.5 | Y | Y |
| F.FQPVNPILQAY.G (SEQ ID NO: 638) | [166-176] | 1288.7 | 1288.5 | Y | Y |

Example 29

Use of Reversible Inhibitors to Reduce LAS-Induced Degradation of ASP

In this Example, experiments conducted to assess the use of reversible inhibitors to reduce LAS-induced degradation of ASP are described. Benzamidine (BZA) is a known reversible inhibitor of serine proteases. Using the standard succ-AAPF-pNA assay as described above, BZA was shown to inhibit the activity of approximately 2 µg/ml ASP, with complete inhibition occurring at 1000 mM (1M), as indicated in Table 29-1, below:

TABLE 29-1

Inhibition of ASP

| BZA Conc. mM | Assay Rate |
|---|---|
| 0 | 0.83 |
| 1 | 0.85 |
| 10 | 0.82 |
| 100 | 0.42 |
| 1000 | 0.02 |

Approximately 200 µg/ml ASP was then incubated with 0.1% LAS and with, and without 1M BZA for up to 4 days. Enzyme activity was measured at different time points by addition of 10 µl incubated sample to 990 µl of assay solution. This reduces the BZA concentration to 10 mM, which by reference to the table above is not inhibitory. Therefore, any loss of activity will be due to enzyme degradation. As indicated in the results below, enzyme incubated with 0.1% LAS and without BZA lost all activity (i.e., it was degraded), while enzyme incubated with 0.1% LAS and 1M BZA, retained activity over the 4 day time-course of the study, demonstrating that inhibition of ASP activity prevents degradation by LAS.

TABLE 29-2

Assay Rate Results for Enzyme Incubated with 0.1% LAS, With/Without BZA

| Time | ASP + 0.1% LAS | ASP + 0.1% LAS + 1M BZA |
|---|---|---|
| 30 secs | 0.755 | 0.761 |
| 30 mins | 0.685 | 0.781 |
| 18 hrs | 0.067 | 0.761 |
| 4 days | 0.004 | 0.853 |

Example 30

Testing of Mutant ASPs

In addition to the tests described above, tests were conducted on various mutants of ASP. The methods described above in Example 1 were used. In the following Tables, "Variant Code" provides the wild-type amino acid, the position in the amino acid sequence, and the replacement amino acid (i.e., "F001A" indicates that the phenylalanine at position 1 in the amino acid sequence has been replaced by alanine in this particular variant).

Keratin Hydrolysis

The table (Table 30-1) below provides the keratin hydrolysis data obtained for the ASP variants which show activity on this substrate in the keratin assay as described above ("Protease Assay with Keratin in Microtiter Plates"). The values are relative to wild type (WT) and calculated as described in the assay procedure. Values greater than 1 are indicative of better activity than WT ASP.

TABLE 30-1

Keratin Hydrolysis Results

| Variant code | Keratin hydrolysis relative |
|---|---|
| F001T | 1.24 |
| F001D | 1.13 |
| F001H | 1.04 |
| F001M | 1.01 |
| F001E | 1.01 |
| V003L | 1.08 |
| I004E | 1.00 |
| N007L | 1.18 |
| A008E | 1.18 |

TABLE 30-1-continued

Keratin Hydrolysis Results

| Variant code | Keratin hydrolysis relative |
|---|---|
| A008G | 1.13 |
| A008D | 1.04 |
| T010N | 1.27 |
| T010E | 1.20 |
| T010D | 1.13 |
| T010G | 1.04 |
| I011A | 1.01 |
| G012D | 1.17 |
| G013S | 1.16 |
| G013M | 1.03 |
| G013A | 1.01 |
| R014L | 1.52 |
| R014Q | 1.49 |
| R014I | 1.40 |
| R014D | 1.36 |
| R014N | 1.29 |
| R014G | 1.28 |
| R014T | 1.21 |
| R014M | 1.21 |
| R014K | 1.18 |
| R014A | 1.12 |
| R014S | 1.12 |
| R014W | 1.07 |
| R014P | 1.04 |
| R014H | 1.03 |
| S015W | 1.20 |
| S015T | 1.05 |
| R016A | 1.04 |
| R016S | 1.03 |
| R016Q | 1.03 |
| I019V | 1.11 |
| N024E | 2.44 |
| N024A | 1.72 |
| N024T | 1.55 |
| N024Q | 1.40 |
| N024V | 1.28 |
| N024L | 1.26 |
| N024H | 1.26 |
| N024M | 1.14 |
| N024F | 1.05 |
| N024S | 1.03 |
| R035E | 1.60 |
| R035L | 1.47 |
| R035Q | 1.42 |
| R035F | 1.41 |
| R035A | 1.37 |
| R035K | 1.26 |
| R035T | 1.22 |
| R035H | 1.18 |
| R035M | 1.17 |
| R035Y | 1.16 |
| R035W | 1.13 |
| R035S | 1.12 |
| R035D | 1.07 |
| R035N | 1.03 |
| R035V | 1.02 |
| T036I | 6.82 |
| T036S | 1.34 |
| T036G | 1.34 |
| T036N | 1.22 |
| T036D | 1.16 |
| T036H | 1.13 |
| T036P | 1.03 |
| T036L | 1.01 |
| A038R | 1.77 |
| A038D | 1.51 |
| A038H | 1.30 |
| A038N | 1.28 |
| A038F | 1.22 |
| A038L | 1.19 |
| A038S | 1.18 |
| A038Y | 1.17 |
| A038T | 1.10 |
| A038V | 1.07 |
| A038G | 1.03 |
| A038I | 1.01 |
| T040V | 1.11 |
| A041N | 1.17 |
| A041D | 1.17 |
| A041I | 1.07 |
| A041L | 1.03 |
| T044E | 1.03 |
| A048E | 1.09 |
| G049A | 1.36 |
| G049S | 1.26 |
| G049H | 1.16 |
| G049F | 1.13 |
| G049L | 1.04 |
| G049T | 1.00 |
| S051D | 1.33 |
| S051Q | 1.18 |
| S051H | 1.12 |
| S051V | 1.11 |
| S051T | 1.09 |
| S051M | 1.01 |
| G054D | 1.71 |
| G054E | 1.23 |
| G054N | 1.06 |
| G054L | 1.02 |
| G054I | 1.00 |
| N055E | 1.30 |
| N055F | 1.25 |
| N055Q | 1.05 |
| R061M | 1.20 |
| R061T | 1.16 |
| R061E | 1.15 |
| R061H | 1.10 |
| R061S | 1.09 |
| R061N | 1.08 |
| R061K | 1.07 |
| R061V | 1.01 |
| T062I | 1.00 |
| G063D | 1.18 |
| G063V | 1.07 |
| A064I | 1.40 |
| A064N | 1.21 |
| A064Y | 1.19 |
| A064L | 1.17 |
| A064V | 1.17 |
| A064H | 1.16 |
| A064F | 1.15 |
| A064P | 1.15 |
| A064T | 1.13 |
| A064Q | 1.13 |
| A064M | 1.13 |
| A064S | 1.11 |
| A064W | 1.09 |
| A064G | 1.01 |
| G065P | 1.42 |
| G065D | 1.29 |
| G065Q | 1.29 |
| G065S | 1.25 |
| G065T | 1.25 |
| G065V | 1.23 |
| G065L | 1.21 |
| G065Y | 1.16 |
| G065A | 1.05 |
| G065R | 1.02 |
| N067D | 1.36 |
| N067G | 1.20 |
| N067T | 1.12 |
| N067E | 1.12 |
| N067S | 1.10 |
| N067H | 1.09 |
| N067A | 1.08 |
| N067Q | 1.07 |
| N067L | 1.05 |
| L068H | 1.07 |

TABLE 30-1-continued

Keratin Hydrolysis Results

| Variant code | Keratin hydrolysis relative |
|---|---|
| L069S | 1.35 |
| L069H | 1.23 |
| L069V | 1.03 |
| A070D | 1.20 |
| A070H | 1.16 |
| A070G | 1.13 |
| A070S | 1.04 |
| Q071G | 1.20 |
| Q071H | 1.14 |
| Q071D | 1.13 |
| Q071S | 1.10 |
| Q071A | 1.07 |
| Q071N | 1.06 |
| Q071I | 1.06 |
| V072I | 1.11 |
| N073T | 1.95 |
| N073S | 1.07 |
| N074G | 1.75 |
| Y075G | 1.42 |
| Y075F | 1.24 |
| S076D | 1.69 |
| S076V | 1.48 |
| S076E | 1.47 |
| S076Y | 1.45 |
| S076T | 1.25 |
| S076L | 1.25 |
| S076N | 1.24 |
| S076I | 1.22 |
| S076W | 1.17 |
| S076Q | 1.13 |
| S076A | 1.08 |
| G077T | 2.13 |
| G077S | 1.21 |
| G077N | 1.06 |
| G078D | 1.35 |
| G078A | 1.27 |
| G078S | 1.07 |
| G078N | 1.07 |
| G078V | 1.03 |
| G078T | 1.00 |
| R079G | 1.48 |
| R079D | 1.44 |
| R079P | 1.43 |
| R079A | 1.31 |
| R079E | 1.31 |
| R079L | 1.25 |
| R079V | 1.25 |
| R079T | 1.23 |
| R079M | 1.23 |
| R079S | 1.23 |
| R079C | 1.02 |
| V080L | 1.03 |
| Q081E | 1.22 |
| Q081D | 1.12 |
| Q081V | 1.10 |
| Q081H | 1.10 |
| Q081P | 1.01 |
| A083E | 1.27 |
| A083L | 1.05 |
| A083I | 1.03 |
| H085Q | 1.26 |
| H085T | 1.22 |
| H085L | 1.14 |
| H085M | 1.10 |
| H085A | 1.06 |
| H085S | 1.02 |
| T086D | 1.33 |
| T086E | 1.24 |
| T086I | 1.08 |
| T086L | 1.07 |
| T086Q | 1.07 |
| T086G | 1.06 |
| T086A | 1.05 |
| T086N | 1.01 |
| A088E | 1.01 |
| A088F | 1.00 |
| P089E | 1.04 |
| V090P | 1.51 |
| V090S | 1.42 |
| V090I | 1.34 |
| V090T | 1.22 |
| V090N | 1.10 |
| V090A | 1.08 |
| V090L | 1.06 |
| S092G | 1.20 |
| S092A | 1.12 |
| S092C | 1.06 |
| A093D | 1.20 |
| A093S | 1.12 |
| A093E | 1.09 |
| S099N | 1.27 |
| S099V | 1.23 |
| S099D | 1.21 |
| S099T | 1.21 |
| S099I | 1.08 |
| T101S | 1.14 |
| W103M | 1.17 |
| T107E | 1.32 |
| T107S | 1.30 |
| T107V | 1.23 |
| T107H | 1.23 |
| T107M | 1.21 |
| T107I | 1.17 |
| T107N | 1.12 |
| T107A | 1.10 |
| T107Q | 1.03 |
| T107K | 1.01 |
| T109E | 1.36 |
| T109I | 1.11 |
| T109G | 1.10 |
| T109A | 1.10 |
| T109L | 1.08 |
| T109P | 1.05 |
| T109H | 1.03 |
| T109N | 1.00 |
| A110S | 1.10 |
| A110T | 1.03 |
| A110H | 1.01 |
| L111E | 1.08 |
| N112E | 1.61 |
| N112D | 1.42 |
| N112Q | 1.36 |
| N112L | 1.27 |
| N112V | 1.23 |
| N112Y | 1.20 |
| N112I | 1.13 |
| N112S | 1.06 |
| N112R | 1.04 |
| S113T | 1.21 |
| S114A | 1.12 |
| V115A | 1.15 |
| T116E | 1.34 |
| T116Q | 1.28 |
| T116F | 1.09 |
| T116S | 1.02 |
| T121E | 1.35 |
| T121D | 1.15 |
| T121S | 1.05 |
| R123E | 1.63 |
| R123D | 1.57 |
| R123I | 1.48 |
| R123F | 1.40 |
| R123A | 1.30 |
| R123L | 1.30 |
| R123Q | 1.29 |
| R123N | 1.24 |
| R123H | 1.22 |
| R123T | 1.16 |

TABLE 30-1-continued

Keratin Hydrolysis Results

| Variant code | Keratin hydrolysis relative |
|---|---|
| R123Y | 1.15 |
| R123S | 1.12 |
| R123G | 1.11 |
| R123V | 1.09 |
| R123W | 1.07 |
| R123K | 1.07 |
| G124A | 1.06 |
| I126L | 1.06 |
| R127A | 1.38 |
| R127Q | 1.23 |
| R127H | 1.19 |
| R127S | 1.19 |
| R127K | 1.17 |
| R127Y | 1.15 |
| R127E | 1.14 |
| R127F | 1.11 |
| R127T | 1.04 |
| R127C | 1.01 |
| T129S | 1.31 |
| A132S | 1.03 |
| P134A | 1.04 |
| S140A | 1.02 |
| L142V | 1.31 |
| A143N | 1.07 |
| N145E | 1.33 |
| N145D | 1.14 |
| N145T | 1.10 |
| N145S | 1.07 |
| N145Q | 1.07 |
| V150L | 1.01 |
| N157D | 1.01 |
| R159E | 1.61 |
| R159F | 1.37 |
| R159N | 1.30 |
| R159Q | 1.28 |
| R159D | 1.23 |
| R159K | 1.20 |
| R159C | 1.19 |
| R159S | 1.10 |
| R159A | 1.10 |
| R159L | 1.09 |
| R159Y | 1.08 |
| R159H | 1.08 |
| R159V | 1.08 |
| R159G | 1.06 |
| R159M | 1.06 |
| T160E | 1.19 |
| T160D | 1.02 |
| G161K | 1.04 |
| T163D | 1.11 |
| T163I | 1.08 |
| T163C | 1.03 |
| Q167T | 1.02 |
| N170Y | 2.23 |
| N170D | 1.38 |
| N170L | 1.12 |
| N170A | 1.06 |
| N170C | 1.04 |
| N170G | 1.04 |
| I172T | 6.27 |
| A175E | 1.04 |
| G177M | 1.01 |
| R179V | 1.60 |
| R179T | 1.53 |
| R179D | 1.48 |
| R179N | 1.42 |
| R179E | 1.42 |
| R179M | 1.41 |
| R179A | 1.39 |
| R179I | 1.38 |
| R179K | 1.32 |
| R179Y | 1.27 |
| R179L | 1.11 |
| R179W | 1.06 |
| I181L | 1.96 |
| I181S | 1.07 |
| T182V | 1.14 |
| T182L | 1.02 |
| T183E | 1.19 |
| T183I | 1.17 |
| T183Q | 1.07 |
| T183D | 1.05 |
| D184E | 1.02 |
| S185N | 1.11 |
| S185D | 1.03 |
| S185M | 1.03 |
| S185G | 1.01 |
| G186N | 2.05 |
| S187H | 1.05 |
| S187E | 1.01 |
| S188E | 1.08 |

DMC Assay

The following table (Table 30-2) provides the variants with improved specific activity on casein. The activity on casein as substrate for all variants was determined as described above ("Protease Assay with Dimethylcasein (96 wells), With or Without Preheating of the Protease for Activity and Thermostability Assays"). The values in the table provide relative values for each variant compared to the activity of the WT enzyme (i.e., each value is the quotient of (variant activity)/(wild type activity)). Every variant with a value higher than 1 is better than WT.

TABLE 30-2

DMC Assay Results

| Variant code | Casein specific activity relative to wild type |
|---|---|
| F001T | 1.19 |
| F001A | 1.11 |
| F001G | 1.00 |
| D002G | 1.24 |
| D002Q | 1.24 |
| D002A | 1.12 |
| D002H | 1.10 |
| D002N | 1.10 |
| V003L | 1.33 |
| V003I | 1.28 |
| V003T | 1.17 |
| I004V | 1.07 |
| I004Q | 1.02 |
| N007L | 1.56 |
| N007S | 1.25 |
| N007A | 1.22 |
| N007H | 1.11 |
| N007I | 1.11 |
| N007V | 1.06 |
| A008G | 1.12 |
| A008K | 1.09 |
| Y009V | 1.06 |
| T010G | 1.18 |
| T010K | 1.12 |
| T010Q | 1.01 |
| I011Q | 1.28 |
| I011A | 1.26 |
| I011T | 1.16 |
| I011S | 1.11 |
| I011L | 1.06 |
| G012W | 1.11 |
| G012R | 1.02 |

TABLE 30-2-continued

DMC Assay Results

| Variant code | Casein specific activity relative to wild type |
|---|---|
| G013M | 1.09 |
| G013S | 1.08 |
| R014E | 1.27 |
| S015F | 1.09 |
| S015A | 1.03 |
| I019V | 1.04 |
| N024A | 2.48 |
| N024E | 2.37 |
| N024T | 1.70 |
| N024Q | 1.70 |
| N024V | 1.62 |
| N024M | 1.48 |
| N024H | 1.45 |
| N024L | 1.34 |
| N024F | 1.21 |
| N024S | 1.10 |
| I028L | 1.16 |
| A030S | 1.11 |
| R035F | 1.20 |
| R035D | 1.01 |
| T036I | 14.08 |
| T036G | 2.46 |
| T036N | 2.13 |
| T036S | 2.08 |
| T036W | 1.84 |
| T036P | 1.69 |
| T036H | 1.67 |
| T036D | 1.61 |
| T036Y | 1.48 |
| T036V | 1.48 |
| T036R | 1.38 |
| T036F | 1.36 |
| T036L | 1.33 |
| T036C | 1.12 |
| A038R | 3.72 |
| A038F | 1.45 |
| A038D | 1.39 |
| A038S | 1.38 |
| A038H | 1.36 |
| A038L | 1.30 |
| A038N | 1.24 |
| A038K | 1.17 |
| A038V | 1.17 |
| A038Y | 1.14 |
| A038I | 1.11 |
| A038I | 1.11 |
| A038G | 1.09 |
| A038T | 1.00 |
| T039A | 1.01 |
| T040V | 1.21 |
| T040S | 1.09 |
| A041N | 1.13 |
| A041I | 1.02 |
| N042H | 1.18 |
| N042K | 1.01 |
| T046K | 1.01 |
| F047I | 1.17 |
| F047M | 1.13 |
| F047V | 1.01 |
| G049F | 1.32 |
| G049K | 1.16 |
| G049A | 1.16 |
| G049L | 1.12 |
| G049W | 1.08 |
| G049H | 1.07 |
| G049T | 1.06 |
| G049S | 1.01 |
| S051A | 1.47 |
| S051Q | 1.14 |
| S051F | 1.13 |
| S051H | 1.09 |
| G054D | 1.66 |
| G054R | 1.33 |
| G054L | 1.32 |
| G054H | 1.32 |
| G054K | 1.24 |
| G054M | 1.24 |
| G054A | 1.23 |
| G054I | 1.22 |
| G054Q | 1.21 |
| G054N | 1.05 |
| G054E | 1.03 |
| N055F | 1.54 |
| N055Q | 1.17 |
| N055K | 1.11 |
| N055H | 1.09 |
| N055E | 1.00 |
| Y057M | 1.00 |
| R061M | 1.20 |
| R061S | 1.08 |
| R061T | 1.02 |
| T062I | 1.22 |
| G063V | 1.21 |
| G063W | 1.12 |
| G063Q | 1.09 |
| G063D | 1.08 |
| G063H | 1.07 |
| G063R | 1.05 |
| A064W | 1.34 |
| A064H | 1.28 |
| A064N | 1.26 |
| A064Y | 1.26 |
| A064R | 1.22 |
| A064F | 1.21 |
| A064K | 1.19 |
| A064M | 1.19 |
| A064S | 1.18 |
| A064L | 1.18 |
| A064I | 1.16 |
| A064Q | 1.11 |
| A064T | 1.11 |
| A064V | 1.10 |
| A064P | 1.01 |
| A064G | 1.00 |
| G065P | 1.57 |
| G065R | 1.56 |
| G065V | 1.48 |
| G065Y | 1.46 |
| G065S | 1.40 |
| G065T | 1.38 |
| G065Q | 1.37 |
| G065L | 1.26 |
| G065A | 1.16 |
| G065H | 1.12 |
| G065I | 1.07 |
| G065D | 1.05 |
| V066H | 1.46 |
| V066D | 1.45 |
| V066I | 1.29 |
| V066L | 1.25 |
| V066E | 1.24 |
| V066A | 1.23 |
| V066M | 1.10 |
| V066N | 1.10 |
| V066G | 1.08 |
| V066T | 1.03 |
| N067G | 1.38 |
| N067L | 1.30 |
| N067K | 1.29 |
| N067A | 1.25 |
| N067H | 1.22 |
| N067T | 1.19 |
| N067D | 1.18 |
| N067S | 1.16 |
| N067Q | 1.14 |
| N067R | 1.13 |
| N067Y | 1.12 |
| N067V | 1.12 |

TABLE 30-2-continued

DMC Assay Results

| Variant code | Casein specific activity relative to wild type |
|---|---|
| N067F | 1.11 |
| N067M | 1.06 |
| N067E | 1.05 |
| L068W | 1.10 |
| L068H | 1.05 |
| L068P | 1.04 |
| L069S | 2.13 |
| L069H | 1.60 |
| L069V | 1.27 |
| L069W | 1.14 |
| L069K | 1.05 |
| L069R | 1.02 |
| L069N | 1.01 |
| A070H | 1.53 |
| A070S | 1.33 |
| A070D | 1.24 |
| A070G | 1.09 |
| A070P | 1.07 |
| A070W | 1.04 |
| Q071I | 1.46 |
| Q071K | 1.41 |
| Q071G | 1.40 |
| Q071M | 1.33 |
| Q071H | 1.28 |
| Q071A | 1.26 |
| Q071N | 1.26 |
| Q071S | 1.19 |
| Q071D | 1.16 |
| Q071F | 1.14 |
| Q071L | 1.11 |
| Q071R | 1.10 |
| Q071T | 1.06 |
| V072I | 1.17 |
| N073T | 2.73 |
| N073S | 1.28 |
| N073H | 1.12 |
| N074G | 1.87 |
| Y075I | 1.37 |
| Y075G | 1.36 |
| Y075F | 1.34 |
| S076W | 1.77 |
| S076Y | 1.69 |
| S076V | 1.51 |
| S076L | 1.44 |
| S076N | 1.20 |
| S076T | 1.18 |
| S076I | 1.18 |
| S076E | 1.17 |
| S076R | 1.14 |
| S076A | 1.13 |
| S076Q | 1.11 |
| S076K | 1.09 |
| S076K | 1.09 |
| S076H | 1.05 |
| G077T | 2.50 |
| G077S | 1.34 |
| G077Y | 1.21 |
| G077N | 1.18 |
| G077Q | 1.02 |
| G077R | 1.02 |
| G078A | 1.64 |
| G078S | 1.35 |
| G078H | 1.31 |
| G078T | 1.29 |
| G078D | 1.25 |
| G078N | 1.23 |
| G078I | 1.19 |
| G078V | 1.19 |
| G078R | 1.18 |
| G078M | 1.01 |
| R079P | 1.24 |
| R079G | 1.20 |
| V080H | 1.24 |
| V080L | 1.22 |
| V080F | 1.15 |
| Q081V | 1.33 |
| Q081K | 1.30 |
| Q081H | 1.24 |
| Q081I | 1.13 |
| Q081D | 1.11 |
| Q081P | 1.07 |
| Q081E | 1.03 |
| Q081R | 1.01 |
| A083N | 1.13 |
| A083M | 1.09 |
| A083G | 1.08 |
| A083L | 1.08 |
| A083H | 1.07 |
| A083I | 1.03 |
| A083E | 1.02 |
| A083V | 1.02 |
| H085Q | 1.41 |
| H085T | 1.26 |
| H085R | 1.22 |
| H085L | 1.22 |
| H085K | 1.15 |
| H085M | 1.01 |
| T086A | 1.21 |
| T086G | 1.08 |
| T086N | 1.08 |
| T086I | 1.08 |
| T086L | 1.08 |
| T086E | 1.03 |
| T086K | 1.03 |
| T086H | 1.02 |
| A088K | 1.05 |
| P089N | 1.19 |
| P089V | 1.05 |
| P089Y | 1.02 |
| P089T | 1.00 |
| V090P | 1.62 |
| V090I | 1.30 |
| V090S | 1.26 |
| V090A | 1.12 |
| V090T | 1.11 |
| V090L | 1.10 |
| V090F | 1.02 |
| S092G | 1.25 |
| S092C | 1.07 |
| A093Q | 1.08 |
| A093T | 1.07 |
| A093H | 1.01 |
| S099T | 1.02 |
| G102Q | 1.09 |
| W103M | 1.54 |
| W103I | 1.33 |
| W103Y | 1.01 |
| H104K | 1.22 |
| H104R | 1.04 |
| T107S | 1.17 |
| T107V | 1.14 |
| T107M | 1.12 |
| T107H | 1.12 |
| T107R | 1.07 |
| T107K | 1.03 |
| T107N | 1.01 |
| T107Q | 1.01 |
| T109I | 1.30 |
| T109H | 1.23 |
| T109A | 1.22 |
| T109P | 1.20 |
| T109R | 1.19 |
| T109L | 1.19 |
| T109G | 1.16 |
| T109N | 1.09 |
| T109V | 1.07 |
| T109E | 1.06 |
| A110T | 1.11 |

TABLE 30-2-continued

DMC Assay Results

| Variant code | Casein specific activity relative to wild type |
|---|---|
| A110S | 1.11 |
| N112I | 1.11 |
| N112R | 1.08 |
| N112G | 1.06 |
| N112L | 1.04 |
| N112Q | 1.03 |
| N112H | 1.00 |
| S114G | 1.37 |
| T116F | 1.45 |
| T116R | 1.06 |
| T116H | 1.04 |
| T116G | 1.01 |
| P118A | 1.45 |
| P118F | 1.39 |
| P118R | 1.37 |
| P118H | 1.24 |
| P118I | 1.19 |
| P118Q | 1.17 |
| P118K | 1.16 |
| P118E | 1.13 |
| P118G | 1.00 |
| E119R | 1.94 |
| E119K | 1.28 |
| E119Q | 1.04 |
| E119G | 1.02 |
| E119L | 1.00 |
| R123E | 1.20 |
| R123I | 1.11 |
| R123K | 1.05 |
| R123D | 1.03 |
| I126L | 1.20 |
| R127F | 1.20 |
| T129S | 1.20 |
| E133Q | 1.10 |
| P134R | 1.06 |
| S140G | 1.03 |
| L142V | 1.12 |
| L142M | 1.08 |
| A143N | 1.12 |
| A143S | 1.11 |
| N145I | 1.26 |
| N145Q | 1.25 |
| N145E | 1.24 |
| N145G | 1.16 |
| N145T | 1.14 |
| N145L | 1.11 |
| N145S | 1.07 |
| N145F | 1.04 |
| N145R | 1.04 |
| N145P | 1.00 |
| Q146D | 1.06 |
| V150L | 1.26 |
| V150M | 1.14 |
| T151L | 1.13 |
| S155H | 1.01 |
| R159F | 1.49 |
| R159E | 1.10 |
| R159Y | 1.07 |
| R159K | 1.04 |
| R159N | 1.01 |
| G161K | 1.08 |
| T163I | 1.13 |
| F166Y | 1.07 |
| Q167N | 1.16 |
| Q167E | 1.09 |
| N170Y | 2.76 |
| N170D | 1.15 |
| N170L | 1.12 |
| N170A | 1.11 |
| N170C | 1.05 |
| N170R | 1.03 |
| N170P | 1.01 |
| P171T | 1.02 |
| Q174I | 1.08 |
| Q174L | 1.02 |
| A175V | 1.04 |
| A175T | 1.02 |
| A175H | 1.02 |
| G177M | 1.42 |
| G177S | 1.09 |
| G177R | 1.04 |
| R179V | 1.63 |
| R179M | 1.36 |
| R179D | 1.33 |
| R179I | 1.31 |
| R179N | 1.29 |
| R179Y | 1.29 |
| R179T | 1.27 |
| R179L | 1.23 |
| R179K | 1.23 |
| R179A | 1.22 |
| R179E | 1.22 |
| R179W | 1.06 |
| R179F | 1.06 |
| T182V | 1.20 |
| T182W | 1.02 |
| T182Q | 1.01 |
| T183I | 1.35 |
| T183K | 1.19 |
| T183M | 1.14 |
| T183R | 1.09 |
| T183L | 1.07 |
| T183Q | 1.07 |
| T183E | 1.05 |
| T183H | 1.02 |
| D184F | 1.18 |
| D184R | 1.18 |
| D184H | 1.14 |
| D184Q | 1.10 |
| D184T | 1.03 |
| D184I | 1.03 |
| D184V | 1.01 |
| S185I | 1.15 |
| S185V | 1.11 |
| S185W | 1.09 |
| S185N | 1.07 |
| S185K | 1.06 |
| S185P | 1.03 |
| S185L | 1.02 |
| P189Y | 1.06 |
| P189W | 1.02 |
| P189R | 1.01 |
| I181H | 1.37 |
| I181G | 1.12 |
| I181N | 1.15 |
| G186V | 1.49 |
| G186E | 1.54 |
| G186I | 1.41 |
| G186L | 1.05 |
| G186N | 1.01 |
| S187P | 1.63 |
| S187E | 1.12 |
| S187T | 1.29 |
| S187L | 1.12 |
| S188M | 1.25 |
| S188L | 1.04 |

Thermostability Assays

The data in the following table (Table 30-3) represent the relative thermostability data of variants of ASP relative to the stability of the WT ASP stability under these conditions. The stability was measured by determining casein activity before and after incubation at elevated temperature (See, "Thermostability Assays" above). The table contains the relative thermostability values compared to WT under these conditions. It is the quotient of (Variant residual activity/WT residual activity). A value greater than one indicates higher thermostability.

TABLE 30-3

Thermostability Assay Results

| Variant code | Thermostability relative |
|---|---|
| V003R | 1.53 |
| I004D | 1.89 |
| I004P | 1.89 |
| I004G | 1.66 |
| A008G | 1.16 |
| Y009E | 2.04 |
| Y009P | 2.04 |
| T010Y | 1.64 |
| T010F | 1.53 |
| T010W | 1.49 |
| T010L | 1.26 |
| T010C | 1.21 |
| T010E | 1.10 |
| T010D | 1.09 |
| T010M | 1.06 |
| T010V | 1.06 |
| T010S | 1.03 |
| G012D | 1.86 |
| G012A | 1.15 |
| G012H | 1.14 |
| G012V | 1.06 |
| G012I | 1.06 |
| G012S | 1.00 |
| R014H | 1.08 |
| R014I | 1.08 |
| R014K | 1.08 |
| R014N | 1.08 |
| R014Q | 1.08 |
| R014S | 1.08 |
| R014T | 1.08 |
| S015Q | 1.23 |
| S015R | 1.23 |
| S015C | 1.22 |
| S015T | 1.16 |
| S015N | 1.16 |
| S015H | 1.13 |
| S015F | 1.07 |
| S015A | 1.04 |
| S015M | 1.04 |
| S015I | 1.03 |
| R016K | 1.07 |
| R016I | 1.06 |
| S018E | 2.18 |
| A022C | 2.27 |
| A022S | 1.94 |
| A022T | 1.55 |
| N024T | 1.49 |
| N024S | 1.25 |
| N024E | 1.12 |
| N024G | 1.12 |
| N024Q | 1.04 |
| N024K | 1.04 |
| N024A | 1.01 |
| N024V | 1.01 |
| G025S | 1.25 |
| G026I | 2.50 |
| G026K | 2.50 |
| G026L | 2.50 |
| G026Q | 2.50 |
| G026V | 2.50 |
| G026W | 2.50 |
| G026E | 2.11 |
| F027V | 2.50 |
| F027W | 2.50 |
| F027I | 1.36 |
| I028P | 2.50 |
| I028W | 1.99 |
| I028T | 1.78 |
| T029E | 2.50 |
| A030M | 2.13 |
| A030N | 2.13 |
| A030P | 1.75 |
| A030Y | 1.57 |
| G031M | 2.13 |
| G031H | 1.65 |
| G031V | 1.63 |
| G031N | 1.55 |
| G031A | 1.15 |
| H032A | 1.37 |
| H032C | 1.01 |
| H032R | 1.01 |
| C033M | 2.13 |
| C033L | 2.04 |
| C033N | 1.85 |
| C033E | 1.85 |
| C033D | 1.36 |
| C033T | 1.01 |
| C033K | 1.01 |
| R035H | 1.08 |
| R035Q | 1.08 |
| R035V | 1.08 |
| R035W | 1.08 |
| R035H | 1.08 |
| R035T | 1.08 |
| R035Y | 1.05 |
| T036V | 1.13 |
| T036I | 1.09 |
| T036K | 1.08 |
| T036P | 1.08 |
| A038D | 1.60 |
| A038C | 1.43 |
| A038Y | 1.07 |
| T039R | 1.72 |
| T039V | 1.19 |
| T039Q | 1.11 |
| T039K | 1.07 |
| T039W | 1.07 |
| T039L | 1.03 |
| T039P | 1.03 |
| T040D | 2.33 |
| T040Q | 2.33 |
| T040H | 2.24 |
| T040P | 1.73 |
| T040N | 1.55 |
| T040G | 1.07 |
| A041S | 1.31 |
| A041D | 1.07 |
| P043D | 2.33 |
| P043H | 2.33 |
| P043K | 2.33 |
| P043L | 2.33 |
| P043N | 2.12 |
| P043G | 1.53 |
| T044V | 1.03 |
| G045V | 2.06 |
| G045A | 1.82 |
| T046Y | 1.68 |
| T046V | 1.66 |
| T046W | 1.43 |
| T046F | 1.32 |
| T046Q | 1.01 |
| A048P | 1.96 |
| A048V | 1.05 |
| A048E | 1.04 |
| G049A | 1.22 |
| S051V | 1.32 |
| S051C | 0.99 |
| P053N | 1.00 |
| G054E | 1.00 |
| Y057N | 1.65 |
| Y057M | 1.55 |
| F059K | 2.17 |
| F059W | 1.33 |
| F059C | 1.07 |
| T062R | 1.92 |
| T062G | 1.44 |

TABLE 30-3-continued

Thermostability Assay Results

| Variant code | Thermostability relative |
|---|---|
| A070P | 1.89 |
| A070G | 1.43 |
| Q071Y | 1.35 |
| Q071A | 1.21 |
| Q071F | 1.06 |
| N073P | 2.08 |
| N074F | 1.36 |
| S076A | 1.00 |
| R079T | 1.58 |
| R079V | 1.31 |
| R079M | 1.01 |
| Q081A | 1.92 |
| Q081S | 1.65 |
| Q081P | 1.57 |
| Q081G | 1.54 |
| Q081H | 1.52 |
| Q081D | 1.51 |
| Q081F | 1.43 |
| Q081E | 1.39 |
| Q081C | 1.13 |
| Q081T | 1.08 |
| A083H | 1.62 |
| A083M | 1.35 |
| A083E | 1.23 |
| A083F | 1.20 |
| A083R | 1.14 |
| A083S | 1.00 |
| G084C | 2.08 |
| G084P | 2.08 |
| G084V | 1.17 |
| G084M | 1.17 |
| T086S | 1.39 |
| T086I | 1.20 |
| T086M | 1.12 |
| T086A | 1.11 |
| T086H | 1.08 |
| T086D | 1.06 |
| T086N | 1.05 |
| T086V | 1.04 |
| A087S | 1.20 |
| A087E | 1.12 |
| P089W | 2.22 |
| P089A | 1.27 |
| V090A | 1.35 |
| V090M | 1.18 |
| V090I | 1.11 |
| V090T | 1.03 |
| G091L | 2.22 |
| G091K | 1.06 |
| S092T | 1.14 |
| A093S | 1.66 |
| A093D | 1.19 |
| A093Q | 1.06 |
| A093Q | 1.06 |
| A093N | 1.06 |
| A093G | 1.02 |
| R096C | 1.92 |
| R096F | 1.75 |
| R096E | 1.57 |
| S099A | 1.80 |
| S099G | 1.17 |
| T100A | 1.70 |
| T100D | 1.18 |
| T100Q | 1.16 |
| T100E | 1.08 |
| T101S | 1.14 |
| W103N | 1.20 |
| C105E | 1.89 |
| C105G | 1.89 |
| C105K | 1.89 |
| C105M | 1.89 |
| C105N | 1.89 |
| C105S | 1.89 |
| C105P | 1.72 |
| C105W | 1.69 |
| C105T | 1.28 |
| C105Y | 1.22 |
| C105A | 1.21 |
| C105L | 1.18 |
| T107S | 1.30 |
| T107L | 1.24 |
| T107Q | 1.24 |
| T107A | 1.17 |
| T107F | 1.14 |
| T107R | 1.11 |
| T107K | 1.10 |
| T107H | 1.02 |
| T107M | 1.00 |
| A110G | 1.15 |
| L111K | 1.17 |
| L111R | 1.10 |
| N112D | 1.08 |
| N112E | 1.08 |
| N112G | 1.08 |
| N112H | 1.08 |
| N112Q | 1.08 |
| N112R | 1.07 |
| N112L | 1.03 |
| N112P | 1.03 |
| N112F | 1.01 |
| S113M | 1.08 |
| S113N | 1.08 |
| S113R | 1.08 |
| S113T | 1.08 |
| S113C | 1.04 |
| S113H | 1.01 |
| S113F | 1.00 |
| S113I | 0.99 |
| V115I | 1.18 |
| V115L | 1.14 |
| V115T | 1.05 |
| T116Q | 1.13 |
| T116E | 1.09 |
| T116L | 1.03 |
| Y117K | 1.41 |
| Y117Q | 1.41 |
| Y117R | 1.41 |
| Y117V | 1.41 |
| P118T | 1.12 |
| P118R | 1.08 |
| P118Q | 1.03 |
| P118S | 1.02 |
| E119L | 1.24 |
| E119V | 1.03 |
| T121E | 1.54 |
| T121D | 1.23 |
| T121A | 1.15 |
| T121S | 1.05 |
| T121H | 1.03 |
| V122C | 1.02 |
| R123W | 1.73 |
| R123F | 1.67 |
| R123Y | 1.58 |
| R123N | 1.53 |
| R123L | 1.39 |
| R123I | 1.39 |
| R123T | 1.35 |
| R123Q | 1.20 |
| R123K | 1.18 |
| R123V | 1.11 |
| L125A | 1.45 |
| L125M | 1.38 |
| R127K | 1.41 |
| R127Q | 1.41 |
| R127F | 1.21 |
| R127Y | 1.09 |
| R127D | 1.03 |
| R127E | 1.03 |
| T128A | 1.89 |
| T128V | 1.89 |

TABLE 30-3-continued

Thermostability Assay Results

| Variant code | Thermostability relative |
|---|---|
| T128G | 1.88 |
| T128S | 1.48 |
| T128C | 1.47 |
| T129W | 2.50 |
| T129Y | 1.30 |
| V130T | 1.13 |
| V130C | 1.07 |
| A132C | 1.19 |
| P134W | 1.18 |
| S137R | 1.92 |
| S140P | 1.88 |
| L141C | 1.33 |
| L142M | 1.10 |
| A143H | 1.19 |
| G144A | 1.14 |
| G144V | 1.10 |
| G144D | 1.02 |
| G144I | 1.00 |
| G144E | 0.99 |
| Q146P | 1.53 |
| Q146Y | 1.02 |
| A147E | 2.00 |
| A147C | 1.08 |
| V150N | 1.12 |
| T151C | 1.30 |
| T151A | 1.07 |
| G153K | 1.23 |
| G153V | 1.23 |
| G154L | 1.17 |
| G154R | 1.14 |
| G154E | 1.13 |
| S155P | 1.92 |
| S155R | 1.92 |
| S155W | 1.78 |
| S155K | 1.69 |
| S155Y | 1.66 |
| S155F | 1.48 |
| S155T | 1.18 |
| S155V | 0.99 |
| G156I | 1.92 |
| G156L | 1.92 |
| G156P | 1.81 |
| G156V | 1.08 |
| G156E | 1.03 |
| C158H | 2.00 |
| C158G | 1.57 |
| C158M | 1.49 |
| R159K | 1.56 |
| R159T | 1.26 |
| R159V | 1.15 |
| R159Q | 1.14 |
| T160I | 1.48 |
| T160E | 1.27 |
| T160Q | 1.14 |
| T160L | 1.09 |
| T160D | 1.04 |
| T160R | 1.04 |
| G161L | 2.13 |
| G161V | 2.13 |
| G161I | 1.50 |
| G161K | 1.24 |
| G162P | 1.32 |
| G162L | 1.11 |
| T163I | 1.19 |
| T163V | 1.02 |
| T164G | 1.83 |
| T164L | 1.54 |
| F165T | 1.01 |
| F165D | 0.99 |
| F166S | 1.44 |
| F166C | 1.29 |
| F166A | 1.20 |
| F166G | 1.01 |
| Q167L | 1.79 |
| Q167N | 1.08 |
| P168Y | 1.45 |
| P168I | 1.17 |
| N170E | 1.32 |
| N170D | 1.17 |
| N170L | 1.06 |
| N170V | 0.99 |
| Q174H | 1.11 |
| Q174L | 1.06 |
| Q174R | 1.06 |
| Q174V | 1.03 |
| Y176P | 1.48 |
| Y176K | 1.06 |
| Y176D | 1.03 |
| G177N | 1.18 |
| G177K | 1.03 |
| R179K | 1.21 |
| M180L | 1.30 |
| T182L | 1.14 |
| T182V | 1.01 |
| T183P | 1.26 |
| T183I | 1.17 |
| T183A | 1.13 |
| T183S | 1.11 |
| T183V | 1.06 |
| D184E | 1.04 |
| S185R | 1.32 |
| S185Q | 1.08 |
| G186S | 1.65 |
| G186P | 1.23 |
| S187R | 1.02 |
| S187G | 1.00 |
| S188A | 1.44 |
| S188E | 1.42 |
| S188V | 1.42 |
| S188T | 1.36 |
| S188M | 1.26 |
| S188G | 1.23 |
| S188C | 1.16 |
| S188H | 1.01 |
| P189S | 1.16 |
| P189S | 1.16 |
| P189D | 1.04 |
| P189K | 1.04 |
| P189Y | 1.03 |
| P189F | 0.99 |

BMI-LVJ 1 Performance Assays

The following table (Table 30-4) provides the data obtained for selected variants in the BMI-LVJ 1 performance assay (See, "Microswatch Assay for Testing Protease Performance"). The table shows performance indices, which where calculated as described above for the variants, which show improved performance compare to the WT enzyme. Those variants, which have a performance index greater than 1, have an improved performance.

TABLE 30-4

BMI-LVJ 1 Performance Assay Results

| Variant code | BMI US LVJ-1 liquid detergent [perf. Index] |
|---|---|
| F001T | 1.06 |
| D002Q | 1.14 |
| D002E | 1.05 |
| D002P | 1.01 |
| V003L | 1.24 |
| V003I | 1.12 |
| N007L | 1.14 |

TABLE 30-4-continued

BMI-LVJ 1 Performance Assay Results

| Variant code | BMI US LVJ-1 liquid detergent [perf. Index] |
|---|---|
| A008G | 1.09 |
| A008D | 1.07 |
| A008E | 1.04 |
| A008M | 1.03 |
| A008K | 1.01 |
| T010E | 1.10 |
| T010Q | 1.08 |
| T010L | 1.08 |
| T010D | 1.02 |
| T010G | 1.01 |
| I011Q | 1.18 |
| I011A | 1.13 |
| I011T | 1.12 |
| I011S | 1.11 |
| I011L | 1.06 |
| G012D | 1.08 |
| G012Y | 1.07 |
| G012N | 1.05 |
| G012L | 1.03 |
| G012Q | 1.00 |
| R014I | 1.25 |
| R014M | 1.20 |
| R014L | 1.11 |
| R014E | 1.09 |
| R014N | 1.08 |
| R014P | 1.08 |
| R014G | 1.03 |
| R014Q | 1.03 |
| S015E | 1.09 |
| S015G | 1.04 |
| R016Q | 1.14 |
| R016L | 1.14 |
| R016N | 1.11 |
| R016G | 1.11 |
| R016I | 1.09 |
| R016A | 1.09 |
| R016M | 1.03 |
| I019V | 1.02 |
| N024E | 1.36 |
| N024A | 1.31 |
| N024T | 1.21 |
| N024Q | 1.19 |
| N024V | 1.17 |
| N024H | 1.14 |
| N024M | 1.13 |
| N024L | 1.12 |
| N024S | 1.07 |
| N024W | 1.00 |
| R035F | 1.23 |
| R035L | 1.14 |
| R035A | 1.06 |
| R035D | 1.03 |
| R035H | 1.03 |
| T036I | 9.16 |
| T036N | 1.77 |
| T036G | 1.64 |
| T036S | 1.61 |
| T036P | 1.49 |
| T036D | 1.41 |
| T036H | 1.25 |
| T036Y | 1.25 |
| T036L | 1.18 |
| T036W | 1.15 |
| T036F | 1.05 |
| A038R | 1.55 |
| A038L | 1.18 |
| A038S | 1.16 |
| A038Y | 1.12 |
| A038N | 1.10 |
| A038D | 1.09 |
| A038F | 1.08 |
| A038V | 1.06 |
| T040V | 1.10 |
| T040S | 1.02 |
| A041N | 1.09 |
| A041I | 1.04 |
| N042H | 1.11 |
| T046Q | 1.05 |
| F047V | 1.02 |
| A048Q | 1.26 |
| G049A | 1.15 |
| G049F | 1.11 |
| G049H | 1.09 |
| G049S | 1.07 |
| G049T | 1.02 |
| G049V | 1.01 |
| S050F | 1.04 |
| S051Q | 1.10 |
| S051T | 1.07 |
| S051D | 1.05 |
| S051A | 1.05 |
| S051V | 1.03 |
| S051M | 1.01 |
| S051H | 1.01 |
| G054D | 1.48 |
| G054Q | 1.17 |
| G054E | 1.16 |
| G054N | 1.14 |
| G054I | 1.14 |
| G054L | 1.11 |
| G054M | 1.09 |
| G054A | 1.08 |
| G054H | 1.00 |
| N055F | 1.07 |
| N055E | 1.01 |
| Y057M | 1.00 |
| R061V | 1.13 |
| R061K | 1.12 |
| R061M | 1.11 |
| R061H | 1.08 |
| R061S | 1.06 |
| R061T | 1.06 |
| T062I | 1.02 |
| A064H | 1.15 |
| A064F | 1.14 |
| A064Y | 1.13 |
| A064W | 1.10 |
| A064N | 1.10 |
| A064T | 1.09 |
| A064S | 1.08 |
| A064V | 1.06 |
| A064Q | 1.04 |
| A064I | 1.04 |
| A064L | 1.02 |
| A064G | 1.02 |
| G065P | 1.28 |
| G065Q | 1.27 |
| G065T | 1.19 |
| G065Y | 1.19 |
| G065S | 1.17 |
| G065L | 1.13 |
| G065V | 1.11 |
| G065R | 1.10 |
| V066H | 1.15 |
| V066D | 1.07 |
| V066E | 1.02 |
| N067L | 1.25 |
| N067S | 1.23 |
| N067A | 1.19 |
| N067Y | 1.16 |
| N067G | 1.14 |
| N067V | 1.14 |
| N067Q | 1.13 |
| N067T | 1.10 |
| N067F | 1.08 |
| N067M | 1.07 |
| N067K | 1.06 |
| N067D | 1.02 |

TABLE 30-4-continued

BMI-LVJ 1 Performance Assay Results

| Variant code | BMI US LVJ-1 liquid detergent [perf. Index] |
|---|---|
| N067H | 1.02 |
| N067C | 1.01 |
| L068H | 1.02 |
| L069S | 1.29 |
| L069H | 1.14 |
| L069W | 1.06 |
| L069V | 1.02 |
| A070G | 1.12 |
| A070P | 1.09 |
| A070D | 1.01 |
| Q071I | 1.14 |
| Q071H | 1.13 |
| Q071F | 1.12 |
| Q071D | 1.11 |
| Q071L | 1.09 |
| Q071T | 1.06 |
| Q071Y | 1.04 |
| Q071S | 1.04 |
| Q071A | 1.03 |
| V072I | 1.04 |
| N073T | 1.67 |
| N074G | 1.28 |
| Y075G | 1.37 |
| Y075F | 1.30 |
| Y075I | 1.18 |
| S076W | 1.49 |
| S076L | 1.39 |
| S076Y | 1.37 |
| S076T | 1.30 |
| S076V | 1.30 |
| S076I | 1.25 |
| S076D | 1.22 |
| S076N | 1.20 |
| S076A | 1.16 |
| S076E | 1.14 |
| G077T | 1.48 |
| G077S | 1.11 |
| G077N | 1.07 |
| G078D | 1.24 |
| G078A | 1.12 |
| G078N | 1.10 |
| G078H | 1.04 |
| G078S | 1.02 |
| R079P | 1.20 |
| R079G | 1.13 |
| R079D | 1.12 |
| R079C | 1.02 |
| V080L | 1.11 |
| V080H | 1.09 |
| V080Q | 1.04 |
| Q081P | 1.22 |
| Q081V | 1.02 |
| Q081K | 1.01 |
| Q081H | 1.01 |
| A083N | 1.03 |
| A083E | 1.03 |
| H085Q | 1.42 |
| H085L | 1.30 |
| H085R | 1.23 |
| H085K | 1.19 |
| H085F | 1.13 |
| H085Y | 1.11 |
| H085T | 1.10 |
| H085M | 1.05 |
| H085V | 1.02 |
| T086N | 1.07 |
| T086D | 1.05 |
| T086R | 1.01 |
| T086Q | 1.00 |
| T086I | 1.00 |
| T086V | 1.00 |
| A088F | 1.12 |
| A088H | 1.04 |
| P089D | 2.85 |
| P089N | 1.11 |
| P089V | 1.07 |
| P089T | 1.00 |
| V090I | 1.12 |
| V090P | 1.10 |
| V090T | 1.06 |
| V090L | 1.01 |
| S092A | 1.21 |
| S092G | 1.11 |
| A093T | 2.26 |
| A093S | 2.15 |
| A093D | 1.10 |
| A093E | 1.06 |
| A093Q | 1.05 |
| A093H | 1.00 |
| R096K | 1.02 |
| S099W | 1.50 |
| S099N | 1.38 |
| S099A | 1.22 |
| S099D | 1.15 |
| S099T | 1.14 |
| S099G | 1.09 |
| S099E | 1.03 |
| S099V | 1.01 |
| G102Q | 1.01 |
| W103M | 1.01 |
| H104S | 1.05 |
| T107H | 1.02 |
| T107N | 1.01 |
| T107S | 1.01 |
| T109E | 1.15 |
| T109N | 1.03 |
| T109I | 1.02 |
| L111E | 1.10 |
| L111D | 1.07 |
| L111T | 1.01 |
| N112E | 1.14 |
| N112L | 1.11 |
| N112Q | 1.09 |
| N112D | 1.08 |
| N112G | 1.07 |
| N112A | 1.01 |
| N112H | 1.01 |
| S113A | 1.13 |
| S113G | 1.12 |
| S113M | 1.04 |
| S114G | 1.25 |
| S114A | 1.05 |
| V115T | 1.03 |
| T116F | 1.15 |
| T116E | 1.02 |
| P118E | 1.02 |
| T121D | 1.13 |
| T121E | 1.11 |
| T121S | 1.04 |
| R123I | 1.24 |
| R123F | 1.22 |
| R123L | 1.15 |
| R123Q | 1.12 |
| R123E | 1.10 |
| R123K | 1.07 |
| R123P | 1.03 |
| R123W | 1.02 |
| R123H | 1.01 |
| G124A | 1.01 |
| L125V | 1.06 |
| R127A | 1.44 |
| R127S | 1.36 |
| R127Q | 1.36 |
| R127K | 1.28 |
| R127L | 1.25 |
| R127H | 1.25 |
| R127Y | 1.23 |
| R127F | 1.22 |

TABLE 30-4-continued

BMI-LVJ 1 Performance Assay Results

| Variant code | BMI US LVJ-1 liquid detergent [perf. Index] |
|---|---|
| R127T | 1.19 |
| R127G | 1.16 |
| R127V | 1.01 |
| T129S | 1.03 |
| A132V | 1.22 |
| A132C | 1.03 |
| P134E | 1.14 |
| P134G | 1.06 |
| P134A | 1.01 |
| S140A | 1.07 |
| L142V | 1.09 |
| L142M | 1.02 |
| A143N | 1.21 |
| A143S | 1.05 |
| A143H | 1.01 |
| N145D | 1.06 |
| N145S | 1.02 |
| V150L | 1.07 |
| N157D | 1.17 |
| R159F | 1.63 |
| R159E | 1.43 |
| R159K | 1.29 |
| R159H | 1.28 |
| R159N | 1.22 |
| R159Y | 1.17 |
| R159D | 1.17 |
| R159V | 1.12 |
| R159C | 1.11 |
| R159L | 1.10 |
| R159A | 1.06 |
| R159W | 1.02 |
| T160E | 1.12 |
| T160D | 1.02 |
| G161K | 1.15 |
| G161E | 1.10 |
| T163D | 1.13 |
| T163I | 1.06 |
| N170Y | 1.34 |
| N170D | 1.09 |
| N170L | 1.08 |
| N170G | 1.03 |
| N170A | 1.00 |
| P171S | 1.03 |
| P171V | 1.01 |
| A175V | 1.05 |
| G177M | 1.03 |
| R179V | 1.19 |
| R179T | 1.11 |
| R179K | 1.10 |
| R179N | 1.09 |
| R179D | 1.07 |
| R179E | 1.06 |
| R179A | 1.03 |
| R179I | 1.01 |
| R179M | 1.01 |
| R179F | 1.00 |
| I181Q | 1.24 |
| I181H | 1.07 |
| I181T | 1.00 |
| T182V | 1.05 |
| T182L | 1.00 |
| T183I | 1.10 |
| T183V | 1.03 |
| T183S | 1.01 |
| D184F | 1.34 |
| D184H | 1.15 |
| D184R | 1.11 |
| D184T | 1.08 |
| D184I | 1.07 |
| D184Q | 1.06 |
| D184L | 1.05 |
| S185I | 1.09 |
| S185W | 1.08 |
| S185L | 1.05 |
| S185L | 1.05 |
| S185M | 1.04 |
| S185G | 1.01 |
| G186V | 1.27 |
| G186E | 1.20 |
| G186I | 1.17 |
| G186L | 1.06 |
| G186T | 1.03 |
| G186Q | 1.01 |
| G186R | 1.00 |
| S187P | 1.24 |
| S187Q | 1.13 |
| S187E | 1.08 |
| S187T | 1.04 |
| S188Q | 1.06 |
| S188M | 1.03 |
| S188L | 1.01 |
| P189T | 1.05 |
| P189N | 1.02 |
| P189I | 1.01 |

BMI-Low pH Performance Assays

The table below (Table 30-5) provides the data obtained for the ASP variants which show activity on this substrate in the microswatch assays under low pH conditions (See, Microswatch Assay for Testing Protease Performance) using TIDE®. The table provides performance indices, which were calculated as described above for the variants which show improved performance compared to WT. Variants that have a performance index greater than 1 have improved performance.

TABLE 30-5

BMI-Low pH Performance Assays

| Variant code | BMI US LVJ-1 liquid detergent [perf. Index] |
|---|---|
| F001T | 1.06 |
| V003L | 1.11 |
| V003I | 1.03 |
| I004M | 1.11 |
| N007L | 1.08 |
| A008R | 1.53 |
| A008V | 1.46 |
| A008T | 1.44 |
| A008S | 1.25 |
| A008E | 1.20 |
| A008L | 1.20 |
| A008N | 1.19 |
| A008H | 1.15 |
| A008P | 1.13 |
| A008D | 1.08 |
| A008Q | 1.07 |
| T010Q | 1.04 |
| T010L | 1.04 |
| T010D | 1.01 |
| I011T | 1.14 |
| I011S | 1.05 |
| G012D | 1.00 |
| R014L | 1.32 |
| R014M | 1.25 |
| R014E | 1.21 |
| R014I | 1.16 |
| R014Q | 1.16 |
| R014N | 1.07 |
| R014K | 1.05 |
| R014D | 1.01 |

TABLE 30-5-continued

BMI-Low pH Performance Assays

| Variant code | BMI US LVJ-1 liquid detergent [perf. Index] |
|---|---|
| S015E | 1.05 |
| R016Q | 1.22 |
| R016L | 1.08 |
| R016I | 1.07 |
| R016W | 1.05 |
| R016N | 1.02 |
| I019V | 1.04 |
| N024E | 1.61 |
| N024A | 1.52 |
| N024T | 1.35 |
| N024Q | 1.25 |
| N024L | 1.21 |
| N024M | 1.15 |
| N024V | 1.15 |
| N024H | 1.14 |
| N024F | 1.06 |
| N024S | 1.03 |
| R035F | 1.36 |
| R035L | 1.21 |
| R035A | 1.14 |
| R035E | 1.13 |
| R035D | 1.08 |
| R035H | 1.07 |
| T036I | 9.02 |
| T036N | 1.69 |
| T036G | 1.63 |
| T036S | 1.59 |
| T036P | 1.41 |
| T036D | 1.28 |
| T036V | 1.19 |
| T036W | 1.07 |
| T036H | 1.06 |
| T036L | 1.02 |
| T036F | 1.02 |
| A038R | 1.89 |
| A038F | 1.41 |
| A038S | 1.32 |
| A038L | 1.26 |
| A038D | 1.25 |
| A038H | 1.20 |
| A038N | 1.13 |
| A038I | 1.10 |
| A038Y | 1.08 |
| A038V | 1.02 |
| A038T | 1.00 |
| T040V | 1.14 |
| T040S | 1.01 |
| A041N | 1.10 |
| A041I | 1.04 |
| F047I | 1.01 |
| A048E | 1.04 |
| G049L | 1.16 |
| G049A | 1.10 |
| G049F | 1.06 |
| G049N | 1.06 |
| G049T | 1.04 |
| G049S | 1.04 |
| S051A | 1.35 |
| S051D | 1.25 |
| S051Q | 1.12 |
| S051F | 1.09 |
| S051T | 1.08 |
| S051H | 1.06 |
| G054D | 1.67 |
| G054I | 1.22 |
| G054L | 1.21 |
| G054E | 1.20 |
| G054Q | 1.16 |
| G054A | 1.16 |
| G054M | 1.10 |
| G054N | 1.06 |
| G054H | 1.01 |
| G054K | 1.01 |
| N055F | 1.69 |
| N055E | 1.35 |
| N055S | 1.25 |
| N055Q | 1.15 |
| N055V | 1.09 |
| N055T | 1.02 |
| F059W | 1.01 |
| R061M | 1.35 |
| R061T | 1.22 |
| R061V | 1.15 |
| R061S | 1.07 |
| R061N | 1.02 |
| R061K | 1.02 |
| R061Q | 1.02 |
| T062I | 1.14 |
| G063V | 1.25 |
| G063D | 1.18 |
| G063P | 1.13 |
| G063Q | 1.12 |
| A064N | 1.28 |
| A064H | 1.24 |
| A064S | 1.23 |
| A064Q | 1.21 |
| A064R | 1.19 |
| A064M | 1.15 |
| A064T | 1.15 |
| A064I | 1.14 |
| A064W | 1.14 |
| A064F | 1.11 |
| A064L | 1.11 |
| A064V | 1.09 |
| A064K | 1.06 |
| A064Y | 1.05 |
| G065P | 1.66 |
| G065Q | 1.49 |
| G065S | 1.35 |
| G065Y | 1.32 |
| G065T | 1.26 |
| G065R | 1.22 |
| G065D | 1.16 |
| G065A | 1.12 |
| G065L | 1.05 |
| G065V | 1.04 |
| V066D | 1.21 |
| V066E | 1.08 |
| N067G | 1.41 |
| N067V | 1.39 |
| N067L | 1.32 |
| N067T | 1.31 |
| N067D | 1.25 |
| N067M | 1.25 |
| N067F | 1.24 |
| N067S | 1.24 |
| N067Y | 1.23 |
| N067C | 1.20 |
| N067A | 1.18 |
| N067Q | 1.13 |
| N067R | 1.11 |
| N067K | 1.07 |
| N067E | 1.07 |
| N067H | 1.06 |
| L068T | 1.03 |
| L068H | 1.01 |
| L069S | 1.79 |
| L069H | 1.64 |
| L069W | 1.26 |
| L069V | 1.21 |
| L069Q | 1.12 |
| A070S | 1.18 |
| A070P | 1.12 |
| A070G | 1.10 |
| Q071M | 1.15 |
| Q071D | 1.10 |
| Q071S | 1.03 |
| N073T | 1.77 |

TABLE 30-5-continued

BMI-Low pH Performance Assays

| Variant code | BMI US LVJ-1 liquid detergent [perf. Index] |
|---|---|
| N074G | 1.61 |
| Y075G | 1.58 |
| Y075F | 1.40 |
| S076V | 1.71 |
| S076Y | 1.71 |
| S076I | 1.55 |
| S076D | 1.55 |
| S076L | 1.46 |
| S076W | 1.42 |
| S076N | 1.40 |
| S076E | 1.25 |
| S076C | 1.22 |
| S076T | 1.18 |
| S076Q | 1.17 |
| S076A | 1.11 |
| S076K | 1.07 |
| S076H | 1.00 |
| G077T | 1.86 |
| G077Q | 1.13 |
| G077N | 1.10 |
| G077S | 1.03 |
| G078D | 1.23 |
| R079P | 1.89 |
| R079C | 1.34 |
| R079G | 1.32 |
| R079E | 1.29 |
| R079D | 1.28 |
| R079L | 1.12 |
| R079A | 1.02 |
| Q081V | 1.31 |
| Q081I | 1.11 |
| Q081E | 1.10 |
| Q081H | 1.10 |
| Q081L | 1.07 |
| Q081K | 1.06 |
| Q081D | 1.06 |
| Q081A | 1.01 |
| A083N | 1.27 |
| A083I | 1.16 |
| A083D | 1.12 |
| A083M | 1.07 |
| A083L | 1.04 |
| A083E | 1.02 |
| A083G | 1.00 |
| H085Q | 1.24 |
| H085L | 1.19 |
| H085R | 1.12 |
| H085N | 1.08 |
| H085T | 1.08 |
| H085F | 1.05 |
| H085K | 1.04 |
| T086A | 1.27 |
| T086I | 1.24 |
| T086L | 1.22 |
| T086F | 1.21 |
| T086E | 1.15 |
| T086M | 1.11 |
| T086D | 1.07 |
| 1086C | 1.04 |
| T086Q | 1.04 |
| T086G | 1.03 |
| A088F | 1.15 |
| P089V | 1.07 |
| P089T | 1.07 |
| V090P | 1.50 |
| V090S | 1.38 |
| V090I | 1.32 |
| V090T | 1.23 |
| V090N | 1.22 |
| V090L | 1.16 |
| V090A | 1.07 |
| S092C | 1.20 |
| S092G | 1.12 |
| S092A | 1.02 |
| A093D | 1.31 |
| A093E | 1.30 |
| A093Q | 1.09 |
| R096K | 1.15 |
| T101S | 1.16 |
| W103M | 1.18 |
| W103Y | 1.18 |
| H104M | 1.01 |
| H104K | 1.00 |
| T107N | 1.42 |
| T107S | 1.30 |
| T107M | 1.24 |
| T107A | 1.20 |
| T107E | 1.20 |
| T107Q | 1.15 |
| T107H | 1.11 |
| T107V | 1.10 |
| T109E | 1.46 |
| T109I | 1.31 |
| T109A | 1.28 |
| T109G | 1.21 |
| T109H | 1.13 |
| T109N | 1.13 |
| T109L | 1.10 |
| T109F | 1.01 |
| A110S | 1.19 |
| A110T | 1.13 |
| A110N | 1.05 |
| N112E | 1.24 |
| N112D | 1.20 |
| N112Q | 1.07 |
| N112A | 1.05 |
| N112L | 1.04 |
| S113A | 1.07 |
| S113G | 1.04 |
| S113M | 1.03 |
| S113E | 1.00 |
| S114G | 1.20 |
| S114T | 1.05 |
| S114A | 1.03 |
| T116F | 1.12 |
| T116G | 1.06 |
| T116E | 1.06 |
| T116Q | 1.00 |
| P118E | 1.00 |
| T121E | 1.46 |
| T121D | 1.31 |
| T121L | 1.12 |
| T121G | 1.06 |
| R123E | 1.42 |
| R123D | 1.35 |
| R123I | 1.34 |
| R123F | 1.29 |
| R123L | 1.20 |
| R123P | 1.18 |
| R123Q | 1.14 |
| R123A | 1.12 |
| R123H | 1.12 |
| R123K | 1.11 |
| R123N | 1.01 |
| G124N | 1.04 |
| G124T | 1.00 |
| L125V | 1.17 |
| I126L | 1.26 |
| R127A | 1.38 |
| R127S | 1.31 |
| R127Q | 1.26 |
| R127L | 1.26 |
| R127K | 1.26 |
| R127H | 1.25 |
| R127Y | 1.21 |
| R127T | 1.19 |
| R127F | 1.18 |
| R127G | 1.06 |

TABLE 30-5-continued

BMI-Low pH Performance Assays

| Variant code | BMI US LVJ-1 liquid detergent [perf. Index] |
|---|---|
| R127V | 1.04 |
| T129S | 1.20 |
| T129G | 1.14 |
| A132V | 1.19 |
| A132S | 1.08 |
| E133D | 1.06 |
| P134A | 1.25 |
| P134E | 1.23 |
| P134D | 1.15 |
| P134G | 1.09 |
| S140A | 1.15 |
| L142V | 1.28 |
| L142M | 1.02 |
| A143N | 1.25 |
| A143M | 1.03 |
| A143S | 1.03 |
| N145S | 1.36 |
| N145E | 1.32 |
| N145Q | 1.15 |
| N145G | 1.13 |
| N145P | 1.12 |
| N145T | 1.09 |
| N145L | 1.06 |
| N145F | 1.01 |
| Q146D | 1.12 |
| Q146F | 1.02 |
| T151V | 1.18 |
| N157D | 1.04 |
| R159F | 1.67 |
| R159E | 1.60 |
| R159C | 1.50 |
| R159Y | 1.31 |
| R159D | 1.30 |
| R159K | 1.25 |
| R159Q | 1.22 |
| R159N | 1.20 |
| R159H | 1.17 |
| R159A | 1.16 |
| R159L | 1.09 |
| R159V | 1.08 |
| R159W | 1.06 |
| R159P | 1.06 |
| R159M | 1.03 |
| T160E | 1.08 |
| G161E | 1.33 |
| G161K | 1.11 |
| G161Q | 1.05 |
| T163D | 1.25 |
| T163I | 1.00 |
| T163C | 1.00 |
| F166Y | 1.12 |
| P168S | 1.06 |
| N170Y | 2.54 |
| N170D | 1.20 |
| N170C | 1.19 |
| N170L | 1.06 |
| N170L | 1.06 |
| N170P | 1.02 |
| N170H | 1.00 |
| P171M | 1.18 |
| P171V | 1.03 |
| I172V | 1.28 |
| A175T | 1.13 |
| A175V | 1.12 |
| A175F | 1.02 |
| Y176L | 1.08 |
| G177M | 1.62 |
| G177S | 1.08 |
| G177Q | 1.08 |
| R179V | 1.70 |
| R179M | 1.44 |
| R179I | 1.39 |
| R179Y | 1.37 |
| R179N | 1.35 |
| R179T | 1.30 |
| R179L | 1.30 |
| R179K | 1.30 |
| R179A | 1.30 |
| R179D | 1.27 |
| R179E | 1.22 |
| R179W | 1.20 |
| R179G | 1.08 |
| R179F | 1.06 |
| M180D | 1.31 |
| I181Q | 1.07 |
| I181C | 1.01 |
| I181L | 1.00 |
| I181T | 1.00 |
| T182V | 1.23 |
| T182W | 1.11 |
| T182L | 1.07 |
| T182Q | 1.06 |
| T182P | 1.05 |
| T183I | 1.25 |
| T183E | 1.16 |
| T183Q | 1.14 |
| T183K | 1.10 |
| T183L | 1.10 |
| T183A | 1.05 |
| T183D | 1.05 |
| T183V | 1.05 |
| T183R | 1.04 |
| T183M | 1.03 |
| D184F | 1.00 |
| G186E | 1.42 |
| G186V | 1.34 |
| G186I | 1.21 |
| G186L | 1.11 |
| G186P | 1.09 |
| G186T | 1.09 |
| G186A | 1.03 |
| S187P | 1.39 |
| S187T | 1.18 |
| S187E | 1.11 |
| S187L | 1.07 |
| S187Q | 1.04 |
| S187V | 1.02 |
| S188E | 1.09 |
| S188P | 1.04 |

Scrambled Egg Assay (ADW) Performance

The following table (Table 30-6) provides the data obtained for selected variants in the scrambled egg performance assay (See, "Scrambled Egg Assay") using Detergent Composition I. The table shows performance indices, which where calculated as described above for the variants, which show improved performance compare to the WT enzyme. Those variants, which have a performance index greater than 1, have an improved performance.

TABLE 30-6

Scrambled Egg Assay Performance Results

| Variant code | ADW [perf. Index] |
|---|---|
| F001T | 1.00 |
| D002A | 1.06 |
| D002N | 1.05 |
| T010G | 1.36 |
| T010A | 1.25 |
| T010L | 1.14 |
| T010F | 1.03 |

TABLE 30-6-continued

Scrambled Egg Assay Performance Results

| Variant code | ADW [perf. Index] |
|---|---|
| T010M | 1.03 |
| T010V | 1.03 |
| T010Q | 1.02 |
| T010S | 1.01 |
| I011A | 1.20 |
| I011S | 1.20 |
| I011T | 1.18 |
| I011L | 1.02 |
| G012I | 1.12 |
| G012Y | 1.08 |
| G012R | 1.05 |
| G012Q | 1.04 |
| R014M | 1.26 |
| R014G | 1.14 |
| R014A | 1.10 |
| S015G | 1.14 |
| S015F | 1.14 |
| S015E | 1.13 |
| S015H | 1.08 |
| R016K | 1.15 |
| R016N | 1.12 |
| R016A | 1.10 |
| R016H | 1.03 |
| I019V | 1.02 |
| A022V | 1.23 |
| N024E | 1.67 |
| N024T | 1.46 |
| N024Q | 1.31 |
| N024A | 1.28 |
| N024L | 1.15 |
| N024V | 1.12 |
| N024H | 1.03 |
| G034A | 1.28 |
| T036I | 6.72 |
| T036S | 1.32 |
| T036G | 1.30 |
| T036N | 1.18 |
| T036V | 1.11 |
| T036W | 1.06 |
| T036Y | 1.05 |
| T036D | 1.02 |
| T036P | 1.02 |
| T036F | 1.01 |
| A038T | 1.27 |
| A038F | 1.24 |
| A038M | 1.00 |
| T046K | 1.10 |
| F047I | 1.05 |
| F047V | 1.02 |
| G049F | 1.17 |
| G049A | 1.13 |
| G049L | 1.10 |
| G049H | 1.05 |
| G049S | 1.02 |
| G049V | 1.01 |
| S051A | 1.13 |
| Y057M | 1.05 |
| G063V | 1.08 |
| G063W | 1.01 |
| G063D | 1.01 |
| A064H | 1.11 |
| A064R | 1.08 |
| A064Y | 1.07 |
| A064W | 1.07 |
| A064V | 1.06 |
| A064T | 1.05 |
| A064N | 1.05 |
| A064K | 1.04 |
| A064Q | 1.04 |
| A064L | 1.04 |
| A064I | 1.02 |
| G065V | 1.17 |
| G065T | 1.11 |
| G065S | 1.10 |
| G065L | 1.10 |
| G065A | 1.07 |
| G065P | 1.04 |
| G065D | 1.03 |
| L069S | 1.39 |
| L069H | 1.19 |
| L069V | 1.06 |
| A070S | 1.09 |
| Q071I | 1.15 |
| Q071F | 1.09 |
| Q071M | 1.05 |
| Q071H | 1.03 |
| Q071D | 1.02 |
| Q071L | 1.01 |
| N073T | 1.89 |
| N074G | 1.12 |
| Y075F | 1.10 |
| Y075G | 1.07 |
| S076W | 1.26 |
| S076V | 1.22 |
| S076Y | 1.21 |
| S076D | 1.13 |
| S076L | 1.12 |
| S076E | 1.09 |
| S076R | 1.09 |
| S076N | 1.08 |
| S076A | 1.07 |
| S076Q | 1.05 |
| S076H | 1.05 |
| S076T | 1.05 |
| S076I | 1.04 |
| S076K | 1.04 |
| G077T | 1.87 |
| G078T | 1.08 |
| G078A | 1.06 |
| G078S | 1.05 |
| G078R | 1.03 |
| G078D | 1.00 |
| R079L | 1.07 |
| R079G | 1.07 |
| R079S | 1.05 |
| R079T | 1.04 |
| R079V | 1.03 |
| R079D | 1.01 |
| R079A | 1.01 |
| V080A | 1.13 |
| V080L | 1.11 |
| H085T | 1.05 |
| T086Q | 1.03 |
| T086A | 1.02 |
| A088F | 1.04 |
| P089A | 1.03 |
| V090I | 1.17 |
| V090P | 1.13 |
| A093S | 1.04 |
| A093Q | 1.02 |
| S099N | 1.14 |
| S099V | 1.12 |
| S099Q | 1.05 |
| S099I | 1.01 |
| T107R | 1.13 |
| T107K | 1.12 |
| T107S | 1.10 |
| T107H | 1.09 |
| T107F | 1.09 |
| T107I | 1.07 |
| T107M | 1.07 |
| T107V | 1.06 |
| T107A | 1.06 |
| T107L | 1.04 |
| T107W | 1.02 |
| T109R | 1.07 |
| T109I | 1.06 |
| T109V | 1.02 |
| A110S | 1.01 |
| N112S | 1.31 |

TABLE 30-6-continued

Scrambled Egg Assay Performance Results

| Variant code | ADW [perf. Index] |
|---|---|
| S114A | 1.11 |
| S114T | 1.09 |
| V115A | 1.04 |
| T116A | 1.10 |
| T116S | 1.03 |
| P118F | 1.06 |
| P118R | 1.05 |
| E119R | 1.27 |
| T121L | 1.05 |
| T121S | 1.03 |
| T121Q | 1.02 |
| G124T | 1.03 |
| L125Q | 1.02 |
| R127F | 1.15 |
| T128S | 1.10 |
| T129S | 1.11 |
| P134R | 1.89 |
| P134E | 1.49 |
| P134L | 1.48 |
| P134H | 1.29 |
| P134V | 1.23 |
| P134D | 1.13 |
| P134T | 1.11 |
| P134S | 1.08 |
| S140A | 1.33 |
| L142V | 1.24 |
| A143S | 1.06 |
| N145D | 1.01 |
| V150L | 1.12 |
| T151L | 1.07 |
| G154S | 1.01 |
| R159F | 1.39 |
| R159K | 1.15 |
| R159Y | 1.06 |
| R159Q | 1.00 |
| G161K | 1.11 |
| T163I | 1.15 |
| T164G | 1.11 |
| F166Y | 1.13 |
| F166V | 1.07 |
| Q167N | 1.13 |
| N170Y | 1.24 |
| N170D | 1.03 |
| N170G | 1.02 |
| L178V | 1.08 |
| R179V | 1.16 |
| R179K | 1.10 |
| R179T | 1.05 |
| T182V | 1.22 |
| T182L | 1.04 |
| T183I | 1.08 |
| T183S | 1.02 |
| D184T | 1.05 |
| D184Q | 1.03 |
| G186S | 1.34 |
| G186E | 1.26 |
| G186V | 1.19 |
| G186I | 1.11 |
| G186A | 1.05 |
| G186L | 1.02 |
| S187E | 1.02 |
| S187T | 1.02 |
| S188A | 1.19 |
| S188M | 1.07 |
| S188G | 1.02 |

Las Stability

The following table (Table 30-7) shows all variants, which have an improved stability compared to the WT-ASP. All variants were tested and the calculations determined according to the protocol shown above (See, "LAS Stability Assay"). The table provides the residual activity after incubation for the variants. Under these conditions the average of the WT value was found to be 10.59% residual activity. All variants with a higher activity are improved with respect to the WT molecule.

TABLE 30-7

LAS Stability Assay Results

| Variant code | LAS stability [residual Activity (%)] |
|---|---|
| F001P | 21.73 |
| F001N | 16.59 |
| F001R | 11.13 |
| D002P | 22.43 |
| D002I | 20.86 |
| D002V | 20.15 |
| D002T | 19.97 |
| D002M | 15.20 |
| D002N | 13.27 |
| D002F | 12.71 |
| D002A | 12.13 |
| D002C | 11.50 |
| A008G | 33.00 |
| A008T | 20.39 |
| A008R | 18.33 |
| A008P | 14.19 |
| T010L | 24.24 |
| T010C | 24.00 |
| T010Y | 20.40 |
| T010Q | 19.48 |
| T010D | 18.06 |
| T010E | 17.48 |
| T010F | 17.10 |
| T010M | 14.94 |
| T010W | 12.63 |
| I011W | 50.85 |
| I011E | 26.05 |
| I011T | 23.20 |
| I011Q | 22.59 |
| G012D | 41.99 |
| G012Q | 28.25 |
| G012N | 27.52 |
| G012V | 27.44 |
| G012S | 24.06 |
| G012I | 23.30 |
| G012H | 19.43 |
| G012Y | 16.33 |
| G012P | 15.10 |
| G012R | 13.43 |
| G012A | 12.15 |
| G012L | 11.15 |
| G012W | 10.66 |
| G013E | 18.82 |
| G013D | 16.72 |
| G013K | 10.79 |
| G013K | 10.79 |
| R014E | 71.80 |
| R014D | 64.85 |
| R014T | 45.51 |
| R014G | 31.47 |
| R014S | 30.62 |
| R014I | 26.03 |
| R014A | 25.60 |
| R014Q | 25.38 |
| R014C | 23.91 |
| R014N | 23.61 |
| R014M | 18.47 |
| R014H | 15.72 |
| R014L | 15.35 |
| R014P | 12.43 |
| S015R | 57.77 |
| S015H | 53.39 |
| S015C | 50.38 |
| S015E | 25.99 |
| S015Y | 23.97 |
| S015M | 19.73 |
| S015F | 17.11 |

TABLE 30-7-continued

LAS Stability Assay Results

| Variant code | LAS stability [residual Activity (%)] |
|---|---|
| S015N | 16.21 |
| S015G | 14.44 |
| S015L | 12.00 |
| S015A | 11.84 |
| S015T | 11.83 |
| S015I | 10.89 |
| R016E | 34.61 |
| R016T | 27.36 |
| R016C | 25.97 |
| R016V | 25.79 |
| R016D | 22.22 |
| R016Q | 19.87 |
| R016I | 19.83 |
| R016S | 10.71 |
| A022C | 27.48 |
| A022S | 25.99 |
| N024E | 23.54 |
| N024T | 18.16 |
| N024G | 15.54 |
| N024S | 14.04 |
| N024F | 13.05 |
| N024V | 11.86 |
| I028V | 14.49 |
| R035E | 88.92 |
| R035D | 76.48 |
| R035Q | 49.08 |
| R035V | 49.02 |
| R035S | 47.13 |
| R035T | 44.84 |
| R035N | 42.49 |
| R035A | 42.38 |
| R035C | 41.31 |
| R035P | 32.50 |
| R035H | 27.88 |
| R035M | 25.29 |
| R035K | 15.26 |
| T036C | 25.91 |
| T036V | 20.77 |
| A038D | 47.40 |
| A038C | 34.28 |
| A038T | 12.27 |
| A041D | 24.80 |
| A041C | 23.37 |
| A041T | 18.58 |
| A041S | 15.58 |
| N042D | 15.04 |
| N042C | 13.16 |
| T044E | 33.74 |
| T044C | 17.24 |
| T046V | 40.22 |
| T046F | 34.46 |
| T046E | 34.01 |
| T046Y | 27.10 |
| T046C | 23.20 |
| F047R | 46.98 |
| F047V | 20.38 |
| F047I | 12.72 |
| A048E | 29.23 |
| G049C | 64.06 |
| G049Q | 49.53 |
| G049E | 48.76 |
| G049H | 47.79 |
| G049A | 43.93 |
| G049V | 43.28 |
| G049N | 29.58 |
| G049L | 24.93 |
| G049S | 19.86 |
| G049F | 16.65 |
| G049K | 15.46 |
| G049T | 11.73 |
| S051L | 19.79 |
| S051A | 15.12 |
| S051C | 14.59 |
| S051G | 14.33 |
| P053C | 11.51 |
| P053N | 10.68 |
| G054C | 26.41 |
| G054E | 19.88 |
| G054Q | 12.71 |
| G054K | 11.71 |
| N055G | 33.29 |
| N055A | 15.31 |
| D056L | 42.96 |
| D056F | 17.11 |
| Y057G | 27.33 |
| F059W | 31.25 |
| R061E | 30.95 |
| R061V | 26.22 |
| R061M | 26.01 |
| R061T | 23.33 |
| R061K | 20.21 |
| R061Q | 18.05 |
| G063D | 13.79 |
| A064C | 15.65 |
| G065D | 14.73 |
| V066N | 16.37 |
| A070M | 21.09 |
| A070G | 15.83 |
| A070P | 14.86 |
| Q071L | 11.17 |
| Y075W | 10.97 |
| G078H | 12.06 |
| R079T | 16.18 |
| R079V | 15.24 |
| R079L | 12.03 |
| V080E | 10.65 |
| Q081P | 18.28 |
| Q081G | 15.49 |
| Q081A | 14.60 |
| Q081E | 14.36 |
| Q081H | 14.02 |
| Q081S | 13.51 |
| Q081D | 13.17 |
| Q081Y | 13.15 |
| Q081F | 12.61 |
| Q081I | 11.93 |
| Q081W | 11.89 |
| Q081C | 11.40 |
| A083H | 17.04 |
| A083D | 15.14 |
| A083E | 14.66 |
| A083Y | 12.54 |
| A083V | 11.93 |
| A083N | 11.52 |
| A083M | 11.35 |
| A083F | 11.21 |
| A083I | 10.80 |
| H085P | 10.62 |
| T086E | 16.60 |
| T086I | 13.95 |
| T086C | 13.70 |
| T086W | 13.45 |
| T086V | 12.92 |
| T086Y | 10.97 |
| T086F | 10.78 |
| T086D | 10.70 |
| A087E | 20.99 |
| A087C | 17.19 |
| A087P | 11.78 |
| A088F | 18.06 |
| A088E | 14.11 |
| A088V | 13.47 |
| A088H | 10.95 |
| P089D | 10.88 |

TABLE 30-7-continued

LAS Stability Assay Results

| Variant code | LAS stability [residual Activity (%)] |
|---|---|
| V090C | 12.71 |
| G091Q | 23.98 |
| S092T | 17.35 |
| S092I | 11.15 |
| S092C | 10.93 |
| S092L | 10.60 |
| A093H | 14.05 |
| S099A | 28.58 |
| S099G | 22.20 |
| S099K | 17.98 |
| S099Q | 17.50 |
| S099H | 15.09 |
| T100A | 27.16 |
| T100R | 22.31 |
| T100K | 22.07 |
| T100Q | 15.53 |
| T100C | 11.47 |
| W103L | 20.25 |
| H104M | 10.65 |
| T107R | 26.61 |
| T107H | 12.35 |
| T109E | 24.23 |
| T109K | 17.25 |
| N112P | 25.16 |
| N112E | 17.68 |
| N112D | 15.90 |
| S113C | 35.77 |
| S113A | 16.28 |
| S113D | 14.68 |
| S113H | 13.27 |
| S114C | 22.24 |
| S114E | 16.60 |
| S114D | 11.86 |
| T116C | 16.41 |
| T116N | 14.90 |
| T116G | 14.42 |
| T116A | 11.29 |
| P118R | 28.25 |
| P118K | 23.28 |
| P118C | 16.70 |
| P118A | 15.98 |
| P118W | 15.50 |
| P118G | 14.55 |
| P118H | 13.73 |
| P118F | 12.80 |
| P118Y | 11.29 |
| E119G | 32.98 |
| E119Y | 29.43 |
| E119R | 26.97 |
| E119T | 26.28 |
| E119V | 24.47 |
| E119N | 20.71 |
| E119A | 19.95 |
| E119L | 15.83 |
| E119S | 15.80 |
| E119Q | 14.68 |
| T121E | 36.49 |
| T121L | 34.33 |
| T121F | 23.82 |
| T121A | 17.78 |
| T121D | 16.73 |
| T121V | 14.25 |
| T121Q | 12.39 |
| T121G | 12.17 |
| T121S | 11.93 |
| T121N | 11.51 |
| R123D | 48.24 |
| R123Y | 47.97 |
| R123C | 46.46 |
| R123E | 44.33 |
| R123N | 40.60 |
| R123H | 39.41 |
| R123T | 34.97 |
| R123W | 33.83 |
| R123F | 30.58 |
| R123S | 30.56 |
| R123Q | 25.60 |
| R123V | 24.71 |
| R123M | 18.54 |
| R123A | 17.24 |
| R123K | 16.38 |
| R123G | 16.12 |
| R123I | 16.04 |
| G124D | 25.10 |
| G124N | 12.84 |
| L125Q | 25.77 |
| L125M | 14.90 |
| R127E | 36.18 |
| R127S | 31.24 |
| R127D | 29.46 |
| R127Q | 27.92 |
| R127K | 25.25 |
| R127A | 21.74 |
| R127C | 16.40 |
| R127T | 14.31 |
| R127Y | 13.61 |
| R127H | 12.89 |
| R127F | 10.69 |
| T128A | 21.49 |
| T128V | 12.94 |
| V130C | 12.97 |
| A132S | 19.09 |
| A132P | 11.71 |
| P134R | 22.20 |
| S140P | 21.06 |
| L141M | 18.59 |
| L141C | 12.46 |
| A143H | 10.95 |
| G144E | 12.63 |
| N145E | 12.29 |
| Q146D | 12.05 |
| T151L | 46.42 |
| T151C | 26.57 |
| T151V | 17.57 |
| S155C | 38.40 |
| S155W | 30.61 |
| S155Y | 23.95 |
| S155I | 22.60 |
| S155V | 21.53 |
| S155E | 19.78 |
| S155T | 17.58 |
| S155F | 17.11 |
| S155Q | 12.59 |
| N157D | 18.83 |
| R159T | 28.61 |
| R159E | 27.00 |
| R159Q | 25.25 |
| R159D | 23.12 |
| R159V | 22.92 |
| R159S | 22.29 |
| R159K | 20.78 |
| R159N | 19.95 |
| R159C | 19.24 |
| R159A | 19.09 |
| R159M | 15.74 |
| R159L | 14.00 |
| R159H | 12.56 |
| R159Y | 11.23 |
| T160D | 15.18 |
| T160E | 11.72 |
| T163D | 23.84 |
| T163C | 19.09 |
| T163Q | 14.20 |
| T163R | 11.15 |

TABLE 30-7-continued

LAS Stability Assay Results

| Variant code | LAS stability [residual Activity (%)] |
|---|---|
| F165W | 28.00 |
| F165E | 23.57 |
| F165H | 21.46 |
| F165S | 14.33 |
| Q167E | 64.13 |
| Q167S | 12.59 |
| V169A | 12.75 |
| N170D | 29.08 |
| N170C | 23.07 |
| N170L | 14.63 |
| N170G | 13.30 |
| N170A | 12.77 |
| N170P | 12.72 |
| I172A | 20.40 |
| Q174C | 16.62 |
| Q174S | 14.76 |
| Q174T | 14.54 |
| Q174V | 13.40 |
| Q174H | 11.18 |
| A175T | 16.19 |
| G177D | 24.74 |
| G177E | 21.37 |
| G177C | 14.01 |
| G177N | 11.53 |
| R179E | 25.06 |
| R179D | 24.16 |
| R179C | 20.71 |
| R179V | 20.09 |
| R179I | 19.51 |
| R179T | 19.20 |
| R179Y | 17.89 |
| R179M | 16.74 |
| R179S | 16.12 |
| R179N | 16.11 |
| R179F | 15.67 |
| R179W | 15.56 |
| R179L | 15.12 |
| R179A | 14.35 |
| R179K | 12.30 |
| M180L | 25.64 |
| M180I | 12.31 |
| I181C | 11.51 |
| T182L | 12.63 |
| T183D | 13.51 |
| T183E | 13.32 |
| S185D | 14.31 |
| S185C | 13.10 |
| S185Y | 10.74 |
| S185N | 10.73 |
| G186E | 14.36 |
| G186P | 13.48 |
| G186C | 11.96 |
| S187E | 15.92 |
| S187F | 13.28 |
| S187L | 12.26 |
| S187C | 11.34 |
| S187W | 11.21 |
| S187G | 10.83 |
| S187A | 10.72 |
| S187V | 10.71 |
| S187H | 10.66 |
| S188E | 15.00 |
| S188C | 12.56 |
| S188T | 11.89 |
| S188G | 11.15 |
| S188V | 10.68 |

Example 31

Determination of ASP Cleaning Activity

In this Example, experiments conducted to determine the cleaning activity of ASP under various conditions, as well as the properties of the various wash conditions are described.

There is a wide variety of wash conditions including varying detergent formulations, wash water volume, wash water temperature, and length of wash time. Thus, detergent components such as proteases must be able to tolerate and function under adverse environmental conditions. For example, detergent formulations used in different areas have different concentrations of their relevant components present in the wash water. For example, a European detergent typically has about 3000-8000 ppm of detergent components in the wash water, while a Japanese detergent typically has less than 800 (e.g., 667 ppm) of detergent components in the wash water. In North America, particularly the United States, detergent typically have about 800 to 2000 (e.g., 975 ppm) of detergent components present in the wash water.

Latin American detergents are generally high suds phosphate builder detergents and the range of detergents used in Latin America can fall in both the medium and high detergent concentrations, as they range from 1500 ppm to 6000 ppm of detergent components in the wash water. Brazilian detergents typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 3000 ppm to about 8000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution, about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan can be between 10 and 30° C. (e.g., about 20° C.), whereas the temperature of wash water in Europe is a typically between 30 and 50° C. (e.g., about 40° C.).

As a further example, different geographies may have different water hardness. Water hardness is typically described as grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies from area to area. Moderately hard (60-120 ppm) to hard (121-181 ppm) water has 60 to 181 parts per million (i.e., parts per million converted to grains per U.S. gallon is ppm # divided by 17.1 equals grains per gallon) of hardness minerals. Table 31-1 provides ranges of water hardness.

TABLE 31-1

Water Hardness Ranges

| Water | Grains per Gallon | Parts per Million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than 10.5 (e.g., 10.5-20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between 3 to 10 grains, 3-8 grains or about 6 grains. Japanese water hardness is typically lower than North American water hardness, typically less than 4, for example 3 grains per gallon mixed $Ca^{2+}/Mg^{2+}$.

The present invention provides protease variants that provide improved wash performance in at least one set of wash conditions and typically in multiple wash conditions.

As described herein, the protease variants are tested for performance in different types of detergent and wash conditions using a microswatch assay (See above, and U.S. patent application Ser. No. 09/554,992; and WO 99/34011, both of which are incorporated by reference herein). Protease variants are tested for other soil substrates also in a similar fashion.

In the experiments conducted to determine cleaning activity of ASP, the following methods were used. Incubators (Innova 4330 Model Incubator, New Brunswick) was pre-warmed for 60 minutes to 40° C. for "European" conditions and for 20° C. for "Japanese" conditions. Blood-Milk-Ink swatches (EMPA 116) were obtained from the Swiss Federal Laboratories for Material Testing and from CFT Research, and were modified by exposure to 0.03% hydrogen peroxide for 30 minutes at 60° C., then dried. Circles of ¼" diameter were cut from the dried swatches and placed vertically, one per well, in a 96 well microplate.

Protease samples of ASP were diluted in 10 mM NaCl, 0.005% TWEEN®-80 to provide the desired concentration of 10 ppm (protein). To provide "North American wash conditions," 1 gram per liter TIDE® laundry detergent (Procter & Gamble) without bleach was prepared in deionized water, and a concentrated stock of calcium and magnesium was added to result in a final water hardness value of 6 grains per gallon. To provide "European wash conditions," 7.6 gram per liter ARIEL® REGULAR laundry detergent (Procter & Gamble) without bleach was prepared in deionized water, and a concentrated stock of calcium and magnesium was added to result in a final water hardness value of 15 grains per gallon. To provide "Japanese wash conditions," 0.67 gram per liter PURE CLEAN laundry detergent (Procter & Gamble) without bleach was prepared in deionized water, and a concentrated stock of calcium and magnesium was added to result in a final water hardness value of 3 grains per gallon.

In yet another detergent composition to provide "Japanese wash conditions with North American detergent formulation," 0.66 gram per liter Detergent Composition III without bleach was prepared in deionized water, and a concentrated stock of calcium and magnesium was added to result in a final water hardness value of 3 grains per gallon.

The detergent solutions were allowed to mix for 15 minutes and were then filtered through a 0.2 micron cellulose acetate filter. A 190 ul of the respective detergent solution was then added to the appropriate wells of a microplate. Then, 10 ul of the enzyme preparation were added to the filtered detergent in order to obtain a final concentration 0.25-3.0 ppm (micrograms per milliliter) of enzyme, for a total volume of 200 µl. The microplate was then sealed to prevent leakage, placed in a holder on an incubator/shaker set to 20° C. and 350/400 RPM and allowed to shake for one hour.

The plate was then removed from the incubator/shaker and an aliquot of 100 µl of solution was removed from each well, and placed on a fresh Costar microtiter plate (Corning). The absorbance at 405 nm wavelength was read for each aliquot on a Microtiter plate reader (SpectraMax 340, Molecular Devices), and reported. The detergent composition and incubation conditions in the microswatch assay are set forth in Table 31-2.

TABLE 31-2

Detergent Composition and Incubation Conditions

| Geography | Detergent | Water Hardness | Enzyme dosage | Temperature | Swatch |
|---|---|---|---|---|---|
| Powder detergent | | | | | |
| European | Ariel Regular 7.6 g/l | 15 gpg Ca/Mg = 4/1 | 0.25-3.0 ppm | 40° | Superfix |
| North American | Detergent Comp. III 1.0 g/l | 6 gpg Ca/Mg = 3/1 | 0.25-3.0 ppm | 20° | 3K |
| Japanese | Pure Clean 0.66 g/l | 3 gpg Ca/Mg = 3/1 | 0.25-3.0 ppm | 20° | 3K |
| Japanese (pseudo) | Detergent Comp. III 0.66 g/l | 3 gpg Ca/Mg = 3/1 | 0.25-3.0 ppm | 20° | 3K |
| Liquid detergent (1.5 ml/L) | Liquid-Tide ® | 6 gpg | 0.25-3.0 ppm | 20° | 3K |

The dose response curves depicting absorbance at 405 nm as a function of concentration (ppm in well), for PURAFECT® (Genencor), OPTIMASE® (Genencor), RELASE™ (Genencor; GG36-variant described above), and ASP are provided in FIGS. 23-27).

Figure 26:
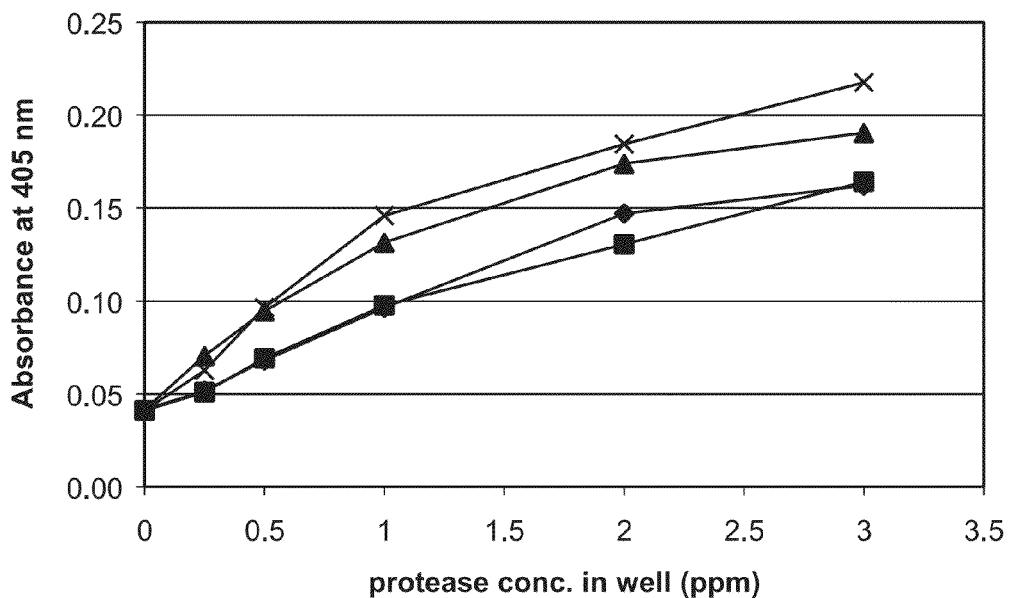
FIG. 26 compares the cleaning activity (absorbance at 405 nm) dose (ppm) response curves of certain serine proteases (69B4 [-x-]; PURAFECT® [-♦-]; RELASE™ [-▲]; and OPTIMASE™ [-■-] in liquid TIDE® detergent under North American wash conditions.
Figure 27:
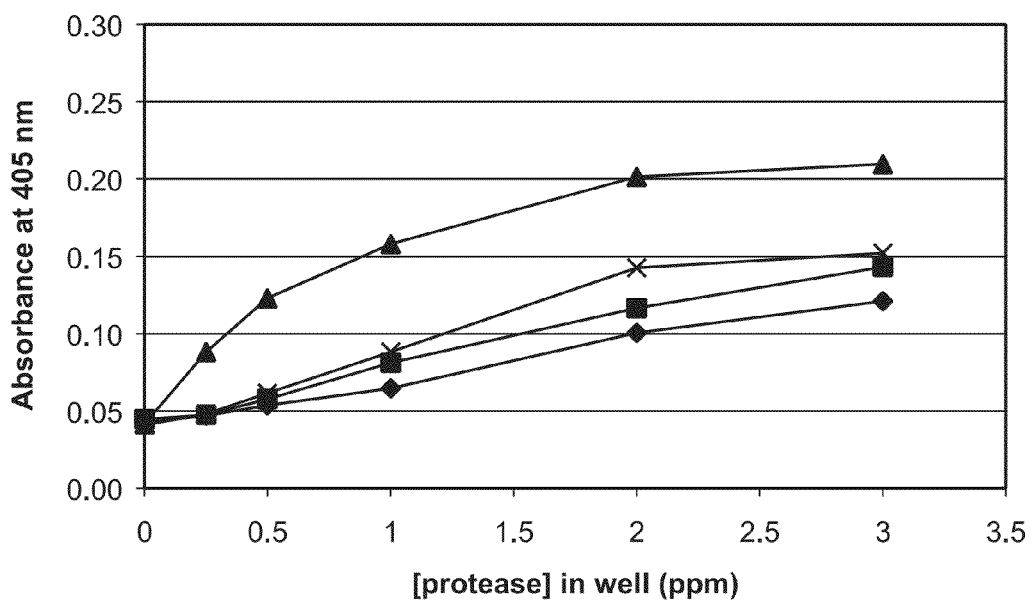
FIG. 27 provides a graph that compares the cleaning activity (absorbance at 405 nm) dose (ppm) response curves of certain serine proteases (69B4 [-x-]; PURAFECT® [-♦-]; RELASE™ [-▲-]; and OPTIMASE™ [-■-] in Detergent Composition III powder detergent (0.66 g/l) North American concentration/detergent formulation under Japanese wash conditions.
Figure 28:
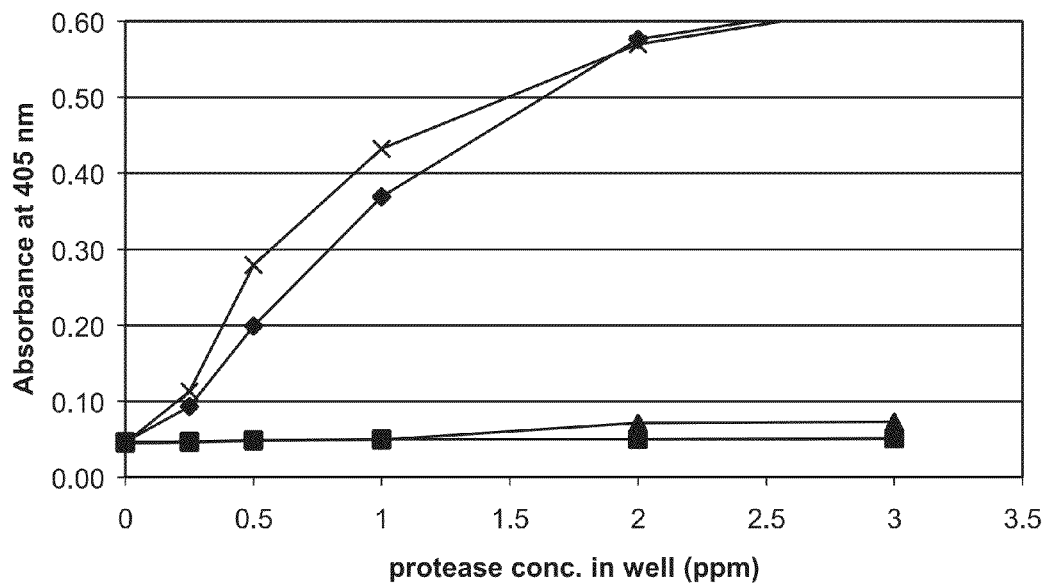
FIG. 28 provides a graph that compares the cleaning activity (absorbance at 405 nm) dose (ppm) response curves of certain serine proteases (69B4 [-x-]; PURAFECT® [-♦-]; RELASE™ [-▲]; and OPTIMASE™ [-■-] in ARIEL® REGULAR detergent powder under European wash conditions.
Figure 29:
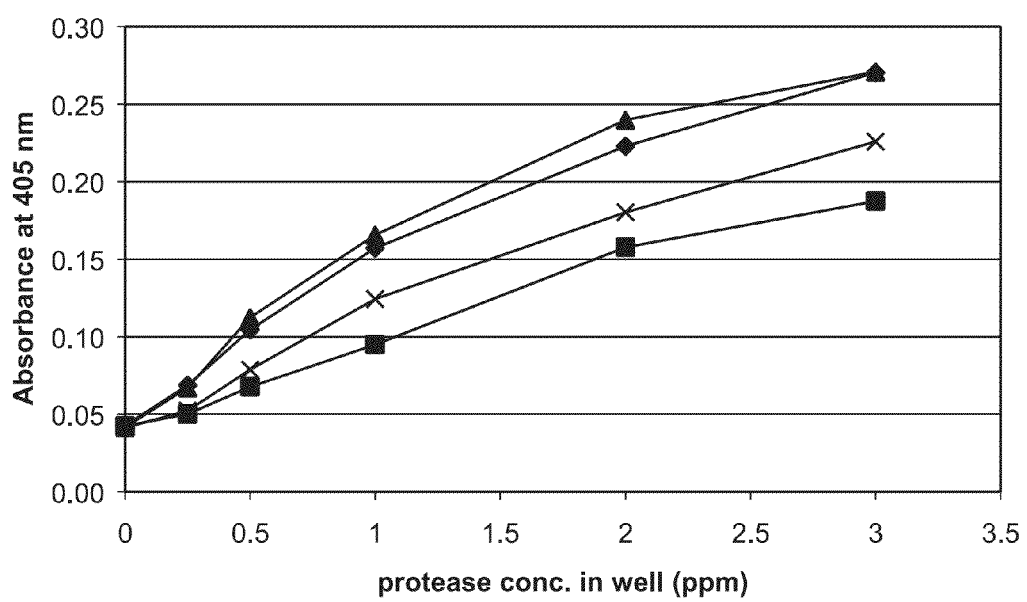
FIG. 29 provides a graph that compares the cleaning activity (absorbance at 405 nm) dose (ppm) response curves of certain serine protease (69B4 [-x-]; PURAFECT® [-♦-]; RELASE™ [-▲-]; and OPTIMASE™ [-■-] in PURE CLEAN detergent powder under Japanese conditions.
Figure 30:
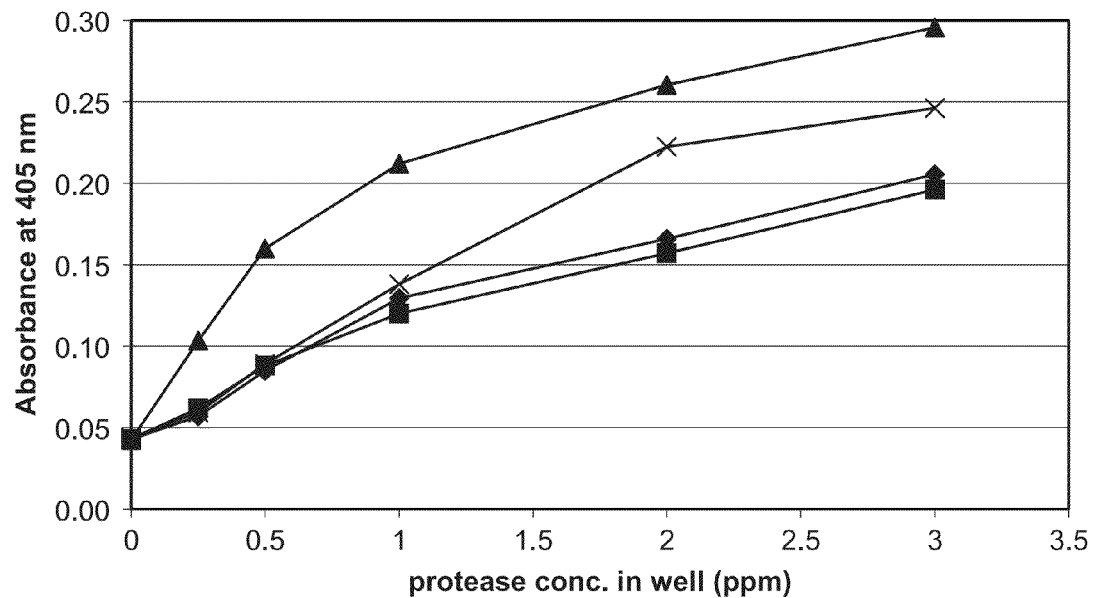
FIG. 30 provides a graph that compares the cleaning activity (absorbance at 405 nm) dose (ppm) response curves of certain serine proteases (69B4 [-x-]; PURAFECT® [-♦-]; RELASE™ [-▲-]; and OPTIMASE™ [-■] in Detergent Composition III powder (1.00 g/l) under North American conditions.

As indicated in FIG. 26, under North American conditions, in liquid TIDE® detergent, the ASP protease showed enhanced cleaning performance as compared to PURAFECT®, RELASE™ and OPTIMASE™ proteases under the same conditions. Under Japanese conditions, in Detergent Comp. III powder (0.66 g/l), ASP showed enhanced or the same cleaning performance as compared to PURAFECT®, RELASE™ and OPTIMASE™ proteases under the same conditions (See, FIG. 27). Under European conditions, in ARIEL® REGULAR powder detergent, the ASP protease showed enhanced cleaning performance as compared to PURAFECT®, RELASE™ and OPTIMASE™ proteases under the same conditions (See, FIG. 28). In both tests, ASP and OPTIMASE™ provided results that were 2 to 10 times the absorbance at 405 nm as compared to PURAFECT® and RELASE™. Under Japanese conditions, in PURE CLEAN powder detergent (See, FIG. 29), the ASP protease showed enhanced and comparative cleaning performance as compared to PURAFECT®, RELASE™ and OPTIMASE™ proteases under the same conditions. Under North American conditions, in Detergent Composition III powder detergent (See, FIG. 30), the ASP protease showed enhanced or comparative cleaning performance as compared to PURAFECT®, RELASE™ and OPTIMASE™ proteases under the same conditions.

Example 32

Liquid Fabric Cleaning Compositions

This Example provides liquid fabric cleaning compositions that find use in conjunction with the present invention. These compositions are contemplated to find particular utility under Japanese machine wash conditions, as well as for applications involving cleaning of fine and/or delicate fabrics. Table 32-1 provides a suitable composition. However, it is not intended that the present invention be limited to this specific formulation, as many other formulations find use with the present invention.

TABLE 32-1

Liquid Fabric Cleaning Composition

| Component | Amount (%) |
|---|---|
| AE2.5S | 2.16 |
| AS | 3.30 |
| N-Cocoyl N-methyl glucamine | 1.10 |
| Nonionic surfactant | 10.00 |
| Citric acid | 0.40 |
| Fatty acid | 0.70 |
| Base | 0.85 |
| Monoethanolamine | 1.01 |
| 1,2-Propanediol | 1.92 |
| EtOH | 0.24 |
| HXS | 2.09 |
| Protease.sup.1 | 0.01 |
| Amylase | 0.06 |
| Minors/inerts to 100% | |

Example 33

Liquid Dishwashing Compositions

This Example provides liquid dishwashing compositions that find use in conjunction with the present invention. These compositions are contemplated to find particular utility under Japanese dish washing conditions. Table 33-1 provide suitable compositions. However, it is not intended that the present invention be limited to this specific formulation, as many other formulations find use with the present invention.

TABLE 33-1

Liquid Dishwashing Compositions

| Component | A | B |
|---|---|---|
| AE1.4S | 24.69 | 24.69 |
| N-cocoyl N-methyl glucamine | 3.09 | 3.09 |
| Amine oxide | 2.06 | 2.06 |
| Betaine | 2.06 | 2.06 |
| Nonionic surfactant | 4.11 | 4.11 |
| Hydrotrope | 4.47 | 4.47 |
| Magnesium | 0.49 | 0.49 |
| Ethanol | 7.2 | 7.2 |
| LemonEase | 0.45 | 0.45 |
| Geraniol/BHT | — | 0.60/0.02 |
| Amylase | 0.03 | 0.005 |
| Protease | 0.01 | 0.43 |
| Balance to 100% | | |

Example 34

Liquid Fabric Cleaning Compositions

The proteases of the present invention find particular use in cleaning compositions. For example, it is contemplated that liquid fabric cleaning composition of particular utility under Japanese machine wash conditions be prepared in accordance with the invention. In some preferred embodiments, these compositions comprise the following components shown in Table 34-1.

TABLE 34-1

Liquid Fabric Cleaning Composition

| Component | Amount (%) |
|---|---|
| AE2.5S | 15.00 |
| AS | 5.50 |
| N-Cocoyl N-methyl glucamine | 5.50 |
| Nonionic surfactant | 4.50 |
| Citric acid | 3.00 |
| Fatty acid | 5.00 |
| Base | 0.97 |
| Monoethanolamine | 5.10 |
| 1,2-Propanediol | 7.44 |
| EtOH | 5.50 |
| HXS | 1.90 |
| Boric Acid | 3.50 |
| Ethoxylated tetraethylenepentaimine | 3.00 |
| SRP | 0.30 |
| Protease | 0.069 |
| Amylase | 0.06 |
| Cellulase | 0.08 |
| Lipase | 0.18 |
| Brightener | 0.10 |
| Minors/inerts to 100% | |

Example 35

Granular Fabric Cleaning Compositions

In this Example, various granular fabric cleaning compositions that find use with the present invention are provided. The following Tables provide suitable compositions. However, it is not intended that the present invention be limited to these specific formulations, as many other formulations find use with the present invention.

TABLE 35-1

Granular Fabric Cleaning Compositions

| | Formulations | | | |
|---|---|---|---|---|
| Component | A | B | C | D |
| Protease1 | 0.10 | 0.20 | 0.03 | 0.05 |
| Protease2 | | | 0.2 | 0.15 |
| C13 linear alkyl benzene sulfonate | 22.00 | 22.00 | 22.00 | 22.00 |
| Phosphate (as sodium tripolyphosphate) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-petaacetic acid) | 0.40 | 0.40 | 0.40 | 0.40 |
| Sodium sulfate | 5.50 | 5.50 | 5.50 | 5.50 |
| Water | Balance to 100% | | | |

TABLE 35-2

Granular Fabric Cleaning Compositions

| Component | A | B | C | D |
|---|---|---|---|---|
| Protease1 | 0.10 | 0.20 | 0.30 | 0.05 |
| Protease2 | | | 0.2 | 0.1 |
| C12 alkyl benzene sulfonate | 12.00 | 12.00 | 12.00 | 12.00 |
| Zeolite A (1-10 micrometer) | 26.00 | 26.00 | 26.00 | 26.00 |
| C12-C14 secondary (2,3) alkyl sulfate, Na salt | 5.00 | 5.00 | 5.00 | 5.00 |
| Sodium citrate | 5.00 | 5.00 | 5.00 | 5.00 |
| Optical brightenere | 0.10 | 0.10 | 0.10 | 0.10 |
| Sodium sulfate | 17.00 | 17.00 | 17.00 | 17.00 |
| Fillers, water, minors | Balance to 100% | | | |

The following laundry detergent compositions are contemplated to provide particular utility under European machine wash conditions.

TABLE 35-3

Granular Fabric Cleaning Compositions

| Component | A | B | C |
|---|---|---|---|
| LAS | 7.0 | 5.61 | 4.76 |
| TAS | | | 1.57 |
| C45AS | 6.0 | 2.24 | 3.89 |
| C25E25 | 1.0 | 0.76 | 1.18 |
| C45E7 | | | 2.0 |
| C25E3 | 4.0 | 5.5 | |
| QAS | 0.8 | 2.0 | 2.0 |
| STPP | | | |
| Zeolite | 25.0 | 19.5 | 19.5 |
| Citric acid | 2.0 | 2.0 | 2.0 |
| NaSKS-6 | 8.0 | 10.6 | 10.6 |
| Carbonate I | 8.0 | 10.0 | 8.6 |
| MA/AA | 1.0 | 2.6 | 1.6 |
| CMC | 0.5 | 0.4 | 0.4 |
| PB4 | | 12.7 | |
| Percarbonate | | | 19.7 |
| TAED | | 3.1 | 5.0 |
| Citrate | 7.0 | | |
| DTPMP | 0.25 | 0.2 | 0.3 |
| HEDP | 0.3 | 0.3 | 0.3 |
| QEA 1 | 0.9 | 1.2 | 1.0 |
| Protease1 | 0.02 | 0.05 | 0.035 |
| Lipase | 0.15 | 0.25 | 0.15 |
| Cellulase | 0.28 | 0.28 | 0.28 |
| Amylase | 0.4 | 0.7 | 0.3 |
| PVPI/PVNO | 0.4 | | 0.1 |
| Photoactivated bleach (ppm) | 15 ppm | 27 ppm | 27 ppm |
| Brightener 1 | 0.08 | 0.19 | 0.19 |
| Brightener 2 | | 0.04 | 0.04 |
| Perfume | 0.3 | 0.3 | 0.3 |
| Effervescent granules (malic acid 40%, sodium bicarbonate 40%, sodium carbonate 20%) | 15 | 15 | 5 |
| Silicon antifoam | 0.5 | 2.4 | 2.4 |
| Minors/inerts to 100% | Balance to 100% | | |

Example 36

Detergent Formulations

In this Example, various detergent formulations which find use with ASP and/or ASP variants are provided. It is understood that the test methods provided in this section must be used to determine the respective values of the parameters of the present invention.

In the exemplified detergent compositions, the enzymes levels are expressed by pure enzyme by weight of the total composition and unless otherwise specified, the detergent ingredients are expressed by weight of the total compositions. The abbreviated component identifications therein have the following meanings:

TABLE 36-1

Definitions Used in this Example

| | |
|---|---|
| LAS | Sodium linear $C_{11-13}$ alkyl benzene sulfonate. |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \bullet N+(CH_3)_2(C_2H_4OH)$ with $R_2 = C_{12}$-$C_{14}$. |
| Silicate | Amorphous Sodium Silicate ($SiO_2:Na_2O$ ratio = 1.6-3.2:1). |
| Metasilicate | Sodium metasilicate ($SiO_2:Na_2O$ ratio = 1.0). |
| Zeolite A | Hydrated Aluminosilicate of formula $Na_{12}(AlO_2SiO_2)_{12} \bullet 27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |
| AA | Sodium polyacrylate polymer of average molecular weight 4,500. |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3 \bullet 4H_2O$. |
| Percarbonate | Sodium percarbonate of nominal formula $2Na_2CO_3 \bullet 3H_2O_2$. |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD: | 5,12-diethyl-1,5,8,12-tetraazabicyclo[6,6,2] hexadecane, dichloride, Mn(II) salt |
| PAAC | Pentaamine acetate cobalt (III) salt. |
| Paraffin | Paraffin oil sold under the tradename Winog 70 by Wintershall. |

TABLE 36-1-continued

Definitions Used in this Example

| | |
|---|---|
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| Protease: | Proteolytic enzyme sold under the tradename Savinase, Alcalase, Everlase by Novo Nordisk A/S, and the following from Genencor International, Inc: "Protease A" described in U.S. RE 34,606 in FIGS. 1A, 1B, and 7, and at column 11, lines 11-37; "Protease B" described in U.S. Pat. No. 5,955,340 and U.S. Pat. No. 5,700,676 in FIGS. 1A, 1B and 5, as well as Table 1; and "Protease C" described in U.S. Pat. No. 6,312,936 and U.S. Pat. No. 6,482,628 in FIGS. 1-3 [SEQ ID 3], and at column 25, line 12, "Protease D" being the variant 101G/103A/104I/159D/232V/236H/245R/248D/252K (BPN' numbering) described in WO 99/20723. |
| Amylase | Amylolytic enzyme sold under the tradename Purafect ® Ox Am described in WO 94/18314, WO96/05295 sold by Genencor; Natalase ®, Termamyl ®, Fungamyl ® and Duramyl ®, all available from Novozymes A/S. |
| Lipase | Lipolytic enzyme sold under the tradename Lipolase Lipolase Ultra by Novozymes A/S and Lipomax by Gist-Brocades. |
| Cellulase | Cellulytic enzyme sold under the tradename Carezyme, Celluzyme and/or Endolase by Novozymes A/S. |
| Pectin Lyase | Pectaway ® and Pectawash ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Silicone antifoam: | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetreaethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |
| Clay | A hydrated aluminumu silicate in a general formula $Al_2O_3SiO_2 \cdot xH_2O$. Types: Kaolinite, montmorillonite, atapulgite, illite, bentonite, halloysite. |
| pH | Measured as a 1% solution in distilled water at 20° C. |

The following Table (Table 36-2) provides liquid laundry detergent compositions that are prepared.

TABLE 36-2

Liquid Laundry Detergent Compositions

| Component | I | II | III | IV | V |
|---|---|---|---|---|---|
| LAS | 24.0 | 32.0 | 6.0 | 8.0 | 6.0 |
| $C_{12}$-$C_{15}$ $AE_{1.8}S$ | — | — | 8.0 | 11.0 | 5.0 |
| $C_8$-$C_{10}$ amido propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | — | 17.0 | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 3.0 | — | 4.0 | 4.0 | 3.0 |
| Citric acid (anhydrous) | 6.0 | 5.0 | 3.0 | 3.0 | 2.0 |
| DETPMP | — | — | 1.0 | 1.0 | 0.5 |
| Monoethanolamine | # | # | 5.0 | 5.0 | 2.0 |
| Sodium hydroxide | — | — | 2.5 | 1.0 | 1.5 |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| ASP | 0.05 | 0.3 | 0.08 | 0.5 | 0.2 |
| Protease A | — | — | — | — | 0.1 |
| Aldose Oxidase | — | — | 0.3 | — | 0.003 |
| DETBCHD | — | — | 0.02 | 0.01 | — |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | | added to product to adjust the neat pH of the product to about 4.2 for (I) and about 3.8 for (II).

The following Table (36-3) provides hand dish liquid detergent compositions that are prepared.

TABLE 36-3

Hand Dish Liquid Detergent Compositions

| Component | I | II | III | IV | V | VI |
|---|---|---|---|---|---|---|
| $C_{12}$-$C_{15}AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | — | 3.0 | — | 1.0 | 3.0 | 1.0 |

TABLE 36-3-continued

Hand Dish Liquid Detergent Compositions

| Component | I | II | III | IV | V | VI |
|---|---|---|---|---|---|---|
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| ASP | 0.02 | 0.01 | 0.03 | 0.01 | 0.02 | 0.05 |
| Protease A | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water. | | | | | | |

The pH of these compositions is about 8 to about 11

Table 36-4 provides liquid automatic dishwashing detergent compositions that are prepared.

TABLE 36-4

Liquid Automatic Dishwashing Detergent Compositions

| Component | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | 4.0 | 3.0 | 3.0 | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| ASP | 0.1 | 0.03 | 0.05 | 0.03 | 0.06 |
| Protease B | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Table 36-5 provides laundry compositions which may be prepared in the form of granules or tablets that are prepared.

TABLE 36-5

Laundry Compositions

| Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2$H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |

TABLE 36-5-continued

Laundry Compositions

| Base Product | I | II | III | IV | V |
|---|---|---|---|---|---|
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | 8.0 | 15.0 | 15.0 |
| Sulfate | 5.0 | 12.0 | 2.0 | 17.0 | 3.0 |
| Silicate | — | 1.0 | — | — | 8.0 |
| ASP | 0.03 | 0.05 | 1.0 | 0.06 | 0.1 |
| Protease B | — | 0.01 | — | — | — |
| Protease C | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, Dye, Brightener/SRP1/Na Carboxymethylcellulose/Photobleach/$MgSO_4$/PVPVI/Suds suppressor/High Molecular PEG/Clay.

Table 36-6 provides liquid laundry detergent formulations which are prepared.

TABLE 36-6

Liquid Laundry Detergent Formulations

| Component | I | I | II | III | IV | V |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na Hydroxide | 6.0 | 6.0 | 2.0 | 3.5 | 4.0 | 3.0 |

TABLE 36-6-continued

Liquid Laundry Detergent Formulations

| Component | I | I | II | III | IV | V |
|---|---|---|---|---|---|---|
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Mono-ethanolamine | 3.0 | 3.0 | 1.5 | 1.0 | 2.5 | 1.0 |
| TEPAE | 2.0 | 2.0 | — | 1.0 | 1.0 | 1.0 |
| ASP | 0.03 | 0.05 | 0.01 | 0.03 | 0.08 | 0.02 |
| Protease A | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Table 36-7 provides compact high density dishwashing detergents that are prepared.

TABLE 36-7

Compact High Density Dishwashing Detergents

| Component | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| ASP | 0.072 | 0.053 | 0.053 | 0.026 | 0.059 | 0.01 |
| Protease B | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/Dye/SRP1/Na Carboxymethylcellulose/Photobleach/MgSO$_4$/PVPVI/Suds suppressor/High Molecular PEG/Clay.

The pH of the above compositions is from about 9.6 to about 11.3.

Table 36-8 provides tablet detergent compositions of the present invention that are prepared by compression of a granular dishwashing detergent composition at a pressure of 13KN/cm$^2$ using a standard 12 head rotary press:

TABLE 36-8

Tablet Detergent Compositions

| Component | I | II | III | IV | V | VI | VII | VIII |
|---|---|---|---|---|---|---|---|---|
| STPP | — | 48.8 | 44.7 | 38.2 | — | 42.4 | 46.1 | 36.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4:3 | 4.2 |
| Lipase | 0.001 | — | 0.01 | — | 0.02 | — | — | — |
| Protease B | 0.01 | — | — | — | — | — | — | — |
| Protease C | — | — | — | — | — | 0.01 | — | — |
| ASP | 0.01 | 0.08 | 0.05 | 0.04 | 0.052 | 0.023 | 0.023 | 0.029 |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 8.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na Carboxymethylcellulose/Photobleach/MgSO$_4$/PVPVI/Suds suppressor/High Molecular PEG/Clay.

The pH of these compositions is from about 10 to about 11.5. The tablet weight of these compositions is from about 20 grams to about 30 grams.

Table 36-9 provides liquid hard surface cleaning detergent compositions of the present invention that are prepared.

TABLE 36-9

Liquid Hard Surface Cleaning Detergent Compositions

| Component | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| $Na_2CO_3$ | 0.6 | 0.13 | 0.6 | 0.1 | 0.2 | 0.6 | 0.2 |
| 3Na Citrate $2H_2O$ | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| ASP | 0.07 | 0.05 | 0.08 | 0.03 | 0.06 | 0.01 | 0.04 |
| Protease B | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of these compositions is from about 7.4 to about 9.5.

Example 37

Animal Feed Comprising ASP

The present invention also provides animal feed compositions comprising ASP and/or ASP variants. In this Example, one such feed, suitable for poultry is provided. However, it is not intended that the present invention be limited to this specific formulation, as the proteases of the present invention find use with numerous other feed formulations. It is further intended that the feeds of the present invention be suitable for administration to any animal, including but not limited to livestock (e.g., cattle, pigs, sheep, etc.), as well as companion animals (e.g., dogs, cats, horses, rodents, etc.). The following Table provides a formulation for a mash, namely a maize-based starter feed suitable for administration to turkey poults up to 3 weeks of age.

TABLE 37-1

Animal Feed Composition

| Ingredient Amount | (wt. %) |
|---|---|
| Maize | 36.65 |
| Soybean meal (45.6% CP) | 55.4 |
| Animal-vegetable fat | 3.2 |
| Dicalcium phosphate | 2.3 |
| Limestone | 1.5 |
| Mineral premix | 0.3 |
| Vitamin premix | 0.3 |
| Sodium chloride | 0.15 |
| DL methionine | 0.2 |

In some embodiments, this feed formulation is supplemented with various concentrations of the protease(s) of the present invention (e.g., 2,000 units/kg, 4,000 units/kg and 6,000 units/kg).

All patents and publications mentioned in the specification are indicative of the levels of those skilled in the art to which the invention pertains. All patents and publications are herein incorporated by reference to the same extent as if each individual publication was specifically and individually indicated to be incorporated by reference. However, the citation of any publication is not to be construed as an admission that it is prior art with respect to the present invention.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. An isolated serine protease obtained from a member of the suborder *Micrococcineae* having at least 95% amino acid identity with the amino acid sequence set forth in SEQ ID NO: 8 and having the serine protease activity of the *Cellulomonas* 69B4 protease set forth by SEQ ID NO: 8.

2. The serine protease of claim 1, wherein said protease is a cellulomonadin.

3. The serine protease of claim 1, wherein said protease is obtained from a *Cellulomonas* species.

4. The serine protease of claim 3, wherein said protease is obtained from *Cellulomonas* 69B4.

5. The serine protease of claim 4, wherein said protease comprises the amino acid sequence set forth in SEQ ID NO: 8.

6. A composition comprising an isolated serine protease having immunological cross-reactivity with said serine protease of claim 4.

7. A composition comprising an isolated serine protease having immunological cross-reactivity with said serine protease of claim 1.

8. A cleaning composition comprising the serine protease of claim 1.

9. The cleaning composition of claim 8, wherein said protease is a serine protease obtained from a *Cellulomonas* organism.

10. The cleaning composition of claim 9, wherein said protease is obtained from *Cellulomonas* 69B4.

11. The cleaning composition of claim 10, wherein said protease comprises the amino acid sequence set forth in SEQ ID NO: 8.

12. A cleaning composition comprising a serine protease, wherein said serine protease has immunological cross-reactivity with the serine protease of claim 8.

13. A cleaning composition comprising a serine protease, wherein said serine protease has immunological cross-reactivity with the serine protease of claim 10.

14. A composition comprising the serine protease of claim 1 and at least one stabilizing agent.

15. The composition of claim 14, wherein said stabilizing agent is selected from the group consisting of borax, glycerol, and competitive inhibitors.

16. The composition of claim 15, wherein said competitive inhibitors stabilize said serine protease to anionic surfactants.

17. The cleaning composition according to claim 8, said composition comprising a sufficient amount of a pH modifier to provide said composition with a neat pH of from about 3 to about 5, said composition being essentially free of materials that hydrolyze at a pH of from about 3 to about 5.

18. The cleaning composition according to claim 17, wherein said materials that hydrolyze comprise a surfactant material.

19. The cleaning composition according to claim 17, said cleaning composition being a liquid composition.

20. The cleaning composition according to claim 18, wherein said surfactant material comprises a sodium alkyl sulfate surfactant that comprises an ethylene oxide moiety.

21. A cleaning composition that comprises at least one acid stable enzyme, said cleaning composition comprising a sufficient amount of a pH modifier to provide said composition with a neat pH of from about 3 to about 5, said composition being essentially free of materials that hydrolyze at a pH of from about 3 to about 5, and wherein said acid stable enzyme is stable at the neat pH of from about 3 to about 5.

22. The cleaning composition according to claim 21, wherein said materials that hydrolyze comprise a surfactant material.

23. The cleaning composition according to claim 21, said cleaning composition being a liquid composition.

24. The cleaning composition according to claim 21, wherein said surfactant material comprises a sodium alkyl sulfate surfactant that comprises an ethylene oxide moiety.

25. The composition according to claim 17, said composition comprising from about 0.001 to about 0.5 weight % of SEQ ID NO: 8.

26. The composition according to claim 25, said composition comprising from about 0.01 to about 0.1 weight percent of SEQ ID NO: 8.

27. The composition of claim 8, said composition being a granule cleaning composition, powder cleaning composition, or tablet cleaning composition.

28. The composition of claim 27, said composition comprising a bleaching material.

29. The composition of claim 27, said composition being a granule cleaning composition.

30. The composition of claim 27, said composition being a powder cleaning composition.

31. The composition of claim 27, said composition being a tablet cleaning composition.

* * * * *